United States Patent
Bedian et al.

(10) Patent No.: US 12,110,344 B2
(45) Date of Patent: Oct. 8, 2024

(54) ANTIBODIES THAT BIND TO C1S AND USES THEREOF

(71) Applicant: DIANTHUS THERAPEUTICS OPCO, INC., New York, NY (US)

(72) Inventors: Vahe Bedian, Waltham, MA (US); Charles A. Omer, Waltham, MA (US)

(73) Assignee: DIANTHUS THERAPEUTICS OPCO, INC., New York, NY (US)

( * ) Notice: Subject to any disclaimer, the term of this patent is extended or adjusted under 35 U.S.C. 154(b) by 0 days.

(21) Appl. No.: 18/515,714

(22) Filed: Nov. 21, 2023

(65) Prior Publication Data

US 2024/0166769 A1    May 23, 2024

Related U.S. Application Data

(60) Provisional application No. 63/590,980, filed on Oct. 17, 2023, provisional application No. 63/501,807, filed on May 12, 2023, provisional application No. 63/485,765, filed on Feb. 17, 2023, provisional application No. 63/384,537, filed on Nov. 21, 2022.

(51) Int. Cl.
| | |
|---|---|
| C07K 16/40 | (2006.01) |
| A61P 25/28 | (2006.01) |
| A61K 39/00 | (2006.01) |

(52) U.S. Cl.
CPC .............. *C07K 16/40* (2013.01); *A61P 25/28* (2018.01); *A61K 39/00* (2013.01)

(58) Field of Classification Search
None
See application file for complete search history.

(56) References Cited

U.S. PATENT DOCUMENTS

| | | | |
|---|---|---|---|
| 4,439,196 A | 3/1984 | Higuchi | |
| 4,447,224 A | 5/1984 | DeCant, Jr. et al. | |
| 4,447,233 A | 5/1984 | Mayfield | |
| 4,487,603 A | 12/1984 | Harris | |
| 4,596,556 A | 6/1986 | Morrow et al. | |
| 4,790,824 A | 12/1988 | Morrow et al. | |
| 4,816,567 A | 3/1989 | Cabilly et al. | |
| 4,941,880 A | 7/1990 | Burns | |
| 4,946,778 A | 8/1990 | Ladner et al. | |
| 5,064,413 A | 11/1991 | McKinnon et al. | |
| 5,260,203 A | 11/1993 | Ladner et al. | |
| 5,312,335 A | 5/1994 | McKinnon et al. | |
| 5,383,851 A | 1/1995 | McKinnon, Jr. et al. | |
| 5,399,163 A | 3/1995 | Peterson et al. | |
| 6,005,079 A | 12/1999 | Casterman et al. | |
| 6,096,002 A | 8/2000 | Landau | |
| 6,620,135 B1 | 9/2003 | Weston et al. | |
| 7,670,600 B2 | 3/2010 | Dall'Acqua et al. | |
| 8,394,925 B2 | 3/2013 | Chamberlain et al. | |
| 2016/0053002 A1 | 2/2016 | Van Vlasselaer et al. | |
| 2016/0090425 A1 | 3/2016 | Rosenthal et al. | |
| 2019/0010233 A1 | 1/2019 | Liu et al. | |
| 2020/0048332 A1 | 2/2020 | Panicker et al. | |
| 2021/0115116 A1 | 4/2021 | Van Vlasselaer et al. | |
| 2022/0380483 A1 | 12/2022 | Bedian | |

FOREIGN PATENT DOCUMENTS

| | | |
|---|---|---|
| EP | 404097 A2 | 12/1990 |
| WO | 1988001649 A1 | 3/1988 |
| WO | 1993011161 A1 | 6/1993 |
| WO | 1994004678 A1 | 3/1994 |
| WO | 1994025591 A1 | 11/1994 |
| WO | 2012148497 A2 | 11/2012 |
| WO | 2015054670 A1 | 4/2015 |
| WO | 2018071676 A1 | 4/2018 |
| WO | 2018091661 A1 | 5/2018 |
| WO | 2022046888 A1 | 3/2022 |
| WO | 2022246154 A2 | 11/2022 |

OTHER PUBLICATIONS

Alegre et al., "Effect of a Single Amino Acid Mutation on the Activating and Immunosuppressive Properties of a "Humanized" OKT3 Monoclonal Antibody," J Immunol, 148(1):3461-3468 (1992).
Baert et al., "Influence of Immunogenicity on the Long-Term Efficacy of Infliximab in Crohn's Disease," (2003) New Engl. J. Med. 348:601-608.
Bayly-Jones, et al. The mystery behind membrane insertion: a review of the complement membrane attacl complex, Phil. Trans. R. Soc.; vol. 372, Feb. 21, 2016.
Beniaminovitz et al., "Prevention of Rejection in Cardiac Transplantation by Blockade of the Interleukin-2 Receptor with a Monoclonal Antibody," (2000) New Engl. J. Med. 342(9):613-619.
Brown et al., "The Classical Pathway is the Dominant Complement Pathway Required for Innate Immunity to Streptococcus Pneumoniae Infection in Mice," Proc Natl Acad Sci USA 99(26):16969-16974, 2002.
Budayova-Spano et al., "The Crystal Structure of the Zymogen Catalytic Domain of Complement Protease C1r Reveals that a Disruptive Mechanical Stress is Required to Trigger Activation of the C1 Complex," EMBO J. (2002) 21(3):231-239.
Cella, et al., Brief measures of health-related quality of life for clinical research in neurology, Qual. Life Clin. Res. Neurol. 2012; 78:1860-1867.
Chalder T. et al., Development of a Fatigue Scale, Journal of Psychosom Resarch 1993; vol. 37, No. 2. pp 147-153.
Chothia et al., "Canonical Structures for the Hypervariable Regions of Immunoglobulins," (1987) J. Mol. Biol. 196:901-917.
Chothia et al., "Conformations of Immunoglobulin Hypervariable Regions," (1989) Nature 342: 877-883.

(Continued)

*Primary Examiner* — Sharon X Wen
(74) *Attorney, Agent, or Firm* — Goodwin Procter LLP

(57) ABSTRACT

Embodiments that are provided for herein relate to antibodies and compositions that bind to C1s. Also provided are methods of producing the antibodies of the present disclosure, as well as uses of the provided antibodies and compositions for the treatment of C1s mediated diseases and disorders.

25 Claims, 14 Drawing Sheets

Specification includes a Sequence Listing.

(56) References Cited

OTHER PUBLICATIONS

Clackson et al., "Making Antibody Fragments Using Phage Display Libraries," (1991) Nature 352:624-628. (Abstract Only).
Dall'Acqua et al., "Increasing the Affinity of a Human IgG1 for the Neonatal Fc Receptor: Biological Consequences," J Immunol, 169(9): 5171-5180 (2002).
David et al., "Protein Iodination with Solid State Lactoperoxidase," (1974) Biochemistry 13(5): 1014-1021. (Abstract Only).
Dombrowski et al., "Direct Submission," Marine Science Institute (Feb. 9, 2016) pp. 1-2.
Fernandez-Quintero, et al., Germline-Dependent Antibody Paratope States and Pairing Specific VH-VL Interface Dynamics, Frontiers in Immunology, vol. 12, 2021.
Fisk J.D et al., Measuring the functional impact of fatigue: initial validation of the fatigue impact scale. Clin Infect Dis. 1994; 1: S79-S83.
Ghosh et al., "Natalizumab for Active Crohn's Disease," (2003) New Engl. J. Med. 348:24-32.
Grohar-Murray, et al. Self-care to manage fatigue among myasthenia gravis patients, Journal of Neuroscience Nusring, vol. 30 Issue 3, Jun. 1998.
Herold et al., "Anti-CD3 Monoclonal Antibody in New-Onset Type 1 Diabetes Mellitus," (2002) New Engl. J. Med. 346 (22):1692-1698.
Holliger et al., "Diabodies: Small Bivalent and Bispecific Antibody Fragments," (1993) Proc. Natl. Acad. Sci. USA 90:6444-6448.
Holliger et al., "Engineered Antibody Fragments and the Rise of Single Domains," (2005) Nat. Biotechnol. 23(9):1126-1136.
International Search Report and Written Opinion for International PCT Application No. PCT/US2022/030189 dated Nov. 10, 2022.
Kabat et al., "Unusual Distributions of Amino Acids in Complementarity-Determining (Hypervariable) Segments of Heavy and Light Chains of Immunoglobulins and Their Possible Roles in Specificity of Antibody-Combining Sites," (1977) J. Biol. Chem. 252(19):6609-6616.
Kabat, "The Structural Basis for Antibody Complementarity," Adv. Prot. Chem. (1978) 32:1-75. (Abstract Only).
Kohler, G., et al., Continuous cultures of fused cells secreting antibody of predefined specificity, Nature, vol. 256, Aug. 1975, pp. 495-497.
Krupp, et al., The Fatigue Severity Scale Application to Patients With Multiple Scelrosis and Systemic Lupus Erythematosus, Arch Neurol, vol. 46, Oct. 1989.
Kusumoto, et al., Human genes for complement components C1r and C1s in a close tail-to-tail arrangement, Proc. Natl. Acad. Sci. USA 85(19), 7307-7311 (1988).
Lathe, "Synthetic Oligonucleotide Probes Deduced from Amino Acid Sequence Data," J. Molec. Biol. (1985) 183:1-12.
Lee et al., "Prolonged Circulating Lives of Single Chain Fv Proteins Conjugated with Polyethylene Glycol: A Comparison of Conjugation Chemistries and Compounds," (1999) Bioconj. Chem. 10(6): 973-981. (Abstract Only).
Lipsky et al., "Infliximab and Methotrexate in the Treatment of Rheumatoid Arthritis," (2000) New Engl. J. Med. 343 (22): 1594-1602.
Liu et al., "Chimeric Mouse-Human IgG1 Antibody that can Mediate Lysis of Cancer Cells," Proc Natl. Acad. Sci., USA (1987) 84:3439-3443.
Liu et al., "Production of a Mouse-Human Chimeric Monoclonal Antibody to CD20 with Potent Fc-Dependent Biologic Activity," J. Immunology (1987) 139(10):3521-3526.
Liu et al., "Randomised, Double Blind, Placebo Controlled Study of Interferon Beta-1a in Relapsing-Remitting Multiple Sclerosis Analysed by Area under Disability/Time Curves," J. Neurol. Neurosurg. Psych. (1999) 67:451-456.
Marks et al., "By-Passing Immunization," J. Mol. Biol. (1991) 222: 581-597.
Milgrom et al., "Treatment of Allergic Asthma with Monoclonal Anti-IgE Antibody," New Engl. J. Med. (1999) 341:1966-1973.
Morrison, et al. Chimeric Human Antibody Molecules: Mouse Antigen-Binding Domains with Human Constant Region Domains, Pro. Natl. Aca. Sci. USA, vol. 81, pp. 6851-6855, Nov. 1984, Immunology.
Muller, "[43] Determination of Affinity and Specificity of Anti-Hapten Antibodies by Competitive Radioimmunoassay," Meth. Enzymol. (1983) 92:589-601. (Abstract Only).
Muyldermans et al., "Recognition of Antigens by Single-Domain Antibody Fragments: the Superfluous Luxury of Paired Domains," (2001) Trends Biochem. Sci. 26(4):230-235.
Pain et al., "Preparation of Protein A-Peroxidase Monoconjugate Using a Heterobifunctional Reagent, and its Use in Enzyme Immunoassays," (1981) J. Immunol. Meth. 40(2): 219-230. (Abstract Only).
Penner, I., et al., The Fatigue Scale for Motor and Cognitive Functions (FSMC): validation of a new instrument to assess multiple sclerosis-related fatigue, Multiple Sclerosis, 2009; 15 (12), pp. 1509-1517.
Pluckthun, "Antibodies from *Escherichia Coli*," Nature (Oct. 4, 1990) vol. 347, No. 6292, pp. 497-498.
Portielji et al., "IL-12: A Promising Adjuvant for Cancer Vaccination," Cancer Immunol. Immunother. (2003) 52:133-144.
Presta, "Selection, Design, and Engineering of Therapeutic Antibodies," J. Allergy Clin. Immunol. (2005) 116 (4):731-736.
Rabia, L., et al. (2018) Understanding and overcoming trade-offs between antibody affinity, specificity, stability, and solubility, Biochem Eng. J. 15(137(; 365-374.
Reichmann et al., "Reshaping Human Antibodies for Therapy." (1988) Nature 332(6162): 323-327.
Rowley et al., "A Protein Epitope Targeted by the Antibody Response to Kawasaki Disease," Pediatrics, Northwestern (Jan. 10, 2019) pp. 1-2.
Silva, et al. The S228P Mutation Prevents in Vivo and in Vitro IgG4 Fab-arm Exchange as Demonstrated using a Combination of Novel Quantitative Immunoassays and Physiological Matrix Preparation, The The Journal of Biological Chemistry, vol. 290, No. 9, pp. 5462-5469, Feb. 27, 2015.
Slamon et al., "Use of Chemotherapy Plus a Monoclonal Antibody against HER2 for Metastatic Breast Cancer that Overexpresses HER2," (2001) New Engl. J. Med. 344(11):783-792.
Tsurushita, N., et al., Humanization of a chicken anti-IL-12 monoclonal antibody, Journal of Immunological Methods, 295 (2004) pp. 9-19.
U.S. Appl. No. 17/749,362 Non-Final Office Action dated Mar. 14, 2024.
Wen et al., "Poly(ethylene glycol)-Conjugated Anti-EGF Receptor Antibody C225 with Radiometal Chelator Attached to the Termini of Polymer Chains," (2001) Bioconj. Chem. 12(4): 545-553. (Abstract Only).
Xie, "A Highly Resolved Spatial and Functional Map of the Ruminant Gastrointestinal Microbiome," Unpublished (Nov. 20, 2020) pp. 1-4.
Yang, et al., A Randomized Trial of Bevacizumab, an Anti-Vascular Endothelial Growth Factor Antibody, for Metastatic Renal Cancer, New England Journal of Medicine, Jul. 3, 20031; 349(5); 427-434.

MEWSWVFLFFLSVTTGVHSEPTMYGEILSPNYPQAYPSEVEKSWDIEVPEGYGIHLYFTHLDIELSENCAYDSVQIISGDT
EEGRLCGQRSSNNPHSPIVEEFQVPYNKLQVIFKSDFSNEERFTGFAAYYVATDINECTDFVDVPCSHFCNNFIGGYFCSC
PPEYFLHDDMKNCGVNCSGDVFTALIGEIASPNYPKPYPENSRCEYQIRLEKGFQVVVTLRREDFDVEAADSAGNCLDSLV
FVAGDRQFGPYCGHGFPGPLNIETKSNALDIIFQTDLTGQKKGWKLRYHGDPMPCPKEDTPNSVWEPAKAKYVFRDVVQIT
CLDGFEVVEGRVGATSFYSTCQSNGKWSNSKLKCQPVDCGIPESIENGKVEDPESTLFGSVIRYTCEEPYYYMENGGGGEY
HCAGNGSWVNEVLGPELPKCVPVCGVPREPFEEKQQIIGGSDADIKNFPWQVFFDNPWAGGALINEYWVLTAAHVVEGNRE
PTMYVGSTSVQTSRLAKSKMLTPEHVFIHPGWKLLEVPEGRTNFDNDIALVRLKDPVKMGPTVSPICLPGTSSDYNLMDGD
LGLISGWGRTEKRDRAVRLKAARLPVAPLRKCKEVKVEKPTADAEAYVFTPNMICAGGEKGMDSCKGDSGGAFAVQDPNDK
TKFYAAGLVSWGPQCGTYGLYTRVKNYVDWIMKTMQENSTPRED*GGGGAGGGGHHHHHHHH**

FIG. 1

Anti-capsular antibody (α-Nm)
mimics N. meningitidis vaccination
(note: 80% human sera was used in the assay)

FIG. 11

SEQUENCE LISTING

```
Sequence total quantity: 455
SEQ ID NO: 1            moltype = AA  length = 118
FEATURE                 Location/Qualifiers
source                  1..118
                        mol_type = protein
                        organism = synthetic construct
SEQUENCE: 1
QVQLVESGGG LVKPGGSLRL SCAASGFTFS DYYMSWIRQA PGKGLEWVSY ISRSGSTKYY  60
ADSVKGRFTI SRDNAKNSLY LQMNSLRAED TAVYYCARDQ EDYALDYWGQ GTLVTVSS    118

SEQ ID NO: 2            moltype = AA  length = 107
FEATURE                 Location/Qualifiers
source                  1..107
                        mol_type = protein
                        organism = synthetic construct
SEQUENCE: 2
DIQMTQSPSS LSASVGDRVT ITCQASQDIS NYLNWYQQKP GKAPKLLIYD ASNLETGVPS  60
RFSGSGSGTD FTFTISSLQP EDIATYYCEQ YEDYPLTFGG GTKVEIK                107

SEQ ID NO: 3            moltype = AA  length = 118
FEATURE                 Location/Qualifiers
```

```
source                        1..118
                              mol_type = protein
                              organism = synthetic construct
SEQUENCE: 3
QVQLVESGGG LVKPGGSLRL SCAASGFTFS DYYMSWIRQA PGKGLEWVSY ISRSGSTKYY    60
ADSVKGRFTI SRDNAKNSLY LQMNSLRAED TAVYYCARDE TDYGWDYWGQ GTLVTVSS    118

SEQ ID NO: 4                  moltype = AA  length = 107
FEATURE                       Location/Qualifiers
source                        1..107
                              mol_type = protein
                              organism = synthetic construct
SEQUENCE: 4
DIQMTQSPSS LSASVGDRVT ITCQASQDIS NYLNWYQQKP GKAPKLLIYD ASNLETGVPS    60
RFSGSGSGTD FTFTISSLQP EDIATYYCEQ YEDYPLTFGG GTKVEIK                107

SEQ ID NO: 5                  moltype = AA  length = 118
FEATURE                       Location/Qualifiers
source                        1..118
                              mol_type = protein
                              organism = synthetic construct
SEQUENCE: 5
QVQLVESGGG LVKPGGSLRL SCAASGFTFS DYYMSWIRQA PGKGLEWVSY ISRSGSTKYY    60
ADSVKGRFTI SRDNAKNSLY LQMNSLRAED TAVYYCARDE TDYAFDEWGQ GTLVTVSS    118

SEQ ID NO: 6                  moltype = AA  length = 107
FEATURE                       Location/Qualifiers
source                        1..107
                              mol_type = protein
                              organism = synthetic construct
SEQUENCE: 6
DIQMTQSPSS LSASVGDRVT ITCQASQDIS NYLNWYQQKP GKAPKLLIYD ASNLETGVPS    60
RFSGSGSGTD FTFTISSLQP EDIATYYCKQ YEDYPLTFGG GTKVEIK                107

SEQ ID NO: 7                  moltype = AA  length = 118
FEATURE                       Location/Qualifiers
source                        1..118
                              mol_type = protein
                              organism = synthetic construct
SEQUENCE: 7
QVQLVESGGG LVKPGGSLRL SCAASGFTFS DYYMSWIRQA PGKGLEWVSY ISRSGSTKYY    60
ADSVKGRFTI SRDNAKNSLY LQMNSLRAED TAVYYCARDE SQYALDYWGQ GTLVTVSS    118

SEQ ID NO: 8                  moltype = AA  length = 107
FEATURE                       Location/Qualifiers
source                        1..107
                              mol_type = protein
                              organism = synthetic construct
SEQUENCE: 8
DIQMTQSPSS LSASVGDRVT ITCQASQDIS NYLNWYQQKP GKAPKLLIYD ASNLETGVPS    60
RFSGSGSGTD FTFTISSLQP EDIATYYCHQ YEDYPLTFGG GTKVEIK                107

SEQ ID NO: 9                  moltype = AA  length = 118
FEATURE                       Location/Qualifiers
source                        1..118
                              mol_type = protein
                              organism = synthetic construct
SEQUENCE: 9
QVQLVESGGG LVKPGGSLRL SCAASGFTFS DYYMSWIRQA PGKGLEWVSY ISRSGSTKYY    60
AHSVKGRFTI SRDNAKNSLY LQMNSLRAED TAVYYCARDN TDYALDLWGQ GTLVTVSS    118

SEQ ID NO: 10                 moltype = AA  length = 107
FEATURE                       Location/Qualifiers
source                        1..107
                              mol_type = protein
                              organism = synthetic construct
SEQUENCE: 10
DIQMTQSPSS LSASVGDRVT ITCQASQDIS NYLNWYQQKP GKAPKLLIYD ASNLETGVPS    60
RFSGSGSGTD FTFTISSLQP EDIATYYCHQ YEDYPLTFGG GTKVEIK                107

SEQ ID NO: 11                 moltype = AA  length = 118
FEATURE                       Location/Qualifiers
source                        1..118
                              mol_type = protein
                              organism = synthetic construct
SEQUENCE: 11
QVQLVESGGG LVKPGGSLRL SCAASGFTFS DYYMSWIRQA PGKGLEWVSY ISRSGSTKYY    60
AHSVKGRFTI SRDNAKNSLY LQMNSLRAED TAVYYCARDE TDYAYDEWGQ GTLVTVSS    118
```

```
SEQ ID NO: 12              moltype = AA   length = 107
FEATURE                    Location/Qualifiers
source                     1..107
                           mol_type = protein
                           organism = synthetic construct
SEQUENCE: 12
DIQMTQSPSS LSASVGDRVT ITCQASQDIS NYLNWYQQKP GKAPKLLIYD ASNLETGVPS    60
RFSGSGSGTD FTFTISSLQP EDIATYYCHQ YEDYPLTFGG GTKVEIK                 107

SEQ ID NO: 13              moltype = AA   length = 118
FEATURE                    Location/Qualifiers
source                     1..118
                           mol_type = protein
                           organism = synthetic construct
SEQUENCE: 13
QVQLVESGGG LVKPGGSLRL SCAASGFTFS DYYMSWIRQA PGKGLEWVSY ISRSGSTKYY    60
ADSVKGRFTI SRDNAKNSLY LQMNSLRAED TAVYYCARDE TDYAYDNWGQ GTLVTVSS    118

SEQ ID NO: 14              moltype = AA   length = 107
FEATURE                    Location/Qualifiers
source                     1..107
                           mol_type = protein
                           organism = synthetic construct
SEQUENCE: 14
DIQMTQSPSS LSASVGDRVT ITCQASQDIS NYLNWYQQKP GKAPKLLIYD ASNLETGVPS    60
RFSGSGSGTD FTFTISSLQP EDIATYYCQQ YEDYPLVFGG GTKVEIK                 107

SEQ ID NO: 15              moltype = AA   length = 118
FEATURE                    Location/Qualifiers
source                     1..118
                           mol_type = protein
                           organism = synthetic construct
SEQUENCE: 15
QVQLVESGGG LVKPGGSLRL SCAASGFTFS DYYMSWIRQA PGKGLEWVSY ISRSGSTKYY    60
ADSVKGRFTI SRDNAKNSLY LQMNSLRAED TAVYYCARDE SDYAYDYWGQ GTLVTVSS    118

SEQ ID NO: 16              moltype = AA   length = 107
FEATURE                    Location/Qualifiers
source                     1..107
                           mol_type = protein
                           organism = synthetic construct
SEQUENCE: 16
DIQMTQSPSS LSASVGDRVT ITCQASQDIS NYLNWYQQKP GKAPKLLIYD ASNLETGVPS    60
RFSGSGSGTD FTFTISSLQP EDIATYYCQQ HEDYPLTFGG GTKVEIK                 107

SEQ ID NO: 17              moltype = AA   length = 117
FEATURE                    Location/Qualifiers
source                     1..117
                           mol_type = protein
                           organism = synthetic construct
SEQUENCE: 17
QVQLVESGGG LVKPGGSLRL SCAASGFTFS DYYMSWIRQA PGKGLEWVSY ISRSGSTKYY    60
ADSVKGRFTI SRDNAKNSLY LQMNSLRAED TAVYYCARDE NYALDWWGQG TLVTVSS     117

SEQ ID NO: 18              moltype = AA   length = 107
FEATURE                    Location/Qualifiers
source                     1..107
                           mol_type = protein
                           organism = synthetic construct
SEQUENCE: 18
DIQMTQSPSS LSASVGDRVT ITCQASQDIS NYLNWYQQKP GKAPKLLIYD ASNLETGVPS    60
RFSGSGSGTD FTFTISSLQP EDIATYYCQQ HEDYPLTFGG GTKVEIK                 107

SEQ ID NO: 19              moltype = AA   length = 118
FEATURE                    Location/Qualifiers
source                     1..118
                           mol_type = protein
                           organism = synthetic construct
SEQUENCE: 19
QVQLVESGGG LVKPGGSLRL SCAASGFTFS DYYMSWIRQA PGKGLEWVSY ISRSGSTKYY    60
ADSVKGRFTI SRDNAKNSLY LQMNSLRAED TAVYYCARDE SDYALDFWGQ GTLVTVSS    118

SEQ ID NO: 20              moltype = AA   length = 107
FEATURE                    Location/Qualifiers
source                     1..107
                           mol_type = protein
                           organism = synthetic construct
SEQUENCE: 20
DIQMTQSPSS LSASVGDRVT ITCQASQDIS NYLNWYQQKP GKAPKLLIYD ASNLETGVPS    60
```

```
RFSGSGSGTD FTFTISSLQP EDIATYYCQQ YEDLIPTFGG GTKVEIK                      107

SEQ ID NO: 21            moltype = AA   length = 119
FEATURE                  Location/Qualifiers
source                   1..119
                         mol_type = protein
                         organism = synthetic construct
SEQUENCE: 21
QVQLVQSGAE VKKPGASVKV SCKVSGDTLT ELSMHWVRQA PGKGLEWMGT FDPEEGETIY         60
AQKFQGRVTM TEDTSTDTAY MELSSLRSED TAVYYCVTEG LAGVPFDLWG QGTLVTVSS         119

SEQ ID NO: 22            moltype = AA   length = 107
FEATURE                  Location/Qualifiers
source                   1..107
                         mol_type = protein
                         organism = synthetic construct
SEQUENCE: 22
DIQMTQSPST LSASVGDRVT ITCRASQSIS SWLAWYQQKP GKAPKLLIYK ASSLESGVPS         60
RFSGSGSGTE FTLTISSLQP DDFATYYCQS YNSYVWTFGQ GTKVEIK                      107

SEQ ID NO: 23            moltype = AA   length = 119
FEATURE                  Location/Qualifiers
source                   1..119
                         mol_type = protein
                         organism = synthetic construct
SEQUENCE: 23
QVQLVQSGAE VKKPGASVKV SCKVSGDTLT ELSMHWVRQA PGKGLEWMGT FDPEEGETIY         60
AQKFQGRVTM TEDTSTDTAY MELSSLRSED TAVYYCVTEG LGGRPFDHWG QGTLVTVSS         119

SEQ ID NO: 24            moltype = AA   length = 107
FEATURE                  Location/Qualifiers
source                   1..107
                         mol_type = protein
                         organism = synthetic construct
SEQUENCE: 24
DIQMTQSPST LSASVGDRVT ITCRASQSIS SWLAWYQQKP GKAPKLLIYK ASSLESGVPS         60
RFSGSGSGTE FTLTISSLQP DDFATYYCQQ VNSYDWTFGQ GTKVEIK                      107

SEQ ID NO: 25            moltype = AA   length = 119
FEATURE                  Location/Qualifiers
source                   1..119
                         mol_type = protein
                         organism = synthetic construct
SEQUENCE: 25
QVQLVQSGAE VKKPGASVKV SCKVSGDTLT ELSMHWVRQA PGKGLEWMGT FDPEEGETIY         60
AQKFQGRVTM TEDTSTDTAY MELSSLRSED TAVYYCVTEG LAGFPFDIWG QGTLVTVSS         119

SEQ ID NO: 26            moltype = AA   length = 107
FEATURE                  Location/Qualifiers
source                   1..107
                         mol_type = protein
                         organism = synthetic construct
SEQUENCE: 26
DIQMTQSPST LSASVGDRVT ITCRASQSIS SWLAWYQQKP GKAPKLLIYK ASSLESGVPS         60
RFSGSGSGTE FTLTISSLQP DDFATYYCQQ VNSYDWTFGQ GTKVEIK                      107

SEQ ID NO: 27            moltype = AA   length = 119
FEATURE                  Location/Qualifiers
source                   1..119
                         mol_type = protein
                         organism = synthetic construct
SEQUENCE: 27
QVQLVQSGAE VKKPGASVKV SCKVSGDTLT ELSMHWVRQA PGKGLEWMGT FDPEEGETIY         60
AQKFQGRVTM TEDTSTDTAY MELSSLRSED TAVYYCVTEG LAWRPTDSWG QGTLVTVSS         119

SEQ ID NO: 28            moltype = AA   length = 107
FEATURE                  Location/Qualifiers
source                   1..107
                         mol_type = protein
                         organism = synthetic construct
SEQUENCE: 28
DIQMTQSPST LSASVGDRVT ITCRASQSIS SWLAWYQQKP GKAPKLLIYK ASSLESGVPS         60
RFSGSGSGTE FTLTISSLQP DDFATYYCQQ VNSYDWTFGQ GTKVEIK                      107

SEQ ID NO: 29            moltype = AA   length = 119
FEATURE                  Location/Qualifiers
source                   1..119
                         mol_type = protein
                         organism = synthetic construct
```

```
SEQUENCE: 29
QVQLVQSGAE VKKPGASVKV SCKVSGDTLT ELSMHWVRQA PGKGLEWMGT FDPEEGETIY    60
AQKFQGRVTM TEDTSTDTAY MELSSLRSED TAVYYCVTKG LAWLPYYSWG QGTLVTVSS    119

SEQ ID NO: 30           moltype = AA  length = 107
FEATURE                 Location/Qualifiers
source                  1..107
                        mol_type = protein
                        organism = synthetic construct
SEQUENCE: 30
DIQMTQSPST LSASVGDRVT ITCRASQSIS SWLAWYQQKP GKAPKLLIYK ASSLESGVPS    60
RFSGSGSGTE FTLTISSLQP DDFATYYCQQ ARSYSWTFGQ GTKVEIK                 107

SEQ ID NO: 31           moltype = AA  length = 119
FEATURE                 Location/Qualifiers
source                  1..119
                        mol_type = protein
                        organism = synthetic construct
SEQUENCE: 31
QVQLVQSGAE VKKPGASVKV SCKVSGDTLT ELSMHWVRQA PGKGLEWMGT FDPEEGETIY    60
AQKFQGRVTM TEDTSTDTAY MELSSLRSED TAVYYCVTEG LAGVPFDLWG QGTLVTVSS    119

SEQ ID NO: 32           moltype = AA  length = 107
FEATURE                 Location/Qualifiers
source                  1..107
                        mol_type = protein
                        organism = synthetic construct
SEQUENCE: 32
DIQMTQSPST LSASVGDRVT ITCRASQSIS SWLAWYQQKP GKAPKLLIYK ASSLESGVPS    60
RFSGSGSGTE FTLTISSLQP DDFATYYCQQ HNSYRWTFGQ GTKVEIK                 107

SEQ ID NO: 33           moltype = AA  length = 119
FEATURE                 Location/Qualifiers
source                  1..119
                        mol_type = protein
                        organism = synthetic construct
SEQUENCE: 33
QVQLVQSGAE VKKPGASVKV SCKVSGDTLT ELSMHWVRQA PGKGLEWMGT FDPEEGETIY    60
AQKFQGRVTM TEDTSTDTAY MELSSLRSED TAVYYCVTEG EAGRPFDAWG QGTLVTVSS    119

SEQ ID NO: 34           moltype = AA  length = 107
FEATURE                 Location/Qualifiers
source                  1..107
                        mol_type = protein
                        organism = synthetic construct
SEQUENCE: 34
DIQMTQSPST LSASVGDRVT ITCRASQSIS SWLAWYQQKP GKAPKLLIYK ASSLESGVPS    60
RFSGSGSGTE FTLTISSLQP DDFATYYCVQ YPSYSWTFGQ GTKVEIK                 107

SEQ ID NO: 35           moltype = AA  length = 119
FEATURE                 Location/Qualifiers
source                  1..119
                        mol_type = protein
                        organism = synthetic construct
SEQUENCE: 35
QVQLVQSGAE VKKPGASVKV SCKVSGDTLT ELSMHWVRQA PGKGLEWMGT FDPEEGETIY    60
AQKFQGRVTM TEDTSTDTAY MELSSLRSED TAVYYCVTEG LAGRPYDVWG QGTLVTVSS    119

SEQ ID NO: 36           moltype = AA  length = 107
FEATURE                 Location/Qualifiers
source                  1..107
                        mol_type = protein
                        organism = synthetic construct
SEQUENCE: 36
DIQMTQSPST LSASVGDRVT ITCRASQSIS SWLAWYQQKP GKAPKLLIYK ASSLESGVPS    60
RFSGSGSGTE FTLTISSLQP DDFATYYCQQ YNSYKLTFGQ GTKVEIK                 107

SEQ ID NO: 37           moltype = AA  length = 119
FEATURE                 Location/Qualifiers
source                  1..119
                        mol_type = protein
                        organism = synthetic construct
SEQUENCE: 37
QVQLVQSGAE VKKPGASVKV SCKVSGDTLT ELSMHWVRQA PGKGLEWMGT FDPEEGETIY    60
AQKFQGRVTM TEDTSTDTAY MELSYLRSED TAVYYCVTEG LAGIPFDSWG QGTLVTVSS    119

SEQ ID NO: 38           moltype = AA  length = 107
FEATURE                 Location/Qualifiers
source                  1..107
```

```
                                mol_type = protein
                                organism = synthetic construct
SEQUENCE: 38
DIQMTQSPST LSASVGDRVT ITCRASQSIS SWLAWYQQKP GKAPKLLIYK ASSLESGVPS    60
RFSGSGSGTE FTLTISSLQP DDFATYYCQQ YNSPSWLFGQ GTKVEIK                 107

SEQ ID NO: 39              moltype = AA   length = 119
FEATURE                    Location/Qualifiers
source                     1..119
                           mol_type = protein
                           organism = synthetic construct
SEQUENCE: 39
QVQLVQSGAE VKKPGASVKV SCKVSGDTLT ELSMHWVRQA PGKGLEWMGT FDPEEGETIY    60
AQKFQGRVTM TEDTSTDTAY MELSYLRSED TAVYYCVTEG LAGIPFDSWG QGTLVTVSS    119

SEQ ID NO: 40              moltype = AA   length = 107
FEATURE                    Location/Qualifiers
source                     1..107
                           mol_type = protein
                           organism = synthetic construct
SEQUENCE: 40
DIQMTQSPST LSASVGDRVT ITCRASQSIS SWLAWYQQKP GKAPKLLIYK ASSLESGVPS    60
RFSGSGSGTE FTLTISSLQP DDFATYYCQQ VNSLSWTFGQ GTKVEIK                 107

SEQ ID NO: 41              moltype = AA   length = 125
FEATURE                    Location/Qualifiers
source                     1..125
                           mol_type = protein
                           organism = synthetic construct
SEQUENCE: 41
EVQLVESGGG VVRPGGSLRL SCAASGFTFD DYGMSWVRQA PGKGLEWVSG INWEGGSTGY    60
ADSVKGRFTI SRDNAKNSLY LQMNSLRAED TALYYCARDE QLGGTTYYYY YMDVWGKGTT   120
VTVSS                                                              125

SEQ ID NO: 42              moltype = AA   length = 107
FEATURE                    Location/Qualifiers
source                     1..107
                           mol_type = protein
                           organism = synthetic construct
SEQUENCE: 42
DIQMTQSPSS LSASVGDRVT ITCRASQGIR NDLGWYQQKP GKAPKRLIYT ASNLQSGVPS    60
RFSGSGSGTE FTLTISSLQP EDFATYYCFQ YNSYPLGFGG GTKVEIK                107

SEQ ID NO: 43              moltype = AA   length = 125
FEATURE                    Location/Qualifiers
source                     1..125
                           mol_type = protein
                           organism = synthetic construct
SEQUENCE: 43
EVQLVESGGG VVRPGGSLRL SCAASGFTFD DYGMSWVRQA PGKGLEWVSG INWEGGSTGY    60
ADSVKGRFTI SRDNAKNSLY LQMNSLRAED TALYYCARDE QLGGKYYYYY YMDVWGKGTT   120
VTVSS                                                              125

SEQ ID NO: 44              moltype = AA   length = 107
FEATURE                    Location/Qualifiers
source                     1..107
                           mol_type = protein
                           organism = synthetic construct
SEQUENCE: 44
DIQMTQSPSS LSASVGDRVT ITCRASQGIR NDLGWYQQKP GKAPKRLIYT ASNLQSGVPS    60
RFSGSGSGTE FTLTISSLQP EDFATYYCLQ YRSHPLTFGG GTKVEIK                107

SEQ ID NO: 45              moltype = AA   length = 125
FEATURE                    Location/Qualifiers
source                     1..125
                           mol_type = protein
                           organism = synthetic construct
SEQUENCE: 45
EVQLVESGGG VVRPGGSLRL SCAASGFTFD DYGMSWVRQA PGKGLEWVSG INWEGGSTGY    60
ADSVKGRFTI SRDNAKNSLY LQMNSLRAED TALYYCARDE QLGGQTYYYY YMDVWGKGTT   120
VTVSS                                                              125

SEQ ID NO: 46              moltype = AA   length = 107
FEATURE                    Location/Qualifiers
source                     1..107
                           mol_type = protein
                           organism = synthetic construct
SEQUENCE: 46
DIQMTQSPSS LSASVGDRVT ITCRASQGIR NDLGWYQQKP GKAPKRLIYT ASNLQSGVPS    60
```

```
RFSGSGSGTE FTLTISSLQP EDFATYYCLQ YNQVPLTFGG GTKVEIK                    107

SEQ ID NO: 47           moltype = AA  length = 125
FEATURE                 Location/Qualifiers
source                  1..125
                        mol_type = protein
                        organism = synthetic construct
SEQUENCE: 47
EVQLVESGGG VVRPGGSLRL SCAASGFTFD DYGMSWVRQA PGKGLEWVSG INWEGGSTGY       60
ADSVKGRFTI SRDNAKNSLY LQMNSLRAED TALYYCARDE QLGGTTYYYY YMDVWGKGTT      120
VTVSS                                                                 125

SEQ ID NO: 48           moltype = AA  length = 107
FEATURE                 Location/Qualifiers
source                  1..107
                        mol_type = protein
                        organism = synthetic construct
SEQUENCE: 48
DIQMTQSPSS LSASVGDRVT ITCRASQGIR NDLGWYQQKP GKAPKRLIYT ASNLQSGVPS       60
RFSGSGSGTE FTLTISSLQP EDFATYYCLQ TNIYPLTFGG GTKVEIK                    107

SEQ ID NO: 49           moltype = AA  length = 125
FEATURE                 Location/Qualifiers
source                  1..125
                        mol_type = protein
                        organism = synthetic construct
SEQUENCE: 49
EVQLVESGGG VVRPGGSLRL SCAASGFTFD DYGMSWVRQA PGKGLEWVSG INWEGGSTGY       60
ADSVKGRFTI SRDNAKNSLY LQMNSLRAED TALYYCARDE QLGGIKYYYY YMDVWGKGTT      120
VTVSS                                                                 125

SEQ ID NO: 50           moltype = AA  length = 107
FEATURE                 Location/Qualifiers
source                  1..107
                        mol_type = protein
                        organism = synthetic construct
SEQUENCE: 50
DIQMTQSPSS LSASVGDRVT ITCRASQGIR NDLGWYQQKP GKAPKRLIYT ASNLQSGVPS       60
RFSGSGSGTE FTLTISSLQP EDFATYYCLQ YKQVPLTFGG GTKVEIK                    107

SEQ ID NO: 51           moltype = AA  length = 125
FEATURE                 Location/Qualifiers
source                  1..125
                        mol_type = protein
                        organism = synthetic construct
SEQUENCE: 51
EVQLVESGGG VVRPGGSLRL SCAASGFTFD DYGMSWVRQA PGKGLEWVSG INWEGGSTGY       60
ADSVKGRFSI SRDNAKNSLY LQMNSLRAED TALYYCARDE QLGGLKYYYY YMDVWGKGTT      120
VTVSS                                                                 125

SEQ ID NO: 52           moltype = AA  length = 107
FEATURE                 Location/Qualifiers
source                  1..107
                        mol_type = protein
                        organism = synthetic construct
SEQUENCE: 52
DIQMTQSPSS LSASVGDRVT ITCRASQGIR NDLGWYQQKP GKAPKRLIYT ASNLQSGVPS       60
RFSGSGSGTE FTLTISSLQP EDFATYYCLQ TNIYPLTFGG GTKVEIK                    107

SEQ ID NO: 53           moltype = AA  length = 125
FEATURE                 Location/Qualifiers
source                  1..125
                        mol_type = protein
                        organism = synthetic construct
SEQUENCE: 53
EVQLVESGGG VVRPGGSLRL SCAASGFTFD DYGMSWVRQA PGKGLEWVSG INWEGGSTGY       60
ADSVKGRFTI SRDNAKNSLY LQMNSLRAED TALYYCARDE QLGGKVYYYY YMDVWGKGTT      120
VTVSS                                                                 125

SEQ ID NO: 54           moltype = AA  length = 107
FEATURE                 Location/Qualifiers
source                  1..107
                        mol_type = protein
                        organism = synthetic construct
SEQUENCE: 54
DIQMTQSPSS LSASVGDRVT ITCRASQGIR NDLGWYQQKP GKAPKRLIYT ASNLQSGVPS       60
RFSGSGSGTE FTLTISSLQP EDFATYYCLQ YNSYPLAFGG GTKVEIK                    107

SEQ ID NO: 55           moltype = AA  length = 125
```

```
FEATURE             Location/Qualifiers
source              1..125
                    mol_type = protein
                    organism = synthetic construct
SEQUENCE: 55
EVQLVESGGG VVRPGGSLRL SCAASGFTFD DYGMSWVRQA PGKGLEWVSG INWEGGSTGY    60
ADSVKGRFSI SRDNAKNSLY LQMNSLRAED TALYYCARDE QLGGLKYYYY YMDVWGKGTT   120
VTVSS                                                              125

SEQ ID NO: 56       moltype = AA   length = 107
FEATURE             Location/Qualifiers
source              1..107
                    mol_type = protein
                    organism = synthetic construct
SEQUENCE: 56
DIQMTQSPSS LSASVGDRVT ITCRASQGIR NDLGWYQQKP GKAPKRLIYT ASNLQSGVPS    60
RFSGSGSGTE FTLTISSLQP EDFATYYCLQ YHSYPLRFGG GTKVEIK                107

SEQ ID NO: 57       moltype = AA   length = 125
FEATURE             Location/Qualifiers
source              1..125
                    mol_type = protein
                    organism = synthetic construct
SEQUENCE: 57
EVQLVESGGG VVRPGGSLRL SCAASGFTFD DYGMSWVRQA PGKGLEWVSG INWEGGSTGY    60
ADSVKGRFTI SRDNAKNSLY LQMNSLRAED TALYYCARDE QLGGNHYYYY YMDAWGKGTT   120
VTVSS                                                              125

SEQ ID NO: 58       moltype = AA   length = 107
FEATURE             Location/Qualifiers
source              1..107
                    mol_type = protein
                    organism = synthetic construct
SEQUENCE: 58
DIQMTQSPSS LSASVGDRVT ITCRASQGIR NDLGWYQQKP GKAPKRLIYT ASNLQSGVPS    60
RFSGSGSGTE FTLTISSLQP EDFATYYCLQ YASYPLKFGG GTKVEIK                107

SEQ ID NO: 59       moltype = AA   length = 125
FEATURE             Location/Qualifiers
source              1..125
                    mol_type = protein
                    organism = synthetic construct
SEQUENCE: 59
EVQLVESGGG VVRPGGSLRL SCAASGFTFD DYGMSWVRQA PGKGLEWVSG INWEGGSTGY    60
ADSVKGRFTI SRDNAKNSLY LQMNSLRAED TALYYCARDE QLGGRHYYYY YMDVWGKGTT   120
VTVSS                                                              125

SEQ ID NO: 60       moltype = AA   length = 107
FEATURE             Location/Qualifiers
source              1..107
                    mol_type = protein
                    organism = synthetic construct
SEQUENCE: 60
DIQMTQSPSS LSASVGDRVT ITCRASQGIR NDLGWYQQKP GKAPKRLIYT ASNLQSGVPS    60
RFSGSGSGTE FTLTISSLQP EDFATYYCLQ YNAYPLIFGG GTKVEIK                107

SEQ ID NO: 61       moltype = AA   length = 5
FEATURE             Location/Qualifiers
source              1..5
                    mol_type = protein
                    organism = synthetic construct
SEQUENCE: 61
DYYMS                                                                5

SEQ ID NO: 62       moltype = AA   length = 17
FEATURE             Location/Qualifiers
source              1..17
                    mol_type = protein
                    organism = synthetic construct
SEQUENCE: 62
YISRSGSTKY YADSVKG                                                  17

SEQ ID NO: 63       moltype = AA   length = 9
FEATURE             Location/Qualifiers
source              1..9
                    mol_type = protein
                    organism = synthetic construct
SEQUENCE: 63
DQEDYALDY                                                            9
```

```
SEQ ID NO: 64            moltype = AA  length = 11
FEATURE                  Location/Qualifiers
source                   1..11
                         mol_type = protein
                         organism = synthetic construct
SEQUENCE: 64
QASQDISNYL N                                                              11

SEQ ID NO: 65            moltype = AA  length = 7
FEATURE                  Location/Qualifiers
source                   1..7
                         mol_type = protein
                         organism = synthetic construct
SEQUENCE: 65
DASNLET                                                                   7

SEQ ID NO: 66            moltype = AA  length = 9
FEATURE                  Location/Qualifiers
source                   1..9
                         mol_type = protein
                         organism = synthetic construct
SEQUENCE: 66
EQYEDYPLT                                                                 9

SEQ ID NO: 67            moltype = AA  length = 9
FEATURE                  Location/Qualifiers
source                   1..9
                         mol_type = protein
                         organism = synthetic construct
SEQUENCE: 67
DETDYGWDY                                                                 9

SEQ ID NO: 68            moltype = AA  length = 9
FEATURE                  Location/Qualifiers
source                   1..9
                         mol_type = protein
                         organism = synthetic construct
SEQUENCE: 68
KQYEDYPLT                                                                 9

SEQ ID NO: 69            moltype = AA  length = 9
FEATURE                  Location/Qualifiers
source                   1..9
                         mol_type = protein
                         organism = synthetic construct
SEQUENCE: 69
DETDYAFDE                                                                 9

SEQ ID NO: 70            moltype = AA  length = 9
FEATURE                  Location/Qualifiers
source                   1..9
                         mol_type = protein
                         organism = synthetic construct
SEQUENCE: 70
DESQYALDY                                                                 9

SEQ ID NO: 71            moltype = AA  length = 9
FEATURE                  Location/Qualifiers
source                   1..9
                         mol_type = protein
                         organism = synthetic construct
SEQUENCE: 71
HQYEDYPLT                                                                 9

SEQ ID NO: 72            moltype = AA  length = 9
FEATURE                  Location/Qualifiers
source                   1..9
                         mol_type = protein
                         organism = synthetic construct
SEQUENCE: 72
DNTDYALDL                                                                 9

SEQ ID NO: 73            moltype = AA  length = 9
FEATURE                  Location/Qualifiers
source                   1..9
                         mol_type = protein
                         organism = synthetic construct
SEQUENCE: 73
```

```
DETDYAYDE                                                                9

SEQ ID NO: 74           moltype = AA   length = 9
FEATURE                 Location/Qualifiers
source                  1..9
                        mol_type = protein
                        organism = synthetic construct
SEQUENCE: 74
DETDYAYDN                                                                9

SEQ ID NO: 75           moltype = AA   length = 9
FEATURE                 Location/Qualifiers
source                  1..9
                        mol_type = protein
                        organism = synthetic construct
SEQUENCE: 75
QQYEDYPLV                                                                9

SEQ ID NO: 76           moltype = AA   length = 9
FEATURE                 Location/Qualifiers
source                  1..9
                        mol_type = protein
                        organism = synthetic construct
SEQUENCE: 76
DESDYAYDY                                                                9

SEQ ID NO: 77           moltype = AA   length = 8
FEATURE                 Location/Qualifiers
source                  1..8
                        mol_type = protein
                        organism = synthetic construct
SEQUENCE: 77
QQHEDYPL                                                                 8

SEQ ID NO: 78           moltype = AA   length = 8
FEATURE                 Location/Qualifiers
source                  1..8
                        mol_type = protein
                        organism = synthetic construct
SEQUENCE: 78
DENYALDW                                                                 8

SEQ ID NO: 79           moltype = AA   length = 8
FEATURE                 Location/Qualifiers
source                  1..8
                        mol_type = protein
                        organism = synthetic construct
SEQUENCE: 79
QHYEDYPL                                                                 8

SEQ ID NO: 80           moltype = AA   length = 9
FEATURE                 Location/Qualifiers
source                  1..9
                        mol_type = protein
                        organism = synthetic construct
SEQUENCE: 80
DESDYALDF                                                                9

SEQ ID NO: 81           moltype = AA   length = 9
FEATURE                 Location/Qualifiers
source                  1..9
                        mol_type = protein
                        organism = synthetic construct
SEQUENCE: 81
QQYEDLIPT                                                                9

SEQ ID NO: 82           moltype = AA   length = 5
FEATURE                 Location/Qualifiers
source                  1..5
                        mol_type = protein
                        organism = synthetic construct
SEQUENCE: 82
ELSMH                                                                    5

SEQ ID NO: 83           moltype = AA   length = 17
FEATURE                 Location/Qualifiers
source                  1..17
                        mol_type = protein
                        organism = synthetic construct
```

```
SEQUENCE: 83
TFDPEEGETI YAQKFQG                                                                  17

SEQ ID NO: 84          moltype = AA  length = 10
FEATURE                Location/Qualifiers
source                 1..10
                       mol_type = protein
                       organism = synthetic construct
SEQUENCE: 84
EGLAGVPFDL                                                                          10

SEQ ID NO: 85          moltype = AA  length = 11
FEATURE                Location/Qualifiers
source                 1..11
                       mol_type = protein
                       organism = synthetic construct
SEQUENCE: 85
RASQSISSWL A                                                                        11

SEQ ID NO: 86          moltype = AA  length = 7
FEATURE                Location/Qualifiers
source                 1..7
                       mol_type = protein
                       organism = synthetic construct
SEQUENCE: 86
KASSLES                                                                             7

SEQ ID NO: 87          moltype = AA  length = 9
FEATURE                Location/Qualifiers
source                 1..9
                       mol_type = protein
                       organism = synthetic construct
SEQUENCE: 87
QSYNSYVWT                                                                           9

SEQ ID NO: 88          moltype = AA  length = 10
FEATURE                Location/Qualifiers
source                 1..10
                       mol_type = protein
                       organism = synthetic construct
SEQUENCE: 88
EGLGGRPFDH                                                                          10

SEQ ID NO: 89          moltype = AA  length = 9
FEATURE                Location/Qualifiers
source                 1..9
                       mol_type = protein
                       organism = synthetic construct
SEQUENCE: 89
QQVNSYDWT                                                                           9

SEQ ID NO: 90          moltype = AA  length = 10
FEATURE                Location/Qualifiers
source                 1..10
                       mol_type = protein
                       organism = synthetic construct
SEQUENCE: 90
EGLAGFPFDI                                                                          10

SEQ ID NO: 91          moltype = AA  length = 10
FEATURE                Location/Qualifiers
source                 1..10
                       mol_type = protein
                       organism = synthetic construct
SEQUENCE: 91
EGLAWRPTDS                                                                          10

SEQ ID NO: 92          moltype = AA  length = 9
FEATURE                Location/Qualifiers
source                 1..9
                       mol_type = protein
                       organism = synthetic construct
SEQUENCE: 92
QQYSSYAWT                                                                           9

SEQ ID NO: 93          moltype = AA  length = 10
FEATURE                Location/Qualifiers
source                 1..10
                       mol_type = protein
```

```
                                                 -continued

SEQUENCE: 93
KGLAWLPYYS                                                                          10

SEQ ID NO: 94          moltype = AA  length = 9
FEATURE                Location/Qualifiers
source                 1..9
                       mol_type = protein
                       organism = synthetic construct
SEQUENCE: 94
QQARSYSWT                                                                            9

SEQ ID NO: 95          moltype = AA  length = 9
FEATURE                Location/Qualifiers
source                 1..9
                       mol_type = protein
                       organism = synthetic construct
SEQUENCE: 95
QQHNSYRWT                                                                            9

SEQ ID NO: 96          moltype = AA  length = 10
FEATURE                Location/Qualifiers
source                 1..10
                       mol_type = protein
                       organism = synthetic construct
SEQUENCE: 96
EGEAGRPFDA                                                                          10

SEQ ID NO: 97          moltype = AA  length = 9
FEATURE                Location/Qualifiers
source                 1..9
                       mol_type = protein
                       organism = synthetic construct
SEQUENCE: 97
VQYPSYSWT                                                                            9

SEQ ID NO: 98          moltype = AA  length = 10
FEATURE                Location/Qualifiers
source                 1..10
                       mol_type = protein
                       organism = synthetic construct
SEQUENCE: 98
EGLAGRPYDV                                                                          10

SEQ ID NO: 99          moltype = AA  length = 9
FEATURE                Location/Qualifiers
source                 1..9
                       mol_type = protein
                       organism = synthetic construct
SEQUENCE: 99
QQYNSYKLT                                                                            9

SEQ ID NO: 100         moltype = AA  length = 11
FEATURE                Location/Qualifiers
source                 1..11
                       mol_type = protein
                       organism = synthetic construct
SEQUENCE: 100
EGLAGIPFDS W                                                                        11

SEQ ID NO: 101         moltype = AA  length = 9
FEATURE                Location/Qualifiers
source                 1..9
                       mol_type = protein
                       organism = synthetic construct
SEQUENCE: 101
QQYNSPSWL                                                                            9

SEQ ID NO: 102         moltype = AA  length = 9
FEATURE                Location/Qualifiers
source                 1..9
                       mol_type = protein
                       organism = synthetic construct
SEQUENCE: 102
QQVNSLSWT                                                                            9

SEQ ID NO: 103         moltype = AA  length = 5
FEATURE                Location/Qualifiers
source                 1..5
```

```
                              -continued mol_type = protein
                       organism = synthetic construct
SEQUENCE: 103
DYGMS                                                                5

SEQ ID NO: 104         moltype = AA   length = 17
FEATURE                Location/Qualifiers
source                 1..17
                       mol_type = protein
                       organism = synthetic construct
SEQUENCE: 104
GINWEGGSTG YADSVKG                                                  17

SEQ ID NO: 105         moltype = AA   length = 16
FEATURE                Location/Qualifiers
source                 1..16
                       mol_type = protein
                       organism = synthetic construct
SEQUENCE: 105
DEQLGGTTYY YYYMDV                                                   16

SEQ ID NO: 106         moltype = AA   length = 11
FEATURE                Location/Qualifiers
source                 1..11
                       mol_type = protein
                       organism = synthetic construct
SEQUENCE: 106
RASQGIRNDL G                                                        11

SEQ ID NO: 107         moltype = AA   length = 7
FEATURE                Location/Qualifiers
source                 1..7
                       mol_type = protein
                       organism = synthetic construct
SEQUENCE: 107
TASNLQS                                                              7

SEQ ID NO: 108         moltype = AA   length = 9
FEATURE                Location/Qualifiers
source                 1..9
                       mol_type = protein
                       organism = synthetic construct
SEQUENCE: 108
FQYNSYPLG                                                            9

SEQ ID NO: 109         moltype = AA   length = 16
FEATURE                Location/Qualifiers
source                 1..16
                       mol_type = protein
                       organism = synthetic construct
SEQUENCE: 109
DEQLGGKYYY YYYMDV                                                   16

SEQ ID NO: 110         moltype = AA   length = 9
FEATURE                Location/Qualifiers
source                 1..9
                       mol_type = protein
                       organism = synthetic construct
SEQUENCE: 110
LQYRSHPLT                                                            9

SEQ ID NO: 111         moltype = AA   length = 16
FEATURE                Location/Qualifiers
source                 1..16
                       mol_type = protein
                       organism = synthetic construct
SEQUENCE: 111
DEQLGGQTYY YYYMDV                                                   16

SEQ ID NO: 112         moltype = AA   length = 9
FEATURE                Location/Qualifiers
source                 1..9
                       mol_type = protein
                       organism = synthetic construct
SEQUENCE: 112
LQYNQVPLT                                                            9

SEQ ID NO: 113         moltype = AA   length = 9
FEATURE                Location/Qualifiers
```

```
source                      1..9
                            mol_type = protein
                            organism = synthetic construct
SEQUENCE: 113
LQTNIYPLT                                                                      9

SEQ ID NO: 114              moltype = AA   length = 16
FEATURE                     Location/Qualifiers
source                      1..16
                            mol_type = protein
                            organism = synthetic construct
SEQUENCE: 114
DEQLGGIKYY YYYMDV                                                              16

SEQ ID NO: 115              moltype = AA   length = 9
FEATURE                     Location/Qualifiers
source                      1..9
                            mol_type = protein
                            organism = synthetic construct
SEQUENCE: 115
LQYKQYPLT                                                                      9

SEQ ID NO: 116              moltype = AA   length = 16
FEATURE                     Location/Qualifiers
source                      1..16
                            mol_type = protein
                            organism = synthetic construct
SEQUENCE: 116
DEQLGGLKYY YYYMDV                                                              16

SEQ ID NO: 117              moltype = AA   length = 16
FEATURE                     Location/Qualifiers
source                      1..16
                            mol_type = protein
                            organism = synthetic construct
SEQUENCE: 117
DEQLGGKVYY YYYMDV                                                              16

SEQ ID NO: 118              moltype = AA   length = 9
FEATURE                     Location/Qualifiers
source                      1..9
                            mol_type = protein
                            organism = synthetic construct
SEQUENCE: 118
LQYNSYPLA                                                                      9

SEQ ID NO: 119              moltype = AA   length = 9
FEATURE                     Location/Qualifiers
source                      1..9
                            mol_type = protein
                            organism = synthetic construct
SEQUENCE: 119
LQYHSYPLR                                                                      9

SEQ ID NO: 120              moltype = AA   length = 16
FEATURE                     Location/Qualifiers
source                      1..16
                            mol_type = protein
                            organism = synthetic construct
SEQUENCE: 120
DEQLGGNHYY YYYMDA                                                              16

SEQ ID NO: 121              moltype = AA   length = 9
FEATURE                     Location/Qualifiers
source                      1..9
                            mol_type = protein
                            organism = synthetic construct
SEQUENCE: 121
LQYASYPLK                                                                      9

SEQ ID NO: 122              moltype = AA   length = 16
FEATURE                     Location/Qualifiers
source                      1..16
                            mol_type = protein
                            organism = synthetic construct
SEQUENCE: 122
DEQLGGRHYY YYYMDV                                                              16

SEQ ID NO: 123              moltype = AA   length = 9
```

```
FEATURE                 Location/Qualifiers
source                  1..9
                        mol_type = protein
                        organism = synthetic construct
SEQUENCE: 123
LQYNAYPLI                                                                    9

SEQ ID NO: 124          moltype = AA  length = 7
FEATURE                 Location/Qualifiers
source                  1..7
                        mol_type = protein
                        organism = synthetic construct
SEQUENCE: 124
GFTFSDY                                                                      7

SEQ ID NO: 125          moltype = AA  length = 6
FEATURE                 Location/Qualifiers
source                  1..6
                        mol_type = protein
                        organism = synthetic construct
SEQUENCE: 125
SRSGST                                                                       6

SEQ ID NO: 126          moltype = AA  length = 7
FEATURE                 Location/Qualifiers
source                  1..7
                        mol_type = protein
                        organism = synthetic construct
SEQUENCE: 126
GDTLTEL                                                                      7

SEQ ID NO: 127          moltype = AA  length = 6
FEATURE                 Location/Qualifiers
source                  1..6
                        mol_type = protein
                        organism = synthetic construct
SEQUENCE: 127
DPEEGE                                                                       6

SEQ ID NO: 128          moltype = AA  length = 7
FEATURE                 Location/Qualifiers
source                  1..7
                        mol_type = protein
                        organism = synthetic construct
SEQUENCE: 128
GFTFDDY                                                                      7

SEQ ID NO: 129          moltype = AA  length = 6
FEATURE                 Location/Qualifiers
source                  1..6
                        mol_type = protein
                        organism = synthetic construct
SEQUENCE: 129
NWEGGS                                                                       6

SEQ ID NO: 130          moltype = AA  length = 8
FEATURE                 Location/Qualifiers
source                  1..8
                        mol_type = protein
                        organism = synthetic construct
SEQUENCE: 130
GFTFSDYY                                                                     8

SEQ ID NO: 131          moltype = AA  length = 8
FEATURE                 Location/Qualifiers
source                  1..8
                        mol_type = protein
                        organism = synthetic construct
SEQUENCE: 131
ISRSGSTK                                                                     8

SEQ ID NO: 132          moltype = AA  length = 11
FEATURE                 Location/Qualifiers
source                  1..11
                        mol_type = protein
                        organism = synthetic construct
SEQUENCE: 132
ARDQEDYALD Y                                                                11
```

```
SEQ ID NO: 133         moltype = AA   length = 6
FEATURE                Location/Qualifiers
source                 1..6
                       mol_type = protein
                       organism = synthetic construct
SEQUENCE: 133
QDISNY                                                                    6

SEQ ID NO: 134         moltype =      length =
SEQUENCE: 134
000

SEQ ID NO: 135         moltype = AA   length = 11
FEATURE                Location/Qualifiers
source                 1..11
                       mol_type = protein
                       organism = synthetic construct
SEQUENCE: 135
ARDETDYGWD Y                                                             11

SEQ ID NO: 136         moltype = AA   length = 11
FEATURE                Location/Qualifiers
source                 1..11
                       mol_type = protein
                       organism = synthetic construct
SEQUENCE: 136
ARDETDYAFD E                                                             11

SEQ ID NO: 137         moltype = AA   length = 11
FEATURE                Location/Qualifiers
source                 1..11
                       mol_type = protein
                       organism = synthetic construct
SEQUENCE: 137
ARDESQYALD Y                                                             11

SEQ ID NO: 138         moltype = AA   length = 11
FEATURE                Location/Qualifiers
source                 1..11
                       mol_type = protein
                       organism = synthetic construct
SEQUENCE: 138
ARDNTDYALD L                                                             11

SEQ ID NO: 139         moltype = AA   length = 11
FEATURE                Location/Qualifiers
source                 1..11
                       mol_type = protein
                       organism = synthetic construct
SEQUENCE: 139
ARDETDYAYD E                                                             11

SEQ ID NO: 140         moltype = AA   length = 11
FEATURE                Location/Qualifiers
source                 1..11
                       mol_type = protein
                       organism = synthetic construct
SEQUENCE: 140
ARDETDYAYD N                                                             11

SEQ ID NO: 141         moltype = AA   length = 11
FEATURE                Location/Qualifiers
source                 1..11
                       mol_type = protein
                       organism = synthetic construct
SEQUENCE: 141
ARDESDYAYD Y                                                             11

SEQ ID NO: 142         moltype = AA   length = 10
FEATURE                Location/Qualifiers
source                 1..10
                       mol_type = protein
                       organism = synthetic construct
SEQUENCE: 142
ARDENYALDW                                                               10

SEQ ID NO: 143         moltype = AA   length = 11
FEATURE                Location/Qualifiers
source                 1..11
```

```
                          mol_type = protein
                          organism = synthetic construct
SEQUENCE: 143
ARDESDYALD F                                                          11

SEQ ID NO: 144            moltype = AA  length = 8
FEATURE                   Location/Qualifiers
source                    1..8
                          mol_type = protein
                          organism = synthetic construct
SEQUENCE: 144
GDTLTELS                                                              8

SEQ ID NO: 145            moltype = AA  length = 8
FEATURE                   Location/Qualifiers
source                    1..8
                          mol_type = protein
                          organism = synthetic construct
SEQUENCE: 145
FDPEEGET                                                              8

SEQ ID NO: 146            moltype = AA  length = 12
FEATURE                   Location/Qualifiers
source                    1..12
                          mol_type = protein
                          organism = synthetic construct
SEQUENCE: 146
VTEGLAGVPF DL                                                         12

SEQ ID NO: 147            moltype = AA  length = 6
FEATURE                   Location/Qualifiers
source                    1..6
                          mol_type = protein
                          organism = synthetic construct
SEQUENCE: 147
QSISSW                                                                6

SEQ ID NO: 148            moltype =    length =
SEQUENCE: 148
000

SEQ ID NO: 149            moltype = AA  length = 12
FEATURE                   Location/Qualifiers
source                    1..12
                          mol_type = protein
                          organism = synthetic construct
SEQUENCE: 149
VTEGLGGRPF DH                                                         12

SEQ ID NO: 150            moltype = AA  length = 12
FEATURE                   Location/Qualifiers
source                    1..12
                          mol_type = protein
                          organism = synthetic construct
SEQUENCE: 150
VTEGLAGFPF DI                                                         12

SEQ ID NO: 151            moltype = AA  length = 12
FEATURE                   Location/Qualifiers
source                    1..12
                          mol_type = protein
                          organism = synthetic construct
SEQUENCE: 151
VTEGLAWRPT DS                                                         12

SEQ ID NO: 152            moltype = AA  length = 12
FEATURE                   Location/Qualifiers
source                    1..12
                          mol_type = protein
                          organism = synthetic construct
SEQUENCE: 152
VTKGLAWLPY YS                                                         12

SEQ ID NO: 153            moltype = AA  length = 12
FEATURE                   Location/Qualifiers
source                    1..12
                          mol_type = protein
                          organism = synthetic construct
SEQUENCE: 153
```

-continued

```
VTEGEAGRPF DA                                                                12

SEQ ID NO: 154          moltype = AA  length = 12
FEATURE                 Location/Qualifiers
source                  1..12
                        mol_type = protein
                        organism = synthetic construct
SEQUENCE: 154
VTEGLAGRPY DV                                                                12

SEQ ID NO: 155          moltype = AA  length = 13
FEATURE                 Location/Qualifiers
source                  1..13
                        mol_type = protein
                        organism = synthetic construct
SEQUENCE: 155
VTEGLAGIPF DSW                                                               13

SEQ ID NO: 156          moltype = AA  length = 8
FEATURE                 Location/Qualifiers
source                  1..8
                        mol_type = protein
                        organism = synthetic construct
SEQUENCE: 156
GFTFDDYG                                                                      8

SEQ ID NO: 157          moltype = AA  length = 8
FEATURE                 Location/Qualifiers
source                  1..8
                        mol_type = protein
                        organism = synthetic construct
SEQUENCE: 157
INWEGGST                                                                      8

SEQ ID NO: 158          moltype = AA  length = 18
FEATURE                 Location/Qualifiers
source                  1..18
                        mol_type = protein
                        organism = synthetic construct
SEQUENCE: 158
ARDEQLGGTT YYYYYMDV                                                          18

SEQ ID NO: 159          moltype = AA  length = 6
FEATURE                 Location/Qualifiers
source                  1..6
                        mol_type = protein
                        organism = synthetic construct
SEQUENCE: 159
QGIRND                                                                        6

SEQ ID NO: 160          moltype =     length =
SEQUENCE: 160
000

SEQ ID NO: 161          moltype = AA  length = 17
FEATURE                 Location/Qualifiers
source                  1..17
                        mol_type = protein
                        organism = synthetic construct
SEQUENCE: 161
ARDEQLGGKY YYYYMDV                                                           17

SEQ ID NO: 162          moltype = AA  length = 18
FEATURE                 Location/Qualifiers
source                  1..18
                        mol_type = protein
                        organism = synthetic construct
SEQUENCE: 162
ARDEQLGGQT YYYYYMDV                                                          18

SEQ ID NO: 163          moltype = AA  length = 18
FEATURE                 Location/Qualifiers
source                  1..18
                        mol_type = protein
                        organism = synthetic construct
SEQUENCE: 163
ARDEQLGGIK YYYYYMDV                                                          18

SEQ ID NO: 164          moltype = AA  length = 18
```

```
FEATURE                 Location/Qualifiers
source                  1..18
                        mol_type = protein
                        organism = synthetic construct
SEQUENCE: 164
ARDEQLGGLK YYYYYMDV                                                       18

SEQ ID NO: 165          moltype = AA  length = 18
FEATURE                 Location/Qualifiers
source                  1..18
                        mol_type = protein
                        organism = synthetic construct
SEQUENCE: 165
ARDEQLGGKV YYYYYMDV                                                       18

SEQ ID NO: 166          moltype = AA  length = 18
FEATURE                 Location/Qualifiers
source                  1..18
                        mol_type = protein
                        organism = synthetic construct
SEQUENCE: 166
ARDEQLGGNH YYYYYMDA                                                       18

SEQ ID NO: 167          moltype = AA  length = 18
FEATURE                 Location/Qualifiers
source                  1..18
                        mol_type = protein
                        organism = synthetic construct
SEQUENCE: 167
ARDEQLGGRH YYYYYMDV                                                       18

SEQ ID NO: 168          moltype = AA  length = 444
FEATURE                 Location/Qualifiers
source                  1..444
                        mol_type = protein
                        organism = synthetic construct
SEQUENCE: 168
QVQLVESGGG LVKPGGSLRL SCAASGFTFS DYYMSWIRQA PGKGLEWVSY ISRSGSTKYY          60
ADSVKGRFTI SRDNAKNSLY LQMNSLRAED TAVYYCARDQ EDYALDYWGQ GTLVTVSSAS         120
TKGPSVFPLA PCSRSTSEST AALGCLVKDY FPEPVTVSWN SGALTSGVHT FPAVLQSSGL         180
YSLSSVVTVP SSSLGTKTYT CNVDHKPSNT KVDKRVESKY GPPCPPCPAP EFEGGPSVFL         240
FPPKPKDTLM ISRTPEVTCV VVDVSQEDPE VQFNWYVDGV EVHNAKTKPR EEQFNSTYRV         300
VSVLTVLHQD WLNGKEYKCK VSNKGLPSSI EKTISKAKGQ PREPQVYTLP PSQEEMTKNQ         360
VSLTCLVKGF YPSDIAVEWE SNGQPENNYK TTPPVLDSDG SFFLYSRLTV DKSRWQEGNV         420
FSCSVLHEAL HSHYTQKSLS LSLG                                               444

SEQ ID NO: 169          moltype = AA  length = 444
FEATURE                 Location/Qualifiers
source                  1..444
                        mol_type = protein
                        organism = synthetic construct
SEQUENCE: 169
QVQLVESGGG LVKPGGSLRL SCAASGFTFS DYYMSWIRQA PGKGLEWVSY ISRSGSTKYY          60
ADSVKGRFTI SRDNAKNSLY LQMNSLRAED TAVYYCARDQ EDYALDYWGQ GTLVTVSSAS         120
TKGPSVFPLA PCSRSTSEST AALGCLVKDY FPEPVTVSWN SGALTSGVHT FPAVLQSSGL         180
YSLSSVVTVP SSSLGTKTYT CNVDHKPSNT KVDKRVESKY GPPCPPCPAP EFEGGPSVFL         240
FPPKPKDTLY ITREPEVTCV VVDVSQEDPE VQFNWYVDGV EVHNAKTKPR EEQFNSTYRV         300
VSVLTVLHQD WLNGKEYKCK VSNKGLPSSI EKTISKAKGQ PREPQVYTLP PSQEEMTKNQ         360
VSLTCLVKGF YPSDIAVEWE SNGQPENNYK TTPPVLDSDG SFFLYSRLTV DKSRWQEGNV         420
FSCSVMHEAL HNHYTQKSLS LSLG                                               444

SEQ ID NO: 170          moltype = AA  length = 444
FEATURE                 Location/Qualifiers
source                  1..444
                        mol_type = protein
                        organism = synthetic construct
SEQUENCE: 170
QVQLVESGGG LVKPGGSLRL SCAASGFTFS DYYMSWIRQA PGKGLEWVSY ISRSGSTKYY          60
ADSVKGRFTI SRDNAKNSLY LQMNSLRAED TAVYYCARDE TDYGWDYWGQ GTLVTVSSAS         120
TKGPSVFPLA PCSRSTSEST AALGCLVKDY FPEPVTVSWN SGALTSGVHT FPAVLQSSGL         180
YSLSSVVTVP SSSLGTKTYT CNVDHKPSNT KVDKRVESKY GPPCPPCPAP EFEGGPSVFL         240
FPPKPKDTLM ISRTPEVTCV VVDVSQEDPE VQFNWYVDGV EVHNAKTKPR EEQFNSTYRV         300
VSVLTVLHQD WLNGKEYKCK VSNKGLPSSI EKTISKAKGQ PREPQVYTLP PSQEEMTKNQ         360
VSLTCLVKGF YPSDIAVEWE SNGQPENNYK TTPPVLDSDG SFFLYSRLTV DKSRWQEGNV         420
FSCSVLHEAL HSHYTQKSLS LSLG                                               444

SEQ ID NO: 171          moltype = AA  length = 444
FEATURE                 Location/Qualifiers
source                  1..444
```

```
                        mol_type = protein
                        organism = synthetic construct
SEQUENCE: 171
QVQLVESGGG LVKPGGSLRL SCAASGFTFS DYYMSWIRQA PGKGLEWVSY ISRSGSTKYY    60
ADSVKGRFTI SRDNAKNSLY LQMNSLRAED TAVYYCARDE TDYGWDYWGQ GTLVTVSSAS   120
TKGPSVFPLA PCSRSTSEST AALGCLVKDY FPEPVTVSWN SGALTSGVHT FPAVLQSSGL   180
YSLSSVVTVP SSSLGTKTYT CNVDHKPSNT KVDKRVESKY GPPCPPCPAP EFEGGPSVFL   240
FPPKPKDTLY ITREPEVTCV VVDVSQEDPE VQFNWYVDGV EVHNAKTKPR EEQFNSTYRV   300
VSVLTVLHQD WLNGKEYKCK VSNKGLPSSI EKTISKAKGQ PREPQVYTLP PSQEEMTKNQ   360
VSLTCLVKGF YPSDIAVEWE SNGQPENNYK TTPPVLDSDG SFFLYSRLTV DKSRWQEGNV   420
FSCSVMHEAL HNHYTQKSLS LSLG                                          444

SEQ ID NO: 172          moltype = AA  length = 444
FEATURE                 Location/Qualifiers
source                  1..444
                        mol_type = protein
                        organism = synthetic construct
SEQUENCE: 172
QVQLVESGGG LVKPGGSLRL SCAASGFTFS DYYMSWIRQA PGKGLEWVSY ISRSGSTKYY    60
ADSVKGRFTI SRDNAKNSLY LQMNSLRAED TAVYYCARDE TDYAFDEWGQ GTLVTVSSAS   120
TKGPSVFPLA PCSRSTSEST AALGCLVKDY FPEPVTVSWN SGALTSGVHT FPAVLQSSGL   180
YSLSSVVTVP SSSLGTKTYT CNVDHKPSNT KVDKRVESKY GPPCPPCPAP EFEGGPSVFL   240
FPPKPKDTLM ISRTPEVTCV VVDVSQEDPE VQFNWYVDGV EVHNAKTKPR EEQFNSTYRV   300
VSVLTVLHQD WLNGKEYKCK VSNKGLPSSI EKTISKAKGQ PREPQVYTLP PSQEEMTKNQ   360
VSLTCLVKGF YPSDIAVEWE SNGQPENNYK TTPPVLDSDG SFFLYSRLTV DKSRWQEGNV   420
FSCSVLHEAL HSHYTQKSLS LSLG                                          444

SEQ ID NO: 173          moltype = AA  length = 444
FEATURE                 Location/Qualifiers
source                  1..444
                        mol_type = protein
                        organism = synthetic construct
SEQUENCE: 173
QVQLVESGGG LVKPGGSLRL SCAASGFTFS DYYMSWIRQA PGKGLEWVSY ISRSGSTKYY    60
ADSVKGRFTI SRDNAKNSLY LQMNSLRAED TAVYYCARDE TDYAFDEWGQ GTLVTVSSAS   120
TKGPSVFPLA PCSRSTSEST AALGCLVKDY FPEPVTVSWN SGALTSGVHT FPAVLQSSGL   180
YSLSSVVTVP SSSLGTKTYT CNVDHKPSNT KVDKRVESKY GPPCPPCPAP EFEGGPSVFL   240
FPPKPKDTLY ITREPEVTCV VVDVSQEDPE VQFNWYVDGV EVHNAKTKPR EEQFNSTYRV   300
VSVLTVLHQD WLNGKEYKCK VSNKGLPSSI EKTISKAKGQ PREPQVYTLP PSQEEMTKNQ   360
VSLTCLVKGF YPSDIAVEWE SNGQPENNYK TTPPVLDSDG SFFLYSRLTV DKSRWQEGNV   420
FSCSVMHEAL HNHYTQKSLS LSLG                                          444

SEQ ID NO: 174          moltype = AA  length = 444
FEATURE                 Location/Qualifiers
source                  1..444
                        mol_type = protein
                        organism = synthetic construct
SEQUENCE: 174
QVQLVESGGG LVKPGGSLRL SCAASGFTFS DYYMSWIRQA PGKGLEWVSY ISRSGSTKYY    60
ADSVKGRFTI SRDNAKNSLY LQMNSLRAED TAVYYCARDE SQYALDYWGQ GTLVTVSSAS   120
TKGPSVFPLA PCSRSTSEST AALGCLVKDY FPEPVTVSWN SGALTSGVHT FPAVLQSSGL   180
YSLSSVVTVP SSSLGTKTYT CNVDHKPSNT KVDKRVESKY GPPCPPCPAP EFEGGPSVFL   240
FPPKPKDTLM ISRTPEVTCV VVDVSQEDPE VQFNWYVDGV EVHNAKTKPR EEQFNSTYRV   300
VSVLTVLHQD WLNGKEYKCK VSNKGLPSSI EKTISKAKGQ PREPQVYTLP PSQEEMTKNQ   360
VSLTCLVKGF YPSDIAVEWE SNGQPENNYK TTPPVLDSDG SFFLYSRLTV DKSRWQEGNV   420
FSCSVLHEAL HSHYTQKSLS LSLG                                          444

SEQ ID NO: 175          moltype = AA  length = 444
FEATURE                 Location/Qualifiers
source                  1..444
                        mol_type = protein
                        organism = synthetic construct
SEQUENCE: 175
QVQLVESGGG LVKPGGSLRL SCAASGFTFS DYYMSWIRQA PGKGLEWVSY ISRSGSTKYY    60
ADSVKGRFTI SRDNAKNSLY LQMNSLRAED TAVYYCARDE SQYALDYWGQ GTLVTVSSAS   120
TKGPSVFPLA PCSRSTSEST AALGCLVKDY FPEPVTVSWN SGALTSGVHT FPAVLQSSGL   180
YSLSSVVTVP SSSLGTKTYT CNVDHKPSNT KVDKRVESKY GPPCPPCPAP EFEGGPSVFL   240
FPPKPKDTLY ITREPEVTCV VVDVSQEDPE VQFNWYVDGV EVHNAKTKPR EEQFNSTYRV   300
VSVLTVLHQD WLNGKEYKCK VSNKGLPSSI EKTISKAKGQ PREPQVYTLP PSQEEMTKNQ   360
VSLTCLVKGF YPSDIAVEWE SNGQPENNYK TTPPVLDSDG SFFLYSRLTV DKSRWQEGNV   420
FSCSVMHEAL HNHYTQKSLS LSLG                                          444

SEQ ID NO: 176          moltype = AA  length = 444
FEATURE                 Location/Qualifiers
source                  1..444
                        mol_type = protein
                        organism = synthetic construct
SEQUENCE: 176
QVQLVESGGG LVKPGGSLRL SCAASGFTFS DYYMSWIRQA PGKGLEWVSY ISRSGSTKYY    60
```

```
AHSVKGRFTI SRDNAKNSLY LQMNSLRAED TAVYYCARDN TDYALDLWGQ GTLVTVSSAS  120
TKGPSVFPLA PCSRSTSEST AALGCLVKDY FPEPVTVSWN SGALTSGVHT FPAVLQSSGL  180
YSLSSVVTVP SSSLGTKTYT CNVDHKPSNT KVDKRVESKY GPPCPPCPAP EFEGGPSVFL  240
FPPKPKDTLM ISRTPEVTCV VVDVSQEDPE VQFNWYVDGV EVHNAKTKPR EEQFNSTYRV  300
VSVLTVLHQD WLNGKEYKCK VSNKGLPSSI EKTISKAKGQ PREPQVYTLP PSQEEMTKNQ  360
VSLTCLVKGF YPSDIAVEWE SNGQPENNYK TTPPVLDSDG SFFLYSRLTV DKSRWQEGNV  420
FSCSVLHEAL HSHYTQKSLS LSLG                                        444

SEQ ID NO: 177            moltype = AA   length = 444
FEATURE                   Location/Qualifiers
source                    1..444
                          mol_type = protein
                          organism = synthetic construct
SEQUENCE: 177
QVQLVESGGG LVKPGGSLRL SCAASGFTFS DYYMSWIRQA PGKGLEWVSY ISRSGSTKYY  60
AHSVKGRFTI SRDNAKNSLY LQMNSLRAED TAVYYCARDN TDYALDLWGQ GTLVTVSSAS  120
TKGPSVFPLA PCSRSTSEST AALGCLVKDY FPEPVTVSWN SGALTSGVHT FPAVLQSSGL  180
YSLSSVVTVP SSSLGTKTYT CNVDHKPSNT KVDKRVESKY GPPCPPCPAP EFEGGPSVFL  240
FPPKPKDTLY ITREPEVTCV VVDVSQEDPE VQFNWYVDGV EVHNAKTKPR EEQFNSTYRV  300
VSVLTVLHQD WLNGKEYKCK VSNKGLPSSI EKTISKAKGQ PREPQVYTLP PSQEEMTKNQ  360
VSLTCLVKGF YPSDIAVEWE SNGQPENNYK TTPPVLDSDG SFFLYSRLTV DKSRWQEGNV  420
FSCSVMHEAL HNHYTQKSLS LSLG                                        444

SEQ ID NO: 178            moltype = AA   length = 444
FEATURE                   Location/Qualifiers
source                    1..444
                          mol_type = protein
                          organism = synthetic construct
SEQUENCE: 178
QVQLVESGGG LVKPGGSLRL SCAASGFTFS DYYMSWIRQA PGKGLEWVSY ISRSGSTKYY  60
AHSVKGRFTI SRDNAKNSLY LQMNSLRAED TAVYYCARDE TDYAYDEWGQ GTLVTVSSAS  120
TKGPSVFPLA PCSRSTSEST AALGCLVKDY FPEPVTVSWN SGALTSGVHT FPAVLQSSGL  180
YSLSSVVTVP SSSLGTKTYT CNVDHKPSNT KVDKRVESKY GPPCPPCPAP EFEGGPSVFL  240
FPPKPKDTLM ISRTPEVTCV VVDVSQEDPE VQFNWYVDGV EVHNAKTKPR EEQFNSTYRV  300
VSVLTVLHQD WLNGKEYKCK VSNKGLPSSI EKTISKAKGQ PREPQVYTLP PSQEEMTKNQ  360
VSLTCLVKGF YPSDIAVEWE SNGQPENNYK TTPPVLDSDG SFFLYSRLTV DKSRWQEGNV  420
FSCSVLHEAL HSHYTQKSLS LSLG                                        444

SEQ ID NO: 179            moltype = AA   length = 444
FEATURE                   Location/Qualifiers
source                    1..444
                          mol_type = protein
                          organism = synthetic construct
SEQUENCE: 179
QVQLVESGGG LVKPGGSLRL SCAASGFTFS DYYMSWIRQA PGKGLEWVSY ISRSGSTKYY  60
AHSVKGRFTI SRDNAKNSLY LQMNSLRAED TAVYYCARDE TDYAYDEWGQ GTLVTVSSAS  120
TKGPSVFPLA PCSRSTSEST AALGCLVKDY FPEPVTVSWN SGALTSGVHT FPAVLQSSGL  180
YSLSSVVTVP SSSLGTKTYT CNVDHKPSNT KVDKRVESKY GPPCPPCPAP EFEGGPSVFL  240
FPPKPKDTLY ITREPEVTCV VVDVSQEDPE VQFNWYVDGV EVHNAKTKPR EEQFNSTYRV  300
VSVLTVLHQD WLNGKEYKCK VSNKGLPSSI EKTISKAKGQ PREPQVYTLP PSQEEMTKNQ  360
VSLTCLVKGF YPSDIAVEWE SNGQPENNYK TTPPVLDSDG SFFLYSRLTV DKSRWQEGNV  420
FSCSVMHEAL HNHYTQKSLS LSLG                                        444

SEQ ID NO: 180            moltype = AA   length = 444
FEATURE                   Location/Qualifiers
source                    1..444
                          mol_type = protein
                          organism = synthetic construct
SEQUENCE: 180
QVQLVESGGG LVKPGGSLRL SCAASGFTFS DYYMSWIRQA PGKGLEWVSY ISRSGSTKYY  60
ADSVKGRFTI SRDNAKNSLY LQMNSLRAED TAVYYCARDE TDYAYDNWGQ GTLVTVSSAS  120
TKGPSVFPLA PCSRSTSEST AALGCLVKDY FPEPVTVSWN SGALTSGVHT FPAVLQSSGL  180
YSLSSVVTVP SSSLGTKTYT CNVDHKPSNT KVDKRVESKY GPPCPPCPAP EFEGGPSVFL  240
FPPKPKDTLM ISRTPEVTCV VVDVSQEDPE VQFNWYVDGV EVHNAKTKPR EEQFNSTYRV  300
VSVLTVLHQD WLNGKEYKCK VSNKGLPSSI EKTISKAKGQ PREPQVYTLP PSQEEMTKNQ  360
VSLTCLVKGF YPSDIAVEWE SNGQPENNYK TTPPVLDSDG SFFLYSRLTV DKSRWQEGNV  420
FSCSVLHEAL HSHYTQKSLS LSLG                                        444

SEQ ID NO: 181            moltype = AA   length = 444
FEATURE                   Location/Qualifiers
source                    1..444
                          mol_type = protein
                          organism = synthetic construct
SEQUENCE: 181
QVQLVESGGG LVKPGGSLRL SCAASGFTFS DYYMSWIRQA PGKGLEWVSY ISRSGSTKYY  60
ADSVKGRFTI SRDNAKNSLY LQMNSLRAED TAVYYCARDE TDYAYDNWGQ GTLVTVSSAS  120
TKGPSVFPLA PCSRSTSEST AALGCLVKDY FPEPVTVSWN SGALTSGVHT FPAVLQSSGL  180
YSLSSVVTVP SSSLGTKTYT CNVDHKPSNT KVDKRVESKY GPPCPPCPAP EFEGGPSVFL  240
FPPKPKDTLY ITREPEVTCV VVDVSQEDPE VQFNWYVDGV EVHNAKTKPR EEQFNSTYRV  300
```

```
VSVLTVLHQD WLNGKEYKCK VSNKGLPSSI EKTISKAKGQ PREPQVYTLP PSQEEMTKNQ    360
VSLTCLVKGF YPSDIAVEWE SNGQPENNYK TTPPVLDSDG SFFLYSRLTV DKSRWQEGNV    420
FSCSVMHEAL HNHYTQKSLS LSLG                                          444

SEQ ID NO: 182            moltype = AA   length = 444
FEATURE                   Location/Qualifiers
source                    1..444
                          mol_type = protein
                          organism = synthetic construct
SEQUENCE: 182
QVQLVESGGG LVKPGGSLRL SCAASGFTFS DYYMSWIRQA PGKGLEWVSY ISRSGSTKYY     60
ADSVKGRFTI SRDNAKNSLY LQMNSLRAED TAVYYCARDE SDYAYDYWGQ GTLVTVSSAS    120
TKGPSVFPLA PCSRSTSEST AALGCLVKDY FPEPVTVSWN SGALTSGVHT FPAVLQSSGL    180
YSLSSVVTVP SSSLGTKTYT CNVDHKPSNT KVDKRVESKY GPPCPPCPAP EFEGGPSVFL    240
FPPKPKDTLM ISRTPEVTCV VVDVSQEDPE VQFNWYVDGV EVHNAKTKPR EEQFNSTYRV    300
VSVLTVLHQD WLNGKEYKCK VSNKGLPSSI EKTISKAKGQ PREPQVYTLP PSQEEMTKNQ    360
VSLTCLVKGF YPSDIAVEWE SNGQPENNYK TTPPVLDSDG SFFLYSRLTV DKSRWQEGNV    420
FSCSVLHEAL HSHYTQKSLS LSLG                                          444

SEQ ID NO: 183            moltype = AA   length = 444
FEATURE                   Location/Qualifiers
source                    1..444
                          mol_type = protein
                          organism = synthetic construct
SEQUENCE: 183
QVQLVESGGG LVKPGGSLRL SCAASGFTFS DYYMSWIRQA PGKGLEWVSY ISRSGSTKYY     60
ADSVKGRFTI SRDNAKNSLY LQMNSLRAED TAVYYCARDE SDYAYDYWGQ GTLVTVSSAS    120
TKGPSVFPLA PCSRSTSEST AALGCLVKDY FPEPVTVSWN SGALTSGVHT FPAVLQSSGL    180
YSLSSVVTVP SSSLGTKTYT CNVDHKPSNT KVDKRVESKY GPPCPPCPAP EFEGGPSVFL    240
FPPKPKDTLY ITREPEVTCV VVDVSQEDPE VQFNWYVDGV EVHNAKTKPR EEQFNSTYRV    300
VSVLTVLHQD WLNGKEYKCK VSNKGLPSSI EKTISKAKGQ PREPQVYTLP PSQEEMTKNQ    360
VSLTCLVKGF YPSDIAVEWE SNGQPENNYK TTPPVLDSDG SFFLYSRLTV DKSRWQEGNV    420
FSCSVMHEAL HNHYTQKSLS LSLG                                          444

SEQ ID NO: 184            moltype = AA   length = 443
FEATURE                   Location/Qualifiers
source                    1..443
                          mol_type = protein
                          organism = synthetic construct
SEQUENCE: 184
QVQLVESGGG LVKPGGSLRL SCAASGFTFS DYYMSWIRQA PGKGLEWVSY ISRSGSTKYY     60
ADSVKGRFTI SRDNAKNSLY LQMNSLRAED TAVYYCARDE NYALDWWGQG TLVTVSSAST    120
KGPSVFPLAP CSRSTSESTA ALGCLVKDYF PEPVTVSWNS GALTSGVHTF PAVLQSSGLY    180
SLSSVVTVPS SSLGTKTYTC NVDHKPSNTK VDKRVESKYG PPCPPCPAPE FEGGPSVFLF    240
PPKPKDTLMI SRTPEVTCVV VDVSQEDPEV QFNWYVDGVE VHNAKTKPRE EQFNSTYRVV    300
SVLTVLHQDW LNGKEYKCKV SNKGLPSSIE KTISKAKGQP REPQVYTLPP SQEEMTKNQV    360
SLTCLVKGFY PSDIAVEWES NGQPENNYKT TPPVLDSDGS FFLYSRLTVD KSRWQEGNVF    420
SCSVLHEALH SHYTQKSLSL SLG                                           443

SEQ ID NO: 185            moltype = AA   length = 443
FEATURE                   Location/Qualifiers
source                    1..443
                          mol_type = protein
                          organism = synthetic construct
SEQUENCE: 185
QVQLVESGGG LVKPGGSLRL SCAASGFTFS DYYMSWIRQA PGKGLEWVSY ISRSGSTKYY     60
ADSVKGRFTI SRDNAKNSLY LQMNSLRAED TAVYYCARDE NYALDWWGQG TLVTVSSAST    120
KGPSVFPLAP CSRSTSESTA ALGCLVKDYF PEPVTVSWNS GALTSGVHTF PAVLQSSGLY    180
SLSSVVTVPS SSLGTKTYTC NVDHKPSNTK VDKRVESKYG PPCPPCPAPE FEGGPSVFLF    240
PPKPKDTLYI TREPEVTCVV VDVSQEDPEV QFNWYVDGVE VHNAKTKPRE EQFNSTYRVV    300
SVLTVLHQDW LNGKEYKCKV SNKGLPSSIE KTISKAKGQP REPQVYTLPP SQEEMTKNQV    360
SLTCLVKGFY PSDIAVEWES NGQPENNYKT TPPVLDSDGS FFLYSRLTVD KSRWQEGNVF    420
SCSVMHEALH NHYTQKSLSL SLG                                           443

SEQ ID NO: 186            moltype = AA   length = 444
FEATURE                   Location/Qualifiers
source                    1..444
                          mol_type = protein
                          organism = synthetic construct
SEQUENCE: 186
QVQLVESGGG LVKPGGSLRL SCAASGFTFS DYYMSWIRQA PGKGLEWVSY ISRSGSTKYY     60
ADSVKGRFTI SRDNAKNSLY LQMNSLRAED TAVYYCARDE SDYALDFWGQ GTLVTVSSAS    120
TKGPSVFPLA PCSRSTSEST AALGCLVKDY FPEPVTVSWN SGALTSGVHT FPAVLQSSGL    180
YSLSSVVTVP SSSLGTKTYT CNVDHKPSNT KVDKRVESKY GPPCPPCPAP EFEGGPSVFL    240
FPPKPKDTLM ISRTPEVTCV VVDVSQEDPE VQFNWYVDGV EVHNAKTKPR EEQFNSTYRV    300
VSVLTVLHQD WLNGKEYKCK VSNKGLPSSI EKTISKAKGQ PREPQVYTLP PSQEEMTKNQ    360
VSLTCLVKGF YPSDIAVEWE SNGQPENNYK TTPPVLDSDG SFFLYSRLTV DKSRWQEGNV    420
FSCSVLHEAL HSHYTQKSLS LSLG                                          444
```

```
SEQ ID NO: 187              moltype = AA   length = 444
FEATURE                     Location/Qualifiers
source                      1..444
                            mol_type = protein
                            organism = synthetic construct
SEQUENCE: 187
QVQLVESGGG LVKPGGSLRL SCAASGFTFS DYYMSWIRQA PGKGLEWVSY ISRSGSTKYY    60
ADSVKGRFTI SRDNAKNSLY LQMNSLRAED TAVYYCARDE SDYALDFWGQ GTLVTVSSAS   120
TKGPSVFPLA PCSRSTSEST AALGCLVKDY FPEPVTVSWN SGALTSGVHT FPAVLQSSGL   180
YSLSSVVTVP SSSLGTKTYT CNVDHKPSNT KVDKRVESKY GPPCPPCPAP EFEGGPSVFL   240
FPPKPKDTLY ITREPEVTCV VVDVSQEDPE VQFNWYVDGV EVHNAKTKPR EEQFNSTYRV   300
VSVLTVLHQD WLNGKEYKCK VSNKGLPSSI EKTISKAKGQ PREPQVYTLP PSQEEMTKNQ   360
VSLTCLVKGF YPSDIAVEWE SNGQPENNYK TTPPVLDSDG SFFLYSRLTV DKSRWQEGNV   420
FSCSVMHEAL HNHYTQKSLS LSLG                                         444

SEQ ID NO: 188              moltype = AA   length = 445
FEATURE                     Location/Qualifiers
source                      1..445
                            mol_type = protein
                            organism = synthetic construct
SEQUENCE: 188
QVQLVQSGAE VKKPGASVKV SCKVSGDTLT ELSMHWVRQA PGKGLEWMGT FDPEEGETIY    60
AQKFQGRVTM TEDTSTDTAY MELSSLRSED TAVYYCVTEG LAGVPFDLWG QGTLVTVSSA   120
STKGPSVFPL APCSRSTSES TAALGCLVKD YFPEPVTVSW NSGALTSGVH TFPAVLQSSG   180
LYSLSSVVTV PSSSLGTKTY TCNVDHKPSN TKVDKRVESK YGPPCPPCPA PEFEGGPSVF   240
LFPPKPKDTL MISRTPEVTC VVVDVSQEDP EVQFNWYVDG VEVHNAKTKP REEQFNSTYR   300
VVSVLTVLHQ DWLNGKEYKC KVSNKGLPSS IEKTISKAKG QPREPQVYTL PPSQEEMTKN   360
QVSLTCLVKG FYPSDIAVEW ESNGQPENNY KTTPPVLDSD GSFFLYSRLT VDKSRWQEGN   420
VFSCSVLHEA LHSHYTQKSL SLSLG                                        445

SEQ ID NO: 189              moltype = AA   length = 445
FEATURE                     Location/Qualifiers
source                      1..445
                            mol_type = protein
                            organism = synthetic construct
SEQUENCE: 189
QVQLVQSGAE VKKPGASVKV SCKVSGDTLT ELSMHWVRQA PGKGLEWMGT FDPEEGETIY    60
AQKFQGRVTM TEDTSTDTAY MELSSLRSED TAVYYCVTEG LAGVPFDLWG QGTLVTVSSA   120
STKGPSVFPL APCSRSTSES TAALGCLVKD YFPEPVTVSW NSGALTSGVH TFPAVLQSSG   180
LYSLSSVVTV PSSSLGTKTY TCNVDHKPSN TKVDKRVESK YGPPCPPCPA PEFEGGPSVF   240
LFPPKPKDTL YITREPEVTC VVVDVSQEDP EVQFNWYVDG VEVHNAKTKP REEQFNSTYR   300
VVSVLTVLHQ DWLNGKEYKC KVSNKGLPSS IEKTISKAKG QPREPQVYTL PPSQEEMTKN   360
QVSLTCLVKG FYPSDIAVEW ESNGQPENNY KTTPPVLDSD GSFFLYSRLT VDKSRWQEGN   420
VFSCSVMHEA LHNHYTQKSL SLSLG                                        445

SEQ ID NO: 190              moltype = AA   length = 445
FEATURE                     Location/Qualifiers
source                      1..445
                            mol_type = protein
                            organism = synthetic construct
SEQUENCE: 190
QVQLVQSGAE VKKPGASVKV SCKVSGDTLT ELSMHWVRQA PGKGLEWMGT FDPEEGETIY    60
AQKFQGRVTM TEDTSTDTAY MELSSLRSED TAVYYCVTEG LGGRPFDHWG QGTLVTVSSA   120
STKGPSVFPL APCSRSTSES TAALGCLVKD YFPEPVTVSW NSGALTSGVH TFPAVLQSSG   180
LYSLSSVVTV PSSSLGTKTY TCNVDHKPSN TKVDKRVESK YGPPCPPCPA PEFEGGPSVF   240
LFPPKPKDTL MISRTPEVTC VVVDVSQEDP EVQFNWYVDG VEVHNAKTKP REEQFNSTYR   300
VVSVLTVLHQ DWLNGKEYKC KVSNKGLPSS IEKTISKAKG QPREPQVYTL PPSQEEMTKN   360
QVSLTCLVKG FYPSDIAVEW ESNGQPENNY KTTPPVLDSD GSFFLYSRLT VDKSRWQEGN   420
VFSCSVLHEA LHSHYTQKSL SLSLG                                        445

SEQ ID NO: 191              moltype = AA   length = 445
FEATURE                     Location/Qualifiers
source                      1..445
                            mol_type = protein
                            organism = synthetic construct
SEQUENCE: 191
QVQLVQSGAE VKKPGASVKV SCKVSGDTLT ELSMHWVRQA PGKGLEWMGT FDPEEGETIY    60
AQKFQGRVTM TEDTSTDTAY MELSSLRSED TAVYYCVTEG LGGRPFDHWG QGTLVTVSSA   120
STKGPSVFPL APCSRSTSES TAALGCLVKD YFPEPVTVSW NSGALTSGVH TFPAVLQSSG   180
LYSLSSVVTV PSSSLGTKTY TCNVDHKPSN TKVDKRVESK YGPPCPPCPA PEFEGGPSVF   240
LFPPKPKDTL YITREPEVTC VVVDVSQEDP EVQFNWYVDG VEVHNAKTKP REEQFNSTYR   300
VVSVLTVLHQ DWLNGKEYKC KVSNKGLPSS IEKTISKAKG QPREPQVYTL PPSQEEMTKN   360
QVSLTCLVKG FYPSDIAVEW ESNGQPENNY KTTPPVLDSD GSFFLYSRLT VDKSRWQEGN   420
VFSCSVMHEA LHNHYTQKSL SLSLG                                        445

SEQ ID NO: 192              moltype = AA   length = 445
FEATURE                     Location/Qualifiers
source                      1..445
                            mol_type = protein
```

```
                        organism = synthetic construct
SEQUENCE: 192
QVQLVQSGAE VKKPGASVKV SCKVSGDTLT ELSMHWVRQA PGKGLEWMGT FDPEEGETIY    60
AQKFQGRVTM TEDTSTDTAY MELSSLRSED TAVYYCVTEG LAGFPFDIWG QGTLVTVSSA   120
STKGPSVFPL APCSRSTSES TAALGCLVKD YFPEPVTVSW NSGALTSGVH TFPAVLQSSG   180
LYSLSSVVTV PSSSLGTKTY TCNVDHKPSN TKVDKRVESK YGPPCPPCPA PEFEGGPSVF   240
LFPPKPKDTL MISRTPEVTC VVVDVSQEDP EVQFNWYVDG VEVHNAKTKP REEQFNSTYR   300
VVSVLTVLHQ DWLNGKEYKC KVSNKGLPSS IEKTISKAKG QPREPQVYTL PPSQEEMTKN   360
QVSLTCLVKG FYPSDIAVEW ESNGQPENNY KTTPPVLDSD GSFFLYSRLT VDKSRWQEGN   420
VFSCSVLHEA LHSHYTQKSL SLSLG                                        445

SEQ ID NO: 193          moltype = AA  length = 445
FEATURE                 Location/Qualifiers
source                  1..445
                        mol_type = protein
                        organism = synthetic construct
SEQUENCE: 193
QVQLVQSGAE VKKPGASVKV SCKVSGDTLT ELSMHWVRQA PGKGLEWMGT FDPEEGETIY    60
AQKFQGRVTM TEDTSTDTAY MELSSLRSED TAVYYCVTEG LAGFPFDIWG QGTLVTVSSA   120
STKGPSVFPL APCSRSTSES TAALGCLVKD YFPEPVTVSW NSGALTSGVH TFPAVLQSSG   180
LYSLSSVVTV PSSSLGTKTY TCNVDHKPSN TKVDKRVESK YGPPCPPCPA PEFEGGPSVF   240
LFPPKPKDTL YITREPEVTC VVVDVSQEDP EVQFNWYVDG VEVHNAKTKP REEQFNSTYR   300
VVSVLTVLHQ DWLNGKEYKC KVSNKGLPSS IEKTISKAKG QPREPQVYTL PPSQEEMTKN   360
QVSLTCLVKG FYPSDIAVEW ESNGQPENNY KTTPPVLDSD GSFFLYSRLT VDKSRWQEGN   420
VFSCSVMHEA LHNHYTQKSL SLSLG                                        445

SEQ ID NO: 194          moltype = AA  length = 444
FEATURE                 Location/Qualifiers
source                  1..444
                        mol_type = protein
                        organism = synthetic construct
SEQUENCE: 194
QVQLVQSGAE VKKPGASVKV SCKVSGDTLT ELSMHWVRQA PGKGLEWMGT FDPEEGETIY    60
AQKFQGRVTM TEDTSTDTAY MELSSLRSED TAVYYCVTEG LAWRPTDSWG QGTLVTVSSA   120
STKGPSVFPL APCSRSTSES TAALGCLVKD YFPEPVTVSW NSGALTSGVH TFPAVLQSSG   180
LYSLSSVVTV PSSSLGTKTY TCNVDHKPSN TKVDKRVESK YGPPCPPCPA PEFEGGPSVF   240
LFPPKPKDTL MISRTPEVTC VVVDVSQEDP EVQFNWYVDG VEVHNAKTKP REEQFNSTYR   300
VVSVLTVLHQ DWLNGKEYKC KVSNKGLPSS IEKTISKAKG QPREPQVYTL PPSQEEMTKN   360
QVSLTCLVKG FYPSDIAVEW ESNGQPENNY KTTPPVLDSD GSFFLYSRLT VDKSRWQEGN   420
VFSCSVLHEA LHSHYTQKSL SLSL                                         444

SEQ ID NO: 195          moltype = AA  length = 445
FEATURE                 Location/Qualifiers
source                  1..445
                        mol_type = protein
                        organism = synthetic construct
SEQUENCE: 195
QVQLVQSGAE VKKPGASVKV SCKVSGDTLT ELSMHWVRQA PGKGLEWMGT FDPEEGETIY    60
AQKFQGRVTM TEDTSTDTAY MELSSLRSED TAVYYCVTEG LAWRPTDSWG QGTLVTVSSA   120
STKGPSVFPL APCSRSTSES TAALGCLVKD YFPEPVTVSW NSGALTSGVH TFPAVLQSSG   180
LYSLSSVVTV PSSSLGTKTY TCNVDHKPSN TKVDKRVESK YGPPCPPCPA PEFEGGPSVF   240
LFPPKPKDTL YITREPEVTC VVVDVSQEDP EVQFNWYVDG VEVHNAKTKP REEQFNSTYR   300
VVSVLTVLHQ DWLNGKEYKC KVSNKGLPSS IEKTISKAKG QPREPQVYTL PPSQEEMTKN   360
QVSLTCLVKG FYPSDIAVEW ESNGQPENNY KTTPPVLDSD GSFFLYSRLT VDKSRWQEGN   420
VFSCSVMHEA LHNHYTQKSL SLSLG                                        445

SEQ ID NO: 196          moltype = AA  length = 445
FEATURE                 Location/Qualifiers
source                  1..445
                        mol_type = protein
                        organism = synthetic construct
SEQUENCE: 196
QVQLVQSGAE VKKPGASVKV SCKVSGDTLT ELSMHWVRQA PGKGLEWMGT FDPEEGETIY    60
AQKFQGRVTM TEDTSTDTAY MELSSLRSED TAVYYCVTKG LAWLPYYSWG QGTLVTVSSA   120
STKGPSVFPL APCSRSTSES TAALGCLVKD YFPEPVTVSW NSGALTSGVH TFPAVLQSSG   180
LYSLSSVVTV PSSSLGTKTY TCNVDHKPSN TKVDKRVESK YGPPCPPCPA PEFEGGPSVF   240
LFPPKPKDTL MISRTPEVTC VVVDVSQEDP EVQFNWYVDG VEVHNAKTKP REEQFNSTYR   300
VVSVLTVLHQ DWLNGKEYKC KVSNKGLPSS IEKTISKAKG QPREPQVYTL PPSQEEMTKN   360
QVSLTCLVKG FYPSDIAVEW ESNGQPENNY KTTPPVLDSD GSFFLYSRLT VDKSRWQEGN   420
VFSCSVLHEA LHSHYTQKSL SLSLG                                        445

SEQ ID NO: 197          moltype = AA  length = 445
FEATURE                 Location/Qualifiers
source                  1..445
                        mol_type = protein
                        organism = synthetic construct
SEQUENCE: 197
QVQLVQSGAE VKKPGASVKV SCKVSGDTLT ELSMHWVRQA PGKGLEWMGT FDPEEGETIY    60
AQKFQGRVTM TEDTSTDTAY MELSSLRSED TAVYYCVTKG LAWLPYYSWG QGTLVTVSSA   120
```

```
STKGPSVFPL APCSRSTSES TAALGCLVKD YFPEPVTVSW NSGALTSGVH TFPAVLQSSG    180
LYSLSSVVTV PSSSLGTKTY TCNVDHKPSN TKVDKRVESK YGPPCPPCPA PEFEGGPSVF    240
LFPPKPKDTL YITREPEVTC VVVDVSQEDP EVQFNWYVDG VEVHNAKTKP REEQFNSTYR    300
VVSVLTVLHQ DWLNGKEYKC KVSNKGLPSS IEKTISKAKG QPREPQVYTL PPSQEEMTKN    360
QVSLTCLVKG FYPSDIAVEW ESNGQPENNY KTTPPVLDSD GSFFLYSRLT VDKSRWQEGN    420
VFSCSVMHEA LHNHYTQKSL SLSLG                                         445

SEQ ID NO: 198          moltype = AA  length = 445
FEATURE                 Location/Qualifiers
source                  1..445
                        mol_type = protein
                        organism = synthetic construct
SEQUENCE: 198
QVQLVQSGAE VKKPGASVKV SCKVSGDTLT ELSMHWVRQA PGKGLEWMGT FDPEEGETIY     60
AQKFQGRVTM TEDTSTDTAY MELSSLRSED TAVYYCVTEG LAGVPFDLWG QGTLVTVSSA    120
STKGPSVFPL APCSRSTSES TAALGCLVKD YFPEPVTVSW NSGALTSGVH TFPAVLQSSG    180
LYSLSSVVTV PSSSLGTKTY TCNVDHKPSN TKVDKRVESK YGPPCPPCPA PEFEGGPSVF    240
LFPPKPKDTL MISRTPEVTC VVVDVSQEDP EVQFNWYVDG VEVHNAKTKP REEQFNSTYR    300
VVSVLTVLHQ DWLNGKEYKC KVSNKGLPSS IEKTISKAKG QPREPQVYTL PPSQEEMTKN    360
QVSLTCLVKG FYPSDIAVEW ESNGQPENNY KTTPPVLDSD GSFFLYSRLT VDKSRWQEGN    420
VFSCSVMHEA LHSHYTQKSL SLSLG                                         445

SEQ ID NO: 199          moltype = AA  length = 445
FEATURE                 Location/Qualifiers
source                  1..445
                        mol_type = protein
                        organism = synthetic construct
SEQUENCE: 199
QVQLVQSGAE VKKPGASVKV SCKVSGDTLT ELSMHWVRQA PGKGLEWMGT FDPEEGETIY     60
AQKFQGRVTM TEDTSTDTAY MELSSLRSED TAVYYCVTEG LAGVPFDLWG QGTLVTVSSA    120
STKGPSVFPL APCSRSTSES TAALGCLVKD YFPEPVTVSW NSGALTSGVH TFPAVLQSSG    180
LYSLSSVVTV PSSSLGTKTY TCNVDHKPSN TKVDKRVESK YGPPCPPCPA PEFEGGPSVF    240
LFPPKPKDTL YITREPEVTC VVVDVSQEDP EVQFNWYVDG VEVHNAKTKP REEQFNSTYR    300
VVSVLTVLHQ DWLNGKEYKC KVSNKGLPSS IEKTISKAKG QPREPQVYTL PPSQEEMTKN    360
QVSLTCLVKG FYPSDIAVEW ESNGQPENNY KTTPPVLDSD GSFFLYSRLT VDKSRWQEGN    420
VFSCSVMHEA LHNHYTQKSL SLSLG                                         445

SEQ ID NO: 200          moltype = AA  length = 445
FEATURE                 Location/Qualifiers
source                  1..445
                        mol_type = protein
                        organism = synthetic construct
SEQUENCE: 200
QVQLVQSGAE VKKPGASVKV SCKVSGDTLT ELSMHWVRQA PGKGLEWMGT FDPEEGETIY     60
AQKFQGRVTM TEDTSTDTAY MELSSLRSED TAVYYCVTEG EAGRPFDAWG QGTLVTVSSA    120
STKGPSVFPL APCSRSTSES TAALGCLVKD YFPEPVTVSW NSGALTSGVH TFPAVLQSSG    180
LYSLSSVVTV PSSSLGTKTY TCNVDHKPSN TKVDKRVESK YGPPCPPCPA PEFEGGPSVF    240
LFPPKPKDTL MISRTPEVTC VVVDVSQEDP EVQFNWYVDG VEVHNAKTKP REEQFNSTYR    300
VVSVLTVLHQ DWLNGKEYKC KVSNKGLPSS IEKTISKAKG QPREPQVYTL PPSQEEMTKN    360
QVSLTCLVKG FYPSDIAVEW ESNGQPENNY KTTPPVLDSD GSFFLYSRLT VDKSRWQEGN    420
VFSCSVMHEA LHSHYTQKSL SLSLG                                         445

SEQ ID NO: 201          moltype = AA  length = 445
FEATURE                 Location/Qualifiers
source                  1..445
                        mol_type = protein
                        organism = synthetic construct
SEQUENCE: 201
QVQLVQSGAE VKKPGASVKV SCKVSGDTLT ELSMHWVRQA PGKGLEWMGT FDPEEGETIY     60
AQKFQGRVTM TEDTSTDTAY MELSSLRSED TAVYYCVTEG EAGRPFDAWG QGTLVTVSSA    120
STKGPSVFPL APCSRSTSES TAALGCLVKD YFPEPVTVSW NSGALTSGVH TFPAVLQSSG    180
LYSLSSVVTV PSSSLGTKTY TCNVDHKPSN TKVDKRVESK YGPPCPPCPA PEFEGGPSVF    240
LFPPKPKDTL YITREPEVTC VVVDVSQEDP EVQFNWYVDG VEVHNAKTKP REEQFNSTYR    300
VVSVLTVLHQ DWLNGKEYKC KVSNKGLPSS IEKTISKAKG QPREPQVYTL PPSQEEMTKN    360
QVSLTCLVKG FYPSDIAVEW ESNGQPENNY KTTPPVLDSD GSFFLYSRLT VDKSRWQEGN    420
VFSCSVMHEA LHNHYTQKSL SLSLG                                         445

SEQ ID NO: 202          moltype = AA  length = 445
FEATURE                 Location/Qualifiers
source                  1..445
                        mol_type = protein
                        organism = synthetic construct
SEQUENCE: 202
QVQLVQSGAE VKKPGASVKV SCKVSGDTLT ELSMHWVRQA PGKGLEWMGT FDPEEGETIY     60
AQKFQGRVTM TEDTSTDTAY MELSSLRSED TAVYYCVTEG LAGRPYDVWG QGTLVTVSSA    120
STKGPSVFPL APCSRSTSES TAALGCLVKD YFPEPVTVSW NSGALTSGVH TFPAVLQSSG    180
LYSLSSVVTV PSSSLGTKTY TCNVDHKPSN TKVDKRVESK YGPPCPPCPA PEFEGGPSVF    240
LFPPKPKDTL MISRTPEVTC VVVDVSQEDP EVQFNWYVDG VEVHNAKTKP REEQFNSTYR    300
VVSVLTVLHQ DWLNGKEYKC KVSNKGLPSS IEKTISKAKG QPREPQVYTL PPSQEEMTKN    360
```

```
QVSLTCLVKG FYPSDIAVEW ESNGQPENNY KTTPPVLDSD GSFFLYSRLT VDKSRWQEGN    420
VFSCSVLHEA LHSHYTQKSL SLSLG                                         445

SEQ ID NO: 203              moltype = AA  length = 445
FEATURE                     Location/Qualifiers
source                      1..445
                            mol_type = protein
                            organism = synthetic construct
SEQUENCE: 203
QVQLVQSGAE VKKPGASVKV SCKVSGDTLT ELSMHWVRQA PGKGLEWMGT FDPEEGETIY    60
AQKFQGRVTM TEDTSTDTAY MELSSLRSED TAVYYCVTEG LAGRPYDVWG QGTLVTVSSA    120
STKGPSVFPL APCSRSTSES TAALGCLVKD YFPEPVTVSW NSGALTSGVH TFPAVLQSSG    180
LYSLSSVVTV PSSSLGTKTY TCNVDHKPSN TKVDKRVESK YGPPCPPCPA PEFEGGPSVF    240
LFPPKPKDTL YITREPEVTC VVVDVSQEDP EVQFNWYVDG VEVHNAKTKP REEQFNSTYR    300
VVSVLTVLHQ DWLNGKEYKC KVSNKGLPSS IEKTISKAKG QPREPQVYTL PPSQEEMTKN    360
QVSLTCLVKG FYPSDIAVEW ESNGQPENNY KTTPPVLDSD GSFFLYSRLT VDKSRWQEGN    420
VFSCSVMHEA LHNHYTQKSL SLSLG                                         445

SEQ ID NO: 204              moltype = AA  length = 445
FEATURE                     Location/Qualifiers
source                      1..445
                            mol_type = protein
                            organism = synthetic construct
SEQUENCE: 204
QVQLVQSGAE VKKPGASVKV SCKVSGDTLT ELSMHWVRQA PGKGLEWMGT FDPEEGETIY    60
AQKFQGRVTM TEDTSTDTAY MELSYLRSED TAVYYCVTEG LAGIPFDSWG QGTLVTVSSA    120
STKGPSVFPL APCSRSTSES TAALGCLVKD YFPEPVTVSW NSGALTSGVH TFPAVLQSSG    180
LYSLSSVVTV PSSSLGTKTY TCNVDHKPSN TKVDKRVESK YGPPCPPCPA PEFEGGPSVF    240
LFPPKPKDTL MISRTPEVTC VVVDVSQEDP EVQFNWYVDG VEVHNAKTKP REEQFNSTYR    300
VVSVLTVLHQ DWLNGKEYKC KVSNKGLPSS IEKTISKAKG QPREPQVYTL PPSQEEMTKN    360
QVSLTCLVKG FYPSDIAVEW ESNGQPENNY KTTPPVLDSD GSFFLYSRLT VDKSRWQEGN    420
VFSCSVLHEA LHSHYTQKSL SLSLG                                         445

SEQ ID NO: 205              moltype = AA  length = 445
FEATURE                     Location/Qualifiers
source                      1..445
                            mol_type = protein
                            organism = synthetic construct
SEQUENCE: 205
QVQLVQSGAE VKKPGASVKV SCKVSGDTLT ELSMHWVRQA PGKGLEWMGT FDPEEGETIY    60
AQKFQGRVTM TEDTSTDTAY MELSYLRSED TAVYYCVTEG LAGIPFDSWG QGTLVTVSSA    120
STKGPSVFPL APCSRSTSES TAALGCLVKD YFPEPVTVSW NSGALTSGVH TFPAVLQSSG    180
LYSLSSVVTV PSSSLGTKTY TCNVDHKPSN TKVDKRVESK YGPPCPPCPA PEFEGGPSVF    240
LFPPKPKDTL YITREPEVTC VVVDVSQEDP EVQFNWYVDG VEVHNAKTKP REEQFNSTYR    300
VVSVLTVLHQ DWLNGKEYKC KVSNKGLPSS IEKTISKAKG QPREPQVYTL PPSQEEMTKN    360
QVSLTCLVKG FYPSDIAVEW ESNGQPENNY KTTPPVLDSD GSFFLYSRLT VDKSRWQEGN    420
VFSCSVMHEA LHNHYTQKSL SLSLG                                         445

SEQ ID NO: 206              moltype = AA  length = 445
FEATURE                     Location/Qualifiers
source                      1..445
                            mol_type = protein
                            organism = synthetic construct
SEQUENCE: 206
QVQLVQSGAE VKKPGASVKV SCKVSGDTLT ELSMHWVRQA PGKGLEWMGT FDPEEGETIY    60
AQKFQGRVTM TEDTSTDTAY MELSRLRSED TAVYYCVTEG LAGIPFDSWG QGTLVTVSSA    120
STKGPSVFPL APCSRSTSES TAALGCLVKD YFPEPVTVSW NSGALTSGVH TFPAVLQSSG    180
LYSLSSVVTV PSSSLGTKTY TCNVDHKPSN TKVDKRVESK YGPPCPPCPA PEFEGGPSVF    240
LFPPKPKDTL MISRTPEVTC VVVDVSQEDP EVQFNWYVDG VEVHNAKTKP REEQFNSTYR    300
VVSVLTVLHQ DWLNGKEYKC KVSNKGLPSS IEKTISKAKG QPREPQVYTL PPSQEEMTKN    360
QVSLTCLVKG FYPSDIAVEW ESNGQPENNY KTTPPVLDSD GSFFLYSRLT VDKSRWQEGN    420
VFSCSVLHEA LHSHYTQKSL SLSLG                                         445

SEQ ID NO: 207              moltype = AA  length = 445
FEATURE                     Location/Qualifiers
source                      1..445
                            mol_type = protein
                            organism = synthetic construct
SEQUENCE: 207
QVQLVQSGAE VKKPGASVKV SCKVSGDTLT ELSMHWVRQA PGKGLEWMGT FDPEEGETIY    60
AQKFQGRVTM TEDTSTDTAY MELSRLRSED TAVYYCVTEG LAGIPFDSWG QGTLVTVSSA    120
STKGPSVFPL APCSRSTSES TAALGCLVKD YFPEPVTVSW NSGALTSGVH TFPAVLQSSG    180
LYSLSSVVTV PSSSLGTKTY TCNVDHKPSN TKVDKRVESK YGPPCPPCPA PEFEGGPSVF    240
LFPPKPKDTL YITREPEVTC VVVDVSQEDP EVQFNWYVDG VEVHNAKTKP REEQFNSTYR    300
VVSVLTVLHQ DWLNGKEYKC KVSNKGLPSS IEKTISKAKG QPREPQVYTL PPSQEEMTKN    360
QVSLTCLVKG FYPSDIAVEW ESNGQPENNY KTTPPVLDSD GSFFLYSRLT VDKSRWQEGN    420
VFSCSVMHEA LHNHYTQKSL SLSLG                                         445

SEQ ID NO: 208              moltype = AA  length = 451
```

```
FEATURE               Location/Qualifiers
source                1..451
                      mol_type = protein
                      organism = synthetic construct
SEQUENCE: 208
EVQLVESGGG VVRPGGSLRL SCAASGFTFD DYGMSWVRQA PGKGLEWVSG INWEGGSTGY    60
ADSVKGRFTI SRDNAKNSLY LQMNSLRAED TALYYCARDE QLGGTTYYYY YMDVWGKGTT   120
VTVSSASTKG PSVFPLAPCS RSTSESTAAL GCLVKDYFPE PVTVSWNSGA LTSGVHTFPA   180
VLQSSGLYSL SSVVTVPSSS LGTKTYTCNV DHKPSNTKVD KRVESKYGPP CPPCPAPEFE   240
GGPSVFLFPP KPKDTLMISR TPEVTCVVVD VSQEDPEVQF NWYVDGVEVH NAKTKPREEQ   300
FNSTYRVVSV LTVLHQDWLN GKEYKCKVSN KGLPSSIEKT ISKAKGQPRE PQVYTLPPSQ   360
EEMTKNQVSL TCLVKGFYPS DIAVEWESNG QPENNYKTTP PVLDSDGSFF LYSRLTVDKS   420
RWQEGNVFSC SVLHEALHSH YTQKSLSLSL G                                  451

SEQ ID NO: 209        moltype = AA  length = 451
FEATURE               Location/Qualifiers
source                1..451
                      mol_type = protein
                      organism = synthetic construct
SEQUENCE: 209
EVQLVESGGG VVRPGGSLRL SCAASGFTFD DYGMSWVRQA PGKGLEWVSG INWEGGSTGY    60
ADSVKGRFTI SRDNAKNSLY LQMNSLRAED TALYYCARDE QLGGTTYYYY YMDVWGKGTT   120
VTVSSASTKG PSVFPLAPCS RSTSESTAAL GCLVKDYFPE PVTVSWNSGA LTSGVHTFPA   180
VLQSSGLYSL SSVVTVPSSS LGTKTYTCNV DHKPSNTKVD KRVESKYGPP CPPCPAPEFE   240
GGPSVFLFPP KPKDTLYITR EPEVTCVVVD VSQEDPEVQF NWYVDGVEVH NAKTKPREEQ   300
FNSTYRVVSV LTVLHQDWLN GKEYKCKVSN KGLPSSIEKT ISKAKGQPRE PQVYTLPPSQ   360
EEMTKNQVSL TCLVKGFYPS DIAVEWESNG QPENNYKTTP PVLDSDGSFF LYSRLTVDKS   420
RWQEGNVFSC SVMHEALHNH YTQKSLSLSL G                                  451

SEQ ID NO: 210        moltype = AA  length = 451
FEATURE               Location/Qualifiers
source                1..451
                      mol_type = protein
                      organism = synthetic construct
SEQUENCE: 210
EVQLVESGGG VVRPGGSLRL SCAASGFTFD DYGMSWVRQA PGKGLEWVSG INWEGGSTGY    60
ADSVKGRFTI SRDNAKNSLY LQMNSLRAED TALYYCARDE QLGGKYYYYY YMDVWGKGTT   120
VTVSSASTKG PSVFPLAPCS RSTSESTAAL GCLVKDYFPE PVTVSWNSGA LTSGVHTFPA   180
VLQSSGLYSL SSVVTVPSSS LGTKTYTCNV DHKPSNTKVD KRVESKYGPP CPPCPAPEFE   240
GGPSVFLFPP KPKDTLMISR TPEVTCVVVD VSQEDPEVQF NWYVDGVEVH NAKTKPREEQ   300
FNSTYRVVSV LTVLHQDWLN GKEYKCKVSN KGLPSSIEKT ISKAKGQPRE PQVYTLPPSQ   360
EEMTKNQVSL TCLVKGFYPS DIAVEWESNG QPENNYKTTP PVLDSDGSFF LYSRLTVDKS   420
RWQEGNVFSC SVLHEALHSH YTQKSLSLSL G                                  451

SEQ ID NO: 211        moltype = AA  length = 451
FEATURE               Location/Qualifiers
source                1..451
                      mol_type = protein
                      organism = synthetic construct
SEQUENCE: 211
EVQLVESGGG VVRPGGSLRL SCAASGFTFD DYGMSWVRQA PGKGLEWVSG INWEGGSTGY    60
ADSVKGRFTI SRDNAKNSLY LQMNSLRAED TALYYCARDE QLGGKYYYYY YMDVWGKGTT   120
VTVSSASTKG PSVFPLAPCS RSTSESTAAL GCLVKDYFPE PVTVSWNSGA LTSGVHTFPA   180
VLQSSGLYSL SSVVTVPSSS LGTKTYTCNV DHKPSNTKVD KRVESKYGPP CPPCPAPEFE   240
GGPSVFLFPP KPKDTLYITR EPEVTCVVVD VSQEDPEVQF NWYVDGVEVH NAKTKPREEQ   300
FNSTYRVVSV LTVLHQDWLN GKEYKCKVSN KGLPSSIEKT ISKAKGQPRE PQVYTLPPSQ   360
EEMTKNQVSL TCLVKGFYPS DIAVEWESNG QPENNYKTTP PVLDSDGSFF LYSRLTVDKS   420
RWQEGNVFSC SVMHEALHNH YTQKSLSLSL G                                  451

SEQ ID NO: 212        moltype = AA  length = 451
FEATURE               Location/Qualifiers
source                1..451
                      mol_type = protein
                      organism = synthetic construct
SEQUENCE: 212
EVQLVESGGG VVRPGGSLRL SCAASGFTFD DYGMSWVRQA PGKGLEWVSG INWEGGSTGY    60
ADSVKGRFTI SRDNAKNSLY LQMNSLRAED TALYYCARDE QLGGQTYYYY YMDVWGKGTT   120
VTVSSASTKG PSVFPLAPCS RSTSESTAAL GCLVKDYFPE PVTVSWNSGA LTSGVHTFPA   180
VLQSSGLYSL SSVVTVPSSS LGTKTYTCNV DHKPSNTKVD KRVESKYGPP CPPCPAPEFE   240
GGPSVFLFPP KPKDTLMISR TPEVTCVVVD VSQEDPEVQF NWYVDGVEVH NAKTKPREEQ   300
FNSTYRVVSV LTVLHQDWLN GKEYKCKVSN KGLPSSIEKT ISKAKGQPRE PQVYTLPPSQ   360
EEMTKNQVSL TCLVKGFYPS DIAVEWESNG QPENNYKTTP PVLDSDGSFF LYSRLTVDKS   420
RWQEGNVFSC SVLHEALHSH YTQKSLSLSL G                                  451

SEQ ID NO: 213        moltype = AA  length = 451
FEATURE               Location/Qualifiers
source                1..451
                      mol_type = protein
                      organism = synthetic construct
```

```
SEQUENCE: 213
EVQLVESGGG VVRPGGSLRL SCAASGFTFD DYGMSWVRQA PGKGLEWVSG INWEGGSTGY    60
ADSVKGRFTI SRDNAKNSLY LQMNSLRAED TALYYCARDE QLGGQTYYYY YMDVWGKGTT   120
VTVSSASTKG PSVFPLAPCS RSTSESTAAL GCLVKDYFPE PVTVSWNSGA LTSGVHTFPA   180
VLQSSGLYSL SSVVTVPSSS LGTKTYTCNV DHKPSNTKVD KRVESKYGPP CPPCPAPEFE   240
GGPSVFLFPP KPKDTLYITR EPEVTCVVVD VSQEDPEVQF NWYVDGVEVH NAKTKPREEQ   300
FNSTYRVVSV LTVLHQDWLN GKEYKCKVSN KGLPSSIEKT ISKAKGQPRE PQVYTLPPSQ   360
EEMTKNQVSL TCLVKGFYPS DIAVEWESNG QPENNYKTTP PVLDSDGSFF LYSRLTVDKS   420
RWQEGNVFSC SVMHEALHNH YTQKSLSLSL G                                 451

SEQ ID NO: 214         moltype = AA   length = 451
FEATURE                Location/Qualifiers
source                 1..451
                       mol_type = protein
                       organism = synthetic construct
SEQUENCE: 214
EVQLVESGGG VVRPGGSLRL SCAASGFTFD DYGMSWVRQA PGKGLEWVSG INWEGGSTGY    60
ADSVKGRFTI SRDNAKNSLY LQMNSLRAED TALYYCARDE QLGGTTYYYY YMDVWGKGTT   120
VTVSSASTKG PSVFPLAPCS RSTSESTAAL GCLVKDYFPE PVTVSWNSGA LTSGVHTFPA   180
VLQSSGLYSL SSVVTVPSSS LGTKTYTCNV DHKPSNTKVD KRVESKYGPP CPPCPAPEFE   240
GGPSVFLFPP KPKDTLMISR TPEVTCVVVD VSQEDPEVQF NWYVDGVEVH NAKTKPREEQ   300
FNSTYRVVSV LTVLHQDWLN GKEYKCKVSN KGLPSSIEKT ISKAKGQPRE PQVYTLPPSQ   360
EEMTKNQVSL TCLVKGFYPS DIAVEWESNG QPENNYKTTP PVLDSDGSFF LYSRLTVDKS   420
RWQEGNVFSC SVLHEALHSH YTQKSLSLSL G                                 451

SEQ ID NO: 215         moltype = AA   length = 451
FEATURE                Location/Qualifiers
source                 1..451
                       mol_type = protein
                       organism = synthetic construct
SEQUENCE: 215
EVQLVESGGG VVRPGGSLRL SCAASGFTFD DYGMSWVRQA PGKGLEWVSG INWEGGSTGY    60
ADSVKGRFTI SRDNAKNSLY LQMNSLRAED TALYYCARDE QLGGTTYYYY YMDVWGKGTT   120
VTVSSASTKG PSVFPLAPCS RSTSESTAAL GCLVKDYFPE PVTVSWNSGA LTSGVHTFPA   180
VLQSSGLYSL SSVVTVPSSS LGTKTYTCNV DHKPSNTKVD KRVESKYGPP CPPCPAPEFE   240
GGPSVFLFPP KPKDTLYITR EPEVTCVVVD VSQEDPEVQF NWYVDGVEVH NAKTKPREEQ   300
FNSTYRVVSV LTVLHQDWLN GKEYKCKVSN KGLPSSIEKT ISKAKGQPRE PQVYTLPPSQ   360
EEMTKNQVSL TCLVKGFYPS DIAVEWESNG QPENNYKTTP PVLDSDGSFF LYSRLTVDKS   420
RWQEGNVFSC SVMHEALHNH YTQKSLSLSL G                                 451

SEQ ID NO: 216         moltype = AA   length = 451
FEATURE                Location/Qualifiers
source                 1..451
                       mol_type = protein
                       organism = synthetic construct
SEQUENCE: 216
EVQLVESGGG VVRPGGSLRL SCAASGFTFD DYGMSWVRQA PGKGLEWVSG INWEGGSTGY    60
ADSVKGRFTI SRDNAKNSLY LQMNSLRAED TALYYCARDE QLGGIKYYYY YMDVWGKGTT   120
VTVSSASTKG PSVFPLAPCS RSTSESTAAL GCLVKDYFPE PVTVSWNSGA LTSGVHTFPA   180
VLQSSGLYSL SSVVTVPSSS LGTKTYTCNV DHKPSNTKVD KRVESKYGPP CPPCPAPEFE   240
GGPSVFLFPP KPKDTLMISR TPEVTCVVVD VSQEDPEVQF NWYVDGVEVH NAKTKPREEQ   300
FNSTYRVVSV LTVLHQDWLN GKEYKCKVSN KGLPSSIEKT ISKAKGQPRE PQVYTLPPSQ   360
EEMTKNQVSL TCLVKGFYPS DIAVEWESNG QPENNYKTTP PVLDSDGSFF LYSRLTVDKS   420
RWQEGNVFSC SVLHEALHSH YTQKSLSLSL G                                 451

SEQ ID NO: 217         moltype = AA   length = 451
FEATURE                Location/Qualifiers
source                 1..451
                       mol_type = protein
                       organism = synthetic construct
SEQUENCE: 217
EVQLVESGGG VVRPGGSLRL SCAASGFTFD DYGMSWVRQA PGKGLEWVSG INWEGGSTGY    60
ADSVKGRFTI SRDNAKNSLY LQMNSLRAED TALYYCARDE QLGGIKYYYY YMDVWGKGTT   120
VTVSSASTKG PSVFPLAPCS RSTSESTAAL GCLVKDYFPE PVTVSWNSGA LTSGVHTFPA   180
VLQSSGLYSL SSVVTVPSSS LGTKTYTCNV DHKPSNTKVD KRVESKYGPP CPPCPAPEFE   240
GGPSVFLFPP KPKDTLYITR EPEVTCVVVD VSQEDPEVQF NWYVDGVEVH NAKTKPREEQ   300
FNSTYRVVSV LTVLHQDWLN GKEYKCKVSN KGLPSSIEKT ISKAKGQPRE PQVYTLPPSQ   360
EEMTKNQVSL TCLVKGFYPS DIAVEWESNG QPENNYKTTP PVLDSDGSFF LYSRLTVDKS   420
RWQEGNVFSC SVMHEALHNH YTQKSLSLSL G                                 451

SEQ ID NO: 218         moltype = AA   length = 451
FEATURE                Location/Qualifiers
source                 1..451
                       mol_type = protein
                       organism = synthetic construct
SEQUENCE: 218
EVQLVESGGG VVRPGGSLRL SCAASGFTFD DYGMSWVRQA PGKGLEWVSG INWEGGSTGY    60
ADSVKGRFSI SRDNAKNSLY LQMNSLRAED TALYYCARDE QLGGLKYYYY YMDVWGKGTT   120
VTVSSASTKG PSVFPLAPCS RSTSESTAAL GCLVKDYFPE PVTVSWNSGA LTSGVHTFPA   180
```

```
VLQSSGLYSL SSVVTVPSSS LGTKTYTCNV DHKPSNTKVD KRVESKYGPP CPPCPAPEFE   240
GGPSVFLFPP KPKDTLMISR TPEVTCVVVD VSQEDPEVQF NWYVDGVEVH NAKTKPREEQ   300
FNSTYRVVSV LTVLHQDWLN GKEYKCKVSN KGLPSSIEKT ISKAKGQPRE PQVYTLPPSQ   360
EEMTKNQVSL TCLVKGFYPS DIAVEWESNG QPENNYKTTP PVLDSDGSFF LYSRLTVDKS   420
RWQEGNVFSC SVLHEALHSH YTQKSLSLSL G                                 451

SEQ ID NO: 219          moltype = AA  length = 451
FEATURE                 Location/Qualifiers
source                  1..451
                        mol_type = protein
                        organism = synthetic construct
SEQUENCE: 219
EVQLVESGGG VVRPGGSLRL SCAASGFTFD DYGMSWVRQA PGKGLEWVSG INWEGGSTGY   60
ADSVKGRFSI SRDNAKNSLY LQMNSLRAED TALYYCARDE QLGGLKYYYY YMDVWGKGTT   120
VTVSSASTKG PSVFPLAPCS RSTSESTAAL GCLVKDYFPE PVTVSWNSGA LTSGVHTFPA   180
VLQSSGLYSL SSVVTVPSSS LGTKTYTCNV DHKPSNTKVD KRVESKYGPP CPPCPAPEFE   240
GGPSVFLFPP KPKDTLYITR EPEVTCVVVD VSQEDPEVQF NWYVDGVEVH NAKTKPREEQ   300
FNSTYRVVSV LTVLHQDWLN GKEYKCKVSN KGLPSSIEKT ISKAKGQPRE PQVYTLPPSQ   360
EEMTKNQVSL TCLVKGFYPS DIAVEWESNG QPENNYKTTP PVLDSDGSFF LYSRLTVDKS   420
RWQEGNVFSC SVMHEALHNH YTQKSLSLSL G                                 451

SEQ ID NO: 220          moltype = AA  length = 451
FEATURE                 Location/Qualifiers
source                  1..451
                        mol_type = protein
                        organism = synthetic construct
SEQUENCE: 220
EVQLVESGGG VVRPGGSLRL SCAASGFTFD DYGMSWVRQA PGKGLEWVSG INWEGGSTGY   60
ADSVKGRFTI SRDNAKNSLY LQMNSLRAED TALYYCARDE QLGGKVYYYY YMDVWGKGTT   120
VTVSSASTKG PSVFPLAPCS RSTSESTAAL GCLVKDYFPE PVTVSWNSGA LTSGVHTFPA   180
VLQSSGLYSL SSVVTVPSSS LGTKTYTCNV DHKPSNTKVD KRVESKYGPP CPPCPAPEFE   240
GGPSVFLFPP KPKDTLMISR TPEVTCVVVD VSQEDPEVQF NWYVDGVEVH NAKTKPREEQ   300
FNSTYRVVSV LTVLHQDWLN GKEYKCKVSN KGLPSSIEKT ISKAKGQPRE PQVYTLPPSQ   360
EEMTKNQVSL TCLVKGFYPS DIAVEWESNG QPENNYKTTP PVLDSDGSFF LYSRLTVDKS   420
RWQEGNVFSC SVLHEALHSH YTQKSLSLSL G                                 451

SEQ ID NO: 221          moltype = AA  length = 451
FEATURE                 Location/Qualifiers
source                  1..451
                        mol_type = protein
                        organism = synthetic construct
SEQUENCE: 221
EVQLVESGGG VVRPGGSLRL SCAASGFTFD DYGMSWVRQA PGKGLEWVSG INWEGGSTGY   60
ADSVKGRFTI SRDNAKNSLY LQMNSLRAED TALYYCARDE QLGGKVYYYY YMDVWGKGTT   120
VTVSSASTKG PSVFPLAPCS RSTSESTAAL GCLVKDYFPE PVTVSWNSGA LTSGVHTFPA   180
VLQSSGLYSL SSVVTVPSSS LGTKTYTCNV DHKPSNTKVD KRVESKYGPP CPPCPAPEFE   240
GGPSVFLFPP KPKDTLYITR EPEVTCVVVD VSQEDPEVQF NWYVDGVEVH NAKTKPREEQ   300
FNSTYRVVSV LTVLHQDWLN GKEYKCKVSN KGLPSSIEKT ISKAKGQPRE PQVYTLPPSQ   360
EEMTKNQVSL TCLVKGFYPS DIAVEWESNG QPENNYKTTP PVLDSDGSFF LYSRLTVDKS   420
RWQEGNVFSC SVMHEALHNH YTQKSLSLSL G                                 451

SEQ ID NO: 222          moltype = AA  length = 451
FEATURE                 Location/Qualifiers
source                  1..451
                        mol_type = protein
                        organism = synthetic construct
SEQUENCE: 222
EVQLVESGGG VVRPGGSLRL SCAASGFTFD DYGMSWVRQA PGKGLEWVSG INWEGGSTGY   60
ADSVKGRFSI SRDNAKNSLY LQMNSLRAED TALYYCARDE QLGGLKYYYY YMDVWGKGTT   120
VTVSSASTKG PSVFPLAPCS RSTSESTAAL GCLVKDYFPE PVTVSWNSGA LTSGVHTFPA   180
VLQSSGLYSL SSVVTVPSSS LGTKTYTCNV DHKPSNTKVD KRVESKYGPP CPPCPAPEFE   240
GGPSVFLFPP KPKDTLMISR TPEVTCVVVD VSQEDPEVQF NWYVDGVEVH NAKTKPREEQ   300
FNSTYRVVSV LTVLHQDWLN GKEYKCKVSN KGLPSSIEKT ISKAKGQPRE PQVYTLPPSQ   360
EEMTKNQVSL TCLVKGFYPS DIAVEWESNG QPENNYKTTP PVLDSDGSFF LYSRLTVDKS   420
RWQEGNVFSC SVLHEALHSH YTQKSLSLSL G                                 451

SEQ ID NO: 223          moltype = AA  length = 451
FEATURE                 Location/Qualifiers
source                  1..451
                        mol_type = protein
                        organism = synthetic construct
SEQUENCE: 223
EVQLVESGGG VVRPGGSLRL SCAASGFTFD DYGMSWVRQA PGKGLEWVSG INWEGGSTGY   60
ADSVKGRFSI SRDNAKNSLY LQMNSLRAED TALYYCARDE QLGGLKYYYY YMDVWGKGTT   120
VTVSSASTKG PSVFPLAPCS RSTSESTAAL GCLVKDYFPE PVTVSWNSGA LTSGVHTFPA   180
VLQSSGLYSL SSVVTVPSSS LGTKTYTCNV DHKPSNTKVD KRVESKYGPP CPPCPAPEFE   240
GGPSVFLFPP KPKDTLYITR EPEVTCVVVD VSQEDPEVQF NWYVDGVEVH NAKTKPREEQ   300
FNSTYRVVSV LTVLHQDWLN GKEYKCKVSN KGLPSSIEKT ISKAKGQPRE PQVYTLPPSQ   360
EEMTKNQVSL TCLVKGFYPS DIAVEWESNG QPENNYKTTP PVLDSDGSFF LYSRLTVDKS   420
```

```
RWQEGNVFSC SVMHEALHNH YTQKSLSLSL G                                 451

SEQ ID NO: 224              moltype = AA   length = 451
FEATURE                     Location/Qualifiers
source                      1..451
                            mol_type = protein
                            organism = synthetic construct
SEQUENCE: 224
EVQLVESGGG VVRPGGSLRL SCAASGFTFD DYGMSWVRQA PGKGLEWVSG INWEGGSTGY   60
ADSVKGRFTI SRDNAKNSLY LQMNSLRAED TALYYCARDE QLGGNHYYYY YMDAWGKGTT  120
VTVSSASTKG PSVFPLAPCS RSTSESTAAL GCLVKDYFPE PVTVSWNSGA LTSGVHTFPA  180
VLQSSGLYSL SSVVTVPSSS LGTKTYTCNV DHKPSNTKVD KRVESKYGPP CPPCPAPEFE  240
GGPSVFLFPP KPKDTLMISR TPEVTCVVVD VSQEDPEVQF NWYVDGVEVH NAKTKPREEQ  300
FNSTYRVVSV LTVLHQDWLN GKEYKCKVSN KGLPSSIEKT ISKAKGQPRE PQVYTLPPSQ  360
EEMTKNQVSL TCLVKGFYPS DIAVEWESNG QPENNYKTTP PVLDSDGSFF LYSRLTVDKS  420
RWQEGNVFSC SVLHEALHSH YTQKSLSLSL G                                 451

SEQ ID NO: 225              moltype = AA   length = 451
FEATURE                     Location/Qualifiers
source                      1..451
                            mol_type = protein
                            organism = synthetic construct
SEQUENCE: 225
EVQLVESGGG VVRPGGSLRL SCAASGFTFD DYGMSWVRQA PGKGLEWVSG INWEGGSTGY   60
ADSVKGRFTI SRDNAKNSLY LQMNSLRAED TALYYCARDE QLGGNHYYYY YMDAWGKGTT  120
VTVSSASTKG PSVFPLAPCS RSTSESTAAL GCLVKDYFPE PVTVSWNSGA LTSGVHTFPA  180
VLQSSGLYSL SSVVTVPSSS LGTKTYTCNV DHKPSNTKVD KRVESKYGPP CPPCPAPEFE  240
GGPSVFLFPP KPKDTLYITR EPEVTCVVVD VSQEDPEVQF NWYVDGVEVH NAKTKPREEQ  300
FNSTYRVVSV LTVLHQDWLN GKEYKCKVSN KGLPSSIEKT ISKAKGQPRE PQVYTLPPSQ  360
EEMTKNQVSL TCLVKGFYPS DIAVEWESNG QPENNYKTTP PVLDSDGSFF LYSRLTVDKS  420
RWQEGNVFSC SVMHEALHNH YTQKSLSLSL G                                 451

SEQ ID NO: 226              moltype = AA   length = 451
FEATURE                     Location/Qualifiers
source                      1..451
                            mol_type = protein
                            organism = synthetic construct
SEQUENCE: 226
EVQLVESGGG VVRPGGSLRL SCAASGFTFD DYGMSWVRQA PGKGLEWVSG INWEGGSTGY   60
ADSVKGRFTI SRDNAKNSLY LQMNSLRAED TALYYCARDE QLGGRHYYYY YMDVWGKGTT  120
VTVSSASTKG PSVFPLAPCS RSTSESTAAL GCLVKDYFPE PVTVSWNSGA LTSGVHTFPA  180
VLQSSGLYSL SSVVTVPSSS LGTKTYTCNV DHKPSNTKVD KRVESKYGPP CPPCPAPEFE  240
GGPSVFLFPP KPKDTLMISR TPEVTCVVVD VSQEDPEVQF NWYVDGVEVH NAKTKPREEQ  300
FNSTYRVVSV LTVLHQDWLN GKEYKCKVSN KGLPSSIEKT ISKAKGQPRE PQVYTLPPSQ  360
EEMTKNQVSL TCLVKGFYPS DIAVEWESNG QPENNYKTTP PVLDSDGSFF LYSRLTVDKS  420
RWQEGNVFSC SVLHEALHSH YTQKSLSLSL G                                 451

SEQ ID NO: 227              moltype = AA   length = 451
FEATURE                     Location/Qualifiers
source                      1..451
                            mol_type = protein
                            organism = synthetic construct
SEQUENCE: 227
EVQLVESGGG VVRPGGSLRL SCAASGFTFD DYGMSWVRQA PGKGLEWVSG INWEGGSTGY   60
ADSVKGRFTI SRDNAKNSLY LQMNSLRAED TALYYCARDE QLGGRHYYYY YMDVWGKGTT  120
VTVSSASTKG PSVFPLAPCS RSTSESTAAL GCLVKDYFPE PVTVSWNSGA LTSGVHTFPA  180
VLQSSGLYSL SSVVTVPSSS LGTKTYTCNV DHKPSNTKVD KRVESKYGPP CPPCPAPEFE  240
GGPSVFLFPP KPKDTLYITR EPEVTCVVVD VSQEDPEVQF NWYVDGVEVH NAKTKPREEQ  300
FNSTYRVVSV LTVLHQDWLN GKEYKCKVSN KGLPSSIEKT ISKAKGQPRE PQVYTLPPSQ  360
EEMTKNQVSL TCLVKGFYPS DIAVEWESNG QPENNYKTTP PVLDSDGSFF LYSRLTVDKS  420
RWQEGNVFSC SVMHEALHNH YTQKSLSLSL G                                 451

SEQ ID NO: 228              moltype = AA   length = 214
FEATURE                     Location/Qualifiers
source                      1..214
                            mol_type = protein
                            organism = synthetic construct
SEQUENCE: 228
DIQMTQSPSS LSASVGDRVT ITCQASQDIS NYLNWYQQKP GKAPKLLIYD ASNLETGVPS   60
RFSGSGSGTD FTFTISSLQP EDIATYYCEQ YEDYPLTFGG GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 229              moltype = AA   length = 214
FEATURE                     Location/Qualifiers
source                      1..214
                            mol_type = protein
                            organism = synthetic construct
SEQUENCE: 229
```

```
DIQMTQSPSS LSASVGDRVT ITCQASQDIS NYLNWYQQKP GKAPKLLIYD ASNLETGVPS   60
RFSGSGSGTD FTFTISSLQP EDIATYYCKQ YEDYPLTFGG GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 230          moltype = AA   length = 214
FEATURE                 Location/Qualifiers
source                  1..214
                        mol_type = protein
                        organism = synthetic construct
SEQUENCE: 230
DIQMTQSPSS LSASVGDRVT ITCQASQDIS NYLNWYQQKP GKAPKLLIYD ASNLETGVPS   60
RFSGSGSGTD FTFTISSLQP EDIATYYCKQ YEDYPLTFGG GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 231          moltype = AA   length = 214
FEATURE                 Location/Qualifiers
source                  1..214
                        mol_type = protein
                        organism = synthetic construct
SEQUENCE: 231
DIQMTQSPSS LSASVGDRVT ITCQASQDIS NYLNWYQQKP GKAPKLLIYD ASNLETGVPS   60
RFSGSGSGTD FTFTISSLQP EDIATYYCHQ YEDYPLTFGG GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 232          moltype = AA   length = 214
FEATURE                 Location/Qualifiers
source                  1..214
                        mol_type = protein
                        organism = synthetic construct
SEQUENCE: 232
DIQMTQSPSS LSASVGDRVT ITCQASQDIS NYLNWYQQKP GKAPKLLIYD ASNLETGVPS   60
RFSGSGSGTD FTFTISSLQP EDIATYYCHQ YEDYPLTFGG GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 233          moltype = AA   length = 214
FEATURE                 Location/Qualifiers
source                  1..214
                        mol_type = protein
                        organism = synthetic construct
SEQUENCE: 233
DIQMTQSPSS LSASVGDRVT ITCQASQDIS NYLNWYQQKP GKAPKLLIYD ASNLETGVPS   60
RFSGSGSGTD FTFTISSLQP EDIATYYCHQ YEDYPLTFGG GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 234          moltype = AA   length = 214
FEATURE                 Location/Qualifiers
source                  1..214
                        mol_type = protein
                        organism = synthetic construct
SEQUENCE: 234
DIQMTQSPSS LSASVGDRVT ITCQASQDIS NYLNWYQQKP GKAPKLLIYD ASNLETGVPS   60
RFSGSGSGTD FTFTISSLQP EDIATYYCQQ YEDYPLVFGG GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 235          moltype = AA   length = 214
FEATURE                 Location/Qualifiers
source                  1..214
                        mol_type = protein
                        organism = synthetic construct
SEQUENCE: 235
DIQMTQSPSS LSASVGDRVT ITCQASQDIS NYLNWYQQKP GKAPKLLIYD ASNLETGVPS   60
RFSGSGSGTD FTFTISSLQP EDIATYYCQQ HEDYPLTFGG GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 236          moltype = AA   length = 214
FEATURE                 Location/Qualifiers
source                  1..214
                        mol_type = protein
                        organism = synthetic construct
SEQUENCE: 236
DIQMTQSPSS LSASVGDRVT ITCQASQDIS NYLNWYQQKP GKAPKLLIYD ASNLETGVPS   60
RFSGSGSGTD FTFTISSLQP EDIATYYCQH YEDYPLTFGG GTKVEIKRTV AAPSVFIFPP  120
```

```
SDEQLKSGTA SVVCLLNNFY PREAKVQWKV DNALQSGNSQ ESVTEQDSKD STYSLSSTLT    180
LSKADYEKHK VYACEVTHQG LSSPVTKSFN RGEC                                214

SEQ ID NO: 237              moltype = AA  length = 214
FEATURE                     Location/Qualifiers
source                      1..214
                            mol_type = protein
                            organism = synthetic construct
SEQUENCE: 237
DIQMTQSPSS LSASVGDRVT ITCQASQDIS NYLNWYQQKP GKAPKLLIYD ASNLETGVPS    60
RFSGSGSGTD FTFTISSLQP EDIATYYCQQ YEDLIPTFGG GTKVEIKRTV AAPSVFIFPP    120
SDEQLKSGTA SVVCLLNNFY PREAKVQWKV DNALQSGNSQ ESVTEQDSKD STYSLSSTLT    180
LSKADYEKHK VYACEVTHQG LSSPVTKSFN RGEC                                214

SEQ ID NO: 238              moltype = AA  length = 214
FEATURE                     Location/Qualifiers
source                      1..214
                            mol_type = protein
                            organism = synthetic construct
SEQUENCE: 238
DIQMTQSPST LSASVGDRVT ITCRASQSIS SWLAWYQQKP GKAPKLLIYK ASSLESGVPS    60
RFSGSGSGTE FTLTISSLQP DDFATYYCQS YNSYVWTFGQ GTKVEIKRTV AAPSVFIFPP    120
SDEQLKSGTA SVVCLLNNFY PREAKVQWKV DNALQSGNSQ ESVTEQDSKD STYSLSSTLT    180
LSKADYEKHK VYACEVTHQG LSSPVTKSFN RGEC                                214

SEQ ID NO: 239              moltype = AA  length = 214
FEATURE                     Location/Qualifiers
source                      1..214
                            mol_type = protein
                            organism = synthetic construct
SEQUENCE: 239
DIQMTQSPST LSASVGDRVT ITCRASQSIS SWLAWYQQKP GKAPKLLIYK ASSLESGVPS    60
RFSGSGSGTE FTLTISSLQP DDFATYYCQQ VNSYDWTFGQ GTKVEIKRTV AAPSVFIFPP    120
SDEQLKSGTA SVVCLLNNFY PREAKVQWKV DNALQSGNSQ ESVTEQDSKD STYSLSSTLT    180
LSKADYEKHK VYACEVTHQG LSSPVTKSFN RGEC                                214

SEQ ID NO: 240              moltype = AA  length = 214
FEATURE                     Location/Qualifiers
source                      1..214
                            mol_type = protein
                            organism = synthetic construct
SEQUENCE: 240
DIQMTQSPST LSASVGDRVT ITCRASQSIS SWLAWYQQKP GKAPKLLIYK ASSLESGVPS    60
RFSGSGSGTE FTLTISSLQP DDFATYYCQQ VNSYDWTFGQ GTKVEIKRTV AAPSVFIFPP    120
SDEQLKSGTA SVVCLLNNFY PREAKVQWKV DNALQSGNSQ ESVTEQDSKD STYSLSSTLT    180
LSKADYEKHK VYACEVTHQG LSSPVTKSFN RGEC                                214

SEQ ID NO: 241              moltype = AA  length = 214
FEATURE                     Location/Qualifiers
source                      1..214
                            mol_type = protein
                            organism = synthetic construct
SEQUENCE: 241
DIQMTQSPST LSASVGDRVT ITCRASQSIS SWLAWYQQKP GKAPKLLIYK ASSLESGVPS    60
RFSGSGSGTE FTLTISSLQP DDFATYYCQQ YSSYAWTFGQ GTKVEIKRTV AAPSVFIFPP    120
SDEQLKSGTA SVVCLLNNFY PREAKVQWKV DNALQSGNSQ ESVTEQDSKD STYSLSSTLT    180
LSKADYEKHK VYACEVTHQG LSSPVTKSFN RGEC                                214

SEQ ID NO: 242              moltype = AA  length = 214
FEATURE                     Location/Qualifiers
source                      1..214
                            mol_type = protein
                            organism = synthetic construct
SEQUENCE: 242
DIQMTQSPST LSASVGDRVT ITCRASQSIS SWLAWYQQKP GKAPKLLIYK ASSLESGVPS    60
RFSGSGSGTE FTLTISSLQP DDFATYYCQQ ARSYSWTFGQ GTKVEIKRTV AAPSVFIFPP    120
SDEQLKSGTA SVVCLLNNFY PREAKVQWKV DNALQSGNSQ ESVTEQDSKD STYSLSSTLT    180
LSKADYEKHK VYACEVTHQG LSSPVTKSFN RGEC                                214

SEQ ID NO: 243              moltype = AA  length = 214
FEATURE                     Location/Qualifiers
source                      1..214
                            mol_type = protein
                            organism = synthetic construct
SEQUENCE: 243
DIQMTQSPST LSASVGDRVT ITCRASQSIS SWLAWYQQKP GKAPKLLIYK ASSLESGVPS    60
RFSGSGSGTE FTLTISSLQP DDFATYYCQQ HNSYRWTFGQ GTKVEIKRTV AAPSVFIFPP    120
SDEQLKSGTA SVVCLLNNFY PREAKVQWKV DNALQSGNSQ ESVTEQDSKD STYSLSSTLT    180
LSKADYEKHK VYACEVTHQG LSSPVTKSFN RGEC                                214
```

```
SEQ ID NO: 244          moltype = AA  length = 214
FEATURE                 Location/Qualifiers
source                  1..214
                        mol_type = protein
                        organism = synthetic construct
SEQUENCE: 244
DIQMTQSPST LSASVGDRVT ITCRASQSIS SWLAWYQQKP GKAPKLLIYK ASSLESGVPS    60
RFSGSGSGTE FTLTISSLQP DDFATYYCVQ YPSYSWTFGQ GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 245          moltype = AA  length = 214
FEATURE                 Location/Qualifiers
source                  1..214
                        mol_type = protein
                        organism = synthetic construct
SEQUENCE: 245
DIQMTQSPST LSASVGDRVT ITCRASQSIS SWLAWYQQKP GKAPKLLIYK ASSLESGVPS    60
RFSGSGSGTE FTLTISSLQP DDFATYYCQQ YNSYKLTFGQ GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 246          moltype = AA  length = 214
FEATURE                 Location/Qualifiers
source                  1..214
                        mol_type = protein
                        organism = synthetic construct
SEQUENCE: 246
DIQMTQSPST LSASVGDRVT ITCRASQSIS SWLAWYQQKP GKAPKLLIYK ASSLESGVPS    60
RFSGSGSGTE FTLTISSLQP DDFATYYCQQ YNSPSWLFGQ GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 247          moltype = AA  length = 214
FEATURE                 Location/Qualifiers
source                  1..214
                        mol_type = protein
                        organism = synthetic construct
SEQUENCE: 247
DIQMTQSPST LSASVGDRVT ITCRASQSIS SWLAWYQQKP GKAPKLLIYK ASSLESGVPS    60
RFSGSGSGTE FTLTISSLQP DDFATYYCQQ VNSLSWTFGQ GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 248          moltype = AA  length = 214
FEATURE                 Location/Qualifiers
source                  1..214
                        mol_type = protein
                        organism = synthetic construct
SEQUENCE: 248
DIQMTQSPSS LSASVGDRVT ITCRASQGIR NDLGWYQQKP GKAPKRLIYT ASNLQSGVPS    60
RFSGSGSGTE FTLTISSLQP EDFATYYCFQ YNSYPLGFGG GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 249          moltype = AA  length = 214
FEATURE                 Location/Qualifiers
source                  1..214
                        mol_type = protein
                        organism = synthetic construct
SEQUENCE: 249
DIQMTQSPSS LSASVGDRVT ITCRASQGIR NDLGWYQQKP GKAPKRLIYT ASNLQSGVPS    60
RFSGSGSGTE FTLTISSLQP EDFATYYCLQ YRSHPLTFGG GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 250          moltype = AA  length = 214
FEATURE                 Location/Qualifiers
source                  1..214
                        mol_type = protein
                        organism = synthetic construct
SEQUENCE: 250
DIQMTQSPSS LSASVGDRVT ITCRASQGIR NDLGWYQQKP GKAPKRLIYT ASNLQSGVPS    60
RFSGSGSGTE FTLTISSLQP EDFATYYCLQ YNQVPLTFGG GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 251          moltype = AA  length = 214
```

```
FEATURE                 Location/Qualifiers
source                  1..214
                        mol_type = protein
                        organism = synthetic construct
SEQUENCE: 251
DIQMTQSPSS LSASVGDRVT ITCRASQGIR NDLGWYQQKP GKAPKRLIYT ASNLQSGVPS    60
RFSGSGSGTE FTLTISSLQP EDFATYYCLQ TNIYPLTFGG GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 252          moltype = AA  length = 214
FEATURE                 Location/Qualifiers
source                  1..214
                        mol_type = protein
                        organism = synthetic construct
SEQUENCE: 252
DIQMTQSPSS LSASVGDRVT ITCRASQGIR NDLGWYQQKP GKAPKRLIYT ASNLQSGVPS    60
RFSGSGSGTE FTLTISSLQP EDFATYYCLQ YKQYPLTFGG GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 253          moltype = AA  length = 214
FEATURE                 Location/Qualifiers
source                  1..214
                        mol_type = protein
                        organism = synthetic construct
SEQUENCE: 253
DIQMTQSPSS LSASVGDRVT ITCRASQGIR NDLGWYQQKP GKAPKRLIYT ASNLQSGVPS    60
RFSGSGSGTE FTLTISSLQP EDFATYYCLQ TNIYPLTFGG GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 254          moltype = AA  length = 214
FEATURE                 Location/Qualifiers
source                  1..214
                        mol_type = protein
                        organism = synthetic construct
SEQUENCE: 254
DIQMTQSPSS LSASVGDRVT ITCRASQGIR NDLGWYQQKP GKAPKRLIYT ASNLQSGVPS    60
RFSGSGSGTE FTLTISSLQP EDFATYYCLQ YNSYPLAFGG GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 255          moltype = AA  length = 214
FEATURE                 Location/Qualifiers
source                  1..214
                        mol_type = protein
                        organism = synthetic construct
SEQUENCE: 255
DIQMTQSPSS LSASVGDRVT ITCRASQGIR NDLGWYQQKP GKAPKRLIYT ASNLQSGVPS    60
RFSGSGSGTE FTLTISSLQP EDFATYYCLQ YHSYPLRFGG GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 256          moltype = AA  length = 214
FEATURE                 Location/Qualifiers
source                  1..214
                        mol_type = protein
                        organism = synthetic construct
SEQUENCE: 256
DIQMTQSPSS LSASVGDRVT ITCRASQGIR NDLGWYQQKP GKAPKRLIYT ASNLQSGVPS    60
RFSGSGSGTE FTLTISSLQP EDFATYYCLQ YASYPLKFGG GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 257          moltype = AA  length = 214
FEATURE                 Location/Qualifiers
source                  1..214
                        mol_type = protein
                        organism = synthetic construct
SEQUENCE: 257
DIQMTQSPSS LSASVGDRVT ITCRASQGIR NDLGWYQQKP GKAPKRLIYT ASNLQSGVPS    60
RFSGSGSGTE FTLTISSLQP EDFATYYCLQ YNAYPLIFGG GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 258          moltype = AA  length = 688
FEATURE                 Location/Qualifiers
source                  1..688
```

```
                              mol_type = protein
                              organism = Homo sapiens
SEQUENCE: 258
MWCIVLFSLL AWVYAEPTMY GEILSPNYPQ AYPSEVEKSW DIEVPEGYGI HLYFTHLDIE   60
LSENCAYDSV QIISGDTEEG RLCGQRSSNN PHSPIVEEFQ VPYNKLQVIF KSDFSNEERF  120
TGFAAYYVAT DINECTDFVD VPCSHFCNNF IGGYFCSCPP EYFLHDDMKN CGVNCSGDVF  180
TALIGEIASP NYPKPYPENS RCEYQIRLEK GFQVVVTLRR EDFDVEAADS AGNCLDSLVF  240
VAGDRQFGPY CGHGFPGPLN IETKSNALDI IFQTDLTGQK KGWKLRYHGD PMPCPKEDTP  300
NSVWEPAKAK YVFRDVVQIT CLDGFEVVEG RVGATSFYST CQSNGKWSNS KLKCQPVDCG  360
IPESIENGKV EDPESTLFGS VIRYTCEEPY YYMENGGGGE YHCAGNGSWV NEVLGPELPK  420
CVPVCGVPRE PFEEKQRIIG GSDADIKNFP WQVFFDNPWA GGALINEYWV LTAAHVVEGN  480
REPTMYVGST SVQTSRLAKS KMLTPEHVFI HPGWKLLEVP EGRTNFDNDI ALVRLKDPVK  540
MGPTVSPICL PGTSSDYNLM DGDLGLISGW GRTEKRDRAV RLKAARLPVA PLRKCKEVKV  600
EKPTADAEAY VFTPNMICAG GEKGMDSCKG DSGGAFAVQD PNDKTKFYAA GLVSWGPQCG  660
TYGLYTRVKN YVDWIMKTMQ ENSTPRED                                    688

SEQ ID NO: 259         moltype = AA  length = 15
FEATURE                Location/Qualifiers
source                 1..15
                       mol_type = protein
                       organism = synthetic construct
SEQUENCE: 259
MWCIVLFSLL AWVYA                                                   15

SEQ ID NO: 260         moltype = AA  length = 673
FEATURE                Location/Qualifiers
source                 1..673
                       mol_type = protein
                       organism = Homo sapiens
SEQUENCE: 260
EPTMYGEILS PNYPQAYPSE VEKSWDIEVP EGYGIHLYFT HLDIELSENC AYDSVQIISG   60
DTEEGRLCGQ RSSNNPHSPI VEEFQVPYNK LQVIFKSDFS NEERFTGFAA YYVATDINEC  120
TDFVDVPCSH FCNNFIGGYF CSCPPEYFLH DDMKNCGVNC SGDVFTALIG EIASPNYPKP  180
YPENSRCEYQ IRLEKGFQVV VTLRREDFDV EAADSAGNCL DSLVFVAGDR QFGPYCGHGF  240
PGPLNIETKS NALDIIFQTD LTGQKKGWKL RYHGDPMPCP KEDTPNSVWE PAKAKYVFRD  300
VVQITCLDGF EVVEGRVGAT SFYSTCQSNG KWSNSKLKCQ PVDCGIPESI ENGKVEDPES  360
TLFGSVIRYT CEEPYYYMEN GGGGEYHCAG NGSWVNEVLG PELPKCVPVC GVPREPFEEK  420
QRIIGGSDAD IKNFPWQVFF DNPWAGGALI NEYWVLTAAH VVEGNREPTM YVGSTSVQTS  480
RLAKSKMLTP EHVFIHPGWK LLEVPEGRTN FDNDIALVRL KDPVKMGPTV SPICLPGTSS  540
DYNLMDGDLG LISGWGRTEK RDRAVRLKAA RLPVAPLRKC KEVKVEKPTA DAEAYVFTPN  600
MICAGGEKGM DSCKGDSGGA FAVQDPNDKT KFYAAGLVSW GPQCGTYGLY TRVKNYVDWI  660
MKTMQENSTP RED                                                    673

SEQ ID NO: 261         moltype = AA  length = 327
FEATURE                Location/Qualifiers
source                 1..327
                       mol_type = protein
                       organism = synthetic construct
SEQUENCE: 261
ASTKGPSVFP LAPCSRSTSE STAALGCLVK DYFPEPVTVS WNSGALTSGV HTFPAVLQSS   60
GLYSLSSVVT VPSSSLGTKT YTCNVDHKPS NTKVDKRVES KYGPPCPPCP APEFEGGPSV  120
FLFPPKPKDT LMISRTPEVT CVVVDVSQED PEVQFNWYVD GVEVHNAKTK PREEQFNSTY  180
RVVSVLTVLH QDWLNGKEYK CKVSNKGLPS SIEKTISKAK GQPREPQVYT LPPSQEEMTK  240
NQVSLTCLVK GFYPSDIAVE WESNGQPENN YKTTPPVLDS DGSFFLYSRL TVDKSRWQEG  300
NVFSCSVLHE ALHSHYTQKS LSLSLGK                                     327

SEQ ID NO: 262         moltype = AA  length = 327
FEATURE                Location/Qualifiers
source                 1..327
                       mol_type = protein
                       organism = synthetic construct
SEQUENCE: 262
ASTKGPSVFP LAPCSRSTSE STAALGCLVK DYFPEPVTVS WNSGALTSGV HTFPAVLQSS   60
GLYSLSSVVT VPSSSLGTKT YTCNVDHKPS NTKVDKRVES KYGPPCPPCP APEFEGGPSV  120
FLFPPKPKDT LYITREPEVT CVVVDVSQED PEVQFNWYVD GVEVHNAKTK PREEQFNSTY  180
RVVSVLTVLH QDWLNGKEYK CKVSNKGLPS SIEKTISKAK GQPREPQVYT LPPSQEEMTK  240
NQVSLTCLVK GFYPSDIAVE WESNGQPENN YKTTPPVLDS DGSFFLYSRL TVDKSRWQEG  300
NVFSCSVMHE ALHNHYTQKS LSLSLGK                                     327

SEQ ID NO: 263         moltype = AA  length = 326
FEATURE                Location/Qualifiers
source                 1..326
                       mol_type = protein
                       organism = synthetic construct
SEQUENCE: 263
ASTKGPSVFP LAPCSRSTSE STAALGCLVK DYFPEPVTVS WNSGALTSGV HTFPAVLQSS   60
GLYSLSSVVT VPSSSLGTKT YTCNVDHKPS NTKVDKRVES KYGPPCPPCP APEFEGGPSV  120
FLFPPKPKDT LMISRTPEVT CVVVDVSQED PEVQFNWYVD GVEVHNAKTK PREEQFNSTY  180
RVVSVLTVLH QDWLNGKEYK CKVSNKGLPS SIEKTISKAK GQPREPQVYT LPPSQEEMTK  240
```

```
NQVSLTCLVK GFYPSDIAVE WESNGQPENN YKTTPPVLDS DGSFFLYSRL TVDKSRWQEG    300
NVFSCSVLHE ALHSHYTQKS LSLSLG                                        326

SEQ ID NO: 264          moltype = AA  length = 326
FEATURE                 Location/Qualifiers
source                  1..326
                        mol_type = protein
                        organism = synthetic construct
SEQUENCE: 264
ASTKGPSVFP LAPCSRSTSE STAALGCLVK DYFPEPVTVS WNSGALTSGV HTFPAVLQSS    60
GLYSLSSVVT VPSSSLGTKT YTCNVDHKPS NTKVDKRVES KYGPPCPPCP APEFEGGPSV    120
FLFPPKPKDT LYITREPEVT CVVVDVSQED PEVQFNWYVD GVEVHNAKTK PREEQFNSTY    180
RVVSVLTVLH QDWLNGKEYK CKVSNKGLPS SIEKTISKAK GQPREPQVYT LPPSQEEMTK    240
NQVSLTCLVK GFYPSDIAVE WESNGQPENN YKTTPPVLDS DGSFFLYSRL TVDKSRWQEG    300
NVFSCSVMHE ALHNHYTQKS LSLSLG                                        326

SEQ ID NO: 265          moltype = AA  length = 107
FEATURE                 Location/Qualifiers
source                  1..107
                        mol_type = protein
                        organism = Homo sapiens
SEQUENCE: 265
RTVAAPSVFI FPPSDEQLKS GTASVVCLLN NFYPREAKVQ WKVDNALQSG NSQESVTEQD    60
SKDSTYSLSS TLTLSKADYE KHKVYACEVT HQGLSSPVTK SFNRGEC                 107

SEQ ID NO: 266          moltype = AA  length = 5
FEATURE                 Location/Qualifiers
source                  1..5
                        mol_type = protein
                        organism = synthetic construct
REPEAT                  1..5
                        note = The sequence can be repeated 1 time, 2 times, 3
                         times, 4 times, or 5 times
SEQUENCE: 266
GGGGS                                                               5

SEQ ID NO: 267          moltype = AA  length = 5
FEATURE                 Location/Qualifiers
source                  1..5
                        mol_type = protein
                        organism = synthetic construct
REPEAT                  1..5
                        note = The sequence can be repeated 1 time, 2 times, 3
                         times, 4 times, or 5 times
SEQUENCE: 267
GGGGA                                                               5

SEQ ID NO: 268          moltype = DNA  length = 348
FEATURE                 Location/Qualifiers
source                  1..348
                        mol_type = other DNA
                        organism = synthetic construct
SEQUENCE: 268
caggtgcagc ttgttgaaag tggtgggggt tggttaaac ctggcggttc ccttcgactt     60
agctgcgcgg cgtcagggtt cacattctca gattattaca tgtcttggat tcggcaagtc    120
cctggtaagg gactggagtg ggtaagctac atatctcggt caggaagtac aaagtactat    180
gcagattcag tgaagggcag gtttacgatt agccgagaca acgcaaagaa ctctctttat    240
ctgcagatga attcactgag agcagaagat accgctgtct attattgtgc cagagaccag    300
gaagattacg ctcttgacta ctggggccaa ggtacgctgg ttacggtc                 348

SEQ ID NO: 269          moltype = DNA  length = 327
FEATURE                 Location/Qualifiers
source                  1..327
                        mol_type = other DNA
                        organism = synthetic construct
SEQUENCE: 269
gacattcaga tgacgcaaag cccctctagc ttgtccgcta gtgtgggtga cagggtcacc     60
attacctgcc aggcttcaca agacatcagt aattacctca actggtatca gcagaaacct    120
gggaaggccc ctaagctgtt gatttacgat gctagtaact ggagaccgg ggtacccagc     180
agatttagcg ggagcggaag tggtacggat tttacgtta ccattagcag cttgcagccc     240
gaggacatcg ctacatatta ctgtgaacag tatgaggact accctcttac cttcggcggt    300
ggaacgaaag ttgagattaa gcgaacc                                       327

SEQ ID NO: 270          moltype = DNA  length = 348
FEATURE                 Location/Qualifiers
source                  1..348
                        mol_type = other DNA
                        organism = synthetic construct
SEQUENCE: 270
```

```
caggtgcagc ttgttgaaag tggtgggggt ttggttaaac ctggcggttc ccttcgactt    60
agctgcgcgg cgtcagggtt cacattctca gattattaca tgtcttggat tcggcaagcc   120
cctggtaagg gactggagtg ggtaagctac atatctcggt caggaagtac aaagtactat   180
gcagattcag tgaagggcag gtttacgatt agccgagaca acgcaaagaa ctctctttat   240
ctgcagatga attcactgag agcagaagat accgctgtct attattgtgc cagagacgag   300
accgattacg gctgggacta ctggggccaa ggtacgctgg ttacggtc                348
```

```
SEQ ID NO: 271          moltype = DNA   length = 327
FEATURE                 Location/Qualifiers
source                  1..327
                        mol_type = other DNA
                        organism = synthetic construct
SEQUENCE: 271
gacattcaga tgacgcaaag cccctctagc ttgtccgcta gtgtgggtga cagggtcacc    60
attacctgcc aggcttcaca agacatcagt aattacctca actggtatca gcagaaacct   120
gggaaggccc ctaagctgtt gatttacgat gctagtaact tggagaccgg ggtacccagc   180
agatttagcg ggagcggaag tggtacggat tttacgttta ccattagcag cttgcagccc   240
gaggacatcg ctacatatta ctgtaagcag tatgaggact accctcttac cttcggcggt   300
ggaacgaaag ttgagattaa gcgaacc                                       327
```

```
SEQ ID NO: 272          moltype = DNA   length = 327
FEATURE                 Location/Qualifiers
source                  1..327
                        mol_type = other DNA
                        organism = synthetic construct
SEQUENCE: 272
gacattcaga tgacgcaaag cccctctagc ttgtccgcta gtgtgggtga cagggtcacc    60
attacctgcc aggcttcaca agacatcagt aattacctca actggtatca gcagaaacct   120
gggaaggccc ctaagctgtt gatttacgat gctagtaact tggagaccgg ggtacccagc   180
agatttagcg ggagcggaag tggtacggat tttacgttta ccattagcag cttgcagccc   240
gaggacatcg ctacatatta ctgtaagcag tatgaggact accctcttac cttcggcggt   300
ggaacgaaag ttgagattaa gcgaacc                                       327
```

```
SEQ ID NO: 273          moltype = DNA   length = 327
FEATURE                 Location/Qualifiers
source                  1..327
                        mol_type = other DNA
                        organism = synthetic construct
SEQUENCE: 273
gacattcaga tgacgcaaag cccctctagc ttgtccgcta gtgtgggtga cagggtcacc    60
attacctgcc aggcttcaca agacatcagt aattacctca actggtatca gcagaaacct   120
gggaaggccc ctaagctgtt gatttacgat gctagtaact tggagaccgg ggtacccagc   180
agatttagcg ggagcggaag tggtacggat tttacgttta ccattagcag cttgcagccc   240
gaggacatcg ctacatatta ctgtaagcag tatgaggact accctcttac cttcggcggt   300
ggaacgaaag ttgagattaa gcgaacc                                       327
```

```
SEQ ID NO: 274          moltype = DNA   length = 348
FEATURE                 Location/Qualifiers
source                  1..348
                        mol_type = other DNA
                        organism = synthetic construct
SEQUENCE: 274
caggtgcagc ttgttgaaag tggtgggggt ttggttaaac ctggcggttc ccttcgactt    60
agctgcgcgg cgtcagggtt cacattctca gattattaca tgtcttggat tcggcaagcc   120
cctggtaagg gactggagtg ggtaagctac atatctcggt caggaagtac aaagtactat   180
gcagattcag tgaagggcag gtttacgatt agccgagaca acgcaaagaa ctctctttat   240
ctgcagatga attcactgag agcagaagat accgctgtct attattgtgc cagagacgag   300
agtcagtacg ctcttgacta ctggggccaa ggtacgctgg ttacggtc                348
```

```
SEQ ID NO: 275          moltype = DNA   length = 327
FEATURE                 Location/Qualifiers
source                  1..327
                        mol_type = other DNA
                        organism = synthetic construct
SEQUENCE: 275
gacattcaga tgacgcaaag cccctctagc ttgtccgcta gtgtgggtga cagggtcacc    60
attacctgcc aggcttcaca agacatcagt aattacctca actggtatca gcagaaacct   120
gggaaggccc ctaagctgtt gatttacgat gctagtaact tggagaccgg ggtacccagc   180
agatttagcg ggagcggaag tggtacggat tttacgttta ccattagcag cttgcagccc   240
gaggacatcg ctacatatta ctgtcaccag tatgaggact accctcttac cttcggcggt   300
ggaacgaaag ttgagattaa gcgaacc                                       327
```

```
SEQ ID NO: 276          moltype = DNA   length = 348
FEATURE                 Location/Qualifiers
source                  1..348
                        mol_type = other DNA
                        organism = synthetic construct
SEQUENCE: 276
caggtgcagc ttgttgaaag tggtgggggt ttggttaaac ctggcggttc ccttcgactt    60
```

```
agctgcgcgg cgtcagggtt cacattctca gattattaca tgtcttggat tcggcaagcc   120
cctggtaagg gactgagtg ggtaagctac atatctcggt caggaagtac aaagtactat   180
gcacattcag tgaagggcag gtttacgatt agccgagaca acgcaaagaa ctctctttat   240
ctgcagatga attcactgag agcagaagat accgctgtct attattgtgc cagagacaac   300
accgattacg ctcttgacct gtggggccaa ggtacgctgg ttacggtc                348

SEQ ID NO: 277          moltype = DNA  length = 327
FEATURE                 Location/Qualifiers
source                  1..327
                        mol_type = other DNA
                        organism = synthetic construct
SEQUENCE: 277
gacattcaga tgacgcaaag cccctctagc ttgtccgcta gtgtgggtga cagggtcacc    60
attacctgcc aggcttcaca agacatcagt aattacctca actggtatca gcagaaacct   120
gggaaggccc ctaagctgtt gatttacgat gctagtaact ggagaccgg ggtacccagc   180
agatttagcg ggagcggaag tggtacggat tttacgttta ccattagcag cttgcagccc   240
gaggacatcg ctacatatta ctgtcaccag tatgaggact accctcttac cttcggcggt   300
ggaacgaaag ttgagattaa gcgaacc                                       327

SEQ ID NO: 278          moltype = DNA  length = 348
FEATURE                 Location/Qualifiers
source                  1..348
                        mol_type = other DNA
                        organism = synthetic construct
SEQUENCE: 278
caggtgcagc ttgttgaaag tggtgggggt tggttaaac ctggcggttc ccttcgactt     60
agctgcgcgg cgtcagggtt cacattctca gattattaca tgtcttggat tcggcaagcc   120
cctggtaagg gactgagtg ggtaagctac atatctcggt caggaagtac aaagtactat   180
gcacattcag tgaagggcag gtttacgatt agccgagaca acgcaaagaa ctctctttat   240
ctgcagatga attcactgag agcagaagat accgctgtct attattgtgc cagagacgag   300
accgattacg cttacgacga atggggccaa ggtacgctgg ttacggtc                348

SEQ ID NO: 279          moltype = DNA  length = 327
FEATURE                 Location/Qualifiers
source                  1..327
                        mol_type = other DNA
                        organism = synthetic construct
SEQUENCE: 279
gacattcaga tgacgcaaag cccctctagc ttgtccgcta gtgtgggtga cagggtcacc    60
attacctgcc aggcttcaca agacatcagt aattacctca actggtatca gcagaaacct   120
gggaaggccc ctaagctgtt gatttacgat gctagtaact ggagaccgg ggtacccagc   180
agatttagcg ggagcggaag tggtacggat tttacgttta ccattagcag cttgcagccc   240
gaggacatcg ctacatatta ctgtcaccag tatgaggact accctcttac cttcggcggt   300
ggaacgaaag ttgagattaa gcgaacc                                       327

SEQ ID NO: 280          moltype = DNA  length = 348
FEATURE                 Location/Qualifiers
source                  1..348
                        mol_type = other DNA
                        organism = synthetic construct
SEQUENCE: 280
caggtgcagc ttgttgaaag tggtgggggt tggttaaac ctggcggttc ccttcgactt     60
agctgcgcgg cgtcagggtt cacattctca gattattaca tgtcttggat tcggcaagcc   120
cctggtaagg gactggagtg ggtaagctac atatctcggt caggaagtac aaagtactat   180
gcagattcag tgaagggcag gtttacgatt agccgagaca acgcaaagaa ctctctttat   240
ctgcagatga attcactgag agcagaagat accgctgtct attattgtgc cagagacgag   300
accgattacg cttacgacaa ctggggccaa ggtacgctgg ttacggtc                348

SEQ ID NO: 281          moltype = DNA  length = 327
FEATURE                 Location/Qualifiers
source                  1..327
                        mol_type = other DNA
                        organism = synthetic construct
SEQUENCE: 281
gacattcaga tgacgcaaag cccctctagc ttgtccgcta gtgtgggtga cagggtcacc    60
attacctgcc aggcttcaca agacatcagt aattacctca actggtatca gcagaaacct   120
gggaaggccc ctaagctgtt gatttacgat gctagtaact ggagaccgg ggtacccagc   180
agatttagcg ggagcggaag tggtacggat tttacgttta ccattagcag cttgcagccc   240
gaggacatcg ctacatatta ctgtcagcag tatgaggact accctcttgt gttcggcggt   300
ggaacgaaag ttgagattaa gcgaacc                                       327

SEQ ID NO: 282          moltype = DNA  length = 348
FEATURE                 Location/Qualifiers
source                  1..348
                        mol_type = other DNA
                        organism = synthetic construct
SEQUENCE: 282
caggtgcagc ttgttgaaag tggtgggggt tggttaaac ctggcggttc ccttcgactt     60
agctgcgcgg cgtcagggtt cacattctca gattattaca tgtcttggat tcggcaagcc   120
```

```
cctggtaagg gactggagtg ggtaagctac atatctcggt caggaagtac aaagtactat    180
gcagattcag tgaagggcag gtttacgatt agccgagaca acgcaaagaa ctctctttat    240
ctgcagatga attcactgag agcagaagat accgctgtct attattgtgc cagagacgag    300
agtgattacg cttacgacta ctggggccaa ggtacgctgg ttacggtc                 348

SEQ ID NO: 283           moltype = DNA   length = 327
FEATURE                  Location/Qualifiers
source                   1..327
                         mol_type = other DNA
                         organism = synthetic construct
SEQUENCE: 283
gacattcaga tgacgcaaag ccctctagc ttgtccgcta gtgtgggtga cagggtcacc     60
attacctgcc aggcttcaca agacatcagt aattacctca actggtatca gcagaaacct    120
gggaaggccc ctaagctgtt gatttacgat gctagtaact tggagaccgg ggtacccagc    180
agatttagcg ggagcggaag tggtacggat tttacgttta ccattagcag cttgcagccc    240
gaggacatcg ctacatatta ctgtcagcag cacgaggact accctcttac cttcggcggt    300
ggaacgaaag ttgagattaa gcgaacc                                        327

SEQ ID NO: 284           moltype = DNA   length = 348
FEATURE                  Location/Qualifiers
source                   1..348
                         mol_type = other DNA
                         organism = synthetic construct
SEQUENCE: 284
caggtgcagc ttgttgaaag tggtgggggt ttggttaaac ctggcggttc ccttcgactt     60
agctgcgcgg cgtcagggtt cacattctca gattattaca tgtcttggat tcggcaagcc    120
cctggtaagg gactggagtg ggtaagctac atatctcggt caggaagtac aaagtactat    180
gcagattcag tgaagggcag gtttacgatt agccgagaca acgcaaagaa ctctctttat    240
ctgcagatga attcactgag agcagaagat accgctgtct attattgtgc cagagacgag    300
aattacgctc ttgactggtg gggccaaggt acgctggtta cggtctcg                 348

SEQ ID NO: 285           moltype = DNA   length = 327
FEATURE                  Location/Qualifiers
source                   1..327
                         mol_type = other DNA
                         organism = synthetic construct
SEQUENCE: 285
gacattcaga tgacgcaaag ccctctagc ttgtccgcta gtgtgggtga cagggtcacc     60
attacctgcc aggcttcaca agacatcagt aattacctca actggtatca gcagaaacct    120
gggaaggccc ctaagctgtt gatttacgat gctagtaact tggagaccgg ggtacccagc    180
agatttagcg ggagcggaag tggtacggat tttacgttta ccattagcag cttgcagccc    240
gaggacatcg ctacatatta ctgtcagcac tatgaggact accctcttac cttcggcggt    300
ggaacgaaag ttgagattaa gcgaacc                                        327

SEQ ID NO: 286           moltype = DNA   length = 348
FEATURE                  Location/Qualifiers
source                   1..348
                         mol_type = other DNA
                         organism = synthetic construct
SEQUENCE: 286
caggtgcagc ttgttgaaag tggtgggggt ttggttaaac ctggcggttc ccttcgactt     60
agctgcgcgg cgtcagggtt cacattctca gattattaca tgtcttggat tcggcaagcc    120
cctggtaagg gactggagtg ggtaagctac atatctcggt caggaagtac aaagtactat    180
gcagattcag tgaagggcag gtttacgatt agccgagaca acgcaaagaa ctctctttat    240
ctgcagatga attcactgag agcagaagat accgctgtct attattgtgc cagagacgag    300
agtgattacg ctcttgactt ctggggccaa ggtacgctgg ttacggtc                 348

SEQ ID NO: 287           moltype = DNA   length = 327
FEATURE                  Location/Qualifiers
source                   1..327
                         mol_type = other DNA
                         organism = synthetic construct
SEQUENCE: 287
gacattcaga tgacgcaaag ccctctagc ttgtccgcta gtgtgggtga cagggtcacc     60
attacctgcc aggcttcaca agacatcagt aattacctca actggtatca gcagaaacct    120
gggaaggccc ctaagctgtt gatttacgat gctagtaact tggagaccgg ggtacccagc    180
agatttagcg ggagcggaag tggtacggat tttacgttta ccattagcag cttgcagccc    240
gaggacatcg ctacatatta ctgtcagcag tatgaggacc tcatcccac cttcggcggt     300
ggaacgaaag ttgagattaa gcgaacc                                        327

SEQ ID NO: 288           moltype = DNA   length = 357
FEATURE                  Location/Qualifiers
source                   1..357
                         mol_type = other DNA
                         organism = synthetic construct
SEQUENCE: 288
caagttcaac tggttcaaag cggggccgag gtaaagaagc caggcgcttc tgtgaaagtc     60
agttgcaagg tgagtgggga tacattgacc gagctgagta tgcactgggt ccggcaagct    120
cctggcaagg gtttggaatg gatgggtact tttgacccgc aggagggaga gaccatctac    180
```

```
gcgcaaaaat tccaaggtag ggtgaccatg acggaggata ccagcacgga tactgcttac    240
atggagctca gctccctcag aagtgaagat actgccgtct actactgtgt gaccgagggt    300
ttggccgggg tgccgtttga tctgtggggg caggggacgc tggtaacggt ctcgagt       357

SEQ ID NO: 289           moltype = DNA   length = 327
FEATURE                  Location/Qualifiers
source                   1..327
                         mol_type = other DNA
                         organism = synthetic construct
SEQUENCE: 289
gacatacaaa tgactcaatc accctctaca ctttccgcct ctgtcggcga cagggtaacg    60
ataacttgcc gggcaagtca atcaatcagc tcctggcttg cttggtatca acaaaaacca   120
ggcaaggcac ctaagctcct catttacaag gcgtcatcac ttgaatcagg ggtgccttca   180
cgattcagtg gatcaggatc tggtactgaa ttcactctga ccatttcaag tcttcagcct   240
gatgactttg cgacctatta ttgccagagc tacaatagct acgtgtggac gttcgggcag   300
ggtactaaag tcgagattaa acgaacc                                       327

SEQ ID NO: 290           moltype = DNA   length = 357
FEATURE                  Location/Qualifiers
source                   1..357
                         mol_type = other DNA
                         organism = synthetic construct
SEQUENCE: 290
caagttcaac tggttcaaag cggggccgag gtaaagaagc caggcgcttc tgtgaaagtc    60
agttgcaagg tgagtgggga tacattgacc gagctgagta tgcactgggt ccggcaagct   120
cctggcaagg gtttggaatg gatgggtact tttgacccgg aggagggaga gaccatctac   180
gcgcaaaaat tccaaggtag ggtgaccatg acggaggata ccagcacgga tactgcttac   240
atggagctca gctccctcag aagtgaagat actgccgtct actactgtgt gaccgagggt   300
ttgggcgggc gcccgtttga tcactggggg caggggacgc tggtaacggt ctcgagt      357

SEQ ID NO: 291           moltype = DNA   length = 327
FEATURE                  Location/Qualifiers
source                   1..327
                         mol_type = other DNA
                         organism = synthetic construct
SEQUENCE: 291
gacatacaaa tgactcaatc accctctaca ctttccgcct ctgtcggcga cagggtaacg    60
ataacttgcc gggcaagtca atcaatcagc tcctggcttg cttggtatca acaaaaacca   120
ggcaaggcac ctaagctcct catttacaag gcgtcatcac ttgaatcagg ggtgccttca   180
cgattcagtg gatcaggatc tggtactgaa ttcactctga ccatttcaag tcttcagcct   240
gatgactttg cgacctatta ttgccagcag gtgaatagct acgactggac gttcgggcag   300
ggtactaaag tcgagattaa acgaacc                                       327

SEQ ID NO: 292           moltype = DNA   length = 357
FEATURE                  Location/Qualifiers
source                   1..357
                         mol_type = other DNA
                         organism = synthetic construct
SEQUENCE: 292
caagttcaac tggttcaaag cggggccgag gtaaagaagc caggcgcttc tgtgaaagtc    60
agttgcaagg tgagtgggga tacattgacc gagctgagta tgcactgggt ccggcaagct   120
cctggcaagg gtttggaatg gatgggtact tttgacccgg aggagggaga gaccatctac   180
gcgcaaaaat tccaaggtag ggtgaccatg acggaggata ccagcacgga tactgcttac   240
atggagctca gctccctcag aagtgaagat actgccgtct actactgtgt gaccgagggt   300
ttggccgggt cccgtttga tatctggggg caggggacgc tggtaacggt ctcgagt       357

SEQ ID NO: 293           moltype = DNA   length = 327
FEATURE                  Location/Qualifiers
source                   1..327
                         mol_type = other DNA
                         organism = synthetic construct
SEQUENCE: 293
gacatacaaa tgactcaatc accctctaca ctttccgcct ctgtcggcga cagggtaacg    60
ataacttgcc gggcaagtca atcaatcagc tcctggcttg cttggtatca acaaaaacca   120
ggcaaggcac ctaagctcct catttacaag gcgtcatcac ttgaatcagg ggtgccttca   180
cgattcagtg gatcaggatc tggtactgaa ttcactctga ccatttcaag tcttcagcct   240
gatgactttg cgacctatta ttgccagcag gtgaatagct acgactggac gttcgggcag   300
ggtactaaag tcgagattaa acgaacc                                       327

SEQ ID NO: 294           moltype = DNA   length = 357
FEATURE                  Location/Qualifiers
source                   1..357
                         mol_type = other DNA
                         organism = synthetic construct
SEQUENCE: 294
caagttcaac tggttcaaag cggggccgag gtaaagaagc caggcgcttc tgtgaaagtc    60
agttgcaagg tgagtgggga tacattgacc gagctgagta tgcactgggt ccggcaagct   120
cctggcaagg gtttggaatg gatgggtact tttgacccgg aggagggaga gaccatctac   180
gcgcaaaaat tccaaggtag ggtgaccatg acggaggata ccagcacgga tactgcttac   240
```

```
atggagctca gctccctcag aagtgaagat actgccgtct actactgtgt gaccgagggt    300
ttggcctggc gcccgaccga ttcatggggg caggggacgc tggtaacggt ctcgagt       357
```

| SEQ ID NO: 295 | moltype = DNA   length = 327 |
|---|---|
| FEATURE | Location/Qualifiers |
| source | 1..327 |
| | mol_type = other DNA |
| | organism = synthetic construct |

SEQUENCE: 295
```
gacatacaaa tgactcaatc accctctaca ctttccgcct ctgtcggcga cagggtaacg    60
ataacttgcc gggcaagtca atcaatcagc tcctggcttg cttggtatca acaaaaacca   120
ggcaaggcac ctaagctcct catttacaag gcgtcatcac ttgaatcagg ggtgccttca   180
cgattcagcg gatcaggatc tggtactgaa ttcactctga ccatttcaag tcttcagcct   240
gatgactttg cgacctatta ttgccagcag tacagcagct acgcctggac gttcgggcag   300
ggtactaaag tcgagattaa acgaacc                                      327
```

| SEQ ID NO: 296 | moltype = DNA   length = 357 |
|---|---|
| FEATURE | Location/Qualifiers |
| source | 1..357 |
| | mol_type = other DNA |
| | organism = synthetic construct |

SEQUENCE: 296
```
caagttcaac tggttcaaag cggggccgag gtaaagaagt caggcgcttc tgtgaaagtc    60
agttgcaagg tgagtgggga tacattgacc gagctgagta tgcactgggt ccggcaagct   120
cctggcaagg gtttggaatg gatgggtact tttgacccgg aggagggaga gaccatctac   180
gcgcaaaaat tccaaggtag ggtgaccatg acggaggata ccagcacgga tactgcttac   240
atggagctca gctccctcag aagtgaagat actgccgtct actactgtgt gaccaagggt   300
ttggccgggc tgccgtacta ctcatggggg caggggacgc tggtaacggt ctcgagt      357
```

| SEQ ID NO: 297 | moltype = DNA   length = 327 |
|---|---|
| FEATURE | Location/Qualifiers |
| source | 1..327 |
| | mol_type = other DNA |
| | organism = synthetic construct |

SEQUENCE: 297
```
gacatacaaa tgactcaatc accctctaca ctttccgcct ctgtcggcga cagggtaacg    60
ataacttgcc gggcaagtca atcaatcagc tcctggcttg cttggtatca acaaaaacca   120
ggcaaggcac ctaagctcct catttacaag gcgtcatcac ttgaatcagg ggtgccttca   180
cgattcagcg gatcaggatc tggtactgaa ttcactctga ccatttcaag tcttcagcct   240
gatgactttg cgacctatta ttgccagcag gcccgcagct actcatggac gttcgggcag   300
ggtactaaag tcgagattaa acgaacc                                      327
```

| SEQ ID NO: 298 | moltype = DNA   length = 357 |
|---|---|
| FEATURE | Location/Qualifiers |
| source | 1..357 |
| | mol_type = other DNA |
| | organism = synthetic construct |

SEQUENCE: 298
```
caagttcaac tggttcaaag cggggccgag gtaaagaagc caggcgcttc tgtgaaagtc    60
agttgcaagg tgagtgggga tacattgacc gagctgagta tgcactgggt ccggcaagct   120
cctggcaagg gtttggaatg gatgggtact tttgacccgg aggagggaga gaccatctac   180
gcgcaaaaat tccaaggtag ggtgaccatg acggaggata ccagcacgga tactgcttac   240
atggagctca gctccctcag aagtgaagat actgccgtct actactgtgt gaccgagggt   300
ttggccgggg tgccgtttga tctgtggggg caggggacgc tggtaacggt ctcgagt      357
```

| SEQ ID NO: 299 | moltype = DNA   length = 327 |
|---|---|
| FEATURE | Location/Qualifiers |
| source | 1..327 |
| | mol_type = other DNA |
| | organism = synthetic construct |

SEQUENCE: 299
```
gacatacaaa tgactcaatc accctctaca ctttccgcct ctgtcggcga cagggtaacg    60
ataacttgcc gggcaagtca atcaatcagc tcctggcttg cttggtatca acaaaaacca   120
ggcaaggcac ctaagctcct catttacaag gcgtcatcac ttgaatcagg ggtgccttca   180
cgattcagcg gatcaggatc tggtactgaa ttcactctga ccatttcaag tcttcagcct   240
gatgactttg cgacctatta ttgccagcag cacaatagct accgctggac gttcgggcag   300
ggtactaaag tcgagattaa acgaacc                                      327
```

| SEQ ID NO: 300 | moltype = DNA   length = 357 |
|---|---|
| FEATURE | Location/Qualifiers |
| source | 1..357 |
| | mol_type = other DNA |
| | organism = synthetic construct |

SEQUENCE: 300
```
caagttcaac tggttcaaag cggggccgag gtaaagaagc caggcgcttc tgtgaaagtc    60
agttgcaagg tgagtgggga tacattgacc gagctgagta tgcactgggt ccggcaagct   120
cctggcaagg gtttggaatg gatgggtact tttgacccgg aggagggaga gaccatctac   180
gcgcaaaaat tccaaggtag ggtgaccatg acggaggata ccagcacgga tactgcttac   240
atggagctca gctccctcag aagtgaagat actgccgtct actactgtgt gaccgagggt   300
```

```
gaggccgggc gcccgtttga tgcctggggg caggggacgc tggtaacggt ctcgagt      357

SEQ ID NO: 301           moltype = DNA  length = 327
FEATURE                  Location/Qualifiers
source                   1..327
                         mol_type = other DNA
                         organism = synthetic construct
SEQUENCE: 301
gacatacaaa tgactcaatc accctctaca ctttccgcct ctgtcggcga cagggtaacg   60
ataacttgcc gggcaagtca atcaatcagc tcctggcttg cttggtatca acaaaaacca  120
ggcaaggcac ctaagctcct catttacaag gcgtcatcac ttgaatcagg ggtgccttca  180
cgattcagcg gatcaggatc tggtactgaa ttcactctga ccatttcaag tcttcagcct  240
gatgactttg cgacctatta ttgcgtgcag taccccagct actcatggac gttcgggcag  300
ggtactaaag tcgagattaa acgaacc                                      327

SEQ ID NO: 302           moltype = DNA  length = 357
FEATURE                  Location/Qualifiers
source                   1..357
                         mol_type = other DNA
                         organism = synthetic construct
SEQUENCE: 302
caagttcaac tggttcaaag cggggccgag gtaaagaagc caggcgcttc tgtgaaagtc   60
agttgcaagg tgagtgggga tacattgacc gagctgagta tgcactgggt ccggcaagct  120
cctggcaagg gtttggaatg gatgggtact tttgacccgg aggagggaga gaccatctac  180
gcgcaaaaat tccaaggtag ggtgaccatg acggaggata ccagcacgga tactgcttac  240
atggagctca gctccctcag aagtgaagat actgccgtct actactgtgt gaccgagggt  300
ttggccgggc gcccgtacga tgtgtggggg caggggacgc tggtaacggt ctcgagt     357

SEQ ID NO: 303           moltype = DNA  length = 327
FEATURE                  Location/Qualifiers
source                   1..327
                         mol_type = other DNA
                         organism = synthetic construct
SEQUENCE: 303
gacatacaaa tgactcaatc accctctaca ctttccgcct ctgtcggcga cagggtaacg   60
ataacttgcc gggcaagtca atcaatcagc tcctggcttg cttggtatca acaaaaacca  120
ggcaaggcac ctaagctcct catttacaag gcgtcatcac ttgaatcagg ggtgccttca  180
cgattcagcg gatcaggatc tggtactgaa ttcactctga ccatttcaag tcttcagcct  240
gatgactttg cgacctatta ttgccagcag tacaatagct acaagctgac gttcgggcag  300
ggtactaaag tcgagattaa acgaacc                                      327

SEQ ID NO: 304           moltype = DNA  length = 357
FEATURE                  Location/Qualifiers
source                   1..357
                         mol_type = other DNA
                         organism = synthetic construct
SEQUENCE: 304
caagttcaac tggttcaaag cggggccgag gtaaagaagc caggcgcttc tgtgaaagtc   60
agttgcaagg tgagtgggga tacattgacc gagctgagta tgcactgggt ccggcaagct  120
cctggcaagg gtttggaatg gatgggtact tttgacccgg aggagggaga gaccatctac  180
gcgcaaaaat tccaaggtag ggtgaccatg acggaggata ccagcacgga tactgcttac  240
atggagctca gctacctcag aagtgaagat actgccgtct actactgtgt gaccgagggt  300
ttggccggga tccgtttga ttcatggggg caggggacgc tggtaacggt ctcgagt      357

SEQ ID NO: 305           moltype = DNA  length = 327
FEATURE                  Location/Qualifiers
source                   1..327
                         mol_type = other DNA
                         organism = synthetic construct
SEQUENCE: 305
gacatacaaa tgactcaatc accctctaca ctttccgcct ctgtcggcga cagggtaacg   60
ataacttgcc gggcaagtca atcaatcagc tcctggcttg cttggtatca acaaaaacca  120
ggcaaggcac ctaagctcct catttacaag gcgtcatcac ttgaatcagg ggtgccttca  180
cgattcagcg gatcaggatc tggtactgaa ttcactctga ccatttcaag tcttcagcct  240
gatgactttg cgacctatta ttgccagcag tacaatagcc cctcatggct gttcgggcag  300
ggtactaaag tcgagattaa acgaacc                                      327

SEQ ID NO: 306           moltype = DNA  length = 357
FEATURE                  Location/Qualifiers
source                   1..357
                         mol_type = other DNA
                         organism = synthetic construct
SEQUENCE: 306
caagttcaac tggttcaaag cggggccgag gtaaagaagc caggcgcttc tgtgaaagtc   60
agttgcaagg tgagtgggga tacattgacc gagctgagta tgcactgggt ccggcaagct  120
cctggcaagg gtttggaatg gatgggtact tttgacccgg aggagggaga gaccatctac  180
gcgcaaaaat tccaaggtag ggtgaccatg acggaggata ccagcacgga tactgcttac  240
atggagctca gctacctcag aagtgaagat actgccgtct actactgtgt gaccgagggt  300
ttggccggga tccgtttga ttcatggggg caggggacgc tggtaacggt ctcgagt      357
```

```
SEQ ID NO: 307         moltype = DNA  length = 327
FEATURE                Location/Qualifiers
source                 1..327
                       mol_type = other DNA
                       organism = synthetic construct
SEQUENCE: 307
gacatacaaa tgactcaatc accctctaca ctttccgcct ctgtcggcga cagggtaacg    60
ataacttgcc gggcaagtca atcaatcagc tcctggcttg cttggtatca acaaaaacca   120
ggcaaggcac ctaagctcct catttacaag gcgtcatcac ttgaatcagg ggtgccttca   180
cgattcagcg gatcaggatc tggtactgaa ttcactctga ccatttcaag tcttcagcct   240
gatgactttg cgacctatta ttgccagcag gtgaatagcc tgtcatggac gttcgggcag   300
ggtactaaag tcgagattaa acgaacc                                        327

SEQ ID NO: 308         moltype = DNA  length = 369
FEATURE                Location/Qualifiers
source                 1..369
                       mol_type = other DNA
                       organism = synthetic construct
SEQUENCE: 308
gaagtccagc ttgttgagtc tggcggaggg gtggttaggc caggaggttc ccttaggctt    60
tcctgtgcgg catcaggatt taccttcgat gactacggaa tgtcatgggt acgacaagct   120
cccggcaaag gcctcgaatg ggtttctggc atcaactggg agggcggttc cactggctac   180
gcggactcag ttaagggtag gttcaccata agcaggaca atgcgaagaa ctcactgtat    240
ctccaaatga acagtctccg cgccgaggat acagcccttt actattgtgc acgagatgag   300
caattggggg ggactactta ttattactat tacatgacg tgtggggtaa aggaacgacc    360
gtcacagtc                                                            369

SEQ ID NO: 309         moltype = DNA  length = 327
FEATURE                Location/Qualifiers
source                 1..327
                       mol_type = other DNA
                       organism = synthetic construct
SEQUENCE: 309
gacatacaga tgactcagtc cccaagtagt ctgagcgcct ctgtcggcga ccgcgttacc    60
attacttgcc gggcgagtca agggatacgc aacgatttgg gttggtatca gcaaaagccc   120
ggaaaggccc caaagcggct gatatacacc gcctcaaacc tccagtctgg agttccatca   180
aggtttagtg gatctggatc tggcactgag tttactctca ctataagctc ccttcagcct   240
gaagacttcg caacttatta ttgcttccag tataatagtt atcctctcgg ctttggcggt   300
ggcaccaaag tggagattaa gcgaacc                                        327

SEQ ID NO: 310         moltype = DNA  length = 369
FEATURE                Location/Qualifiers
source                 1..369
                       mol_type = other DNA
                       organism = synthetic construct
SEQUENCE: 310
gaagtccagc ttgttgagtc tggcggaggg gtggttaggc caggaggttc ccttaggctt    60
tcctgtgcgg catcaggatt taccttcgat gactacggaa tgtcatgggt acgacaagct   120
cccggcaaag gcctcgaatg ggtttctggc atcaactggg agggcggttc cactggctac   180
gcggactcag ttaagggtag gttcaccata agcaggaca atgcgaagaa ctcactgtat    240
ctccaaatga acagtctccg cgccgaggat acagcccttt actattgtgc acgagatgag   300
caattggggg ggaagtatta ctattactat tacatggacg tgtggggtaa aggaacgacc   360
gtcacagtc                                                            369

SEQ ID NO: 311         moltype = DNA  length = 330
FEATURE                Location/Qualifiers
source                 1..330
                       mol_type = other DNA
                       organism = synthetic construct
SEQUENCE: 311
gacatacaga tgactcagtc cccaagtagt ctgagcgcct ctgtcggcga ccgcgttacc    60
attacttgcc gggcgagtca agggatacgc aacgatttgg gttggtatca gcaaaagccc   120
ggaaaggccc caaagcggct gatatacacc gcctcaaacc tccagtctgg agttccatca   180
aggtttagtg gatctggatc tggcactgag tttactctca ctataagctc ccttcagcct   240
gaagacttcg caacttatta ttgcttgcag taccgcagtc actatcctct cacttttggc   300
ggtggcacca aagtggagat taagcgaacc                                     330

SEQ ID NO: 312         moltype = DNA  length = 369
FEATURE                Location/Qualifiers
source                 1..369
                       mol_type = other DNA
                       organism = synthetic construct
SEQUENCE: 312
gaagtccagc ttgttgagtc tggcggaggg gtggttaggc caggaggttc ccttaggctt    60
tcctgtgcgg catcaggatt taccttcgat gactacggaa tgtcatgggt acgacaagct   120
cccggcaaag gcctcgaatg ggtttctggc atcaactggg agggcggttc cactggctac   180
gcggactcag ttaagggtag gttcaccata agcaggaca atgcgaagaa ctcactgtat    240
ctccaaatga acagtctccg cgccgaggat acagcccttt actattgtgc acgagatgag   300
```

```
caattggggg ggcagactta ttattactat tacatggacg tgtggggtaa aggaacgacc    360
gtcacagtc                                                            369

SEQ ID NO: 313          moltype = DNA  length = 327
FEATURE                 Location/Qualifiers
source                  1..327
                        mol_type = other DNA
                        organism = synthetic construct
SEQUENCE: 313
gacatacaga tgactcagtc cccaagtagt ctgagcgcct ctgtcggcga ccgcgttacc    60
attacttgcc gggcgagtca agggatacgc aacgatttgg gttggtatca gcaaaagccc   120
ggaaaggccc caaagcggct gatatacacc gcctcaaacc tccagtctgg agttccatca   180
aggtttagtg gatctggatc tggcactgag tttactctca ctataagctc ccttcagcct   240
gaagacttcg caacttatta ttgcttgcag tataatcagg tgcctctcac ttttggcggt   300
ggcaccaaag tggagattaa gcgaacc                                       327

SEQ ID NO: 314          moltype = DNA  length = 369
FEATURE                 Location/Qualifiers
source                  1..369
                        mol_type = other DNA
                        organism = synthetic construct
SEQUENCE: 314
gaagtccagc ttgttgagtc tggcggaggg gtggttaggc caggaggttc ccttaggctt    60
tcctgtgcgg catcaggatt taccttcgat gactacggaa tgtcatgggt acgacaagct   120
cccggcaaag gcctcgaatg ggtttctggc atcaactggg agggcggttc cactggctac   180
gcggactcag ttaagggtag gttcaccata agcagggaca acgaagaa ctcactgtat     240
ctccaaatga acagtctccg cgccgaggat acagcccttt actattgtgc acgagatgag   300
caattggggg ggaccaccta ttattactat tacatggacg tgtggggtaa aggaacgacc   360
gtcacagtc                                                            369

SEQ ID NO: 315          moltype = DNA  length = 327
FEATURE                 Location/Qualifiers
source                  1..327
                        mol_type = other DNA
                        organism = synthetic construct
SEQUENCE: 315
gacatacaga tgactcagtc cccaagtagt ctgagcgcct ctgtcggcga ccgcgttacc    60
attacttgcc gggcgagtca agggatacgc aacgatttgg gttggtatca gcaaaagccc   120
ggaaaggccc caaagcggct gatatacacc gcctcaaacc tccagtctgg agttccatca   180
aggtttagtg gatctggatc tggcactgag tttactctca ctataagctc ccttcagcct   240
gaagacttcg caacttatta ttgcttgcag accaatatct atcctctcac ttttggcggt   300
ggcaccaaag tggagattaa gcgaacc                                       327

SEQ ID NO: 316          moltype = DNA  length = 369
FEATURE                 Location/Qualifiers
source                  1..369
                        mol_type = other DNA
                        organism = synthetic construct
SEQUENCE: 316
gaagtccagc ttgttgagtc tggcggaggg gtggttaggc caggaggttc ccttaggctt    60
tcctgtgcgg catcaggatt taccttcgat gactacggaa tgtcatgggt acgacaagct   120
cccggcaaag gcctcgaatg ggtttctggc atcaactggg agggcggttc cactggctac   180
gcggactcag ttaagggtag gttcaccata agcagggaca atgcgaagaa ctcactgtat   240
ctccaaatga acagtctccg cgccgaggat acagcccttt actattgtgc acgagatgag   300
caattggggg ggatcaagta ttattactat tacatggacg tgtggggtaa aggaacgacc   360
gtcacagtc                                                            369

SEQ ID NO: 317          moltype = DNA  length = 327
FEATURE                 Location/Qualifiers
source                  1..327
                        mol_type = other DNA
                        organism = synthetic construct
SEQUENCE: 317
gacatacaga tgactcagtc cccaagtagt ctgagcgcct ctgtcggcga ccgcgttacc    60
attacttgcc gggcgagtca agggatacgc aacgatttgg gttggtatca gcaaaagccc   120
ggaaaggccc caaagcggct gatatacacc gcctcaaacc tccagtctgg agttccatca   180
aggtttagtg gatctggatc tggcactgag tttactctca ctataagctc ccttcagcct   240
gaagacttcg caacttatta ttgcttgcag tataagcagt atcctctcac ttttggcggt   300
ggcaccaaag tggagattaa gcgaacc                                       327

SEQ ID NO: 318          moltype = DNA  length = 369
FEATURE                 Location/Qualifiers
source                  1..369
                        mol_type = other DNA
                        organism = synthetic construct
SEQUENCE: 318
gaagtccagc ttgttgagtc tggcggaggg gtggttaggc caggaggttc ccttaggctt    60
tcctgtgcgg catcaggatt tactttcgat gactacggaa tgtcatgggt acgacaagct   120
cccggcaaag gccttgaatg ggtttctggc atcaactggg agggcggttc cactggctac   180
```

```
gcggactcag ttaagggtag gttcagcata agcagggaca atgcgaagaa ctcactgtat    240
ctccaaatga acagtctccg cgccgaggat acagcccttt actattgtgc acgagatgag    300
caattggggg ggctgaagta ttattactat tacatggacg tgtggggtaa aggaacgacc    360
gtcacagtc                                                            369

SEQ ID NO: 319          moltype = DNA   length = 327
FEATURE                 Location/Qualifiers
source                  1..327
                        mol_type = other DNA
                        organism = synthetic construct
SEQUENCE: 319
gacatacaga tgactcagtc cccaagtagt ctgagcgcct ctgtcggcga ccgcgttacc    60
attacttgcc gggcgagtca aggatacgc aacgatttgg gttggtatca gcaaaagccc    120
ggaaaggccc caaagcggct gatatacacc gcctcaaacc tccagtctgg agttccatca    180
aggtttagtg gatctggatc tggcactgag tttactctca ctataagctc ccttcagcct    240
gaagacttcg caacttatta ttgcttgcag accaatatct atcctctcac ttttggcggt    300
ggcaccaaag tggagattaa gcgaacc                                         327

SEQ ID NO: 320          moltype = DNA   length = 369
FEATURE                 Location/Qualifiers
source                  1..369
                        mol_type = other DNA
                        organism = synthetic construct
SEQUENCE: 320
gaagtccagc ttgttgagtc tggcggaggg gtggttaggc caggaggttc ccttaggctt    60
tcctgtgcgg catcaggatt taccttcgat gactacggaa tgtcatgggt acgacaagct    120
cccggcaaag gcctcgaatg ggtttctggc atcaactggg agggcggttc cactggctac    180
gcggactcag ttaagggtag gttcaccata agcagggaca atgcgaagaa ctcactgtat    240
ctccaaatga acagtctccg cgccgaggat acagcccttt actattgtgc acgagatgag    300
caattggggg ggaaggtgta ttattactat tacatggacg tgtggggtaa aggaacgacc    360
gtcacagtc                                                            369

SEQ ID NO: 321          moltype = DNA   length = 327
FEATURE                 Location/Qualifiers
source                  1..327
                        mol_type = other DNA
                        organism = synthetic construct
SEQUENCE: 321
gacatacaga tgactcagtc cccaagtagt ctgagcgcct ctgtcggcga ccgcgttacc    60
attacttgcc gggcgagtca aggatacgc aacgatttgg gttggtatca gcaaaagccc    120
ggaaaggccc caaagcggct gatatacacc gcctcaaacc tccagtctgg agttccatca    180
aggtttagtg gatctggatc tggcactgag tttactctca ctataagctc ccttcagcct    240
gaagacttcg caacttatta ttgcttgcag tataatagtt atcctctcgc ctttggcggt    300
ggcaccaaag tggagattaa gcgaacc                                         327

SEQ ID NO: 322          moltype = DNA   length = 369
FEATURE                 Location/Qualifiers
source                  1..369
                        mol_type = other DNA
                        organism = synthetic construct
SEQUENCE: 322
gaagtccagc ttgttgagtc tggcggaggg gtggttaggc caggaggttc ccttaggctt    60
tcctgtgcgg catcaggatt tactttcgat gactacggaa tgtcatgggt acgacaagct    120
cccggcaaag gccttgaatg ggtttctggc atcaactggg agggcggttc cactggctac    180
gcggactcag ttaagggtag gttcagcata agcagggaca atgcgaagaa ctcactgtat    240
ctccaaatga acagtctccg cgccgaggat acagcccttt actattgtgc acgagatgag    300
caattggggg ggctgaagta ttattactat tacatggacg tgtggggtaa aggaacgacc    360
gtcacagtc                                                            369

SEQ ID NO: 323          moltype = DNA   length = 327
FEATURE                 Location/Qualifiers
source                  1..327
                        mol_type = other DNA
                        organism = synthetic construct
SEQUENCE: 323
gacatacaga tgactcagtc cccaagtagt ctgagcgcct ctgtcggcga ccgcgttacc    60
attacttgcc gggcgagtca aggatacgc aacgatttgg gttggtatca gcaaaagccc    120
ggaaaggccc caaagcggct gatatacacc gcctcaaacc tccagtctgg agttccatca    180
aggtttagtg gatctggatc tggcactgag tttactctca ctataagctc ccttcagcct    240
gaagacttcg caacttatta ttgcttgcag tatcacagtt atcctctccg ctttggcggt    300
ggcaccaaag tggagattaa gcgaacc                                         327

SEQ ID NO: 324          moltype = DNA   length = 369
FEATURE                 Location/Qualifiers
source                  1..369
                        mol_type = other DNA
                        organism = synthetic construct
SEQUENCE: 324
gaagtccagc ttgttgagtc tggcggaggg gtggttaggc caggaggttc ccttaggctt    60
```

```
tcctgtgcgg catcaggatt taccttcgat gactacggaa tgtcatgggt acgacaagct    120
cccggcaaag gcctcgaatg ggtttctggc atcaactggg agggcggttc cactggctac    180
gcggactcag ttaagggtag gttcaccata agcagggaca atgcgaagaa ctcactgtat    240
ctccaaatga acagtctccg cgccaggat acagccttt actattgtgc acgagatgag     300
caattggggg ggaatcacta ttattactat tacatggacg cttggggtaa aggaacgacc    360
gtcacagtc                                                            369

SEQ ID NO: 325           moltype = DNA    length = 327
FEATURE                  Location/Qualifiers
source                   1..327
                         mol_type = other DNA
                         organism = synthetic construct
SEQUENCE: 325
gacatacaga tgactcagtc cccaagtagt ctgagcgcct ctgtcggcga ccgcgttacc    60
attacttgcc gggcgagtca agggatacgc aacgatttgg gttggtatca gcaaaagccc    120
ggaaaggccc caaagcggct gatatacacc gcctcaaacc tccagtctgg agttccatca    180
aggtttagtg gatctggatc tggcactgag tttactctca ctataagctc ccttcagcct    240
gaagacttcg caacttatta ttgcttgcag tatgccagtt atcctctcaa gtttggcggt    300
ggcaccaaag tggagattaa gcgaacc                                         327

SEQ ID NO: 326           moltype = DNA    length = 369
FEATURE                  Location/Qualifiers
source                   1..369
                         mol_type = other DNA
                         organism = synthetic construct
SEQUENCE: 326
gaagtccagc ttgttgagtc tggcggaggg gtggttaggc caggaggttc ccttaggctt    60
tcctgtgcgg catcaggatt taccttcgat gactacggaa tgtcatgggt acgacaagct    120
cccggcaaag gcctcgaatg ggtttctggc atcaactggg agggcggttc cactggctac    180
gcggactcag ttaagggtag gttcaccata agcagggaca atgcgaagaa ctcactgtat    240
ctccaaatga acagtctccg cgccaggat acagccttt actattgtgc acgagatgag     300
caattggggg ggcgccacta ttattactat tacatggacg tgtggggtaa aggaacgacc    360
gtcacagtc                                                            369

SEQ ID NO: 327           moltype = DNA    length = 327
FEATURE                  Location/Qualifiers
source                   1..327
                         mol_type = other DNA
                         organism = synthetic construct
SEQUENCE: 327
gacatacaga tgactcagtc cccaagtagt ctgagcgcct ctgtcggcga ccgcgttacc    60
attacttgcc gggcgagtca agggatacgc aacgatttgg gttggtatca gcaaaagccc    120
ggaaaggccc caaagcggct gatatacacc gcctcaaacc tccagtctgg agttccatca    180
aggtttagtg gatctggatc tggcactgag tttactctca ctataagctc ccttcagcct    240
gaagacttcg caacttatta ttgcttgcag tataatgcct atcctctcat ctttggcggt    300
ggcaccaaag tggagattaa gcgaacc                                         327

SEQ ID NO: 328           moltype =         length =
SEQUENCE: 328
000

SEQ ID NO: 329           moltype =         length =
SEQUENCE: 329
000

SEQ ID NO: 330           moltype =         length =
SEQUENCE: 330
000

SEQ ID NO: 331           moltype =         length =
SEQUENCE: 331
000

SEQ ID NO: 332           moltype =         length =
SEQUENCE: 332
000

SEQ ID NO: 333           moltype = AA     length = 16
FEATURE                  Location/Qualifiers
source                   1..16
                         mol_type = protein
                         organism = synthetic construct
VARIANT                  7
                         note = X can be N, T, I, Q, L, K, or R
VARIANT                  8
                         note = X can be Y, T, K, H, or V
VARIANT                  16
                         note = X can be V or A
SEQUENCE: 333
```

DEQLGGXXYY YYYMDX 16

```
SEQ ID NO: 334         moltype = AA  length = 118
FEATURE                Location/Qualifiers
source                 1..118
                       mol_type = protein
                       organism = synthetic construct
SEQUENCE: 334
EVQLVESGGG LVKPGGSLRL SCAASGFTFS DYYMSWIRQA PGKGLEWVSY ISRSGSTKYY  60
ADSVKGRFTI SRDNAKNSLY LQMNSLRAED TAVYYCARDQ EDYALDYWGQ GTLVTVSS  118

SEQ ID NO: 335         moltype = AA  length = 118
FEATURE                Location/Qualifiers
source                 1..118
                       mol_type = protein
                       organism = synthetic construct
SEQUENCE: 335
EVQLVESGGG LVKPGGSLRL SCAASGFTFS DYYMSWIRQA PGKGLEWVSY ISRSGSTKYY  60
ADSVKGRFTI SRDNAKNSLY LQMNSLRAED TAVYYCARDE TDYGWDYWGQ GTLVTVSS  118

SEQ ID NO: 336         moltype = AA  length = 118
FEATURE                Location/Qualifiers
source                 1..118
                       mol_type = protein
                       organism = synthetic construct
SEQUENCE: 336
EVQLVESGGG LVKPGGSLRL SCAASGFTFS DYYMSWIRQA PGKGLEWVSY ISRSGSTKYY  60
ADSVKGRFTI SRDNAKNSLY LQMNSLRAED TAVYYCARDE TDYAFDEWGQ GTLVTVSS  118

SEQ ID NO: 337         moltype = AA  length = 118
FEATURE                Location/Qualifiers
source                 1..118
                       mol_type = protein
                       organism = synthetic construct
SEQUENCE: 337
EVQLVESGGG LVKPGGSLRL SCAASGFTFS DYYMSWIRQA PGKGLEWVSY ISRSGSTKYY  60
ADSVKGRFTI SRDNAKNSLY LQMNSLRAED TAVYYCARDE SQYALDYWGQ GTLVTVSS  118

SEQ ID NO: 338         moltype = AA  length = 118
FEATURE                Location/Qualifiers
source                 1..118
                       mol_type = protein
                       organism = synthetic construct
SEQUENCE: 338
EVQLVESGGG LVKPGGSLRL SCAASGFTFS DYYMSWIRQA PGKGLEWVSY ISRSGSTKYY  60
AHSVKGRFTI SRDNAKNSLY LQMNSLRAED TAVYYCARDN TDYALDLWGQ GTLVTVSS  118

SEQ ID NO: 339         moltype = AA  length = 118
FEATURE                Location/Qualifiers
source                 1..118
                       mol_type = protein
                       organism = synthetic construct
SEQUENCE: 339
EVQLVESGGG LVKPGGSLRL SCAASGFTFS DYYMSWIRQA PGKGLEWVSY ISRSGSTKYY  60
AHSVKGRFTI SRDNAKNSLY LQMNSLRAED TAVYYCARDE TDYAYDEWGQ GTLVTVSS  118

SEQ ID NO: 340         moltype = AA  length = 118
FEATURE                Location/Qualifiers
source                 1..118
                       mol_type = protein
                       organism = synthetic construct
SEQUENCE: 340
EVQLVESGGG LVKPGGSLRL SCAASGFTFS DYYMSWIRQA PGKGLEWVSY ISRSGSTKYY  60
ADSVKGRFTI SRDNAKNSLY LQMNSLRAED TAVYYCARDE TDYAYDNWGQ GTLVTVSS  118

SEQ ID NO: 341         moltype = AA  length = 118
FEATURE                Location/Qualifiers
source                 1..118
                       mol_type = protein
                       organism = synthetic construct
SEQUENCE: 341
EVQLVESGGG LVKPGGSLRL SCAASGFTFS DYYMSWIRQA PGKGLEWVSY ISRSGSTKYY  60
ADSVKGRFTI SRDNAKNSLY LQMNSLRAED TAVYYCARDE SDYAYDYWGQ GTLVTVSS  118

SEQ ID NO: 342         moltype = AA  length = 117
FEATURE                Location/Qualifiers
source                 1..117
                       mol_type = protein
                       organism = synthetic construct
```

```
SEQUENCE: 342
EVQLVESGGG LVKPGGSLRL SCAASGFTFS DYYMSWIRQA PGKGLEWVSY ISRSGSTKYY    60
ADSVKGRFTI SRDNAKNSLY LQMNSLRAED TAVYYCARDE NYALDWWGQG TLVTVSS      117

SEQ ID NO: 343          moltype = AA   length = 118
FEATURE                 Location/Qualifiers
source                  1..118
                        mol_type = protein
                        organism = synthetic construct
SEQUENCE: 343
EVQLVESGGG LVKPGGSLRL SCAASGFTFS DYYMSWIRQA PGKGLEWVSY ISRSGSTKYY    60
ADSVKGRFTI SRDNAKNSLY LQMNSLRAED TAVYYCARDE SDYALDFWGQ GTLVTVSS     118

SEQ ID NO: 344          moltype = AA   length = 119
FEATURE                 Location/Qualifiers
source                  1..119
                        mol_type = protein
                        organism = synthetic construct
SEQUENCE: 344
EVQLVQSGAE VKKPGASVKV SCKVSGDTLT ELSMHWVRQA PGKGLEWMGT FDPEEGETIY    60
AQKFQGRVTM TEDTSTDTAY MELSSLRSED TAVYYCVTEG LAGVPFDLWG QGTLVTVSS    119

SEQ ID NO: 345          moltype = AA   length = 119
FEATURE                 Location/Qualifiers
source                  1..119
                        mol_type = protein
                        organism = synthetic construct
SEQUENCE: 345
EVQLVQSGAE VKKPGASVKV SCKVSGDTLT ELSMHWVRQA PGKGLEWMGT FDPEEGETIY    60
AQKFQGRVTM TEDTSTDTAY MELSSLRSED TAVYYCVTEG LGGRPFDHWG QGTLVTVSS    119

SEQ ID NO: 346          moltype = AA   length = 119
FEATURE                 Location/Qualifiers
source                  1..119
                        mol_type = protein
                        organism = synthetic construct
SEQUENCE: 346
EVQLVQSGAE VKKPGASVKV SCKVSGDTLT ELSMHWVRQA PGKGLEWMGT FDPEEGETIY    60
AQKFQGRVTM TEDTSTDTAY MELSSLRSED TAVYYCVTEG LAGFPFDIWG QGTLVTVSS    119

SEQ ID NO: 347          moltype = AA   length = 119
FEATURE                 Location/Qualifiers
source                  1..119
                        mol_type = protein
                        organism = synthetic construct
SEQUENCE: 347
EVQLVQSGAE VKKPGASVKV SCKVSGDTLT ELSMHWVRQA PGKGLEWMGT FDPEEGETIY    60
AQKFQGRVTM TEDTSTDTAY MELSSLRSED TAVYYCVTEG LAWRPTDSWG QGTLVTVSS    119

SEQ ID NO: 348          moltype = AA   length = 119
FEATURE                 Location/Qualifiers
source                  1..119
                        mol_type = protein
                        organism = synthetic construct
SEQUENCE: 348
EVQLVQSGAE VKKPGASVKV SCKVSGDTLT ELSMHWVRQA PGKGLEWMGT FDPEEGETIY    60
AQKFQGRVTM TEDTSTDTAY MELSSLRSED TAVYYCVTKG LAWLPYYSWG QGTLVTVSS    119

SEQ ID NO: 349          moltype = AA   length = 119
FEATURE                 Location/Qualifiers
source                  1..119
                        mol_type = protein
                        organism = synthetic construct
SEQUENCE: 349
EVQLVQSGAE VKKPGASVKV SCKVSGDTLT ELSMHWVRQA PGKGLEWMGT FDPEEGETIY    60
AQKFQGRVTM TEDTSTDTAY MELSSLRSED TAVYYCVTEG LAGVPFDLWG QGTLVTVSS    119

SEQ ID NO: 350          moltype = AA   length = 119
FEATURE                 Location/Qualifiers
source                  1..119
                        mol_type = protein
                        organism = synthetic construct
SEQUENCE: 350
EVQLVQSGAE VKKPGASVKV SCKVSGDTLT ELSMHWVRQA PGKGLEWMGT FDPEEGETIY    60
AQKFQGRVTM TEDTSTDTAY MELSSLRSED TAVYYCVTEG EAGRPFDAWG QGTLVTVSS    119

SEQ ID NO: 351          moltype = AA   length = 119
FEATURE                 Location/Qualifiers
source                  1..119
```

```
                        mol_type = protein
                        organism = synthetic construct
SEQUENCE: 351
EVQLVQSGAE VKKPGASVKV SCKVSGDTLT ELSMHWVRQA PGKGLEWMGT FDPEEGETIY    60
AQKFQGRVTM TEDTSTDTAY MELSSLRSED TAVYYCVTEG LAGRPYDVWG QGTLVTVSS    119

SEQ ID NO: 352          moltype = AA   length = 119
FEATURE                 Location/Qualifiers
source                  1..119
                        mol_type = protein
                        organism = synthetic construct
SEQUENCE: 352
EVQLVQSGAE VKKPGASVKV SCKVSGDTLT ELSMHWVRQA PGKGLEWMGT FDPEEGETIY    60
AQKFQGRVTM TEDTSTDTAY MELSYLRSED TAVYYCVTEG LAGIPFDSWG QGTLVTVSS    119

SEQ ID NO: 353          moltype = AA   length = 119
FEATURE                 Location/Qualifiers
source                  1..119
                        mol_type = protein
                        organism = synthetic construct
SEQUENCE: 353
EVQLVQSGAE VKKPGASVKV SCKVSGDTLT ELSMHWVRQA PGKGLEWMGT FDPEEGETIY    60
AQKFQGRVTM TEDTSTDTAY MELSYLRSED TAVYYCVTEG LAGIPFDSWG QGTLVTVSS    119

SEQ ID NO: 354          moltype = AA   length = 124
FEATURE                 Location/Qualifiers
source                  1..124
                        mol_type = protein
                        organism = synthetic construct
SEQUENCE: 354
EVQLVESGGG VVRPGGSLRL SCAASGFTFD DYGMSWVRQA PGKGLEWVSG INWEGGSTGY    60
ADSVKGRFTI SRDNAKNSLY LQMNSLRAED TALYYCARDE QLGGTTYYYY YMDVWGKGTT   120
VTVS                                                                124

SEQ ID NO: 355          moltype = AA   length = 125
FEATURE                 Location/Qualifiers
source                  1..125
                        mol_type = protein
                        organism = synthetic construct
SEQUENCE: 355
QVQLVESGGG VVRPGGSLRL SCAASGFTFD DYGMSWVRQA PGKGLEWVSG INWEGGSTGY    60
ADSVKGRFTI SRDNAKNSLY LQMNSLRAED TALYYCARDE QLGGKYYYYY YMDVWGKGTT   120
VTVSS                                                               125

SEQ ID NO: 356          moltype = AA   length = 125
FEATURE                 Location/Qualifiers
source                  1..125
                        mol_type = protein
                        organism = synthetic construct
SEQUENCE: 356
QVQLVESGGG VVRPGGSLRL SCAASGFTFD DYGMSWVRQA PGKGLEWVSG INWEGGSTGY    60
ADSVKGRFTI SRDNAKNSLY LQMNSLRAED TALYYCARDE QLGGQTYYYY YMDVWGKGTT   120
VTVSS                                                               125

SEQ ID NO: 357          moltype = AA   length = 125
FEATURE                 Location/Qualifiers
source                  1..125
                        mol_type = protein
                        organism = synthetic construct
SEQUENCE: 357
QVQLVESGGG VVRPGGSLRL SCAASGFTFD DYGMSWVRQA PGKGLEWVSG INWEGGSTGY    60
ADSVKGRFTI SRDNAKNSLY LQMNSLRAED TALYYCARDE QLGGTTYYYY YMDVWGKGTT   120
VTVSS                                                               125

SEQ ID NO: 358          moltype = AA   length = 125
FEATURE                 Location/Qualifiers
source                  1..125
                        mol_type = protein
                        organism = synthetic construct
SEQUENCE: 358
QVQLVESGGG VVRPGGSLRL SCAASGFTFD DYGMSWVRQA PGKGLEWVSG INWEGGSTGY    60
ADSVKGRFTI SRDNAKNSLY LQMNSLRAED TALYYCARDE QLGGIKYYYY YMDVWGKGTT   120
VTVSS                                                               125

SEQ ID NO: 359          moltype = AA   length = 125
FEATURE                 Location/Qualifiers
source                  1..125
                        mol_type = protein
                        organism = synthetic construct
```

```
SEQUENCE: 359
QVQLVESGGG VVRPGGSLRL SCAASGFTFD DYGMSWVRQA PGKGLEWVSG INWEGGSTGY    60
ADSVKGRFSI SRDNAKNSLY LQMNSLRAED TALYYCARDE QLGGLKYYYY YMDVWGKGTT   120
VTVSS                                                              125

SEQ ID NO: 360          moltype = AA   length = 125
FEATURE                 Location/Qualifiers
source                  1..125
                        mol_type = protein
                        organism = synthetic construct
SEQUENCE: 360
QVQLVESGGG VVRPGGSLRL SCAASGFTFD DYGMSWVRQA PGKGLEWVSG INWEGGSTGY    60
ADSVKGRFTI SRDNAKNSLY LQMNSLRAED TALYYCARDE QLGGKVYYYY YMDVWGKGTT   120
VTVSS                                                              125

SEQ ID NO: 361          moltype = AA   length = 125
FEATURE                 Location/Qualifiers
source                  1..125
                        mol_type = protein
                        organism = synthetic construct
SEQUENCE: 361
QVQLVESGGG VVRPGGSLRL SCAASGFTFD DYGMSWVRQA PGKGLEWVSG INWEGGSTGY    60
ADSVKGRFSI SRDNAKNSLY LQMNSLRAED TALYYCARDE QLGGLKYYYY YMDVWGKGTT   120
VTVSS                                                              125

SEQ ID NO: 362          moltype = AA   length = 125
FEATURE                 Location/Qualifiers
source                  1..125
                        mol_type = protein
                        organism = synthetic construct
SEQUENCE: 362
QVQLVESGGG VVRPGGSLRL SCAASGFTFD DYGMSWVRQA PGKGLEWVSG INWEGGSTGY    60
ADSVKGRFTI SRDNAKNSLY LQMNSLRAED TALYYCARDE QLGGNHYYYY YMDAWGKGTT   120
VTVSS                                                              125

SEQ ID NO: 363          moltype = AA   length = 125
FEATURE                 Location/Qualifiers
source                  1..125
                        mol_type = protein
                        organism = synthetic construct
SEQUENCE: 363
QVQLVESGGG VVRPGGSLRL SCAASGFTFD DYGMSWVRQA PGKGLEWVSG INWEGGSTGY    60
ADSVKGRFTI SRDNAKNSLY LQMNSLRAED TALYYCARDE QLGGRHYYYY YMDVWGKGTT   120
VTVSS                                                              125

SEQ ID NO: 364          moltype = AA   length = 444
FEATURE                 Location/Qualifiers
source                  1..444
                        mol_type = protein
                        organism = synthetic construct
SEQUENCE: 364
EVQLVESGGG LVKPGGSLRL SCAASGFTFS DYYMSWIRQA PGKGLEWVSY ISRSGSTKYY    60
ADSVKGRFTI SRDNAKNSLY LQMNSLRAED TAVYYCARDQ EDYALDYWGQ GTLVTVSSAS   120
TKGPSVFPLA PCSRSTSEST AALGCLVKDY FPEPVTVSWN SGALTSGVHT FPAVLQSSGL   180
YSLSSVVTVP SSSLGTKTYT CNVDHKPSNT KVDKRVESKY GPPCPPCPAP EFEGGPSVFL   240
FPPKPKDTLM ISRTPEVTCV VVDVSQEDPE VQFNWYVDGV EVHNAKTKPR EEQFNSTYRV   300
VSVLTVLHQD WLNGKEYKCK VSNKGLPSSI EKTISKAKGQ PREPQVYTLP PSQEEMTKNQ   360
VSLTCLVKGF YPSDIAVEWE SNGQPENNYK TTPPVLDSDG SFFLYSRLTV DKSRWQEGNV   420
FSCSVLHEAL HSHYTQKSLS LSLG                                         444

SEQ ID NO: 365          moltype = AA   length = 444
FEATURE                 Location/Qualifiers
source                  1..444
                        mol_type = protein
                        organism = synthetic construct
SEQUENCE: 365
EVQLVESGGG LVKPGGSLRL SCAASGFTFS DYYMSWIRQA PGKGLEWVSY ISRSGSTKYY    60
ADSVKGRFTI SRDNAKNSLY LQMNSLRAED TAVYYCARDQ EDYALDYWGQ GTLVTVSSAS   120
TKGPSVFPLA PCSRSTSEST AALGCLVKDY FPEPVTVSWN SGALTSGVHT FPAVLQSSGL   180
YSLSSVVTVP SSSLGTKTYT CNVDHKPSNT KVDKRVESKY GPPCPPCPAP EFEGGPSVFL   240
FPPKPKDTLY ITREPEVTCV VVDVSQEDPE VQFNWYVDGV EVHNAKTKPR EEQFNSTYRV   300
VSVLTVLHQD WLNGKEYKCK VSNKGLPSSI EKTISKAKGQ PREPQVYTLP PSQEEMTKNQ   360
VSLTCLVKGF YPSDIAVEWE SNGQPENNYK TTPPVLDSDG SFFLYSRLTV DKSRWQEGNV   420
FSCSVMHEAL HNHYTQKSLS LSLG                                         444

SEQ ID NO: 366          moltype = AA   length = 444
FEATURE                 Location/Qualifiers
source                  1..444
                        mol_type = protein
```

```
                        organism = synthetic construct
SEQUENCE: 366
EVQLVESGGG LVKPGGSLRL SCAASGFTFS DYYMSWIRQA PGKGLEWVSY ISRSGSTKYY      60
ADSVKGRFTI SRDNAKNSLY LQMNSLRAED TAVYYCARDE TDYGWDYWGQ GTLVTVSSAS     120
TKGPSVFPLA PCSRSTSEST AALGCLVKDY FPEPVTVSWN SGALTSGVHT FPAVLQSSGL     180
YSLSSVVTVP SSSLGTKTYT CNVDHKPSNT KVDKRVESKY GPPCPPCPAP EFEGGPSVFL     240
FPPKPKDTLM ISRTPEVTCV VVDVSQEDPE VQFNWYVDGV EVHNAKTKPR EEQFNSTYRV     300
VSVLTVLHQD WLNGKEYKCK VSNKGLPSSI EKTISKAKGQ PREPQVYTLP PSQEEMTKNQ     360
VSLTCLVKGF YPSDIAVEWE SNGQPENNYK TTPPVLDSDG SFFLYSRLTV DKSRWQEGNV     420
FSCSVLHEAL HSHYTQKSLS LSLG                                           444

SEQ ID NO: 367          moltype = AA  length = 444
FEATURE                 Location/Qualifiers
source                  1..444
                        mol_type = protein
                        organism = synthetic construct
SEQUENCE: 367
EVQLVESGGG LVKPGGSLRL SCAASGFTFS DYYMSWIRQA PGKGLEWVSY ISRSGSTKYY      60
ADSVKGRFTI SRDNAKNSLY LQMNSLRAED TAVYYCARDE TDYGWDYWGQ GTLVTVSSAS     120
TKGPSVFPLA PCSRSTSEST AALGCLVKDY FPEPVTVSWN SGALTSGVHT FPAVLQSSGL     180
YSLSSVVTVP SSSLGTKTYT CNVDHKPSNT KVDKRVESKY GPPCPPCPAP EFEGGPSVFL     240
FPPKPKDTLY ITREPEVTCV VVDVSQEDPE VQFNWYVDGV EVHNAKTKPR EEQFNSTYRV     300
VSVLTVLHQD WLNGKEYKCK VSNKGLPSSI EKTISKAKGQ PREPQVYTLP PSQEEMTKNQ     360
VSLTCLVKGF YPSDIAVEWE SNGQPENNYK TTPPVLDSDG SFFLYSRLTV DKSRWQEGNV     420
FSCSVMHEAL HNHYTQKSLS LSLG                                           444

SEQ ID NO: 368          moltype = AA  length = 444
FEATURE                 Location/Qualifiers
source                  1..444
                        mol_type = protein
                        organism = synthetic construct
SEQUENCE: 368
EVQLVESGGG LVKPGGSLRL SCAASGFTFS DYYMSWIRQA PGKGLEWVSY ISRSGSTKYY      60
ADSVKGRFTI SRDNAKNSLY LQMNSLRAED TAVYYCARDE TDYAFDEWGQ GTLVTVSSAS     120
TKGPSVFPLA PCSRSTSEST AALGCLVKDY FPEPVTVSWN SGALTSGVHT FPAVLQSSGL     180
YSLSSVVTVP SSSLGTKTYT CNVDHKPSNT KVDKRVESKY GPPCPPCPAP EFEGGPSVFL     240
FPPKPKDTLM ISRTPEVTCV VVDVSQEDPE VQFNWYVDGV EVHNAKTKPR EEQFNSTYRV     300
VSVLTVLHQD WLNGKEYKCK VSNKGLPSSI EKTISKAKGQ PREPQVYTLP PSQEEMTKNQ     360
VSLTCLVKGF YPSDIAVEWE SNGQPENNYK TTPPVLDSDG SFFLYSRLTV DKSRWQEGNV     420
FSCSVLHEAL HSHYTQKSLS LSLG                                           444

SEQ ID NO: 369          moltype = AA  length = 444
FEATURE                 Location/Qualifiers
source                  1..444
                        mol_type = protein
                        organism = synthetic construct
SEQUENCE: 369
EVQLVESGGG LVKPGGSLRL SCAASGFTFS DYYMSWIRQA PGKGLEWVSY ISRSGSTKYY      60
ADSVKGRFTI SRDNAKNSLY LQMNSLRAED TAVYYCARDE TDYAFDEWGQ GTLVTVSSAS     120
TKGPSVFPLA PCSRSTSEST AALGCLVKDY FPEPVTVSWN SGALTSGVHT FPAVLQSSGL     180
YSLSSVVTVP SSSLGTKTYT CNVDHKPSNT KVDKRVESKY GPPCPPCPAP EFEGGPSVFL     240
FPPKPKDTLY ITREPEVTCV VVDVSQEDPE VQFNWYVDGV EVHNAKTKPR EEQFNSTYRV     300
VSVLTVLHQD WLNGKEYKCK VSNKGLPSSI EKTISKAKGQ PREPQVYTLP PSQEEMTKNQ     360
VSLTCLVKGF YPSDIAVEWE SNGQPENNYK TTPPVLDSDG SFFLYSRLTV DKSRWQEGNV     420
FSCSVMHEAL HNHYTQKSLS LSLG                                           444

SEQ ID NO: 370          moltype = AA  length = 444
FEATURE                 Location/Qualifiers
source                  1..444
                        mol_type = protein
                        organism = synthetic construct
SEQUENCE: 370
EVQLVESGGG LVKPGGSLRL SCAASGFTFS DYYMSWIRQA PGKGLEWVSY ISRSGSTKYY      60
ADSVKGRFTI SRDNAKNSLY LQMNSLRAED TAVYYCARDE SQYALDYWGQ GTLVTVSSAS     120
TKGPSVFPLA PCSRSTSEST AALGCLVKDY FPEPVTVSWN SGALTSGVHT FPAVLQSSGL     180
YSLSSVVTVP SSSLGTKTYT CNVDHKPSNT KVDKRVESKY GPPCPPCPAP EFEGGPSVFL     240
FPPKPKDTLM ISRTPEVTCV VVDVSQEDPE VQFNWYVDGV EVHNAKTKPR EEQFNSTYRV     300
VSVLTVLHQD WLNGKEYKCK VSNKGLPSSI EKTISKAKGQ PREPQVYTLP PSQEEMTKNQ     360
VSLTCLVKGF YPSDIAVEWE SNGQPENNYK TTPPVLDSDG SFFLYSRLTV DKSRWQEGNV     420
FSCSVLHEAL HSHYTQKSLS LSLG                                           444

SEQ ID NO: 371          moltype = AA  length = 444
FEATURE                 Location/Qualifiers
source                  1..444
                        mol_type = protein
                        organism = synthetic construct
SEQUENCE: 371
EVQLVESGGG LVKPGGSLRL SCAASGFTFS DYYMSWIRQA PGKGLEWVSY ISRSGSTKYY      60
ADSVKGRFTI SRDNAKNSLY LQMNSLRAED TAVYYCARDE SQYALDYWGQ GTLVTVSSAS     120
```

```
TKGPSVFPLA PCSRSTSEST AALGCLVKDY FPEPVTVSWN SGALTSGVHT FPAVLQSSGL   180
YSLSSVVTVP SSSLGTKTYT CNVDHKPSNT KVDKRVESKY GPPCPPCPAP EFEGGPSVFL   240
FPPKPKDTLY ITREPEVTCV VVDVSQEDPE VQFNWYVDGV EVHNAKTKPR EEQFNSTYRV   300
VSVLTVLHQD WLNGKEYKCK VSNKGLPSSI EKTISKAKGQ PREPQVYTLP PSQEEMTKNQ   360
VSLTCLVKGF YPSDIAVEWE SNGQPENNYK TTPPVLDSDG SFFLYSRLTV DKSRWQEGNV   420
FSCSVMHEAL HNHYTQKSLS LSLG                                         444

SEQ ID NO: 372        moltype = AA  length = 444
FEATURE               Location/Qualifiers
source                1..444
                      mol_type = protein
                      organism = synthetic construct
SEQUENCE: 372
EVQLVESGGG LVKPGGSLRL SCAASGFTFS DYYMSWIRQA PGKGLEWVSY ISRSGSTKYY    60
AHSVKGRFTI SRDNAKNSLY LQMNSLRAED TAVYYCARDN TDYALDLWGQ GTLVTVSSAS   120
TKGPSVFPLA PCSRSTSEST AALGCLVKDY FPEPVTVSWN SGALTSGVHT FPAVLQSSGL   180
YSLSSVVTVP SSSLGTKTYT CNVDHKPSNT KVDKRVESKY GPPCPPCPAP EFEGGPSVFL   240
FPPKPKDTLM ISRTPEVTCV VVDVSQEDPE VQFNWYVDGV EVHNAKTKPR EEQFNSTYRV   300
VSVLTVLHQD WLNGKEYKCK VSNKGLPSSI EKTISKAKGQ PREPQVYTLP PSQEEMTKNQ   360
VSLTCLVKGF YPSDIAVEWE SNGQPENNYK TTPPVLDSDG SFFLYSRLTV DKSRWQEGNV   420
FSCSVLHEAL HSHYTQKSLS LSLG                                         444

SEQ ID NO: 373        moltype = AA  length = 444
FEATURE               Location/Qualifiers
source                1..444
                      mol_type = protein
                      organism = synthetic construct
SEQUENCE: 373
EVQLVESGGG LVKPGGSLRL SCAASGFTFS DYYMSWIRQA PGKGLEWVSY ISRSGSTKYY    60
AHSVKGRFTI SRDNAKNSLY LQMNSLRAED TAVYYCARDN TDYALDLWGQ GTLVTVSSAS   120
TKGPSVFPLA PCSRSTSEST AALGCLVKDY FPEPVTVSWN SGALTSGVHT FPAVLQSSGL   180
YSLSSVVTVP SSSLGTKTYT CNVDHKPSNT KVDKRVESKY GPPCPPCPAP EFEGGPSVFL   240
FPPKPKDTLY ITREPEVTCV VVDVSQEDPE VQFNWYVDGV EVHNAKTKPR EEQFNSTYRV   300
VSVLTVLHQD WLNGKEYKCK VSNKGLPSSI EKTISKAKGQ PREPQVYTLP PSQEEMTKNQ   360
VSLTCLVKGF YPSDIAVEWE SNGQPENNYK TTPPVLDSDG SFFLYSRLTV DKSRWQEGNV   420
FSCSVMHEAL HNHYTQKSLS LSLG                                         444

SEQ ID NO: 374        moltype = AA  length = 444
FEATURE               Location/Qualifiers
source                1..444
                      mol_type = protein
                      organism = synthetic construct
SEQUENCE: 374
EVQLVESGGG LVKPGGSLRL SCAASGFTFS DYYMSWIRQA PGKGLEWVSY ISRSGSTKYY    60
AHSVKGRFTI SRDNAKNSLY LQMNSLRAED TAVYYCARDE TDYAYDEWGQ GTLVTVSSAS   120
TKGPSVFPLA PCSRSTSEST AALGCLVKDY FPEPVTVSWN SGALTSGVHT FPAVLQSSGL   180
YSLSSVVTVP SSSLGTKTYT CNVDHKPSNT KVDKRVESKY GPPCPPCPAP EFEGGPSVFL   240
FPPKPKDTLM ISRTPEVTCV VVDVSQEDPE VQFNWYVDGV EVHNAKTKPR EEQFNSTYRV   300
VSVLTVLHQD WLNGKEYKCK VSNKGLPSSI EKTISKAKGQ PREPQVYTLP PSQEEMTKNQ   360
VSLTCLVKGF YPSDIAVEWE SNGQPENNYK TTPPVLDSDG SFFLYSRLTV DKSRWQEGNV   420
FSCSVLHEAL HSHYTQKSLS LSLG                                         444

SEQ ID NO: 375        moltype = AA  length = 444
FEATURE               Location/Qualifiers
source                1..444
                      mol_type = protein
                      organism = synthetic construct
SEQUENCE: 375
EVQLVESGGG LVKPGGSLRL SCAASGFTFS DYYMSWIRQA PGKGLEWVSY ISRSGSTKYY    60
AHSVKGRFTI SRDNAKNSLY LQMNSLRAED TAVYYCARDE TDYAYDEWGQ GTLVTVSSAS   120
TKGPSVFPLA PCSRSTSEST AALGCLVKDY FPEPVTVSWN SGALTSGVHT FPAVLQSSGL   180
YSLSSVVTVP SSSLGTKTYT CNVDHKPSNT KVDKRVESKY GPPCPPCPAP EFEGGPSVFL   240
FPPKPKDTLY ITREPEVTCV VVDVSQEDPE VQFNWYVDGV EVHNAKTKPR EEQFNSTYRV   300
VSVLTVLHQD WLNGKEYKCK VSNKGLPSSI EKTISKAKGQ PREPQVYTLP PSQEEMTKNQ   360
VSLTCLVKGF YPSDIAVEWE SNGQPENNYK TTPPVLDSDG SFFLYSRLTV DKSRWQEGNV   420
FSCSVMHEAL HNHYTQKSLS LSLG                                         444

SEQ ID NO: 376        moltype = AA  length = 444
FEATURE               Location/Qualifiers
source                1..444
                      mol_type = protein
                      organism = synthetic construct
SEQUENCE: 376
EVQLVESGGG LVKPGGSLRL SCAASGFTFS DYYMSWIRQA PGKGLEWVSY ISRSGSTKYY    60
ADSVKGRFTI SRDNAKNSLY LQMNSLRAED TAVYYCARDE TDYAYDNWGQ GTLVTVSSAS   120
TKGPSVFPLA PCSRSTSEST AALGCLVKDY FPEPVTVSWN SGALTSGVHT FPAVLQSSGL   180
YSLSSVVTVP SSSLGTKTYT CNVDHKPSNT KVDKRVESKY GPPCPPCPAP EFEGGPSVFL   240
FPPKPKDTLM ISRTPEVTCV VVDVSQEDPE VQFNWYVDGV EVHNAKTKPR EEQFNSTYRV   300
VSVLTVLHQD WLNGKEYKCK VSNKGLPSSI EKTISKAKGQ PREPQVYTLP PSQEEMTKNQ   360
```

```
VSLTCLVKGF YPSDIAVEWE SNGQPENNYK TTPPVLDSDG SFFLYSRLTV DKSRWQEGNV   420
FSCSVLHEAL HSHYTQKSLS LSLG                                         444

SEQ ID NO: 377          moltype = AA  length = 444
FEATURE                 Location/Qualifiers
source                  1..444
                        mol_type = protein
                        organism = synthetic construct
SEQUENCE: 377
EVQLVESGGG LVKPGGSLRL SCAASGFTFS DYYMSWIRQA PGKGLEWVSY ISRSGSTKYY    60
ADSVKGRFTI SRDNAKNSLY LQMNSLRAED TAVYYCARDE TDYAYDNWGQ GTLVTVSSAS   120
TKGPSVFPLA PCSRSTSEST AALGCLVKDY FPEPVTVSWN SGALTSGVHT FPAVLQSSGL   180
YSLSSVVTVP SSSLGTKTYT CNVDHKPSNT KVDKRVESKY GPPCPPCPAP EFEGGPSVFL   240
FPPKPKDTLY ITREPEVTCV VVDVSQEDPE VQFNWYVDGV EVHNAKTKPR EEQFNSTYRV   300
VSVLTVLHQD WLNGKEYKCK VSNKGLPSSI EKTISKAKGQ PREPQVYTLP PSQEEMTKNQ   360
VSLTCLVKGF YPSDIAVEWE SNGQPENNYK TTPPVLDSDG SFFLYSRLTV DKSRWQEGNV   420
FSCSVMHEAL HNHYTQKSLS LSLG                                         444

SEQ ID NO: 378          moltype = AA  length = 444
FEATURE                 Location/Qualifiers
source                  1..444
                        mol_type = protein
                        organism = synthetic construct
SEQUENCE: 378
EVQLVESGGG LVKPGGSLRL SCAASGFTFS DYYMSWIRQA PGKGLEWVSY ISRSGSTKYY    60
ADSVKGRFTI SRDNAKNSLY LQMNSLRAED TAVYYCARDE SDYAYDYWGQ GTLVTVSSAS   120
TKGPSVFPLA PCSRSTSEST AALGCLVKDY FPEPVTVSWN SGALTSGVHT FPAVLQSSGL   180
YSLSSVVTVP SSSLGTKTYT CNVDHKPSNT KVDKRVESKY GPPCPPCPAP EFEGGPSVFL   240
FPPKPKDTLM ISRTPEVTCV VVDVSQEDPE VQFNWYVDGV EVHNAKTKPR EEQFNSTYRV   300
VSVLTVLHQD WLNGKEYKCK VSNKGLPSSI EKTISKAKGQ PREPQVYTLP PSQEEMTKNQ   360
VSLTCLVKGF YPSDIAVEWE SNGQPENNYK TTPPVLDSDG SFFLYSRLTV DKSRWQEGNV   420
FSCSVLHEAL HSHYTQKSLS LSLG                                         444

SEQ ID NO: 379          moltype = AA  length = 444
FEATURE                 Location/Qualifiers
source                  1..444
                        mol_type = protein
                        organism = synthetic construct
SEQUENCE: 379
EVQLVESGGG LVKPGGSLRL SCAASGFTFS DYYMSWIRQA PGKGLEWVSY ISRSGSTKYY    60
ADSVKGRFTI SRDNAKNSLY LQMNSLRAED TAVYYCARDE SDYAYDYWGQ GTLVTVSSAS   120
TKGPSVFPLA PCSRSTSEST AALGCLVKDY FPEPVTVSWN SGALTSGVHT FPAVLQSSGL   180
YSLSSVVTVP SSSLGTKTYT CNVDHKPSNT KVDKRVESKY GPPCPPCPAP EFEGGPSVFL   240
FPPKPKDTLY ITREPEVTCV VVDVSQEDPE VQFNWYVDGV EVHNAKTKPR EEQFNSTYRV   300
VSVLTVLHQD WLNGKEYKCK VSNKGLPSSI EKTISKAKGQ PREPQVYTLP PSQEEMTKNQ   360
VSLTCLVKGF YPSDIAVEWE SNGQPENNYK TTPPVLDSDG SFFLYSRLTV DKSRWQEGNV   420
FSCSVMHEAL HNHYTQKSLS LSLG                                         444

SEQ ID NO: 380          moltype = AA  length = 443
FEATURE                 Location/Qualifiers
source                  1..443
                        mol_type = protein
                        organism = synthetic construct
SEQUENCE: 380
EVQLVESGGG LVKPGGSLRL SCAASGFTFS DYYMSWIRQA PGKGLEWVSY ISRSGSTKYY    60
ADSVKGRFTI SRDNAKNSLY LQMNSLRAED TAVYYCARDE NYALDWWGQG TLVTVSSAST   120
KGPSVFPLAP CSRSTSESTA ALGCLVKDYF PEPVTVSWNS GALTSGVHTF PAVLQSSGLY   180
SLSSVVTVPS SSLGTKTYTC NVDHKPSNTK VDKRVESKYG PPCPPCPAPE FEGGPSVFLF   240
PPKPKDTLMI SRTPEVTCVV VDVSQEDPEV QFNWYVDGVE VHNAKTKPRE EQFNSTYRVV   300
SVLTVLHQDW LNGKEYKCKV SNKGLPSSIE KTISKAKGQP REPQVYTLPP SQEEMTKNQV   360
SLTCLVKGFY PSDIAVEWES NGQPENNYKT TPPVLDSDGS FFLYSRLTVD KSRWQEGNVF   420
SCSVLHEALH SHYTQKSLSL SLG                                          443

SEQ ID NO: 381          moltype = AA  length = 443
FEATURE                 Location/Qualifiers
source                  1..443
                        mol_type = protein
                        organism = synthetic construct
SEQUENCE: 381
EVQLVESGGG LVKPGGSLRL SCAASGFTFS DYYMSWIRQA PGKGLEWVSY ISRSGSTKYY    60
ADSVKGRFTI SRDNAKNSLY LQMNSLRAED TAVYYCARDE NYALDWWGQG TLVTVSSAST   120
KGPSVFPLAP CSRSTSESTA ALGCLVKDYF PEPVTVSWNS GALTSGVHTF PAVLQSSGLY   180
SLSSVVTVPS SSLGTKTYTC NVDHKPSNTK VDKRVESKYG PPCPPCPAPE FEGGPSVFLF   240
PPKPKDTLYI TREPEVTCVV VDVSQEDPEV QFNWYVDGVE VHNAKTKPRE EQFNSTYRVV   300
SVLTVLHQDW LNGKEYKCKV SNKGLPSSIE KTISKAKGQP REPQVYTLPP SQEEMTKNQV   360
SLTCLVKGFY PSDIAVEWES NGQPENNYKT TPPVLDSDGS FFLYSRLTVD KSRWQEGNVF   420
SCSVMHEALH NHYTQKSLSL SLG                                          443

SEQ ID NO: 382          moltype = AA  length = 444
```

```
FEATURE                 Location/Qualifiers
source                  1..444
                        mol_type = protein
                        organism = synthetic construct
SEQUENCE: 382
EVQLVESGGG LVKPGGSLRL SCAASGFTFS DYYMSWIRQA PGKGLEWVSY ISRSGSTKYY    60
ADSVKGRFTI SRDNAKNSLY LQMNSLRAED TAVYYCARDE SDYALDFWGQ GTLVTVSSAS   120
TKGPSVFPLA PCSRSTSEST AALGCLVKDY FPEPVTVSWN SGALTSGVHT FPAVLQSSGL   180
YSLSSVVTVP SSSLGTKTYT CNVDHKPSNT KVDKRVESKY GPPCPPCPAP EFEGGPSVFL   240
FPPKPKDTLM ISRTPEVTCV VVDVSQEDPE VQFNWYVDGV EVHNAKTKPR EEQFNSTYRV   300
VSVLTVLHQD WLNGKEYKCK VSNKGLPSSI EKTISKAKGQ PREPQVYTLP PSQEEMTKNQ   360
VSLTCLVKGF YPSDIAVEWE SNGQPENNYK TTPPVLDSDG SFFLYSRLTV DKSRWQEGNV   420
FSCSVLHEAL HSHYTQKSLS LSLG                                         444

SEQ ID NO: 383          moltype = AA  length = 444
FEATURE                 Location/Qualifiers
source                  1..444
                        mol_type = protein
                        organism = synthetic construct
SEQUENCE: 383
EVQLVESGGG LVKPGGSLRL SCAASGFTFS DYYMSWIRQA PGKGLEWVSY ISRSGSTKYY    60
ADSVKGRFTI SRDNAKNSLY LQMNSLRAED TAVYYCARDE SDYALDFWGQ GTLVTVSSAS   120
TKGPSVFPLA PCSRSTSEST AALGCLVKDY FPEPVTVSWN SGALTSGVHT FPAVLQSSGL   180
YSLSSVVTVP SSSLGTKTYT CNVDHKPSNT KVDKRVESKY GPPCPPCPAP EFEGGPSVFL   240
FPPKPKDTLY ITREPEVTCV VVDVSQEDPE VQFNWYVDGV EVHNAKTKPR EEQFNSTYRV   300
VSVLTVLHQD WLNGKEYKCK VSNKGLPSSI EKTISKAKGQ PREPQVYTLP PSQEEMTKNQ   360
VSLTCLVKGF YPSDIAVEWE SNGQPENNYK TTPPVLDSDG SFFLYSRLTV DKSRWQEGNV   420
FSCSVMHEAL HNHYTQKSLS LSLG                                         444

SEQ ID NO: 384          moltype = AA  length = 445
FEATURE                 Location/Qualifiers
source                  1..445
                        mol_type = protein
                        organism = synthetic construct
SEQUENCE: 384
EVQLVQSGAE VKKPGASVKV SCKVSGDTLT ELSMHWVRQA PGKGLEWMGT FDPEEGETIY    60
AQKFQGRVTM TEDTSTDTAY MELSSLRSED TAVYYCVTEG LAGVPFDLWG QGTLVTVSSA   120
STKGPSVFPL APCSRSTSES TAALGCLVKD YFPEPVTVSW NSGALTSGVH TFPAVLQSSG   180
LYSLSSVVTV PSSSLGTKTY TCNVDHKPSN TKVDKRVESK YGPPCPPCPA PEFEGGPSVF   240
LFPPKPKDTL MISRTPEVTC VVVDVSQEDP EVQFNWYVDG VEVHNAKTKP REEQFNSTYR   300
VVSVLTVLHQ DWLNGKEYKC KVSNKGLPSS IEKTISKAKG QPREPQVYTL PPSQEEMTKN   360
QVSLTCLVKG FYPSDIAVEW ESNGQPENNY KTTPPVLDSD GSFFLYSRLT VDKSRWQEGN   420
VFSCSVLHEA LHSHYTQKSL SLSLG                                        445

SEQ ID NO: 385          moltype = AA  length = 445
FEATURE                 Location/Qualifiers
source                  1..445
                        mol_type = protein
                        organism = synthetic construct
SEQUENCE: 385
EVQLVQSGAE VKKPGASVKV SCKVSGDTLT ELSMHWVRQA PGKGLEWMGT FDPEEGETIY    60
AQKFQGRVTM TEDTSTDTAY MELSSLRSED TAVYYCVTEG LAGVPFDLWG QGTLVTVSSA   120
STKGPSVFPL APCSRSTSES TAALGCLVKD YFPEPVTVSW NSGALTSGVH TFPAVLQSSG   180
LYSLSSVVTV PSSSLGTKTY TCNVDHKPSN TKVDKRVESK YGPPCPPCPA PEFEGGPSVF   240
LFPPKPKDTL YITREPEVTC VVVDVSQEDP EVQFNWYVDG VEVHNAKTKP REEQFNSTYR   300
VVSVLTVLHQ DWLNGKEYKC KVSNKGLPSS IEKTISKAKG QPREPQVYTL PPSQEEMTKN   360
QVSLTCLVKG FYPSDIAVEW ESNGQPENNY KTTPPVLDSD GSFFLYSRLT VDKSRWQEGN   420
VFSCSVMHEA LHNHYTQKSL SLSLG                                        445

SEQ ID NO: 386          moltype = AA  length = 445
FEATURE                 Location/Qualifiers
source                  1..445
                        mol_type = protein
                        organism = synthetic construct
SEQUENCE: 386
EVQLVQSGAE VKKPGASVKV SCKVSGDTLT ELSMHWVRQA PGKGLEWMGT FDPEEGETIY    60
AQKFQGRVTM TEDTSTDTAY MELSSLRSED TAVYYCVTEG LGGRPFDHWG QGTLVTVSSA   120
STKGPSVFPL APCSRSTSES TAALGCLVKD YFPEPVTVSW NSGALTSGVH TFPAVLQSSG   180
LYSLSSVVTV PSSSLGTKTY TCNVDHKPSN TKVDKRVESK YGPPCPPCPA PEFEGGPSVF   240
LFPPKPKDTL MISRTPEVTC VVVDVSQEDP EVQFNWYVDG VEVHNAKTKP REEQFNSTYR   300
VVSVLTVLHQ DWLNGKEYKC KVSNKGLPSS IEKTISKAKG QPREPQVYTL PPSQEEMTKN   360
QVSLTCLVKG FYPSDIAVEW ESNGQPENNY KTTPPVLDSD GSFFLYSRLT VDKSRWQEGN   420
VFSCSVLHEA LHSHYTQKSL SLSLG                                        445

SEQ ID NO: 387          moltype = AA  length = 483
FEATURE                 Location/Qualifiers
source                  1..483
                        mol_type = protein
                        organism = synthetic construct
```

```
SEQUENCE: 387
MABWITHCON STANTDOMAI NPEANDYTEM UTATIONSEV QLVQSGAEVK KPGASVKVSC    60
KVSGDTLTEL SMHWVRQAPG KGLEWMGTFD PEEGETIYAQ KFQGRVTMTE DTSTDTAYME   120
LSSLRSEDTA VYYCVTEGLG GRPFDHWGQG TLVTVSSAST KGPSVFPLAP CSRSTSESTA   180
ALGCLVKDYF PEPVTVSWNS GALTSGVHTF PAVLQSSGLY SLSSVVTVPS SSLGTKTYTC   240
NVDHKPSNTK VDKRVESKYG PPCPPCPAPE FEGGPSVFLF PPKPKDTLYI TREPEVTCVV   300
VDVSQEDPEV QFNWYVDGVE VHNAKTKPRE EQFNSTYRVV SVLTVLHQDW LNGKEYKCKV   360
SNKGLPSSIE KTISKAKGQP REPQVYTLPP SQEEMTKNQV SLTCLVKGFY PSDIAVEWES   420
NGQPENNYKT TPPVLDSDGS FFLYSRLTVD KSRWQEGNVF SCSVMHEALH NHYTQKSLSL   480
SLG                                                                483

SEQ ID NO: 388           moltype = AA  length = 445
FEATURE                  Location/Qualifiers
source                   1..445
                         mol_type = protein
                         organism = synthetic construct
SEQUENCE: 388
EVQLVQSGAE VKKPGASVKV SCKVSGDTLT ELSMHWVRQA PGKGLEWMGT FDPEEGETIY    60
AQKFQGRVTM TEDTSTDTAY MELSSLRSED TAVYYCVTEG LAGFPFDIWG QGTLVTVSSA   120
STKGPSVFPL APCSRSTSES TAALGCLVKD YFPEPVTVSW NSGALTSGVH TFPAVLQSSG   180
LYSLSSVVTV PSSSLGTKTY TCNVDHKPSN TKVDKRVESK YGPPCPPCPA PEFEGGPSVF   240
LFPPKPKDTL MISRTPEVTC VVVDVSQEDP EVQFNWYVDG VEVHNAKTKP REEQFNSTYR   300
VVSVLTVLHQ DWLNGKEYKC KVSNKGLPSS IEKTISKAKG QPREPQVYTL PPSQEEMTKN   360
QVSLTCLVKG FYPSDIAVEW ESNGQPENNY KTTPPVLDSD GSFFLYSRLT VDKSRWQEGN   420
VFSCSVHEA LHSHYTQKSL SLSLG                                         445

SEQ ID NO: 389           moltype = AA  length = 445
FEATURE                  Location/Qualifiers
source                   1..445
                         mol_type = protein
                         organism = synthetic construct
SEQUENCE: 389
EVQLVQSGAE VKKPGASVKV SCKVSGDTLT ELSMHWVRQA PGKGLEWMGT FDPEEGETIY    60
AQKFQGRVTM TEDTSTDTAY MELSSLRSED TAVYYCVTEG LAGFPFDIWG QGTLVTVSSA   120
STKGPSVFPL APCSRSTSES TAALGCLVKD YFPEPVTVSW NSGALTSGVH TFPAVLQSSG   180
LYSLSSVVTV PSSSLGTKTY TCNVDHKPSN TKVDKRVESK YGPPCPPCPA PEFEGGPSVF   240
LFPPKPKDTL YITREPEVTC VVVDVSQEDP EVQFNWYVDG VEVHNAKTKP REEQFNSTYR   300
VVSVLTVLHQ DWLNGKEYKC KVSNKGLPSS IEKTISKAKG QPREPQVYTL PPSQEEMTKN   360
QVSLTCLVKG FYPSDIAVEW ESNGQPENNY KTTPPVLDSD GSFFLYSRLT VDKSRWQEGN   420
VFSCSVMHEA LHNHYTQKSL SLSLG                                        445

SEQ ID NO: 390           moltype = AA  length = 445
FEATURE                  Location/Qualifiers
source                   1..445
                         mol_type = protein
                         organism = synthetic construct
SEQUENCE: 390
EVQLVQSGAE VKKPGASVKV SCKVSGDTLT ELSMHWVRQA PGKGLEWMGT FDPEEGETIY    60
AQKFQGRVTM TEDTSTDTAY MELSSLRSED TAVYYCVTEG LAWRPTDSWG QGTLVTVSSA   120
STKGPSVFPL APCSRSTSES TAALGCLVKD YFPEPVTVSW NSGALTSGVH TFPAVLQSSG   180
LYSLSSVVTV PSSSLGTKTY TCNVDHKPSN TKVDKRVESK YGPPCPPCPA PEFEGGPSVF   240
LFPPKPKDTL MISRTPEVTC VVVDVSQEDP EVQFNWYVDG VEVHNAKTKP REEQFNSTYR   300
VVSVLTVLHQ DWLNGKEYKC KVSNKGLPSS IEKTISKAKG QPREPQVYTL PPSQEEMTKN   360
QVSLTCLVKG FYPSDIAVEW ESNGQPENNY KTTPPVLDSD GSFFLYSRLT VDKSRWQEGN   420
VFSCSVHEA LHSHYTQKSL SLSLG                                         445

SEQ ID NO: 391           moltype = AA  length = 445
FEATURE                  Location/Qualifiers
source                   1..445
                         mol_type = protein
                         organism = synthetic construct
SEQUENCE: 391
EVQLVQSGAE VKKPGASVKV SCKVSGDTLT ELSMHWVRQA PGKGLEWMGT FDPEEGETIY    60
AQKFQGRVTM TEDTSTDTAY MELSSLRSED TAVYYCVTEG LAWRPTDSWG QGTLVTVSSA   120
STKGPSVFPL APCSRSTSES TAALGCLVKD YFPEPVTVSW NSGALTSGVH TFPAVLQSSG   180
LYSLSSVVTV PSSSLGTKTY TCNVDHKPSN TKVDKRVESK YGPPCPPCPA PEFEGGPSVF   240
LFPPKPKDTL YITREPEVTC VVVDVSQEDP EVQFNWYVDG VEVHNAKTKP REEQFNSTYR   300
VVSVLTVLHQ DWLNGKEYKC KVSNKGLPSS IEKTISKAKG QPREPQVYTL PPSQEEMTKN   360
QVSLTCLVKG FYPSDIAVEW ESNGQPENNY KTTPPVLDSD GSFFLYSRLT VDKSRWQEGN   420
VFSCSVMHEA LHNHYTQKSL SLSLG                                        445

SEQ ID NO: 392           moltype = AA  length = 445
FEATURE                  Location/Qualifiers
source                   1..445
                         mol_type = protein
                         organism = synthetic construct
SEQUENCE: 392
EVQLVQSGAE VKKPGASVKV SCKVSGDTLT ELSMHWVRQA PGKGLEWMGT FDPEEGETIY    60
AQKFQGRVTM TEDTSTDTAY MELSSLRSED TAVYYCVTKG LAWLPYYSWG QGTLVTVSSA   120
```

```
                                        -continued
STKGPSVFPL APCSRSTSES TAALGCLVKD YFPEPVTVSW NSGALTSGVH TFPAVLQSSG     180
LYSLSSVVTV PSSSLGTKTY TCNVDHKPSN TKVDKRVESK YGPPCPPCPA PEFEGGPSVF     240
LFPPKPKDTL MISRTPEVTC VVVDVSQEDP EVQFNWYVDG VEVHNAKTKP REEQFNSTYR     300
VVSVLTVLHQ DWLNGKEYKC KVSNKGLPSS IEKTISKAKG QPREPQVYTL PPSQEEMTKN     360
QVSLTCLVKG FYPSDIAVEW ESNGQPENNY KTTPPVLDSD GSFFLYSRLT VDKSRWQEGN     420
VFSCSVLHEA LHSHYTQKSL SLSLG                                          445

SEQ ID NO: 393          moltype = AA  length = 445
FEATURE                 Location/Qualifiers
source                  1..445
                        mol_type = protein
                        organism = synthetic construct
SEQUENCE: 393
EVQLVQSGAE VKKPGASVKV SCKVSGDTLT ELSMHWVRQA PGKGLEWMGT FDPEEGETIY      60
AQKFQGRVTM TEDTSTDTAY MELSSLRSED TAVYYCVTKG LAWLPYYSWG QGTLVTVSSA     120
STKGPSVFPL APCSRSTSES TAALGCLVKD YFPEPVTVSW NSGALTSGVH TFPAVLQSSG     180
LYSLSSVVTV PSSSLGTKTY TCNVDHKPSN TKVDKRVESK YGPPCPPCPA PEFEGGPSVF     240
LFPPKPKDTL YITREPEVTC VVVDVSQEDP EVQFNWYVDG VEVHNAKTKP REEQFNSTYR     300
VVSVLTVLHQ DWLNGKEYKC KVSNKGLPSS IEKTISKAKG QPREPQVYTL PPSQEEMTKN     360
QVSLTCLVKG FYPSDIAVEW ESNGQPENNY KTTPPVLDSD GSFFLYSRLT VDKSRWQEGN     420
VFSCSVMHEA LHNHYTQKSL SLSLG                                          445

SEQ ID NO: 394          moltype = AA  length = 445
FEATURE                 Location/Qualifiers
source                  1..445
                        mol_type = protein
                        organism = synthetic construct
SEQUENCE: 394
EVQLVQSGAE VKKPGASVKV SCKVSGDTLT ELSMHWVRQA PGKGLEWMGT FDPEEGETIY      60
AQKFQGRVTM TEDTSTDTAY MELSSLRSED TAVYYCVTEG LAGVPFDLWG QGTLVTVSSA     120
STKGPSVFPL APCSRSTSES TAALGCLVKD YFPEPVTVSW NSGALTSGVH TFPAVLQSSG     180
LYSLSSVVTV PSSSLGTKTY TCNVDHKPSN TKVDKRVESK YGPPCPPCPA PEFEGGPSVF     240
LFPPKPKDTL MISRTPEVTC VVVDVSQEDP EVQFNWYVDG VEVHNAKTKP REEQFNSTYR     300
VVSVLTVLHQ DWLNGKEYKC KVSNKGLPSS IEKTISKAKG QPREPQVYTL PPSQEEMTKN     360
QVSLTCLVKG FYPSDIAVEW ESNGQPENNY KTTPPVLDSD GSFFLYSRLT VDKSRWQEGN     420
VFSCSVLHEA LHSHYTQKSL SLSLG                                          445

SEQ ID NO: 395          moltype = AA  length = 445
FEATURE                 Location/Qualifiers
source                  1..445
                        mol_type = protein
                        organism = synthetic construct
SEQUENCE: 395
EVQLVQSGAE VKKPGASVKV SCKVSGDTLT ELSMHWVRQA PGKGLEWMGT FDPEEGETIY      60
AQKFQGRVTM TEDTSTDTAY MELSSLRSED TAVYYCVTEG LAGVPFDLWG QGTLVTVSSA     120
STKGPSVFPL APCSRSTSES TAALGCLVKD YFPEPVTVSW NSGALTSGVH TFPAVLQSSG     180
LYSLSSVVTV PSSSLGTKTY TCNVDHKPSN TKVDKRVESK YGPPCPPCPA PEFEGGPSVF     240
LFPPKPKDTL YITREPEVTC VVVDVSQEDP EVQFNWYVDG VEVHNAKTKP REEQFNSTYR     300
VVSVLTVLHQ DWLNGKEYKC KVSNKGLPSS IEKTISKAKG QPREPQVYTL PPSQEEMTKN     360
QVSLTCLVKG FYPSDIAVEW ESNGQPENNY KTTPPVLDSD GSFFLYSRLT VDKSRWQEGN     420
VFSCSVMHEA LHNHYTQKSL SLSLG                                          445

SEQ ID NO: 396          moltype = AA  length = 445
FEATURE                 Location/Qualifiers
source                  1..445
                        mol_type = protein
                        organism = synthetic construct
SEQUENCE: 396
EVQLVQSGAE VKKPGASVKV SCKVSGDTLT ELSMHWVRQA PGKGLEWMGT FDPEEGETIY      60
AQKFQGRVTM TEDTSTDTAY MELSSLRSED TAVYYCVTEG EAGRPFDAWG QGTLVTVSSA     120
STKGPSVFPL APCSRSTSES TAALGCLVKD YFPEPVTVSW NSGALTSGVH TFPAVLQSSG     180
LYSLSSVVTV PSSSLGTKTY TCNVDHKPSN TKVDKRVESK YGPPCPPCPA PEFEGGPSVF     240
LFPPKPKDTL MISRTPEVTC VVVDVSQEDP EVQFNWYVDG VEVHNAKTKP REEQFNSTYR     300
VVSVLTVLHQ DWLNGKEYKC KVSNKGLPSS IEKTISKAKG QPREPQVYTL PPSQEEMTKN     360
QVSLTCLVKG FYPSDIAVEW ESNGQPENNY KTTPPVLDSD GSFFLYSRLT VDKSRWQEGN     420
VFSCSVLHEA LHSHYTQKSL SLSLG                                          445

SEQ ID NO: 397          moltype = AA  length = 445
FEATURE                 Location/Qualifiers
source                  1..445
                        mol_type = protein
                        organism = synthetic construct
SEQUENCE: 397
EVQLVQSGAE VKKPGASVKV SCKVSGDTLT ELSMHWVRQA PGKGLEWMGT FDPEEGETIY      60
AQKFQGRVTM TEDTSTDTAY MELSSLRSED TAVYYCVTEG EAGRPFDAWG QGTLVTVSSA     120
STKGPSVFPL APCSRSTSES TAALGCLVKD YFPEPVTVSW NSGALTSGVH TFPAVLQSSG     180
LYSLSSVVTV PSSSLGTKTY TCNVDHKPSN TKVDKRVESK YGPPCPPCPA PEFEGGPSVF     240
LFPPKPKDTL YITREPEVTC VVVDVSQEDP EVQFNWYVDG VEVHNAKTKP REEQFNSTYR     300
VVSVLTVLHQ DWLNGKEYKC KVSNKGLPSS IEKTISKAKG QPREPQVYTL PPSQEEMTKN     360
```

```
QVSLTCLVKG FYPSDIAVEW ESNGQPENNY KTTPPVLDSD GSFFLYSRLT VDKSRWQEGN    420
VFSCSVMHEA LHNHYTQKSL SLSLG                                          445

SEQ ID NO: 398             moltype = AA  length = 445
FEATURE                    Location/Qualifiers
source                     1..445
                           mol_type = protein
                           organism = synthetic construct
SEQUENCE: 398
EVQLVQSGAE VKKPGASVKV SCKVSGDTLT ELSMHWVRQA PGKGLEWMGT FDPEEGETIY     60
AQKFQGRVTM TEDTSTDTAY MELSSLRSED TAVYYCVTEG LAGRPYDVWG QGTLVTVSSA    120
STKGPSVFPL APCSRSTSES TAALGCLVKD YFPEPVTVSW NSGALTSGVH TFPAVLQSSG    180
LYSLSSVVTV PSSSLGTKTY TCNVDHKPSN TKVDKRVESK YGPPCPPCPA PEFEGGPSVF    240
LFPPKPKDTL MISRTPEVTC VVVDVSQEDP EVQFNWYVDG VEVHNAKTKP REEQFNSTYR    300
VVSVLTVLHQ DWLNGKEYKC KVSNKGLPSS IEKTISKAKG QPREPQVYTL PPSQEEMTKN    360
QVSLTCLVKG FYPSDIAVEW ESNGQPENNY KTTPPVLDSD GSFFLYSRLT VDKSRWQEGN    420
VFSCSVMHEA LHSHYTQKSL SLSLG                                          445

SEQ ID NO: 399             moltype = AA  length = 445
FEATURE                    Location/Qualifiers
source                     1..445
                           mol_type = protein
                           organism = synthetic construct
SEQUENCE: 399
EVQLVQSGAE VKKPGASVKV SCKVSGDTLT ELSMHWVRQA PGKGLEWMGT FDPEEGETIY     60
AQKFQGRVTM TEDTSTDTAY MELSSLRSED TAVYYCVTEG LAGRPYDVWG QGTLVTVSSA    120
STKGPSVFPL APCSRSTSES TAALGCLVKD YFPEPVTVSW NSGALTSGVH TFPAVLQSSG    180
LYSLSSVVTV PSSSLGTKTY TCNVDHKPSN TKVDKRVESK YGPPCPPCPA PEFEGGPSVF    240
LFPPKPKDTL YITREPEVTC VVVDVSQEDP EVQFNWYVDG VEVHNAKTKP REEQFNSTYR    300
VVSVLTVLHQ DWLNGKEYKC KVSNKGLPSS IEKTISKAKG QPREPQVYTL PPSQEEMTKN    360
QVSLTCLVKG FYPSDIAVEW ESNGQPENNY KTTPPVLDSD GSFFLYSRLT VDKSRWQEGN    420
VFSCSVMHEA LHNHYTQKSL SLSLG                                          445

SEQ ID NO: 400             moltype = AA  length = 445
FEATURE                    Location/Qualifiers
source                     1..445
                           mol_type = protein
                           organism = synthetic construct
SEQUENCE: 400
EVQLVQSGAE VKKPGASVKV SCKVSGDTLT ELSMHWVRQA PGKGLEWMGT FDPEEGETIY     60
AQKFQGRVTM TEDTSTDTAY MELSYLRSED TAVYYCVTEG LAGIPFDSWG QGTLVTVSSA    120
STKGPSVFPL APCSRSTSES TAALGCLVKD YFPEPVTVSW NSGALTSGVH TFPAVLQSSG    180
LYSLSSVVTV PSSSLGTKTY TCNVDHKPSN TKVDKRVESK YGPPCPPCPA PEFEGGPSVF    240
LFPPKPKDTL MISRTPEVTC VVVDVSQEDP EVQFNWYVDG VEVHNAKTKP REEQFNSTYR    300
VVSVLTVLHQ DWLNGKEYKC KVSNKGLPSS IEKTISKAKG QPREPQVYTL PPSQEEMTKN    360
QVSLTCLVKG FYPSDIAVEW ESNGQPENNY KTTPPVLDSD GSFFLYSRLT VDKSRWQEGN    420
VFSCSVMHEA LHSHYTQKSL SLSLG                                          445

SEQ ID NO: 401             moltype = AA  length = 445
FEATURE                    Location/Qualifiers
source                     1..445
                           mol_type = protein
                           organism = synthetic construct
SEQUENCE: 401
EVQLVQSGAE VKKPGASVKV SCKVSGDTLT ELSMHWVRQA PGKGLEWMGT FDPEEGETIY     60
AQKFQGRVTM TEDTSTDTAY MELSYLRSED TAVYYCVTEG LAGIPFDSWG QGTLVTVSSA    120
STKGPSVFPL APCSRSTSES TAALGCLVKD YFPEPVTVSW NSGALTSGVH TFPAVLQSSG    180
LYSLSSVVTV PSSSLGTKTY TCNVDHKPSN TKVDKRVESK YGPPCPPCPA PEFEGGPSVF    240
LFPPKPKDTL YITREPEVTC VVVDVSQEDP EVQFNWYVDG VEVHNAKTKP REEQFNSTYR    300
VVSVLTVLHQ DWLNGKEYKC KVSNKGLPSS IEKTISKAKG QPREPQVYTL PPSQEEMTKN    360
QVSLTCLVKG FYPSDIAVEW ESNGQPENNY KTTPPVLDSD GSFFLYSRLT VDKSRWQEGN    420
VFSCSVMHEA LHNHYTQKSL SLSLG                                          445

SEQ ID NO: 402             moltype = AA  length = 445
FEATURE                    Location/Qualifiers
source                     1..445
                           mol_type = protein
                           organism = synthetic construct
SEQUENCE: 402
EVQLVQSGAE VKKPGASVKV SCKVSGDTLT ELSMHWVRQA PGKGLEWMGT FDPEEGETIY     60
AQKFQGRVTM TEDTSTDTAY MELSYLRSED TAVYYCVTEG LAGIPFDSWG QGTLVTVSSA    120
STKGPSVFPL APCSRSTSES TAALGCLVKD YFPEPVTVSW NSGALTSGVH TFPAVLQSSG    180
LYSLSSVVTV PSSSLGTKTY TCNVDHKPSN TKVDKRVESK YGPPCPPCPA PEFEGGPSVF    240
LFPPKPKDTL MISRTPEVTC VVVDVSQEDP EVQFNWYVDG VEVHNAKTKP REEQFNSTYR    300
VVSVLTVLHQ DWLNGKEYKC KVSNKGLPSS IEKTISKAKG QPREPQVYTL PPSQEEMTKN    360
QVSLTCLVKG FYPSDIAVEW ESNGQPENNY KTTPPVLDSD GSFFLYSRLT VDKSRWQEGN    420
VFSCSVMHEA LHNHYTQKSL SLSLG                                          445

SEQ ID NO: 403             moltype = AA  length = 445
```

```
FEATURE                 Location/Qualifiers
source                  1..445
                        mol_type = protein
                        organism = synthetic construct
SEQUENCE: 403
EVQLVQSGAE VKKPGASVKV SCKVSGDTLT ELSMHWVRQA PGKGLEWMGT FDPEEGETIY    60
AQKFQGRVTM TEDTSTDTAY MELSYLRSED TAVYYCVTEG LAGIPFDSWG QGTLVTVSSA   120
STKGPSVFPL APCSRSTSES TAALGCLVKD YFPEPVTVSW NSGALTSGVH TFPAVLQSSG   180
LYSLSSVVTV PSSSLGTKTY TCNVDHKPSN TKVDKRVESK YGPPCPPCPA PEFEGGPSVF   240
LFPPKPKDTL YITREPEVTC VVVDVSQEDP EVQFNWYVDG VEVHNAKTKP REEQFNSTYR   300
VVSVLTVLHQ DWLNGKEYKC KVSNKGLPSS IEKTISKAKG QPREPQVYTL PPSQEEMTKN   360
QVSLTCLVKG FYPSDIAVEW ESNGQPENNY KTTPPVLDSD GSFFLYSRLT VDKSRWQEGN   420
VFSCSVMHEA LHNHYTQKSL SLSLG                                        445

SEQ ID NO: 404          moltype = AA  length = 451
FEATURE                 Location/Qualifiers
source                  1..451
                        mol_type = protein
                        organism = synthetic construct
SEQUENCE: 404
QVQLVESGGG VVRPGGSLRL SCAASGFTFD DYGMSWVRQA PGKGLEWVSG INWEGGSTGY    60
ADSVKGRFTI SRDNAKNSLY LQMNSLRAED TALYYCARDE QLGGTTYYYY YMDVWGKGTT   120
VTVSSASTKG PSVFPLAPCS RSTSESTAAL GCLVKDYFPE PVTVSWNSGA LTSGVHTFPA   180
VLQSSGLYSL SSVVTVPSSS LGTKTYTCNV DHKPSNTKVD KRVESKYGPP CPPCPAPEFE   240
GGPSVFLFPP KPKDTLMISR TPEVTCVVVD VSQEDPEVQF NWYVDGVEVH NAKTKPREEQ   300
FNSTYRVVSV LTVLHQDWLN GKEYKCKVSN KGLPSSIEKT ISKAKGQPRE PQVYTLPPSQ   360
EEMTKNQVSL TCLVKGFYPS DIAVEWESNG QPENNYKTTP PVLDSDGSFF LYSRLTVDKS   420
RWQEGNVFSC SVLHEALHSH YTQKSLSLSL G                                 451

SEQ ID NO: 405          moltype = AA  length = 451
FEATURE                 Location/Qualifiers
source                  1..451
                        mol_type = protein
                        organism = synthetic construct
SEQUENCE: 405
QVQLVESGGG VVRPGGSLRL SCAASGFTFD DYGMSWVRQA PGKGLEWVSG INWEGGSTGY    60
ADSVKGRFTI SRDNAKNSLY LQMNSLRAED TALYYCARDE QLGGTTYYYY YMDVWGKGTT   120
VTVSSASTKG PSVFPLAPCS RSTSESTAAL GCLVKDYFPE PVTVSWNSGA LTSGVHTFPA   180
VLQSSGLYSL SSVVTVPSSS LGTKTYTCNV DHKPSNTKVD KRVESKYGPP CPPCPAPEFE   240
GGPSVFLFPP KPKDTLYITR EPEVTCVVVD VSQEDPEVQF NWYVDGVEVH NAKTKPREEQ   300
FNSTYRVVSV LTVLHQDWLN GKEYKCKVSN KGLPSSIEKT ISKAKGQPRE PQVYTLPPSQ   360
EEMTKNQVSL TCLVKGFYPS DIAVEWESNG QPENNYKTTP PVLDSDGSFF LYSRLTVDKS   420
RWQEGNVFSC SVMHEALHNH YTQKSLSLSL G                                 451

SEQ ID NO: 406          moltype = AA  length = 451
FEATURE                 Location/Qualifiers
source                  1..451
                        mol_type = protein
                        organism = synthetic construct
SEQUENCE: 406
QVQLVESGGG VVRPGGSLRL SCAASGFTFD DYGMSWVRQA PGKGLEWVSG INWEGGSTGY    60
ADSVKGRFTI SRDNAKNSLY LQMNSLRAED TALYYCARDE QLGGKYYYYY YMDVWGKGTT   120
VTVSSASTKG PSVFPLAPCS RSTSESTAAL GCLVKDYFPE PVTVSWNSGA LTSGVHTFPA   180
VLQSSGLYSL SSVVTVPSSS LGTKTYTCNV DHKPSNTKVD KRVESKYGPP CPPCPAPEFE   240
GGPSVFLFPP KPKDTLMISR TPEVTCVVVD VSQEDPEVQF NWYVDGVEVH NAKTKPREEQ   300
FNSTYRVVSV LTVLHQDWLN GKEYKCKVSN KGLPSSIEKT ISKAKGQPRE PQVYTLPPSQ   360
EEMTKNQVSL TCLVKGFYPS DIAVEWESNG QPENNYKTTP PVLDSDGSFF LYSRLTVDKS   420
RWQEGNVFSC SVLHEALHSH YTQKSLSLSL G                                 451

SEQ ID NO: 407          moltype = AA  length = 451
FEATURE                 Location/Qualifiers
source                  1..451
                        mol_type = protein
                        organism = synthetic construct
SEQUENCE: 407
QVQLVESGGG VVRPGGSLRL SCAASGFTFD DYGMSWVRQA PGKGLEWVSG INWEGGSTGY    60
ADSVKGRFTI SRDNAKNSLY LQMNSLRAED TALYYCARDE QLGGKYYYYY YMDVWGKGTT   120
VTVSSASTKG PSVFPLAPCS RSTSESTAAL GCLVKDYFPE PVTVSWNSGA LTSGVHTFPA   180
VLQSSGLYSL SSVVTVPSSS LGTKTYTCNV DHKPSNTKVD KRVESKYGPP CPPCPAPEFE   240
GGPSVFLFPP KPKDTLYITR EPEVTCVVVD VSQEDPEVQF NWYVDGVEVH NAKTKPREEQ   300
FNSTYRVVSV LTVLHQDWLN GKEYKCKVSN KGLPSSIEKT ISKAKGQPRE PQVYTLPPSQ   360
EEMTKNQVSL TCLVKGFYPS DIAVEWESNG QPENNYKTTP PVLDSDGSFF LYSRLTVDKS   420
RWQEGNVFSC SVMHEALHNH YTQKSLSLSL G                                 451

SEQ ID NO: 408          moltype = AA  length = 451
FEATURE                 Location/Qualifiers
source                  1..451
                        mol_type = protein
                        organism = synthetic construct
```

```
SEQUENCE: 408
QVQLVESGGG VVRPGGSLRL SCAASGFTFD DYGMSWVRQA PGKGLEWVSG INWEGGSTGY  60
ADSVKGRFTI SRDNAKNSLY LQMNSLRAED TALYYCARDE QLGGQTYYYY YMDVWGKGTT 120
VTVSSASTKG PSVFPLAPCS RSTSESTAAL GCLVKDYFPE PVTVSWNSGA LTSGVHTFPA 180
VLQSSGLYSL SSVVTVPSSS LGTKTYTCNV DHKPSNTKVD KRVESKYGPP CPPCPAPEFE 240
GGPSVFLFPP KPKDTLMISR TPEVTCVVVD VSQEDPEVQF NWYVDGVEVH NAKTKPREEQ 300
FNSTYRVVSV LTVLHQDWLN GKEYKCKVSN KGLPSSIEKT ISKAKGQPRE PQVYTLPPSQ 360
EEMTKNQVSL TCLVKGFYPS DIAVEWESNG QPENNYKTTP PVLDSDGSFF LYSRLTVDKS 420
RWQEGNVFSC SVLHEALHSH YTQKSLSLSL G                                451

SEQ ID NO: 409          moltype = AA   length = 451
FEATURE                 Location/Qualifiers
source                  1..451
                        mol_type = protein
                        organism = synthetic construct
SEQUENCE: 409
QVQLVESGGG VVRPGGSLRL SCAASGFTFD DYGMSWVRQA PGKGLEWVSG INWEGGSTGY  60
ADSVKGRFTI SRDNAKNSLY LQMNSLRAED TALYYCARDE QLGGQTYYYY YMDVWGKGTT 120
VTVSSASTKG PSVFPLAPCS RSTSESTAAL GCLVKDYFPE PVTVSWNSGA LTSGVHTFPA 180
VLQSSGLYSL SSVVTVPSSS LGTKTYTCNV DHKPSNTKVD KRVESKYGPP CPPCPAPEFE 240
GGPSVFLFPP KPKDTLYITR EPEVTCVVVD VSQEDPEVQF NWYVDGVEVH NAKTKPREEQ 300
FNSTYRVVSV LTVLHQDWLN GKEYKCKVSN KGLPSSIEKT ISKAKGQPRE PQVYTLPPSQ 360
EEMTKNQVSL TCLVKGFYPS DIAVEWESNG QPENNYKTTP PVLDSDGSFF LYSRLTVDKS 420
RWQEGNVFSC SVMHEALHNH YTQKSLSLSL G                                451

SEQ ID NO: 410          moltype = AA   length = 451
FEATURE                 Location/Qualifiers
source                  1..451
                        mol_type = protein
                        organism = synthetic construct
SEQUENCE: 410
QVQLVESGGG VVRPGGSLRL SCAASGFTFD DYGMSWVRQA PGKGLEWVSG INWEGGSTGY  60
ADSVKGRFTI SRDNAKNSLY LQMNSLRAED TALYYCARDE QLGGTTYYYY YMDVWGKGTT 120
VTVSSASTKG PSVFPLAPCS RSTSESTAAL GCLVKDYFPE PVTVSWNSGA LTSGVHTFPA 180
VLQSSGLYSL SSVVTVPSSS LGTKTYTCNV DHKPSNTKVD KRVESKYGPP CPPCPAPEFE 240
GGPSVFLFPP KPKDTLMISR TPEVTCVVVD VSQEDPEVQF NWYVDGVEVH NAKTKPREEQ 300
FNSTYRVVSV LTVLHQDWLN GKEYKCKVSN KGLPSSIEKT ISKAKGQPRE PQVYTLPPSQ 360
EEMTKNQVSL TCLVKGFYPS DIAVEWESNG QPENNYKTTP PVLDSDGSFF LYSRLTVDKS 420
RWQEGNVFSC SVLHEALHSH YTQKSLSLSL G                                451

SEQ ID NO: 411          moltype = AA   length = 451
FEATURE                 Location/Qualifiers
source                  1..451
                        mol_type = protein
                        organism = synthetic construct
SEQUENCE: 411
QVQLVESGGG VVRPGGSLRL SCAASGFTFD DYGMSWVRQA PGKGLEWVSG INWEGGSTGY  60
ADSVKGRFTI SRDNAKNSLY LQMNSLRAED TALYYCARDE QLGGTTYYYY YMDVWGKGTT 120
VTVSSASTKG PSVFPLAPCS RSTSESTAAL GCLVKDYFPE PVTVSWNSGA LTSGVHTFPA 180
VLQSSGLYSL SSVVTVPSSS LGTKTYTCNV DHKPSNTKVD KRVESKYGPP CPPCPAPEFE 240
GGPSVFLFPP KPKDTLYITR EPEVTCVVVD VSQEDPEVQF NWYVDGVEVH NAKTKPREEQ 300
FNSTYRVVSV LTVLHQDWLN GKEYKCKVSN KGLPSSIEKT ISKAKGQPRE PQVYTLPPSQ 360
EEMTKNQVSL TCLVKGFYPS DIAVEWESNG QPENNYKTTP PVLDSDGSFF LYSRLTVDKS 420
RWQEGNVFSC SVMHEALHNH YTQKSLSLSL G                                451

SEQ ID NO: 412          moltype = AA   length = 451
FEATURE                 Location/Qualifiers
source                  1..451
                        mol_type = protein
                        organism = synthetic construct
SEQUENCE: 412
QVQLVESGGG VVRPGGSLRL SCAASGFTFD DYGMSWVRQA PGKGLEWVSG INWEGGSTGY  60
ADSVKGRFTI SRDNAKNSLY LQMNSLRAED TALYYCARDE QLGGIKYYYY YMDVWGKGTT 120
VTVSSASTKG PSVFPLAPCS RSTSESTAAL GCLVKDYFPE PVTVSWNSGA LTSGVHTFPA 180
VLQSSGLYSL SSVVTVPSSS LGTKTYTCNV DHKPSNTKVD KRVESKYGPP CPPCPAPEFE 240
GGPSVFLFPP KPKDTLMISR TPEVTCVVVD VSQEDPEVQF NWYVDGVEVH NAKTKPREEQ 300
FNSTYRVVSV LTVLHQDWLN GKEYKCKVSN KGLPSSIEKT ISKAKGQPRE PQVYTLPPSQ 360
EEMTKNQVSL TCLVKGFYPS DIAVEWESNG QPENNYKTTP PVLDSDGSFF LYSRLTVDKS 420
RWQEGNVFSC SVLHEALHSH YTQKSLSLSL G                                451

SEQ ID NO: 413          moltype = AA   length = 451
FEATURE                 Location/Qualifiers
source                  1..451
                        mol_type = protein
                        organism = synthetic construct
SEQUENCE: 413
QVQLVESGGG VVRPGGSLRL SCAASGFTFD DYGMSWVRQA PGKGLEWVSG INWEGGSTGY  60
ADSVKGRFTI SRDNAKNSLY LQMNSLRAED TALYYCARDE QLGGIKYYYY YMDVWGKGTT 120
VTVSSASTKG PSVFPLAPCS RSTSESTAAL GCLVKDYFPE PVTVSWNSGA LTSGVHTFPA 180
```

```
VLQSSGLYSL SSVVTVPSSS LGTKTYTCNV DHKPSNTKVD KRVESKYGPP CPPCPAPEFE    240
GGPSVFLFPP KPKDTLYITR EPEVTCVVVD VSQEDPEVQF NWYVDGVEVH NAKTKPREEQ    300
FNSTYRVVSV LTVLHQDWLN GKEYKCKVSN KGLPSSIEKT ISKAKGQPRE PQVYTLPPSQ    360
EEMTKNQVSL TCLVKGFYPS DIAVEWESNG QPENNYKTTP PVLDSDGSFF LYSRLTVDKS    420
RWQEGNVFSC SVMHEALHNH YTQKSLSLSL G                                  451

SEQ ID NO: 414         moltype = AA  length = 451
FEATURE                Location/Qualifiers
source                 1..451
                       mol_type = protein
                       organism = synthetic construct
SEQUENCE: 414
QVQLVESGGG VVRPGGSLRL SCAASGFTFD DYGMSWVRQA PGKGLEWVSG INWEGGSTGY    60
ADSVKGRFSI SRDNAKNSLY LQMNSLRAED TALYYCARDE QLGGLKYYYY YMDVWGKGTT    120
VTVSSASTKG PSVFPLAPCS RSTSESTAAL GCLVKDYFPE PVTVSWNSGA LTSGVHTFPA    180
VLQSSGLYSL SSVVTVPSSS LGTKTYTCNV DHKPSNTKVD KRVESKYGPP CPPCPAPEFE    240
GGPSVFLFPP KPKDTLMISR TPEVTCVVVD VSQEDPEVQF NWYVDGVEVH NAKTKPREEQ    300
FNSTYRVVSV LTVLHQDWLN GKEYKCKVSN KGLPSSIEKT ISKAKGQPRE PQVYTLPPSQ    360
EEMTKNQVSL TCLVKGFYPS DIAVEWESNG QPENNYKTTP PVLDSDGSFF LYSRLTVDKS    420
RWQEGNVFSC SVLHEALHSH YTQKSLSLSL G                                  451

SEQ ID NO: 415         moltype = AA  length = 451
FEATURE                Location/Qualifiers
source                 1..451
                       mol_type = protein
                       organism = synthetic construct
SEQUENCE: 415
QVQLVESGGG VVRPGGSLRL SCAASGFTFD DYGMSWVRQA PGKGLEWVSG INWEGGSTGY    60
ADSVKGRFSI SRDNAKNSLY LQMNSLRAED TALYYCARDE QLGGLKYYYY YMDVWGKGTT    120
VTVSSASTKG PSVFPLAPCS RSTSESTAAL GCLVKDYFPE PVTVSWNSGA LTSGVHTFPA    180
VLQSSGLYSL SSVVTVPSSS LGTKTYTCNV DHKPSNTKVD KRVESKYGPP CPPCPAPEFE    240
GGPSVFLFPP KPKDTLYITR EPEVTCVVVD VSQEDPEVQF NWYVDGVEVH NAKTKPREEQ    300
FNSTYRVVSV LTVLHQDWLN GKEYKCKVSN KGLPSSIEKT ISKAKGQPRE PQVYTLPPSQ    360
EEMTKNQVSL TCLVKGFYPS DIAVEWESNG QPENNYKTTP PVLDSDGSFF LYSRLTVDKS    420
RWQEGNVFSC SVMHEALHNH YTQKSLSLSL G                                  451

SEQ ID NO: 416         moltype = AA  length = 451
FEATURE                Location/Qualifiers
source                 1..451
                       mol_type = protein
                       organism = synthetic construct
SEQUENCE: 416
QVQLVESGGG VVRPGGSLRL SCAASGFTFD DYGMSWVRQA PGKGLEWVSG INWEGGSTGY    60
ADSVKGRFTI SRDNAKNSLY LQMNSLRAED TALYYCARDE QLGGKVYYYY YMDVWGKGTT    120
VTVSSASTKG PSVFPLAPCS RSTSESTAAL GCLVKDYFPE PVTVSWNSGA LTSGVHTFPA    180
VLQSSGLYSL SSVVTVPSSS LGTKTYTCNV DHKPSNTKVD KRVESKYGPP CPPCPAPEFE    240
GGPSVFLFPP KPKDTLMISR TPEVTCVVVD VSQEDPEVQF NWYVDGVEVH NAKTKPREEQ    300
FNSTYRVVSV LTVLHQDWLN GKEYKCKVSN KGLPSSIEKT ISKAKGQPRE PQVYTLPPSQ    360
EEMTKNQVSL TCLVKGFYPS DIAVEWESNG QPENNYKTTP PVLDSDGSFF LYSRLTVDKS    420
RWQEGNVFSC SVLHEALHSH YTQKSLSLSL G                                  451

SEQ ID NO: 417         moltype = AA  length = 451
FEATURE                Location/Qualifiers
source                 1..451
                       mol_type = protein
                       organism = synthetic construct
SEQUENCE: 417
QVQLVESGGG VVRPGGSLRL SCAASGFTFD DYGMSWVRQA PGKGLEWVSG INWEGGSTGY    60
ADSVKGRFTI SRDNAKNSLY LQMNSLRAED TALYYCARDE QLGGKVYYYY YMDVWGKGTT    120
VTVSSASTKG PSVFPLAPCS RSTSESTAAL GCLVKDYFPE PVTVSWNSGA LTSGVHTFPA    180
VLQSSGLYSL SSVVTVPSSS LGTKTYTCNV DHKPSNTKVD KRVESKYGPP CPPCPAPEFE    240
GGPSVFLFPP KPKDTLYITR EPEVTCVVVD VSQEDPEVQF NWYVDGVEVH NAKTKPREEQ    300
FNSTYRVVSV LTVLHQDWLN GKEYKCKVSN KGLPSSIEKT ISKAKGQPRE PQVYTLPPSQ    360
EEMTKNQVSL TCLVKGFYPS DIAVEWESNG QPENNYKTTP PVLDSDGSFF LYSRLTVDKS    420
RWQEGNVFSC SVMHEALHNH YTQKSLSLSL G                                  451

SEQ ID NO: 418         moltype = AA  length = 451
FEATURE                Location/Qualifiers
source                 1..451
                       mol_type = protein
                       organism = synthetic construct
SEQUENCE: 418
QVQLVESGGG VVRPGGSLRL SCAASGFTFD DYGMSWVRQA PGKGLEWVSG INWEGGSTGY    60
ADSVKGRFSI SRDNAKNSLY LQMNSLRAED TALYYCARDE QLGGLKYYYY YMDVWGKGTT    120
VTVSSASTKG PSVFPLAPCS RSTSESTAAL GCLVKDYFPE PVTVSWNSGA LTSGVHTFPA    180
VLQSSGLYSL SSVVTVPSSS LGTKTYTCNV DHKPSNTKVD KRVESKYGPP CPPCPAPEFE    240
GGPSVFLFPP KPKDTLMISR TPEVTCVVVD VSQEDPEVQF NWYVDGVEVH NAKTKPREEQ    300
FNSTYRVVSV LTVLHQDWLN GKEYKCKVSN KGLPSSIEKT ISKAKGQPRE PQVYTLPPSQ    360
EEMTKNQVSL TCLVKGFYPS DIAVEWESNG QPENNYKTTP PVLDSDGSFF LYSRLTVDKS    420
```

```
RWQEGNVFSC SVLHEALHSH YTQKSLSLSL G                           451

SEQ ID NO: 419          moltype = AA  length = 451
FEATURE                 Location/Qualifiers
source                  1..451
                        mol_type = protein
                        organism = synthetic construct
SEQUENCE: 419
QVQLVESGGG VVRPGGSLRL SCAASGFTFD DYGMSWVRQA PGKGLEWVSG INWEGGSTGY  60
ADSVKGRFSI SRDNAKNSLY LQMNSLRAED TALYYCARDE QLGGLKYYYY YMDVWGKGTT 120
VTVSSASTKG PSVFPLAPCS RSTSESTAAL GCLVKDYFPE PVTVSWNSGA LTSGVHTFPA 180
VLQSSGLYSL SSVVTVPSSS LGTKTYTCNV DHKPSNTKVD KRVESKYGPP CPPCPAPEFE 240
GGPSVFLFPP KPKDTLYITR EPEVTCVVVD VSQEDPEVQF NWYVDGVEVH NAKTKPREEQ 300
FNSTYRVVSV LTVLHQDWLN GKEYKCKVSN KGLPSSIEKT ISKAKGQPRE PQVYTLPPSQ 360
EEMTKNQVSL TCLVKGFYPS DIAVEWESNG QPENNYKTTP PVLDSDGSFF LYSRLTVDKS 420
RWQEGNVFSC SVMHEALHNH YTQKSLSLSL G                           451

SEQ ID NO: 420          moltype = AA  length = 451
FEATURE                 Location/Qualifiers
source                  1..451
                        mol_type = protein
                        organism = synthetic construct
SEQUENCE: 420
QVQLVESGGG VVRPGGSLRL SCAASGFTFD DYGMSWVRQA PGKGLEWVSG INWEGGSTGY  60
ADSVKGRFTI SRDNAKNSLY LQMNSLRAED TALYYCARDE QLGGNHYYYY YMDAWGKGTT 120
VTVSSASTKG PSVFPLAPCS RSTSESTAAL GCLVKDYFPE PVTVSWNSGA LTSGVHTFPA 180
VLQSSGLYSL SSVVTVPSSS LGTKTYTCNV DHKPSNTKVD KRVESKYGPP CPPCPAPEFE 240
GGPSVFLFPP KPKDTLMISR TPEVTCVVVD VSQEDPEVQF NWYVDGVEVH NAKTKPREEQ 300
FNSTYRVVSV LTVLHQDWLN GKEYKCKVSN KGLPSSIEKT ISKAKGQPRE PQVYTLPPSQ 360
EEMTKNQVSL TCLVKGFYPS DIAVEWESNG QPENNYKTTP PVLDSDGSFF LYSRLTVDKS 420
RWQEGNVFSC SVLHEALHSH YTQKSLSLSL G                           451

SEQ ID NO: 421          moltype = AA  length = 451
FEATURE                 Location/Qualifiers
source                  1..451
                        mol_type = protein
                        organism = synthetic construct
SEQUENCE: 421
QVQLVESGGG VVRPGGSLRL SCAASGFTFD DYGMSWVRQA PGKGLEWVSG INWEGGSTGY  60
ADSVKGRFTI SRDNAKNSLY LQMNSLRAED TALYYCARDE QLGGNHYYYY YMDAWGKGTT 120
VTVSSASTKG PSVFPLAPCS RSTSESTAAL GCLVKDYFPE PVTVSWNSGA LTSGVHTFPA 180
VLQSSGLYSL SSVVTVPSSS LGTKTYTCNV DHKPSNTKVD KRVESKYGPP CPPCPAPEFE 240
GGPSVFLFPP KPKDTLYITR EPEVTCVVVD VSQEDPEVQF NWYVDGVEVH NAKTKPREEQ 300
FNSTYRVVSV LTVLHQDWLN GKEYKCKVSN KGLPSSIEKT ISKAKGQPRE PQVYTLPPSQ 360
EEMTKNQVSL TCLVKGFYPS DIAVEWESNG QPENNYKTTP PVLDSDGSFF LYSRLTVDKS 420
RWQEGNVFSC SVMHEALHNH YTQKSLSLSL G                           451

SEQ ID NO: 422          moltype = AA  length = 451
FEATURE                 Location/Qualifiers
source                  1..451
                        mol_type = protein
                        organism = synthetic construct
SEQUENCE: 422
QVQLVESGGG VVRPGGSLRL SCAASGFTFD DYGMSWVRQA PGKGLEWVSG INWEGGSTGY  60
ADSVKGRFTI SRDNAKNSLY LQMNSLRAED TALYYCARDE QLGGRHYYYY YMDVWGKGTT 120
VTVSSASTKG PSVFPLAPCS RSTSESTAAL GCLVKDYFPE PVTVSWNSGA LTSGVHTFPA 180
VLQSSGLYSL SSVVTVPSSS LGTKTYTCNV DHKPSNTKVD KRVESKYGPP CPPCPAPEFE 240
GGPSVFLFPP KPKDTLMISR TPEVTCVVVD VSQEDPEVQF NWYVDGVEVH NAKTKPREEQ 300
FNSTYRVVSV LTVLHQDWLN GKEYKCKVSN KGLPSSIEKT ISKAKGQPRE PQVYTLPPSQ 360
EEMTKNQVSL TCLVKGFYPS DIAVEWESNG QPENNYKTTP PVLDSDGSFF LYSRLTVDKS 420
RWQEGNVFSC SVLHEALHSH YTQKSLSLSL G                           451

SEQ ID NO: 423          moltype = AA  length = 451
FEATURE                 Location/Qualifiers
source                  1..451
                        mol_type = protein
                        organism = synthetic construct
SEQUENCE: 423
QVQLVESGGG VVRPGGSLRL SCAASGFTFD DYGMSWVRQA PGKGLEWVSG INWEGGSTGY  60
ADSVKGRFTI SRDNAKNSLY LQMNSLRAED TALYYCARDE QLGGRHYYYY YMDVWGKGTT 120
VTVSSASTKG PSVFPLAPCS RSTSESTAAL GCLVKDYFPE PVTVSWNSGA LTSGVHTFPA 180
VLQSSGLYSL SSVVTVPSSS LGTKTYTCNV DHKPSNTKVD KRVESKYGPP CPPCPAPEFE 240
GGPSVFLFPP KPKDTLYITR EPEVTCVVVD VSQEDPEVQF NWYVDGVEVH NAKTKPREEQ 300
FNSTYRVVSV LTVLHQDWLN GKEYKCKVSN KGLPSSIEKT ISKAKGQPRE PQVYTLPPSQ 360
EEMTKNQVSL TCLVKGFYPS DIAVEWESNG QPENNYKTTP PVLDSDGSFF LYSRLTVDKS 420
RWQEGNVFSC SVMHEALHNH YTQKSLSLSL G                           451

SEQ ID NO: 424          moltype = DNA  length = 348
FEATURE                 Location/Qualifiers
```

```
source                          1..348
                                mol_type = other DNA
                                organism = synthetic construct
SEQUENCE: 424
gaagtgcagc ttgttgaaag tggtgggggt ttggttaaac ctggcggttc ccttcgactt    60
agctgcgcgg cgtcagggtt cacattctca gattattaca tgtcttggat tcggcaagcc   120
cctggtaagg gactggagtg ggtaagctac atatctcggt caggaagtac aaagtactat   180
gcagattcag tgaagggcag gtttacgatt agccgagaca acgcaaagaa ctctctttat   240
ctgcagatga attcactgag agcagaagat accgctgtct attattgtgc cagagaccag   300
gaaagattacg ctcttgacta ctggggccaa ggtacgctgg ttacggtc               348

SEQ ID NO: 425                  moltype = DNA   length = 348
FEATURE                         Location/Qualifiers
source                          1..348
                                mol_type = other DNA
                                organism = synthetic construct
SEQUENCE: 425
gaagtgcagc ttgttgaaag tggtgggggt ttggttaaac ctggcggttc ccttcgactt    60
agctgcgcgg cgtcagggtt cacattctca gattattaca tgtcttggat tcggcaagcc   120
cctggtaagg gactggagtg ggtaagctac atatctcggt caggaagtac aaagtactat   180
gcagattcag tgaagggcag gtttacgatt agccgagaca acgcaaagaa ctctctttat   240
ctgcagatga attcactgag agcagaagat accgctgtct attattgtgc cagagacgag   300
accgattacg gctgggacta ctggggccaa ggtacgctgg ttacggtc                348

SEQ ID NO: 426                  moltype = DNA   length = 348
FEATURE                         Location/Qualifiers
source                          1..348
                                mol_type = other DNA
                                organism = synthetic construct
SEQUENCE: 426
gaagtgcagc ttgttgaaag tggtgggggt ttggttaaac ctggcggttc ccttcgactt    60
agctgcgcgg cgtcagggtt cacattctca gattattaca tgtcttggat tcggcaagcc   120
cctggtaagg gactggagtg ggtaagctac atatctcggt caggaagtac aaagtactat   180
gcagattcag tgaagggcag gtttacgatt agccgagaca acgcaaagaa ctctctttat   240
ctgcagatga attcactgag agcagaagat accgctgtct attattgtgc cagagacgag   300
accgattacg ctttcgacga atggggccaa ggtacgctgg ttacggtc                348

SEQ ID NO: 427                  moltype = DNA   length = 348
FEATURE                         Location/Qualifiers
source                          1..348
                                mol_type = other DNA
                                organism = synthetic construct
SEQUENCE: 427
gaagtgcagc ttgttgaaag tggtgggggt ttggttaaac ctggcggttc ccttcgactt    60
agctgcgcgg cgtcagggtt cacattctca gattattaca tgtcttggat tcggcaagcc   120
cctggtaagg gactggagtg ggtaagctac atatctcggt caggaagtac aaagtactat   180
gcagattcag tgaagggcag gtttacgatt agccgagaca acgcaaagaa ctctctttat   240
ctgcagatga attcactgag agcagaagat accgctgtct attattgtgc cagagacgag   300
agtcagtacg ctcttgacta ctggggccaa ggtacgctgg ttacggtc                348

SEQ ID NO: 428                  moltype = DNA   length = 348
FEATURE                         Location/Qualifiers
source                          1..348
                                mol_type = other DNA
                                organism = synthetic construct
SEQUENCE: 428
gaagtgcagc ttgttgaaag tggtgggggt ttggttaaac ctggcggttc ccttcgactt    60
agctgcgcgg cgtcagggtt cacattctca gattattaca tgtcttggat tcggcaagcc   120
cctggtaagg gactggagtg ggtaagctac atatctcggt caggaagtac aaagtactat   180
gcacattcag tgaagggcag gtttacgatt agccgagaca acgcaaagaa ctctctttat   240
ctgcagatga attcactgag agcagaagat accgctgtct attattgtgc cagagacaac   300
accgattacg ctcttgacct gtggggccaa ggtacgctgg ttacggtc                348

SEQ ID NO: 429                  moltype = DNA   length = 348
FEATURE                         Location/Qualifiers
source                          1..348
                                mol_type = other DNA
                                organism = synthetic construct
SEQUENCE: 429
gaagtgcagc ttgttgaaag tggtgggggt ttggttaaac ctggcggttc ccttcgactt    60
agctgcgcgg cgtcagggtt cacattctca gattattaca tgtcttggat tcggcaagcc   120
cctggtaagg gactggagtg ggtaagctac atatctcggt caggaagtac aaagtactat   180
gcacattcag tgaagggcag gtttacgatt agccgagaca acgcaaagaa ctctctttat   240
ctgcagatga attcactgag agcagaagat accgctgtct attattgtgc cagagacgag   300
accgattacg cttacgacga atggggccaa ggtacgctgg ttacggtc                348

SEQ ID NO: 430                  moltype = DNA   length = 348
FEATURE                         Location/Qualifiers
source                          1..348
```

```
                          mol_type = other DNA
                          organism = synthetic construct
SEQUENCE: 430
gaagtgcagc ttgttgaaag tggtgggggt ttggttaaac ctggcggttc ccttcgactt    60
agctgcgcgg cgtcagggtt cacattctca gattattaca tgtcttggat tcggcaagcc   120
cctggtaagg gactggagtg ggtaagctac atatctcggt caggaagtac aaagtactat   180
gcagattcag tgaagggcag gtttacgatt agccgagaca acgcaaagaa ctctctttat   240
ctgcagatga attcactgag agcagaagat accgctgtct attattgtgc cagagacgag   300
accgattacg cttacgacaa ctggggccaa ggtacgctgg ttacggtc                348

SEQ ID NO: 431          moltype = DNA   length = 348
FEATURE                 Location/Qualifiers
source                  1..348
                        mol_type = other DNA
                        organism = synthetic construct
SEQUENCE: 431
gaagtgcagc ttgttgaaag tggtgggggt ttggttaaac ctggcggttc ccttcgactt    60
agctgcgcgg cgtcagggtt cacattctca gattattaca tgtcttggat tcggcaagcc   120
cctggtaagg gactggagtg ggtaagctac atatctcggt caggaagtac aaagtactat   180
gcagattcag tgaagggcag gtttacgatt agccgagaca acgcaaagaa ctctctttat   240
ctgcagatga attcactgag agcagaagat accgctgtct attattgtgc cagagacgag   300
agtgattacg cttacgacta ctggggccaa ggtacgctgg ttacggtc                348

SEQ ID NO: 432          moltype = DNA   length = 348
FEATURE                 Location/Qualifiers
source                  1..348
                        mol_type = other DNA
                        organism = synthetic construct
SEQUENCE: 432
gaagtgcagc ttgttgaaag tggtgggggt ttggttaaac ctggcggttc ccttcgactt    60
agctgcgcgg cgtcagggtt cacattctca gattattaca tgtcttggat tcggcaagcc   120
cctggtaagg gactggagtg ggtaagctac atatctcggt caggaagtac aaagtactat   180
gcagattcag tgaagggcag gtttacgatt agccgagaca acgcaaagaa ctctctttat   240
ctgcagatga attcactgag agcagaagat accgctgtct attattgtgc cagagacgag   300
aattacgctc ttgactggtg gggccaaggt acgctggtta cggtctcg                348

SEQ ID NO: 433          moltype = DNA   length = 348
FEATURE                 Location/Qualifiers
source                  1..348
                        mol_type = other DNA
                        organism = synthetic construct
SEQUENCE: 433
gaagtgcagc ttgttgaaag tggtgggggt ttggttaaac ctggcggttc ccttcgactt    60
agctgcgcgg cgtcagggtt cacattctca gattattaca tgtcttggat tcggcaagcc   120
cctggtaagg gactggagtg ggtaagctac atatctcggt caggaagtac aaagtactat   180
gcagattcag tgaagggcag gtttacgatt agccgagaca acgcaaagaa ctctctttat   240
ctgcagatga attcactgag agcagaagat accgctgtct attattgtgc cagagacgag   300
agtgattacg ctcttgactt ctggggccaa ggtacgctgg ttacggtc                348

SEQ ID NO: 434          moltype = DNA   length = 357
FEATURE                 Location/Qualifiers
source                  1..357
                        mol_type = other DNA
                        organism = synthetic construct
SEQUENCE: 434
gaagttcaac tggttcaaag cggggccgag gtaaagaagc caggcgcttc tgtgaaagtc    60
agttgcaagg tgagtgggga tacattgacc gagctgagta tgcactgggt ccggcaagct   120
cctggcaagg gtttggaatg gatgggtact tttgacccgg aggagggaga gaccatctac   180
gcgcaaaaat tccaaggtag ggtgaccatg acggaggata ccagcacgga tactgcttac   240
atggagctca gctccctcag aagtgaagat actgccgtct actactgtgt gaccgagggt   300
ttggccgggg tgccgtttga tctgtggggg caggggacgc tggtaacggt ctcgagt      357

SEQ ID NO: 435          moltype = DNA   length = 357
FEATURE                 Location/Qualifiers
source                  1..357
                        mol_type = other DNA
                        organism = synthetic construct
SEQUENCE: 435
gaagttcaac tggttcaaag cggggccgag gtaaagaagc caggcgcttc tgtgaaagtc    60
agttgcaagg tgagtgggga tacattgacc gagctgagta tgcactgggt ccggcaagct   120
cctggcaagg gtttggaatg gatgggtact tttgacccgg aggagggaga gaccatctac   180
gcgcaaaaat tccaaggtag ggtgaccatg acggaggata ccagcacgga tactgcttac   240
atggagctca gctccctcag aagtgaagat actgccgtct actactgtgt gaccgagggt   300
ttgggcgggc gcccgtttga tcactggggg caggggacgc tggtaacggt ctcgagt      357

SEQ ID NO: 436          moltype = DNA   length = 357
FEATURE                 Location/Qualifiers
source                  1..357
                        mol_type = other DNA
``` organism = synthetic construct
SEQUENCE: 436
gaagttcaac tggttcaaag cggggccgag gtaaagaagc caggcgcttc tgtgaaagtc 60
agttgcaagg tgagtgggga tacattgacc gagctgagta tgcactgggt ccggcaagct 120
cctggcaagg gtttggaatg gatgggtact tttgacccgg aggagggaga gaccatctac 180
gcgcaaaaat tccaaggtag ggtgaccatg acggaggata ccagcacgga tactgcttac 240
atggagctca gctccctcag aagtgaagat actgccgtct actactgtgt gaccgagggt 300
ttggccgggt tcccgtttga tatctggggg caggggacgc tggtaacggt ctcgagt 357

SEQ ID NO: 437           moltype = DNA  length = 357
FEATURE                  Location/Qualifiers
source                   1..357
                         mol_type = other DNA
                         organism = synthetic construct
SEQUENCE: 437
gaagttcaac tggttcaaag cggggccgag gtaaagaagc caggcgcttc tgtgaaagtc 60
agttgcaagg tgagtgggga tacattgacc gagctgagta tgcactgggt ccggcaagct 120
cctggcaagg gtttggaatg gatgggtact tttgacccgg aggagggaga gaccatctac 180
gcgcaaaaat tccaaggtag ggtgaccatg acggaggata ccagcacgga tactgcttac 240
atggagctca gctccctcag aagtgaagat actgccgtct actactgtgt gaccgagggt 300
ttggcctggc gcccgaccga ttcatggggg caggggacgc tggtaacggt ctcgagt 357

SEQ ID NO: 438           moltype = DNA  length = 357
FEATURE                  Location/Qualifiers
source                   1..357
                         mol_type = other DNA
                         organism = synthetic construct
SEQUENCE: 438
gaagttcaac tggttcaaag cggggccgag gtaaagaagt caggcgcttc tgtgaaagtc 60
agttgcaagg tgagtgggga tacattgacc gagctgagta tgcactgggt ccggcaagct 120
cctggcaagg gtttggaatg gatgggtact tttgacccgg aggagggaga gaccatctac 180
gcgcaaaaat tccaaggtag ggtgaccatg acggaggata ccagcacgga tactgcttac 240
atggagctca gctccctcag aagtgaagat actgccgtct actactgtgt gaccaagggt 300
ttggccgggc tgccgtacta ctcatggggg caggggacgc tggtaacggt ctcgagt 357

SEQ ID NO: 439           moltype = DNA  length = 357
FEATURE                  Location/Qualifiers
source                   1..357
                         mol_type = other DNA
                         organism = synthetic construct
SEQUENCE: 439
gaagttcaac tggttcaaag cggggccgag gtaaagaagc caggcgcttc tgtgaaagtc 60
agttgcaagg tgagtgggga tacattgacc gagctgagta tgcactgggt ccggcaagct 120
cctggcaagg gtttggaatg gatgggtact tttgacccgg aggagggaga gaccatctac 180
gcgcaaaaat tccaaggtag ggtgaccatg acggaggata ccagcacgga tactgcttac 240
atggagctca gctccctcag aagtgaagat actgccgtct actactgtgt gaccgagggt 300
ttggccgggg tgccgtttga tctgtggggg caggggacgc tggtaacggt ctcgagt 357

SEQ ID NO: 440           moltype = DNA  length = 357
FEATURE                  Location/Qualifiers
source                   1..357
                         mol_type = other DNA
                         organism = synthetic construct
SEQUENCE: 440
gaagttcaac tggttcaaag cggggccgag gtaaagaagc caggcgcttc tgtgaaagtc 60
agttgcaagg tgagtgggga tacattgacc gagctgagta tgcactgggt ccggcaagct 120
cctggcaagg gtttggaatg gatgggtact tttgacccgg aggagggaga gaccatctac 180
gcgcaaaaat tccaaggtag ggtgaccatg acggaggata ccagcacgga tactgcttac 240
atggagctca gctccctcag aagtgaagat actgccgtct actactgtgt gaccgagggt 300
gaggccgggc gcccgtttga tgcctggggg caggggacgc tggtaacggt ctcgagt 357

SEQ ID NO: 441           moltype = DNA  length = 357
FEATURE                  Location/Qualifiers
source                   1..357
                         mol_type = other DNA
                         organism = synthetic construct
SEQUENCE: 441
gaagttcaac tggttcaaag cggggccgag gtaaagaagc caggcgcttc tgtgaaagtc 60
agttgcaagg tgagtgggga tacattgacc gagctgagta tgcactgggt ccggcaagct 120
cctggcaagg gtttggaatg gatgggtact tttgacccgg aggagggaga gaccatctac 180
gcgcaaaaat tccaaggtag ggtgaccatg acggaggata ccagcacgga tactgcttac 240
atggagctca gctccctcag aagtgaagat actgccgtct actactgtgt gaccgagggt 300
ttggccgggc gcccgtacga tgtgtggggg caggggacgc tggtaacggt ctcgagt 357

SEQ ID NO: 442           moltype = DNA  length = 357
FEATURE                  Location/Qualifiers
source                   1..357
                         mol_type = other DNA
                         organism = synthetic construct SEQUENCE: 442
```
gaagttcaac tggttcaaag cggggccgag gtaaagaagc caggcgcttc tgtgaaagtc    60
agttgcaagg tgagtgggga tacattgacc gagctgagta tgcactgggt ccggcaagct   120
cctggcaagg gtttgaatg gatgggtact tttgacccgg aggagggaga gaccatctac   180
gcgcaaaaat tccaaggtag ggtgaccatg acggaggata ccagcacgga tactgcttac   240
atggagctca gctacctcag aagtgaagat actgccgtct actactgtgt gaccgagggt   300
ttggccggga tcccgtttga ttcatggggg cagggacgc tggtaacggt ctcgagt      357
```

| | | |
|---|---|---|
| SEQ ID NO: 443 | moltype = DNA length = 357 | |
| FEATURE | Location/Qualifiers | |
| source | 1..357 | |
| | mol_type = other DNA | |
| | organism = synthetic construct | |

SEQUENCE: 443
```
gaagttcaac tggttcaaag cggggccgag gtaaagaagc caggcgcttc tgtgaaagtc    60
agttgcaagg tgagtgggga tacattgacc gagctgagta tgcactgggt ccggcaagct   120
cctggcaagg gtttgaatg gatgggtact tttgacccgg aggagggaga gaccatctac   180
gcgcaaaaat tccaaggtag ggtgaccatg acggaggata ccagcacgga tactgcttac   240
atggagctca gctacctcag aagtgaagat actgccgtct actactgtgt gaccgagggt   300
ttggccggga tcccgtttga ttcatggggg cagggacgc tggtaacggt ctcgagt      357
```

| | | |
|---|---|---|
| SEQ ID NO: 444 | moltype = DNA length = 369 | |
| FEATURE | Location/Qualifiers | |
| source | 1..369 | |
| | mol_type = other DNA | |
| | organism = synthetic construct | |

SEQUENCE: 444
```
caagtccagc ttgttgagtc tggcggaggg gtggttaggc caggaggttc ccttaggctt    60
tcctgtgcgg catcaggatt taccttcgat gactacggaa tgtcatgggt acgacaagct   120
cccggcaaag gcctcgaatg ggtttctggc atcaactggg agggcggttc cactggctac   180
gcggactcag ttaagggtag gttcaccata agcagggaca atgcgaagaa ctcactgtat   240
ctccaaatga acagtctccg cgccgaggat acagcccttt actattgtgc acgagatgag   300
caattggggg ggactactta ttattactat tacatggacg tgtggggtaa aggaacgacc   360
gtcacagtc                                                          369
```

| | | |
|---|---|---|
| SEQ ID NO: 445 | moltype = DNA length = 369 | |
| FEATURE | Location/Qualifiers | |
| source | 1..369 | |
| | mol_type = other DNA | |
| | organism = synthetic construct | |

SEQUENCE: 445
```
caagtccagc ttgttgagtc tggcggaggg gtggttaggc caggaggttc ccttaggctt    60
tcctgtgcgg catcaggatt taccttcgat gactacggaa tgtcatgggt acgacaagct   120
cccggcaaag gcctcgaatg ggtttctggc atcaactggg agggcggttc cactggctac   180
gcggactcag ttaagggtag gttcaccata agcagggaca atgcgaagaa ctcactgtat   240
ctccaaatga acagtctccg cgccgaggat acagcccttt actattgtgc acgagatgag   300
caattggggg ggaagtatta ctattactat tacatggacg tgtggggtaa aggaacgacc   360
gtcacagtc                                                          369
```

| | | |
|---|---|---|
| SEQ ID NO: 446 | moltype = DNA length = 369 | |
| FEATURE | Location/Qualifiers | |
| source | 1..369 | |
| | mol_type = other DNA | |
| | organism = synthetic construct | |

SEQUENCE: 446
```
caagtccagc ttgttgagtc tggcggaggg gtggttaggc caggaggttc ccttaggctt    60
tcctgtgcgg catcaggatt taccttcgat gactacggaa tgtcatgggt acgacaagct   120
cccggcaaag gcctcgaatg ggtttctggc atcaactggg agggcggttc cactggctac   180
gcggactcag ttaagggtag gttcaccata agcagggaca atgcgaagaa ctcactgtat   240
ctccaaatga acagtctccg cgccgaggat acagcccttt actattgtgc acgagatgag   300
caattggggg ggcagactta ttattactat tacatggacg tgtggggtaa aggaacgacc   360
gtcacagtc                                                          369
```

| | | |
|---|---|---|
| SEQ ID NO: 447 | moltype = DNA length = 369 | |
| FEATURE | Location/Qualifiers | |
| source | 1..369 | |
| | mol_type = other DNA | |
| | organism = synthetic construct | |

SEQUENCE: 447
```
caagtccagc ttgttgagtc tggcggaggg gtggttaggc caggaggttc ccttaggctt    60
tcctgtgcgg catcaggatt taccttcgat gactacggaa tgtcatgggt acgacaagct   120
cccggcaaag gcctcgaatg ggtttctggc atcaactggg agggcggttc cactggctac   180
gcggactcag ttaagggtag gttcaccata agcagggaca atgcgaagaa ctcactgtat   240
ctccaaatga acagtctccg cgccgaggat acagcccttt actattgtgc acgagatgag   300
caattggggg ggaccaccta ttattactat tacatggacg tgtggggtaa aggaacgacc   360
gtcacagtc                                                          369
```

| | | |
|---|---|---|
| SEQ ID NO: 448 | moltype = DNA length = 369 | |
| FEATURE | Location/Qualifiers | |

```
source                   1..369
                         mol_type = other DNA
                         organism = synthetic construct
SEQUENCE: 448
caagtccagc ttgttgagtc tggcggaggg gtggttaggc caggaggttc ccttaggctt    60
tcctgtgcgg catcaggatt taccttcgat gactacggaa tgtcatgggt acgacaagct   120
cccggcaaag gcctcgaatg ggtttctggc atcaactggg agggcggttc cactggctac   180
gcggactcag ttaagggtag gttcaccata agcagggaca atgcgaagaa ctcactgtat   240
ctccaaatga acagtctccg cgccgaggat acagcccttt actattgtgc acgagatgag   300
caattggggg ggatcaagta ttattactat tacatggacg tgtggggtaa aggaacgacc   360
gtcacagtc                                                           369

SEQ ID NO: 449            moltype = DNA   length = 369
FEATURE                   Location/Qualifiers
source                    1..369
                          mol_type = other DNA
                          organism = synthetic construct
SEQUENCE: 449
caagtccagc ttgttgagtc tggcggaggg gtggttaggc caggaggttc ccttaggctt    60
tcctgtgcgg catcaggatt tactttcgat gactacggaa tgtcatgggt acgacaagct   120
cccggcaaag gccttgaatg ggtttctggc atcaactggg agggcggttc cactggctac   180
gcggactcag ttaagggtag gttcagcata agcagggaca atgcgaagaa ctcactgtat   240
ctccaaatga acagtctccg cgccgaggat acagcccttt actattgtgc acgagatgag   300
caattggggg ggctgaagta ttattactat tacatggacg tgtggggtaa aggaacgacc   360
gtcacagtc                                                           369

SEQ ID NO: 450            moltype = DNA   length = 369
FEATURE                   Location/Qualifiers
source                    1..369
                          mol_type = other DNA
                          organism = synthetic construct
SEQUENCE: 450
caagtccagc ttgttgagtc tggcggaggg gtggttaggc caggaggttc ccttaggctt    60
tcctgtgcgg catcaggatt taccttcgat gactacggaa tgtcatgggt acgacaagct   120
cccggcaaag gcctcgaatg ggtttctggc atcaactggg agggcggttc cactggctac   180
gcggactcag ttaagggtag gttcaccata agcagggaca atgcgaagaa ctcactgtat   240
ctccaaatga acagtctccg cgccgaggat acagcccttt actattgtgc acgagatgag   300
caattggggg ggaaggtgta ttattactat tacatggacg tgtggggtaa aggaacgacc   360
gtcacagtc                                                           369

SEQ ID NO: 451            moltype = DNA   length = 369
FEATURE                   Location/Qualifiers
source                    1..369
                          mol_type = other DNA
                          organism = synthetic construct
SEQUENCE: 451
caagtccagc ttgttgagtc tggcggaggg gtggttaggc caggaggttc ccttaggctt    60
tcctgtgcgg catcaggatt tactttcgat gactacggaa tgtcatgggt acgacaagct   120
cccggcaaag gccttgaatg ggtttctggc atcaactggg agggcggttc cactggctac   180
gcggactcag ttaagggtag gttcagcata agcagggaca atgcgaagaa ctcactgtat   240
ctccaaatga acagtctccg cgccgaggat acagcccttt actattgtgc acgagatgag   300
caattggggg ggctgaagta ttattactat tacatggacg tgtggggtaa aggaacgacc   360
gtcacagtc                                                           369

SEQ ID NO: 452            moltype = DNA   length = 369
FEATURE                   Location/Qualifiers
source                    1..369
                          mol_type = other DNA
                          organism = synthetic construct
SEQUENCE: 452
caagtccagc ttgttgagtc tggcggaggg gtggttaggc caggaggttc ccttaggctt    60
tcctgtgcgg catcaggatt taccttcgat gactacggaa tgtcatgggt acgacaagct   120
cccggcaaag gcctcgaatg ggtttctggc atcaactggg agggcggttc cactggctac   180
gcggactcag ttaagggtag gttcaccata agcagggaca atgcgaagaa ctcactgtat   240
ctccaaatga acagtctccg cgccgaggat acagcccttt actattgtgc acgagatgag   300
caattggggg ggaatcacta ttattactat tacatggacg cttggggtaa aggaacgacc   360
gtcacagtc                                                           369

SEQ ID NO: 453            moltype = DNA   length = 369
FEATURE                   Location/Qualifiers
source                    1..369
                          mol_type = other DNA
                          organism = synthetic construct
SEQUENCE: 453
caagtccagc ttgttgagtc tggcggaggg gtggttaggc caggaggttc ccttaggctt    60
tcctgtgcgg catcaggatt taccttcgat gactacggaa tgtcatgggt acgacaagct   120
cccggcaaag gcctcgaatg ggtttctggc atcaactggg agggcggttc cactggctac   180
gcggactcag ttaagggtag gttcaccata agcagggaca atgcgaagaa ctcactgtat   240
ctccaaatga acagtctccg cgccgaggat acagcccttt actattgtgc acgagatgag   300
```

```
caattggggg ggcgccacta ttattactat tacatggacg tgtggggtaa aggaacgacc    360
gtcacagtc                                                            369

SEQ ID NO: 454           moltype = AA   length = 116
FEATURE                  Location/Qualifiers
source                   1..116
                         mol_type = protein
                         organism = synthetic construct
SEQUENCE: 454
VQLVESGGGL VKPGGSLRLS CAASGFTFSD YYMSWIRQAP GKGLEWVSYI SRSGSTKYYA     60
DSVKGRFTIS RDNAKNSLYL QMNSLRAEDT AVYYCARDEN YALDWWGQGT LVTVSS        116

SEQ ID NO: 455           moltype = AA   length = 442
FEATURE                  Location/Qualifiers
source                   1..442
                         mol_type = protein
                         organism = synthetic construct
SEQUENCE: 455
VQLVESGGGL VKPGGSLRLS CAASGFTFSD YYMSWIRQAP GKGLEWVSYI SRSGSTKYYA     60
DSVKGRFTIS RDNAKNSLYL QMNSLRAEDT AVYYCARDEN YALDWWGQGT LVTVSSASTK    120
GPSVFPLAPC SRSTSESTAA LGCLVKDYFP EPVTVSWNSG ALTSGVHTFP AVLQSSGLYS    180
LSSVVTVPSS SLGTKTYTCN VDHKPSNTKV DKRVESKYGP PCPPCPAPEF EGGPSVFLFP    240
PKPKDTLYIT REPEVTCVVV DVSQEDPEVQ FNWYVDGVEV HNAKTKPREE QFNSTYRVVS    300
VLTVLHQDWL NGKEYKCKVS NKGLPSSIEK TISKAKGQPR EPQVYTLPPS QEEMTKNQVS    360
LTCLVKGFYP SDIAVEWESN GQPENNYKTT PPVLDSDGSF FLYSRLTVDK SRWQEGNVFS    420
CSVMHEALHN HYTQKSLSLS LG                                            442
```

ANTIBODIES THAT BIND TO C1S AND USES THEREOF

CROSS-REFERENCE TO RELATED APPLICATIONS

This application claims the benefit of U.S. Provisional Application No. 63/590,980, filed on Oct. 17, 2023, U.S. Provisional Application No. 63/501,807, filed May 12, 2023, U.S. Provisional Application No. 63/485,765, filed on Feb. 17, 2023, and U.S. Provisional Application No. 63/384,537, filed on Nov. 21, 2022, each of which is hereby incorporated by reference in their entirety.

REFERENCE TO AN ELECTRONIC SEQUENCE LISTING

This application contains a Sequence Listing which has been submitted electronically in XML format and is hereby incorporated by reference in its entirety. The Sequence Listing is named "DIN002WOsequencelisting.xml", was created on Nov. 17, 2023, and is 495,158 bytes in size.

FIELD OF THE INVENTION

The field of the invention is immunology, in particular therapeutic antibodies, and treatment of disease with those antibodies.

BACKGROUND

The complement system is a well-known effector mechanism of the innate immune response, providing not only protection against pathogens and other harmful agents but also recovery from injury. Complement activation due to autoantibodies and alloantibodies can lead to damage to normal cells or rejection of transplanted tissue. The complement pathway is comprised of a number of proteins that typically exist in the body in an inactive form. Complement is comprised of the alternative, classical and lectin pathways, and are critical for immune defense. The classical complement pathway is triggered by activation of the first component of complement, referred to as the C1 complex, which consists of C1q, C1r, and C1s proteins. Upon binding of C1 to an immune complex or other activator, the C1s component, a diisopropyl fluorophosphate (DFP)-sensitive serine protease, cleaves complement components C4 and C2 to initiate activation of the classical complement pathway. Binding of C1 to antigen-antibody complexes induces cleavage of proenzyme C1s to active C1s enzyme, and the eventual formation of the pore-forming membrane attack complex (MAC) that is responsible for the destruction of the neuromuscular junction. The classical complement pathway appears to play a role in many diseases and disorders.

For example, sutimlimab (TNT009), marketed as EnJaymo®, is an antibody that inhibits C1s for treatment of hemolysis in adults with cold agglutinin disease.

However, sutimlimab binds to both the active form of C1s, and the inactive zymogen proC1s, and due to the lack of specificity of sutimlimab for either form of C1s, a very high dose must be administered to overcome circulating levels of proC1s, which may limit the clinical use of sutimlimab.

Myasthenia gravis (MG) is a rare and chronic autoimmune disease caused by autoantibodies that target proteins at the neuromuscular junction, which lead to impaired neurotransmission, muscle fatigue, and weakness. The most prevalent autoantibody in myasthenia gravis is against the nicotinic acetylcholine receptor (AChR), which is proposed to induce pathology through three different mechanisms, including activation of the complement system. Treatments for MG lack in their effectiveness.

Therefore, there is a need in the art for compounds that treat a complement classical pathway-mediated disease or disorder with specificity for active forms of the complement proteins. The embodiments provided for herein satisfy these needs as well as others.

SUMMARY

In some embodiments, an antibody, or antigen binding fragment thereof, is provided that binds to the active form of C1s. In some embodiments, an antibody, or antigen binding fragment thereof, is provided that specifically binds to the active form of C1s. In some embodiments, the antibody, or antigen binding fragment thereof, is as provided herein.

In some embodiments, a variant of an antibody, or antigen binding fragment thereof, is provided, wherein the variant has 1-10 substitutions, deletions, or insertions.

In some embodiments, a variant of an antibody, or antigen binding fragment thereof, is provided, wherein the variant has 1-10 conservative substitutions.

In some embodiments, a recombinant antibody, or antigen binding fragment thereof, is provided, wherein the recombinant antibody, or antigen binding fragment thereof, binds to C1s. In some embodiments, the recombinant antibody, or antigen binding fragment thereof, is an antibody, or antigen binding fragment thereof, as provided for herein.

In some embodiments, an isolated nucleic acid molecule is provided. In some embodiments, the isolated nucleic acid molecule encodes an antibody or antigen binding fragment thereof, a heavy chain variable region, a light chain variable region, a heavy chain, a light chain, or a combination thereof. In some embodiments, the antibody or antigen binding fragment thereof, a heavy chain variable region, a light chain variable region, a heavy chain, or light chain are as provided for herein.

In some embodiments, an expression vector is provided. In some embodiments, the expression vector comprises a nucleic acid molecule as provided for herein.

In some embodiments a host cell is provided. In some embodiments, the host cell comprises a nucleic acid molecule or expression vector as provided for herein. In some embodiments, the host cell comprises a nucleic acid molecule as provided for herein. In some embodiments, the host cell comprises an expression vector as provided for herein.

In some embodiments, an antibody, or antigen binding fragment thereof, is provided, wherein the antibody, or antigen binding fragment thereof, is produced by the host cell.

In some embodiments, a pharmaceutical composition is provided. In some embodiments, the pharmaceutical composition comprises an antibody, or antigen binding fragment thereof, as provided for herein.

In some embodiments, a method of producing a polypeptide comprising a heavy chain variable region or a light chain variable region is provided. In some embodiments, the method comprises (a) growing a host cell as provided for herein under conditions so that the host cell expresses the polypeptide comprising the heavy chain variable region or the light chain variable region; and (b) purifying the polypeptide comprising the heavy chain or the light chain variable regions. In some embodiments, the heavy chain variable region is as provided for herein. In some embodiments, the light chain variable region is as provided for herein.

In some embodiments, a method of producing an antibody or an antigen binding fragment of the antibody is provided. In some embodiments, the antibody or antigen binding fragment bind to human C1s. In some embodiments, the method comprises (a) growing a host cell as provided for herein under conditions so that the host cell expresses a polypeptide or polypeptides comprising the immunoglobulin heavy chain variable region and/or the immunoglobulin light chain variable region, thereby producing the antibody or the antigen binding fragment of the antibody; and (b) purifying the antibody or the antigen-binding fragment of the antibody.

In some embodiments, a method of treating a subject with a C1s mediated disorder is provided. In some embodiments, the method comprises administering to the subject an antibody, or antigen binding fragment thereof, as provided for herein, or a pharmaceutical composition as provided for herein.

In some embodiments, an antibody, or antigen binding fragment thereof, or a pharmaceutical composition is provided, wherein the antibody, or antigen binding fragment thereof, or the pharmaceutical composition are for the use in the treatment of a C1s mediated disorder. In some embodiments, the antibody, or antigen binding fragment thereof, is as provided for herein. In some embodiments, the pharmaceutical composition is as provided for herein. In some embodiments, the C1s mediated disorder is as provided for herein. In some embodiments, the C1s mediated disorder is hemolysis, Cold Agglutinin Disease, Immune Thrombocytopenia (ITP), Myasthenia Gravis, Glomerulopathies, Atypical Hemolytic uremic syndrome, antiphospholipid antibody syndrome, transplant rejection, Chronic inflammatory demyelinating polyneuropathy (CIDP), Multifocal motor neuropathy (MMN), Dermatomyositis, or Anti MAG neuropathy. In some embodiments, the condition can be caused by a stroke or spinal cord injury.

In some embodiments, an antibody, or antigen binding fragment thereof, or a pharmaceutical composition is provided, wherein the antibody, or antigen binding fragment thereof, or the pharmaceutical composition are for the use as a medicament. In some embodiments, the antibody, or antigen binding fragment thereof, is as provided for herein. In some embodiments, the pharmaceutical composition is as provided for herein.

In some embodiments, a use of an antibody, or antigen binding fragment thereof, or a pharmaceutical composition is provided, wherein the use is for the treatment of a C1s mediated disorder. In some embodiments, the antibody, or antigen binding fragment thereof, is as provided for herein. In some embodiments, the pharmaceutical composition is as provided for herein. In some embodiments, the C1s mediated disorder is as provided for herein.

BRIEF DESCRIPTION OF THE DRAWINGS

FIG. 1 illustrates the amino acid sequence of hProC1s RQ, in which the underlined portion denotes the expressed protein-secreting signal sequence (first 19 amino acids), the bolded portion denotes the sequence in which arginine 437 has been changed to glutamine, and the italicized region denotes the spacer and 10 histidine residues used in the purification of the protein (last 19 amino acids).

FIG. 2A shows binding to antibody 4011 g and derivatives. FIG. 2B shows binding to antibody 5 L3 g and derivatives. FIG. 2C shows binding to antibody 191 g and derivatives.

FIG. 11 shows percent (%) bacterial survival of *N. meningitidis* in complement-containing sera and anticapsular antibody with heat-inactivation, anti-C7 antibody, ravulizumab, or MAB39.

DETAILED DESCRIPTION

Figure 2A:
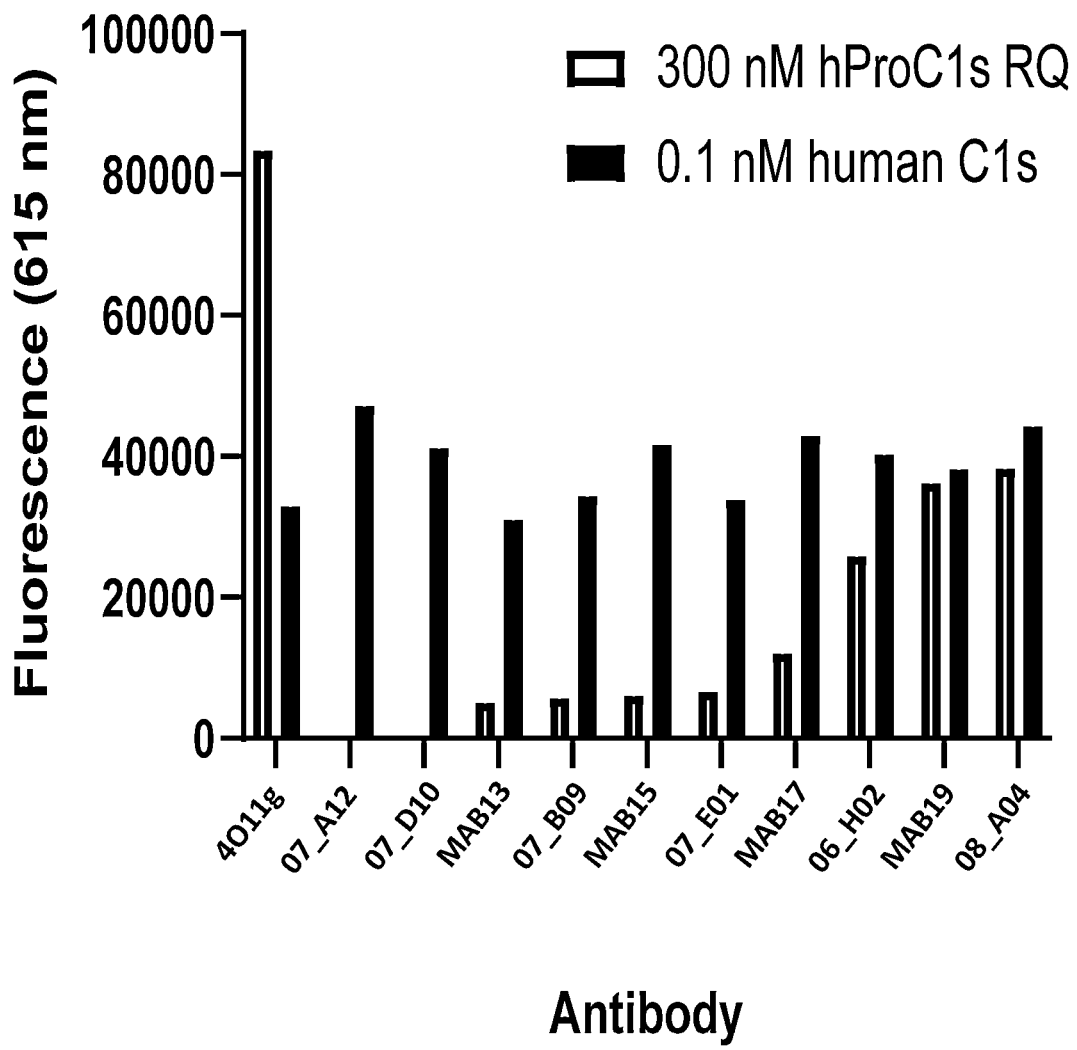
FIGS. 2A-2C show binding of hProC1s RQ and human C1s to the antibodies disclosed herein.

Provided herein are binding proteins, e.g., antibodies, or fragments, thereof, that selectively bind to C1s and have low binding to the zymogen proC1s. In some embodiments, the antibodies inhibit activation of the classical complement pathway and can be used in methods to treat complement mediated disorders, such as, but not limited to those provided for herein. In some embodiments, the selectivity for C1s over proC1s can be used to reduce or prevent target mediated clearance of the therapeutic antibody, thus requiring lower doses and a reduction in the frequency of administration of the antibody.

Before the present compositions and methods are described, it is to be understood that the scope of the invention is not limited to the particular processes, compositions, or methodologies described herein, as these may vary. It is also to be understood that the terminology used in the description is for the purpose of describing the particular versions or embodiments only, and is not intended to limit the scope of the present invention. Unless defined otherwise, all technical and scientific terms used herein have the same meanings as commonly understood by one of ordinary skill in the art. Although any methods and materials similar or equivalent to those described herein can be used in the practice or testing of embodiments of the methods and systems disclosed herein, the preferred methods, devices, and materials are now described.

The following explanations of terms and methods are provided to better describe the present disclosure and to guide those of ordinary skill in the art in the practice of the present disclosure.

Those of ordinary skill in the art will understand that given the amino acid sequence of a variable region of the binding molecules (e.g., antibodies) set forth herein can determine the CDR sequences therein by these or any other conventions used to define CDR, such as, for example, IMGT, Kabat, Chothia, or Contact using web-based tools are available for determining the CDRs in such variable regions based on any known convention. Such tools include those found at www.abysis.org/abysis/sequence_input/key_annotation/key_annotation.cgi and www.novoprolabs.com/tools/cdr.

Accordingly, the disclosure herein of a set of three CDRs in a heavy or light chain variable region based upon one CDR convention is considered the equivalent of that same set of CDRs as determined by any other convention, which can be referred to as "convention equivalents" or "convention equivalent CDRs".

As used herein, "comprising" means "including" and the singular forms "a" or "an" or "the" include plural references unless the context clearly dictates otherwise. For example, reference to "comprising a therapeutic agent" includes one or a plurality of such therapeutic agents. The term "or" refers to a single element of stated alternative elements, unless the context clearly indicates otherwise. For example, the phrase "A or B" refers to A alone or B alone. The phrase "A, B, or a combination thereof" refers to A alone, B alone, or a combination of A and B. Similarly, "one or more of A and B" refers to A, B, or a combination of both A and B. The phrase "A and B" refers to a combination of A and B. Furthermore, the various elements, features and steps discussed herein, as well as other known equivalents for each such element, feature or step, can be mixed and matched by one of ordinary skill in this art to perform methods in accordance with principles described herein. Among the various elements, features, and steps some will be specifically included and others specifically excluded in particular examples.

Unless otherwise defined, all technical and scientific terms used herein have the same meaning as commonly understood to one of ordinary skill in the art. Although methods and materials similar or equivalent to those described herein can be used in the practice or testing of the present disclosure, suitable methods and materials are described below. The materials, methods, and examples are illustrative only and not intended to be limiting. All references cited herein are incorporated by reference in their entirety.

As used herein, the term "antibody" refers to any form of antibody that exhibits the desired biological activity. Thus, it is used in the broadest sense and specifically covers, but is not limited to, monoclonal antibodies (including full length monoclonal antibodies), polyclonal antibodies, multispecific antibodies (e.g., bispecific antibodies), humanized, fully human antibodies, chimeric antibodies and camelized single domain antibodies. "Parental antibodies" are antibodies obtained by exposure of an immune system to an antigen prior to modification of the antibodies for an intended use, such as humanization of an antibody for use as a human therapeutic antibody.

As used herein, unless otherwise indicated, "antibody fragment" or "antigen binding fragment" refers to antigen binding fragments of antibodies, i.e. antibody fragments that retain the ability to bind specifically to the antigen bound by the full-length antibody, e.g. fragments that retain one or more CDR regions. Examples of antibody binding fragments include, but are not limited to, Fab, Fab', F(ab')2, and Fv fragments; diabodies; linear antibodies; single-chain antibody molecules, e.g., sc-Fv; nanobodies (single domain antibody) and multispecific antibodies formed from antibody fragments.

A "Fab fragment" is comprised of one light chain and the $C_H1$ and variable regions of one heavy chain. The heavy chain of a Fab molecule cannot form a disulfide bond with another heavy chain molecule.

An "Fc" region contains two heavy chain fragments comprising the $C_H2$ and $C_H3$ domains of an antibody. The two heavy chain fragments are held together by two or more disulfide bonds and by hydrophobic interactions of the CH3 domains.

A "Fab' fragment" contains one light chain and a portion or fragment of one heavy chain that contains the $V_H$ domain and the $C_H1$ domain and also the region between the $C_H1$ and $C_H2$ domains, such that an interchain disulfide bond can be formed between the two heavy chains of two Fab' fragments to form a F(ab')$_2$ molecule.

A "F(ab')$_2$ fragment" contains two light chains and two heavy chains containing a portion of the constant region between the $C_H1$ and $C_H2$ domains, such that an interchain disulfide bond is formed between the two heavy chains. A F(ab')$_2$ fragment thus is composed of two Fab' fragments that are held together by a disulfide bond between the two heavy chains.

The "Fv region" comprises the variable regions from both the heavy and light chains, but lacks the constant regions.

The term "single-chain Fv" or "scFv" antibody refers to antibody fragments comprising the $V_H$ and $V_L$ domains of an antibody, wherein these domains are present in a single polypeptide chain. Generally, the Fv polypeptide further comprises a polypeptide linker between the $V_H$ and $V_L$ domains which enables the scFv to form the desired structure for antigen binding. For a review of scFv, see Pluckthun (1994) THE PHARMACOLOGY OF MONOCLONAL ANTIBODIES, vol. 113, Rosenburg and Moore eds. Springer-Verlag, New York, pp. 269-315. See also, International Patent Application Publication No. WO 88/01649 and U.S. Pat. Nos. 4,946,778 and 5,260,203.

A "single-domain antibody" is an immunologically functional immunoglobulin fragment containing only the variable region of a heavy chain or the variable region of a light chain. In some instances, two or more $V_H$ regions are covalently joined with a peptide linker to create a bivalent domain antibody. The two $V_H$ regions of a bivalent domain antibody may target the same or different antigens.

A "bivalent antibody" comprises two antigen binding sites. In some instances, the two binding sites have the same antigen specificities. However, bivalent antibodies may be bispecific (see below).

In certain embodiments, monoclonal antibodies herein also include camelized single domain antibodies. See, e.g., Muyldermans et al. (2001) Trends Biochem. Sci. 26:230; Reichmann et al. (1999) J. Immunol. Methods 231:25; WO 94/04678; WO 94/25591; U.S. Pat. No. 6,005,079). In one embodiment, the present invention provides single domain antibodies comprising two $V_H$ domains with modifications such that single domain antibodies are formed.

As used herein, the term "diabodies" refers to small antibody fragments with two antigen-binding sites, which fragments comprise a heavy chain variable domain ($V_H$) connected to a light chain variable domain ($V_L$) in the same polypeptide chain ($V_H$-$V_L$ or $V_L$-$V_H$). By using a linker that is too short to allow pairing between the two domains on the same chain, the domains are forced to pair with the complementary domains of another chain and create two antigen-binding sites. Diabodies are described more fully in, e.g., EP 404,097; WO 93/11161; and Holliger et al. (1993) Proc. Natl. Acad. Sci. USA 90: 6444-6448. For a review of engineered antibody variants generally see Holliger and Hudson (2005) Nat. Biotechnol. 23:1126-1136.

Typically, a variant antibody or antigen binding fragment of the antibodies provided herein retain at least 10% of its C1s binding activity (when compared to a parental antibody that is modified) when that activity is expressed on a molar basis. In some embodiments, a variant antibody (or antigen fragment thereof), or antigen binding fragment of an antibody provided herein, retains at least 20%, 50%, 70%, 80%, 90%, 95% or 100% or more of the C1s binding affinity as the parental antibody. As described herein, it is also intended that an antibody or antigen binding fragment of the invention can include conservative or non-conservative amino acid substitutions, which can also be referred to as "conservative variants" or "function conserved variants" of the antibody, that do not substantially alter its biologic activity.

"Isolated antibody" refers to the purification status of a binding compound and in such context means the molecule is substantially free of other biological molecules such as nucleic acids, proteins, lipids, carbohydrates, or other material such as cellular debris and growth media. Generally, the term "isolated" is not intended to refer to a complete absence of such material or to an absence of water, buffers, or salts, unless they are present in amounts that substantially interfere with experimental or therapeutic use of the binding compound as described herein.

The term "monoclonal antibody", as used herein, refers to population of substantially homogeneous antibodies, i.e., the antibody molecules comprising the population are identical in amino acid sequence except for possible naturally occurring mutations and/or post-translational modifications that may be present in minor amounts. In contrast, conventional (polyclonal) antibody preparations typically include a multitude of different antibodies having different amino acid sequences in their variable domains, particularly their CDRs, that are often specific for different epitopes. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al. (1975) Nature 256: 495, or may be made by recombinant DNA methods (see, e.g., U.S. Pat. No. 4,816,567). The "monoclonal antibodies" may also be isolated from phage antibody libraries using the techniques described in Clackson et al. (1991) Nature 352: 624-628 and Marks et al. (1991) J. Mol. Biol. 222: 581-597, for example. See also Presta (2005) J. Allergy Clin. Immunol. 116:731.

As used herein, a "chimeric antibody" is an antibody having the variable domain from a first antibody and constant domain from a second antibody, where the first and second antibodies are from different species. (U.S. Pat. No. 4,816,567; and Morrison et al., (1984) Proc. Natl. Acad. Sci. USA 81: 6851-6855). Typically, the variable domains are obtained from an antibody from an experimental animal (the "parental antibody"), such as a rodent, and the constant domain sequences are obtained from human antibodies, so that the resulting chimeric antibody will be less likely to elicit an adverse immune response in a human subject than the parental (e.g. rodent) antibody.

As used herein, the term "humanized antibody" refers to forms of antibodies that contain sequences from both human and non-human (e.g., murine, rat) antibodies. In general, the humanized antibody will comprise substantially all of at least one, and typically two, variable domains, in which all or substantially all of the hypervariable loops correspond to those of a non-human immunoglobulin, and all or substantially all of the framework (FR) regions are those of a human immunoglobulin sequence. The humanized antibody may optionally comprise at least a portion of a human immunoglobulin constant region (Fc).

The term "fully human antibody" refers to an antibody that comprises human immunoglobulin protein sequences only. A fully human antibody may contain murine carbohydrate chains if produced in a mouse, in a mouse cell, or in a hybridoma derived from a mouse cell. Similarly, "mouse antibody" refers to an antibody that comprises mouse immunoglobulin sequences only. Alternatively, a fully human antibody may contain rat carbohydrate chains if produced in a rat, in a rat cell, or in a hybridoma derived from a rat cell. Similarly, "rat antibody" refers to an antibody that comprises rat immunoglobulin sequences only.

In some embodiments, the basic antibody structural unit comprises a tetramer. Each tetramer includes two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of the heavy chain may define a constant region primarily responsible for effector function. Typically, human light chains are classified as kappa and lambda light chains. Furthermore, human heavy chains are typically classified as mu, delta, gamma, alpha, or epsilon, and define the antibody's isotype as IgM, IgD, IgG, IgA, and IgE, respectively. Within light and heavy chains, the variable and constant regions are joined by a "J" region of about 12 or more amino acids, with the heavy chain also including a "D" region of about 10 more amino acids. See generally, *Fundamental Immunology* Ch. 7 (Paul, W., ed., 2nd ed. Raven Press, N.Y. (1989).

The variable regions of each light/heavy chain pair form the antibody binding site. Thus, in general, an intact antibody has two binding sites. However, in bifunctional or bispecific antibodies, the two binding sites are, in general, not the same.

Typically, the variable domains of both the heavy and light chains comprise three hypervariable regions, also called complementarity determining regions (CDRs), located within relatively conserved framework regions (FR). The CDRs are usually aligned by the framework regions, enabling binding to a specific epitope. In general, from N-terminal to C-terminal, both light and heavy chains variable domains comprise FR1, CDR1, FR2, CDR2, FR3, CDR3 and FR4. The assignment of amino acids to each domain is, generally, in accordance with the definitions of *Sequences of Proteins of Immunological Interest*, Kabat, et al.; National Institutes of Health, Bethesda, Md.; 5$^{th}$ ed.; NIH Publ. No. 91-3242 (1991); Kabat (1978) Adv. Prot. Chem. 32:1-75; Kabat, et al., (1977) J. Biol. Chem. 252: 6609-6616; Chothia, et al., (1987) J Mol. Biol. 196:901-917 or Chothia, et al., (1989) Nature 342:878-883.

As used herein, the term "hypervariable region" refers to the amino acid residues of an antibody that are responsible for antigen-binding. The hypervariable region comprises amino acid residues from a "complementarity determining region" or "CDR" (i.e. residues 24-34 (CDRL1), 50-56 (CDRL2) and 89-97 (CDRL3) in the light chain variable domain and residues 31-35 (CDRH1), 50-65 (CDRH2) and 95-102 (CDRH3) in the heavy chain variable domain; Kabat et al. (1991) Sequences of Proteins of Immunological Interest, 5th Ed. Public Health Service, National Institutes of Health, Bethesda, Md.) and/or those residues from a "hypervariable loop" (i.e. residues 26-32 (CDRL1), 50-52 (CDRL2) and 91-96 (CDRL3) in the light chain variable domain and 26-32 (CDRH1), 53-55 (CDRH2) and 96-101 (CDRH3) in the heavy chain variable domain; Chothia and Lesk (1987) *J. Mol. Biol.* 196: 901-917). The CDRs can also be referenced according to the IMGT system for the identification of CDRs, which is described in Lefranc MP. Unique database numbering system for immunogenetic analysis. Immunol Today (1997) 18:509. As used herein, the term "framework" or "FR" residues refers to those variable domain residues other than the hypervariable region residues defined herein as CDR residues. CDRs provide the majority of contact residues for the binding of the antibody to the antigen or epitope. CDRs of interest can be derived from donor antibody variable heavy and light chain sequences, and include analogs of the naturally occurring CDRs, which analogs also share or retain the same antigen binding specificity and/or neutralizing ability as the donor antibody from which they were derived.

As used herein, "specific binding" or "immunospecific binding" or "binds immunospecifically" refer to antibody binding to a predetermined antigen at a much higher affinity than for another antigen(s) (e.g. selectively binds the active form of complement component C1s as compared to inactive C1s, which can also be referred to as proC1s zymogen). In some embodiments, the antibody binds the predetermined antigen with a dissociation constant ($K_D$) of $10^{-7}$ M or less, and such $K_D$ is at least two-fold less than its $K_D$ for binding to a non-specific antigen (e.g., BSA, casein, or another non-specific polypeptide).

The phrases "an antibody recognizing C1s" and "an antibody specific for C1s" are used interchangeably herein with the term "an antibody which binds immunospecifically to C1s." In some embodiments, the antibody binds specifically or preferentially to C1s, such as the active form of C1s over other proteins, such as, but not limited to, the inactive form of C1s (proC1s). The degree of specificity necessary for an anti-C1s antibody may depend on the intended use of the antibody, and at any rate is defined by its suitability for use for an intended purpose. In some embodiments, the antibody, or binding compound derived from the antigen-binding site of an antibody, of the contemplated method binds to its antigen (active form of C1s), with an affinity that is at least two-fold greater, at least ten times greater, at least 20-times greater, or at least 100-times greater than the affinity with any other antigen, including, but not limited to inactive Cis.

Methods for determining mAb specificity and affinity by competitive inhibition can be found in Harlow, et al., Antibodies: A Laboratory Manual, Cold Spring Harbor Laboratory Press, Cold Spring Harbor, N.Y., 1988), Colligan et al., eds., Current Protocols in Immunology, Greene Publishing Assoc. and Wiley Interscience, N.Y., (1992, 1993), and Muller, Meth. Enzymol. 92:589 601 (1983), which references are entirely incorporated herein by reference.

The term "homolog" means protein sequences having between 40% and 100% sequence identity to a reference sequence. Percent identity between two peptide chains can be determined by pair wise alignment using the default settings of the AlignX module of Vector NTI v.9.0.0 (Invitrogen Corp., Carlsbad, Calif.) or other suitable alignment software, such as BLAST. In some embodiments, the antibody, or antigen binding fragment thereof has, at least 50, 60, 70, 80, 90, 91, 92, 93, 94, 95, 96, 97, 98, or 99% homology or identity to a sequence described herein. In some embodiments, the antibody has conservative substitutions as compared to a sequence described herein. Exemplary conservative substitutions are illustrated in Table 1 and are encompassed within the scope of the disclosed subject matter. The conservative substitution may reside in the framework regions, or in antigen-binding sites, as long they do not adversely affect the properties of the antibody. Substitutions may be made to improve antibody properties, for example stability or affinity. Conservative substitutions will produce molecules having functional and chemical characteristics similar to those molecules into which such modifications are made. Exemplary amino acid substitutions are shown in the table below.

TABLE 1

Table: Exemplary Conservative Substitutions:

| Original Residue | Exemplary Conservative Substitutions |
|---|---|
| Ala | Val, Leu, Ile |
| Arg | Lys, Gln, Asn |
| Asn | Gln |
| Asp | Glu |
| Cys | Ser, Ala |
| Gln | Asn |
| Gly | Pro, Ala |
| His | Asn, Gln, Lys, Arg |
| Ile | Leu, Val, Met, Ala, Phe |
| Leu | Ile, Val, Met, Ala, Phe |
| Lys | Arg, Gln, Asn |
| Met | Leu, Phe, Ile |
| Phe | Leu, Val, Ile, Ala, Tyr |
| Pro | Ala |

TABLE 1-continued

Table: Exemplary Conservative Substitutions:

| Original Residue | Exemplary Conservative Substitutions |
|---|---|
| Ser | Thr, Ala, Cys |
| Thr | Ser |
| Trp | Tyr, Phe |
| Tyr | Trp, Phe, Thr, Ser |
| Val | Ile, Met, Leu, Phe, Ala |

In some embodiments, variants of the proteins and peptides provided herein are provided. In some embodiments, a variant comprises a substitution, deletions, or insertion. In some embodiments, the variant comprises 1, 2, 3, 4, 5, 6, 7, 8, 9, or 10 (e.g., 1-10) substitutions. As described herein, the substitutions can be conservative substitutions. In some embodiments, the substitution is non-conservative. In some embodiments, the variant comprises 1, 2, 3, 4, 5, 6, 7, 8, 9, or 10 (e.g., 1-10) deletions. In some embodiments, the variant comprises 1, 2, 3, 4, 5, 6, 7, 8, 9, or 10 (e.g., 1-10) insertions. In some embodiments, the substitutions, deletions, or insertions are present in the CDRs provided for herein. In some embodiments, the substitutions, deletions, or insertions are not present in the CDRs provided for herein.

The term "in combination with" as used herein means that the described agents can be administered to an animal or subject together in a mixture, concurrently as single agents or sequentially as single agents in any order.

The term "epitope" is meant to refer to that portion of any molecule capable of being recognized by and bound by an antibody at one or more of the Ab's antigen binding regions. Epitopes usually consist of chemically active surface groupings of molecules such as amino acids or sugar side chains and have specific three-dimensional structural characteristics as well as specific charge characteristics.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., Sendai viruses, lentiviruses, retroviruses, adenoviruses, and adeno-associated viruses) that incorporate the recombinant polynucleotide.

In some embodiments, the antibody is a monoclonal antibody which binds to C1s. The sequence of active C1s is as follows (SEQ ID NO: 258): residues 1-15 (SEQ ID NO: 259) constitute the signal peptide which is cleaved during translation, and residues 16-688 (SEQ ID NO: 260) constitute the mature protein, as shown in (SEQ ID NO: 258)
MWCIVLFSLLAWVYAEPTMYGEILSPNYPQAYPSEVEKSWDIEVP

EGYGIHLYFTHLDIELSENCAYDSVQIISGDTEEGRLCGQRSSNN

PHSPIVEEFQVPYNKLQVIFKSDFSNEERFTGFAAYYVATDINEC

TDFVDVPCSHFCNNFIGGYFCSCPPEYFLHDDMKNCGVNCSGDVF

TALIGEIASPNYPKPYPENSRCEYQIRLEKGFQVVVTLRREDFDV

EAADSAGNCLDSLVFVAGDRQFGPYCGHGFPGPLNIETKSNALDI

IFQTDLTGQKKGWKLRYHGDPMPCPKEDTPNSVWEPAKAKYVFRD

VVQITCLDGFEVVEGRVGATSFYSTCQSNGKWSNSKLKCQPVDCG

IPESIENGKVEDPESTLFGSVIRYTCEEPYYYMENGGGGEYHCAG

NGSWVNEVLGPELPKCVPVCGVPREPFEEKQRIIGGSDADIKNFP

WQVFFDNPWAGGALINEYWVLTAAHVVEGNREPTMYVGSTSVQTS

RLAKSKMLTPEHVFIHPGWKLLEVPEGRTNFDNDIALVRLKDPVK

MGPTVSPICLPGTSSDYNLMDGDLGLISGWGRTEKRDRAVRLKAA

RLPVAPLRKCKEVKVEKPTADAEAYVFTPNMICAGGEKGMDSCKG

DSGGAFAVQDPNDKTKFYAAGLVSWGPQCGTYGLYTRVKNYVDWI

MKTMQENSTPRED;

(SEQ ID NO: 259)
MWCIVLFSLLAWVYA;

(SEQ ID NO: 260)
EPTMYGEILSPNYPQAYPSEVEKSWDIEVPEGYGIHLYFTHLDIE

LSENCAYDSVQIISGDTEEGRLCGQRSSNNPHSPIVEEFQVPYNK

LQVIFKSDFSNEERFTGFAAYYVATDINECTDFVDVPCSHFCNNF

IGGYFCSCPPEYFLHDDMKNCGVNCSGDVFTALIGEIASPNYPKP

YPENSRCEYQIRLEKGFQVVVTLRREDFDVEAADSAGNCLDSLVF

VAGDRQFGPYCGHGFPGPLNIETKSNALDIIFQTDLTGQKKGWKL

RYHGDPMPCPKEDTPNSVWEPAKAKYVFRDVVQITCLDGFEVVEG

RVGATSFYSTCQSNGKWSNSKLKCQPVDCGIPESIENGKVEDPES

TLFGSVIRYTCEEPYYYMENGGGGEYHCAGNGSWVNEVLGPELPK

CVPVCGVPREPFEEKQRIIGGSDADIKNFPWQVFFDNPWAGGALI

NEYWVLTAAHVVEGNREPTMYVGSTSVQTSRLAKSKMLTPEHVFI

HPGWKLLEVPEGRTNFDNDIALVRLKDPVKMGPTVSPICLPGTSS

DYNLMDGDLGLISGWGRTEKRDRAVRLKAARLPVAPLRKCKEVKV

EKPTADAEAYVFTPNMICAGGEKGMDSCKGDSGGAFAVQDPNDKT

KFYAAGLVSWGPQCGTYGLYTRVKNYVDWIMKTMQENSTPRED.

The difference between inactive C1s and active C1s is that inactive proC1s is cleaved at the peptide bond between R437 and I438 and undergoes a conformational change. The two fragments generated by this cleavage remain associated by a disulfide bond. Without wishing to be bound by a particular theory, proC1s is a single chain 86,000 Da protein that is the native form of C1s proteins (e.g. serine protease). C1s is a subunit of the C1 complex which is the first complement component in the cascade referred to as the classical pathway of complement. ProC1s is an inactive zymogen until C1 is activated. C1 complex binds to and is activated by antigen-antibody complexes (immune complexes) yielding C1r enzyme. C1r enzyme in the C1 complex activates proC1s generating C1s enzyme. C1 complex is a non-covalent calcium-dependent complex of one C1q, two C1r and two C1s molecules. C1q binds through two or more of its six arms to the Fc domains of IgG or IgM. The binding of multiple arms to immune complexes causes the two C1r proteins in the complex (protease zymogens) to activate producing two proteases that cleave and activate the two proC1s in the complex (Morikis, D. and Lambris, J. D.

(2005)). This activation of proC1s is caused by cleavage into the two chain C1s enzyme with 58,000 and 28,000 Dalton fragments.

In some embodiments, the antibodies provided herein do not inhibit, or significantly inhibit, the proteolytic cleavage of non-complement substrates. Examples of non-complement substrates, include but are not limited to, collagen, HMC I, HMGB1, IGFBP5, LRP6, NCL, and NPM1. Without being bound to any theory, such substrates are important in the clearance of antigens on apoptotic cells or in the hemostasis of bone, muscle, and connective tissues. Accordingly, an antibody that does not inhibit, or significantly inhibit, the proteolytic cleavage of non-complement substrates, such as those provided for herein, can allow the antibody to be utilized with fewer side effects or at higher doses. In some embodiments, the non-complement substrate is collagen. In some embodiments, the non-complement substrate is HMC I. In some embodiments, the non-complement substrate is HMGB1. In some embodiments, the non-complement substrate is IGFBP5. In some embodiments, the non-complement substrate is LRP6. In some embodiments, the non-complement substrate is NCL. In some embodiments, the non-complement substrate is NPM1.

In some embodiments, the antibody comprises an Fc domain. The Fc domain can be linked to the heavy or light chain of the antibody. In some embodiments, the Fc domain comprises a mutation to extend the half-life of the antibody. In some embodiments, the Fc domain comprises a mutation such as those described in U.S. Pat. No. 7,670,600, which is hereby incorporated by reference in its entirety. In some embodiment, the constant region comprises a mutation at position at amino acid residue 428 relative to a wild-type human IgG constant domain, numbered according to the EU numbering index of Kabat ("EU Numbering"). Without being bound to any particular theory, an antibody comprising a mutation that corresponds to residue 428 can have an increased half-life compared to the half-life of an IgG having the wild-type human IgG constant domain. In some embodiments, the mutation is a substitution of the native residue with a threonine, leucine, phenylalanine or serine. In some embodiments, the antibody further comprises one or more amino acid substitutions relative to the corresponding wild-type human IgG constant domain at one or more of amino acid residues 251-256, 285-290, 308-314, 385-389, and 429-436, numbered according to the Kabat EU numbering index. The specific mutations or substitutions at these positions are described in U.S. Pat. No. 7,670,600, which is hereby incorporated by reference in its entirety.

Other mutations can be used in the Fc domain, such as those provided for in U.S. Pat. No. 8,394,925, which is hereby incorporated by reference in its entirety. In some embodiments, the Fc region is a variant Fc region comprising amino acid substitutions at positions 428 and 434, wherein the amino acid substitutions are a leucine that is not the wild-type amino acid at position 428 and a serine that is not the wild-type amino acid at position 434, wherein the polypeptide is an antibody and wherein numbering is according to the EU Index in Kabat et al. In some embodiments, the Fc region comprises a S228P, L235E, M428L, or N434S substitution. In some embodiments, the Fc region comprises a M428L substitution. In some embodiments, the Fc region comprises a N434S substitution. In some embodiments, the Fc region comprises a M428L and a N434S substitution (EU Numbering), which can be collectively referred to as "LS mutations" or "LS". In some embodiments, the Fc region comprises a M252Y, S254T, and/or T256E substitution (EU Numbering). In some embodiments, the Fc region comprises a M252Y, S254T, and T256E substitutions. When all three of the mutations of M252Y, S254T, and T256E are present in the Fc region, it can be referred to as "YTE" or "YTE mutations."

In some embodiments, the antibody comprises a constant region as set forth below with or without the mutations provided for in the list below:

>IgG4 S228P L235E LS
(SEQ ID NO: 261)
ASTKGPSVFPLAPCSRSTSESTAALGCLVKDYFPEPVTVSWNSGA

LTSGVHTFPAVLQSSGLYSLSSVVTVPSSSLGTKTYTCNVDHKPS

NTKVDKRVESKYGPPCPPCPAPEFEGGPSVFLFPPKPKDTLMISR

TPEVTCVVVDVSQEDPEVQFNWYVDGVEVHNAKTKPREEQFNSTY

RVVSVLTVLHQDWLNGKEYKCKVSNKGLPSSIEKTISKAKGQPRE

PQVYTLPPSQEEMTKNQVSLTCLVKGFYPSDIAVEWESNGQPENN

YKTTPPVLDSDGSFFLYSRLTVDKSRWQEGNVFSCSVLHEALHSH

YTQKSLSLSLGK;

>IgG4 S228P L235E YTE
(SEQ ID NO: 262)
ASTKGPSVFPLAPCSRSTSESTAALGCLVKDYFPEPVTVSWNSGA

LTSGVHTFPAVLQSSGLYSLSSVVTVPSSSLGTKTYTCNVDHKPS

NTKVDKRVESKYGPPCPPCPAPEFEGGPSVFLFPPKPKDTLYITR

EPEVTCVVVDVSQEDPEVQFNWYVDGVEVHNAKTKPREEQFNSTY

RVVSVLTVLHQDWLNGKEYKCKVSNKGLPSSIEKTISKAKGQPRE

PQVYTLPPSQEEMTKNQVSLTCLVKGFYPSDIAVEWESNGQPENN

YKTTPPVLDSDGSFFLYSRLTVDKSRWQEGNVFSCSVMHEALHNH

YTQKSLSLSLGK.

In some embodiments, the antibody comprises a constant region as provided herein, wherein the C-terminal lysine (K) amino acid has been deleted. In some embodiments, the antibody comprises a constant region as set follows:

>IgG4 S228P L235E LS-trunc
(SEQ ID NO: 263)
ASTKGPSVFPLAPCSRSTSESTAALGCLVKDYFPEPVTVSWNSGA

LTSGVHTFPAVLQSSGLYSLSSVVTVPSSSLGTKTYTCNVDHKPS

NTKVDKRVESKYGPPCPPCPAPEFEGGPSVFLFPPKPKDTLMISR

TPEVTCVVVDVSQEDPEVQFNWYVDGVEVHNAKTKPREEQFNSTY

RVVSVLTVLHQDWLNGKEYKCKVSNKGLPSSIEKTISKAKGQPRE

PQVYTLPPSQEEMTKNQVSLTCLVKGFYPSDIAVEWESNGQPENN

YKTTPPVLDSDGSFFLYSRLTVDKSRWQEGNVFSCSVLHEALHSH

YTQKSLSLSLG;

>IgG4 S228P L235E YTE-trunc
(SEQ ID NO: 264)
ASTKGPSVFPLAPCSRSTSESTAALGCLVKDYFPEPVTVSWNSGA

LTSGVHTFPAVLQSSGLYSLSSVVTVPSSSLGTKTYTCNVDHKPS

NTKVDKRVESKYGPPCPPCPAPEFEGGPSVFLFPPKPKDTLYITR

EPEVTCVVVDVSQEDPEVQFNWYVDGVEVHNAKTKPREEQFNSTY

```
RVVSVLTVLHQDWLNGKEYKCKVSNKGLPSSIEKTISKAKGQPRE

PQVYTLPPSQEEMTKNQVSLTCLVKGFYPSDIAVEWESNGQPENN

YKTTPPVLDSDGSFFLYSRLTVDKSRWQEGNVFSCSVMHEALHNH

YTQKSLSLSLG.
```

In some embodiments, the antibody, such as the light chain, comprises a kappa constant region, such as the human constant domain, which can comprise a sequence of:

```
RTVAAPSVFIFPPSDEQLKSGTASVVCLLNNFYPREAKVQW

KVDNALQSGNSQESVTEQDSKDSTYSLSSTLTLSKADYEKH

KVYACEVTHQGLSSPVTKSFNRGEC
(human kappa constant domain, SEQ ID NO: 265).
```

As used herein and unless otherwise indicated, the term "about" is intended to mean±5% of the value it modifies. Thus, about 100 means 95 to 105.

In some embodiments, the antibodies described herein are used to detect the presence of the antigen. The present antibody can be used in any device or method to detect the presence of the antigen. In some embodiments, the antibodies are used to detect the active form of C1s. In some embodiments, the antibodies are used to detect the active form preferentially (specifically) over the inactive form of C1s.

The term "purified" when referenced to an antibody refers to an antibody that is substantially free of other material that associates with the molecule in its natural environment. For instance, a purified protein is substantially free of the cellular material or other proteins from the cell or tissue from which it is derived. The term refers to preparations where the isolated protein is sufficiently pure to be analyzed, or at least 70% to 80% (w/w) pure, at least 80%-90% (w/w) pure, 90-95% pure; and, at least 95%, 96%, 97%, 98%, 99%, or 100% (w/w) pure. In some embodiments, the antibody is purified.

Antibody Conjugates

The antibodies provided for herein may also be conjugated to a chemical moiety. The chemical moiety may be, inter alia, a polymer, a radionuclide or a cytotoxic factor. In some embodiments, this can be referred to as an antibody drug conjugate. In some embodiments, the chemical moiety is a polymer which increases the half-life of the antibody molecule in the body of a subject. Suitable polymers include, but are not limited to, polyethylene glycol (PEG) (e.g., PEG with a molecular weight of 2 kDa, 5 kDa, 10 kDa, 12 kDa, 20 kDa, 30 kDa or 40 kDa), dextran and monomethoxypolyethylene glycol (mPEG). Lee, et al., (1999) (Bioconj. Chem. 10:973-981) discloses PEG conjugated single-chain antibodies. Wen, et al., (2001) (Bioconj. Chem. 12:545-553) disclose conjugating antibodies with PEG which is attached to a radiometal chelator (diethylenetriaminpentaacetic acid (DTPA)). Examples of chemical moieties include, but are not limited to, anti-mitotics, such as calicheamicins (e.g. ozogamicin), monomethyl auristatin E, mertansine, and the like. Other examples include, but are not limited to, biologically active anti-microtubule agents, alkylating agents and DNA minor groove binding agents. Other examples thereof are provided herein and below. The chemical moiety can be linked to the antibody through a linking group (maleimide), a cleavable linker, such as a cathepsin cleavable linkers (valine-citrulline), and in some embodiments, one or more spacers (e.g. para-aminobenzyl-carbamate).

The antibodies and antibody fragments of the invention may also be conjugated with labels such as $^{99}$Tc, $^{90}$Y $^{111}$In, $^{32}$P, $^{14}$C, $^{125}$I, $^{3}$H, $^{131}$I, $^{11}$C, $^{15}$O, $^{13}$N, $^{18}$F, $^{35}$S, $^{51}$Cr, $^{57}$To, $^{226}$Ra, $^{60}$Co, $^{59}$Fe, $^{57}$Se, $^{152}$Eu, $^{67}$CU, $^{217}$Ci, $^{211}$At, $^{212}$Pb, $^{47}$Sc, $^{109}$Pd, $^{234}$Th, and $^{40}$K, $^{157}$Gd, $^{55}$Mn, $^{52}$Tr and $^{56}$Fe.

The antibodies and antibody fragments may also be conjugated with fluorescent or chemiluminescent labels, including fluorophores such as rare earth chelates, fluorescein and its derivatives, rhodamine and its derivatives, isothiocyanate, phycoerythrin, phycocyanin, allophycocyanin, o-phthaladehyde, fluorescamine, $^{152}$Eu, dansyl, umbelliferone, luciferin, luminal label, isoluminal label, an aromatic acridinium ester label, an imidazole label, an acridimium salt label, an oxalate ester label, an aequorin label, 2,3-dihydrophthalazinediones, biotin/avidin, spin labels and stable free radicals.

The antibody molecules may also be conjugated to a cytotoxic factor such as diphtheria toxin, *Pseudomonas aeruginosa* exotoxin A chain, ricin A chain, abrin A chain, modeccin A chain, alpha-sarcin, *Aleurites fordii* proteins and compounds (e.g., fatty acids), dianthin proteins, *Phytoiacca americana* proteins PAPI, PAPII, and PAP-S, *Momordica charantia* inhibitor, curcin, crotin, *Saponaria officinalis* inhibitor, mitogellin, restrictocin, phenomycin, and neomycin.

Any method known in the art for conjugating the antibody molecules of the invention to the various moieties may be employed, including those methods described by Hunter, et al., (1962) Nature 144:945; David, et al., (1974) Biochemistry 13:1014; Pain, et al., (1981) J. Immunol. Meth. 40:219; and Nygren, J., (1982) Histochem. and Cytochem. 30:407. Methods for conjugating antibodies are conventional and very well known in the art.

In some embodiments, antibodies (e.g. an anti-C1s antibody) are provided herein. In some embodiments, the antibody is a recombinant antibody that binds to C1s. In some embodiments, the antibody binds to the active form of C1s. In some embodiments, the antibody binds to active form preferentially over the inactive form of C1s. In some embodiments, the antibody binds to the active form with an affinity that is at least 10, 20, 30, 40, 50, 60, 70, 80, 90, 100, or 200% higher as compared to its affinity for the inactive form of C1s. In some embodiments, the C1s protein is a human C1s protein, such as the active form of C1s. In some embodiments, the antibody does not specifically bind to the inactive form of the C1s protein. As used herein, the term "recombinant antibody" refers to an antibody that is not naturally occurring. In some embodiments, the term "recombinant antibody" refers to an antibody that is not isolated from a human subject. In some embodiments, the antibody binds with at least 100 times more affinity to the active form of C1s as compared to proC1s.

In some embodiments, an antibody, or antigen binding fragment thereof is provided, wherein the antibody or antibody fragment comprises a peptide selected from the following table, which illustrates the CDRs based on Kabat numbering.

TABLE 2

| Kabat CDRs | | | | | | |
|---|---|---|---|---|---|---|
| Ab ID No | HCDR1 | HCDR2 | HCDR3 | LCDR1 | LCDR2 | LCDR3 |
| MAB1 | DYYMS (SEQ ID NO: 61) | YISRSGSTKYYADSVKG (SEQ ID NO: 62) | DQEDYALDY (SEQ ID NO: 63) | QASQDISNYLN (SEQ ID NO: 64) | DASNLET (SEQ ID NO: 65) | EQYEDYPLT (SEQ ID NO: 66) |
| MAB2 | DYYMS (SEQ ID NO: 61) | YISRSGSTKYYADSVKG (SEQ ID NO: 62) | DETDYGWDY (SEQ ID NO: 67) | QASQDISNYLN (SEQ ID NO: 64) | DASNLET (SEQ ID NO: 65) | KQYEDYPLT (SEQ ID NO: 68) |
| MAB3 | DYYMS (SEQ ID NO: 61) | YISRSGSTKYYADSVKG (SEQ ID NO: 62) | DETDYAFDE (SEQ ID NO: 69) | QASQDISNYLN (SEQ ID NO: 64) | DASNLET (SEQ ID NO: 65) | KQYEDYPLT (SEQ ID NO: 68) |
| MAB4 | DYYMS (SEQ ID NO: 61) | YISRSGSTKYYADSVKG (SEQ ID NO: 62) | DESQYALDY (SEQ ID NO: 70) | QASQDISNYLN (SEQ ID NO: 64) | DASNLET (SEQ ID NO: 65) | HQYEDYPLT (SEQ ID NO: 71) |
| MAB5 | DYYMS (SEQ ID NO: 61) | YISRSGSTKYYADSVKG (SEQ ID NO: 62) | DNTDYALDL (SEQ ID NO: 72) | QASQDISNYLN (SEQ ID NO: 64) | DASNLET (SEQ ID NO: 65) | HQYEDYPLT (SEQ ID NO: 71) |
| MAB6 | DYYMS (SEQ ID NO: 61) | YISRSGSTKYYADSVKG (SEQ ID NO: 62) | DETDYAYDE (SEQ ID NO: 73) | QASQDISNYLN (SEQ ID NO: 64) | DASNLET (SEQ ID NO: 65) | HQYEDYPLT (SEQ ID NO: 71) |
| MAB7 | DYYMS (SEQ ID NO: 61) | YISRSGSTKYYADSVKG (SEQ ID NO: 62) | DETDYAYDN (SEQ ID NO: 74) | QASQDISNYLN (SEQ ID NO: 64) | DASNLET (SEQ ID NO: 65) | QQYEDYPLV (SEQ ID NO: 75) |
| MAB8 | DYYMS (SEQ ID NO: 61) | YISRSGSTKYYADSVKG (SEQ ID NO: 62) | DESDYAYDY (SEQ ID NO: 76) | QASQDISNYLN (SEQ ID NO: 64) | DASNLET (SEQ ID NO: 65) | QQHEDYPL (SEQ ID NO: 77) |
| MAB9 | DYYMS (SEQ ID NO: 61) | YISRSGSTKYYADSVKG (SEQ ID NO: 62) | DENYALDW (SEQ ID NO: 78) | QASQDISNYLN (SEQ ID NO: 64) | DASNLET (SEQ ID NO: 65) | QHYEDYPL (SEQ ID NO: 79) |
| MAB10 | DYYMS (SEQ ID NO: 61) | YISRSGSTKYYADSVKG (SEQ ID NO: 62) | DESDYALDF (SEQ ID NO: 80) | QASQDISNYLN (SEQ ID NO: 64) | DASNLET (SEQ ID NO: 65) | QQYEDLIPT (SEQ ID NO: 81) |
| MAB11 | ELSMH (SEQ ID NO: 82) | TFDPEEGETIYAQKFQG (SEQ ID NO: 83) | EGLAGVPFDL (SEQ ID NO: 84) | RASQSISSWLA (SEQ ID NO: 85) | KASSLES (SEQ ID NO: 86) | QSYNSYVWT (SEQ ID NO: 87) |
| MAB12 | ELSMH (SEQ ID NO: 82) | TFDPEEGETIYAQKFQG (SEQ ID NO: 83) | EGLGGRPFDH (SEQ ID NO: 88) | RASQSISSWLA (SEQ ID NO: 85) | KASSLES (SEQ ID NO: 86) | QQVNSYDWT (SEQ ID NO 89) |
| MAB13 | ELSMH (SEQ ID NO: 82) | TFDPEEGETIYAQKFQG (SEQ ID NO: 83) | EGLAGFPFDI (SEQ ID NO: 90) | RASQSISSWLA (SEQ ID NO: 85) | KASSLES (SEQ ID NO: 86) | QQVNSYDWT (SEQ ID NO 89) |
| MAB14 | ELSMH (SEQ ID NO: 82) | TFDPEEGETIYAQKFQG (SEQ ID NO: 83) | EGLAWRPTDS (SEQ ID NO: 91) | RASQSISSWLA (SEQ ID NO: 85) | KASSLES (SEQ ID NO: 86) | QQYSSYAWT (SEQ ID NO: 92) |
| MAB15 | ELSMH (SEQ ID NO: 82) | TFDPEEGETIYAQKFQG (SEQ ID NO: 83) | KGLAWLPYYS (SEQ ID NO: 93) | RASQSISSWLA (SEQ ID NO: 85) | KASSLES (SEQ ID NO: 86) | QQARSYSWT (SEQ ID NO: 94) |

TABLE 2-continued

| | Kabat CDRs | | | | | |
|---|---|---|---|---|---|---|
| Ab ID No | HCDR1 | HCDR2 | HCDR3 | LCDR1 | LCDR2 | LCDR3 |
| MAB16 | ELSMH (SEQ ID NO: 82) | TFDPEEGETIYAQKFQG (SEQ ID NO: 83) | EGLAGVPFDL (SEQ ID NO: 84) | RASQSISSWLA (SEQ ID NO: 85) | KASSLES (SEQ ID NO: 86) | QQHNSYRWT (SEQ ID NO: 95) |
| MAB17 | ELSMH (SEQ ID NO: 82) | TFDPEEGETIYAQKFQG (SEQ ID NO: 83) | EGEAGRPFDA (SEQ ID NO: 96) | RASQSISSWLA (SEQ ID NO: 85) | KASSLES (SEQ ID NO: 86) | VQYPSYSWT (SEQ ID NO: 97) |
| MAB18 | ELSMH (SEQ ID NO: 82) | TFDPEEGETIYAQKFQG (SEQ ID NO: 83) | EGLAGRPYDV (SEQ ID NO: 98) | RASQSISSWLA (SEQ ID NO: 85) | KASSLES (SEQ ID NO: 86) | QQYNSYKLT (SEQ ID NO: 99) |
| MAB19 | ELSMH (SEQ ID NO: 82) | TFDPEEGETIYAQKFQG (SEQ ID NO: 83) | EGLAGIPFDSW (SEQ ID NO: 100) | RASQSISSWLA (SEQ ID NO: 85) | KASSLES (SEQ ID NO: 86) | QQYNSPSWL (SEQ ID NO: 101) |
| MAB20 | ELSMH (SEQ ID NO: 82) | TFDPEEGETIYAQKFQG (SEQ ID NO: 83) | EGLAGIPFDSW (SEQ ID NO: 100) | RASQSISSWLA (SEQ ID NO: 85) | KASSLES (SEQ ID NO: 86) | QQVNSLSWT (SEQ ID NO: 102) |
| MAB21 | DYGMS (SEQ ID NO: 103) | GINWEGGSTGYADSVKG (SEQ ID NO: 104) | DEQLGGTTYYYYYMDV (SEQ ID NO: 105) | RASQGIRNDLG (SEQ ID NO: 106) | TASNLQS (SEQ ID NO: 107) | FQYNSYPLG (SEQ ID NO: 108) |
| MAB22 | DYGMS (SEQ ID NO: 103) | GINWEGGSTGYADSVKG (SEQ ID NO: 104) | DEQLGGKYYYYYMDV (SEQ ID NO: 109) | RASQGIRNDLG (SEQ ID NO: 106) | TASNLQS (SEQ ID NO: 107) | LQYRSHPLT (SEQ ID NO: 110) |
| MAB23 | DYGMS (SEQ ID NO: 103) | GINWEGGSTGYADSVKG (SEQ ID NO: 104) | DEQLGGQTYYYYYMDV (SEQ ID NO 111) | RASQGIRNDLG (SEQ ID NO: 106) | TASNLQS (SEQ ID NO: 107) | LQYNQVPLT (SEQ ID NO: 112) |
| MAB24 | DYGMS (SEQ ID NO: 103) | GINWEGGSTGYADSVKG (SEQ ID NO: 104) | DEQLGGTTYYYYYMDV (SEQ ID NO: 105) | RASQGIRNDLG (SEQ ID NO: 106) | TASNLQS (SEQ ID NO: 107) | LQTNIYPLT (SEQ ID NO: 113) |
| MAB25 | DYGMS (SEQ ID NO: 103) | GINWEGGSTGYADSVKG (SEQ ID NO: 104) | DEQLGGIKYYYYYMDV (SEQ ID NO: 114) | RASQGIRNDLG (SEQ ID NO: 106) | TASNLQS (SEQ ID NO: 107) | LQYKQYPLT (SEQ ID NO: 115) |
| MAB26 | DYGMS (SEQ ID NO: 103) | GINWEGGSTGYADSVKG (SEQ ID NO: 104) | DEQLGGLKYYYYYMDV (SEQ ID NO: 116) | RASQGIRNDLG (SEQ ID NO: 106) | TASNLQS (SEQ ID NO: 107) | LQTNIYPLT (SEQ ID NO: 113) |
| MAB27 | DYGMS (SEQ ID NO: 103) | GINWEGGSTGYADSVKG (SEQ ID NO: 104) | DEQLGGKVYYYYYMDV (SEQ ID NO: 117) | RASQGIRNDLG (SEQ ID NO: 106) | TASNLQS (SEQ ID NO: 107) | LQYNSYPLA (SEQ ID NO: 118) |
| MAB28 | DYGMS (SEQ ID NO: 103) | GINWEGGSTGYADSVKG (SEQ ID NO: 104) | DEQLGGLKYYYYYMDV (SEQ ID NO: 116) | RASQGIRNDLG (SEQ ID NO: 106) | TASNLQS (SEQ ID NO: 107) | LQYHSYPLR (SEQ ID NO: 119) |
| MAB29 | DYGMS (SEQ ID NO: 103) | GINWEGGSTGYADSVKG (SEQ ID NO: 104) | DEQLGGNHYYYYYMDA (SEQ ID NO: 120) | RASQGIRNDLG (SEQ ID NO: 106) | TASNLQS (SEQ ID NO: 107) | LQYASYPLK (SEQ ID NO: 121) |
| MAB30 | DYGMS (SEQ ID NO: 103) | GINWEGGSTGYADSVKG (SEQ ID NO: 104) | DEQLGGRHYYYYYMDV (SEQ ID NO: 122) | RASQGIRNDLG (SEQ ID NO: 106) | TASNLQS (SEQ ID NO: 107) | LQYNAYPLI (SEQ ID NO: 123) |

TABLE 2-continued

Kabat CDRs

| Ab ID No | HCDR1 | HCDR2 | HCDR3 | LCDR1 | LCDR2 | LCDR3 |
|---|---|---|---|---|---|---|
| MAB31 | DYYMS (SEQ ID NO: 61) | YISRSGSTKY YADSVKG (SEQ ID NO: 62) | DQEDYALDY (SEQ ID NO: 63) | QASQDISNY LN (SEQ ID NO: 64) | DASNLET (SEQ ID NO: 65) | EQYEDYPLT (SEQ ID NO: 66) |
| MAB32 | DYYMS (SEQ ID NO: 61) | YISRSGSTKY YADSVKG (SEQ ID NO: 62) | DETDYGWDY (SEQ ID NO: 67) | QASQDISNY LN (SEQ ID NO: 64) | DASNLET (SEQ ID NO: 65) | KQYEDYPLT (SEQ ID NO: 68) |
| MAB33 | DYYMS (SEQ ID NO: 61) | YISRSGSTKY YADSVKG (SEQ ID NO: 62) | DETDYAFDE (SEQ ID NO: 69) | QASQDISNY LN (SEQ ID NO: 64) | DASNLET (SEQ ID NO: 65) | KQYEDYPLT (SEQ ID NO: 68) |
| MAB34 | DYYMS (SEQ ID NO: 61) | YISRSGSTKY YADSVKG (SEQ ID NO: 62) | DESQYALDY (SEQ ID NO: 70) | QASQDISNY LN (SEQ ID NO: 64) | DASNLET (SEQ ID NO: 65) | HQYEDYPLT (SEQ ID NO: 71) |
| MAB35 | DYYMS (SEQ ID NO: 61) | YISRSGSTKY YADSVKG (SEQ ID NO: 62) | DNTDYALDL (SEQ ID NO: 72) | QASQDISNY LN (SEQ ID NO: 64) | DASNLET (SEQ ID NO: 65) | HQYEDYPLT (SEQ ID NO: 71) |
| MAB36 | DYYMS (SEQ ID NO: 61) | YISRSGSTKY YADSVKG (SEQ ID NO: 62) | DETDYAYDE (SEQ ID NO: 73) | QASQDISNY LN (SEQ ID NO: 64) | DASNLET (SEQ ID NO: 65) | HQYEDYPLT (SEQ ID NO: 71) |
| MAB37 | DYYMS (SEQ ID NO: 61) | YISRSGSTKY YADSVKG (SEQ ID NO: 62) | DETDYAYDN (SEQ ID NO: 74) | QASQDISNY LN (SEQ ID NO: 64) | DASNLET (SEQ ID NO: 65) | QQYEDYPLV (SEQ ID NO: 75) |
| MAB38 | DYYMS (SEQ ID NO: 61) | YISRSGSTKY YADSVKG (SEQ ID NO: 62) | DESDYAYDY (SEQ ID NO: 76) | QASQDISNY LN (SEQ ID NO: 64) | DASNLET (SEQ ID NO: 65) | QQHEDYPL (SEQ ID NO: 77) |
| MAB39 | DYYMS (SEQ ID NO: 61) | YISRSGSTKY YADSVKG (SEQ ID NO: 62) | DENYALDW (SEQ ID NO: 78) | QASQDISNY LN (SEQ ID NO: 64) | DASNLET (SEQ ID NO: 65) | QHYEDYPL (SEQ ID NO: 79) |
| MAB40 | DYYMS (SEQ ID NO: 61) | YISRSGSTKY YADSVKG (SEQ ID NO: 62) | DESDYALDF (SEQ ID NO: 80) | QASQDISNY LN (SEQ ID NO: 64) | DASNLET (SEQ ID NO: 65) | QQYEDLIPT (SEQ ID NO: 81) |
| MAB41 | ELSMH (SEQ ID NO: 82) | TFDPEEGETI YAQKFQG (SEQ ID NO: 83) | EGLAGVPFDL (SEQ ID NO: 84) | RASQSISSW LA (SEQ ID NO: 85) | KASSLES (SEQ ID NO: 86) | QSYNSYVWT (SEQ ID NO: 87) |
| MAB42 | ELSMH (SEQ ID NO: 82) | TFDPEEGETI YAQKFQG (SEQ ID NO: 83) | EGLGGRPFDH (SEQ ID NO: 88) | RASQSISSW LA (SEQ ID NO: 85) | KASSLES (SEQ ID NO: 86) | QQVNSYDWT (SEQ ID NO 89) |
| MAB43 | ELSMH (SEQ ID NO: 82) | TFDPEEGETI YAQKFQG (SEQ ID NO: 83) | EGLAGFPFDI (SEQ ID NO: 90) | RASQSISSW LA (SEQ ID NO: 85) | KASSLES (SEQ ID NO: 86) | QQVNSYDWT (SEQ ID NO 89) |
| MAB44 | ELSMH (SEQ ID NO: 82) | TFDPEEGETI YAQKFQG (SEQ ID NO: 83) | EGLAWRPTDS (SEQ ID NO: 91) | RASQSISSW LA (SEQ ID NO: 85) | KASSLES (SEQ ID NO: 86) | QQYSSYAWT (SEQ ID NO: 92) |
| MAB45 | ELSMH (SEQ ID NO: 82) | TFDPEEGETI YAQKFQG (SEQ ID NO: 83) | KGLAWLPYY S (SEQ ID NO: 93) | RASQSISSW LA (SEQ ID NO: 85) | KASSLES (SEQ ID NO: 86) | QQARSYSWT (SEQ ID NO: 94) |

TABLE 2-continued

| | | Kabat CDRs | | | | |
|---|---|---|---|---|---|---|
| Ab ID No | HCDR1 | HCDR2 | HCDR3 | LCDR1 | LCDR2 | LCDR3 |
| MAB46 | ELSMH (SEQ ID NO: 82) | TFDPEEGETI YAQKFQG (SEQ ID NO: 83) | EGLAGVPFDL (SEQ ID NO: 84) | RASQSISSW LA (SEQ ID NO: 85) | KASSLES (SEQ ID NO: 86) | QQHNSYRWT (SEQ ID NO: 95) |
| MAB47 | ELSMH (SEQ ID NO: 82) | TFDPEEGETI YAQKFQG (SEQ ID NO: 83) | EGEAGRPFDA (SEQ ID NO: 96) | RASQSISSW LA (SEQ ID NO: 85) | KASSLES (SEQ ID NO: 86) | VQYPSYSWT (SEQ ID NO: 97) |
| MAB48 | ELSMH (SEQ ID NO: 82) | TFDPEEGETI YAQKFQG (SEQ ID NO: 83) | EGLAGRPYDV (SEQ ID NO: 98) | RASQSISSW LA (SEQ ID NO: 85) | KASSLES (SEQ ID NO: 86) | QQYNSYKLT (SEQ ID NO: 99) |
| MAB49 | ELSMH (SEQ ID NO: 82) | TFDPEEGETI YAQKFQG (SEQ ID NO: 83) | EGLAGIPFDS W (SEQ ID NO: 100) | RASQSISSW LA (SEQ ID NO: 85) | KASSLES (SEQ ID NO: 86) | QQYNSPSWL (SEQ ID NO: 101) |
| MAB50 | ELSMH (SEQ ID NO: 82) | TFDPEEGETI YAQKFQG (SEQ ID NO: 83) | EGLAGIPFDS W (SEQ ID NO: 100) | RASQSISSW LA (SEQ ID NO: 85) | KASSLES (SEQ ID NO: 86) | QQVNSLSWT (SEQ ID NO: 102) |
| MAB51 | DYGMS (SEQ ID NO: 103) | GINWEGGST GYADSVKG (SEQ ID NO: 104) | DEQLGGTTYY YYYMDV (SEQ ID NO: 105) | RASQGIRN DLG (SEQ ID NO: 106) | TASNLQS (SEQ ID NO: 107) | FQYNSYPLG (SEQ ID NO: 108) |
| MAB52 | DYGMS (SEQ ID NO: 103) | GINWEGGST GYADSVKG (SEQ ID NO: 104) | DEQLGGKYY YYYMDV (SEQ ID NO: 109) | RASQGIRN DLG (SEQ ID NO: 106) | TASNLQS (SEQ ID NO: 107) | LQYRSHPLT (SEQ ID NO: 110) |
| MAB53 | DYGMS (SEQ ID NO: 103) | GINWEGGST GYADSVKG (SEQ ID NO: 104) | DEQLGGQTY YYYMDV (SEQ ID NO: 111) | RASQGIRN DLG (SEQ ID NO: 106) | TASNLQS (SEQ ID NO: 107) | LQYNQVPLT (SEQ ID NO: 112) |
| MAB54 | DYGMS (SEQ ID NO: 103) | GINWEGGST GYADSVKG (SEQ ID NO: 104) | DEQLGGTTYY YYYMDV (SEQ ID NO: 105) | RASQGIRN DLG (SEQ ID NO: 106) | TASNLQS (SEQ ID NO: 107) | LQTNIYPLT (SEQ ID NO: 113) |
| MAB55 | DYGMS (SEQ ID NO: 103) | GINWEGGST GYADSVKG (SEQ ID NO: 104) | DEQLGGIKYY YYYMDV (SEQ ID NO: 114) | RASQGIRN DLG (SEQ ID NO: 106) | TASNLQS (SEQ ID NO: 107) | LQYKQYPLT (SEQ ID NO: 115) |
| MAB56 | DYGMS (SEQ ID NO: 103) | GINWEGGST GYADSVKG (SEQ ID NO: 104) | DEQLGGLKY YYYMDV (SEQ ID NO: 116) | RASQGIRN DLG (SEQ ID NO: 106) | TASNLQS (SEQ ID NO: 107) | LQTNIYPLT (SEQ ID NO: 113) |
| MAB57 | DYGMS (SEQ ID NO: 103) | GINWEGGST GYADSVKG (SEQ ID NO: 104) | DEQLGGKVY YYYMDV (SEQ ID NO: 117) | RASQGIRN DLG (SEQ ID NO: 106) | TASNLQS (SEQ ID NO: 107) | LQYNSYPLA (SEQ ID NO: 118) |
| MAB58 | DYGMS (SEQ ID NO: 103) | GINWEGGST GYADSVKG (SEQ ID NO: 104) | DEQLGGLKY YYYMDV (SEQ ID NO: 116) | RASQGIRN DLG (SEQ ID NO: 106) | TASNLQS (SEQ ID NO: 107) | LQYHSYPLR (SEQ ID NO: 119) |
| MAB59 | DYGMS (SEQ ID NO: 103) | GINWEGGST GYADSVKG (SEQ ID NO: 104) | DEQLGGNHY YYYMDA (SEQ ID NO: 120) | RASQGIRN DLG (SEQ ID NO: 106) | TASNLQS (SEQ ID NO: 107) | LQYASYPLK (SEQ ID NO: 121) |
| MAB60 | DYGMS (SEQ ID NO: 103) | GINWEGGST GYADSVKG (SEQ ID NO: 104) | DEQLGGRHY YYYMDV (SEQ ID NO: 122) | RASQGIRN DLG (SEQ ID NO: 106) | TASNLQS (SEQ ID NO: 107) | LQYNAYPLI (SEQ ID NO: 123) |

The CDRs in the above-identified table can also be referred to according to Chothia CDRs or IMGT CDRs. These are illustrated in the following tables for the different antibodies. Table 3:

TABLE 3

| CHOTHIA CDRS | | | | | | |
|---|---|---|---|---|---|---|
| Ab ID No | HCDR1 | HCDR2 | HCDR3 | LCDR1 | LCDR2 | LCDR3 |
| MAB1 | GFTFSDY (SEQ ID NO: 124) | SRSGST (SEQ ID NO: 125) | DQEDYALDY (SEQ ID NO: 63) | QASQDISNY LN (SEQ ID NO: 64) | DASNLET (SEQ ID NO: 65) | EQYEDYPLT (SEQ ID NO: 66) |
| MAB2 | GFTFSDY (SEQ ID NO: 124) | SRSGST (SEQ ID NO: 125) | DETDYGWDY (SEQ ID NO: 67) | QASQDISNY LN (SEQ ID NO: 64) | DASNLET (SEQ ID NO: 65) | KQYEDYPLT (SEQ ID NO: 68) |
| MAB3 | GFTFSDY (SEQ ID NO: 124) | SRSGST (SEQ ID NO: 125) | DETDYAFDE (SEQ ID NO: 69) | QASQDISNY LN (SEQ ID NO: 64) | DASNLET (SEQ ID NO: 65) | KQYEDYPLT (SEQ ID NO: 68) |
| MAB4 | GFTFSDY (SEQ ID NO: 124) | SRSGST (SEQ ID NO: 125) | DESQYALDY (SEQ ID NO: 70) | QASQDISNY LN (SEQ ID NO: 64) | DASNLET (SEQ ID NO: 65) | HQYEDYPLT (SEQ ID NO: 71) |
| MAB5 | GFTFSDY (SEQ ID NO: 124) | SRSGST (SEQ ID NO: 125) | DNTDYALDL (SEQ ID NO: 72) | QASQDISNY LN (SEQ ID NO: 64) | DASNLET (SEQ ID NO: 65) | HQYEDYPLT (SEQ ID NO: 71) |
| MAB6 | GFTFSDY (SEQ ID NO: 124) | SRSGST (SEQ ID NO: 125) | DETDYAYDE (SEQ ID NO: 73) | QASQDISNY LN (SEQ ID NO: 64) | DASNLET (SEQ ID NO: 65) | HQYEDYPLT (SEQ ID NO: 71) |
| MAB7 | GFTFSDY (SEQ ID NO: 124) | SRSGST (SEQ ID NO: 125) | DETDYAYDN (SEQ ID NO: 74) | QASQDISNY LN (SEQ ID NO: 64) | DASNLET (SEQ ID NO: 65) | QQYEDYPLV (SEQ ID NO: 75) |
| MAB8 | GFTFSDY (SEQ ID NO: 124) | SRSGST (SEQ ID NO: 125) | DESDYAYDY (SEQ ID NO: 76) | QASQDISNY LN (SEQ ID NO: 64) | DASNLET (SEQ ID NO: 65) | QQHEDYPL (SEQ ID NO: 77) |
| MAB9 | GFTFSDY (SEQ ID NO: 124) | SRSGST (SEQ ID NO: 125) | DENYALDW (SEQ ID NO: 78) | QASQDISNY LN (SEQ ID NO: 64) | DASNLET (SEQ ID NO: 65) | QHYEDYPL (SEQ ID NO: 79) |
| MAB10 | GFTFSDY (SEQ ID NO: 124) | SRSGST (SEQ ID NO: 125) | DESDYALDF (SEQ ID NO: 80) | QASQDISNY LN (SEQ ID NO: 64) | DASNLET (SEQ ID NO: 65) | QQYEDLIPT (SEQ ID NO: 81) |
| MAB11 | GDTLTEL (SEQ ID NO: 126) | DPEEGE (SEQ ID NO: 127) | EGLAGVPFDL (SEQ ID NO: 84) | RASQSISSW LA (SEQ ID NO: 85) | KASSLES (SEQ ID NO: 86) | QSYNSYVWT (SEQ ID NO: 87) |
| MAB12 | GDTLTEL (SEQ ID NO: 126) | DPEEGE (SEQ ID NO: 127) | EGLGGRPFDH (SEQ ID NO: 88) | RASQSISSW LA (SEQ ID NO: 85) | KASSLES (SEQ ID NO: 86) | QQVNSYDWT (SEQ ID NO 89) |
| MAB13 | GDTLTEL (SEQ ID NO: 126) | DPEEGE (SEQ ID NO: 127) | EGLAGFPFDI (SEQ ID NO: 90) | RASQSISSW LA (SEQ ID NO: 85) | KASSLES (SEQ ID NO: 86) | QQVNSYDWT (SEQ ID NO 89) |
| MAB14 | GDTLTEL (SEQ ID NO: 126) | DPEEGE (SEQ ID NO: 127) | EGLAWRPTDS (SEQ ID NO: 91) | RASQSISSW LA (SEQ ID NO: 85) | KASSLES (SEQ ID NO: 86) | QQYSSYAWT (SEQ ID NO: 92) |
| MAB15 | GDTLTEL (SEQ ID NO: 126) | DPEEGE (SEQ ID NO: 127) | KGLAWLPYYS (SEQ ID NO: 93) | RASQSISSW LA (SEQ ID NO: 85) | KASSLES (SEQ ID NO: 86) | QQARSYSWT (SEQ ID NO: 94) |
| MAB16 | GDTLTEL (SEQ ID NO: 126) | DPEEGE (SEQ ID NO: 127) | EGLAGVPFDL (SEQ ID NO: 84) | RASQSISSW LA (SEQ ID NO: 85) | KASSLES (SEQ ID NO: 86) | QQHNSYRWT (SEQ ID NO: 95) |
| MAB17 | GDTLTEL (SEQ ID NO: 126) | DPEEGE (SEQ ID NO: 127) | EGEAGRPFDA (SEQ ID NO: 96) | RASQSISSW LA (SEQ ID NO: 85) | KASSLES (SEQ ID NO: 86) | VQYPSYSWT (SEQ ID NO: 97) |

TABLE 3-continued

| | CHOTHIA CDRS | | | | | |
|---|---|---|---|---|---|---|
| Ab ID No | HCDR1 | HCDR2 | HCDR3 | LCDR1 | LCDR2 | LCDR3 |
| MAB18 | GDTLTEL (SEQ ID NO: 126) | DPEEGE (SEQ ID NO: 127) | EGLAGRPYDV (SEQ ID NO: 98) | RASQSISSW LA (SEQ ID NO: 85) | KASSLES (SEQ ID NO: 86) | QQYNSYKLT (SEQ ID NO: 99) |
| MAB19 | GDTLTEL (SEQ ID NO: 126) | DPEEGE (SEQ ID NO: 127) | EGLAGIPFDS W (SEQ ID NO: 100) | RASQSISSW LA (SEQ ID NO: 85) | KASSLES (SEQ ID NO: 86) | QQYNSPSWL (SEQ ID NO: 101) |
| MAB20 | GDTLTEL (SEQ ID NO: 126) | DPEEGE (SEQ ID NO: 127) | EGLAGIPFDS W (SEQ ID NO: 100) | RASQSISSW LA (SEQ ID NO: 85) | KASSLES (SEQ ID NO: 86) | QQVNSLSWT (SEQ ID NO: 102) |
| MAB21 | GFTFDDY (SEQ ID NO: 128) | NWEGGS (SEQ II NO: 129) | DEQLGGTTYY YYYMDV (SEQ ID NO: 105) | RASQGIRN DLG (SEQ ID NO: 106) | TASNLQS (SEQ ID NO: 107) | FQYNSYPLG (SEQ ID NO: 108) |
| MAB22 | GFTFDDY (SEQ ID NO: 128) | NWEGGS (SEQ ID NO: 129) | DEQLGGKYY YYYYMDV (SEQ ID NO: 109) | RASQGIRN DLG (SEQ ID NO: 106) | TASNLQS (SEQ ID NO: 107) | LQYRSHPLT (SEQ ID NO: 110) |
| MAB23 | GFTFDDY (SEQ ID NO: 128) | NWEGGS (SEQ ID NO: 129) | DEQLGGQTY YYYMDV (SEQ ID NO: 111) | RASQGIRN DLG (SEQ ID NO: 106) | TASNLQS (SEQ ID NO: 107) | LQYNQVPLT (SEQ ID NO: 112) |
| MAB24 | GFTFDDY (SEQ ID NO: 128) | NWEGGS (SEQ ID NO: 129) | DEQLGGTTYY YYYMDV (SEQ ID NO: 105) | RASQGIRN DLG (SEQ ID NO: 106) | TASNLQS (SEQ ID NO: 107) | LQTNIYPLT (SEQ ID NO: 113) |
| MAB25 | GFTFDDY (SEQ ID NO: 128) | NWEGGS (SEQ ID NO: 129) | DEQLGGIKYY YYYMDV (SEQ ID NO: 114) | RASQGIRN DLG (SEQ ID NO: 106) | TASNLQS (SEQ ID NO: 107) | LQYKQYPLT (SEQ ID NO: 115) |
| MAB26 | GFTFDDY (SEQ ID NO: 128) | NWEGGS (SEQ ID NO: 129) | DEQLGGLKY YYYMDV (SEQ ID NO: 116) | RASQGIRN DLG (SEQ ID NO: 106) | TASNLQS (SEQ ID NO: 107) | LQTNIYPLT (SEQ ID NO: 113) |
| MAB27 | GFTFDDY (SEQ ID NO: 128) | NWEGGS (SEQ ID NO: 129) | DEQLGGKVY YYYMDV (SEQ ID NO: 117) | RASQGIRN DLG (SEQ ID NO: 106) | TASNLQS (SEQ ID NO: 107) | LQYNSYPLA (SEQ ID NO: 118) |
| MAB28 | GFTFDDY (SEQ ID NO: 128) | NWEGGS (SEQ ID NO: 129) | DEQLGGLKY YYYMDV (SEQ ID NO: 116) | RASQGIRN DLG (SEQ ID NO: 106) | TASNLQS (SEQ ID NO: 107) | LQYHSYPLR (SEQ ID NO: 119) |
| MAB29 | GFTFDDY (SEQ ID NO: 128) | NWEGGS (SEQ ID NO: 129) | DEQLGGNHY YYYMDA (SEQ ID NO: 120) | RASQGIRN DLG (SEQ ID NO: 106) | TASNLQS (SEQ ID NO: 107) | LQYASYPLK (SEQ ID NO: 121) |
| MAB30 | GFTFDDY (SEQ ID NO: 128) | NWEGGS (SEQ ID NO: 129) | DEQLGGRHY YYYMDV (SEQ ID NO: 122) | RASQGIRN DLG (SEQ ID NO: 106) | TASNLQS (SEQ ID NO: 107) | LOYNAYPLI (SEQ ID NO: 123) |
| MAB31 | GFTFSDY (SEQ ID NO: 124) | SRSGST (SEQ ID NO: 125) | DQEDYALDY (SEQ ID NO: 63) | QASQDISNY LN (SEQ ID NO: 64) | DASNLET (SEQ ID NO: 65) | EQYEDYPLT (SEQ ID NO: 66) |
| MAB32 | GFTFSDY (SEQ ID NO: 124) | SRSGST (SEQ ID NO: 125) | DETDYGWDY (SEQ ID NO: 67) | QASQDISNY LN (SEQ ID NO: 64) | DASNLET (SEQ ID NO: 65) | KQYEDYPLT (SEQ ID NO: 68) |
| MAB33 | GFTFSDY (SEQ ID NO: 124) | SRSGST (SEQ ID NO: 125) | DETDYAFDE (SEQ ID NO: 69) | QASQDISNY LN (SEQ ID NO: 64) | DASNLET (SEQ ID NO: 65) | KQYEDYPLT (SEQ ID NO: 68) |

TABLE 3-continued

| | CHOTHIA CDRS | | | | | |
|---|---|---|---|---|---|---|
| Ab ID No | HCDR1 | HCDR2 | HCDR3 | LCDR1 | LCDR2 | LCDR3 |
| MAB34 | GFTFSDY (SEQ ID NO: 124) | SRSGST (SEQ ID NO: 125) | DESQYALDY (SEQ ID NO: 70) | QASQDISNY LN (SEQ ID NO: 64) | DASNLET (SEQ ID NO: 65) | HQYEDYPLT (SEQ ID NO: 71) |
| MAB35 | GFTFSDY (SEQ ID NO: 124) | SRSGST (SEQ ID NO: 125) | DNTDYALDL (SEQ ID NO: 72) | QASQDISNY LN (SEQ ID NO: 64) | DASNLET (SEQ ID NO: 65) | HQYEDYPLT (SEQ ID NO: 71) |
| MAB36 | GFTFSDY (SEQ ID NO: 124) | SRSGST (SEQ ID NO: 125) | DETDYAYDE (SEQ ID NO: 73) | QASQDISNY LN (SEQ ID NO: 64) | DASNLET (SEQ ID NO: 65) | HQYEDYPLT (SEQ ID NO: 71) |
| MAB37 | GFTFSDY (SEQ ID NO: 124) | SRSGST (SEQ ID NO: 125) | DETDYAYDN (SEQ ID NO: 74) | QASQDISNY LN (SEQ ID NO: 64) | DASNLET (SEQ ID NO: 65) | QQYEDYPLV (SEQ ID NO: 75) |
| MAB38 | GFTFSDY (SEQ ID NO: 124) | SRSGST (SEQ ID NO: 125) | DESDYAYDY (SEQ ID NO: 76) | QASQDISNY LN (SEQ ID NO: 64) | DASNLET (SEQ ID NO: 65) | QQHEDYPL (SEQ ID NO: 77) |
| MAB39 | GFTFSDY (SEQ ID NO: 124) | SRSGST (SEQ ID NO: 125) | DENYALDW (SEQ ID NO: 78) | QASQDISNY LN (SEQ ID NO: 64) | DASNLET (SEQ ID NO: 65) | QHYEDYPL (SEQ ID NO: 79) |
| MAB40 | GFTFSDY (SEQ ID NO: 124) | SRSGST (SEQ ID NO: 125) | DESDYALDF (SEQ ID NO: 80) | QASQDISNY LN (SEQ ID NO: 64) | DASNLET (SEQ ID NO: 65) | QQYEDLIPT (SEQ ID NO: 81) |
| MAB41 | GDTLTEL (SEQ ID NO: 126) | DPEEGE (SEQ ID NO: 127) | EGLAGVPFDL (SEQ ID NO: 84) | RASQSISSW LA (SEQ ID NO: 85) | KASSLES (SEQ ID NO: 86) | QSYNSYVWT (SEQ ID NO: 87) |
| MAB42 | GDTLTEL (SEQ ID NO: 126) | DPEEGE (SEQ ID NO: 127) | EGLGGRPFDH (SEQ ID NO 88) | RASQSISSW LA (SEQ ID NO: 85) | KASSLES (SEQ ID NO: 86) | QQVNSYDWT (SEQ ID NO 89) |
| MAB43 | GDTLTEL (SEQ ID NO: 126) | DPEEGE (SEQ ID NO: 127) | EGLAGFPFDI (SEQ ID NO 90) | RASQSISSW LA (SEQ ID NO: 85) | KASSLES (SEQ ID NO: 86) | QQVNSYDWT (SEQ ID NO 89) |
| MAB44 | GDTLTEL (SEQ ID NO: 126) | DPEEGE (SEQ ID NO: 127) | EGLAWRPTDS (SEQ ID NO: 91) | RASQSISSW LA (SEQ ID NO: 85) | KASSLES (SEQ ID NO: 86) | QQYSSYAWT (SEQ ID NO: 92) |
| MAB45 | GDTLTEL (SEQ ID NO: 126) | DPEEGE (SEQ ID NO: 127) | KGLAWLPYYS (SEQ ID NO: 93) | RASQSISSW LA (SEQ ID NO: 85) | KASSLES (SEQ ID NO: 86) | QQARSYSWT (SEQ ID NO: 94) |
| MAB46 | GDTLTEL (SEQ ID NO: 126) | DPEEGE (SEQ ID NO: 127) | EGLAGVPFDL (SEQ ID NO 84) | RASQSISSW LA (SEQ ID NO: 85) | KASSLES (SEQ ID NO: 86) | QQHNSYRWT (SEQ ID NO: 95) |
| MAB47 | GDTLTEL (SEQ ID NO: 126) | DPEEGE (SEQ ID NO: 127) | EGEAGRPFDA (SEQ ID NO: 96) | RASQSISSW LA (SEQ ID NO: 85) | KASSLES (SEQ ID NO: 86) | VQYPSYSWT (SEQ ID NO 97) |
| MAB48 | GDTLTEL (SEQ ID NO: 126) | DPEEGE (SEQ ID NO: 127) | EGLAGRPYDV (SEQ ID NO: 98) | RASQSISSW LA (SEQ ID NO: 85) | KASSLES (SEQ ID NO: 86) | QQYNSYKLT (SEQ ID NO: 99) |
| MAB49 | GDTLTEL (SEQ ID NO: 126) | DPEEGE (SEQ ID NO: 127) | EGLAGIPFDS W (SEQ ID NO: 100) | RASQSISSW LA (SEQ ID NO: 85) | KASSLES (SEQ ID NO: 86) | QQYNSPSWL (SEQ ID NO: 101) |
| MAB50 | GDTLTEL (SEQ ID NO: 126) | DPEEGE (SEQ ID NO: 127) | EGLAGIPFDS W (SEQ ID NO: 100) | RASQSISSW LA (SEQ ID NO: 85) | KASSLES (SEQ ID NO: 86) | QQVNSLSWT (SEQ ID NO: 102) |
| MAB51 | GFTFDDY (SEQ ID NO: 128) | NWEGGS (SEQ ID NO: 129) | DEQLGGTTYY YYYMDV (SEQ ID NO: 105) | RASQGIRN DLG (SEQ ID NO: 106) | TASNLQS (SEQ ID NO: 107) | FQYNSYPLG (SEQ ID NO: 108) |

TABLE 3-continued

CHOTHIA CDRS

| Ab ID No | HCDR1 | HCDR2 | HCDR3 | LCDR1 | LCDR2 | LCDR3 |
|---|---|---|---|---|---|---|
| MAB52 | GFTFDDY (SEQ ID NO: 128) | NWEGGS (SEQ ID NO: 129) | DEQLGGKYY YYYYMDV (SEQ ID NO: 109) | RASQGIRN DLG (SEQ ID NO: 106) | TASNLQS (SEQ ID NO: 107) | LQYRSHPLT (SEQ ID NO: 110) |
| MAB53 | GFTFDDY (SEQ ID NO: 128) | NWEGGS (SEQ ID NO: 129) | DEQLGGQTY YYYYMDV (SEQ ID NO: 111) | RASQGIRN DLG (SEQ ID NO: 106) | TASNLQS (SEQ ID NO: 107) | LQYNQVPLT (SEQ ID NO: 112) |
| MAB54 | GFTFDDY (SEQ ID NO: 128) | NWEGGS (SEQ ID NO: 129) | DEQLGGTTYY YYYMDV (SEQ ID NO: 105) | RASQGIRN DLG (SEQ ID NO: 106) | TASNLQS (SEQ ID NO: 107) | LQTNIYPLT (SEQ ID NO: 113) |
| MAB55 | GFTFDDY (SEQ ID NO: 128) | NWEGGS (SEQ ID NO: 129) | DEQLGGIKYY YYYMDV (SEQ ID NO: 114) | RASQGIRN DLG (SEQ ID NO: 106) | TASNLQS (SEQ ID NO: 107) | LQYKQYPLT (SEQ ID NO: 115) |
| MAB56 | GFTFDDY (SEQ ID NO: 128) | NWEGGS (SEQ ID NO: 129) | DEQLGGLKY YYYYMDV (SEQ ID NO: 116) | RASQGIRN DLG (SEQ ID NO: 106) | TASNLQS (SEQ ID NO: 107) | LQTNIYPLT (SEQ ID NO: 113) |
| MAB57 | GFTFDDY (SEQ ID NO: 128) | NWEGGS (SEQ ID NO: 129) | DEQLGGKVY YYYYMDV (SEQ ID NO: 117) | RASQGIRN DLG (SEQ ID NO: 106) | TASNLQS (SEQ ID NO: 107) | LQYNSYPLA (SEQ ID NO: 118) |
| MAB58 | GFTFDDY (SEQ ID NO: 128) | NWEGGS (SEQ ID NO: 129) | DEQLGGLKY YYYYMDV (SEQ ID NO: 116) | RASQGIRN DLG (SEQ ID NO: 106) | TASNLQS (SEQ ID NO: 107) | LQYHSYPLR (SEQ ID NO: 119) |
| MAB59 | GFTFDDY (SEQ ID NO: 128) | NWEGGS (SEQ ID NO: 129) | DEQLGGNHY YYYYMDA (SEQ ID NO: 120) | RASQGIRN DLG (SEQ ID NO: 106) | TASNLQS (SEQ ID NO: 107) | LQYASYPLK (SEQ ID NO: 121) |
| MAB60 | GFTFDDY (SEQ ID NO: 128) | NWEGGS (SEQ ID NO: 129) | DEQLGGRHY YYYYMDV (SEQ ID NO: 122) | RASQGIRN DLG (SEQ ID NO: 106) | TASNLQS (SEQ ID NO: 107) | LQYNAYPLI (SEQ ID NO: 123) |

TABLE 4

IMGT CDRS

| Ab ID No | HCDR1 | HCDR2 | HCDR3 | LCDR1 | LCDR2 | LCDR3 |
|---|---|---|---|---|---|---|
| MAB1 | GFTFSDY Y (SEQ ID NO: 130) | ISRSGSTK (SEQ ID NO: 131) | ARDQEDYAL DY (SEQ ID NO: 132) | QDISNY (SEQ ID NO: 133) | DAS (SEQ ID NO: 134) | EQYEDYPLT (SEQ ID NO: 66) |
| MAB2 | GFTFSDY Y (SEQ ID NO: 130) | ISRSGSTK (SEQ ID NO: 131) | ARDETDYGW DY (SEQ ID NO: 135) | QDISNY (SEQ ID NO: 133) | DAS (SEQ ID NO: 134) | KQYEDYPLT (SEQ ID NO: 68) |
| MAB3 | GFTFSDY Y (SEQ ID NO: 130) | ISRSGSTK (SEQ ID NO: 131) | ARDETDYAFD E (SEQ ID NO: 136) | QDISNY (SEQ ID NO: 133) | DAS (SEQ ID NO: 134) | KQYEDYPLT (SEQ ID NO: 68) |
| MAB4 | GFTFSDY Y (SEQ ID NO: 130) | ISRSGSTK (SEQ ID NO: 131) | ARDESQYALD Y (SEQ ID NO: 137) | QDISNY (SEQ ID NO: 133) | DAS (SEQ ID NO: 134) | HQYEDYPLT (SEQ ID NO: 71) |
| MAB5 | GFTFSDY Y (SEQ ID NO: 130) | ISRSGSTK (SEQ ID NO: 131) | ARDNTDYAL DL (SEQ ID NO: 138) | QDISNY (SEQ ID NO: 133) | DAS (SEQ ID NO: 134) | HQYEDYPLT (SEQ ID NO: 71) |

TABLE 4-continued

IMGT CDRS

| Ab ID No | HCDR1 | HCDR2 | HCDR3 | LCDR1 | LCDR2 | LCDR3 |
|---|---|---|---|---|---|---|
| MAB6 | GFTFSDYY (SEQ ID NO: 130) | ISRSGSTK (SEQ ID NO: 131) | ARDETDYAYDE (SEQ ID NO: 139) | QDISNY (SEQ ID NO: 133) | DAS (SEQ ID NO: 134) | HQYEDYPLT (SEQ ID NO: 71) |
| MAB7 | GFTFSDYY (SEQ ID NO: 130) | ISRSGSTK (SEQ ID NO: 131) | ARDETDYAYDN (SEQ ID NO: 140) | QDISNY (SEQ ID NO: 133) | DAS (SEQ ID NO: 134) | QQYEDYPLV (SEQ ID NO: 75) |
| MAB8 | GFTFSDYY (SEQ ID NO: 130) | ISRSGSTK (SEQ ID NO: 131) | ARDESDYAYDY (SEQ ID NO: 141) | QDISNY (SEQ ID NO: 133) | DAS (SEQ ID NO: 134) | QQHEDYPL (SEQ ID NO: 77) |
| MAB9 | GFTFSDYY (SEQ ID NO: 130) | ISRSGSTK (SEQ ID NO: 131) | ARDENYALDW (SEQ ID NO: 142) | QDISNY (SEQ ID NO: 133) | DAS (SEQ ID NO: 134) | QHYEDYPL (SEQ ID NO: 79) |
| MAB10 | GFTFSDYY (SEQ ID NO: 130) | ISRSGSTK (SEQ ID NO: 131) | ARDESDYALDF (SEQ ID NO: 143) | QDISNY (SEQ ID NO: 133) | DAS (SEQ ID NO: 134) | QQYEDLIPT (SEQ ID NO: 81) |
| MAB11 | GDTLTELS (SEQ ID NO: 144) | FDPEEGET (SEQ ID NO: 145) | VTEGLAGVPFDL (SEQ ID NO: 146) | QSISSW (SEQ ID NO: 147) | KAS (SEQ ID NO: 148) | QSYNSYVWT (SEQ ID NO: 87) |
| MAB12 | GDTLTELS (SEQ ID NO: 144) | FDPEEGET (SEQ ID NO: 145) | VTEGLGGRPFDH (SEQ ID NO: 149) | QSISSW (SEQ ID NO: 147) | KAS (SEQ ID NO: 148) | QQVNSYDWT (SEQ ID NO 89) |
| MAB13 | GDTLTELS (SEQ ID NO: 144) | FDPEEGET (SEQ ID NO: 145) | VTEGLAGFPFDI (SEQ ID NO: 150) | QSISSW (SEQ ID NO: 147) | KAS (SEQ ID NO: 148) | QQVNSYDWT (SEQ ID NO 89) |
| MAB14 | GDTLTELS (SEQ ID NO: 144) | FDPEEGET (SEQ ID NO: 145) | VTEGLAWRPTDS (SEQ ID NO: 151) | QSISSW (SEQ ID NO: 147) | KAS (SEQ ID NO: 148) | QQYSSYAWT (SEQ ID NO 92) |
| MAB15 | GDTLTELS (SEQ ID NO: 144) | FDPEEGET (SEQ ID NO: 145) | VTKGLAWLPYYS (SEQ ID NO: 152) | QSISSW (SEQ ID NO: 147) | KAS (SEQ ID NO: 148) | QQARSYSWT (SEQ ID NO: 94) |
| MAB16 | GDTLTELS (SEQ ID NO: 144) | FDPEEGET (SEQ ID NO: 145) | VTEGLAGVPFDL (SEQ ID NO: 146) | QSISSW (SEQ ID NO: 147) | KAS (SEQ ID NO: 148) | QQHNSYRWT (SEQ ID NO: 95) |
| MAB17 | GDTLTELS (SEQ ID NO: 144) | FDPEEGET (SEQ ID NO: 145) | VTEGEAGRPFDA (SEQ ID NO: 153) | QSISSW (SEQ ID NO: 147) | KAS (SEQ ID NO: 148) | VQYPSYSWT (SEQ ID NO: 97) |
| MAB18 | GDTLTELS (SEQ ID NO: 144) | FDPEEGET (SEQ ID NO: 145) | VTEGLAGRPYDV (SEQ ID NO: 154) | QSISSW (SEQ ID NO: 147) | KAS (SEQ ID NO: 148) | QQYNSYKLT (SEQ ID NO: 99) |
| MAB19 | GDTLTELS (SEQ ID NO: 144) | FDPEEGET (SEQ ID NO: 145) | VTEGLAGIPFDSW (SEQ ID NO: 155) | QSISSW (SEQ ID NO: 147) | KAS (SEQ ID NO: 148) | QQYNSPSWL (SEQ ID NO: 101) |
| MAB20 | GDTLTELS (SEQ ID NO: 144) | FDPEEGET (SEQ ID NO: 145) | VTEGLAGIPFDSW (SEQ ID NO: 155) | QSISSW (SEQ ID NO: 147) | KAS (SEQ ID NO: 148) | QQVNSLSWT (SEQ ID NO: 102) |
| MAB21 | GFTFDDYG (SEQ ID NO: 156) | INWEGGST (SEQ ID NO: 157) | ARDEQLGGTTYYYYMDV (SEQ ID NO: 158) | QGIRND (SEQ ID NO: 159) | TAS (SEQ ID NO: 160) | FQYNSYPLG (SEQ ID NO: 108) |
| MAB22 | GFTFDDYG (SEQ ID NO: 156) | INWEGGST (SEQ ID NO: 157) | ARDEQLGGKYYYYMDV (SEQ ID NO: 161) | QGIRND (SEQ ID NO: 159) | TAS (SEQ ID NO: 160) | LQYRSHPLT (SEQ ID NO: 110) |
| MAB23 | GFTFDDYG (SEQ ID NO: 156) | INWEGGST (SEQ ID NO: 157) | ARDEQLGGQTYYYYMDV (SEQ ID NO: 162) | QGIRND (SEQ ID NO: 159) | TAS (SEQ ID NO: 160) | LQYNQVPLT (SEQ ID NO: 112) |

TABLE 4-continued

IMGT CDRS

| Ab ID No | HCDR1 | HCDR2 | HCDR3 | LCDR1 | LCDR2 | LCDR3 |
|---|---|---|---|---|---|---|
| MAB24 | GFTFDDYG (SEQ ID NO: 156) | INWEGGST (SEQ ID NO: 157) | ARDEQLGGTTYYYYYMDV (SEQ ID NO: 158) | QGIRND (SEQ ID NO: 159) | TAS (SEQ ID NO: 160) | LQTNIYPLT (SEQ ID NO: 113) |
| MAB25 | GFTFDDYG (SEQ ID NO: 156) | INWEGGST (SEQ ID NO: 157) | ARDEQLGGIKYYYYYMDV (SEQ ID NO: 163) | QGIRND (SEQ ID NO: 159) | TAS (SEQ ID NO: 160) | LQYKQYPLT (SEQ ID NO: 115) |
| MAB26 | GFTFDDYG (SEQ ID NO: 156) | INWEGGST (SEQ ID NO: 157) | ARDEQLGGLKYYYYYMDV (SEQ ID NO: 164) | QGIRND (SEQ ID NO: 159) | TAS (SEQ ID NO: 160) | LQTNIYPLT (SEQ ID NO: 113) |
| MAB27 | GFTFDDYG (SEQ ID NO: 156) | INWEGGST (SEQ ID NO: 157) | ARDEQLGGKVYYYYYMDV (SEQ ID NO: 165) | QGIRND (SEQ ID NO: 159) | TAS (SEQ ID NO: 160) | LQYNSYPLA (SEQ ID NO: 118) |
| MAB28 | GFTFDDYG (SEQ ID NO: 156) | INWEGGST (SEQ ID NO: 157) | ARDEQLGGLKYYYYYMDV (SEQ ID NO: 164) | QGIRND (SEQ ID NO: 159) | TAS (SEQ ID NO: 160) | LQYHSYPLR (SEQ ID NO: 119) |
| MAB29 | GFTFDDYG (SEQ ID NO: 156) | INWEGGST (SEQ ID NO: 157) | ARDEQLGGNHYYYYYMDA (SEQ ID NO: 166) | QGIRND (SEQ ID NO: 159) | TAS (SEQ ID NO: 160) | LQYASYPLK (SEQ ID NO: 121) |
| MAB30 | GFTFDDYG (SEQ ID NO: 156) | INWEGGST (SEQ ID NO: 157) | ARDEQLGGRHYYYYYMDV (SEQ ID NO 167) | QGIRND (SEQ ID NO 159) | TAS (SEQ ID NO: 160) | LQYNAYPLI (SEQ ID NO: 123) |
| MAB31 | GFTFSDYY (SEQ ID NO: 130) | ISRSGSTK (SEQ ID NO: 131) | ARDQEDYALDY (SEQ ID NO: 132) | QDISNY (SEQ ID NO: 133) | DAS (SEQ ID NO: 134) | EQYEDYPLT (SEQ ID NO: 66) |
| MAB32 | GFTFSDYY (SEQ ID NO: 130) | ISRSGSTK (SEQ ID NO: 131) | ARDETDYGWDY (SEQ ID NO: 135) | QDISNY (SEQ ID NO: 133) | DAS (SEQ ID NO: 134) | KQYEDYPLT (SEQ ID NO: 68) |
| MAB33 | GFTFSDYY (SEQ ID NO: 130) | ISRSGSTK (SEQ ID NO: 131) | ARDETDYAFDE (SEQ ID NO: 136) | QDISNY (SEQ ID NO: 133) | DAS (SEQ ID NO: 134) | KQYEDYPLT (SEQ ID NO: 68) |
| MAB34 | GFTFSDYY (SEQ ID NO: 130) | ISRSGSTK (SEQ ID NO: 131) | ARDESQYALDY (SEQ ID NO: 137) | QDISNY (SEQ ID NO: 133) | DAS (SEQ ID NO: 134) | HQYEDYPLT (SEQ ID NO: 71) |
| MAB35 | GFTFSDYY (SEQ ID NO: 130) | ISRSGSTK (SEQ ID NO: 131) | ARDNTDYALDL (SEQ ID NO: 138) | QDISNY (SEQ ID NO: 133) | DAS (SEQ ID NO: 134) | HQYEDYPLT (SEQ ID NO: 71) |
| MAB36 | GFTFSDYY (SEQ ID NO: 130) | ISRSGSTK (SEQ ID NO: 131) | ARDETDYAYDE (SEQ ID NO: 139) | QDISNY (SEQ ID NO: 133) | DAS (SEQ ID NO: 134) | HQYEDYPLT (SEQ ID NO: 71) |
| MAB37 | GFTFSDYY (SEQ ID NO: 130) | ISRSGSTK (SEQ ID NO: 131) | ARDETDYAYDN (SEQ ID NO: 140) | QDISNY (SEQ ID NO: 133) | DAS (SEQ ID NO: 134) | QQYEDYPLV (SEQ ID NO: 75) |
| MAB38 | GFTFSDYY (SEQ ID NO: 130) | ISRSGSTK (SEQ ID NO: 131) | ARDESDYAYDY (SEQ ID NO: 141) | QDISNY (SEQ ID NO: 133) | DAS (SEQ ID NO: 134) | QQHEDYPL (SEQ ID NO: 77) |
| MAB39 | GFTFSDYY (SEQ ID NO: 130) | ISRSGSTK (SEQ ID NO: 131) | ARDENYALDW (SEQ ID NO: 142) | QDISNY (SEQ ID NO: 133) | DAS (SEQ ID NO: 134) | QHYEDYPL (SEQ ID NO: 79) |

TABLE 4-continued

| Ab ID No | HCDR1 | HCDR2 | HCDR3 | LCDR1 | LCDR2 | LCDR3 |
|---|---|---|---|---|---|---|
| MAB40 | GFTFSDYY (SEQ ID NO: 130) | ISRSGSTK (SEQ ID NO: 131) | ARDESDYALDF (SEQ ID NO: 143) | QDISNY (SEQ ID NO: 133) | DAS (SEQ ID NO: 134) | QQYEDLIPT (SEQ ID NO: 81) |
| MAB41 | GDTLTELS (SEQ ID NO: 144) | FDPEEGET (SEQ ID NO: 145) | VTEGLAGVPFDL (SEQ ID NO: 146) | QSISSW (SEQ ID NO: 147) | KAS (SEQ ID NO: 148) | QSYNSYVWT (SEQ ID NO: 87) |
| MAB42 | GDTLTELS (SEQ ID NO: 144) | FDPEEGET (SEQ ID NO: 145) | VTEGLGGRPFDH (SEQ ID NO: 149) | QSISSW (SEQ ID NO: 147) | KAS (SEQ ID NO: 148) | QQVNSYDWT (SEQ ID NO 89) |
| MAB43 | GDTLTELS (SEQ ID NO: 144) | FDPEEGET (SEQ ID NO: 145) | VTEGLAGFPFDI (SEQ ID NO: 150) | QSISSW (SEQ ID NO: 147) | KAS (SEQ ID NO: 148) | QQVNSYDWT (SEQ ID NO 89) |
| MAB44 | GDTLTELS (SEQ ID NO: 144) | FDPEEGET (SEQ ID 145) | VTEGLAWRPTDS (SEQ ID NO: 151) | QSISSW (SEQ ID NO: 147) | KAS (SEQ ID NO: 148) | QQYSSYAWT (SEQ ID NO: 92) |
| MAB45 | GDTLTELS (SEQ ID NO: 144) | FDPEEGET (SEQ ID NO: 145) | VTKGLAWLPYYS (SEQ ID NO: 152) | QSISSW (SEQ ID NO: 147) | KAS (SEQ ID NO: 148) | QQARSYSWT (SEQ ID NO: 94) |
| MAB46 | GDTLTELS (SEQ ID NO: 144) | FDPEEGET (SEQ ID 145) | VTEGLAGVPFDL (SEQ ID NO: 146) | QSISSW (SEQ ID NO: 147) | KAS (SEQ ID NO: 148) | QQHNSYRWT (SEQ ID NO: 95) |
| MAB47 | GDTLTELS (SEQ ID NO: 144) | FDPEEGET (SEQ ID NO: 145) | VTEGEAGRPFDA (SEQ ID NO: 153) | QSISSW (SEQ ID NO: 147) | KAS (SEQ ID NO: 148) | VQYPSYSWT (SEQ ID NO: 97) |
| MAB48 | GDTLTELS (SEQ ID NO: 144) | FDPEEGET (SEQ ID NO: 145) | VTEGLAGRPYDV (SEQ ID NO: 154) | QSISSW (SEQ ID NO: 147) | KAS (SEQ ID NO: 148) | QQYNSYKLT (SEQ ID NO: 99) |
| MAB49 | GDTLTELS (SEQ ID NO: 144) | FDPEEGET (SEQ ID NO: 145) | VTEGLAGIPFDSW (SEQ ID NO: 155) | QSISSW (SEQ ID NO: 147) | KAS (SEQ ID NO: 148) | QQYNSPSWL (SEQ ID NO: 101) |
| MAB50 | GDTLTELS (SEQ ID NO: 144) | FDPEEGET (SEQ ID NO: 145) | VTEGLAGIPFDSW (SEQ ID NO: 155) | QSISSW (SEQ ID NO: 147) | KAS (SEQ ID NO: 148) | QQVNSLSWT (SEQ ID NO: 102) |
| MAB51 | GFTFDDYG (SEQ ID NO: 156) | INWEGGST (SEQ ID NO 157) | ARDEQLGGTTYYYYYMDV (SEQ ID NO: 158) | QGIRND (SEQ ID NO: 159) | TAS (SEQ ID NO: 160) | FQYNSYPLG (SEQ ID NO: 108) |
| MAB52 | GFTFDDYG (SEQ ID NO: 156) | INWEGGST (SEQ ID NO: 157) | ARDEQLGGKYYYYYMDV (SEQ ID NO: 161) | QGIRND (SEQ ID NO: 159) | TAS (SEQ ID NO: 160) | LQYRSHPLT (SEQ ID NO: 110) |
| MAB53 | GFTFDDYG (SEQ ID NO: 156) | INWEGGST (SEQ ID NO: 157) | ARDEQLGGQTYYYYYMDV (SEQ ID NO: 162) | QGIRND (SEQ ID NO: 159) | TAS (SEQ ID NO: 160) | LQYNQVPLT (SEQ ID NO: 112) |
| MAB54 | GFTFDDYG (SEQ ID NO: 156) | INWEGGST (SEQ ID NO: 157) | ARDEQLGGTTYYYYYMDV (SEQ ID NO: 158) | QGIRND (SEQ ID NO: 159) | TAS (SEQ ID NO: 160) | LQTNIYPLT (SEQ ID NO: 113) |
| MAB55 | GFTFDDYG (SEQ ID NO: 156) | INWEGGST (SEQ ID NO: 157) | ARDEQLGGIKYYYYYMDV (SEQ ID NO: 163) | QGIRND (SEQ ID NO: 159) | TAS (SEQ ID NO: 160) | LQYKQYPLT (SEQ ID NO: 115) |
| MAB56 | GFTFDDYG (SEQ ID NO: 156) | INWEGGST (SEQ ID NO: 157) | ARDEQLGGLKYYYYYMDV (SEQ ID NO: 164) | QGIRND (SEQ ID NO: 159) | TAS (SEQ ID NO: 160) | LQTNIYPLT (SEQ ID NO: 113) |

TABLE 4-continued

IMGT CDRS

| Ab ID No | HCDR1 | HCDR2 | HCDR3 | LCDR1 | LCDR2 | LCDR3 |
|---|---|---|---|---|---|---|
| MAB57 | GFTFDDY G (SEQ ID NO: 156) | INWEGGST (SEQ ID NO: 157) | ARDEQLGGK VYYYYYMDV (SEQ ID NO: 165) | QGIRND (SEQ ID NO: 159) | TAS (SEQ ID NO: 160) | LQYNSYPLA (SEQ ID NO: 118) |
| MAB58 | GFTFDDY G (SEQ ID NO: 156) | INWEGGST (SEQ ID NO: 157) | ARDEQLGGL KYYYYYMDV (SEQ ID NO: 164) | QGIRND (SEQ ID NO: 159) | TAS (SEQ ID NO: 160) | LQYHSYPLR (SEQ ID NO: 119) |
| MAB59 | GFTFDDY G (SEQ ID NO: 156) | INWEGGST (SEQ ID NO: 157) | ARDEQLGGN HYYYYYMDA (SEQ ID NO: 166) | QGIRND (SEQ ID NO: 159) | TAS (SEQ ID NO: 160) | LQYASYPLK (SEQ ID NO: 121) |
| MAB60 | GFTFDDY G (SEQ ID NO: 156) | INWEGGST (SEQ ID NO: 157) | ARDEQLGGR HYYYYYMDV (SEQ ID NO 167) | QGIRND (SEQ ID NO: 159) | TAS (SEQ ID NO: 160) | LQYNAYPLI (SEQ ID NO: 123) |

In some embodiments, the antibody comprises a variable heavy chain comprising a HCDR1 of SEQ ID NO: 128, a HCDR2 of SEQ ID NO: 129, and a HCDR3 of DEQLGGX$_1$X$_2$YYYYYMDX$_3$ (SEQ ID NO: 333), wherein:

$X_1$ is N, T, I, Q, L, K, or R;

$X_2$ is Y, T, K, H, or V; and $X_3$ is V or A.

In some embodiments, $X_1$ is N, T, I, Q, L, K, or R, $X_2$ is Y, and $X_3$ is V. In some embodiments, $X_1$ is N, T, I, Q, L, K, or R, $X_2$ is Y, and $X_3$ is A. In some embodiments, $X_1$ is N, T, I, Q, L, K, or R, $X_2$ is T, and $X_3$ is V. In some embodiments, $X_1$ is N, T, I, Q, L, K, or R, $X_2$ is T, and $X_3$ is A. In some embodiments, $X_1$ is N, T, I, Q, L, K, or R, $X_2$ is K, and $X_3$ is V. In some embodiments, $X_1$ is N, T, I, Q, L, K, or R, $X_2$ is K, and $X_3$ is A.

In some embodiments, $X_1$ is N, T, I, Q, L, K, or R, $X_2$ is H, and $X_3$ is V. In some embodiments, $X_1$ is N, T, I, Q, L, K, or R, $X_2$ is H, and $X_3$ is A. In some embodiments, $X_1$ is N, T, I, Q, L, K, or R, $X_2$ is V, and $X_3$ is V. In some embodiments, $X_1$ is N, T, I, Q, L, K, or R, $X_2$ is V, and $X_3$ is A. In some embodiments, $X_1$ is N, $X_2$ is Y, and $X_3$ is A. In some embodiments, $X_1$ is N, T, I, Q, L, K, or R, $X_2$ is T, and $X_3$ is V. In some embodiments, $X_1$ is N, T, I, Q, L, K, or R, $X_2$ is T, and $X_3$ is A. In some embodiments, $X_1$ is N, T, I, Q, L, K, or R, $X_2$ is K, and $X_3$ is V. In some embodiments, $X_1$ is N, T, I, Q, L, K, or R, $X_2$ is K, and $X_3$ is A.

In some embodiments, $X_1$ is N, T, I, Q, L, K, or R, $X_2$ is H, and $X_3$ is V. In some embodiments, $X_1$ is N, T, I, Q, L, K, or R, $X_2$ is H, and $X_3$ is A. In some embodiments, $X_1$ is N, T, I, Q, L, K, or R, $X_2$ is V, and $X_3$ is V. In some embodiments, $X_1$ is N, T, I, Q, L, K, or R, $X_2$ is V, and $X_3$ is A. In some embodiments, $X_1$ is not N. In some embodiments, $X_1$ is not T. In some embodiments, $X_1$ is not I. In some embodiments, $X_1$ is not Q. In some embodiments, $X_1$ is not L. In some embodiments, $X_1$ is not K. In some embodiments, $X_1$ is not R.

In some embodiments, an antibody is provided comprising a variable light chain LCDR1 of SEQ ID NO: 106, a LCDR2 of SEQ ID NO: 107, and a LCDR3 comprising an amino acid sequence of:

$X_4QX_5X_6X_7X_8PLX_9$ (SEQ ID NO: 332), wherein:

$X_4$ is L or F;

$X_5$ is Y or T;

$X_6$ is N, K, A, H, or R;

$X_7$ is S, Q, I, or A;

$X_8$ is Y, V, or H; and $X_9$ is T, G, K, R, I or A.

In some embodiments, $X_4$ is L; $X_5$ is Y or T; $X_6$ is N, K, A, H, or R; $X_7$ is S, Q, I, or A; $X_8$ is Y, V, or H; and $X_9$ is T, G, K, R, I or A. In some embodiments, $X_4$ is F; $X_5$ is Y or T; $X_6$ is N, K, A, H, or R; $X_7$ is S, Q, I, or A; $X_8$ is Y, V, or H; and $X_9$ is T, G, K, R, I or A. In some embodiments, $X_4$ is L or F; $X_5$ is Y; $X_6$ is N, K, A, H, or R; $X_7$ is S, Q, I, or A; $X_8$ is Y, V, or H; and $X_9$ is T, G, K, R, I or A. In some embodiments, $X_4$ is L or F; $X_5$ is T; $X_6$ is N, K, A, H, or R; $X_7$ is S, Q, I, or A; $X_8$ is Y, V, or H; and $X_9$ is T, G, K, R, I or A. In some embodiments, $X_4$ is L or F; $X_5$ is Y or T; $X_6$ is N; $X_7$ is S, Q, I, or A; $X_8$ is Y, V, or H; and $X_9$ is T, G, K, R, I or A. In some embodiments, $X_4$ is L or F; $X_5$ is Y or T; $X_6$ is K; $X_7$ is S, Q, I, or A; $X_8$ is Y, V, or H; and $X_9$ is T, G, K, R, I or A. In some embodiments, $X_4$ is L or F; $X_5$ is Y or T; $X_6$ is A; $X_7$ is S, Q, I, or A; $X_8$ is Y, V, or H; and $X_9$ is T, G, K, R, I or A. In some embodiments, $X_4$ is L or F; $X_5$ is Y or T; $X_6$ is H; $X_7$ is S, Q, I, or A; $X_8$ is Y, V, or H; and $X_9$ is T, G, K, R, I or A. In some embodiments, $X_4$ is L or F; $X_5$ is Y or T; $X_6$ is R; $X_7$ is S, Q, I, or A; $X_8$ is Y, V, or H; and $X_9$ is T, G, K, R, I or A. In some embodiments, $X_4$ is L or F; $X_5$ is Y or T; $X_6$ is N, K, A, H, or R; $X_7$ is S; $X_8$ is Y, V, or H; and $X_9$ is T, G, K, R, I or A. In some embodiments, $X_4$ is L or F; $X_5$ is Y or T; $X_6$ is N, K, A, H, or R; $X_7$ is Q; $X_8$ is Y, V, or H; and $X_9$ is T, G, K, R, I or A. In some embodiments, $X_4$ is L or F; $X_5$ is Y or T; $X_6$ is N, K, A, H, or R; $X_7$ is I; $X_8$ is Y, V, or H; and $X_9$ is T, G, K, R, I or A. In some embodiments, $X_4$ is L or F; $X_5$ is Y or T; $X_6$ is N, K, A, H, or R; $X_7$ is A; $X_8$ is Y, V, or H; and $X_9$ is T, G, K, R, I or A. In some embodiments, $X_4$ is L or F; $X_5$ is Y or T; $X_6$ is N, K, A, H, or R; $X_7$ is S, Q, I, or A; $X_8$ is Y; and $X_9$ is T, G, K, R, I or A. In some embodiments, $X_4$ is L or F; $X_5$ is Y or T; $X_6$ is N, K, A, H, or R; $X_7$ is S, Q, I, or A; $X_8$ is V; and $X_9$ is T, G, K, R, I or A. In some embodiments, $X_4$ is L or F; $X_5$ is Y or T; $X_6$ is N, K, A, H, or R; $X_7$ is S, Q, I, or A; $X_8$ is H; and $X_9$ is T, G, K, R, I or A. In some embodiments, $X_4$ is L or F; $X_5$ is Y or T; $X_6$ is N, K, A, H, or R; $X_7$ is S, Q, I, or A; $X_8$ is Y, V, or H; and $X_9$ is T. In some embodiments, $X_4$ is L or F; $X_5$ is Y or T; $X_6$ is N, K, A, H, or R; $X_7$ is S, Q, I, or A; $X_8$ is Y, V, or H; and $X_9$ is G. In some embodiments, $X_4$ is L or F; $X_5$ is Y or T; $X_6$ is N, K, A, H, or R; $X_7$ is S, Q, I, or A; $X_8$ is Y, V, or H; and $X_9$ is K. In some embodiments, $X_4$ is L or F; $X_5$ is Y or T; $X_6$ is N, K, A, H, or R; $X_7$ is S, Q, I, or A; $X_8$ is Y, V, or H; and $X_9$ is R. In some embodiments, $X_4$ is L or F; $X_5$ is Y or T; $X_6$ is N, K, A, H, or R; $X_7$ is S, Q, I, or A; $X_8$ is Y, V, or H; and $X_9$ is I. In some embodiments, $X_4$ is L or F; $X_5$ is Y or T; $X_6$ is N, K, A, H, or R; $X_7$ is S, Q, I, or A; $X_8$ is Y, V, or H; and $X_9$ is A.

In some embodiments, an antibody is provided comprising a variable heavy chain comprising a variable heavy chain comprising a HCDR1 of SEQ ID NO: 128, a HCDR2 of SEQ ID NO: 129, and a HCDR3 of DEQLGGX$_1$X$_2$YYYYYMDX$_3$ (SEQ ID NO: 333), wherein $X_1$ is N, T, I, Q, L, K, or R; $X_2$ is Y, T, K, H, or V; and $X_3$ is V or A; and a variable light chain LCDR1 of SEQ ID NO: 106, a LCDR2 of SEQ ID NO: 107, and a LCDR3 comprising an amino acid sequence of $X_4QX_5X_6X_7X_8PLX_9$ (SEQ ID NO: 332), wherein $X_4$ is L or F; $X_5$ is Y or T; $X_6$ is N, K, A, H, or R; $X_7$ is S, Q, I, or A; $X_8$ is Y, V, or H; and $X_9$ is T, G, K, R, I or A. In some embodiments, the variables of the HCDR3 and the LCDR3 are as set forth above.

In some embodiments, the antibody comprises a variable light chain and a heavy chain as set forth for MAB21, MAB22, MAB23, MAB24, MAB25, MAB26, MAB27, MAB28, MAB29, MAB30, MAB51, MAB52, MAB53, MAB54, MAB55, MAB56, MAB57, MAB58, MAB59, or MAB60, provided that the HCDR3 comprises an amino acid sequence of SEQ ID NO: 333 and the LCDR3 comprises as an amino acid sequence of SEQ ID NO: 332 as set forth herein. In some embodiments, the antibody comprises a variable light chain and a heavy chain that are each, independently, at least 85%, 86%, 87%, 88%, 89%, 90%, 91%, 92%, 93%, 94%, 95%, 96%, 97%, 98% or 99% as set forth for the VL and VH of MAB21, MAB22, MAB23, MAB24, MAB25, MAB26, MAB27, MAB28, MAB29, MAB30, MAB51, MAB52, MAB53, MAB54, MAB55, MAB56, MAB57, MAB58, MAB59, or MAB60, provided that the HCDR3 comprises an amino acid sequence of SEQ ID NO: 333 and the LCDR3 comprises as an amino acid sequence of SEQ ID NO: 332 as set forth herein.

In some embodiments, the antibody does not comprise a HCDR3 of EQLGGNYYYYYYMDV and/or a LCDR3 of LQYNSYPLT. In some embodiments, when an antibody comprises a HCDR3 of EQLGGNYYYYYYMDV, the antibody does not comprise a LCDR3 of LQYNSYPLT.

In some embodiments, the antibody comprises a variable heavy chain comprising a HCDR1 of SEQ ID NO: 61, a HCDR2 of SEQ ID NO: 62, and a HCDR3 of DX$_{10}$X$_{11}$X$_{12}$YX$_{13}$X$_{14}$DX$_{15}$ (SEQ ID NO: 329), wherein: $X_{10}$ is E, Q, or N; $X_{11}$ is T, E, S, or N; $X_{12}$ is D or Q; $X_{13}$ is A or G; $X_{14}$ is L, W, F, or Y; and $X_{15}$ is Y, E, L, N, F, or W. In some embodiments, $X_{10}$ is E. In some embodiments, $X_{10}$ is Q. In some embodiments, $X_{10}$ is N. In some embodiments, $X_{11}$ is T. In some embodiments, $X_{11}$ is E. In some embodiments, $X_{11}$ is S. In some embodiments, $X_{11}$ is N. In some embodiments, $X_{12}$ is D. In some embodiments, $X_{12}$ is D. In some embodiments, $X_{13}$ is A. In some embodiments, $X_{13}$ is G. In some embodiments, $X_{14}$ is L. In some embodiments, $X_{14}$ is W. In some embodiments, $X_{14}$ is F. In some embodiments, $X_{14}$ is or Y. In some embodiments, $X_{15}$ is Y. In some embodiments, $X_{15}$ is E. In some embodiments, $X_{15}$ is L. In some embodiments, $X_{15}$ is N. In some embodiments, $X_{15}$ is F. In some embodiments, $X_{15}$ is W.

In some embodiments, the antibody comprises a variable light chain comprising a LCDR1 of SEQ ID NO: 64, a LCDR2 of SEQ ID NO: 65, and a LCDR3 comprising an amino acid sequence of $X_{16}X_{17}X_{18}EDX_{19}X_{20}X_{21}X_{22}$ (SEQ ID NO: 328), wherein $X_{16}$ is Q, E, K, or H; $X_{17}$ is Q or H; $X_{18}$ is Y or H, $X_{19}$ is L or Y; $X_{20}$ is P or I; $X_{21}$ is L or P, and $X_{22}$ is T or V. In some embodiments, $X_{16}$ is Q. In some embodiments, $X_{16}$ is E. In some embodiments, $X_{16}$ is K. In some embodiments, $X_{16}$ is H. In some embodiments, $X_{17}$ is Q. In some embodiments, $X_{17}$ is H. In some embodiments, $X_{18}$ is Y. In some embodiments, $X_{18}$ is H. In some embodiments, $X_{19}$ is L. In some embodiments, $X_{19}$ is Y. In some embodiments, $X_{20}$ is P. In some embodiments, $X_{20}$ is I. In some embodiments, $X_{21}$ is L. In some embodiments, $X_{21}$ is P. In some embodiments, $X_{22}$ is T. In some embodiments, $X_{22}$ is V.

In some embodiments, an antibody is provided comprising a variable heavy chain comprising a variable heavy chain comprising a HCDR1 of SEQ ID NO: 61, a HCDR2 of SEQ ID NO: 62, and a HCDR3 of SEQ ID NO: 329 as set forth herein and a variable light chain LCDR1 of SEQ ID NO: 63, a LCDR2 of SEQ ID NO: 64, and a LCDR3 comprising an amino acid sequence of SEQ ID NO: 328 as set forth herein.

In some embodiments, the antibody comprises a variable light chain and a heavy chain as set forth for MAB1, MAB2, MAB3, MAB4, MAB5, MAB6, MAB7, MAB8, MAB9, MAB10, MAB31, MAB32, MAB33, MAB34, MAB35, MAB36, MAB38, MAB39, or MAB40, provided that the HCDR3 comprises an amino acid sequence of SEQ ID NO: 329 and the LCDR3 comprises as an amino acid sequence of SEQ ID NO: 328 as set forth herein. In some embodiments, the antibody comprises a variable light chain and a heavy chain that are each, independently, at least 85%, 86%, 87%, 88%, 89%, 90%, 91%, 92%, 93%, 94%, 95%, 96%, 97%, 98% or 99% as set forth for the VL and VH of MAB1, MAB2, MAB3, MAB4, MAB5, MAB6, MAB7, MAB8, MAB9, MAB10, MAB31, MAB32, MAB33, MAB34, MAB35, MAB36, MAB38, MAB39, or MAB40, provided that the HCDR3 comprises an amino acid sequence of SEQ ID NO: 329 and the LCDR3 comprises as an amino acid sequence of SEQ ID NO: 328 as set forth herein.

In some embodiments, a VH and VL is provided, provided that when the HCDR3 is DETDYALDY, the LCDR3 is not QQYEDLPLT. In some embodiments, SEQ ID NO: 329 is not DETDYALDY. In some embodiments, SEQ ID NO: 328 is not QQYEDLPLT.

In some embodiments, the antibody comprises a variable heavy chain comprising a HCDR1 of SEQ ID NO: 82, a HCDR2 of SEQ ID NO: 83, and a HCDR3 of $X_{23}GX_{24}X_{25}X_{26}X_{27}PX_{28}X_{29}X_{30}$ (SEQ ID NO: 330), wherein: $X_{23}$ is E or K, $X_{24}$ is L or E; $X_{25}$ is A or G, $X_{26}$ is G or W, $X_{27}$ is R, V, L, I, or F, $X_{28}$ is F, Y, or T, $X_{29}$ is D or Y, and X 30 is A, V, L, S, H, or I. In some embodiments, $X_{23}$ is E. In some embodiments $X_{24}$ is L. In some embodiments, $X_{25}$ is A. In some embodiments $X_{26}$ is G. In some embodiments $X_{27}$ is R. In some embodiments, $X_{27}$ is V. In some embodiments, $X_{27}$ is L. In some embodiments, $X_{27}$ is I. In some embodiments, $X_{27}$ is F. In some embodiments, $X_{28}$ is F. In some embodiments, $X_{28}$ is Y. In some embodiments, In some embodiments, $X_{29}$ is D. In some embodiments, $X_{30}$ is S or L.

In some embodiments, the antibody comprises a variable light chain comprising a LCDR1 of SEQ ID NO: 85, a LCDR2 of SEQ ID NO: 86, and a LCDR3 of X31QX32X33SX34X35X36X37 (SEQ ID NO: 331), wherein X31 is Q or V; X32 is Y, A, V, or H; X33 is N, P, S, or R; X34 is Y, L, or P; X35 is S, K, V, A, D, or R; X36 is W or L; and X37 is T or L. In some embodiments, X31 is Q. In some embodiments, X31 is V. In some embodiments, X32 is Y. In some embodiments, X32 is A. In some embodiments, X32 is V. In some embodiments, X32 is H. In some embodiments, X33 is N. In some embodiments, X33 is P. In some embodiments, X33 is S. In some embodiments, X33 is R. In some embodiments, X34 is Y. In some embodiments, X34 is L. In some embodiments, X34 is P. In some embodiments, X35 is S. In some embodiments, X35 is K. In some embodiments, X35 is V. In some embodiments, X35 is A. In some embodiments, X35 is D. In some embodiments, X35 is R. In some embodiments, X36 is W. In some embodiments, X36 is L. In some embodiments, X37 is T. In some embodiments, X37 is L.

In some embodiments, an antibody is provided comprising a variable heavy chain comprising a variable heavy chain comprising a HCDR1 of SEQ ID NO: 82, a HCDR2 of SEQ ID NO: 83, and a HCDR3 of SEQ ID NO: 330 as set forth herein and a variable light chain comprising a LCDR1 of SEQ ID NO: 84, a LCDR2 of SEQ ID NO: 85, and a LCDR3 comprising an amino acid sequence of SEQ ID NO: 331 as set forth herein.

In some embodiments, the antibody comprises a variable light chain and a heavy chain as set forth for MAB11, MAB12, MAB13, MAB14, MAB15, MAB16, MAB17, MAB18, MAB19, MAB20, MAB41, MAB42, MAB43, MAB44, MAB45, MAB46, MAB47, MAB48, MAB49, or MAB50, provided that the HCDR3 comprises an amino acid sequence of SEQ ID NO: 330 and the LCDR3 comprises as an amino acid sequence of SEQ ID NO: 331 as set forth herein. In some embodiments, the antibody comprises a variable light chain and a heavy chain that are each, independently, at least 85%, 86%, 87%, 88%, 89%, 90%, 91%, 92%, 93%, 94%, 95%, 96%, 97%, 98% or 99% as set forth for the VL and VH of MAB11, MAB12, MAB13, MAB14, MAB15, MAB16, MAB17, MAB18, MAB19, MAB20, MAB41, MAB42, MAB43, MAB44, MAB45, MAB46, MAB47, MAB48, MAB49, or MAB50, provided that the HCDR3 comprises an amino acid sequence of SEQ ID NO: 330 and the LCDR3 comprises as an amino acid sequence of SEQ ID NO: 331 as set forth herein.

In some embodiments, a VH and VL is provided, provided that when the HCDR3 is EGLAGRPFDS, the LCDR3 is not QQYNSYSWTY. In some embodiments, SEQ ID NO: 330 is not EGLAGRPFDS. In some embodiments, SEQ ID NO: 331 is not QQYNSYSWTY.

In some embodiments, an antibody, or antibody binding fragment thereof, comprises a heavy or light chain CDR as provided in the tables above. In some embodiments, an antibody, or antibody binding fragment thereof, comprises a light chain LCDR having a sequence of SEQ ID NO: 64, 65, 66, 68, 71, 75, 77, 79, 81, 85, 86, 87, 89, 92, 94, 95, 97, 99, 101, 102, 106, 107, 108, 110, 112, 113, 115, 118, 119, 121, 123, 133, 134, 147, 148, 159, 160, or a combination thereof. In some embodiments, an antibody, or antibody binding fragment thereof, comprises a heavy chain HCDR having a sequence of SEQ ID NO: 61, 62, 63, 67, 69, 70, 72, 73, 74, 76, 78, 80, 82, 83, 84, 88, 90, 91, 93, 96, 98, 100, 103, 104, 105, 109, 111, 114, 116, 117, 120, 122, 124, 125, 126, 127, 128, 129, 130, 131, 132, 135, 136, 137, 138, 139, 140, 141, 142, 143, 144, 145, 146, 149, 150, 151, 152, 153, 154, 155, 156, 157, 158, 161, 162, 163, 164, 165, 166, 167, or a combination thereof.

In some embodiments, the heavy chain HCDR comprises a sequence that is a combination of one or more of SEQ ID NO: 61, 62, 63, 67, 69, 70, 72, 73, 74, 76, 78, 80, 82, 83, 84, 88, 90, 91, 93, 96, 98, 100, 103, 104, 105, 109, 111, 114, 116, 117, 120,122, 124, 125, 126, 127, 128, 129, 130, 131, 132, 135, 136, 137, 138, 139, 140, 141, 142, 143, 144, 145, 146, 149, 150, 151, 152, 153, 154, 155, 156, 157, 158, 161, 162, 163, 164, 165, 166, and 167.

It is to be understood that the CDRs referenced in the embodiments throughout the present specification can be interchanged with the CDRs that are characterized by different formats, such as Chothia and IMGT, which are illustrated in the tables above.

In some embodiments, an antibody, or antibody binding fragment thereof, comprises a light chain variable region having a LCDR1, a LCDR2, and a LCDR3, wherein the LCDR1 has a sequence of SEQ ID NO: 64, the LCDR2 has a sequence of SEQ ID NO: 65, and the LCDR3 has a sequence of SEQ ID NO: 66.

In some embodiments, an antibody, or antibody binding fragment thereof, comprises a light chain variable region having a LCDR1, a LCDR2, and a LCDR3, wherein the LCDR1 has a sequence of SEQ ID NO: 64, the LCDR2 has a sequence of SEQ ID NO: 65, and the LCDR3 has a sequence of SEQ ID NO: 68.

In some embodiments, an antibody, or antibody binding fragment thereof, comprises a light chain variable region having a LCDR1, a LCDR2, and a LCDR3, wherein the LCDR1 has a sequence of SEQ ID NO: 64, the LCDR2 has a sequence of SEQ ID NO: 65, and the LCDR3 has a sequence of SEQ ID NO: 71.

In some embodiments, an antibody, or antibody binding fragment thereof, comprises a light chain variable region having a LCDR1, a LCDR2, and a LCDR3, wherein the LCDR1 has a sequence of SEQ ID NO: 64, the LCDR2 has a sequence of SEQ ID NO: 65, and the LCDR3 has a sequence of SEQ ID NO: 75.

In some embodiments, an antibody, or antibody binding fragment thereof, comprises a light chain variable region having a LCDR1, a LCDR2, and a LCDR3, wherein the LCDR1 has a sequence of SEQ ID NO: 64, the LCDR2 has a sequence of SEQ ID NO: 65, and the LCDR3 has a sequence of SEQ ID NO: 77.

In some embodiments, an antibody, or antibody binding fragment thereof, comprises a light chain variable region having a LCDR1, a LCDR2, and a LCDR3, wherein the LCDR1 has a sequence of SEQ ID NO: 64, the LCDR2 has a sequence of SEQ ID NO: 65, and the LCDR3 has a sequence of SEQ ID NO: 79.

In some embodiments, an antibody, or antibody binding fragment thereof, comprises a light chain variable region having a LCDR1, a LCDR2, and a LCDR3, wherein the LCDR1 has a sequence of SEQ ID NO: 64, the LCDR2 has a sequence of SEQ ID NO: 65, and the LCDR3 has a sequence of SEQ ID NO: 81.

In some embodiments, an antibody, or antibody binding fragment thereof, comprises a light chain variable region having a LCDR1, a LCDR2, and a LCDR3, wherein the LCDR1 has a sequence of SEQ ID NO: 85, the LCDR2 has a sequence of SEQ ID NO: 86, and the LCDR3 has a sequence of SEQ ID NO: 87.

In some embodiments, an antibody, or antibody binding fragment thereof, comprises a light chain variable region having a LCDR1, a LCDR2, and a LCDR3, wherein the LCDR1 has a sequence of SEQ ID NO: 85, the LCDR2 has a sequence of SEQ ID NO: 86, and the LCDR3 has a sequence of SEQ ID NO: 89.

In some embodiments, an antibody, or antibody binding fragment thereof, comprises a light chain variable region having a LCDR1, a LCDR2, and a LCDR3, wherein the LCDR1 has a sequence of SEQ ID NO: 85, the LCDR2 has a sequence of SEQ ID NO: 86, and the LCDR3 has a sequence of SEQ ID NO: 92.

In some embodiments, an antibody, or antibody binding fragment thereof, comprises a light chain variable region having a LCDR1, a LCDR2, and a LCDR3, wherein the LCDR1 has a sequence of SEQ ID NO: 85, the LCDR2 has a sequence of SEQ ID NO: 86, and the LCDR3 has a sequence of SEQ ID NO: 94.

In some embodiments, an antibody, or antibody binding fragment thereof, comprises a light chain variable region having a LCDR1, a LCDR2, and a LCDR3, wherein the LCDR1 has a sequence of SEQ ID NO: 85, the LCDR2 has a sequence of SEQ ID NO: 86, and the LCDR3 has a sequence of SEQ ID NO: 95.

In some embodiments, an antibody, or antibody binding fragment thereof, comprises a light chain variable region having a LCDR1, a LCDR2, and a LCDR3, wherein the LCDR1 has a sequence of SEQ ID NO: 85, the LCDR2 has a sequence of SEQ ID NO: 86, and the LCDR3 has a sequence of SEQ ID NO: 97.

In some embodiments, an antibody, or antibody binding fragment thereof, comprises a light chain variable region having a LCDR1, a LCDR2, and a LCDR3, wherein the LCDR1 has a sequence of SEQ ID NO: 85, the LCDR2 has a sequence of SEQ ID NO: 86, and the LCDR3 has a sequence of SEQ ID NO: 99.

In some embodiments, an antibody, or antibody binding fragment thereof, comprises a light chain variable region having a LCDR1, a LCDR2, and a LCDR3, wherein the LCDR1 has a sequence of SEQ ID NO: 85, the LCDR2 has a sequence of SEQ ID NO: 86, and the LCDR3 has a sequence of SEQ ID NO: 101.

In some embodiments, an antibody, or antibody binding fragment thereof, comprises a light chain variable region having a LCDR1, a LCDR2, and a LCDR3, wherein the LCDR1 has a sequence of SEQ ID NO: 85, the LCDR2 has a sequence of SEQ ID NO: 86, and the LCDR3 has a sequence of SEQ ID NO: 102.

In some embodiments, an antibody, or antibody binding fragment thereof, comprises a light chain variable region having a LCDR1, a LCDR2, and a LCDR3, wherein the LCDR1 has a sequence of SEQ ID NO: 106, the LCDR2 has a sequence of SEQ ID NO: 107, and the LCDR3 has a sequence of SEQ ID NO: 108.

In some embodiments, an antibody, or antibody binding fragment thereof, comprises a light chain variable region having a LCDR1, a LCDR2, and a LCDR3, wherein the LCDR1 has a sequence of SEQ ID NO: 106, the LCDR2 has a sequence of SEQ ID NO: 107, and the LCDR3 has a sequence of SEQ ID NO: 110.

In some embodiments, an antibody, or antibody binding fragment thereof, comprises a light chain variable region having a LCDR1, a LCDR2, and a LCDR3, wherein the LCDR1 has a sequence of SEQ ID NO: 106, the LCDR2 has a sequence of SEQ ID NO: 107, and the LCDR3 has a sequence of SEQ ID NO: 112.

In some embodiments, an antibody, or antibody binding fragment thereof, comprises a light chain variable region having a LCDR1, a LCDR2, and a LCDR3, wherein the LCDR1 has a sequence of SEQ ID NO: 106, the LCDR2 has a sequence of SEQ ID NO: 107, and the LCDR3 has a sequence of SEQ ID NO: 113.

In some embodiments, an antibody, or antibody binding fragment thereof, comprises a light chain variable region having a LCDR1, a LCDR2, and a LCDR3, wherein the LCDR1 has a sequence of SEQ ID NO: 106, the LCDR2 has a sequence of SEQ ID NO: 107, and the LCDR3 has a sequence of SEQ ID NO: 115.

In some embodiments, an antibody, or antibody binding fragment thereof, comprises a light chain variable region having a LCDR1, a LCDR2, and a LCDR3, wherein the LCDR1 has a sequence of SEQ ID NO: 106, the LCDR2 has a sequence of SEQ ID NO: 107, and the LCDR3 has a sequence of SEQ ID NO: 118.

In some embodiments, an antibody, or antibody binding fragment thereof, comprises a light chain variable region having a LCDR1, a LCDR2, and a LCDR3, wherein the LCDR1 has a sequence of SEQ ID NO: 106, the LCDR2 has a sequence of SEQ ID NO: 107, and the LCDR3 has a sequence of SEQ ID NO: 119.

In some embodiments, an antibody, or antibody binding fragment thereof, comprises a light chain variable region having a LCDR1, a LCDR2, and a LCDR3, wherein the LCDR1 has a sequence of SEQ ID NO: 106, the LCDR2 has a sequence of SEQ ID NO: 107, and the LCDR3 has a sequence of SEQ ID NO: 121.

In some embodiments, an antibody, or antibody binding fragment thereof, comprises a light chain variable region having a LCDR1, a LCDR2, and a LCDR3, wherein the LCDR1 has a sequence of SEQ ID NO: 106, the LCDR2 has a sequence of SEQ ID NO: 107, and the LCDR3 has a sequence of SEQ ID NO: 123.

In some embodiments, an antibody, or antibody binding fragment thereof, comprises a light chain variable region having a LCDR1, a LCDR2, and a LCDR3, wherein the LCDR1 has a sequence of SEQ ID NO: 133, the LCDR2 has a sequence of SEQ ID NO: 134, and the LCDR3 has a sequence of SEQ ID NO: 66.

In some embodiments, an antibody, or antibody binding fragment thereof, comprises a light chain variable region having a LCDR1, a LCDR2, and a LCDR3, wherein the LCDR1 has a sequence of SEQ ID NO: 133, the LCDR2 has a sequence of SEQ ID NO: 134, and the LCDR3 has a sequence of SEQ ID NO: 68.

In some embodiments, an antibody, or antibody binding fragment thereof, comprises a light chain variable region having a LCDR1, a LCDR2, and a LCDR3, wherein the LCDR1 has a sequence of SEQ ID NO: 133, the LCDR2 has a sequence of SEQ ID NO: 134, and the LCDR3 has a sequence of SEQ ID NO: 71.

In some embodiments, an antibody, or antibody binding fragment thereof, comprises a light chain variable region having a LCDR1, a LCDR2, and a LCDR3, wherein the LCDR1 has a sequence of SEQ ID NO: 133, the LCDR2 has a sequence of SEQ ID NO: 134, and the LCDR3 has a sequence of SEQ ID NO: 75.

In some embodiments, an antibody, or antibody binding fragment thereof, comprises a light chain variable region having a LCDR1, a LCDR2, and a LCDR3, wherein the LCDR1 has a sequence of SEQ ID NO: 133, the LCDR2 has a sequence of SEQ ID NO: 134, and the LCDR3 has a sequence of SEQ ID NO: 77.

In some embodiments, an antibody, or antibody binding fragment thereof, comprises a light chain variable region having a LCDR1, a LCDR2, and a LCDR3, wherein the LCDR1 has a sequence of SEQ ID NO: 133, the LCDR2 has a sequence of SEQ ID NO: 134, and the LCDR3 has a sequence of SEQ ID NO: 79.

In some embodiments, an antibody, or antibody binding fragment thereof, comprises a light chain variable region having a LCDR1, a LCDR2, and a LCDR3, wherein the LCDR1 has a sequence of SEQ ID NO: 133, the LCDR2 has a sequence of SEQ ID NO: 134, and the LCDR3 has a sequence of SEQ ID NO: 81.

In some embodiments, an antibody, or antibody binding fragment thereof, comprises a light chain variable region having a LCDR1, a LCDR2, and a LCDR3, wherein the LCDR1 has a sequence of SEQ ID NO: 147, the LCDR2 has a sequence of SEQ ID NO: 148, and the LCDR3 has a sequence of SEQ ID NO: 87.

In some embodiments, an antibody, or antibody binding fragment thereof, comprises a light chain variable region having a LCDR1, a LCDR2, and a LCDR3, wherein the LCDR1 has a sequence of SEQ ID NO: 147, the LCDR2 has a sequence of SEQ ID NO: 148, and the LCDR3 has a sequence of SEQ ID NO: 89.

In some embodiments, an antibody, or antibody binding fragment thereof, comprises a light chain variable region having a LCDR1, a LCDR2, and a LCDR3, wherein the LCDR1 has a sequence of SEQ ID NO: 147, the LCDR2 has a sequence of SEQ ID NO: 148, and the LCDR3 has a sequence of SEQ ID NO: 92.

In some embodiments, an antibody, or antibody binding fragment thereof, comprises a light chain variable region having a LCDR1, a LCDR2, and a LCDR3, wherein the LCDR1 has a sequence of SEQ ID NO: 147, the LCDR2 has a sequence of SEQ ID NO: 148, and the LCDR3 has a sequence of SEQ ID NO: 94.

In some embodiments, an antibody, or antibody binding fragment thereof, comprises a light chain variable region having a LCDR1, a LCDR2, and a LCDR3, wherein the LCDR1 has a sequence of SEQ ID NO: 147, the LCDR2 has a sequence of SEQ ID NO: 148, and the LCDR3 has a sequence of SEQ ID NO: 95.

In some embodiments, an antibody, or antibody binding fragment thereof, comprises a light chain variable region having a LCDR1, a LCDR2, and a LCDR3, wherein the LCDR1 has a sequence of SEQ ID NO: 147, the LCDR2 has a sequence of SEQ ID NO: 148, and the LCDR3 has a sequence of SEQ ID NO: 97.

In some embodiments, an antibody, or antibody binding fragment thereof, comprises a light chain variable region having a LCDR1, a LCDR2, and a LCDR3, wherein the LCDR1 has a sequence of SEQ ID NO: 147, the LCDR2 has a sequence of SEQ ID NO: 148, and the LCDR3 has a sequence of SEQ ID NO: 99.

In some embodiments, an antibody, or antibody binding fragment thereof, comprises a light chain variable region having a LCDR1, a LCDR2, and a LCDR3, wherein the LCDR1 has a sequence of SEQ ID NO: 147, the LCDR2 has a sequence of SEQ ID NO: 148, and the LCDR3 has a sequence of SEQ ID NO: 101.

In some embodiments, an antibody, or antibody binding fragment thereof, comprises a light chain variable region having a LCDR1, a LCDR2, and a LCDR3, wherein the LCDR1 has a sequence of SEQ ID NO: 147, the LCDR2 has a sequence of SEQ ID NO: 148, and the LCDR3 has a sequence of SEQ ID NO: 102.

In some embodiments, an antibody, or antibody binding fragment thereof, comprises a light chain variable region having a LCDR1, a LCDR2, and a LCDR3, wherein the LCDR1 has a sequence of SEQ ID NO: 159, the LCDR2 has a sequence of SEQ ID NO: 160, and the LCDR3 has a sequence of SEQ ID NO: 108.

In some embodiments, an antibody, or antibody binding fragment thereof, comprises a light chain variable region having a LCDR1, a LCDR2, and a LCDR3, wherein the LCDR1 has a sequence of SEQ ID NO: 159, the LCDR2 has a sequence of SEQ ID NO: 160, and the LCDR3 has a sequence of SEQ ID NO: 110.

In some embodiments, an antibody, or antibody binding fragment thereof, comprises a light chain variable region having a LCDR1, a LCDR2, and a LCDR3, wherein the LCDR1 has a sequence of SEQ ID NO: 159, the LCDR2 has a sequence of SEQ ID NO: 160, and the LCDR3 has a sequence of SEQ ID NO: 112.

In some embodiments, an antibody, or antibody binding fragment thereof, comprises a light chain variable region having a LCDR1, a LCDR2, and a LCDR3, wherein the LCDR1 has a sequence of SEQ ID NO: 159, the LCDR2 has a sequence of SEQ ID NO: 160, and the LCDR3 has a sequence of SEQ ID NO: 113.

In some embodiments, an antibody, or antibody binding fragment thereof, comprises a light chain variable region having a LCDR1, a LCDR2, and a LCDR3, wherein the LCDR1 has a sequence of SEQ ID NO: 159, the LCDR2 has a sequence of SEQ ID NO: 160, and the LCDR3 has a sequence of SEQ ID NO: 115.

In some embodiments, an antibody, or antibody binding fragment thereof, comprises a light chain variable region having a LCDR1, a LCDR2, and a LCDR3, wherein the LCDR1 has a sequence of SEQ ID NO: 159, the LCDR2 has a sequence of SEQ ID NO: 160, and the LCDR3 has a sequence of SEQ ID NO: 118.

In some embodiments, an antibody, or antibody binding fragment thereof, comprises a light chain variable region having a LCDR1, a LCDR2, and a LCDR3, wherein the LCDR1 has a sequence of SEQ ID NO: 159, the LCDR2 has a sequence of SEQ ID NO: 160, and the LCDR3 has a sequence of SEQ ID NO: 119.

In some embodiments, an antibody, or antibody binding fragment thereof, comprises a light chain variable region having a LCDR1, a LCDR2, and a LCDR3, wherein the LCDR1 has a sequence of SEQ ID NO: 159, the LCDR2 has a sequence of SEQ ID NO: 160, and the LCDR3 has a sequence of SEQ ID NO: 112.

In some embodiments, an antibody, or antibody binding fragment thereof, comprises a light chain variable region having a LCDR1, a LCDR2, and a LCDR3, wherein the LCDR1 has a sequence of SEQ ID NO: 159, the LCDR2 has a sequence of SEQ ID NO: 160, and the LCDR3 has a sequence of SEQ ID NO: 123.

In some embodiments, an antibody, or antibody binding fragment thereof, comprises a heavy chain variable region having a HCDR1, a HCDR2, and a HCDR3, wherein the HCDR1 has a sequence of SEQ ID NO: 61, the HCDR2 has a sequence of SEQ ID NO: 62, and the HCDR3 has a sequence of SEQ ID NO: 63.

In some embodiments, an antibody, or antibody binding fragment thereof, comprises a heavy chain variable region having a HCDR1, a HCDR2, and a HCDR3, wherein the HCDR1 has a sequence of SEQ ID NO: 61, the HCDR2 has a sequence of SEQ ID NO: 62, and the HCDR3 has a sequence of SEQ ID NO: 67.

In some embodiments, an antibody, or antibody binding fragment thereof, comprises a heavy chain variable region having a HCDR1, a HCDR2, and a HCDR3, wherein the HCDR1 has a sequence of SEQ ID NO: 61, the HCDR2 has a sequence of SEQ ID NO: 62, and the HCDR3 has a sequence of SEQ ID NO: 69.

In some embodiments, an antibody, or antibody binding fragment thereof, comprises a heavy chain variable region having a HCDR1, a HCDR2, and a HCDR3, wherein the HCDR1 has a sequence of SEQ ID NO: 61, the HCDR2 has a sequence of SEQ ID NO: 62, and the HCDR3 has a sequence of SEQ ID NO: 70.

In some embodiments, an antibody, or antibody binding fragment thereof, comprises a heavy chain variable region having a HCDR1, a HCDR2, and a HCDR3, wherein the HCDR1 has a sequence of SEQ ID NO: 61, the HCDR2 has a sequence of SEQ ID NO: 62, and the HCDR3 has a sequence of SEQ ID NO: 72.

In some embodiments, an antibody, or antibody binding fragment thereof, comprises a heavy chain variable region having a HCDR1, a HCDR2, and a HCDR3, wherein the HCDR1 has a sequence of SEQ ID NO: 61, the HCDR2 has a sequence of SEQ ID NO: 62, and the HCDR3 has a sequence of SEQ ID NO: 73.

In some embodiments, an antibody, or antibody binding fragment thereof, comprises a heavy chain variable region having a HCDR1, a HCDR2, and a HCDR3, wherein the HCDR1 has a sequence of SEQ ID NO: 61, the HCDR2 has a sequence of SEQ ID NO: 62, and the HCDR3 has a sequence of SEQ ID NO: 74.

In some embodiments, an antibody, or antibody binding fragment thereof, comprises a heavy chain variable region having a HCDR1, a HCDR2, and a HCDR3, wherein the HCDR1 has a sequence of SEQ ID NO: 61, the HCDR2 has a sequence of SEQ ID NO: 62, and the HCDR3 has a sequence of SEQ ID NO: 76.

In some embodiments, an antibody, or antibody binding fragment thereof, comprises a heavy chain variable region having a HCDR1, a HCDR2, and a HCDR3, wherein the HCDR1 has a sequence of SEQ ID NO: 61, the HCDR2 has a sequence of SEQ ID NO: 62, and the HCDR3 has a sequence of SEQ ID NO: 78.

In some embodiments, an antibody, or antibody binding fragment thereof, comprises a heavy chain variable region having a HCDR1, a HCDR2, and a HCDR3, wherein the HCDR1 has a sequence of SEQ ID NO: 61, the HCDR2 has a sequence of SEQ ID NO: 62, and the HCDR3 has a sequence of SEQ ID NO: 80.

In some embodiments, an antibody, or antibody binding fragment thereof, comprises a heavy chain variable region having a HCDR1, a HCDR2, and a HCDR3, wherein the HCDR1 has a sequence of SEQ ID NO: 82, the HCDR2 has a sequence of SEQ ID NO: 83, and the HCDR3 has a sequence of SEQ ID NO: 84.

In some embodiments, an antibody, or antibody binding fragment thereof, comprises a heavy chain variable region having a HCDR1, a HCDR2, and a HCDR3, wherein the HCDR1 has a sequence of SEQ ID NO: 82, the HCDR2 has a sequence of SEQ ID NO: 83, and the HCDR3 has a sequence of SEQ ID NO: 88.

In some embodiments, an antibody, or antibody binding fragment thereof, comprises a heavy chain variable region having a HCDR1, a HCDR2, and a HCDR3, wherein the HCDR1 has a sequence of SEQ ID NO: 82, the HCDR2 has a sequence of SEQ ID NO: 83, and the HCDR3 has a sequence of SEQ ID NO: 90.

In some embodiments, an antibody, or antibody binding fragment thereof, comprises a heavy chain variable region having a HCDR1, a HCDR2, and a HCDR3, wherein the HCDR1 has a sequence of SEQ ID NO: 82, the HCDR2 has a sequence of SEQ ID NO: 83, and the HCDR3 has a sequence of SEQ ID NO: 91.

In some embodiments, an antibody, or antibody binding fragment thereof, comprises a heavy chain variable region having a HCDR1, a HCDR2, and a HCDR3, wherein the HCDR1 has a sequence of SEQ ID NO: 82, the HCDR2 has a sequence of SEQ ID NO: 83, and the HCDR3 has a sequence of SEQ ID NO: 93.

In some embodiments, an antibody, or antibody binding fragment thereof, comprises a heavy chain variable region having a HCDR1, a HCDR2, and a HCDR3, wherein the HCDR1 has a sequence of SEQ ID NO: 82, the HCDR2 has a sequence of SEQ ID NO: 83, and the HCDR3 has a sequence of SEQ ID NO: 96.

In some embodiments, an antibody, or antibody binding fragment thereof, comprises a heavy chain variable region having a HCDR1, a HCDR2, and a HCDR3, wherein the HCDR1 has a sequence of SEQ ID NO: 82, the HCDR2 has a sequence of SEQ ID NO: 83, and the HCDR3 has a sequence of SEQ ID NO: 98.

In some embodiments, an antibody, or antibody binding fragment thereof, comprises a heavy chain variable region having a HCDR1, a HCDR2, and a HCDR3, wherein the HCDR1 has a sequence of SEQ ID NO: 82, the HCDR2 has a sequence of SEQ ID NO: 83, and the HCDR3 has a sequence of SEQ ID NO: 100.

In some embodiments, an antibody, or antibody binding fragment thereof, comprises a heavy chain variable region having a HCDR1, a HCDR2, and a HCDR3, wherein the HCDR1 has a sequence of SEQ ID NO: 103, the HCDR2 has a sequence of SEQ ID NO: 104, and the HCDR3 has a sequence of SEQ ID NO: 105.

In some embodiments, an antibody, or antibody binding fragment thereof, comprises a heavy chain variable region having a HCDR1, a HCDR2, and a HCDR3, wherein the HCDR1 has a sequence of SEQ ID NO: 103, the HCDR2 has a sequence of SEQ ID NO: 104, and the HCDR3 has a sequence of SEQ ID NO: 109.

In some embodiments, an antibody, or antibody binding fragment thereof, comprises a heavy chain variable region having a HCDR1, a HCDR2, and a HCDR3, wherein the HCDR1 has a sequence of SEQ ID NO: 103, the HCDR2 has a sequence of SEQ ID NO: 104, and the HCDR3 has a sequence of SEQ ID NO: 111.

In some embodiments, an antibody, or antibody binding fragment thereof, comprises a heavy chain variable region having a HCDR1, a HCDR2, and a HCDR3, wherein the HCDR1 has a sequence of SEQ ID NO: 103, the HCDR2 has a sequence of SEQ ID NO: 104, and the HCDR3 has a sequence of SEQ ID NO: 114.

In some embodiments, an antibody, or antibody binding fragment thereof, comprises a heavy chain variable region having a HCDR1, a HCDR2, and a HCDR3, wherein the HCDR1 has a sequence of SEQ ID NO: 103, the HCDR2 has a sequence of SEQ ID NO: 104, and the HCDR3 has a sequence of SEQ ID NO: 116.

In some embodiments, an antibody, or antibody binding fragment thereof, comprises a heavy chain variable region having a HCDR1, a HCDR2, and a HCDR3, wherein the HCDR1 has a sequence of SEQ ID NO: 103, the HCDR2 has a sequence of SEQ ID NO: 104, and the HCDR3 has a sequence of SEQ ID NO: 117.

In some embodiments, an antibody, or antibody binding fragment thereof, comprises a heavy chain variable region having a HCDR1, a HCDR2, and a HCDR3, wherein the HCDR1 has a sequence of SEQ ID NO: 103, the HCDR2 has a sequence of SEQ ID NO: 104, and the HCDR3 has a sequence of SEQ ID NO: 120.

In some embodiments, an antibody, or antibody binding fragment thereof, comprises a heavy chain variable region having a HCDR1, a HCDR2, and a HCDR3, wherein the HCDR1 has a sequence of SEQ ID NO: 103, the HCDR2 has a sequence of SEQ ID NO: 104, and the HCDR3 has a sequence of SEQ ID NO: 122.

In some embodiments, an antibody, or antibody binding fragment thereof, comprises a heavy chain variable region having a HCDR1, a HCDR2, and a HCDR3, wherein the HCDR1 has a sequence of SEQ ID NO: 124, the HCDR2 has a sequence of SEQ ID NO: 125, and the HCDR3 has a sequence of SEQ ID NO: 63.

In some embodiments, an antibody, or antibody binding fragment thereof, comprises a heavy chain variable region having a HCDR1, a HCDR2, and a HCDR3, wherein the HCDR1 has a sequence of SEQ ID NO: 124, the HCDR2 has a sequence of SEQ ID NO: 125, and the HCDR3 has a sequence of SEQ ID NO: 67.

In some embodiments, an antibody, or antibody binding fragment thereof, comprises a heavy chain variable region having a HCDR1, a HCDR2, and a HCDR3, wherein the HCDR1 has a sequence of SEQ ID NO: 124, the HCDR2 has a sequence of SEQ ID NO: 125, and the HCDR3 has a sequence of SEQ ID NO: 69.

In some embodiments, an antibody, or antibody binding fragment thereof, comprises a heavy chain variable region having a HCDR1, a HCDR2, and a HCDR3, wherein the HCDR1 has a sequence of SEQ ID NO: 124, the HCDR2 has a sequence of SEQ ID NO: 125, and the HCDR3 has a sequence of SEQ ID NO: 70.

In some embodiments, an antibody, or antibody binding fragment thereof, comprises a heavy chain variable region having a HCDR1, a HCDR2, and a HCDR3, wherein the HCDR1 has a sequence of SEQ ID NO: 124, the HCDR2 has a sequence of SEQ ID NO: 125, and the HCDR3 has a sequence of SEQ ID NO: 72.

In some embodiments, an antibody, or antibody binding fragment thereof, comprises a heavy chain variable region having a HCDR1, a HCDR2, and a HCDR3, wherein the HCDR1 has a sequence of SEQ ID NO: 124, the HCDR2 has a sequence of SEQ ID NO: 125, and the HCDR3 has a sequence of SEQ ID NO: 73.

In some embodiments, an antibody, or antibody binding fragment thereof, comprises a heavy chain variable region having a HCDR1, a HCDR2, and a HCDR3, wherein the HCDR1 has a sequence of SEQ ID NO: 124, the HCDR2 has a sequence of SEQ ID NO: 125, and the HCDR3 has a sequence of SEQ ID NO: 74.

In some embodiments, an antibody, or antibody binding fragment thereof, comprises a heavy chain variable region having a HCDR1, a HCDR2, and a HCDR3, wherein the HCDR1 has a sequence of SEQ ID NO: 124, the HCDR2 has a sequence of SEQ ID NO: 125, and the HCDR3 has a sequence of SEQ ID NO: 76.

In some embodiments, an antibody, or antibody binding fragment thereof, comprises a heavy chain variable region having a HCDR1, a HCDR2, and a HCDR3, wherein the HCDR1 has a sequence of SEQ ID NO: 124, the HCDR2 has a sequence of SEQ ID NO: 125, and the HCDR3 has a sequence of SEQ ID NO: 78.

In some embodiments, an antibody, or antibody binding fragment thereof, comprises a heavy chain variable region having a HCDR1, a HCDR2, and a HCDR3, wherein the HCDR1 has a sequence of SEQ ID NO: 124, the HCDR2 has a sequence of SEQ ID NO: 125, and the HCDR3 has a sequence of SEQ ID NO: 80.

In some embodiments, an antibody, or antibody binding fragment thereof, comprises a heavy chain variable region having a HCDR1, a HCDR2, and a HCDR3, wherein the HCDR1 has a sequence of SEQ ID NO: 126, the HCDR2 has a sequence of SEQ ID NO: 127, and the HCDR3 has a sequence of SEQ ID NO: 84.

In some embodiments, an antibody, or antibody binding fragment thereof, comprises a heavy chain variable region having a HCDR1, a HCDR2, and a HCDR3, wherein the HCDR1 has a sequence of SEQ ID NO: 126, the HCDR2 has a sequence of SEQ ID NO: 127, and the HCDR3 has a sequence of SEQ ID NO: 88.

In some embodiments, an antibody, or antibody binding fragment thereof, comprises a heavy chain variable region having a HCDR1, a HCDR2, and a HCDR3, wherein the HCDR1 has a sequence of SEQ ID NO: 126, the HCDR2 has a sequence of SEQ ID NO: 127, and the HCDR3 has a sequence of SEQ ID NO: 90.

In some embodiments, an antibody, or antibody binding fragment thereof, comprises a heavy chain variable region having a HCDR1, a HCDR2, and a HCDR3, wherein the HCDR1 has a sequence of SEQ ID NO: 126, the HCDR2 has a sequence of SEQ ID NO: 127, and the HCDR3 has a sequence of SEQ ID NO: 91.

In some embodiments, an antibody, or antibody binding fragment thereof, comprises a heavy chain variable region having a HCDR1, a HCDR2, and a HCDR3, wherein the HCDR1 has a sequence of SEQ ID NO: 126, the HCDR2 has a sequence of SEQ ID NO: 127, and the HCDR3 has a sequence of SEQ ID NO: 93.

In some embodiments, an antibody, or antibody binding fragment thereof, comprises a heavy chain variable region having a HCDR1, a HCDR2, and a HCDR3, wherein the HCDR1 has a sequence of SEQ ID NO: 126, the HCDR2 has a sequence of SEQ ID NO: 127, and the HCDR3 has a sequence of SEQ ID NO: 96.

In some embodiments, an antibody, or antibody binding fragment thereof, comprises a heavy chain variable region having a HCDR1, a HCDR2, and a HCDR3, wherein the HCDR1 has a sequence of SEQ ID NO: 126, the HCDR2 has a sequence of SEQ ID NO: 127, and the HCDR3 has a sequence of SEQ ID NO: 98.

In some embodiments, an antibody, or antibody binding fragment thereof, comprises a heavy chain variable region having a HCDR1, a HCDR2, and a HCDR3, wherein the HCDR1 has a sequence of SEQ ID NO: 126, the HCDR2 has a sequence of SEQ ID NO: 127, and the HCDR3 has a sequence of SEQ ID NO: 100.

In some embodiments, an antibody, or antibody binding fragment thereof, comprises a heavy chain variable region having a HCDR1, a HCDR2, and a HCDR3, wherein the HCDR1 has a sequence of SEQ ID NO: 128, the HCDR2 has a sequence of SEQ ID NO: 129, and the HCDR3 has a sequence of SEQ ID NO: 105.

In some embodiments, an antibody, or antibody binding fragment thereof, comprises a heavy chain variable region having a HCDR1, a HCDR2, and a HCDR3, wherein the HCDR1 has a sequence of SEQ ID NO: 128, the HCDR2 has a sequence of SEQ ID NO: 129, and the HCDR3 has a sequence of SEQ ID NO: 109.

In some embodiments, an antibody, or antibody binding fragment thereof, comprises a heavy chain variable region having a HCDR1, a HCDR2, and a HCDR3, wherein the HCDR1 has a sequence of SEQ ID NO: 128, the HCDR2 has a sequence of SEQ ID NO: 129, and the HCDR3 has a sequence of SEQ ID NO: 111.

In some embodiments, an antibody, or antibody binding fragment thereof, comprises a heavy chain variable region having a HCDR1, a HCDR2, and a HCDR3, wherein the HCDR1 has a sequence of SEQ ID NO: 128, the HCDR2 has a sequence of SEQ ID NO: 129, and the HCDR3 has a sequence of SEQ ID NO: 114.

In some embodiments, an antibody, or antibody binding fragment thereof, comprises a heavy chain variable region having a HCDR1, a HCDR2, and a HCDR3, wherein the HCDR1 has a sequence of SEQ ID NO: 128, the HCDR2 has a sequence of SEQ ID NO: 129, and the HCDR3 has a sequence of SEQ ID NO: 116.

In some embodiments, an antibody, or antibody binding fragment thereof, comprises a heavy chain variable region having a HCDR1, a HCDR2, and a HCDR3, wherein the HCDR1 has a sequence of SEQ ID NO: 128, the HCDR2 has a sequence of SEQ ID NO: 129, and the HCDR3 has a sequence of SEQ ID NO: 117.

In some embodiments, an antibody, or antibody binding fragment thereof, comprises a heavy chain variable region having a HCDR1, a HCDR2, and a HCDR3, wherein the HCDR1 has a sequence of SEQ ID NO: 128, the HCDR2 has a sequence of SEQ ID NO: 129, and the HCDR3 has a sequence of SEQ ID NO: 120.

In some embodiments, an antibody, or antibody binding fragment thereof, comprises a heavy chain variable region having a HCDR1, a HCDR2, and a HCDR3, wherein the HCDR1 has a sequence of SEQ ID NO: 128, the HCDR2 has a sequence of SEQ ID NO: 129, and the HCDR3 has a sequence of SEQ ID NO: 122.

In some embodiments, an antibody, or antibody binding fragment thereof, comprises a heavy chain variable region having a HCDR1, a HCDR2, and a HCDR3, wherein the HCDR1 has a sequence of SEQ ID NO: 130, the HCDR2 has a sequence of SEQ ID NO: 131, and the HCDR3 has a sequence of SEQ ID NO: 132.

In some embodiments, an antibody, or antibody binding fragment thereof, comprises a heavy chain variable region having a HCDR1, a HCDR2, and a HCDR3, wherein the HCDR1 has a sequence of SEQ ID NO: 130, the HCDR2 has a sequence of SEQ ID NO: 131, and the HCDR3 has a sequence of SEQ ID NO: 135.

In some embodiments, an antibody, or antibody binding fragment thereof, comprises a heavy chain variable region having a HCDR1, a HCDR2, and a HCDR3, wherein the HCDR1 has a sequence of SEQ ID NO: 130, the HCDR2 has a sequence of SEQ ID NO: 131, and the HCDR3 has a sequence of SEQ ID NO: 136.

In some embodiments, an antibody, or antibody binding fragment thereof, comprises a heavy chain variable region having a HCDR1, a HCDR2, and a HCDR3, wherein the HCDR1 has a sequence of SEQ ID NO: 130, the HCDR2 has a sequence of SEQ ID NO: 131, and the HCDR3 has a sequence of SEQ ID NO: 137.

In some embodiments, an antibody, or antibody binding fragment thereof, comprises a heavy chain variable region having a HCDR1, a HCDR2, and a HCDR3, wherein the HCDR1 has a sequence of SEQ ID NO: 130, the HCDR2 has a sequence of SEQ ID NO: 131, and the HCDR3 has a sequence of SEQ ID NO: 138.

In some embodiments, an antibody, or antibody binding fragment thereof, comprises a heavy chain variable region having a HCDR1, a HCDR2, and a HCDR3, wherein the HCDR1 has a sequence of SEQ ID NO: 130, the HCDR2 has a sequence of SEQ ID NO: 131, and the HCDR3 has a sequence of SEQ ID NO: 139.

In some embodiments, an antibody, or antibody binding fragment thereof, comprises a heavy chain variable region having a HCDR1, a HCDR2, and a HCDR3, wherein the HCDR1 has a sequence of SEQ ID NO: 130, the HCDR2 has a sequence of SEQ ID NO: 131, and the HCDR3 has a sequence of SEQ ID NO: 140.

In some embodiments, an antibody, or antibody binding fragment thereof, comprises a heavy chain variable region having a HCDR1, a HCDR2, and a HCDR3, wherein the HCDR1 has a sequence of SEQ ID NO: 130, the HCDR2 has a sequence of SEQ ID NO: 131, and the HCDR3 has a sequence of SEQ ID NO: 141.

In some embodiments, an antibody, or antibody binding fragment thereof, comprises a heavy chain variable region having a HCDR1, a HCDR2, and a HCDR3, wherein the HCDR1 has a sequence of SEQ ID NO: 130, the HCDR2 has a sequence of SEQ ID NO: 131, and the HCDR3 has a sequence of SEQ ID NO: 142.

In some embodiments, an antibody, or antibody binding fragment thereof, comprises a heavy chain variable region having a HCDR1, a HCDR2, and a HCDR3, wherein the HCDR1 has a sequence of SEQ ID NO: 130, the HCDR2 has a sequence of SEQ ID NO: 131, and the HCDR3 has a sequence of SEQ ID NO: 143.

In some embodiments, an antibody, or antibody binding fragment thereof, comprises a heavy chain variable region having a HCDR1, a HCDR2, and a HCDR3, wherein the HCDR1 has a sequence of SEQ ID NO: 144, the HCDR2 has a sequence of SEQ ID NO: 145, and the HCDR3 has a sequence of SEQ ID NO: 146.

In some embodiments, an antibody, or antibody binding fragment thereof, comprises a heavy chain variable region having a HCDR1, a HCDR2, and a HCDR3, wherein the HCDR1 has a sequence of SEQ ID NO: 144, the HCDR2 has a sequence of SEQ ID NO: 145, and the HCDR3 has a sequence of SEQ ID NO: 149.

In some embodiments, an antibody, or antibody binding fragment thereof, comprises a heavy chain variable region having a HCDR1, a HCDR2, and a HCDR3, wherein the HCDR1 has a sequence of SEQ ID NO: 144, the HCDR2 has a sequence of SEQ ID NO: 145, and the HCDR3 has a sequence of SEQ ID NO: 150.

In some embodiments, an antibody, or antibody binding fragment thereof, comprises a heavy chain variable region having a HCDR1, a HCDR2, and a HCDR3, wherein the HCDR1 has a sequence of SEQ ID NO: 144, the HCDR2 has a sequence of SEQ ID NO: 145, and the HCDR3 has a sequence of SEQ ID NO: 151.

In some embodiments, an antibody, or antibody binding fragment thereof, comprises a heavy chain variable region having a HCDR1, a HCDR2, and a HCDR3, wherein the HCDR1 has a sequence of SEQ ID NO: 144, the HCDR2 has a sequence of SEQ ID NO: 145, and the HCDR3 has a sequence of SEQ ID NO: 152.

In some embodiments, an antibody, or antibody binding fragment thereof, comprises a heavy chain variable region having a HCDR1, a HCDR2, and a HCDR3, wherein the HCDR1 has a sequence of SEQ ID NO: 144, the HCDR2 has a sequence of SEQ ID NO: 145, and the HCDR3 has a sequence of SEQ ID NO: 153.

In some embodiments, an antibody, or antibody binding fragment thereof, comprises a heavy chain variable region having a HCDR1, a HCDR2, and a HCDR3, wherein the HCDR1 has a sequence of SEQ ID NO: 144, the HCDR2 has a sequence of SEQ ID NO: 145, and the HCDR3 has a sequence of SEQ ID NO: 154.

In some embodiments, an antibody, or antibody binding fragment thereof, comprises a heavy chain variable region having a HCDR1, a HCDR2, and a HCDR3, wherein the HCDR1 has a sequence of SEQ ID NO: 144, the HCDR2 has a sequence of SEQ ID NO: 145, and the HCDR3 has a sequence of SEQ ID NO: 155.

In some embodiments, an antibody, or antibody binding fragment thereof, comprises a heavy chain variable region having a HCDR1, a HCDR2, and a HCDR3, wherein the HCDR1 has a sequence of SEQ ID NO: 156, the HCDR2 has a sequence of SEQ ID NO: 157, and the HCDR3 has a sequence of SEQ ID NO: 158.

In some embodiments, an antibody, or antibody binding fragment thereof, comprises a heavy chain variable region having a HCDR1, a HCDR2, and a HCDR3, wherein the HCDR1 has a sequence of SEQ ID NO: 156, the HCDR2 has a sequence of SEQ ID NO: 157, and the HCDR3 has a sequence of SEQ ID NO: 161.

In some embodiments, an antibody, or antibody binding fragment thereof, comprises a heavy chain variable region having a HCDR1, a HCDR2, and a HCDR3, wherein the HCDR1 has a sequence of SEQ ID NO: 156, the HCDR2 has a sequence of SEQ ID NO: 157, and the HCDR3 has a sequence of SEQ ID NO: 162.

In some embodiments, an antibody, or antibody binding fragment thereof, comprises a heavy chain variable region having a HCDR1, a HCDR2, and a HCDR3, wherein the HCDR1 has a sequence of SEQ ID NO: 156, the HCDR2 has a sequence of SEQ ID NO: 157, and the HCDR3 has a sequence of SEQ ID NO: 163.

In some embodiments, an antibody, or antibody binding fragment thereof, comprises a heavy chain variable region having a HCDR1, a HCDR2, and a HCDR3, wherein the HCDR1 has a sequence of SEQ ID NO: 156, the HCDR2 has a sequence of SEQ ID NO: 157, and the HCDR3 has a sequence of SEQ ID NO: 164.

In some embodiments, an antibody, or antibody binding fragment thereof, comprises a heavy chain variable region having a HCDR1, a HCDR2, and a HCDR3, wherein the HCDR1 has a sequence of SEQ ID NO: 156, the HCDR2 has a sequence of SEQ ID NO: 157, and the HCDR3 has a sequence of SEQ ID NO: 165.

In some embodiments, an antibody, or antibody binding fragment thereof, comprises a heavy chain variable region having a HCDR1, a HCDR2, and a HCDR3, wherein the HCDR1 has a sequence of SEQ ID NO: 156, the HCDR2 has a sequence of SEQ ID NO: 157, and the HCDR3 has a sequence of SEQ ID NO: 166.

In some embodiments, an antibody, or antibody binding fragment thereof, comprises a heavy chain variable region having a HCDR1, a HCDR2, and a HCDR3, wherein the HCDR1 has a sequence of SEQ ID NO: 156, the HCDR2 has a sequence of SEQ ID NO: 157, and the HCDR3 has a sequence of SEQ ID NO: 167.

In some embodiments, an antibody, or antigen binding fragment thereof, comprises: (i) a light chain variable region comprising light chain LCDR1, LCDR2, and LCDR3 sequences, wherein the light chain LCDR1 sequence has the amino acid sequence SEQ ID NO: 64; the light chain LCDR2 sequence has the amino acid sequence of SEQ ID NO: 65; and the light chain LCDR3 sequence has the amino acid sequence of SEQ ID NO: 66 and (ii) a heavy chain variable region comprising heavy chain HCDR1, HCDR2, and HCDR3 sequences, wherein the heavy chain HCDR1 sequence has the amino acid sequence of SEQ ID NO: 61; the heavy chain HCDR2 has the amino acid sequence of SEQ ID NO: 62 and the heavy chain HCDR3 sequence has the amino acid sequence of SEQ ID NO: 63; or variants or convention equivalents of any of the foregoing.

In some embodiments, an antibody, or antigen binding fragment thereof, comprises: (i) a light chain variable region comprising light chain LCDR1, LCDR2, and LCDR3 sequences, wherein the light chain LCDR1 sequence has the amino acid sequence SEQ ID NO: 64; the light chain LCDR2 sequence has the amino acid sequence of SEQ ID NO: 65; and the light chain LCDR3 sequence has the amino acid sequence of SEQ ID NO: 68 and (ii) a heavy chain variable region comprising heavy chain HCDR1, HCDR2, and HCDR3 sequences, wherein the HCDR1 sequence has the amino acid sequence of SEQ ID NO: 61; the HCDR2 has the amino acid sequence of SEQ ID NO: 62 and the HCDR3 sequence has the amino acid sequence of SEQ ID NO: 67; or variants or convention equivalents of any of the foregoing.

In some embodiments, an antibody, or antigen binding fragment thereof, comprises: (i) a light chain variable region comprising light chain LCDR1, LCDR2, and LCDR3 sequences, wherein the light chain LCDR1 sequence has the amino acid sequence SEQ ID NO: 64; the light chain LCDR2 sequence has the amino acid sequence of SEQ ID NO: 65; and the light chain LCDR3 sequence has the amino acid sequence of SEQ ID NO: 68 and (ii) a heavy chain variable region comprising heavy chain HCDR1, HCDR2, and HCDR3 sequences, wherein the heavy chain HCDR1 sequence has the amino acid sequence of SEQ ID NO: 61; the heavy chain HCDR2 has the amino acid sequence of SEQ ID NO: 62 and the heavy chain HCDR3 sequence has the amino acid sequence of SEQ ID NO: 69; or variants or convention equivalents of any of the foregoing.

In some embodiments, an antibody, or antigen binding fragment thereof, comprises: (i) a light chain variable region comprising light chain LCDR1, LCDR2, and LCDR3 sequences, wherein the light chain LCDR1 sequence has the amino acid sequence SEQ ID NO: 64; the light chain LCDR2 sequence has the amino acid sequence of SEQ ID NO: 65 and (ii) a heavy chain variable region comprising heavy chain HCDR1, HCDR2, and HCDR3 sequences, wherein the HCDR1 sequence has the amino acid sequence of SEQ ID NO: 61; the HCDR2 has the amino acid sequence of SEQ ID NO: 62 and the HCDR3 sequence has the amino acid sequence of SEQ ID NO: 70; or variants or convention equivalents of any of the foregoing.

In some embodiments, an antibody, or antigen binding fragment thereof, comprises: (i) a light chain variable region comprising light chain LCDR1, LCDR2, and LCDR3 sequences, wherein the light chain LCDR1 sequence has the amino acid sequence SEQ ID NO: 64; the light chain LCDR2 sequence has the amino acid sequence of SEQ ID NO: 65; and the light chain LCDR3 sequence has the amino acid sequence of SEQ ID NO: 71 and (ii) a heavy chain variable region comprising heavy chain HCDR1, HCDR2, and HCDR3 sequences, wherein the HCDR1 sequence has the amino acid sequence of SEQ ID NO: 61; the HCDR2 has the amino acid sequence of SEQ ID NO: 62 and the HCDR3 sequence has the amino acid sequence of SEQ ID NO: 72; or variants or convention equivalents of any of the foregoing.

In some embodiments, an antibody, or antigen binding fragment thereof, comprises: (i) a light chain variable region comprising light chain LCDR1, LCDR2, and LCDR3 sequences, wherein the light chain LCDR1 sequence has the amino acid sequence SEQ ID NO: 64; the light chain LCDR2 sequence has the amino acid sequence of SEQ ID NO: 65; and the light chain LCDR3 sequence has the amino acid sequence of SEQ ID NO: 71 and (ii) a heavy chain variable region comprising heavy chain HCDR1, HCDR2, and HCDR3 sequences, wherein the HCDR1 sequence has the amino acid sequence of SEQ ID NO: 61; the HCDR2 has the amino acid sequence of SEQ ID NO: 62 and the HCDR3 sequence has the amino acid sequence of SEQ ID NO: 73; or variants or convention equivalents of any of the foregoing.

In some embodiments, an antibody, or antigen binding fragment thereof, comprises: (i) a light chain variable region comprising light chain LCDR1, LCDR2, and LCDR3 sequences, wherein the light chain LCDR1 sequence has the amino acid sequence SEQ ID NO: 64; the light chain LCDR2 sequence has the amino acid sequence of SEQ ID NO: 65; and the light chain LCDR3 sequence has the amino acid sequence of SEQ ID NO: 75 and (ii) a heavy chain variable region comprising heavy chain HCDR1, HCDR2, and HCDR3 sequences, wherein the HCDR1 sequence has the amino acid sequence of SEQ ID NO: 61; the HCDR2 has the amino acid sequence of SEQ ID NO: 62 and the HCDR3 sequence has the amino acid sequence of SEQ ID NO: 74; or variants or convention equivalents of any of the foregoing.

In some embodiments, an antibody, or antigen binding fragment thereof, comprises: (i) a light chain variable region comprising light chain LCDR1, LCDR2, and LCDR3 sequences, wherein the light chain LCDR1 sequence has the amino acid sequence SEQ ID NO: 64; the light chain LCDR2 sequence has the amino acid sequence of SEQ ID NO: 65; and the light chain LCDR3 sequence has the amino acid sequence of SEQ ID NO: 77 and (ii) a heavy chain variable region comprising heavy chain HCDR1, HCDR2, and HCDR3 sequences, wherein the HCDR1 sequence has the amino acid sequence of SEQ ID NO: 61; the HCDR2 has the amino acid sequence of SEQ ID NO: 62 and the HCDR3 sequence has the amino acid sequence of SEQ ID NO: 76; or variants or convention equivalents of any of the foregoing.

In some embodiments, an antibody, or antigen binding fragment thereof, comprises: (i) a light chain variable region comprising light chain LCDR1, LCDR2, and LCDR3 sequences, wherein the light chain LCDR1 sequence has the amino acid sequence SEQ ID NO: 64; the light chain LCDR2 sequence has the amino acid sequence of SEQ ID NO: 65; and the light chain LCDR3 sequence has the amino acid sequence of SEQ ID NO: 79 and (ii) a heavy chain variable region comprising heavy chain HCDR1, HCDR2, and HCDR3 sequences, wherein the HCDR1 sequence has the amino acid sequence of SEQ ID NO: 61; the HCDR2 has the amino acid sequence of SEQ ID NO: 62 and the HCDR3 sequence has the amino acid sequence of SEQ ID NO: 78; or variants or convention equivalents of any of the foregoing.

In some embodiments, an antibody, or antigen binding fragment thereof, comprises: (i) a light chain variable region comprising light chain LCDR1, LCDR2, and LCDR3 sequences, wherein the light chain LCDR1 sequence has the amino acid sequence SEQ ID NO: 64; the light chain LCDR2 sequence has the amino acid sequence of SEQ ID NO: 65; and the light chain LCDR3 sequence has the amino acid sequence of SEQ ID NO: 81 and (ii) a heavy chain variable region comprising heavy chain HCDR1, HCDR2, and HCDR3 sequences, wherein the HCDR1 sequence has the amino acid sequence of SEQ ID NO: 61; the HCDR2 has the amino acid sequence of SEQ ID NO: 62 and the HCDR3 sequence has the amino acid sequence of SEQ ID NO: 80; or variants or convention equivalents of any of the foregoing.

In some embodiments, an antibody, or antigen binding fragment thereof, comprises: (i) a light chain variable region comprising light chain LCDR1, LCDR2, and LCDR3 sequences, wherein the light chain LCDR1 sequence has the amino acid sequence SEQ ID NO: 85; the light chain LCDR2 sequence has the amino acid sequence of SEQ ID NO: 86; and the light chain LCDR3 sequence has the amino acid sequence of SEQ ID NO: 87 and (ii) a heavy chain variable region comprising heavy chain HCDR1, HCDR2, and HCDR3 sequences, wherein the heavy chain HCDR1 sequence has the amino acid sequence of SEQ ID NO: 82; the heavy chain HCDR2 has the amino acid sequence of SEQ ID NO: 83 and the heavy chain HCDR3 sequence has the amino acid sequence of SEQ ID NO: 84; or variants or convention equivalents of any of the foregoing.

In some embodiments, an antibody, or antigen binding fragment thereof, comprises: (i) a light chain variable region comprising light chain LCDR1, LCDR2, and LCDR3 sequences, wherein the light chain sequence has the amino acid sequence SEQ ID NO: 85; the light chain LCDR2 sequence has the amino acid sequence of SEQ ID NO: 86; and the light chain LCDR3 sequence has the amino acid sequence of SEQ ID NO: 89 and (ii) a heavy chain variable region comprising heavy chain HCDR1, HCDR2, and HCDR3 sequences, wherein the heavy chain HCDR1 sequence has the amino acid sequence of SEQ ID NO: 82; the heavy chain HCDR2 has the amino acid sequence of SEQ ID NO: 83 and the heavy chain HCDR3 sequence has the amino acid sequence of SEQ ID NO: 88; or variants or convention equivalents of any of the foregoing.

In some embodiments, an antibody, or antigen binding fragment thereof, comprises: (i) a light chain variable region comprising light chain LCDR1, LCDR2, and LCDR3 sequences, wherein the light chain LCDR1 sequence has the amino acid sequence SEQ ID NO: 85; the light chain LCDR2 sequence has the amino acid sequence of SEQ ID NO: 86; and the light chain LCDR3 sequence has the amino acid sequence of SEQ ID NO: 89 and (ii) a heavy chain variable region comprising heavy chain HCDR1, HCDR2, and HCDR3 sequences, wherein the heavy chain HCDR1 sequence has the amino acid sequence of SEQ ID NO: 82; the heavy chain HCDR2 has the amino acid sequence of SEQ ID NO: 83 and the heavy chain HCDR3 sequence has the amino acid sequence of SEQ ID NO: 90; or variants or convention equivalents of any of the foregoing.

In some embodiments, an antibody, or antigen binding fragment thereof, comprises: (i) a light chain variable region comprising light chain LCDR1, LCDR2, and LCDR3 sequences, wherein the light chain LCDR1 sequence has the amino acid sequence SEQ ID NO: 85; the light chain LCDR2 sequence has the amino acid sequence of SEQ ID NO: 86; and the light chain LCDR3 sequence has the amino acid sequence of SEQ ID NO: 92 and (ii) a heavy chain variable region comprising heavy chain HCDR1, HCDR2, and HCDR3 sequences, wherein the heavy chain HCDR1 sequence has the amino acid sequence of SEQ ID NO: 82; the heavy chain HCDR2 has the amino acid sequence of SEQ ID NO: 83 and the heavy chain HCDR3 sequence has the amino acid sequence of SEQ ID NO: 91; or variants or convention equivalents of any of the foregoing.

In some embodiments, an antibody, or antigen binding fragment thereof, comprises: (i) a light chain variable region comprising light chain LCDR1, LCDR2, and LCDR3 sequences, wherein the light chain LCDR1 sequence has the amino acid sequence SEQ ID NO: 85; the light chain LCDR2 sequence has the amino acid sequence of SEQ ID NO: 86; and the light chain LCDR3 sequence has the amino acid sequence of SEQ ID NO: 94 and (ii) a heavy chain variable region comprising heavy chain HCDR1, HCDR2, and HCDR3 sequences, wherein the heavy chain HCDR1 sequence has the amino acid sequence of SEQ ID NO: 82; the heavy chain HCDR2 has the amino acid sequence of SEQ ID NO: 83 and the heavy chain HCDR3 sequence has the amino acid sequence of SEQ ID NO: 93; or variants or convention equivalents of any of the foregoing.

In some embodiments, an antibody, or antigen binding fragment thereof, comprises: (i) a light chain variable region comprising light chain LCDR1, LCDR2, and LCDR3 sequences, wherein the light chain LCDR1 sequence has the amino acid sequence SEQ ID NO: 85; the light chain LCDR2 sequence has the amino acid sequence of SEQ ID NO: 86; and the light chain LCDR3 sequence has the amino acid sequence of SEQ ID NO: 95 and (ii) a heavy chain variable region comprising heavy chain HCDR1, HCDR2, and HCDR3 sequences, wherein the heavy chain HCDR1 sequence has the amino acid sequence of SEQ ID NO: 82; the heavy chain HCDR2 has the amino acid sequence of SEQ ID NO: 83 and the heavy chain HCDR3 sequence has the amino acid sequence of SEQ ID NO: 84; or variants or convention equivalents of any of the foregoing.

In some embodiments, an antibody, or antigen binding fragment thereof, comprises: (i) a light chain variable region comprising light chain LCDR1, LCDR2, and LCDR3 sequences, wherein the light chain LCDR1 sequence has the amino acid sequence SEQ ID NO: 85; the light chain LCDR2 sequence has the amino acid sequence of SEQ ID NO: 86; and the light chain LCDR3 sequence has the amino acid sequence of SEQ ID NO: 97 and (ii) a heavy chain variable region comprising heavy chain HCDR1, HCDR2, and HCDR3 sequences, wherein the heavy chain HCDR1 sequence has the amino acid sequence of SEQ ID NO: 82; the heavy chain HCDR2 has the amino acid sequence of SEQ ID NO: 83 and the heavy chain HCDR3 sequence has the amino acid sequence of SEQ ID NO: 96; or variants or convention equivalents of any of the foregoing.

In some embodiments, an antibody, or antigen binding fragment thereof, comprises: (i) a light chain variable region comprising light chain LCDR1, LCDR2, and LCDR3 sequences, wherein the light chain LCDR1 sequence has the amino acid sequence SEQ ID NO: 85; the light chain LCDR2 sequence has the amino acid sequence of SEQ ID NO: 86; and the light chain LCDR3 sequence has the amino acid sequence of SEQ ID NO: 99 and (ii) a heavy chain variable region comprising heavy chain HCDR1, HCDR2, and HCDR3 sequences, wherein the heavy chain HCDR1 sequence has the amino acid sequence of SEQ ID NO: 82; the heavy chain HCDR2 has the amino acid sequence of SEQ ID NO: 83 and the heavy chain HCDR3 sequence has the amino acid sequence of SEQ ID NO: 98; or variants or convention equivalents of any of the foregoing.

In some embodiments, an antibody, or antigen binding fragment thereof, comprises: (i) a light chain variable region comprising light chain LCDR1, LCDR2, and LCDR3 sequences, wherein the light chain LCDR1 sequence has the amino acid sequence SEQ ID NO: 85; the light chain LCDR2 sequence has the amino acid sequence of SEQ ID NO: 86; and the light chain LCDR3 sequence has the amino acid sequence of SEQ ID NO: 101 and (ii) a heavy chain variable region comprising heavy chain HCDR1, HCDR2, and HCDR3 sequences, wherein the heavy chain HCDR1 sequence has the amino acid sequence of SEQ ID NO: 82; the heavy chain HCDR2 has the amino acid sequence of SEQ ID NO: 83 and the heavy chain HCDR3 sequence has the amino acid sequence of SEQ ID NO: 100; or variants or convention equivalents of any of the foregoing.

In some embodiments, an antibody, or antigen binding fragment thereof, comprises: (i) a light chain variable region comprising light chain LCDR1, LCDR2, and LCDR3 sequences, wherein the light chain LCDR1 sequence has the amino acid sequence SEQ ID NO: 85; the light chain LCDR2 sequence has the amino acid sequence of SEQ ID NO: 86; and the light chain LCDR3 sequence has the amino acid sequence of SEQ ID NO: 102 and (ii) a heavy chain variable region comprising heavy chain HCDR1, HCDR2, and HCDR3 sequences, wherein the heavy chain HCDR1 sequence has the amino acid sequence of SEQ ID NO: 82; the heavy chain HCDR2 has the amino acid sequence of SEQ ID NO: 83 and the heavy chain HCDR3 sequence has the amino acid sequence of SEQ ID NO: 100; or variants or convention equivalents of any of the foregoing.

In some embodiments, an antibody, or antigen binding fragment thereof, comprises: (i) a light chain variable region comprising light chain LCDR1, LCDR2, and LCDR3 sequences, wherein the light chain LCDR1 sequence has the amino acid sequence SEQ ID NO: 106; the light chain LCDR2 sequence has the amino acid sequence of SEQ ID NO: 107; and the light chain LCDR3 sequence has the amino acid sequence of SEQ ID NO: 108 and (ii) a heavy chain variable region comprising heavy chain HCDR1, HCDR2, and HCDR3 sequences, wherein the heavy chain HCDR1 sequence has the amino acid sequence of SEQ ID NO: 103; the heavy chain HCDR2 has the amino acid sequence of SEQ ID NO: 104 and the heavy chain HCDR3 sequence has the amino acid sequence of SEQ ID NO: 105; or variants or convention equivalents of any of the foregoing.

In some embodiments, an antibody, or antigen binding fragment thereof, comprises: (i) a light chain variable region comprising light chain LCDR1, LCDR2, and LCDR3 sequences, wherein the light chain LCDR1 sequence has the amino acid sequence SEQ ID NO: 106; the light chain LCDR2 sequence has the amino acid sequence of SEQ ID NO: 107; and the light chain LCDR3 sequence has the amino acid sequence of SEQ ID NO: 110 and (ii) a heavy chain variable region comprising heavy chain HCDR1, HCDR2, and HCDR3 sequences, wherein the heavy chain HCDR1 sequence has the amino acid sequence of SEQ ID NO: 103; the heavy chain HCDR2 has the amino acid sequence of SEQ ID NO: 104 and the heavy chain HCDR3 sequence has the amino acid sequence of SEQ ID NO: 109; or variants or convention equivalents of any of the foregoing.

In some embodiments, an antibody, or antigen binding fragment thereof, comprises: (i) a light chain variable region comprising light chain LCDR1, LCDR2, and LCDR3 sequences, wherein the light chain LCDR1 sequence has the amino acid sequence SEQ ID NO: 106; the light chain LCDR2 sequence has the amino acid sequence of SEQ ID NO: 107; and the light chain LCDR3 sequence has the amino acid sequence of SEQ ID NO: 112 and (ii) a heavy chain variable region comprising heavy chain HCDR1, HCDR2, and HCDR3 sequences, wherein the heavy chain HCDR1 sequence has the amino acid sequence of SEQ ID NO: 103; the heavy chain HCDR2 has the amino acid sequence of SEQ ID NO: 104 and the heavy chain HCDR3 sequence has the amino acid sequence of SEQ ID NO: 111; or variants or convention equivalents of any of the foregoing.

In some embodiments, an antibody, or antigen binding fragment thereof, comprises: (i) a light chain variable region comprising light chain LCDR1, LCDR2, and LCDR3 sequences, wherein the light chain LCDR1 sequence has the amino acid sequence SEQ ID NO: 106; the light chain LCDR2 sequence has the amino acid sequence of SEQ ID NO: 107; and the light chain LCDR3 sequence has the amino acid sequence of SEQ ID NO: 113 and (ii) a heavy chain variable region comprising heavy chain HCDR1, HCDR2, and HCDR3 sequences, wherein the heavy chain HCDR1 sequence has the amino acid sequence of SEQ ID NO: 103; the heavy chain HCDR2 has the amino acid sequence of SEQ ID NO: 104 and the heavy chain HCDR3 sequence has the amino acid sequence of SEQ ID NO: 105; or variants or convention equivalents of any of the foregoing.

In some embodiments, an antibody, or antigen binding fragment thereof, comprises: (i) a light chain variable region comprising light chain LCDR1, LCDR2, and LCDR3 sequences, wherein the light chain LCDR1 sequence has the amino acid sequence SEQ ID NO: 106; the light chain LCDR2 sequence has the amino acid sequence of SEQ ID NO: 107; and the light chain LCDR3 sequence has the amino acid sequence of SEQ ID NO: 115 and (ii) a heavy chain variable region comprising heavy chain HCDR1, HCDR2, and HCDR3 sequences, wherein the heavy chain HCDR1 sequence has the amino acid sequence of SEQ ID NO: 103; the heavy chain HCDR2 has the amino acid sequence of SEQ ID NO: 104 and the heavy chain HCDR3 sequence has the amino acid sequence of SEQ ID NO: 114; or variants or convention equivalents of any of the foregoing.

In some embodiments, an antibody, or antigen binding fragment thereof, comprises: (i) a light chain variable region comprising light chain LCDR1, LCDR2, and LCDR3 sequences, wherein the light chain LCDR1 sequence has the amino acid sequence SEQ ID NO: 106; the light chain LCDR2 sequence has the amino acid sequence of SEQ ID NO: 107; and the light chain LCDR3 sequence has the amino acid sequence of SEQ ID NO: 113 and (ii) a heavy chain variable region comprising heavy chain HCDR1, HCDR2, and HCDR3 sequences, wherein the heavy chain HCDR1 sequence has the amino acid sequence of SEQ ID NO: 103; the heavy chain HCDR2 has the amino acid sequence of SEQ ID NO: 104 and the heavy chain HCDR3 sequence has the amino acid sequence of SEQ ID NO: 116; or variants or convention equivalents of any of the foregoing.

In some embodiments, an antibody, or antigen binding fragment thereof, comprises: (i) a light chain variable region comprising light chain LCDR1, LCDR2, and LCDR3 sequences, wherein the light chain LCDR1 sequence has the amino acid sequence SEQ ID NO: 106; the light chain LCDR2 sequence has the amino acid sequence of SEQ ID NO: 107; and the light chain LCDR3 sequence has the amino acid sequence of SEQ ID NO: 118 and (ii) a heavy chain variable region comprising heavy chain HCDR1, HCDR2, and HCDR3 sequences, wherein the heavy chain HCDR1 sequence has the amino acid sequence of SEQ ID NO: 103; the heavy chain HCDR2 has the amino acid sequence of SEQ ID NO: 104 and the heavy chain HCDR3 sequence has the amino acid sequence of SEQ ID NO: 117; or variants or convention equivalents of any of the foregoing.

In some embodiments, an antibody, or antigen binding fragment thereof, comprises: (i) a light chain variable region comprising light chain LCDR1, LCDR2, and LCDR3 sequences, wherein the light chain LCDR1 sequence has the amino acid sequence SEQ ID NO: 106; the light chain LCDR2 sequence has the amino acid sequence of SEQ ID NO: 107; and the light chain LCDR3 sequence has the amino acid sequence of SEQ ID NO: 119 and (ii) a heavy chain variable region comprising heavy chain HCDR1, HCDR2, and HCDR3 sequences, wherein the heavy chain HCDR1 sequence has the amino acid sequence of SEQ ID NO: 103; the heavy chain HCDR2 has the amino acid sequence of SEQ ID NO: 104 and the heavy chain HCDR3 sequence has the amino acid sequence of SEQ ID NO: 116; or variants or convention equivalents of any of the foregoing.

In some embodiments, an antibody, or antigen binding fragment thereof, comprises: (i) a light chain variable region comprising light chain LCDR1, LCDR2, and LCDR3 sequences, wherein the light chain LCDR1 sequence has the amino acid sequence SEQ ID NO: 106; the light chain LCDR2 sequence has the amino acid sequence of SEQ ID NO: 107; and the light chain LCDR3 sequence has the amino acid sequence of SEQ ID NO: 121 and (ii) a heavy chain variable region comprising heavy chain HCDR1, HCDR2, and HCDR3 sequences, wherein the heavy chain HCDR1 sequence has the amino acid sequence of SEQ ID NO: 103; the heavy chain HCDR2 has the amino acid sequence of SEQ ID NO: 104 and the heavy chain HCDR3 sequence has the amino acid sequence of SEQ ID NO: 120; or variants or convention equivalents of any of the foregoing.

In some embodiments, an antibody, or antigen binding fragment thereof, comprises: (i) a light chain variable region comprising light chain LCDR1, LCDR2, and LCDR3 sequences, wherein the light chain LCDR1 sequence has the amino acid sequence SEQ ID NO: 106; the light chain LCDR2 sequence has the amino acid sequence of SEQ ID NO: 107; and the light chain LCDR3 sequence has the amino acid sequence of SEQ ID NO: 123 and (ii) a heavy chain variable region comprising heavy chain HCDR1, HCDR2, and HCDR3 sequences, wherein the heavy chain HCDR1 sequence has the amino acid sequence of SEQ ID NO: 103; the heavy chain HCDR2 has the amino acid sequence of SEQ ID NO: 104 and the heavy chain HCDR3 sequence has the amino acid sequence of SEQ ID NO: 122; or variants or convention equivalents of any of the foregoing.

Although the preceding paragraphs may make reference to CDRs under the Kabat system the equivalent CDR sequences can be used from the IMGT and CHOTHIA designations.

In some embodiments, an antibody or antigen-binding fragment thereof is provided, wherein the HCDR1, HCDR2, and HCDR3 are selected from SEQ ID NO: 61, SEQ ID NO: 62, and SEQ ID NO: 63, respectively, from SEQ ID NO: 124, SEQ ID NO: 125, and SEQ ID NO: 63, respectively, or from SEQ ID NO: 130, SEQ ID NO: 131, and SEQ ID NO: 132, respectively, and the LCDR1, LCDR2, and LCDR3 are selected from SEQ ID NO: 64, SEQ ID NO: 65, and SEQ ID NO: 66, respectively, from SEQ ID NO: 64, SEQ ID NO: 65, and SEQ ID NO: 66, respectively, or from SEQ ID NO: 133, SEQ ID NO: 134, and SEQ ID NO: 66 respectively.

In some embodiments, an antibody or antigen-binding fragment thereof is provided, wherein the HCDR1, HCDR2, and HCDR3 are selected from SEQ ID NO: 61, SEQ ID NO: 62, and SEQ ID NO: 67, respectively, from SEQ ID NO: 124, SEQ ID NO: 125, and SEQ ID NO: 67, respectively, or from SEQ ID NO: 130, SEQ ID NO: 131, and SEQ ID NO: 135, respectively, and the LCDR1, LCDR2, and LCDR3 are selected from SEQ ID NO: 64, SEQ ID NO: 65, and SEQ ID NO: 68, respectively, from SEQ ID NO: 64, SEQ ID NO: 65, and SEQ ID NO: 68, respectively, or from SEQ ID NO: 133, SEQ ID NO: 134, and SEQ ID NO: 68 respectively.

In some embodiments, an antibody or antigen-binding fragment thereof is provided, wherein the HCDR1, HCDR2, and HCDR3 are selected from SEQ ID NO: 61, SEQ ID NO: 62, and SEQ ID NO: 69, respectively, from SEQ ID NO: 124, SEQ ID NO: 125, and SEQ ID NO: 69, respectively, or from SEQ ID NO: 130, SEQ ID NO: 131, and SEQ ID NO: 136, respectively, and the LCDR1, LCDR2, and LCDR3 are selected from SEQ ID NO: 64, SEQ ID NO: 65, and SEQ ID NO: 68, respectively, from SEQ ID NO: 64, SEQ ID NO: 65, and SEQ ID NO: 68, respectively, or from SEQ ID NO: 133, SEQ ID NO: 134, and SEQ ID NO: 68 respectively.

In some embodiments, an antibody or antigen-binding fragment thereof is provided, wherein the HCDR1, HCDR2, and HCDR3 are selected from SEQ ID NO: 61, SEQ ID NO: 62, and SEQ ID NO: 70, respectively, from SEQ ID NO: 124, SEQ ID NO: 125, and SEQ ID NO: 70, respectively, or from SEQ ID NO: 130, SEQ ID NO: 131, and SEQ ID NO: 137, respectively, and the LCDR1, LCDR2, and LCDR3 are selected from SEQ ID NO: 64, SEQ ID NO: 65, and SEQ ID NO: 71, respectively, from SEQ ID NO: 64, SEQ ID NO: 65, and SEQ ID NO: 71, respectively, or from SEQ ID NO: 133, SEQ ID NO: 134, and SEQ ID NO: 71 respectively.

In some embodiments, an antibody or antigen-binding fragment thereof is provided, wherein the HCDR1, HCDR2, and HCDR3 are selected from SEQ ID NO: 61, SEQ ID NO: 62, and SEQ ID NO: 72, respectively, from SEQ ID NO: 124, SEQ ID NO: 125, and SEQ ID NO: 72, respectively, or from SEQ ID NO: 130, SEQ ID NO: 131, and SEQ ID NO: 138, respectively, and the LCDR1, LCDR2, and LCDR3 are selected from SEQ ID NO: 64, SEQ ID NO: 65, and SEQ ID NO: 71, respectively, from SEQ ID NO: 64, SEQ ID NO: 65, and SEQ ID NO: 71, respectively, or from SEQ ID NO: 133, SEQ ID NO: 134, and SEQ ID NO: 71 respectively.

In some embodiments, an antibody or antigen-binding fragment thereof is provided, wherein the HCDR1, HCDR2, and HCDR3 are selected from SEQ ID NO: 61, SEQ ID NO: 62, and SEQ ID NO: 73, respectively, from SEQ ID NO: 124, SEQ ID NO: 125, and SEQ ID NO: 73, respectively, or from SEQ ID NO: 130, SEQ ID NO: 131, and SEQ ID NO: 139, respectively, and the LCDR1, LCDR2, and LCDR3 are selected from SEQ ID NO: 64, SEQ ID NO: 65, and SEQ ID NO: 71, respectively, from SEQ ID NO: 64, SEQ ID NO: 65, and SEQ ID NO: 71, respectively, or from SEQ ID NO: 133, SEQ ID NO: 134, and SEQ ID NO: 71 respectively.

In some embodiments, an antibody or antigen-binding fragment thereof is provided, wherein the HCDR1, HCDR2, and HCDR3 are selected from SEQ ID NO: 61, SEQ ID NO: 62, and SEQ ID NO: 74, respectively, from SEQ ID NO: 124, SEQ ID NO: 125, and SEQ ID NO: 74, respectively, or from SEQ ID NO: 130, SEQ ID NO: 131, and SEQ ID NO: 140, respectively, and the LCDR1, LCDR2, and LCDR3 are selected from SEQ ID NO: 64, SEQ ID NO: 65, and SEQ ID NO: 75, respectively, from SEQ ID NO: 64, SEQ ID NO: 65, and SEQ ID NO: 75, respectively, or from SEQ ID NO: 133, SEQ ID NO: 134, and SEQ ID NO: 75 respectively.

In some embodiments, an antibody or antigen-binding fragment thereof is provided, wherein the HCDR1, HCDR2, and HCDR3 are selected from SEQ ID NO: 61, SEQ ID NO: 62, and SEQ ID NO: 76, respectively, from SEQ ID NO: 124, SEQ ID NO: 125, and SEQ ID NO: 76, respectively, or from SEQ ID NO: 130, SEQ ID NO: 131, and SEQ ID NO: 141, respectively, and the LCDR1, LCDR2, and LCDR3 are selected from SEQ ID NO: 64, SEQ ID NO: 65, and SEQ ID NO: 77, respectively, from SEQ ID NO: 64, SEQ ID NO: 65, and SEQ ID NO: 77, respectively, or from SEQ ID NO: 133, SEQ ID NO: 134, and SEQ ID NO: 77 respectively.

In some embodiments, an antibody or antigen-binding fragment thereof is provided, wherein the HCDR1, HCDR2, and HCDR3 are selected from SEQ ID NO: 61, SEQ ID NO: 62, and SEQ ID NO: 78, respectively, from SEQ ID NO: 124, SEQ ID NO: 125, and SEQ ID NO: 78, respectively, or from SEQ ID NO: 130, SEQ ID NO: 131, and SEQ ID NO: 142, respectively, and the LCDR1, LCDR2, and LCDR3 are selected from SEQ ID NO: 64, SEQ ID NO: 65, and SEQ ID NO: 79, respectively, from SEQ ID NO: 64, SEQ ID NO: 65, and SEQ ID NO: 79, respectively, or from SEQ ID NO: 133, SEQ ID NO: 134, and SEQ ID NO: 79 respectively.

In some embodiments, an antibody or antigen-binding fragment thereof is provided, wherein the HCDR1, HCDR2, and HCDR3 are selected from SEQ ID NO: 61, SEQ ID NO: 62, and SEQ ID NO: 80, respectively, from SEQ ID NO: 124, SEQ ID NO: 125, and SEQ ID NO: 80, respectively, or from SEQ ID NO: 130, SEQ ID NO: 131, and SEQ ID NO: 143, respectively, and the LCDR1, LCDR2, and LCDR3 are selected from SEQ ID NO: 64, SEQ ID NO: 65, and SEQ ID NO: 81, respectively, from SEQ ID NO: 64, SEQ ID NO: 65, and SEQ ID NO: 81, respectively, or from SEQ ID NO: 133, SEQ ID NO: 134, and SEQ ID NO: 81 respectively.

In some embodiments, an antibody or antigen-binding fragment thereof is provided, wherein the HCDR1, HCDR2, and HCDR3 are selected from SEQ ID NO: 82, SEQ ID NO: 83, and SEQ ID NO: 84, respectively, from SEQ ID NO: 126, SEQ ID NO: 127, and SEQ ID NO: 84, respectively, or from SEQ ID NO: 144, SEQ ID NO: 145, and SEQ ID NO: 146, respectively, and the LCDR1, LCDR2, and LCDR3 are selected from SEQ ID NO: 85, SEQ ID NO: 86, and SEQ ID NO: 87, respectively, from SEQ ID NO: 85, SEQ ID NO: 86, and SEQ ID NO: 87, respectively, or from SEQ ID NO: 147, SEQ ID NO: 148, and SEQ ID NO: 87 respectively.

In some embodiments, an antibody or antigen-binding fragment thereof is provided, wherein the HCDR1, HCDR2, and HCDR3 are selected from SEQ ID NO: 82, SEQ ID NO: 83, and SEQ ID NO: 88, respectively, from SEQ ID NO: 126, SEQ ID NO: 127, and SEQ ID NO: 88, respectively, or from SEQ ID NO: 144, SEQ ID NO: 145, and SEQ ID NO: 149, respectively, and the LCDR1, LCDR2, and LCDR3 are selected from SEQ ID NO: 85, SEQ ID NO: 86, and SEQ ID NO: 89, respectively, from SEQ ID NO: 85, SEQ ID NO: 86, and SEQ ID NO: 89, respectively, or from SEQ ID NO: 147, SEQ ID NO: 148, and SEQ ID NO: 89 respectively.

In some embodiments, an antibody or antigen-binding fragment thereof is provided, wherein the HCDR1, HCDR2, and HCDR3 are selected from SEQ ID NO: 82, SEQ ID NO: 83, and SEQ ID NO: 90, respectively, from SEQ ID NO: 126, SEQ ID NO: 127, and SEQ ID NO: 90, respectively, or from SEQ ID NO: 144, SEQ ID NO: 145, and SEQ ID NO: 150, respectively, and the LCDR1, LCDR2, and LCDR3 are selected from SEQ ID NO: 85, SEQ ID NO: 86, and SEQ ID NO: 89, respectively, from SEQ ID NO: 85, SEQ ID NO: 86, and SEQ ID NO: 89, respectively, or from SEQ ID NO: 147, SEQ ID NO: 148, and SEQ ID NO: 89 respectively.

In some embodiments, an antibody or antigen-binding fragment thereof is provided, wherein the HCDR1, HCDR2, and HCDR3 are selected from SEQ ID NO: 82, SEQ ID NO: 83, and SEQ ID NO: 91, respectively, from SEQ ID NO: 126, SEQ ID NO: 127, and SEQ ID NO: 91, respectively, or from SEQ ID NO: 144, SEQ ID NO: 145, and SEQ ID NO: 151, respectively, and the LCDR1, LCDR2, and LCDR3 are selected from SEQ ID NO: 85, SEQ ID NO: 86, and SEQ ID NO: 92, respectively, from SEQ ID NO: 85, SEQ ID NO: 86, and SEQ ID NO: 92, respectively, or from SEQ ID NO: 147, SEQ ID NO: 148, and SEQ ID NO: 92 respectively.

In some embodiments, an antibody or antigen-binding fragment thereof is provided, wherein the HCDR1, HCDR2, and HCDR3 are selected from SEQ ID NO: 82, SEQ ID NO: 83, and SEQ ID NO: 93, respectively, from SEQ ID NO: 126, SEQ ID NO: 127, and SEQ ID NO: 93, respectively, or from SEQ ID NO: 144, SEQ ID NO: 145, and SEQ ID NO: 152, respectively, and the LCDR1, LCDR2, and LCDR3 are selected from SEQ ID NO: 85, SEQ ID NO: 86, and SEQ ID NO: 94, respectively, from SEQ ID NO: 85, SEQ ID NO: 86, and SEQ ID NO: 94, respectively, or from SEQ ID NO: 147, SEQ ID NO: 148, and SEQ ID NO: 94 respectively.

In some embodiments, an antibody or antigen-binding fragment thereof is provided, wherein the HCDR1, HCDR2, and HCDR3 are selected from SEQ ID NO: 82, SEQ ID NO: 83, and SEQ ID NO: 84, respectively, from SEQ ID NO: 126, SEQ ID NO: 127, and SEQ ID NO: 84, respectively, or from SEQ ID NO: 144, SEQ ID NO: 145, and SEQ ID NO: 146, respectively, and the LCDR1, LCDR2, and LCDR3 are selected from SEQ ID NO: 85, SEQ ID NO: 86, and SEQ ID NO: 95, respectively, from SEQ ID NO: 85, SEQ ID NO: 86, and SEQ ID NO: 95, respectively, or from SEQ ID NO: 147, SEQ ID NO: 148, and SEQ ID NO: 95 respectively.

In some embodiments, an antibody or antigen-binding fragment thereof is provided, wherein the HCDR1, HCDR2, and HCDR3 are selected from SEQ ID NO: 82, SEQ ID NO: 83, and SEQ ID NO: 96, respectively, from SEQ ID NO: 126, SEQ ID NO: 127, and SEQ ID NO: 96, respectively, or from SEQ ID NO: 144, SEQ ID NO: 145, and SEQ ID NO: 153, respectively, and the LCDR1, LCDR2, and LCDR3 are selected from SEQ ID NO: 85, SEQ ID NO: 86, and SEQ ID NO: 97, respectively, from SEQ ID NO: 85, SEQ ID NO: 86, and SEQ ID NO: 97, respectively, or from SEQ ID NO: 147, SEQ ID NO: 148, and SEQ ID NO: 97 respectively.

In some embodiments, an antibody or antigen-binding fragment thereof is provided, wherein the HCDR1, HCDR2, and HCDR3 are selected from SEQ ID NO: 82, SEQ ID NO: 83, and SEQ ID NO: 98, respectively, from SEQ ID NO: 126, SEQ ID NO: 127, and SEQ ID NO: 98, respectively, or from SEQ ID NO: 144, SEQ ID NO: 145, and SEQ ID NO: 154, respectively, and the LCDR1, LCDR2, and LCDR3 are selected from SEQ ID NO: 85, SEQ ID NO: 86, and SEQ ID NO: 99, respectively, from SEQ ID NO: 85, SEQ ID NO: 86, and SEQ ID NO: 99, respectively, or from SEQ ID NO: 147, SEQ ID NO: 148, and SEQ ID NO: 99 respectively.

In some embodiments, an antibody or antigen-binding fragment thereof is provided, wherein the HCDR1, HCDR2, and HCDR3 are selected from SEQ ID NO: 82, SEQ ID NO: 83, and SEQ ID NO: 100, respectively, from SEQ ID NO: 126, SEQ ID NO: 127, and SEQ ID NO: 100, respectively, or from SEQ ID NO: 144, SEQ ID NO: 145, and SEQ ID NO: 155, respectively, and the LCDR1, LCDR2, and LCDR3 are selected from SEQ ID NO: 85, SEQ ID NO: 86, and SEQ ID NO: 101, respectively, from SEQ ID NO: 85, SEQ ID NO: 86, and SEQ ID NO: 101, respectively, or from SEQ ID NO: 147, SEQ ID NO: 148, and SEQ ID NO: 101 respectively.

In some embodiments, an antibody or antigen-binding fragment thereof is provided, wherein the HCDR1, HCDR2, and HCDR3 are selected from SEQ ID NO: 82, SEQ ID NO: 83, and SEQ ID NO: 100, respectively, from SEQ ID NO: 126, SEQ ID NO: 127, and SEQ ID NO: 100, respectively, or from SEQ ID NO: 144, SEQ ID NO: 145, and SEQ ID NO: 155, respectively, and the LCDR1, LCDR2, and LCDR3 are selected from SEQ ID NO: 85, SEQ ID NO: 86, and SEQ ID NO: 102, respectively, from SEQ ID NO: 85, SEQ ID NO: 86, and SEQ ID NO: 102, respectively, or from SEQ ID NO: 147, SEQ ID NO: 148, and SEQ ID NO: 102 respectively.

In some embodiments, an antibody or antigen-binding fragment thereof is provided, wherein the HCDR1, HCDR2, and HCDR3 are selected from SEQ ID NO: 103, SEQ ID NO: 104, and SEQ ID NO: 105, respectively, from SEQ ID NO: 128, SEQ ID NO: 129, and SEQ ID NO: 105, respectively, or from SEQ ID NO: 156, SEQ ID NO: 157, and SEQ ID NO: 158, respectively, and the LCDR1, LCDR2, and LCDR3 are selected from SEQ ID NO: 106, SEQ ID NO: 107, and SEQ ID NO: 108, respectively, from SEQ ID NO: 106, SEQ ID NO: 107, and SEQ ID NO: 108, respectively, or from SEQ ID NO: 159, SEQ ID NO: 160, and SEQ ID NO: 108 respectively.

In some embodiments, an antibody or antigen-binding fragment thereof is provided, wherein the HCDR1, HCDR2, and HCDR3 are selected from SEQ ID NO: 103, SEQ ID NO: 104, and SEQ ID NO: 109, respectively, from SEQ ID NO: 128, SEQ ID NO: 129, and SEQ ID NO: 109, respectively, or from SEQ ID NO: 156, SEQ ID NO: 157, and SEQ ID NO: 161, respectively, and the LCDR1, LCDR2, and LCDR3 are selected from SEQ ID NO: 106, SEQ ID NO: 107, and SEQ ID NO: 110, respectively, from SEQ ID NO: 106, SEQ ID NO: 107, and SEQ ID NO: 110, respectively, or from SEQ ID NO: 159, SEQ ID NO: 160, and SEQ ID NO: 110 respectively.

In some embodiments, an antibody or antigen-binding fragment thereof is provided, wherein the HCDR1, HCDR2, and HCDR3 are selected from SEQ ID NO: 103, SEQ ID NO: 104, and SEQ ID NO: 111, respectively, from SEQ ID NO: 128, SEQ ID NO: 129, and SEQ ID NO: 111, respectively, or from SEQ ID NO: 156, SEQ ID NO: 157, and SEQ ID NO: 162, respectively, and the LCDR1, LCDR2, and LCDR3 are selected from SEQ ID NO: 106, SEQ ID NO: 107, and SEQ ID NO: 112, respectively, from SEQ ID NO: 106, SEQ ID NO: 107, and SEQ ID NO: 112, respectively, or from SEQ ID NO: 159, SEQ ID NO: 160, and SEQ ID NO: 112 respectively.

In some embodiments, an antibody or antigen-binding fragment thereof is provided, wherein the HCDR1, HCDR2, and HCDR3 are selected from SEQ ID NO: 103, SEQ ID NO: 104, and SEQ ID NO: 105, respectively, from SEQ ID NO: 128, SEQ ID NO: 129, and SEQ ID NO: 105, respectively, or from SEQ ID NO: 156, SEQ ID NO: 157, and SEQ ID NO: 158, respectively, and the LCDR1, LCDR2, and LCDR3 are selected from SEQ ID NO: 106, SEQ ID NO: 107, and SEQ ID NO: 113, respectively, from SEQ ID NO: 106, SEQ ID NO: 107, and SEQ ID NO: 113, respectively, or from SEQ ID NO: 159, SEQ ID NO: 160, and SEQ ID NO: 113 respectively.

In some embodiments, an antibody or antigen-binding fragment thereof is provided, wherein the HCDR1, HCDR2, and HCDR3 are selected from SEQ ID NO: 103, SEQ ID NO: 104, and SEQ ID NO: 114, respectively, from SEQ ID NO: 128, SEQ ID NO: 129, and SEQ ID NO: 114, respectively, or from SEQ ID NO: 156, SEQ ID NO: 157, and SEQ ID NO: 163, respectively, and the LCDR1, LCDR2, and LCDR3 are selected from SEQ ID NO: 106, SEQ ID NO: 107, and SEQ ID NO: 115, respectively, from SEQ ID NO: 106, SEQ ID NO: 107, and SEQ ID NO: 115, respectively, or from SEQ ID NO: 159, SEQ ID NO: 160, and SEQ ID NO: 115 respectively.

In some embodiments, an antibody or antigen-binding fragment thereof is provided, wherein the HCDR1, HCDR2, and HCDR3 are selected from SEQ ID NO: 103, SEQ ID NO: 104, and SEQ ID NO: 116, respectively, from SEQ ID NO: 128, SEQ ID NO: 129, and SEQ ID NO: 116, respectively, or from SEQ ID NO: 156, SEQ ID NO: 157, and SEQ ID NO: 164, respectively, and the LCDR1, LCDR2, and LCDR3 are selected from SEQ ID NO: 106, SEQ ID NO: 107, and SEQ ID NO: 113, respectively, from SEQ ID NO: 106, SEQ ID NO: 107, and SEQ ID NO: 113, respectively, or from SEQ ID NO: 159, SEQ ID NO: 160, and SEQ ID NO: 113 respectively.

In some embodiments, an antibody or antigen-binding fragment thereof is provided, wherein the HCDR1, HCDR2, and HCDR3 are selected from SEQ ID NO: 103, SEQ ID NO: 104, and SEQ ID NO: 117, respectively, from SEQ ID NO: 128, SEQ ID NO: 129, and SEQ ID NO: 117, respectively, or from SEQ ID NO: 156, SEQ ID NO: 157, and SEQ ID NO: 165, respectively, and the LCDR1, LCDR2, and LCDR3 are selected from SEQ ID NO: 106, SEQ ID NO: 107, and SEQ ID NO: 118, respectively, from SEQ ID NO: 106, SEQ ID NO: 107, and SEQ ID NO: 118, respectively, or from SEQ ID NO: 159, SEQ ID NO: 160, and SEQ ID NO: 118 respectively.

In some embodiments, an antibody or antigen-binding fragment thereof is provided, wherein the HCDR1, HCDR2, and HCDR3 are selected from SEQ ID NO: 103, SEQ ID NO: 104, and SEQ ID NO: 116, respectively, from SEQ ID NO: 128, SEQ ID NO: 129, and SEQ ID NO: 116, respectively, or from SEQ ID NO: 156, SEQ ID NO: 157, and SEQ ID NO: 164, respectively, and the LCDR1, LCDR2, and LCDR3 are selected from SEQ ID NO: 106, SEQ ID NO: 107, and SEQ ID NO: 119, respectively, from SEQ ID NO: 106, SEQ ID NO: 107, and SEQ ID NO: 119, respectively, or from SEQ ID NO: 159, SEQ ID NO: 160, and SEQ ID NO: 119 respectively.

In some embodiments, an antibody or antigen-binding fragment thereof is provided, wherein the HCDR1, HCDR2, and HCDR3 are selected from SEQ ID NO: 103, SEQ ID NO: 104, and SEQ ID NO: 120, respectively, from SEQ ID NO: 128, SEQ ID NO: 129, and SEQ ID NO: 120, respectively, or from SEQ ID NO: 156, SEQ ID NO: 157, and SEQ ID NO: 166, respectively, and the LCDR1, LCDR2, and LCDR3 are selected from SEQ ID NO: 106, SEQ ID NO: 107, and SEQ ID NO: 121, respectively, from SEQ ID NO: 106, SEQ ID NO: 107, and SEQ ID NO: 121, respectively, or from SEQ ID NO: 159, SEQ ID NO: 160, and SEQ ID NO: 121 respectively.

In some embodiments, an antibody or antigen-binding fragment thereof is provided, wherein the HCDR1, HCDR2, and HCDR3 are selected from SEQ ID NO: 103, SEQ ID NO: 104, and SEQ ID NO: 122, respectively, from SEQ ID NO: 128, SEQ ID NO: 129, and SEQ ID NO: 122, respectively, or from SEQ ID NO: 156, SEQ ID NO: 157, and SEQ ID NO: 167, respectively, and the LCDR1, LCDR2, and LCDR3 are selected from SEQ ID NO: 106, SEQ ID NO: 107, and SEQ ID NO: 123, respectively, from SEQ ID NO: 106, SEQ ID NO: 107, and SEQ ID NO: 123, respectively, or from SEQ ID NO: 159, SEQ ID NO: 160, and SEQ ID NO: 123 respectively.

In some embodiments, the antibody comprises a heavy chain variable region peptide having one of the following sequences, or a variant thereof:

TABLE 5

| SEQ ID NO: | AB ID NO. | VH Sequence |
|---|---|---|
| 1 | MAB1 | QVQLVESGGGLVKPGGSLRLSCAASGFTFSDYYMSWIRQAPGKGLEWVSYISRSGSTKYYADSVKGRFTISRDNAKNSLYLQMNSLRAEDTAVYYCARDQEDYALDYWGQGTLVTVSS |
| 3 | MAB2 | QVQLVESGGGLVKPGGSLRLSCAASGFTFSDYYMSWIRQAPGKGLEWVSYISRSGSTKYYADSVKGRFTISRDNAKNSLYLQMNSLRAEDTAVYYCARDETDYGWDYWGQGTLVTVSS |
| 5 | MAB3 | QVQLVESGGGLVKPGGSLRLSCAASGFTFSDYYMSWIRQAPGKGLEWVSYISRSGSTKYYADSVKGRFTISRDNAKNSLYLQMNSLRAEDTAVYYCARDETDYAFDEWGQGTLVTVSS |
| 7 | MAB4 | QVQLVESGGGLVKPGGSLRLSCAASGFTFSDYYMSWIRQAPGKGLEWVSYISRSGSTKYYADSVKGRFTISRDNAKNSLYLQMNSLRAEDTAVYYCARDESQYALDYWGQGTLVTVSS |
| 9 | MAB5 | QVQLVESGGGLVKPGGSLRLSCAASGFTFSDYYMSWIRQAPGKGLEWVSYISRSGSTKYYAHSVKGRFTISRDNAKNSLYLQMNSLRAEDTAVYYCARDNTDYALDLWGQGTLVTVSS |
| 11 | MAB6 | QVQLVESGGGLVKPGGSLRLSCAASGFTFSDYYMSWIRQAPGKGLEWVSYISRSGSTKYYAHSVKGRFTISRDNAKNSLYLQMNSLRAEDTAVYYCARDETDYAYDEWGQGTLVTVSS |
| 13 | MAB7 | QVQLVESGGGLVKPGGSLRLSCAASGFTFSDYYMSWIRQAPGKGLEWVSYISRSGSTKYYADSVKGRFTISRDNAKNSLYLQMNSLRAEDTAVYYCARDETDYAYDNWGQGTLVTVSS |
| 15 | MAB8 | QVQLVESGGGLVKPGGSLRLSCAASGFTFSDYYMSWIRQAPGKGLEWVSYISRSGSTKYYADSVKGRFTISRDNAKNSLYLQMNSLRAEDTAVYYCARDESDYAYDYWGQGTLVTVSS |
| 17 | MAB9 | QVQLVESGGGLVKPGGSLRLSCAASGFTFSDYYMSWIRQAPGKGLEWVSYISRSGSTKYYADSVKGRFTISRDNAKNSLYLQMNSLRAEDTAVYYCARDENYALDWWGQGTLVTVSS |
| 19 | MAB10 | QVQLVESGGGLVKPGGSLRLSCAASGFTFSDYYMSWIRQAPGKGLEWVSYISRSGSTKYYADSVKGRFTISRDNAKNSLYLQMNSLRAEDTAVYYCARDESDYALDFWGQGTLVTVSS |

TABLE 5-continued

| SEQ ID NO: | AB ID NO. | VH Sequence |
|---|---|---|
| 21 | MAB11 | QVQLVQSGAEVKKPGASVKVSCKVSGDTLTELSMHWVRQ APGKGLEWMGTFDPEEGETIYAQKFQGRVTMTEDTSTDTA YMELSSLRSEDTAVYYCVTEGLAGVPFDLWGQGTLVTVSS |
| 23 | MAB12 | QVQLVQSGAEVKKPGASVKVSCKVSGDTLTELSMHWVRQ APGKGLEWMGTFDPEEGETIYAQKFQGRVTMTEDTSTDTA YMELSSLRSEDTAVYYCVTEGLGGRPFDHWGQGTLVTVSS |
| 25 | MAB13 | QVQLVQSGAEVKKPGASVKVSCKVSGDTLTELSMHWVRQ APGKGLEWMGTFDPEEGETIYAQKFQGRVTMTEDTSTDTA YMELSSLRSEDTAVYYCVTEGLAGFPFDIWGQGTLVTVSS |
| 27 | MAB14 | QVQLVQSGAEVKKPGASVKVSCKVSGDTLTELSMHWVRQ APGKGLEWMGTFDPEEGETIYAQKFQGRVTMTEDTSTDTA YMELSSLRSEDTAVYYCVTEGLAWRPTDSWGQGTLVTVSS |
| 29 | MAB15 | QVQLVQSGAEVKKPGASVKVSCKVSGDTLTELSMHWVRQ APGKGLEWMGTFDPEEGETIYAQKFQGRVTMTEDTSTDTA YMELSSLRSEDTAVYYCVTKGLAWLPYYSWGQGTLVTVSS |
| 31 | MAB16 | QVQLVQSGAEVKKPGASVKVSCKVSGDTLTELSMHWVRQ APGKGLEWMGTFDPEEGETIYAQKFQGRVTMTEDTSTDTA YMELSSLRSEDTAVYYCVTEGLAGVPFDLWGQGTLVTVSS |
| 33 | MAB17 | QVQLVQSGAEVKKPGASVKVSCKVSGDTLTELSMHWVRQ APGKGLEWMGTFDPEEGETIYAQKFQGRVTMTEDTSTDTA YMELSSLRSEDTAVYYCVTEGEAGRPFDAWGQGTLVTVSS |
| 35 | MAB18 | QVQLVQSGAEVKKPGASVKVSCKVSGDTLTELSMHWVRQ APGKGLEWMGTFDPEEGETIYAQKFQGRVTMTEDTSTDTA YMELSSLRSEDTAVYYCVTEGLAGRPYDVWGQGTLVTVSS |
| 37 | MAB19 | QVQLVQSGAEVKKPGASVKVSCKVSGDTLTELSMHWVRQ APGKGLEWMGTFDPEEGETIYAQKFQGRVTMTEDTSTDTA YMELSYLRSEDTAVYYCVTEGLAGIPFDSWGQGTLVTVSS |
| 39 | MAB20 | QVQLVQSGAEVKKPGASVKVSCKVSGDTLTELSMHWVRQ APGKGLEWMGTFDPEEGETIYAQKFQGRVTMTEDTSTDTA YMELSYLRSEDTAVYYCVTEGLAGIPFDSWGQGTLVTVSS |
| 41 | MAB21 | EVQLVESGGGVVRPGGSLRLSCAASGFTFDDYGMSWVRQA PGKGLEWVSGINWEGGSTGYADSVKGRFTISRDNAKNSLYL QMNSLRAEDTALYYCARDEQLGGTTYYYYYMDVWGKGTT VTVSS |
| 43 | MAB22 | EVQLVESGGGVVRPGGSLRLSCAASGFTFDDYGMSWVRQA PGKGLEWVSGINWEGGSTGYADSVKGRFTISRDNAKNSLYL QMNSLRAEDTALYYCARDEQLGGKYYYYYMDVWGKGT TVTVSS |
| 45 | MAB23 | EVQLVESGGGVVRPGGSLRLSCAASGFTFDDYGMSWVRQA PGKGLEWVSGINWEGGSTGYADSVKGRFTISRDNAKNSLYL QMNSLRAEDTALYYCARDEQLGGQTYYYYYMDVWGKGT TVTVSS |
| 47 | MAB24 | EVQLVESGGGVVRPGGSLRLSCAASGFTFDDYGMSWVRQA PGKGLEWVSGINWEGGSTGYADSVKGRFTISRDNAKNSLYL QMNSLRAEDTALYYCARDEQLGGTTYYYYYMDVWGKGTT VTVSS |
| 49 | MAB25 | EVQLVESGGGVVRPGGSLRLSCAASGFTFDDYGMSWVRQA PGKGLEWVSGINWEGGSTGYADSVKGRFTISRDNAKNSLYL QMNSLRAEDTALYYCARDEQLGGIKYYYYYMDVWGKGTT VTVSS |
| 51 | MAB26 | EVQLVESGGGVVRPGGSLRLSCAASGFTFDDYGMSWVRQA PGKGLEWVSGINWEGGSTGYADSVKGRFSISRDNAKNSLYL QMNSLRAEDTALYYCARDEQLGGLKYYYYYMDVWGKGT TVTVSS |
| 53 | MAB27 | EVQLVESGGGVVRPGGSLRLSCAASGFTFDDYGMSWVRQA PGKGLEWVSGINWEGGSTGYADSVKGRFTISRDNAKNSLYL QMNSLRAEDTALYYCARDEQLGGKVYYYYYMDVWGKGT TVTVSS |

TABLE 5-continued

| SEQ ID NO: | AB ID NO. | VH Sequence |
|---|---|---|
| 55 | MAB28 | EVQLVESGGGVVRPGGSLRLSCAASGFTFDDYGMSWVRQA PGKGLEWVSGINWEGGSTGYADSVKGRFSISRDNAKNSLYL QMNSLRAEDTALYYCARDEQLGGLKYYYYYMDVWGKGT TVTVSS |
| 57 | MAB29 | EVQLVESGGGVVRPGGSLRLSCAASGFTFDDYGMSWVRQA PGKGLEWVSGINWEGGSTGYADSVKGRFTISRDNAKNSLYL QMNSLRAEDTALYYCARDEQLGGNHYYYYYMDAWGKGT TVTVSS |
| 59 | MAB30 | EVQLVESGGGVVRPGGSLRLSCAASGFTFDDYGMSWVRQA PGKGLEWVSGINWEGGSTGYADSVKGRFTISRDNAKNSLYL QMNSLRAEDTALYYCARDEQLGGRHYYYYYMDVWGKGT TVTVSS |
| 334 | MAB31 | EVQLVESGGGLVKPGGSLRLSCAASGFTFSDYYMSWIRQAP GKGLEWVSYISRSGSTKYYADSVKGRFTISRDNAKNSLYLQ MNSLRAEDTAVYYCARDQEDYALDYWGQGTLVTVSS |
| 335 | MAB32 | EVQLVESGGGLVKPGGSLRLSCAASGFTFSDYYMSWIRQAP GKGLEWVSYISRSGSTKYYADSVKGRFTISRDNAKNSLYLQ MNSLRAEDTAVYYCARDETDYGWDYWGQGTLVTVSS |
| 336 | MAB33 | EVQLVESGGGLVKPGGSLRLSCAASGFTFSDYYMSWIRQAP GKGLEWVSYISRSGSTKYYADSVKGRFTISRDNAKNSLYLQ MNSLRAEDTAVYYCARDETDYAFDEWGQGTLVTVSS |
| 337 | MAB34 | EVQLVESGGGLVKPGGSLRLSCAASGFTFSDYYMSWIRQAP GKGLEWVSYISRSGSTKYYADSVKGRFTISRDNAKNSLYLQ MNSLRAEDTAVYYCARDESQYALDYWGQGTLVTVSS |
| 338 | MAB35 | EVQLVESGGGLVKPGGSLRLSCAASGFTFSDYYMSWIRQAP GKGLEWVSYISRSGSTKYYAHSVKGRFTISRDNAKNSLYLQ MNSLRAEDTAVYYCARDNTDYALDLWGQGTLVTVSS |
| 339 | MAB36 | EVQLVESGGGLVKPGGSLRLSCAASGFTFSDYYMSWIRQAP GKGLEWVSYISRSGSTKYYAHSVKGRFTISRDNAKNSLYLQ MNSLRAEDTAVYYCARDETDYAYDEWGQGTLVTVSS |
| 340 | MAB37 | EVQLVESGGGLVKPGGSLRLSCAASGFTFSDYYMSWIRQAP GKGLEWVSYISRSGSTKYYADSVKGRFTISRDNAKNSLYLQ MNSLRAEDTAVYYCARDETDYAYDNWGQGTLVTVSS |
| 341 | MAB38 | EVQLVESGGGLVKPGGSLRLSCAASGFTFSDYYMSWIRQAP GKGLEWVSYISRSGSTKYYADSVKGRFTISRDNAKNSLYLQ MNSLRAEDTAVYYCARDESDYAYDYWGQGTLVTVSS |
| 342 | MAB39 | EVQLVESGGGLVKPGGSLRLSCAASGFTFSDYYMSWIRQAP GKGLEWVSYISRSGSTKYYADSVKGRFTISRDNAKNSLYLQ MNSLRAEDTAVYYCARDENYALDWWGQGTLVTVSS |
| 343 | MAB40 | EVQLVESGGGLVKPGGSLRLSCAASGFTFSDYYMSWIRQAP GKGLEWVSYISRSGSTKYYADSVKGRFTISRDNAKNSLYLQ MNSLRAEDTAVYYCARDESDYALDFWGQGTLVTVSS |
| 344 | MAB41 | EVQLVQSGAEVKKPGASVKVSCKVSGDTLTELSMHWVRQA PGKGLEWMGTFDPEEGETIYAQKFQGRVTMTEDTSTDTAY MELSSLRSEDTAVYYCVTEGLAGVPFDLWGQGTLVTVSS |
| 345 | MAB42 | EVQLVQSGAEVKKPGASVKVSCKVSGDTLTELSMHWVRQA PGKGLEWMGTFDPEEGETIYAQKFQGRVTMTEDTSTDTAY MELSSLRSEDTAVYYCVTEGLGGRPFDHWGQGTLVTVSS |
| 346 | MAB43 | EVQLVQSGAEVKKPGASVKVSCKVSGDTLTELSMHWVRQA PGKGLEWMGTFDPEEGETIYAQKFQGRVTMTEDTSTDTAY MELSSLRSEDTAVYYCVTEGLAGFPFDIWGQGTLVTVSS |
| 347 | MAB44 | EVQLVQSGAEVKKPGASVKVSCKVSGDTLTELSMHWVRQA PGKGLEWMGTFDPEEGETIYAQKFQGRVTMTEDTSTDTAY MELSSLRSEDTAVYYCVTEGLAWRPTDSWGQGTLVTVSS |
| 348 | MAB45 | EVQLVQSGAEVKKPGASVKVSCKVSGDTLTELSMHWVRQA PGKGLEWMGTFDPEEGETIYAQKFQGRVTMTEDTSTDTAY MELSSLRSEDTAVYYCVTKGLAWLPYYSWGQGTLVTVSS |

TABLE 5-continued

| SEQ ID NO: | AB ID NO. | VH Sequence |
|---|---|---|
| 349 | MAB46 | EVQLVQSGAEVKKPGASVKVSCKVSGDTLTELSMHWVRQAPGKGLEWMGTFDPEEGETIYAQKFQGRVTMTEDTSTDTAYMELSSLRSEDTAVYYCVTEGLAGVPFDLWGQGTLVTVSS |
| 350 | MAB47 | EVQLVQSGAEVKKPGASVKVSCKVSGDTLTELSMHWVRQAPGKGLEWMGTFDPEEGETIYAQKFQGRVTMTEDTSTDTAYMELSSLRSEDTAVYYCVTEGEAGRPFDAWGQGTLVTVSS |
| 351 | MAB48 | EVQLVQSGAEVKKPGASVKVSCKVSGDTLTELSMHWVRQAPGKGLEWMGTFDPEEGETIYAQKFQGRVTMTEDTSTDTAYMELSSLRSEDTAVYYCVTEGLAGRPYDVWGQGTLVTVSS |
| 352 | MAB49 | EVQLVQSGAEVKKPGASVKVSCKVSGDTLTELSMHWVRQAPGKGLEWMGTFDPEEGETIYAQKFQGRVTMTEDTSTDTAYMELSYLRSEDTAVYYCVTEGLAGIPFDSWGQGTLVTVSS |
| 353 | MAB50 | EVQLVQSGAEVKKPGASVKVSCKVSGDTLTELSMHWVRQAPGKGLEWMGTFDPEEGETIYAQKFQGRVTMTEDTSTDTAYMELSYLRSEDTAVYYCVTEGLAGIPFDSWGQGTLVTVSS |
| 354 | MAB51 | EVQLVESGGGVVRPGGSLRLSCAASGFTFDDYGMSWVRQAPGKGLEWVSGINWEGGSTGYADSVKGRFTISRDNAKNSLYLQMNSLRAEDTALYYCARDEQLGGTTYYYYYMDVWGKGTTVTVSS |
| 355 | MAB52 | QVQLVESGGGVVRPGGSLRLSCAASGFTFDDYGMSWVRQAPGKGLEWVSGINWEGGSTGYADSVKGRFTISRDNAKNSLYLQMNSLRAEDTALYYCARDEQLGGKYYYYYMDVWGKGTTVTVSS |
| 356 | MAB53 | QVQLVESGGGVVRPGGSLRLSCAASGFTFDDYGMSWVRQAPGKGLEWVSGINWEGGSTGYADSVKGRFTISRDNAKNSLYLQMNSLRAEDTALYYCARDEQLGGQTYYYYYMDVWGKGTTVTVSS |
| 357 | MAB54 | QVQLVESGGGVVRPGGSLRLSCAASGFTFDDYGMSWVRQAPGKGLEWVSGINWEGGSTGYADSVKGRFTISRDNAKNSLYLQMNSLRAEDTALYYCARDEQLGGTTYYYYYMDVWGKGTTVTVSS |
| 358 | MAB55 | QVQLVESGGGVVRPGGSLRLSCAASGFTFDDYGMSWVRQAPGKGLEWVSGINWEGGSTGYADSVKGRFTISRDNAKNSLYLQMNSLRAEDTALYYCARDEQLGGIKYYYYYMDVWGKGTTVTVSS |
| 359 | MAB56 | QVQLVESGGGVVRPGGSLRLSCAASGFTFDDYGMSWVRQAPGKGLEWVSGINWEGGSTGYADSVKGRFSISRDNAKNSLYLQMNSLRAEDTALYYCARDEQLGGLKYYYYYMDVWGKGTTVTVSS |
| 360 | MAB57 | QVQLVESGGGVVRPGGSLRLSCAASGFTFDDYGMSWVRQAPGKGLEWVSGINWEGGSTGYADSVKGRFTISRDNAKNSLYLQMNSLRAEDTALYYCARDEQLGGKVYYYYYMDVWGKGTTVTVSS |
| 361 | MAB58 | QVQLVESGGGVVRPGGSLRLSCAASGFTFDDYGMSWVRQAPGKGLEWVSGINWEGGSTGYADSVKGRFSISRDNAKNSLYLQMNSLRAEDTALYYCARDEQLGGLKYYYYYMDVWGKGTTVTVSS |
| 362 | MAB59 | QVQLVESGGGVVRPGGSLRLSCAASGFTFDDYGMSWVRQAPGKGLEWVSGINWEGGSTGYADSVKGRFTISRDNAKNSLYLQMNSLRAEDTALYYCARDEQLGGNHYYYYYMDAWGKGTTVTVSS |
| 363 | MAB60 | QVQLVESGGGVVRPGGSLRLSCAASGFTFDDYGMSWVRQAPGKGLEWVSGINWEGGSTGYADSVKGRFTISRDNAKNSLYLQMNSLRAEDTALYYCARDEQLGGRHYYYYYMDVWGKGTTVTVSS |

In some embodiments, the antibody comprises the heavy chain variable chain sequence of:

(SEQ ID NO: 454)
VQLVESGGGLVKPGGSLRLSCAASGFTFSDYYMSWIRQAPGKGLEWVSYI
SRSGSTKYYADSVKGRFTISRDNAKNSLYLQMNSLRAEDTAVYYCARDEN
YALDWWGQGTLVTVSS.

A heavy variable chain comprising this amino acid sequence can be paired with for example, the variable light chain comprising the amino acid sequence of SEQ ID NO 18 or the light chain of SEQ ID NO: 236. A variable heavy chain (VH) comprising the amino acid sequence of SEQ ID NO: 454 can be fused to a constant domain comprising a YTE or LS mutations as exemplified herein. For example, in some embodiments, the constant domain comprises the amino acid sequence of SEQ ID NO: 262 or SEQ ID NO: 261.

In some embodiments, the antibody comprises a heavy chain sequence of:

(SEQ ID NO: 455)
VQLVESGGGLVKPGGSLRLSCAASGFTFSDYYMSWIRQAPGKGLEWVSYI
SRSGSTKYYADSVKGRFTISRDNAKNSLYLQMNSLRAEDTAVYYCARDEN
YALDWWGQGTLVTVSSASTKGPSVFPLAPCSRSTSESTAALGCLVKDYFP
EPVTVSWNSGALTSGVHTFPAVLQSSGLYSLSSVVTVPSSSLGTKTYTCN
VDHKPSNTKVDKRVESKYGPPCPPCPAPEFEGGPSVFLFPPKPKDTLYIT
REPEVTCVVVDVSQEDPEVQFNWYVDGVEVHNAKTKPREEQFNSTYRVVS
VLTVLHQDWLNGKEYKCKVSNKGLPSSIEKTISKAKGQPREPQVYTLPPS
QEEMTKNQVSLTCLVKGFYPSDIAVEWESNGQPENNYKTTPPVLDSDGSF
FLYSRLTVDKSRWQEGNVFSCSVMHEALHNHYTQKSLSLSLG.

In some embodiments, the antibody comprises a light chain variable region peptide having one of the following sequences, or a variant thereof:

TABLE 6

| SEQ ID NO | AB ID NO. | VL Sequence |
| --- | --- | --- |
| 2 | MAB1/MAB31 | DIQMTQSPSSLSASVGDRVTITCQASQDISNYLNWYQQKPG KAPKLLIYDASNLETGVPSRFSGSGSGTDFTFTISSLQPEDIAT YYCEQYEDYPLTFGGGTKVEIK |
| 4 | MAB2/MAB32 | DIQMTQSPSSLSASVGDRVTITCQASQDISNYLNWYQQKPG KAPKLLIYDASNLETGVPSRFSGSGSGTDFTFTISSLQPEDIAT YYCKQYEDYPLTFGGGTKVEIK |
| 6 | MAB3/MAB 33 | DIQMTQSPSSLSASVGDRVTITCQASQDISNYLNWYQQKPG KAPKLLIYDASNLETGVPSRFSGSGSGTDFTFTISSLQPEDIAT YYCKQYEDYPLTFGGGTKVEIK |
| 8 | MAB4/MAB 34 | DIQMTQSPSSLSASVGDRVTITCQASQDISNYLNWYQQKPG KAPKLLIYDASNLETGVPSRFSGSGSGTDFTFTISSLQPEDIAT YYCHQYEDYPLTFGGGTKVEIK |
| 10 | MAB5/MAB 35 | DIQMTQSPSSLSASVGDRVTITCQASQDISNYLNWYQQKPG KAPKLLIYDASNLETGVPSRFSGSGSGTDFTFTISSLQPEDIAT YYCHQYEDYPLTFGGGTKVEIK |
| 12 | MAB6/MAB 36 | DIQMTQSPSSLSASVGDRVTITCQASQDISNYLNWYQQKPG KAPKLLIYDASNLETGVPSRFSGSGSGTDFTFTISSLQPEDIAT YYCHQYEDYPLTFGGGTKVEIK |
| 14 | MAB7/MAB 37 | DIQMTQSPSSLSASVGDRVTITCQASQDISNYLNWYQQKPG KAPKLLIYDASNLETGVPSRFSGSGSGTDFTFTISSLQPEDIAT YYCQQYEDYPLVFGGGTKVEIK |
| 16 | MAB8/MAB 38 | DIQMTQSPSSLSASVGDRVTITCQASQDISNYLNWYQQKPG KAPKLLIYDASNLETGVPSRFSGSGSGTDFTFTISSLQPEDIAT YYCQQHEDYPLTFGGGTKVEIK |
| 18 | MAB9/MAB 39 | DIQMTQSPSSLSASVGDRVTITCQASQDISNYLNWYQQKPG KAPKLLIYDASNLETGVPSRFSGSGSGTDFTFTISSLQPEDIAT YYCQHYEDYPLTFGGGTKVEIK |
| 20 | MAB10/MAB 40 | DIQMTQSPSSLSASVGDRVTITCQASQDISNYLNWYQQKPG KAPKLLIYDASNLETGVPSRFSGSGSGTDFTFTISSLQPEDIAT YYCQQYEDLIPTFGGGTKVEIK |
| 22 | MAB11/MAB 41 | DIQMTQSPSTLSASVGDRVTITCRASQSISSWLAWYQQKPGK APKLLIYKASSLESGVPSRFSGSGSGTEFTLTISSLQPDDFATY YCQSYNSYVWTFGQGTKVEIK |
| 24 | MAB12/MAB 42 | DIQMTQSPSTLSASVGDRVTITCRASQSISSWLAWYQQKPGK APKLLIYKASSLESGVPSRFSGSGSGTEFTLTISSLQPDDFATY YCQQVNSYDWTFGQGTKVEIK |
| 26 | MAB13/MAB 43 | DIQMTQSPSTLSASVGDRVTITCRASQSISSWLAWYQQKPGK APKLLIYKASSLESGVPSRFSGSGSGTEFTLTISSLQPDDFATY YCQQVNSYDWTFGQGTKVEIK |

TABLE 6-continued

| SEQ ID NO: | AB ID NO. | VL Sequence |
|---|---|---|
| 28 | MAB14/MAB 44 | DIQMTQSPSTLSASVGDRVTITCRASQSISSWLAWYQQKPGK<br>APKLLIYKASSLESGVPSRFSGSGSGTEFTLTISSLQPDDFATY<br>YCQQYSSYAWTFGQGTKVEIK |
| 30 | MAB15/MAB 45 | DIQMTQSPSTLSASVGDRVTITCRASQSISSWLAWYQQKPGK<br>APKLLIYKASSLESGVPSRFSGSGSGTEFTLTISSLQPDDFATY<br>YCQQARSYSWTFGQGTKVEIK |
| 32 | MAB16/MAB 46 | DIQMTQSPSTLSASVGDRVTITCRASQSISSWLAWYQQKPGK<br>APKLLIYKASSLESGVPSRFSGSGSGTEFTLTISSLQPDDFATY<br>YCQQHNSYRWTFGQGTKVEIK |
| 34 | MAB17/MAB 47 | DIQMTQSPSTLSASVGDRVTITCRASQSISSWLAWYQQKPGK<br>APKLLIYKASSLESGVPSRFSGSGSGTEFTLTISSLQPDDFATY<br>YCVQYPSYSWTFGQGTKVEIK |
| 36 | MAB18/MAB 48 | DIQMTQSPSTLSASVGDRVTITCRASQSISSWLAWYQQKPGK<br>APKLLIYKASSLESGVPSRFSGSGSGTEFTLTISSLQPDDFATY<br>YCQQYNSYKLTFGQGTKVEIK |
| 38 | MAB19/MAB 49 | DIQMTQSPSTLSASVGDRVTITCRASQSISSWLAWYQQKPGK<br>APKLLIYKASSLESGVPSRFSGSGSGTEFTLTISSLQPDDFATY<br>YCQQYNSPSWLFGQGTKVEIK |
| 40 | MAB20/MAB 50 | DIQMTQSPSTLSASVGDRVTITCRASQSISSWLAWYQQKPGK<br>APKLLIYKASSLESGVPSRFSGSGSGTEFTLTISSLQPDDFATY<br>YCQQVNSLSWTFGQGTKVEIK |
| 42 | MAB21/MAB 51 | DIQMTQSPSSLSASVGDRVTITCRASQGIRNDLGWYQQKPG<br>KAPKRLIYTASNLQSGVPSRFSGSGSGTEFTLTISSLQPEDFAT<br>YYCFQYNSYPLGFGGGTKVEIK |
| 44 | MAB22/MAB 52 | DIQMTQSPSSLSASVGDRVTITCRASQGIRNDLGWYQQKPG<br>KAPKRLIYTASNLQSGVPSRFSGSGSGTEFTLTISSLQPEDFAT<br>YYCLQYRSHPLTFGGGTKVEIK |
| 46 | MAB23/MAB 53 | DIQMTQSPSSLSASVGDRVTITCRASQGIRNDLGWYQQKPG<br>KAPKRLIYTASNLQSGVPSRFSGSGSGTEFTLTISSLQPEDFAT<br>YYCLQYNQVPLTFGGGTKVEIK |
| 48 | MAB24/MAB 54 | DIQMTQSPSSLSASVGDRVTITCRASQGIRNDLGWYQQKPG<br>KAPKRLIYTASNLQSGVPSRFSGSGSGTEFTLTISSLQPEDFAT<br>YYCLQTNIYPLTFGGGTKVEIK |
| 50 | MAB25/MAB 55 | DIQMTQSPSSLSASVGDRVTITCRASQGIRNDLGWYQQKPG<br>KAPKRLIYTASNLQSGVPSRFSGSGSGTEFTLTISSLQPEDFAT<br>YYCLQYKQYPLTFGGGTKVEIK |
| 52 | MAB26/MAB 56 | DIQMTQSPSSLSASVGDRVTITCRASQGIRNDLGWYQQKPG<br>KAPKRLIYTASNLQSGVPSRFSGSGSGTEFTLTISSLQPEDFAT<br>YYCLQTNIYPLTFGGGTKVEIK |
| 54 | MAB27/MAB 57 | DIQMTQSPSSLSASVGDRVTITCRASQGIRNDLGWYQQKPG<br>KAPKRLIYTASNLQSGVPSRFSGSGSGTEFTLTISSLQPEDFAT<br>YYCLQYNSYPLAFGGGTKVEIK |
| 56 | MAB28/MAB 58 | DIQMTQSPSSLSASVGDRVTITCRASQGIRNDLGWYQQKPG<br>KAPKRLIYTASNLQSGVPSRFSGSGSGTEFTLTISSLQPEDFAT<br>YYCLQYHSYPLRFGGGTKVEIK |
| 58 | MAB29/MAB 59 | DIQMTQSPSSLSASVGDRVTITCRASQGIRNDLGWYQQKPG<br>KAPKRLIYTASNLQSGVPSRFSGSGSGTEFTLTISSLQPEDFAT<br>YYCLQYASYPLKFGGGTKVEIK |
| 60 | MAB30/MAB 60 | DIQMTQSPSSLSASVGDRVTITCRASQGIRNDLGWYQQKPG<br>KAPKRLIYTASNLQSGVPSRFSGSGSGTEFTLTISSLQPEDFAT<br>YYCLQYNAYPLIFGGGTKVEIK |

In some embodiments, an antibody, or antigen binding fragment thereof, comprises a sequence selected from one or more of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 334, SEQ ID NO: 335, SEQ ID NO: 336, SEQ ID NO: 337, SEQ ID NO: 338, SEQ ID NO: 339, SEQ ID NO: 340, SEQ ID NO: 341, SEQ ID NO: 342, SEQ ID NO: 343, SEQ ID NO: 344, SEQ ID NO: 345, SEQ ID NO: 346, SEQ ID NO: 347, SEQ ID NO: 348, SEQ ID NO: 349, SEQ ID NO: 350, SEQ ID NO: 351, SEQ ID NO: 352, SEQ ID NO: 353, SEQ ID NO: 354, SEQ ID NO: 355, SEQ ID NO: 356, SEQ ID NO: 357, SEQ ID NO: 358, SEQ ID NO: 359, SEQ ID NO: 360, SEQ ID NO: 361, SEQ ID NO: 362, SEQ ID NO: 363, or any variants thereof.

In some embodiments, an antibody, or antigen binding fragment thereof, comprises a $V_H$ peptide of SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 334, 335, 336, 337, 338, 339, 340, 341, 342, 343, 344, 345, 346, 347, 348, 349, 350, 351, 352, 353, 354, 355, 356, 35358, 359, 360, 361, 362, or 363, or any variant thereof.

In some embodiments, an antibody, or antigen binding fragment thereof, comprises a $V_H$ peptide having at least 85%, 86%, 87%, 88%, 89%, 90%, 91%, 92%, 93%, 94%, 95%, 96%, 97%, 98%, or 99% identity to SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 334, 335, 336, 337, 338, 339, 340, 341, 342, 343, 344, 345, 346, 347, 348, 349, 350, 351, 352, 353, 354, 355, 356, 35358, 359, 360, 361, 362, or 363.

In some embodiments, an antibody, or antigen binding fragment thereof, comprises a $V_H$ peptide of SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 334, 335, 336, 337, 338, 339, 340, 341, 342, 343, 344, 345, 346, 347, 348, 349, 350, 351, 352, 353, 354, 355, 356, 35358, 359, 360, 361, 362, or 363.

In some embodiments, an antibody, or antigen binding fragment thereof, comprises a $V_H$ peptide of SEQ ID NO: 1. In some embodiments, an antibody, or antigen binding fragment thereof, comprises a $V_H$ peptide having at least 85% identity to SEQ ID NO: 1. In some embodiments, an antibody, or antigen binding fragment thereof, comprises a $V_H$ peptide having at least 85%, 86%, 87%, 88%, 89%, 90%, 91%, 92%, 93%, 94%, 95%, 96%, 97%, 98%, or 99% identity to SEQ ID NO: 1.

In some embodiments, an antibody, or antigen binding fragment thereof, comprises a $V_H$ peptide of SEQ ID NO: 3. In some embodiments, an antibody, or antigen binding fragment thereof, comprises a $V_H$ peptide having at least 85% identity to SEQ ID NO: 3.

In some embodiments, an antibody, or antigen binding fragment thereof, comprises a $V_H$ peptide having at least 85%, 86%, 87%, 88%, 89%, 90%, 91%, 92%, 93%, 94%, 95%, 96%, 97%, 98%, or 99% identity to SEQ ID NO: 3.

In some embodiments, an antibody, or antigen binding fragment thereof, comprises a $V_H$ peptide of SEQ ID NO: 5. In some embodiments, an antibody, or antigen binding fragment thereof, comprises a $V_H$ peptide having at least 85% identity to SEQ ID NO: 5. In some embodiments, an antibody, or antigen binding fragment thereof, comprises a $V_H$ peptide having at least 85%, 86%, 87%, 88%, 89%, 90%, 91%, 92%, 93%, 94%, 95%, 96%, 97%, 98%, or 99% identity to SEQ ID NO: 5.

In some embodiments, an antibody, or antigen binding fragment thereof, comprises a $V_H$ peptide of SEQ ID NO: 7. In some embodiments, an antibody, or antigen binding fragment thereof, comprises a $V_H$ peptide having at least 85% identity to SEQ ID NO: 7. In some embodiments, an antibody, or antigen binding fragment thereof, comprises a $V_H$ peptide having at least 85%, 86%, 87%, 88%, 89%, 90%, 91%, 92%, 93%, 94%, 95%, 96%, 97%, 98%, or 99% identity to SEQ ID NO: 7.

In some embodiments, an antibody, or antigen binding fragment thereof, comprises a $V_H$ peptide of SEQ ID NO: 9. In some embodiments, an antibody, or antigen binding fragment thereof, comprises a $V_H$ peptide having at least 85% identity to SEQ ID NO: 9. In some embodiments, an antibody, or antigen binding fragment thereof, comprises a $V_H$ peptide having at least 85%, 86%, 87%, 88%, 89%, 90%, 91%, 92%, 93%, 94%, 95%, 96%, 97%, 98%, or 99% identity to SEQ ID NO: 9.

In some embodiments, an antibody, or antigen binding fragment thereof, comprises a $V_H$ peptide of SEQ ID NO: 11. In some embodiments, an antibody, or antigen binding fragment thereof, comprises a $V_H$ peptide having at least 85% identity to SEQ ID NO: 11. In some embodiments, an antibody, or antigen binding fragment thereof, comprises a $V_H$ peptide having at least 85%, 86%, 87%, 88%, 89%, 90%, 91%, 92%, 93%, 94%, 95%, 96%, 97%, 98%, or 99% identity to SEQ ID NO: 11.

In some embodiments, an antibody, or antigen binding fragment thereof, comprises a $V_H$ peptide of SEQ ID NO: 13. In some embodiments, an antibody, or antigen binding fragment thereof, comprises a $V_H$ peptide having at least 85% identity to SEQ ID NO: 13. In some embodiments, an antibody, or antigen binding fragment thereof, comprises a $V_H$ peptide having at least 85%, 86%, 87%, 88%, 89%, 90%, 91%, 92%, 93%, 94%, 95%, 96%, 97%, 98%, or 99% identity to SEQ ID NO: 13.

In some embodiments, an antibody, or antigen binding fragment thereof, comprises a $V_H$ peptide of SEQ ID NO: 15. In some embodiments, an antibody, or antigen binding fragment thereof, comprises a $V_H$ peptide having at least 85% identity to SEQ ID NO: 15. In some embodiments, an antibody, or antigen binding fragment thereof, comprises a $V_H$ peptide having at least 85%, 86%, 87%, 88%, 89%, 90%, 91%, 92%, 93%, 94%, 95%, 96%, 97%, 98%, or 99% identity to SEQ ID NO: 15.

In some embodiments, an antibody, or antigen binding fragment thereof, comprises a $V_H$ peptide of SEQ ID NO: 17. In some embodiments, an antibody, or antigen binding fragment thereof, comprises a $V_H$ peptide having at least 85% identity to SEQ ID NO: 17. In some embodiments, an antibody, or antigen binding fragment thereof, comprises a $V_H$ peptide having at least 85%, 86%, 87%, 88%, 89%, 90%, 91%, 92%, 93%, 94%, 95%, 96%, 97%, 98%, or 99% identity to SEQ ID NO: 17.

In some embodiments, an antibody, or antigen binding fragment thereof, comprises a $V_H$ peptide of SEQ ID NO: 19. In some embodiments, an antibody, or antigen binding fragment thereof, comprises a $V_H$ peptide having at least 85% identity to SEQ ID NO: 19. In some embodiments, an antibody, or antigen binding fragment thereof, comprises a $V_H$ peptide having at least 85%, 86%, 87%, 88%, 89%, 90%, 91%, 92%, 93%, 94%, 95%, 96%, 97%, 98%, or 99% identity to SEQ ID NO: 19.

In some embodiments, an antibody, or antigen binding fragment thereof, comprises a $V_H$ peptide of SEQ ID NO: 21. In some embodiments, an antibody, or antigen binding fragment thereof, comprises a $V_H$ peptide having at least 85% identity to SEQ ID NO: 21. In some embodiments, an antibody, or antigen binding fragment thereof, comprises a $V_H$ peptide having at least 85%, 86%, 87%, 88%, 89%, 90%, 91%, 92%, 93%, 94%, 95%, 96%, 97%, 98%, or 99% identity to SEQ ID NO: 21.

In some embodiments, an antibody, or antigen binding fragment thereof, comprises a $V_H$ peptide of SEQ ID NO: 23. In some embodiments, an antibody, or antigen binding fragment thereof, comprises a $V_H$ peptide having at least 85% identity to SEQ ID NO: 23. In some embodiments, an antibody, or antigen binding fragment thereof, comprises a $V_H$ peptide having at least 85%, 86%, 87%, 88%, 89%, 90%, 91%, 92%, 93%, 94%, 95%, 96%, 97%, 98%, or 99% identity to SEQ ID NO: 23.

In some embodiments, an antibody, or antigen binding fragment thereof, comprises a $V_H$ peptide of SEQ ID NO: 25. In some embodiments, an antibody, or antigen binding fragment thereof, comprises a $V_H$ peptide having at least 85% identity to SEQ ID NO: 25. In some embodiments, an antibody, or antigen binding fragment thereof, comprises a $V_H$ peptide having at least 85%, 86%, 87%, 88%, 89%, 90%, 91%, 92%, 93%, 94%, 95%, 96%, 97%, 98%, or 99% identity to SEQ ID NO: 25.

In some embodiments, an antibody, or antigen binding fragment thereof, comprises a $V_H$ peptide of SEQ ID NO: 27. In some embodiments, an antibody, or antigen binding fragment thereof, comprises a $V_H$ peptide having at least 85% identity to SEQ ID NO: 27. In some embodiments, an antibody, or antigen binding fragment thereof, comprises a $V_H$ peptide having at least 85%, 86%, 87%, 88%, 89%, 90%, 91%, 92%, 93%, 94%, 95%, 96%, 97%, 98%, or 99% identity to SEQ ID NO: 27.

In some embodiments, an antibody, or antigen binding fragment thereof, comprises a $V_H$ peptide of SEQ ID NO: 29. In some embodiments, an antibody, or antigen binding fragment thereof, comprises a $V_H$ peptide having at least 85% identity to SEQ ID NO: 29. In some embodiments, an antibody, or antigen binding fragment thereof, comprises a $V_H$ peptide having at least 85%, 86%, 87%, 88%, 89%, 90%, 91%, 92%, 93%, 94%, 95%, 96%, 97%, 98%, or 99% identity to SEQ ID NO: 29.

In some embodiments, an antibody, or antigen binding fragment thereof, comprises a $V_H$ peptide of SEQ ID NO: 31. In some embodiments, an antibody, or antigen binding fragment thereof, comprises a $V_H$ peptide having at least 85% identity to SEQ ID NO: 31. In some embodiments, an antibody, or antigen binding fragment thereof, comprises a $V_H$ peptide having at least 85%, 86%, 87%, 88%, 89%, 90%, 91%, 92%, 93%, 94%, 95%, 96%, 97%, 98%, or 99% identity to SEQ ID NO: 31.

In some embodiments, an antibody, or antigen binding fragment thereof, comprises a $V_H$ peptide of SEQ ID NO: 33. In some embodiments, an antibody, or antigen binding fragment thereof, comprises a $V_H$ peptide having at least 85% identity to SEQ ID NO: 33. In some embodiments, an antibody, or antigen binding fragment thereof, comprises a $V_H$ peptide having at least 85%, 86%, 87%, 88%, 89%, 90%, 91%, 92%, 93%, 94%, 95%, 96%, 97%, 98%, or 99% identity to SEQ ID NO: 33.

In some embodiments, an antibody, or antigen binding fragment thereof, comprises a $V_H$ peptide of SEQ ID NO: 35. In some embodiments, an antibody, or antigen binding fragment thereof, comprises a $V_H$ peptide having at least 85% identity to SEQ ID NO: 35. In some embodiments, an antibody, or antigen binding fragment thereof, comprises a $V_H$ peptide having at least 85%, 86%, 87%, 88%, 89%, 90%, 91%, 92%, 93%, 94%, 95%, 96%, 97%, 98%, or 99% identity to SEQ ID NO: 35.

In some embodiments, an antibody, or antigen binding fragment thereof, comprises a $V_H$ peptide of SEQ ID NO: 37. In some embodiments, an antibody, or antigen binding fragment thereof, comprises a $V_H$ peptide having at least 85% identity to SEQ ID NO: 37. In some embodiments, an antibody, or antigen binding fragment thereof, comprises a $V_H$ peptide having at least 85%, 86%, 87%, 88%, 89%, 90%, 91%, 92%, 93%, 94%, 95%, 96%, 97%, 98%, or 99% identity to SEQ ID NO: 37.

In some embodiments, an antibody, or antigen binding fragment thereof, comprises a $V_H$ peptide of SEQ ID NO: 39. In some embodiments, an antibody, or antigen binding fragment thereof, comprises a $V_H$ peptide having at least 85% identity to SEQ ID NO: 39. In some embodiments, an antibody, or antigen binding fragment thereof, comprises a $V_H$ peptide having at least 85%, 86%, 87%, 88%, 89%, 90%, 91%, 92%, 93%, 94%, 95%, 96%, 97%, 98%, or 99% identity to SEQ ID NO: 39.

In some embodiments, an antibody, or antigen binding fragment thereof, comprises a $V_H$ peptide of SEQ ID NO: 41. In some embodiments, an antibody, or antigen binding fragment thereof, comprises a $V_H$ peptide having at least 85% identity to SEQ ID NO: 41. In some embodiments, an antibody, or antigen binding fragment thereof, comprises a $V_H$ peptide having at least 85%, 86%, 87%, 88%, 89%, 90%, 91%, 92%, 93%, 94%, 95%, 96%, 97%, 98%, or 99% identity to SEQ ID NO: 41.

In some embodiments, an antibody, or antigen binding fragment thereof, comprises a $V_H$ peptide of SEQ ID NO: 43. In some embodiments, an antibody, or antigen binding fragment thereof, comprises a $V_H$ peptide having at least 85% identity to SEQ ID NO: 43. In some embodiments, an antibody, or antigen binding fragment thereof, comprises a $V_H$ peptide having at least 85%, 86%, 87%, 88%, 89%, 90%, 91%, 92%, 93%, 94%, 95%, 96%, 97%, 98%, or 99% identity to SEQ ID NO: 43.

In some embodiments, an antibody, or antigen binding fragment thereof, comprises a $V_H$ peptide of SEQ ID NO: 45. In some embodiments, an antibody, or antigen binding fragment thereof, comprises a $V_H$ peptide having at least 85% identity to SEQ ID NO: 45. In some embodiments, an antibody, or antigen binding fragment thereof, comprises a $V_H$ peptide having at least 85%, 86%, 87%, 88%, 89%, 90%, 91%, 92%, 93%, 94%, 95%, 96%, 97%, 98%, or 99% identity to SEQ ID NO: 45.

In some embodiments, an antibody, or antigen binding fragment thereof, comprises a $V_H$ peptide of SEQ ID NO: 47. In some embodiments, an antibody, or antigen binding fragment thereof, comprises a $V_H$ peptide having at least 85% identity to SEQ ID NO: 47. In some embodiments, an antibody, or antigen binding fragment thereof, comprises a $V_H$ peptide having at least 85%, 86%, 87%, 88%, 89%, 90%, 91%, 92%, 93%, 94%, 95%, 96%, 97%, 98%, or 99% identity to SEQ ID NO: 47.

In some embodiments, an antibody, or antigen binding fragment thereof, comprises a $V_H$ peptide of SEQ ID NO: 49. In some embodiments, an antibody, or antigen binding fragment thereof, comprises a $V_H$ peptide having at least 85% identity to SEQ ID NO: 49. In some embodiments, an antibody, or antigen binding fragment thereof, comprises a $V_H$ peptide having at least 85%, 86%, 87%, 88%, 89%, 90%, 91%, 92%, 93%, 94%, 95%, 96%, 97%, 98%, or 99% identity to SEQ ID NO: 49.

In some embodiments, an antibody, or antigen binding fragment thereof, comprises a $V_H$ peptide of SEQ ID NO: 51. In some embodiments, an antibody, or antigen binding fragment thereof, comprises a $V_H$ peptide having at least 85% identity to SEQ ID NO: 51. In some embodiments, an antibody, or antigen binding fragment thereof, comprises a $V_H$ peptide having at least 85%, 86%, 87%, 88%, 89%, 90%, 91%, 92%, 93%, 94%, 95%, 96%, 97%, 98%, or 99% identity to SEQ ID NO: 51.

In some embodiments, an antibody, or antigen binding fragment thereof, comprises a $V_H$ peptide of SEQ ID NO: 53. In some embodiments, an antibody, or antigen binding fragment thereof, comprises a $V_H$ peptide having at least 85% identity to SEQ ID NO: 53. In some embodiments, an antibody, or antigen binding fragment thereof, comprises a $V_H$ peptide having at least 85%, 86%, 87%, 88%, 89%, 90%, 91%, 92%, 93%, 94%, 95%, 96%, 97%, 98%, or 99% identity to SEQ ID NO: 53.

In some embodiments, an antibody, or antigen binding fragment thereof, comprises a $V_H$ peptide of SEQ ID NO: 55. In some embodiments, an antibody, or antigen binding fragment thereof, comprises a $V_H$ peptide having at least 85% identity to SEQ ID NO: 55. In some embodiments, an antibody, or antigen binding fragment thereof, comprises a $V_H$ peptide having at least 85%, 86%, 87%, 88%, 89%, 90%, 91%, 92%, 93%, 94%, 95%, 96%, 97%, 98%, or 99% identity to SEQ ID NO: 55.

In some embodiments, an antibody, or antigen binding fragment thereof, comprises a $V_H$ peptide of SEQ ID NO: 57. In some embodiments, an antibody, or antigen binding fragment thereof, comprises a $V_H$ peptide having at least 85% identity to SEQ ID NO: 57. In some embodiments, an antibody, or antigen binding fragment thereof, comprises a $V_H$ peptide having at least 85%, 86%, 87%, 88%, 89%, 90%, 91%, 92%, 93%, 94%, 95%, 96%, 97%, 98%, or 99% identity to SEQ ID NO: 57.

In some embodiments, an antibody, or antigen binding fragment thereof, comprises a $V_H$ peptide of SEQ ID NO: 59. In some embodiments, an antibody, or antigen binding fragment thereof, comprises a $V_H$ peptide having at least 85% identity to SEQ ID NO: 59. In some embodiments, an antibody, or antigen binding fragment thereof, comprises a $V_H$ peptide having at least 85%, 86%, 87%, 88%, 89%, 90%, 91%, 92%, 93%, 94%, 95%, 96%, 97%, 98%, or 99% identity to SEQ ID NO: 59.

In some embodiments, an antibody, or antigen binding fragment thereof, comprises a $V_H$ peptide of SEQ ID NO: 334. In some embodiments, an antibody, or antigen binding fragment thereof, comprises a $V_H$ peptide having at least 85% identity to SEQ ID NO: 334. In some embodiments, an antibody, or antigen binding fragment thereof, comprises a $V_H$ peptide having at least 85%, 86%, 87%, 88%, 89%, 90%, 91%, 92%, 93%, 94%, 95%, 96%, 97%, 98%, or 99% identity to SEQ ID NO: 334.

In some embodiments, an antibody, or antigen binding fragment thereof, comprises a $V_H$ peptide of SEQ ID NO: 335. In some embodiments, an antibody, or antigen binding fragment thereof, comprises a $V_H$ peptide having at least 85% identity to SEQ ID NO: 335. In some embodiments, an antibody, or antigen binding fragment thereof, comprises a $V_H$ peptide having at least 85%, 86%, 87%, 88%, 89%, 90%, 91%, 92%, 93%, 94%, 95%, 96%, 97%, 98%, or 99% identity to SEQ ID NO: 335.

In some embodiments, an antibody, or antigen binding fragment thereof, comprises a $V_H$ peptide of SEQ ID NO: 336. In some embodiments, an antibody, or antigen binding fragment thereof, comprises a $V_H$ peptide having at least 85% identity to SEQ ID NO: 336. In some embodiments, an antibody, or antigen binding fragment thereof, comprises a $V_H$ peptide having at least 85%, 86%, 87%, 88%, 89%, 90%, 91%, 92%, 93%, 94%, 95%, 96%, 97%, 98%, or 99% identity to SEQ ID NO: 336.

In some embodiments, an antibody, or antigen binding fragment thereof, comprises a $V_H$ peptide of SEQ ID NO: 337. In some embodiments, an antibody, or antigen binding fragment thereof, comprises a $V_H$ peptide having at least 85% identity to SEQ ID NO: 337. In some embodiments, an antibody, or antigen binding fragment thereof, comprises a $V_H$ peptide having at least 85%, 86%, 87%, 88%, 89%, 90%, 91%, 92%, 93%, 94%, 95%, 96%, 97%, 98%, or 99% identity to SEQ ID NO: 337.

In some embodiments, an antibody, or antigen binding fragment thereof, comprises a $V_H$ peptide of SEQ ID NO: 338. In some embodiments, an antibody, or antigen binding fragment thereof, comprises a $V_H$ peptide having at least 85% identity to SEQ ID NO: 338. In some embodiments, an antibody, or antigen binding fragment thereof, comprises a $V_H$ peptide having at least 85%, 86%, 87%, 88%, 89%, 90%, 91%, 92%, 93%, 94%, 95%, 96%, 97%, 98%, or 99% identity to SEQ ID NO: 338.

In some embodiments, an antibody, or antigen binding fragment thereof, comprises a $V_H$ peptide of SEQ ID NO: 339. In some embodiments, an antibody, or antigen binding fragment thereof, comprises a $V_H$ peptide having at least 85% identity to SEQ ID NO: 339. In some embodiments, an antibody, or antigen binding fragment thereof, comprises a $V_H$ peptide having at least 85%, 86%, 87%, 88%, 89%, 90%, 91%, 92%, 93%, 94%, 95%, 96%, 97%, 98%, or 99% identity to SEQ ID NO: 339.

In some embodiments, an antibody, or antigen binding fragment thereof, comprises a $V_H$ peptide of SEQ ID NO: 340. In some embodiments, an antibody, or antigen binding fragment thereof, comprises a $V_H$ peptide having at least 85% identity to SEQ ID NO: 340. In some embodiments, an antibody, or antigen binding fragment thereof, comprises a $V_H$ peptide having at least 85%, 86%, 87%, 88%, 89%, 90%, 91%, 92%, 93%, 94%, 95%, 96%, 97%, 98%, or 99% identity to SEQ ID NO: 340.

In some embodiments, an antibody, or antigen binding fragment thereof, comprises a $V_H$ peptide of SEQ ID NO: 341. In some embodiments, an antibody, or antigen binding fragment thereof, comprises a $V_H$ peptide having at least 85% identity to SEQ ID NO: 341. In some embodiments, an antibody, or antigen binding fragment thereof, comprises a $V_H$ peptide having at least 85%, 86%, 87%, 88%, 89%, 90%, 91%, 92%, 93%, 94%, 95%, 96%, 97%, 98%, or 99% identity to SEQ ID NO: 341.

In some embodiments, an antibody, or antigen binding fragment thereof, comprises a $V_H$ peptide of SEQ ID NO: 342. In some embodiments, an antibody, or antigen binding fragment thereof, comprises a $V_H$ peptide having at least 85% identity to SEQ ID NO: 342. In some embodiments, an antibody, or antigen binding fragment thereof, comprises a $V_H$ peptide having at least 85%, 86%, 87%, 88%, 89%, 90%, 91%, 92%, 93%, 94%, 95%, 96%, 97%, 98%, or 99% identity to SEQ ID NO: 342.

In some embodiments, an antibody, or antigen binding fragment thereof, comprises a $V_H$ peptide of SEQ ID NO: 343. In some embodiments, an antibody, or antigen binding fragment thereof, comprises a $V_H$ peptide having at least 85% identity to SEQ ID NO: 343. In some embodiments, an antibody, or antigen binding fragment thereof, comprises a $V_H$ peptide having at least 85%, 86%, 87%, 88%, 89%, 90%, 91%, 92%, 93%, 94%, 95%, 96%, 97%, 98%, or 99% identity to SEQ ID NO: 343.

In some embodiments, an antibody, or antigen binding fragment thereof, comprises a $V_H$ peptide of SEQ ID NO: 344. In some embodiments, an antibody, or antigen binding fragment thereof, comprises a $V_H$ peptide having at least 85% identity to SEQ ID NO: 344. In some embodiments, an antibody, or antigen binding fragment thereof, comprises a $V_H$ peptide having at least 85%, 86%, 87%, 88%, 89%, 90%, 91%, 92%, 93%, 94%, 95%, 96%, 97%, 98%, or 99% identity to SEQ ID NO: 344.

In some embodiments, an antibody, or antigen binding fragment thereof, comprises a $V_H$ peptide of SEQ ID NO: 345. In some embodiments, an antibody, or antigen binding fragment thereof, comprises a $V_H$ peptide having at least 85% identity to SEQ ID NO: 345. In some embodiments, an antibody, or antigen binding fragment thereof, comprises a $V_H$ peptide having at least 85%, 86%, 87%, 88%, 89%, 90%, 91%, 92%, 93%, 94%, 95%, 96%, 97%, 98%, or 99% identity to SEQ ID NO: 345.

In some embodiments, an antibody, or antigen binding fragment thereof, comprises a $V_H$ peptide of SEQ ID NO: 346. In some embodiments, an antibody, or antigen binding fragment thereof, comprises a $V_H$ peptide having at least 85% identity to SEQ ID NO: 346. In some embodiments, an antibody, or antigen binding fragment thereof, comprises a $V_H$ peptide having at least 85%, 86%, 87%, 88%, 89%, 90%, 91%, 92%, 93%, 94%, 95%, 96%, 97%, 98%, or 99% identity to SEQ ID NO: 346.

In some embodiments, an antibody, or antigen binding fragment thereof, comprises a $V_H$ peptide of SEQ ID NO: 347. In some embodiments, an antibody, or antigen binding fragment thereof, comprises a $V_H$ peptide having at least 85% identity to SEQ ID NO: 347. In some embodiments, an antibody, or antigen binding fragment thereof, comprises a $V_H$ peptide having at least 85%, 86%, 87%, 88%, 89%, 90%, 91%, 92%, 93%, 94%, 95%, 96%, 97%, 98%, or 99% identity to SEQ ID NO: 347.

In some embodiments, an antibody, or antigen binding fragment thereof, comprises a $V_H$ peptide of SEQ ID NO: 348. In some embodiments, an antibody, or antigen binding fragment thereof, comprises a $V_H$ peptide having at least 85% identity to SEQ ID NO: 348. In some embodiments, an antibody, or antigen binding fragment thereof, comprises a $V_H$ peptide having at least 85%, 86%, 87%, 88%, 89%, 90%, 91%, 92%, 93%, 94%, 95%, 96%, 97%, 98%, or 99% identity to SEQ ID NO: 348.

In some embodiments, an antibody, or antigen binding fragment thereof, comprises a $V_H$ peptide of SEQ ID NO: 349. In some embodiments, an antibody, or antigen binding fragment thereof, comprises a $V_H$ peptide having at least 85% identity to SEQ ID NO: 349. In some embodiments, an antibody, or antigen binding fragment thereof, comprises a $V_H$ peptide having at least 85%, 86%, 87%, 88%, 89%, 90%, 91%, 92%, 93%, 94%, 95%, 96%, 97%, 98%, or 99% identity to SEQ ID NO: 349.

In some embodiments, an antibody, or antigen binding fragment thereof, comprises a $V_H$ peptide of SEQ ID NO: 350. In some embodiments, an antibody, or antigen binding fragment thereof, comprises a $V_H$ peptide having at least 85% identity to SEQ ID NO: 350. In some embodiments, an antibody, or antigen binding fragment thereof, comprises a $V_H$ peptide having at least 85%, 86%, 87%, 88%, 89%, 90%, 91%, 92%, 93%, 94%, 95%, 96%, 97%, 98%, or 99% identity to SEQ ID NO: 350.

In some embodiments, an antibody, or antigen binding fragment thereof, comprises a $V_H$ peptide of SEQ ID NO: 351. In some embodiments, an antibody, or antigen binding fragment thereof, comprises a $V_H$ peptide having at least 85% identity to SEQ ID NO: 351. In some embodiments, an antibody, or antigen binding fragment thereof, comprises a $V_H$ peptide having at least 85%, 86%, 87%, 88%, 89%, 90%, 91%, 92%, 93%, 94%, 95%, 96%, 97%, 98%, or 99% identity to SEQ ID NO: 351.

In some embodiments, an antibody, or antigen binding fragment thereof, comprises a $V_H$ peptide of SEQ ID NO: 352. In some embodiments, an antibody, or antigen binding fragment thereof, comprises a $V_H$ peptide having at least 85% identity to SEQ ID NO: 352. In some embodiments, an antibody, or antigen binding fragment thereof, comprises a $V_H$ peptide having at least 85%, 86%, 87%, 88%, 89%, 90%, 91%, 92%, 93%, 94%, 95%, 96%, 97%, 98%, or 99% identity to SEQ ID NO: 352.

In some embodiments, an antibody, or antigen binding fragment thereof, comprises a $V_H$ peptide of SEQ ID NO: 353. In some embodiments, an antibody, or antigen binding fragment thereof, comprises a $V_H$ peptide having at least 85% identity to SEQ ID NO: 353. In some embodiments, an antibody, or antigen binding fragment thereof, comprises a $V_H$ peptide having at least 85%, 86%, 87%, 88%, 89%, 90%, 91%, 92%, 93%, 94%, 95%, 96%, 97%, 98%, or 99% identity to SEQ ID NO: 353.

In some embodiments, an antibody, or antigen binding fragment thereof, comprises a $V_H$ peptide of SEQ ID NO: 354. In some embodiments, an antibody, or antigen binding fragment thereof, comprises a $V_H$ peptide having at least 85% identity to SEQ ID NO: 354. In some embodiments, an antibody, or antigen binding fragment thereof, comprises a $V_H$ peptide having at least 85%, 86%, 87%, 88%, 89%, 90%, 91%, 92%, 93%, 94%, 95%, 96%, 97%, 98%, or 99% identity to SEQ ID NO: 354.

In some embodiments, an antibody, or antigen binding fragment thereof, comprises a $V_H$ peptide of SEQ ID NO: 355. In some embodiments, an antibody, or antigen binding fragment thereof, comprises a $V_H$ peptide having at least 85% identity to SEQ ID NO: 355. In some embodiments, an antibody, or antigen binding fragment thereof, comprises a $V_H$ peptide having at least 85%, 86%, 87%, 88%, 89%, 90%, 91%, 92%, 93%, 94%, 95%, 96%, 97%, 98%, or 99% identity to SEQ ID NO: 355.

In some embodiments, an antibody, or antigen binding fragment thereof, comprises a $V_H$ peptide of SEQ ID NO: 356. In some embodiments, an antibody, or antigen binding fragment thereof, comprises a $V_H$ peptide having at least 85% identity to SEQ ID NO: 356. In some embodiments, an antibody, or antigen binding fragment thereof, comprises a $V_H$ peptide having at least 85%, 86%, 87%, 88%, 89%, 90%, 91%, 92%, 93%, 94%, 95%, 96%, 97%, 98%, or 99% identity to SEQ ID NO: 356.

In some embodiments, an antibody, or antigen binding fragment thereof, comprises a $V_H$ peptide of SEQ ID NO: 357. In some embodiments, an antibody, or antigen binding fragment thereof, comprises a $V_H$ peptide having at least 85% identity to SEQ ID NO: 357. In some embodiments, an antibody, or antigen binding fragment thereof, comprises a $V_H$ peptide having at least 85%, 86%, 87%, 88%, 89%, 90%, 91%, 92%, 93%, 94%, 95%, 96%, 97%, 98%, or 99% identity to SEQ ID NO: 357.

In some embodiments, an antibody, or antigen binding fragment thereof, comprises a $V_H$ peptide of SEQ ID NO: 358. In some embodiments, an antibody, or antigen binding fragment thereof, comprises a $V_H$ peptide having at least 85% identity to SEQ ID NO: 358. In some embodiments, an antibody, or antigen binding fragment thereof, comprises a V$_H$ peptide having at least 85%, 86%, 87%, 88%, 89%, 90%, 91%, 92%, 93%, 94%, 95%, 96%, 97%, 98%, or 99% identity to SEQ ID NO: 358.

In some embodiments, an antibody, or antigen binding fragment thereof, comprises a V$_H$ peptide of SEQ ID NO: 359. In some embodiments, an antibody, or antigen binding fragment thereof, comprises a V$_H$ peptide having at least 85% identity to SEQ ID NO: 359. In some embodiments, an antibody, or antigen binding fragment thereof, comprises a V$_H$ peptide having at least 85%, 86%, 87%, 88%, 89%, 90%, 91%, 92%, 93%, 94%, 95%, 96%, 97%, 98%, or 99% identity to SEQ ID NO: 359.

In some embodiments, an antibody, or antigen binding fragment thereof, comprises a V$_H$ peptide of SEQ ID NO: 360. In some embodiments, an antibody, or antigen binding fragment thereof, comprises a V$_H$ peptide having at least 85% identity to SEQ ID NO: 360. In some embodiments, an antibody, or antigen binding fragment thereof, comprises a V$_H$ peptide having at least 85%, 86%, 87%, 88%, 89%, 90%, 91%, 92%, 93%, 94%, 95%, 96%, 97%, 98%, or 99% identity to SEQ ID NO: 360.

In some embodiments, an antibody, or antigen binding fragment thereof, comprises a V$_H$ peptide of SEQ ID NO: 361. In some embodiments, an antibody, or antigen binding fragment thereof, comprises a V$_H$ peptide having at least 85% identity to SEQ ID NO: 361. In some embodiments, an antibody, or antigen binding fragment thereof, comprises a V$_H$ peptide having at least 85%, 86%, 87%, 88%, 89%, 90%, 91%, 92%, 93%, 94%, 95%, 96%, 97%, 98%, or 99% identity to SEQ ID NO: 361.

In some embodiments, an antibody, or antigen binding fragment thereof, comprises a V$_H$ peptide of SEQ ID NO: 362. In some embodiments, an antibody, or antigen binding fragment thereof, comprises a V$_H$ peptide having at least 85% identity to SEQ ID NO: 362. In some embodiments, an antibody, or antigen binding fragment thereof, comprises a V$_H$ peptide having at least 85%, 86%, 87%, 88%, 89%, 90%, 91%, 92%, 93%, 94%, 95%, 96%, 97%, 98%, or 99% identity to SEQ ID NO: 362.

In some embodiments, an antibody, or antigen binding fragment thereof, comprises a V$_H$ peptide of SEQ ID NO: 363. In some embodiments, an antibody, or antigen binding fragment thereof, comprises a V$_H$ peptide having at least 85% identity to SEQ ID NO: 363. In some embodiments, an antibody, or antigen binding fragment thereof, comprises a V$_H$ peptide having at least 85%, 86%, 87%, 88%, 89%, 90%, 91%, 92%, 93%, 94%, 95%, 96%, 97%, 98%, or 99% identity to SEQ ID NO: 363.

In some embodiments, an antibody, or antigen binding fragment thereof, comprises a V$_L$ peptide of SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, or 60, or any variant thereof. In some embodiments, an antibody, or antigen binding fragment thereof, comprises a V$_L$ peptide having at least 85% identity to SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, or 60. In some embodiments, an antibody, or antigen binding fragment thereof, comprises a V$_L$ peptide having at least 85%, 86%, 87%, 88%, 89%, 90%, 91%, 92%, 93%, 94%, 95%, 96%, 97%, 98%, or 99% identity to SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, or 60. In some embodiments, an antibody, or antigen binding fragment thereof, comprises a V$_L$ peptide of SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, or 60.

In some embodiments, an antibody, or antigen binding fragment thereof, comprises a V$_L$ peptide of SEQ ID NO: 2. In some embodiments, an antibody, or antigen binding fragment thereof, comprises a V$_L$ peptide having at least 85% identity to SEQ ID NO: 2. In some embodiments, an antibody, or antigen binding fragment thereof, comprises a V$_L$ peptide having at least 85%, 86%, 87%, 88%, 89%, 90%, 91%, 92%, 93%, 94%, 95%, 96%, 97%, 98%, or 99% identity to SEQ ID NO: 2.

In some embodiments, an antibody, or antigen binding fragment thereof, comprises a V$_L$ peptide of SEQ ID NO: 4. In some embodiments, an antibody, or antigen binding fragment thereof, comprises a V$_L$ peptide having at least 85% identity to SEQ ID NO: 4. In some embodiments, an antibody, or antigen binding fragment thereof, comprises a V$_L$ peptide having at least 85%, 86%, 87%, 88%, 89%, 90%, 91%, 92%, 93%, 94%, 95%, 96%, 97%, 98%, or 99% identity to SEQ ID NO: 4.

In some embodiments, an antibody, or antigen binding fragment thereof, comprises a V$_L$ peptide of SEQ ID NO: 6. In some embodiments, an antibody, or antigen binding fragment thereof, comprises a V$_L$ peptide having at least 85% identity to SEQ ID NO: 6. In some embodiments, an antibody, or antigen binding fragment thereof, comprises a V$_L$ peptide having at least 85%, 86%, 87%, 88%, 89%, 90%, 91%, 92%, 93%, 94%, 95%, 96%, 97%, 98%, or 99% identity to SEQ ID NO: 6.

In some embodiments, an antibody, or antigen binding fragment thereof, comprises a V$_L$ peptide of SEQ ID NO: 8. In some embodiments, an antibody, or antigen binding fragment thereof, comprises a V$_L$ peptide having at least 85% identity to SEQ ID NO: 8. In some embodiments, an antibody, or antigen binding fragment thereof, comprises a V$_L$ peptide having at least 85%, 86%, 87%, 88%, 89%, 90%, 91%, 92%, 93%, 94%, 95%, 96%, 97%, 98%, or 99% identity to SEQ ID NO: 8.

In some embodiments, an antibody, or antigen binding fragment thereof, comprises a V$_L$ peptide of SEQ ID NO: 10. In some embodiments, an antibody, or antigen binding fragment thereof, comprises a V$_L$ peptide having at least 85% identity to SEQ ID NO: 10. In some embodiments, an antibody, or antigen binding fragment thereof, comprises a V$_L$ peptide having at least 85%, 86%, 87%, 88%, 89%, 90%, 91%, 92%, 93%, 94%, 95%, 96%, 97%, 98%, or 99% identity to SEQ ID NO: 10.

In some embodiments, an antibody, or antigen binding fragment thereof, comprises a V$_L$ peptide of SEQ ID NO: 12. In some embodiments, an antibody, or antigen binding fragment thereof, comprises a V$_L$ peptide having at least 85% identity to SEQ ID NO: 12. In some embodiments, an antibody, or antigen binding fragment thereof, comprises a V$_L$ peptide having at least 85%, 86%, 87%, 88%, 89%, 90%, 91%, 92%, 93%, 94%, 95%, 96%, 97%, 98%, or 99% identity to SEQ ID NO: 12.

In some embodiments, an antibody, or antigen binding fragment thereof, comprises a V$_L$ peptide of SEQ ID NO: 14. In some embodiments, an antibody, or antigen binding fragment thereof, comprises a V$_L$ peptide having at least 85% identity to SEQ ID NO: 14. In some embodiments, an antibody, or antigen binding fragment thereof, comprises a V$_L$ peptide having at least 85%, 86%, 87%, 88%, 89%, 90%, 91%, 92%, 93%, 94%, 95%, 96%, 97%, 98%, or 99% identity to SEQ ID NO: 14.

In some embodiments, an antibody, or antigen binding fragment thereof, comprises a V$_L$ peptide of SEQ ID NO: 16. In some embodiments, an antibody, or antigen binding fragment thereof, comprises a V$_L$ peptide having at least 85% identity to SEQ ID NO: 16. In some embodiments, an antibody, or antigen binding fragment thereof, comprises a $V_L$ peptide having at least 85%, 86%, 87%, 88%, 89%, 90%, 91%, 92%, 93%, 94%, 95%, 96%, 97%, 98%, or 99% identity to SEQ ID NO: 16.

In some embodiments, an antibody, or antigen binding fragment thereof, comprises a $V_L$ peptide of SEQ ID NO: 18. In some embodiments, an antibody, or antigen binding fragment thereof, comprises a $V_L$ peptide having at least 85% identity to SEQ ID NO: 18. In some embodiments, an antibody, or antigen binding fragment thereof, comprises a $V_L$ peptide having at least 85%, 86%, 87%, 88%, 89%, 90%, 91%, 92%, 93%, 94%, 95%, 96%, 97%, 98%, or 99% identity to SEQ ID NO: 18.

In some embodiments, an antibody, or antigen binding fragment thereof, comprises a $V_L$ peptide of SEQ ID NO: 20. In some embodiments, an antibody, or antigen binding fragment thereof, comprises a $V_L$ peptide having at least 85% identity to SEQ ID NO: 20. In some embodiments, an antibody, or antigen binding fragment thereof, comprises a $V_L$ peptide having at least 85%, 86%, 87%, 88%, 89%, 90%, 91%, 92%, 93%, 94%, 95%, 96%, 97%, 98%, or 99% identity to SEQ ID NO: 20.

In some embodiments, an antibody, or antigen binding fragment thereof, comprises a $V_L$ peptide of SEQ ID NO: 22. In some embodiments, an antibody, or antigen binding fragment thereof, comprises a $V_L$ peptide having at least 85% identity to SEQ ID NO: 22. In some embodiments, an antibody, or antigen binding fragment thereof, comprises a $V_L$ peptide having at least 85%, 86%, 87%, 88%, 89%, 90%, 91%, 92%, 93%, 94%, 95%, 96%, 97%, 98%, or 99% identity to SEQ ID NO: 22.

In some embodiments, an antibody, or antigen binding fragment thereof, comprises a $V_L$ peptide of SEQ ID NO: 24. In some embodiments, an antibody, or antigen binding fragment thereof, comprises a $V_L$ peptide having at least 85% identity to SEQ ID NO: 24. In some embodiments, an antibody, or antigen binding fragment thereof, comprises a $V_L$ peptide having at least 85%, 86%, 87%, 88%, 89%, 90%, 91%, 92%, 93%, 94%, 95%, 96%, 97%, 98%, or 99% identity to SEQ ID NO: 24.

In some embodiments, an antibody, or antigen binding fragment thereof, comprises a $V_L$ peptide of SEQ ID NO: 26. In some embodiments, an antibody, or antigen binding fragment thereof, comprises a $V_L$ peptide having at least 85% identity to SEQ ID NO: 26. In some embodiments, an antibody, or antigen binding fragment thereof, comprises a $V_L$ peptide having at least 85%, 86%, 87%, 88%, 89%, 90%, 91%, 92%, 93%, 94%, 95%, 96%, 97%, 98%, or 99% identity to SEQ ID NO: 26.

In some embodiments, an antibody, or antigen binding fragment thereof, comprises a $V_L$ peptide of SEQ ID NO: 28. In some embodiments, an antibody, or antigen binding fragment thereof, comprises a $V_L$ peptide having at least 85% identity to SEQ ID NO: 28. In some embodiments, an antibody, or antigen binding fragment thereof, comprises a $V_L$ peptide having at least 85%, 86%, 87%, 88%, 89%, 90%, 91%, 92%, 93%, 94%, 95%, 96%, 97%, 98%, or 99% identity to SEQ ID NO: 28.

In some embodiments, an antibody, or antigen binding fragment thereof, comprises a $V_L$ peptide of SEQ ID NO: 30. In some embodiments, an antibody, or antigen binding fragment thereof, comprises a $V_L$ peptide having at least 85% identity to SEQ ID NO: 30. In some embodiments, an antibody, or antigen binding fragment thereof, comprises a $V_L$ peptide having at least 85%, 86%, 87%, 88%, 89%, 90%, 91%, 92%, 93%, 94%, 95%, 96%, 97%, 98%, or 99% identity to SEQ ID NO: 30.

In some embodiments, an antibody, or antigen binding fragment thereof, comprises a $V_L$ peptide of SEQ ID NO: 32. In some embodiments, an antibody, or antigen binding fragment thereof, comprises a $V_L$ peptide having at least 85% identity to SEQ ID NO: 32. In some embodiments, an antibody, or antigen binding fragment thereof, comprises a $V_L$ peptide having at least 85%, 86%, 87%, 88%, 89%, 90%, 91%, 92%, 93%, 94%, 95%, 96%, 97%, 98%, or 99% identity to SEQ ID NO: 32.

In some embodiments, an antibody, or antigen binding fragment thereof, comprises a $V_L$ peptide of SEQ ID NO: 34. In some embodiments, an antibody, or antigen binding fragment thereof, comprises a $V_L$ peptide having at least 85% identity to SEQ ID NO: 34. In some embodiments, an antibody, or antigen binding fragment thereof, comprises a $V_L$ peptide having at least 85%, 86%, 87%, 88%, 89%, 90%, 91%, 92%, 93%, 94%, 95%, 96%, 97%, 98%, or 99% identity to SEQ ID NO: 34.

In some embodiments, an antibody, or antigen binding fragment thereof, comprises a $V_L$ peptide of SEQ ID NO: 36. In some embodiments, an antibody, or antigen binding fragment thereof, comprises a $V_L$ peptide having at least 85% identity to SEQ ID NO: 36. In some embodiments, an antibody, or antigen binding fragment thereof, comprises a $V_L$ peptide having at least 85%, 86%, 87%, 88%, 89%, 90%, 91%, 92%, 93%, 94%, 95%, 96%, 97%, 98%, or 99% identity to SEQ ID NO: 36.

In some embodiments, an antibody, or antigen binding fragment thereof, comprises a $V_L$ peptide of SEQ ID NO: 38. In some embodiments, an antibody, or antigen binding fragment thereof, comprises a $V_L$ peptide having at least 85% identity to SEQ ID NO: 38. In some embodiments, an antibody, or antigen binding fragment thereof, comprises a $V_L$ peptide having at least 85%, 86%, 87%, 88%, 89%, 90%, 91%, 92%, 93%, 94%, 95%, 96%, 97%, 98%, or 99% identity to SEQ ID NO: 38.

In some embodiments, an antibody, or antigen binding fragment thereof, comprises a $V_L$ peptide of SEQ ID NO: 40. In some embodiments, an antibody, or antigen binding fragment thereof, comprises a $V_L$ peptide having at least 85% identity to SEQ ID NO: 40. In some embodiments, an antibody, or antigen binding fragment thereof, comprises a $V_L$ peptide having at least 85%, 86%, 87%, 88%, 89%, 90%, 91%, 92%, 93%, 94%, 95%, 96%, 97%, 98%, or 99% identity to SEQ ID NO: 40.

In some embodiments, an antibody, or antigen binding fragment thereof, comprises a $V_L$ peptide of SEQ ID NO: 42. In some embodiments, an antibody, or antigen binding fragment thereof, comprises a $V_L$ peptide having at least 85% identity to SEQ ID NO: 42. In some embodiments, an antibody, or antigen binding fragment thereof, comprises a $V_L$ peptide having at least 85%, 86%, 87%, 88%, 89%, 90%, 91%, 92%, 93%, 94%, 95%, 96%, 97%, 98%, or 99% identity to SEQ ID NO: 42.

In some embodiments, an antibody, or antigen binding fragment thereof, comprises a $V_L$ peptide of SEQ ID NO: 44. In some embodiments, an antibody, or antigen binding fragment thereof, comprises a $V_L$ peptide having at least 85% identity to SEQ ID NO: 44. In some embodiments, an antibody, or antigen binding fragment thereof, comprises a $V_L$ peptide having at least 85%, 86%, 87%, 88%, 89%, 90%, 91%, 92%, 93%, 94%, 95%, 96%, 97%, 98%, or 99% identity to SEQ ID NO: 44.

In some embodiments, an antibody, or antigen binding fragment thereof, comprises a $V_L$ peptide of SEQ ID NO: 46. In some embodiments, an antibody, or antigen binding fragment thereof, comprises a $V_L$ peptide having at least 85% identity to SEQ ID NO: 46. In some embodiments, an antibody, or antigen binding fragment thereof, comprises a $V_L$ peptide having at least 85%, 86%, 87%, 88%, 89%, 90%, 91%, 92%, 93%, 94%, 95%, 96%, 97%, 98%, or 99% identity to SEQ ID NO: 46.

In some embodiments, an antibody, or antigen binding fragment thereof, comprises a $V_L$ peptide of SEQ ID NO: 48. In some embodiments, an antibody, or antigen binding fragment thereof, comprises a $V_L$ peptide having at least 85% identity to SEQ ID NO: 48. In some embodiments, an antibody, or antigen binding fragment thereof, comprises a $V_L$ peptide having at least 85%, 86%, 87%, 88%, 89%, 90%, 91%, 92%, 93%, 94%, 95%, 96%, 97%, 98%, or 99% identity to SEQ ID NO: 48.

In some embodiments, an antibody, or antigen binding fragment thereof, comprises a $V_L$ peptide of SEQ ID NO: 50. In some embodiments, an antibody, or antigen binding fragment thereof, comprises a $V_L$ peptide having at least 85% identity to SEQ ID NO: 50. In some embodiments, an antibody, or antigen binding fragment thereof, comprises a $V_L$ peptide having at least 85%, 86%, 87%, 88%, 89%, 90%, 91%, 92%, 93%, 94%, 95%, 96%, 97%, 98%, or 99% identity to SEQ ID NO: 50.

In some embodiments, an antibody, or antigen binding fragment thereof, comprises a $V_L$ peptide of SEQ ID NO: 52. In some embodiments, an antibody, or antigen binding fragment thereof, comprises a $V_L$ peptide having at least 85% identity to SEQ ID NO: 52. In some embodiments, an antibody, or antigen binding fragment thereof, comprises a $V_L$ peptide having at least 85%, 86%, 87%, 88%, 89%, 90%, 91%, 92%, 93%, 94%, 95%, 96%, 97%, 98%, or 99% identity to SEQ ID NO: 52.

In some embodiments, an antibody, or antigen binding fragment thereof, comprises a $V_L$ peptide of SEQ ID NO: 54. In some embodiments, an antibody, or antigen binding fragment thereof, comprises a $V_L$ peptide having at least 85% identity to SEQ ID NO: 54. In some embodiments, an antibody, or antigen binding fragment thereof, comprises a $V_L$ peptide having at least 85%, 86%, 87%, 88%, 89%, 90%, 91%, 92%, 93%, 94%, 95%, 96%, 97%, 98%, or 99% identity to SEQ ID NO: 54.

In some embodiments, an antibody, or antigen binding fragment thereof, comprises a $V_L$ peptide of SEQ ID NO: 56. In some embodiments, an antibody, or antigen binding fragment thereof, comprises a $V_L$ peptide having at least 85% identity to SEQ ID NO: 56. In some embodiments, an antibody, or antigen binding fragment thereof, comprises a $V_L$ peptide having at least 85%, 86%, 87%, 88%, 89%, 90%, 91%, 92%, 93%, 94%, 95%, 96%, 97%, 98%, or 99% identity to SEQ ID NO: 56.

In some embodiments, an antibody, or antigen binding fragment thereof, comprises a $V_L$ peptide of SEQ ID NO: 58. In some embodiments, an antibody, or antigen binding fragment thereof, comprises a $V_L$ peptide having at least 85% identity to SEQ ID NO: 58. In some embodiments, an antibody, or antigen binding fragment thereof, comprises a $V_L$ peptide having at least 85%, 86%, 87%, 88%, 89%, 90%, 91%, 92%, 93%, 94%, 95%, 96%, 97%, 98%, or 99% identity to SEQ ID NO: 58.

In some embodiments, an antibody, or antigen binding fragment thereof, comprises a $V_L$ peptide of SEQ ID NO: 60. In some embodiments, an antibody, or antigen binding fragment thereof, comprises a $V_L$ peptide having at least 85% identity to SEQ ID NO: 60. In some embodiments, an antibody, or antigen binding fragment thereof, comprises a $V_L$ peptide having at least 85%, 86%, 87%, 88%, 89%, 90%, 91%, 92%, 93%, 94%, 95%, 96%, 97%, 98%, or 99% identity to SEQ ID NO: 60.

In some embodiments, an antibody, or antigen binding fragment thereof, comprises a $V_H$ peptide and a $V_L$ peptide, wherein the wherein the $V_H$ peptide comprises a sequence of SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 334, 335, 336, 337, 338, 339, 340, 341, 342, 343, 344, 345, 346, 347, 348, 349, 350, 351, 352, 353, 354, 355, 356, 35358, 359, 360, 361, 362, or 363, or a variant thereof; and the $V_L$ peptide comprises a sequence of SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, or 60, or a variant thereof. In some embodiments, an antibody, or antigen binding fragment thereof, comprises a $V_H$ peptide and a $V_L$ peptide, wherein the wherein the $V_H$ peptide has at least 85%, 86%, 87%, 88%, 89%, 90%, 91%, 92%, 93%, 94%, 95%, 96%, 97%, 98%, or 99% identity to SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 334, 335, 336, 337, 338, 339, 340, 341, 342, 343, 344, 345, 346, 347, 348, 349, 350, 351, 352, 353, 354, 355, 356, 35358, 359, 360, 361, 362, or 363; and the $V_L$ peptide has at least 85%, 86%, 87%, 88%, 89%, 90%, 91%, 92%, 93%, 94%, 95%, 96%, 97%, 98%, or 99% identity to SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, or 60. In some of these embodiments, the $V_H$ peptide comprises a sequence of SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 334, 335, 336, 337, 338, 339, 340, 341, 342, 343, 344, 345, 346, 347, 348, 349, 350, 351, 352, 353, 354, 355, 356, 35358, 359, 360, 361, 362, or 363; and the $V_L$ peptide comprises a sequence of SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, or 60.

In some embodiments, the heavy chain of the antibody, or antigen binding fragment thereof, comprises a heavy chain variable region having at least 85%, 86%, 87%, 88%, 89%, 90%, 91%, 92%, 93%, 94%, 95%, 96%, 97%, 98%, 99%, or 100% identity to SEQ ID NO: 1, wherein the antibody, or antigen binding fragment thereof, maintains a HCDR1 sequence of SEQ ID NO: 61, SEQ ID NO: 124, or SEQ ID NO: 130, maintains a HCDR2 sequence of SEQ ID NO: 62, SEQ ID NO: 125, or SEQ ID NO: 131, maintains a HCDR3 sequence of SEQ ID NO: 63 or SEQ ID NO: 132, maintains a LCDR1 sequence of SEQ ID NO: 64, or SEQ ID NO: 133, maintains a LCDR2 sequence of SEQ ID NO: 65, or SEQ ID NO: 134, and maintains a LCDR3 sequence of SEQ ID NO: 66

In some embodiments, the heavy chain of the antibody, or antigen binding fragment thereof, comprises a heavy chain variable region having at least 85%, 86%, 87%, 88%, 89%, 90%, 91%, 92%, 93%, 94%, 95%, 96%, 97%, 98%, 99%, or 100% identity to SEQ ID NO: 3, wherein the antibody, or antigen binding fragment thereof, maintains a HCDR1 sequence of SEQ ID NO: 61, SEQ ID NO: 124, or SEQ ID NO: 130, maintains a HCDR2 sequence of SEQ ID NO: 62, SEQ ID NO: 125, or SEQ ID NO: 131, maintains a HCDR3 sequence of SEQ ID NO: 67 or SEQ ID NO: 135, maintains a LCDR1 sequence of SEQ ID NO: 64, or SEQ ID NO: 1339, maintains a LCDR2 sequence of SEQ ID NO: 65, or SEQ ID NO: 134, and maintains a LCDR3 sequence SEQ ID NO: 68.

In some embodiments, the heavy chain of the antibody, or antigen binding fragment thereof, comprises a heavy chain variable region having at least 85%, 86%, 87%, 88%, 89%, 90%, 91%, 92%, 93%, 94%, 95%, 96%, 97%, 98%, 99%, or 100% identity to SEQ ID NO: 5, wherein the antibody, or antigen binding fragment thereof, maintains a HCDR1 sequence of SEQ ID NO: 61, SEQ ID NO: 124, or SEQ ID NO: 130, maintains a HCDR2 sequence of SEQ ID NO: 62, SEQ ID NO: 125, or SEQ ID NO: 131, maintains a HCDR3 sequence of SEQ ID NO: 69 or SEQ ID NO: 136, maintains a LCDR1 sequence of SEQ ID NO: 64, or SEQ ID NO: 133, maintains a LCDR2 sequence of SEQ ID NO: 65, or SEQ ID NO: 134, and maintains a LCDR3 sequence SEQ ID NO: 68.

In some embodiments, the heavy chain of the antibody, or antigen binding fragment thereof, comprises a heavy chain variable region having at least 85%, 86%, 87%, 88%, 89%, 90%, 91%, 92%, 93%, 94%, 95%, 96%, 97%, 98%, 99%, or 100% identity to SEQ ID NO: 7, wherein the antibody, or antigen binding fragment thereof, maintains a HCDR1 sequence of SEQ ID NO: 61, SEQ ID NO: 124, or SEQ ID NO: 130, maintains a HCDR2 sequence of SEQ ID NO: 62, SEQ ID NO: 125, or SEQ ID NO: 131, maintains a HCDR3 sequence of SEQ ID NO: 70 or SEQ ID NO: 137, maintains a LCDR1 sequence of SEQ ID NO: 64, or SEQ ID NO: 133, maintains a LCDR2 sequence of SEQ ID NO: 65, or SEQ ID NO: 134, and maintains a LCDR3 sequence SEQ ID NO: 71.

In some embodiments, the heavy chain of the antibody, or antigen binding fragment thereof, comprises a heavy chain variable region having at least 85%, 86%, 87%, 88%, 89%, 90%, 91%, 92%, 93%, 94%, 95%, 96%, 97%, 98%, 99%, or 100% identity to SEQ ID NO: 9, wherein the antibody, or antigen binding fragment thereof, maintains a HCDR1 sequence of SEQ ID NO: 61, SEQ ID NO: 124, or SEQ ID NO: 130, maintains a HCDR2 sequence of SEQ ID NO: 62, SEQ ID NO: 125, or SEQ ID NO: 131, maintains a HCDR3 sequence of SEQ ID NO: 72 or SEQ ID NO: 138, maintains a LCDR1 sequence of SEQ ID NO: 64, or SEQ ID NO: 133, maintains a LCDR2 sequence of SEQ ID NO: 65, or SEQ ID NO: 134, and maintains a LCDR3 sequence SEQ ID NO: 71.

In some embodiments, the heavy chain of the antibody, or antigen binding fragment thereof, comprises a heavy chain variable region having at least 85%, 86%, 87%, 88%, 89%, 90%, 91%, 92%, 93%, 94%, 95%, 96%, 97%, 98%, 99%, or 100% identity to SEQ ID NO: 11, wherein the antibody, or antigen binding fragment thereof, maintains a HCDR1 sequence of SEQ ID NO: 61, SEQ ID NO: 124, or SEQ ID NO: 130, maintains a HCDR2 sequence of SEQ ID NO: 62, SEQ ID NO: 125, or SEQ ID NO: 131, maintains a HCDR3 sequence of SEQ ID NO: 73 or SEQ ID NO: 139, maintains a LCDR1 sequence of SEQ ID NO: 64, or SEQ ID NO: 133, maintains a LCDR2 sequence of SEQ ID NO: 65, or SEQ ID NO: 134, and maintains a LCDR3 sequence SEQ ID NO: 71.

In some embodiments, the heavy chain of the antibody, or antigen binding fragment thereof, comprises a heavy chain variable region having at least 85%, 86%, 87%, 88%, 89%, 90%, 91%, 92%, 93%, 94%, 95%, 96%, 97%, 98%, 99%, or 100% identity to SEQ ID NO: 13, wherein the antibody, or antigen binding fragment thereof, maintains a HCDR1 sequence of SEQ ID NO: 61, SEQ ID NO: 124, or SEQ ID NO: 130, maintains a HCDR2 sequence of SEQ ID NO: 62, SEQ ID NO: 125, or SEQ ID NO: 131, maintains a HCDR3 sequence of SEQ ID NO: 74 or SEQ ID NO: 140, maintains a LCDR1 sequence of SEQ ID NO: 64, or SEQ ID NO: 133, maintains a LCDR2 sequence of SEQ ID NO: 65, or SEQ ID NO: 134, and maintains a LCDR3 sequence SEQ ID NO: 75.

In some embodiments, the heavy chain of the antibody, or antigen binding fragment thereof, comprises a heavy chain variable region having at least 85%, 86%, 87%, 88%, 89%, 90%, 91%, 92%, 93%, 94%, 95%, 96%, 97%, 98%, 99%, or 100% identity to SEQ ID NO: 15, wherein the antibody, or antigen binding fragment thereof, maintains a HCDR1 sequence of SEQ ID NO: 61, SEQ ID NO: 124, or SEQ ID NO: 130, maintains a HCDR2 sequence of SEQ ID NO: 62, SEQ ID NO: 125, or SEQ ID NO: 131, maintains a HCDR3 sequence of SEQ ID NO: 76 or SEQ ID NO: 141, maintains a LCDR1 sequence of SEQ ID NO: 64, or SEQ ID NO: 133, maintains a LCDR2 sequence of SEQ ID NO: 65, or SEQ ID NO: 134, and maintains a LCDR3 sequence SEQ ID NO: 77.

In some embodiments, the heavy chain of the antibody, or antigen binding fragment thereof, comprises a heavy chain variable region having at least 85%, 86%, 87%, 88%, 89%, 90%, 91%, 92%, 93%, 94%, 95%, 96%, 97%, 98%, 99%, or 100% identity to SEQ ID NO: 17, wherein the antibody, or antigen binding fragment thereof, maintains a HCDR1 sequence of SEQ ID NO: 61, SEQ ID NO: 124, or SEQ ID NO: 130, maintains a HCDR2 sequence of SEQ ID NO: 62, SEQ ID NO: 125, or SEQ ID NO: 131, maintains a HCDR3 sequence of SEQ ID NO: 78 or SEQ ID NO: 142, maintains a LCDR1 sequence of SEQ ID NO: 64, or SEQ ID NO: 133, maintains a LCDR2 sequence of SEQ ID NO: 65, or SEQ ID NO: 134, and maintains a LCDR3 sequence SEQ ID NO: 79.

In some embodiments, the heavy chain of the antibody, or antigen binding fragment thereof, comprises a heavy chain variable region having at least 85%, 86%, 87%, 88%, 89%, 90%, 91%, 92%, 93%, 94%, 95%, 96%, 97%, 98%, 99%, or 100% identity to SEQ ID NO: 19, wherein the antibody, or antigen binding fragment thereof, maintains a HCDR1 sequence of SEQ ID NO: 61, SEQ ID NO: 124, or SEQ ID NO: 130, maintains a HCDR2 sequence of SEQ ID NO: 62, SEQ ID NO: 125, or SEQ ID NO: 131, maintains a HCDR3 sequence of SEQ ID NO: 80 or SEQ ID NO: 143, maintains a LCDR1 sequence of SEQ ID NO: 64, or SEQ ID NO: 133, maintains a LCDR2 sequence of SEQ ID NO: 65, or SEQ ID NO: 134, and maintains a LCDR3 sequence SEQ ID NO: 81.

In some embodiments, the heavy chain of the antibody, or antigen binding fragment thereof, comprises a heavy chain variable region having at least 85%, 86%, 87%, 88%, 89%, 90%, 91%, 92%, 93%, 94%, 95%, 96%, 97%, 98%, 99%, or 100% identity to SEQ ID NO: 21, wherein the antibody, or antigen binding fragment thereof, maintains a HCDR1 sequence of SEQ ID NO: 82, SEQ ID NO: 126, or SEQ ID NO: 144, maintains a HCDR2 sequence of SEQ ID NO: 83, SEQ ID NO: 127, or SEQ ID NO: 145, maintains a HCDR3 sequence of SEQ ID NO: 84 or SEQ ID NO: 146, maintains a LCDR1 sequence of SEQ ID NO: 85, or SEQ ID NO: 147, maintains a LCDR2 sequence of SEQ ID NO: 86, or SEQ ID NO: 148, and maintains a LCDR3 sequence SEQ ID NO: 87.

In some embodiments, the heavy chain of the antibody, or antigen binding fragment thereof, comprises a heavy chain variable region having at least 85%, 86%, 87%, 88%, 89%, 90%, 91%, 92%, 93%, 94%, 95%, 96%, 97%, 98%, 99%, or 100% identity to SEQ ID NO: 23, wherein the antibody, or antigen binding fragment thereof, maintains a HCDR1 sequence of SEQ ID NO: 82, SEQ ID NO: 126, or SEQ ID NO: 144, maintains a HCDR2 sequence of SEQ ID NO: 83, SEQ ID NO: 127, or SEQ ID NO: 145, maintains a HCDR3 sequence of SEQ ID NO: 88 or SEQ ID NO: 149, maintains a LCDR1 sequence of SEQ ID NO: 85, or SEQ ID NO: 147, maintains a LCDR2 sequence of SEQ ID NO: 86, or SEQ ID NO: 148, and maintains a LCDR3 sequence SEQ ID NO: 89.

In some embodiments, the heavy chain of the antibody, or antigen binding fragment thereof, comprises a heavy chain variable region having at least 85%, 86%, 87%, 88%, 89%, 90%, 91%, 92%, 93%, 94%, 95%, 96%, 97%, 98%, 99%, or 100% identity to SEQ ID NO: 25, wherein the antibody, or antigen binding fragment thereof, maintains a HCDR1 sequence of SEQ ID NO: 82, SEQ ID NO: 126, or SEQ ID NO: 144, maintains a HCDR2 sequence of SEQ ID NO: 83, SEQ ID NO: 127, or SEQ ID NO: 145, maintains a HCDR3 sequence of SEQ ID NO: 90 or SEQ ID NO: 150, maintains a LCDR1 sequence of SEQ ID NO: 85, or SEQ ID NO: 147, maintains a LCDR2 sequence of SEQ ID NO: 86, or SEQ ID NO: 148, and maintains a LCDR3 sequence SEQ ID NO: 89.

In some embodiments, the heavy chain of the antibody, or antigen binding fragment thereof, comprises a heavy chain variable region having at least 85%, 86%, 87%, 88%, 89%, 90%, 91%, 92%, 93%, 94%, 95%, 96%, 97%, 98%, 99%, or 100% identity to SEQ ID NO: 27, wherein the antibody, or antigen binding fragment thereof, maintains a HCDR1 sequence of SEQ ID NO: 82, SEQ ID NO: 126, or SEQ ID NO: 144, maintains a HCDR2 sequence of SEQ ID NO: 83, SEQ ID NO: 127, or SEQ ID NO: 145, maintains a HCDR3 sequence of SEQ ID NO: 91 or SEQ ID NO: 151, maintains a LCDR1 sequence of SEQ ID NO: 85, or SEQ ID NO: 147, maintains a LCDR2 sequence of SEQ ID NO: 86, or SEQ ID NO: 148, and maintains a LCDR3 sequence SEQ ID NO: 92.

In some embodiments, the heavy chain of the antibody, or antigen binding fragment thereof, comprises a heavy chain variable region having at least 85%, 86%, 87%, 88%, 89%, 90%, 91%, 92%, 93%, 94%, 95%, 96%, 97%, 98%, 99%, or 100% identity to SEQ ID NO: 29, wherein the antibody, or antigen binding fragment thereof, maintains a HCDR1 sequence of SEQ ID NO: 82, SEQ ID NO: 126, or SEQ ID NO: 144, maintains a HCDR2 sequence of SEQ ID NO: 83, SEQ ID NO: 127, or SEQ ID NO: 145, maintains a HCDR3 sequence of SEQ ID NO: 93 or SEQ ID NO: 152, maintains a LCDR1 sequence of SEQ ID NO: 85, or SEQ ID NO: 147, maintains a LCDR2 sequence of SEQ ID NO: 86, or SEQ ID NO: 148, and maintains a LCDR3 sequence SEQ ID NO: 94.

In some embodiments, the heavy chain of the antibody, or antigen binding fragment thereof, comprises a heavy chain variable region having at least 85%, 86%, 87%, 88%, 89%, 90%, 91%, 92%, 93%, 94%, 95%, 96%, 97%, 98%, 99%, or 100% identity to SEQ ID NO: 31, wherein the antibody, or antigen binding fragment thereof, maintains a HCDR1 sequence of SEQ ID NO: 82, SEQ ID NO: 126, or SEQ ID NO: 144, maintains a HCDR2 sequence of SEQ ID NO: 83, SEQ ID NO: 127, or SEQ ID NO: 145, maintains a HCDR3 sequence of SEQ ID NO: 84 or SEQ ID NO: 146, maintains a LCDR1 sequence of SEQ ID NO: 85, or SEQ ID NO: 147, maintains a LCDR2 sequence of SEQ ID NO: 86, or SEQ ID NO: 148, and maintains a LCDR3 sequence SEQ ID NO: 95.

In some embodiments, the heavy chain of the antibody, or antigen binding fragment thereof, comprises a heavy chain variable region having at least 85%, 86%, 87%, 88%, 89%, 90%, 91%, 92%, 93%, 94%, 95%, 96%, 97%, 98%, 99%, or 100% identity to SEQ ID NO: 33, wherein the antibody, or antigen binding fragment thereof, maintains a HCDR1 sequence of SEQ ID NO: 82, SEQ ID NO: 126, or SEQ ID NO: 144, maintains a HCDR2 sequence of SEQ ID NO: 83, SEQ ID NO: 127, or SEQ ID NO: 145, maintains a HCDR3 sequence of SEQ ID NO: 96 or SEQ ID NO: 153, maintains a LCDR1 sequence of SEQ ID NO: 85, or SEQ ID NO: 147, maintains a LCDR2 sequence of SEQ ID NO: 86, or SEQ ID NO: 148, and maintains a LCDR3 sequence SEQ ID NO: 97.

In some embodiments, the heavy chain of the antibody, or antigen binding fragment thereof, comprises a heavy chain variable region having at least 85%, 86%, 87%, 88%, 89%, 90%, 91%, 92%, 93%, 94%, 95%, 96%, 97%, 98%, 99%, or 100% identity to SEQ ID NO: 35, wherein the antibody, or antigen binding fragment thereof, maintains a HCDR1 sequence of SEQ ID NO: 82, SEQ ID NO: 126, or SEQ ID NO: 144, maintains a HCDR2 sequence of SEQ ID NO: 83, SEQ ID NO: 127, or SEQ ID NO: 145, maintains a HCDR3 sequence of SEQ ID NO: 98 or SEQ ID NO: 154, maintains a LCDR1 sequence of SEQ ID NO: 85, or SEQ ID NO: 147, maintains a LCDR2 sequence of SEQ ID NO: 86, or SEQ ID NO: 148, and maintains a LCDR3 sequence SEQ ID NO: 99.

In some embodiments, the heavy chain of the antibody, or antigen binding fragment thereof, comprises a heavy chain variable region having at least 85%, 86%, 87%, 88%, 89%, 90%, 91%, 92%, 93%, 94%, 95%, 96%, 97%, 98%, 99%, or 100% identity to SEQ ID NO: 37, wherein the antibody, or antigen binding fragment thereof, maintains a HCDR1 sequence of SEQ ID NO: 82, SEQ ID NO: 126, or SEQ ID NO: 144, maintains a HCDR2 sequence of SEQ ID NO: 83, SEQ ID NO: 127, or SEQ ID NO: 145, maintains a HCDR3 sequence of SEQ ID NO: 100 or SEQ ID NO: 155, maintains a LCDR1 sequence of SEQ ID NO: 85, or SEQ ID NO: 147, maintains a LCDR2 sequence of SEQ ID NO: 86, or SEQ ID NO: 148, and maintains a LCDR3 sequence SEQ ID NO: 101.

In some embodiments, the heavy chain of the antibody, or antigen binding fragment thereof, comprises a heavy chain variable region having at least 85%, 86%, 87%, 88%, 89%, 90%, 91%, 92%, 93%, 94%, 95%, 96%, 97%, 98%, 99%, or 100% identity to SEQ ID NO: 39, wherein the antibody, or antigen binding fragment thereof, maintains a HCDR1 sequence of SEQ ID NO: 82, SEQ ID NO: 126, or SEQ ID NO: 144, maintains a HCDR2 sequence of SEQ ID NO: 83, SEQ ID NO: 127, or SEQ ID NO: 145, maintains a HCDR3 sequence of SEQ ID NO: 100 or SEQ ID NO: 155, maintains a LCDR1 sequence of SEQ ID NO: 85, or SEQ ID NO: 147, maintains a LCDR2 sequence of SEQ ID NO: 86, or SEQ ID NO: 148, and maintains a LCDR3 sequence SEQ ID NO: 102.

In some embodiments, the heavy chain of the antibody, or antigen binding fragment thereof, comprises a heavy chain variable region having at least 85%, 86%, 87%, 88%, 89%, 90%, 91%, 92%, 93%, 94%, 95%, 96%, 97%, 98%, 99%, or 100% identity to SEQ ID NO: 41, wherein the antibody, or antigen binding fragment thereof, maintains a HCDR1 sequence of SEQ ID NO: 103, SEQ ID NO: 128, or SEQ ID NO: 156, maintains a HCDR2 sequence of SEQ ID NO: 104, SEQ ID NO: 129, or SEQ ID NO: 157, maintains a HCDR3 sequence of SEQ ID NO: 105 or SEQ ID NO: 158, maintains a LCDR1 sequence of SEQ ID NO: 106, or SEQ ID NO: 159, maintains a LCDR2 sequence of SEQ ID NO: 107, or SEQ ID NO: 160, and maintains a LCDR3 sequence SEQ ID NO: 108.

In some embodiments, the heavy chain of the antibody, or antigen binding fragment thereof, comprises a heavy chain variable region having at least 85%, 86%, 87%, 88%, 89%, 90%, 91%, 92%, 93%, 94%, 95%, 96%, 97%, 98%, 99%, or 100% identity to SEQ ID NO: 43, wherein the antibody, or antigen binding fragment thereof, maintains a HCDR1 sequence of SEQ ID NO: 103, SEQ ID NO: 128, or SEQ ID NO: 156, maintains a HCDR2 sequence of SEQ ID NO: 104, SEQ ID NO: 129, or SEQ ID NO: 157, maintains a HCDR3 sequence of SEQ ID NO: 109 or SEQ ID NO: 161, maintains a LCDR1 sequence of SEQ ID NO: 106, or SEQ ID NO: 159, maintains a LCDR2 sequence of SEQ ID NO: 107, or SEQ ID NO: 160, and maintains a LCDR3 sequence SEQ ID NO: 110.

In some embodiments, the heavy chain of the antibody, or antigen binding fragment thereof, comprises a heavy chain variable region having at least 85%, 86%, 87%, 88%, 89%, 90%, 91%, 92%, 93%, 94%, 95%, 96%, 97%, 98%, 99%, or 100% identity to SEQ ID NO: 45, wherein the antibody, or antigen binding fragment thereof, maintains a HCDR1 sequence of SEQ ID NO: 103, SEQ ID NO: 128, or SEQ ID NO: 156, maintains a HCDR2 sequence of SEQ ID NO: 104, SEQ ID NO: 129, or SEQ ID NO: 157, maintains a HCDR3 sequence of SEQ ID NO: 111 or SEQ ID NO: 162, maintains a LCDR1 sequence of SEQ ID NO: 106, or SEQ ID NO: 159, maintains a LCDR2 sequence of SEQ ID NO: 107, or SEQ ID NO: 160, and maintains a LCDR3 sequence SEQ ID NO: 112.

In some embodiments, the heavy chain of the antibody, or antigen binding fragment thereof, comprises a heavy chain variable region having at least 85%, 86%, 87%, 88%, 89%, 90%, 91%, 92%, 93%, 94%, 95%, 96%, 97%, 98%, 99%, or 100% identity to SEQ ID NO: 47, wherein the antibody, or antigen binding fragment thereof, maintains a HCDR1 sequence of SEQ ID NO: 103, SEQ ID NO: 128, or SEQ ID NO: 156, maintains a HCDR2 sequence of SEQ ID NO: 104, SEQ ID NO: 129, or SEQ ID NO: 157, maintains a HCDR3 sequence of SEQ ID NO: 105 or SEQ ID NO: 158, maintains a LCDR1 sequence of SEQ ID NO: 106, or SEQ ID NO: 159, maintains a LCDR2 sequence of SEQ ID NO: 107, or SEQ ID NO: 160, and maintains a LCDR3 sequence SEQ ID NO: 113.

In some embodiments, the heavy chain of the antibody, or antigen binding fragment thereof, comprises a heavy chain variable region having at least 85%, 86%, 87%, 88%, 89%, 90%, 91%, 92%, 93%, 94%, 95%, 96%, 97%, 98%, 99%, or 100% identity to SEQ ID NO: 49, wherein the antibody, or antigen binding fragment thereof, maintains a HCDR1 sequence of SEQ ID NO: 103, SEQ ID NO: 128, or SEQ ID NO: 156, maintains a HCDR2 sequence of SEQ ID NO: 104, SEQ ID NO: 129, or SEQ ID NO: 157, maintains a HCDR3 sequence of SEQ ID NO: 114 or SEQ ID NO: 163, maintains a LCDR1 sequence of SEQ ID NO: 106, or SEQ ID NO: 159, maintains a LCDR2 sequence of SEQ ID NO: 107, or SEQ ID NO: 160, and maintains a LCDR3 sequence SEQ ID NO: 115.

In some embodiments, the heavy chain of the antibody, or antigen binding fragment thereof, comprises a heavy chain variable region having at least 85%, 86%, 87%, 88%, 89%, 90%, 91%, 92%, 93%, 94%, 95%, 96%, 97%, 98%, 99%, or 100% identity to SEQ ID NO: 51, wherein the antibody, or antigen binding fragment thereof, maintains a HCDR1 sequence of SEQ ID NO: 103, SEQ ID NO: 128, or SEQ ID NO: 156, maintains a HCDR2 sequence of SEQ ID NO: 104, SEQ ID NO: 129, or SEQ ID NO: 157, maintains a HCDR3 sequence of SEQ ID NO: 116 or SEQ ID NO: 164, maintains a LCDR1 sequence of SEQ ID NO: 106, or SEQ ID NO: 159, maintains a LCDR2 sequence of SEQ ID NO: 107, or SEQ ID NO: 160, and maintains a LCDR3 sequence SEQ ID NO: 113.

In some embodiments, the heavy chain of the antibody, or antigen binding fragment thereof, comprises a heavy chain variable region having at least 85%, 86%, 87%, 88%, 89%, 90%, 91%, 92%, 93%, 94%, 95%, 96%, 97%, 98%, 99%, or 100% identity to SEQ ID NO: 53, wherein the antibody, or antigen binding fragment thereof, maintains a HCDR1 sequence of SEQ ID NO: 103, SEQ ID NO: 128, or SEQ ID NO: 156, maintains a HCDR2 sequence of SEQ ID NO: 104, SEQ ID NO: 129, or SEQ ID NO: 157, maintains a HCDR3 sequence of SEQ ID NO: 117 or SEQ ID NO: 165, maintains a LCDR1 sequence of SEQ ID NO: 106, or SEQ ID NO: 159, maintains a LCDR2 sequence of SEQ ID NO: 107, or SEQ ID NO: 160, and maintains a LCDR3 sequence SEQ ID NO: 118.

In some embodiments, the heavy chain of the antibody, or antigen binding fragment thereof, comprises a heavy chain variable region having at least 85%, 86%, 87%, 88%, 89%, 90%, 91%, 92%, 93%, 94%, 95%, 96%, 97%, 98%, 99%, or 100% identity to SEQ ID NO: 55, wherein the antibody, or antigen binding fragment thereof, maintains a HCDR1 sequence of SEQ ID NO: 103, SEQ ID NO: 128, or SEQ ID NO: 156, maintains a HCDR2 sequence of SEQ ID NO: 104, SEQ ID NO: 129, or SEQ ID NO: 157, maintains a HCDR3 sequence of SEQ ID NO: 116 or SEQ ID NO: 164, maintains a LCDR1 sequence of SEQ ID NO: 106, or SEQ ID NO: 159, maintains a LCDR2 sequence of SEQ ID NO: 107, or SEQ ID NO: 160, and maintains a LCDR3 sequence SEQ ID NO: 119.

In some embodiments, the heavy chain of the antibody, or antigen binding fragment thereof, comprises a heavy chain variable region having at least 85%, 86%, 87%, 88%, 89%, 90%, 91%, 92%, 93%, 94%, 95%, 96%, 97%, 98%, 99%, or 100% identity to SEQ ID NO: 57, wherein the antibody, or antigen binding fragment thereof, maintains a HCDR1 sequence of SEQ ID NO: 103, SEQ ID NO: 128, or SEQ ID NO: 156, maintains a HCDR2 sequence of SEQ ID NO: 104, SEQ ID NO: 129, or SEQ ID NO: 157, maintains a HCDR3 sequence of SEQ ID NO: 120 or SEQ ID NO: 166, maintains a LCDR1 sequence of SEQ ID NO: 106, or SEQ ID NO: 159, maintains a LCDR2 sequence of SEQ ID NO: 107, or SEQ ID NO: 160, and maintains a LCDR3 sequence SEQ ID NO: 121.

In some embodiments, the heavy chain of the antibody, or antigen binding fragment thereof, comprises a heavy chain variable region having at least 85%, 86%, 87%, 88%, 89%, 90%, 91%, 92%, 93%, 94%, 95%, 96%, 97%, 98%, 99%, or 100% identity to SEQ ID NO: 59, wherein the antibody, or antigen binding fragment thereof, maintains a HCDR1 sequence of SEQ ID NO: 103, SEQ ID NO: 128, or SEQ ID NO: 156, maintains a HCDR2 sequence of SEQ ID NO: 104, SEQ ID NO: 129, or SEQ ID NO: 157, maintains a HCDR3 sequence of SEQ ID NO: 122 or SEQ ID NO: 167, maintains a LCDR1 sequence of SEQ ID NO: 106, or SEQ ID NO: 159, maintains a LCDR2 sequence of SEQ ID NO: 107, or SEQ ID NO: 160, and maintains a LCDR3 sequence SEQ ID NO: 123.

In some embodiments, the heavy chain of the antibody, or antigen binding fragment thereof, comprises a heavy chain variable region having at least 85%, 86%, 87%, 88%, 89%, 90%, 91%, 92%, 93%, 94%, 95%, 96%, 97%, 98%, 99%, or 100% identity to SEQ ID NO: 334, wherein the antibody, or antigen binding fragment thereof, maintains a HCDR1 sequence of SEQ ID NO: 61, SEQ ID NO: 124, or SEQ ID NO: 130, maintains a HCDR2 sequence of SEQ ID NO: 62, SEQ ID NO: 125, or SEQ ID NO: 131, maintains a HCDR3 sequence of SEQ ID NO: 63 or SEQ ID NO: 132, maintains a LCDR1 sequence of SEQ ID NO: 64, or SEQ ID NO: 133, maintains a LCDR2 sequence of SEQ ID NO: 65, or SEQ ID NO: 134, and maintains a LCDR3 sequence of SEQ ID NO: 66

In some embodiments, the heavy chain of the antibody, or antigen binding fragment thereof, comprises a heavy chain variable region having at least 85%, 86%, 87%, 88%, 89%, 90%, 91%, 92%, 93%, 94%, 95%, 96%, 97%, 98%, 99%, or 100% identity to SEQ ID NO: 335, wherein the antibody, or antigen binding fragment thereof, maintains a HCDR1 sequence of SEQ ID NO: 61, SEQ ID NO: 124, or SEQ ID NO: 130, maintains a HCDR2 sequence of SEQ ID NO: 62, SEQ ID NO: 125, or SEQ ID NO: 131, maintains a HCDR3 sequence of SEQ ID NO: 67 or SEQ ID NO: 135, maintains a LCDR1 sequence of SEQ ID NO: 64, or SEQ ID NO:

1339, maintains a LCDR2 sequence of SEQ ID NO: 65, or SEQ ID NO: 134, and maintains a LCDR3 sequence SEQ ID NO: 68.

In some embodiments, the heavy chain of the antibody, or antigen binding fragment thereof, comprises a heavy chain variable region having at least 85%, 86%, 87%, 88%, 89%, 90%, 91%, 92%, 93%, 94%, 95%, 96%, 97%, 98%, 99%, or 100% identity to SEQ ID NO: 336, wherein the antibody, or antigen binding fragment thereof, maintains a HCDR1 sequence of SEQ ID NO: 61, SEQ ID NO: 124, or SEQ ID NO: 130, maintains a HCDR2 sequence of SEQ ID NO: 62, SEQ ID NO: 125, or SEQ ID NO: 131, maintains a HCDR3 sequence of SEQ ID NO: 69 or SEQ ID NO: 136, maintains a LCDR1 sequence of SEQ ID NO: 64, or SEQ ID NO: 133, maintains a LCDR2 sequence of SEQ ID NO: 65, or SEQ ID NO: 134, and maintains a LCDR3 sequence SEQ ID NO: 68.

In some embodiments, the heavy chain of the antibody, or antigen binding fragment thereof, comprises a heavy chain variable region having at least 85%, 86%, 87%, 88%, 89%, 90%, 91%, 92%, 93%, 94%, 95%, 96%, 97%, 98%, 99%, or 100% identity to SEQ ID NO: 337, wherein the antibody, or antigen binding fragment thereof, maintains a HCDR1 sequence of SEQ ID NO: 61, SEQ ID NO: 124, or SEQ ID NO: 130, maintains a HCDR2 sequence of SEQ ID NO: 62, SEQ ID NO: 125, or SEQ ID NO: 131, maintains a HCDR3 sequence of SEQ ID NO: 70 or SEQ ID NO: 137, maintains a LCDR1 sequence of SEQ ID NO: 64, or SEQ ID NO: 133, maintains a LCDR2 sequence of SEQ ID NO: 65, or SEQ ID NO: 134, and maintains a LCDR3 sequence SEQ ID NO: 71.

In some embodiments, the heavy chain of the antibody, or antigen binding fragment thereof, comprises a heavy chain variable region having at least 85%, 86%, 87%, 88%, 89%, 90%, 91%, 92%, 93%, 94%, 95%, 96%, 97%, 98%, 99%, or 100% identity to SEQ ID NO: 338, wherein the antibody, or antigen binding fragment thereof, maintains a HCDR1 sequence of SEQ ID NO: 61, SEQ ID NO: 124, or SEQ ID NO: 130, maintains a HCDR2 sequence of SEQ ID NO: 62, SEQ ID NO: 125, or SEQ ID NO: 131, maintains a HCDR3 sequence of SEQ ID NO: 72 or SEQ ID NO: 138, maintains a LCDR1 sequence of SEQ ID NO: 64, or SEQ ID NO: 133, maintains a LCDR2 sequence of SEQ ID NO: 65, or SEQ ID NO: 134, and maintains a LCDR3 sequence SEQ ID NO: 71.

In some embodiments, the heavy chain of the antibody, or antigen binding fragment thereof, comprises a heavy chain variable region having at least 85%, 86%, 87%, 88%, 89%, 90%, 91%, 92%, 93%, 94%, 95%, 96%, 97%, 98%, 99%, or 100% identity to SEQ ID NO: 339, wherein the antibody, or antigen binding fragment thereof, maintains a HCDR1 sequence of SEQ ID NO: 61, SEQ ID NO: 124, or SEQ ID NO: 130, maintains a HCDR2 sequence of SEQ ID NO: 62, SEQ ID NO: 125, or SEQ ID NO: 131, maintains a HCDR3 sequence of SEQ ID NO: 73 or SEQ ID NO: 139, maintains a LCDR1 sequence of SEQ ID NO: 64, or SEQ ID NO: 133, maintains a LCDR2 sequence of SEQ ID NO: 65, or SEQ ID NO: 134, and maintains a LCDR3 sequence SEQ ID NO: 71.

In some embodiments, the heavy chain of the antibody, or antigen binding fragment thereof, comprises a heavy chain variable region having at least 85%, 86%, 87%, 88%, 89%, 90%, 91%, 92%, 93%, 94%, 95%, 96%, 97%, 98%, 99%, or 100% identity to SEQ ID NO: 340, wherein the antibody, or antigen binding fragment thereof, maintains a HCDR1 sequence of SEQ ID NO: 61, SEQ ID NO: 124, or SEQ ID NO: 130, maintains a HCDR2 sequence of SEQ ID NO: 62, SEQ ID NO: 125, or SEQ ID NO: 131, maintains a HCDR3 sequence of SEQ ID NO: 74 or SEQ ID NO: 140, maintains a LCDR1 sequence of SEQ ID NO: 64, or SEQ ID NO: 133, maintains a LCDR2 sequence of SEQ ID NO: 65, or SEQ ID NO: 134, and maintains a LCDR3 sequence SEQ ID NO: 75.

In some embodiments, the heavy chain of the antibody, or antigen binding fragment thereof, comprises a heavy chain variable region having at least 85%, 86%, 87%, 88%, 89%, 90%, 91%, 92%, 93%, 94%, 95%, 96%, 97%, 98%, 99%, or 100% identity to SEQ ID NO: 341, wherein the antibody, or antigen binding fragment thereof, maintains a HCDR1 sequence of SEQ ID NO: 61, SEQ ID NO: 124, or SEQ ID NO: 130, maintains a HCDR2 sequence of SEQ ID NO: 62, SEQ ID NO: 125, or SEQ ID NO: 131, maintains a HCDR3 sequence of SEQ ID NO: 76 or SEQ ID NO: 141, maintains a LCDR1 sequence of SEQ ID NO: 64, or SEQ ID NO: 133, maintains a LCDR2 sequence of SEQ ID NO: 65, or SEQ ID NO: 134, and maintains a LCDR3 sequence SEQ ID NO: 77.

In some embodiments, the heavy chain of the antibody, or antigen binding fragment thereof, comprises a heavy chain variable region having at least 85%, 86%, 87%, 88%, 89%, 90%, 91%, 92%, 93%, 94%, 95%, 96%, 97%, 98%, 99%, or 100% identity to SEQ ID NO: 342, wherein the antibody, or antigen binding fragment thereof, maintains a HCDR1 sequence of SEQ ID NO: 61, SEQ ID NO: 124, or SEQ ID NO: 130, maintains a HCDR2 sequence of SEQ ID NO: 62, SEQ ID NO: 125, or SEQ ID NO: 131, maintains a HCDR3 sequence of SEQ ID NO: 78 or SEQ ID NO: 142, maintains a LCDR1 sequence of SEQ ID NO: 64, or SEQ ID NO: 133, maintains a LCDR2 sequence of SEQ ID NO: 65, or SEQ ID NO: 134, and maintains a LCDR3 sequence SEQ ID NO: 79.

In some embodiments, the heavy chain of the antibody, or antigen binding fragment thereof, comprises a heavy chain variable region having at least 85%, 86%, 87%, 88%, 89%, 90%, 91%, 92%, 93%, 94%, 95%, 96%, 97%, 98%, 99%, or 100% identity to SEQ ID NO: 343, wherein the antibody, or antigen binding fragment thereof, maintains a HCDR1 sequence of SEQ ID NO: 61, SEQ ID NO: 124, or SEQ ID NO: 130, maintains a HCDR2 sequence of SEQ ID NO: 62, SEQ ID NO: 125, or SEQ ID NO: 131, maintains a HCDR3 sequence of SEQ ID NO: 80 or SEQ ID NO: 143, maintains a LCDR1 sequence of SEQ ID NO: 64, or SEQ ID NO: 133, maintains a LCDR2 sequence of SEQ ID NO: 65, or SEQ ID NO: 134, and maintains a LCDR3 sequence SEQ ID NO: 81.

In some embodiments, the heavy chain of the antibody, or antigen binding fragment thereof, comprises a heavy chain variable region having at least 85%, 86%, 87%, 88%, 89%, 90%, 91%, 92%, 93%, 94%, 95%, 96%, 97%, 98%, 99%, or 100% identity to SEQ ID NO: 344, wherein the antibody, or antigen binding fragment thereof, maintains a HCDR1 sequence of SEQ ID NO: 82, SEQ ID NO: 126, or SEQ ID NO: 144, maintains a HCDR2 sequence of SEQ ID NO: 83, SEQ ID NO: 127, or SEQ ID NO: 145, maintains a HCDR3 sequence of SEQ ID NO: 84 or SEQ ID NO: 146, maintains a LCDR1 sequence of SEQ ID NO: 85, or SEQ ID NO: 147, maintains a LCDR2 sequence of SEQ ID NO: 86, or SEQ ID NO: 148, and maintains a LCDR3 sequence SEQ ID NO: 87.

In some embodiments, the heavy chain of the antibody, or antigen binding fragment thereof, comprises a heavy chain variable region having at least 85%, 86%, 87%, 88%, 89%, 90%, 91%, 92%, 93%, 94%, 95%, 96%, 97%, 98%, 99%, or 100% identity to SEQ ID NO: 345, wherein the antibody, or antigen binding fragment thereof, maintains a HCDR1 sequence of SEQ ID NO: 82, SEQ ID NO: 126, or SEQ ID NO: 144, maintains a HCDR2 sequence of SEQ ID NO: 83, SEQ ID NO: 127, or SEQ ID NO: 145, maintains a HCDR3 sequence of SEQ ID NO: 88 or SEQ ID NO: 149, maintains a LCDR1 sequence of SEQ ID NO: 85, or SEQ ID NO: 147, maintains a LCDR2 sequence of SEQ ID NO: 86, or SEQ ID NO: 148, and maintains a LCDR3 sequence SEQ ID NO: 89.

In some embodiments, the heavy chain of the antibody, or antigen binding fragment thereof, comprises a heavy chain variable region having at least 85%, 86%, 87%, 88%, 89%, 90%, 91%, 92%, 93%, 94%, 95%, 96%, 97%, 98%, 99%, or 100% identity to SEQ ID NO: 346, wherein the antibody, or antigen binding fragment thereof, maintains a HCDR1 sequence of SEQ ID NO: 82, SEQ ID NO: 126, or SEQ ID NO: 144, maintains a HCDR2 sequence of SEQ ID NO: 83, SEQ ID NO: 127, or SEQ ID NO: 145, maintains a HCDR3 sequence of SEQ ID NO: 90 or SEQ ID NO: 150, maintains a LCDR1 sequence of SEQ ID NO: 85, or SEQ ID NO: 147, maintains a LCDR2 sequence of SEQ ID NO: 86, or SEQ ID NO: 148, and maintains a LCDR3 sequence SEQ ID NO: 89.

In some embodiments, the heavy chain of the antibody, or antigen binding fragment thereof, comprises a heavy chain variable region having at least 85%, 86%, 87%, 88%, 89%, 90%, 91%, 92%, 93%, 94%, 95%, 96%, 97%, 98%, 99%, or 100% identity to SEQ ID NO: 347, wherein the antibody, or antigen binding fragment thereof, maintains a HCDR1 sequence of SEQ ID NO: 82, SEQ ID NO: 126, or SEQ ID NO: 144, maintains a HCDR2 sequence of SEQ ID NO: 83, SEQ ID NO: 127, or SEQ ID NO: 145, maintains a HCDR3 sequence of SEQ ID NO: 91 or SEQ ID NO: 151, maintains a LCDR1 sequence of SEQ ID NO: 85, or SEQ ID NO: 147, maintains a LCDR2 sequence of SEQ ID NO: 86, or SEQ ID NO: 148, and maintains a LCDR3 sequence SEQ ID NO: 92.

In some embodiments, the heavy chain of the antibody, or antigen binding fragment thereof, comprises a heavy chain variable region having at least 85%, 86%, 87%, 88%, 89%, 90%, 91%, 92%, 93%, 94%, 95%, 96%, 97%, 98%, 99%, or 100% identity to SEQ ID NO: 348, wherein the antibody, or antigen binding fragment thereof, maintains a HCDR1 sequence of SEQ ID NO: 82, SEQ ID NO: 126, or SEQ ID NO: 144, maintains a HCDR2 sequence of SEQ ID NO: 83, SEQ ID NO: 127, or SEQ ID NO: 145, maintains a HCDR3 sequence of SEQ ID NO: 93 or SEQ ID NO: 152, maintains a LCDR1 sequence of SEQ ID NO: 85, or SEQ ID NO: 147, maintains a LCDR2 sequence of SEQ ID NO: 86, or SEQ ID NO: 148, and maintains a LCDR3 sequence SEQ ID NO: 94.

In some embodiments, the heavy chain of the antibody, or antigen binding fragment thereof, comprises a heavy chain variable region having at least 85%, 86%, 87%, 88%, 89%, 90%, 91%, 92%, 93%, 94%, 95%, 96%, 97%, 98%, 99%, or 100% identity to SEQ ID NO: 349, wherein the antibody, or antigen binding fragment thereof, maintains a HCDR1 sequence of SEQ ID NO: 82, SEQ ID NO: 126, or SEQ ID NO: 144, maintains a HCDR2 sequence of SEQ ID NO: 83, SEQ ID NO: 127, or SEQ ID NO: 145, maintains a HCDR3 sequence of SEQ ID NO: 84 or SEQ ID NO: 146, maintains a LCDR1 sequence of SEQ ID NO: 85, or SEQ ID NO: 147, maintains a LCDR2 sequence of SEQ ID NO: 86, or SEQ ID NO: 148, and maintains a LCDR3 sequence SEQ ID NO: 95.

In some embodiments, the heavy chain of the antibody, or antigen binding fragment thereof, comprises a heavy chain variable region having at least 85%, 86%, 87%, 88%, 89%, 90%, 91%, 92%, 93%, 94%, 95%, 96%, 97%, 98%, 99%, or 100% identity to SEQ ID NO: 350, wherein the antibody, or antigen binding fragment thereof, maintains a HCDR1 sequence of SEQ ID NO: 82, SEQ ID NO: 126, or SEQ ID NO: 144, maintains a HCDR2 sequence of SEQ ID NO: 83, SEQ ID NO: 127, or SEQ ID NO: 145, maintains a HCDR3 sequence of SEQ ID NO: 96 or SEQ ID NO: 153, maintains a LCDR1 sequence of SEQ ID NO: 85, or SEQ ID NO: 147, maintains a LCDR2 sequence of SEQ ID NO: 86, or SEQ ID NO: 148, and maintains a LCDR3 sequence SEQ ID NO: 97.

In some embodiments, the heavy chain of the antibody, or antigen binding fragment thereof, comprises a heavy chain variable region having at least 85%, 86%, 87%, 88%, 89%, 90%, 91%, 92%, 93%, 94%, 95%, 96%, 97%, 98%, 99%, or 100% identity to SEQ ID NO: 351, wherein the antibody, or antigen binding fragment thereof, maintains a HCDR1 sequence of SEQ ID NO: 82, SEQ ID NO: 126, or SEQ ID NO: 144, maintains a HCDR2 sequence of SEQ ID NO: 83, SEQ ID NO: 127, or SEQ ID NO: 145, maintains a HCDR3 sequence of SEQ ID NO: 98 or SEQ ID NO: 154, maintains a LCDR1 sequence of SEQ ID NO: 85, or SEQ ID NO: 147, maintains a LCDR2 sequence of SEQ ID NO: 86, or SEQ ID NO: 148, and maintains a LCDR3 sequence SEQ ID NO: 99.

In some embodiments, the heavy chain of the antibody, or antigen binding fragment thereof, comprises a heavy chain variable region having at least 85%, 86%, 87%, 88%, 89%, 90%, 91%, 92%, 93%, 94%, 95%, 96%, 97%, 98%, 99%, or 100% identity to SEQ ID NO: 352, wherein the antibody, or antigen binding fragment thereof, maintains a HCDR1 sequence of SEQ ID NO: 82, SEQ ID NO: 126, or SEQ ID NO: 144, maintains a HCDR2 sequence of SEQ ID NO: 83, SEQ ID NO: 127, or SEQ ID NO: 145, maintains a HCDR3 sequence of SEQ ID NO: 100 or SEQ ID NO: 155, maintains a LCDR1 sequence of SEQ ID NO: 85, or SEQ ID NO: 147, maintains a LCDR2 sequence of SEQ ID NO: 86, or SEQ ID NO: 148, and maintains a LCDR3 sequence SEQ ID NO: 101.

In some embodiments, the heavy chain of the antibody, or antigen binding fragment thereof, comprises a heavy chain variable region having at least 85%, 86%, 87%, 88%, 89%, 90%, 91%, 92%, 93%, 94%, 95%, 96%, 97%, 98%, 99%, or 100% identity to SEQ ID NO: 353, wherein the antibody, or antigen binding fragment thereof, maintains a HCDR1 sequence of SEQ ID NO: 82, SEQ ID NO: 126, or SEQ ID NO: 144, maintains a HCDR2 sequence of SEQ ID NO: 83, SEQ ID NO: 127, or SEQ ID NO: 145, maintains a HCDR3 sequence of SEQ ID NO: 100 or SEQ ID NO: 155, maintains a LCDR1 sequence of SEQ ID NO: 85, or SEQ ID NO: 147, maintains a LCDR2 sequence of SEQ ID NO: 86, or SEQ ID NO: 148, and maintains a LCDR3 sequence SEQ ID NO: 102.

In some embodiments, the heavy chain of the antibody, or antigen binding fragment thereof, comprises a heavy chain variable region having at least 85%, 86%, 87%, 88%, 89%, 90%, 91%, 92%, 93%, 94%, 95%, 96%, 97%, 98%, 99%, or 100% identity to SEQ ID NO: 354, wherein the antibody, or antigen binding fragment thereof, maintains a HCDR1 sequence of SEQ ID NO: 103, SEQ ID NO: 128, or SEQ ID NO: 156, maintains a HCDR2 sequence of SEQ ID NO: 104, SEQ ID NO: 129, or SEQ ID NO: 157, maintains a HCDR3 sequence of SEQ ID NO: 105 or SEQ ID NO: 158, maintains a LCDR1 sequence of SEQ ID NO: 106, or SEQ ID NO: 159, maintains a LCDR2 sequence of SEQ ID NO: 107, or SEQ ID NO: 160, and maintains a LCDR3 sequence SEQ ID NO: 108.

In some embodiments, the heavy chain of the antibody, or antigen binding fragment thereof, comprises a heavy chain variable region having at least 85%, 86%, 87%, 88%, 89%, 90%, 91%, 92%, 93%, 94%, 95%, 96%, 97%, 98%, 99%, or 100% identity to SEQ ID NO: 355, wherein the antibody, or antigen binding fragment thereof, maintains a HCDR1 sequence of SEQ ID NO: 103, SEQ ID NO: 128, or SEQ ID NO: 156, maintains a HCDR2 sequence of SEQ ID NO: 104, SEQ ID NO: 129, or SEQ ID NO: 157, maintains a HCDR3 sequence of SEQ ID NO: 109 or SEQ ID NO: 161, maintains a LCDR1 sequence of SEQ ID NO: 106, or SEQ ID NO: 159, maintains a LCDR2 sequence of SEQ ID NO: 107, or SEQ ID NO: 160, and maintains a LCDR3 sequence SEQ ID NO: 110.

In some embodiments, the heavy chain of the antibody, or antigen binding fragment thereof, comprises a heavy chain variable region having at least 85%, 86%, 87%, 88%, 89%, 90%, 91%, 92%, 93%, 94%, 95%, 96%, 97%, 98%, 99%, or 100% identity to SEQ ID NO: 356, wherein the antibody, or antigen binding fragment thereof, maintains a HCDR1 sequence of SEQ ID NO: 103, SEQ ID NO: 128, or SEQ ID NO: 156, maintains a HCDR2 sequence of SEQ ID NO: 104, SEQ ID NO: 129, or SEQ ID NO: 157, maintains a HCDR3 sequence of SEQ ID NO: 111 or SEQ ID NO: 162, maintains a LCDR1 sequence of SEQ ID NO: 106, or SEQ ID NO: 159, maintains a LCDR2 sequence of SEQ ID NO: 107, or SEQ ID NO: 160, and maintains a LCDR3 sequence SEQ ID NO: 112.

In some embodiments, the heavy chain of the antibody, or antigen binding fragment thereof, comprises a heavy chain variable region having at least 85%, 86%, 87%, 88%, 89%, 90%, 91%, 92%, 93%, 94%, 95%, 96%, 97%, 98%, 99%, or 100% identity to SEQ ID NO: 357, wherein the antibody, or antigen binding fragment thereof, maintains a HCDR1 sequence of SEQ ID NO: 103, SEQ ID NO: 128, or SEQ ID NO: 156, maintains a HCDR2 sequence of SEQ ID NO: 104, SEQ ID NO: 129, or SEQ ID NO: 157, maintains a HCDR3 sequence of SEQ ID NO: 105 or SEQ ID NO: 158, maintains a LCDR1 sequence of SEQ ID NO: 106, or SEQ ID NO: 159, maintains a LCDR2 sequence of SEQ ID NO: 107, or SEQ ID NO: 160, and maintains a LCDR3 sequence SEQ ID NO: 113.

In some embodiments, the heavy chain of the antibody, or antigen binding fragment thereof, comprises a heavy chain variable region having at least 85%, 86%, 87%, 88%, 89%, 90%, 91%, 92%, 93%, 94%, 95%, 96%, 97%, 98%, 99%, or 100% identity to SEQ ID NO: 358, wherein the antibody, or antigen binding fragment thereof, maintains a HCDR1 sequence of SEQ ID NO: 103, SEQ ID NO: 128, or SEQ ID NO: 156, maintains a HCDR2 sequence of SEQ ID NO: 104, SEQ ID NO: 129, or SEQ ID NO: 157, maintains a HCDR3 sequence of SEQ ID NO: 114 or SEQ ID NO: 163, maintains a LCDR1 sequence of SEQ ID NO: 106, or SEQ ID NO: 159, maintains a LCDR2 sequence of SEQ ID NO: 107, or SEQ ID NO: 160, and maintains a LCDR3 sequence SEQ ID NO: 115.

In some embodiments, the heavy chain of the antibody, or antigen binding fragment thereof, comprises a heavy chain variable region having at least 85%, 86%, 87%, 88%, 89%, 90%, 91%, 92%, 93%, 94%, 95%, 96%, 97%, 98%, 99%, or 100% identity to SEQ ID NO: 359, wherein the antibody, or antigen binding fragment thereof, maintains a HCDR1 sequence of SEQ ID NO: 103, SEQ ID NO: 128, or SEQ ID NO: 156, maintains a HCDR2 sequence of SEQ ID NO: 104, SEQ ID NO: 129, or SEQ ID NO: 157, maintains a HCDR3 sequence of SEQ ID NO: 116 or SEQ ID NO: 164, maintains a LCDR1 sequence of SEQ ID NO: 106, or SEQ ID NO: 159, maintains a LCDR2 sequence of SEQ ID NO: 107, or SEQ ID NO: 160, and maintains a LCDR3 sequence SEQ ID NO: 113.

In some embodiments, the heavy chain of the antibody, or antigen binding fragment thereof, comprises a heavy chain variable region having at least 85%, 86%, 87%, 88%, 89%, 90%, 91%, 92%, 93%, 94%, 95%, 96%, 97%, 98%, 99%, or 100% identity to SEQ ID NO: 360, wherein the antibody, or antigen binding fragment thereof, maintains a HCDR1 sequence of SEQ ID NO: 103, SEQ ID NO: 128, or SEQ ID NO: 156, maintains a HCDR2 sequence of SEQ ID NO: 104, SEQ ID NO: 129, or SEQ ID NO: 157, maintains a HCDR3 sequence of SEQ ID NO: 117 or SEQ ID NO: 165, maintains a LCDR1 sequence of SEQ ID NO: 106, or SEQ ID NO: 159, maintains a LCDR2 sequence of SEQ ID NO: 107, or SEQ ID NO: 160, and maintains a LCDR3 sequence SEQ ID NO: 118.

In some embodiments, the heavy chain of the antibody, or antigen binding fragment thereof, comprises a heavy chain variable region having at least 85%, 86%, 87%, 88%, 89%, 90%, 91%, 92%, 93%, 94%, 95%, 96%, 97%, 98%, 99%, or 100% identity to SEQ ID NO: 361, wherein the antibody, or antigen binding fragment thereof, maintains a HCDR1 sequence of SEQ ID NO: 103, SEQ ID NO: 128, or SEQ ID NO: 156, maintains a HCDR2 sequence of SEQ ID NO: 104, SEQ ID NO: 129, or SEQ ID NO: 157, maintains a HCDR3 sequence of SEQ ID NO: 116 or SEQ ID NO: 164, maintains a LCDR1 sequence of SEQ ID NO: 106, or SEQ ID NO: 159, maintains a LCDR2 sequence of SEQ ID NO: 107, or SEQ ID NO: 160, and maintains a LCDR3 sequence SEQ ID NO: 119.

In some embodiments, the heavy chain of the antibody, or antigen binding fragment thereof, comprises a heavy chain variable region having at least 85%, 86%, 87%, 88%, 89%, 90%, 91%, 92%, 93%, 94%, 95%, 96%, 97%, 98%, 99%, or 100% identity to SEQ ID NO: 362, wherein the antibody, or antigen binding fragment thereof, maintains a HCDR1 sequence of SEQ ID NO: 103, SEQ ID NO: 128, or SEQ ID NO: 156, maintains a HCDR2 sequence of SEQ ID NO: 104, SEQ ID NO: 129, or SEQ ID NO: 157, maintains a HCDR3 sequence of SEQ ID NO: 120 or SEQ ID NO: 166, maintains a LCDR1 sequence of SEQ ID NO: 106, or SEQ ID NO: 159, maintains a LCDR2 sequence of SEQ ID NO: 107, or SEQ ID NO: 160, and maintains a LCDR3 sequence SEQ ID NO: 121.

In some embodiments, the heavy chain of the antibody, or antigen binding fragment thereof, comprises a heavy chain variable region having at least 85%, 86%, 87%, 88%, 89%, 90%, 91%, 92%, 93%, 94%, 95%, 96%, 97%, 98%, 99%, or 100% identity to SEQ ID NO: 363, wherein the antibody, or antigen binding fragment thereof, maintains a HCDR1 sequence of SEQ ID NO: 103, SEQ ID NO: 128, or SEQ ID NO: 156, maintains a HCDR2 sequence of SEQ ID NO: 104, SEQ ID NO: 129, or SEQ ID NO: 157, maintains a HCDR3 sequence of SEQ ID NO: 122 or SEQ ID NO: 167, maintains a LCDR1 sequence of SEQ ID NO: 106, or SEQ ID NO: 159, maintains a LCDR2 sequence of SEQ ID NO: 107, or SEQ ID NO: 160, and maintains a LCDR3 sequence SEQ ID NO: 123.

In some embodiments, the light chain of the antibody, or antigen binding fragment thereof, comprises a light chain variable region having at least 85%, 86%, 87%, 88%, 89%, 90%, 91%, 92%, 93%, 94%, 95%, 96%, 97%, 98%, 99%, or 100% identity to SEQ ID NO: 2, wherein the antibody, or antigen binding fragment thereof, maintains a HCDR1 sequence of SEQ ID NO: 61, SEQ ID NO: 124, or SEQ ID NO: 130, maintains a HCDR2 sequence of SEQ ID NO: 62, SEQ ID NO: 125, or SEQ ID NO: 131, maintains a HCDR3 sequence of SEQ ID NO: 63 or SEQ ID NO: 132, maintains a LCDR1 sequence of SEQ ID NO: 64, or SEQ ID NO: 133, maintains a LCDR2 sequence of SEQ ID NO: 65, or SEQ ID NO: 134, and maintains a LCDR3 sequence of SEQ ID NO: 66.

In some embodiments, the light chain of the antibody, or antigen binding fragment thereof, comprises a light chain variable region having at least 85%, 86%, 87%, 88%, 89%, 90%, 91%, 92%, 93%, 94%, 95%, 96%, 97%, 98%, 99%, or 100% identity to SEQ ID NO: 4, wherein the antibody, or antigen binding fragment thereof, maintains a HCDR1 sequence of SEQ ID NO: 61, SEQ ID NO: 124, or SEQ ID NO: 130, maintains a HCDR2 sequence of SEQ ID NO: 62, SEQ ID NO: 125, or SEQ ID NO: 131, maintains a HCDR3 sequence of SEQ ID NO: 67 or SEQ ID NO: 135, maintains a LCDR1 sequence of SEQ ID NO: 64, or SEQ ID NO: 1339, maintains a LCDR2 sequence of SEQ ID NO: 65, or SEQ ID NO: 134, and maintains a LCDR3 sequence SEQ ID NO: 68.

In some embodiments, the light chain of the antibody, or antigen binding fragment thereof, comprises a light chain variable region having at least 85%, 86%, 87%, 88%, 89%, 90%, 91%, 92%, 93%, 94%, 95%, 96%, 97%, 98%, 99%, or 100% identity to SEQ ID NO: 6, wherein the antibody, or antigen binding fragment thereof, maintains a HCDR1 sequence of SEQ ID NO: 61, SEQ ID NO: 124, or SEQ ID NO: 130, maintains a HCDR2 sequence of SEQ ID NO: 62, SEQ ID NO: 125, or SEQ ID NO: 131, maintains a HCDR3 sequence of SEQ ID NO: 69 or SEQ ID NO: 136, maintains a LCDR1 sequence of SEQ ID NO: 64, or SEQ ID NO: 133, maintains a LCDR2 sequence of SEQ ID NO: 65, or SEQ ID NO: 134, and maintains a LCDR3 sequence SEQ ID NO: 68.

In some embodiments, the light chain of the antibody, or antigen binding fragment thereof, comprises a light chain variable region having at least 85%, 86%, 87%, 88%, 89%, 90%, 91%, 92%, 93%, 94%, 95%, 96%, 97%, 98%, 99%, or 100% identity to SEQ ID NO: 8, wherein the antibody, or antigen binding fragment thereof, maintains a HCDR1 sequence of SEQ ID NO: 61, SEQ ID NO: 124, or SEQ ID NO: 130, maintains a HCDR2 sequence of SEQ ID NO: 62, SEQ ID NO: 125, or SEQ ID NO: 131, maintains a HCDR3 sequence of SEQ ID NO: 70 or SEQ ID NO: 137, maintains a LCDR1 sequence of SEQ ID NO: 64, or SEQ ID NO: 133, maintains a LCDR2 sequence of SEQ ID NO: 65, or SEQ ID NO: 134, and maintains a LCDR3 sequence SEQ ID NO: 71.

In some embodiments, the light chain of the antibody, or antigen binding fragment thereof, comprises a light chain variable region having at least 85%, 86%, 87%, 88%, 89%, 90%, 91%, 92%, 93%, 94%, 95%, 96%, 97%, 98%, 99%, or 100% identity to SEQ ID NO: 10, wherein the antibody, or antigen binding fragment thereof, maintains a HCDR1 sequence of SEQ ID NO: 61, SEQ ID NO: 124, or SEQ ID NO: 130, maintains a HCDR2 sequence of SEQ ID NO: 62, SEQ ID NO: 125, or SEQ ID NO: 131, maintains a HCDR3 sequence of SEQ ID NO: 72 or SEQ ID NO: 138, maintains a LCDR1 sequence of SEQ ID NO: 64, or SEQ ID NO: 133, maintains a LCDR2 sequence of SEQ ID NO: 65, or SEQ ID NO: 134, and maintains a LCDR3 sequence SEQ ID NO: 71.

In some embodiments, the light chain of the antibody, or antigen binding fragment thereof, comprises a light chain variable region having at least 85%, 86%, 87%, 88%, 89%, 90%, 91%, 92%, 93%, 94%, 95%, 96%, 97%, 98%, 99%, or 100% identity to SEQ ID NO: 12, wherein the antibody, or antigen binding fragment thereof, maintains a HCDR1 sequence of SEQ ID NO: 61, SEQ ID NO: 124, or SEQ ID NO: 130, maintains a HCDR2 sequence of SEQ ID NO: 62, SEQ ID NO: 125, or SEQ ID NO: 131, maintains a HCDR3 sequence of SEQ ID NO: 73 or SEQ ID NO: 139, maintains a LCDR1 sequence of SEQ ID NO: 64, or SEQ ID NO: 133, maintains a LCDR2 sequence of SEQ ID NO: 65, or SEQ ID NO: 134, and maintains a LCDR3 sequence SEQ ID NO: 71.

In some embodiments, the light chain of the antibody, or antigen binding fragment thereof, comprises a light chain variable region having at least 85%, 86%, 87%, 88%, 89%, 90%, 91%, 92%, 93%, 94%, 95%, 96%, 97%, 98%, 99%, or 100% identity to SEQ ID NO: 14, wherein the antibody, or antigen binding fragment thereof, maintains a HCDR1 sequence of SEQ ID NO: 61, SEQ ID NO: 124, or SEQ ID NO: 130, maintains a HCDR2 sequence of SEQ ID NO: 62, SEQ ID NO: 125, or SEQ ID NO: 131, maintains a HCDR3 sequence of SEQ ID NO: 74 or SEQ ID NO: 140, maintains a LCDR1 sequence of SEQ ID NO: 64, or SEQ ID NO: 133, maintains a LCDR2 sequence of SEQ ID NO: 65, or SEQ ID NO: 134, and maintains a LCDR3 sequence SEQ ID NO: 75.

In some embodiments, the light chain of the antibody, or antigen binding fragment thereof, comprises a light chain variable region having at least 85%, 86%, 87%, 88%, 89%, 90%, 91%, 92%, 93%, 94%, 95%, 96%, 97%, 98%, 99%, or 100% identity to SEQ ID NO: 16, wherein the antibody, or antigen binding fragment thereof, maintains a HCDR1 sequence of SEQ ID NO: 61, SEQ ID NO: 124, or SEQ ID NO: 130, maintains a HCDR2 sequence of SEQ ID NO: 62, SEQ ID NO: 125, or SEQ ID NO: 131, maintains a HCDR3 sequence of SEQ ID NO: 76 or SEQ ID NO: 141, maintains a LCDR1 sequence of SEQ ID NO: 64, or SEQ ID NO: 133, maintains a LCDR2 sequence of SEQ ID NO: 65, or SEQ ID NO: 134, and maintains a LCDR3 sequence SEQ ID NO: 77.

In some embodiments, the light chain of the antibody, or antigen binding fragment thereof, comprises a light chain variable region having at least 85%, 86%, 87%, 88%, 89%, 90%, 91%, 92%, 93%, 94%, 95%, 96%, 97%, 98%, 99%, or 100% identity to SEQ ID NO: 18, wherein the antibody, or antigen binding fragment thereof, maintains a HCDR1 sequence of SEQ ID NO: 61, SEQ ID NO: 124, or SEQ ID NO: 130, maintains a HCDR2 sequence of SEQ ID NO: 62, SEQ ID NO: 125, or SEQ ID NO: 131, maintains a HCDR3 sequence of SEQ ID NO: 78 or SEQ ID NO: 142, maintains a LCDR1 sequence of SEQ ID NO: 64, or SEQ ID NO: 133, maintains a LCDR2 sequence of SEQ ID NO: 65, or SEQ ID NO: 134, and maintains a LCDR3 sequence SEQ ID NO: 79.

In some embodiments, the light chain of the antibody, or antigen binding fragment thereof, comprises a light chain variable region having at least 85%, 86%, 87%, 88%, 89%, 90%, 91%, 92%, 93%, 94%, 95%, 96%, 97%, 98%, 99%, or 100% identity to SEQ ID NO: 20, wherein the antibody, or antigen binding fragment thereof, maintains a HCDR1 sequence of SEQ ID NO: 61, SEQ ID NO: 124, or SEQ ID NO: 130, maintains a HCDR2 sequence of SEQ ID NO: 62, SEQ ID NO: 125, or SEQ ID NO: 131, maintains a HCDR3 sequence of SEQ ID NO: 80 or SEQ ID NO: 143, maintains a LCDR1 sequence of SEQ ID NO: 64, or SEQ ID NO: 133, maintains a LCDR2 sequence of SEQ ID NO: 65, or SEQ ID NO: 134, and maintains a LCDR3 sequence SEQ ID NO: 81.

In some embodiments, the light chain of the antibody, or antigen binding fragment thereof, comprises a light chain variable region having at least 85%, 86%, 87%, 88%, 89%, 90%, 91%, 92%, 93%, 94%, 95%, 96%, 97%, 98%, 99%, or 100% identity to SEQ ID NO: 22, wherein the antibody, or antigen binding fragment thereof, maintains a HCDR1 sequence of SEQ ID NO: 82, SEQ ID NO: 126, or SEQ ID NO: 144, maintains a HCDR2 sequence of SEQ ID NO: 83, SEQ ID NO: 127, or SEQ ID NO: 145, maintains a HCDR3 sequence of SEQ ID NO: 84 or SEQ ID NO: 146, maintains a LCDR1 sequence of SEQ ID NO: 85, or SEQ ID NO: 147, maintains a LCDR2 sequence of SEQ ID NO: 86, or SEQ ID NO: 148, and maintains a LCDR3 sequence SEQ ID NO: 87.

In some embodiments, the light chain of the antibody, or antigen binding fragment thereof, comprises a light chain variable region having at least 85%, 86%, 87%, 88%, 89%, 90%, 91%, 92%, 93%, 94%, 95%, 96%, 97%, 98%, 99%, or 100% identity to SEQ ID NO: 24, wherein the antibody, or antigen binding fragment thereof, maintains a HCDR1 sequence of SEQ ID NO: 82, SEQ ID NO: 126, or SEQ ID NO: 144, maintains a HCDR2 sequence of SEQ ID NO: 83, SEQ ID NO: 127, or SEQ ID NO: 145, maintains a HCDR3 sequence of SEQ ID NO: 88 or SEQ ID NO: 149, maintains a LCDR1 sequence of SEQ ID NO: 85, or SEQ ID NO: 147, maintains a LCDR2 sequence of SEQ ID NO: 86, or SEQ ID NO: 148, and maintains a LCDR3 sequence SEQ ID NO: 89.

In some embodiments, the light chain of the antibody, or antigen binding fragment thereof, comprises a light chain variable region having at least 85%, 86%, 87%, 88%, 89%, 90%, 91%, 92%, 93%, 94%, 95%, 96%, 97%, 98%, 99%, or 100% identity to SEQ ID NO: 26, wherein the antibody, or antigen binding fragment thereof, maintains a HCDR1 sequence of SEQ ID NO: 82, SEQ ID NO: 126, or SEQ ID NO: 144, maintains a HCDR2 sequence of SEQ ID NO: 83, SEQ ID NO: 127, or SEQ ID NO: 145, maintains a HCDR3 sequence of SEQ ID NO: 90 or SEQ ID NO: 150, maintains a LCDR1 sequence of SEQ ID NO: 85, or SEQ ID NO: 147, maintains a LCDR2 sequence of SEQ ID NO: 86, or SEQ ID NO: 148, and maintains a LCDR3 sequence SEQ ID NO: 89.

In some embodiments, the light chain of the antibody, or antigen binding fragment thereof, comprises a light chain variable region having at least 85%, 86%, 87%, 88%, 89%, 90%, 91%, 92%, 93%, 94%, 95%, 96%, 97%, 98%, 99%, or 100% identity to SEQ ID NO: 28, wherein the antibody, or antigen binding fragment thereof, maintains a HCDR1 sequence of SEQ ID NO: 82, SEQ ID NO: 126, or SEQ ID NO: 144, maintains a HCDR2 sequence of SEQ ID NO: 83, SEQ ID NO: 127, or SEQ ID NO: 145, maintains a HCDR3 sequence of SEQ ID NO: 91 or SEQ ID NO: 151, maintains a LCDR1 sequence of SEQ ID NO: 85, or SEQ ID NO: 147, maintains a LCDR2 sequence of SEQ ID NO: 86, or SEQ ID NO: 148, and maintains a LCDR3 sequence SEQ ID NO: 92.

In some embodiments, the light chain of the antibody, or antigen binding fragment thereof, comprises a light chain variable region having at least 85%, 86%, 87%, 88%, 89%, 90%, 91%, 92%, 93%, 94%, 95%, 96%, 97%, 98%, 99%, or 100% identity to SEQ ID NO: 30, wherein the antibody, or antigen binding fragment thereof, maintains a HCDR1 sequence of SEQ ID NO: 82, SEQ ID NO: 126, or SEQ ID NO: 144, maintains a HCDR2 sequence of SEQ ID NO: 83, SEQ ID NO: 127, or SEQ ID NO: 145, maintains a HCDR3 sequence of SEQ ID NO: 93 or SEQ ID NO: 152, maintains a LCDR1 sequence of SEQ ID NO: 85, or SEQ ID NO: 147, maintains a LCDR2 sequence of SEQ ID NO: 86, or SEQ ID NO: 148, and maintains a LCDR3 sequence SEQ ID NO: 94.

In some embodiments, the light chain of the antibody, or antigen binding fragment thereof, comprises a light chain variable region having at least 85%, 86%, 87%, 88%, 89%, 90%, 91%, 92%, 93%, 94%, 95%, 96%, 97%, 98%, 99%, or 100% identity to SEQ ID NO: 32, wherein the antibody, or antigen binding fragment thereof, maintains a HCDR1 sequence of SEQ ID NO: 82, SEQ ID NO: 126, or SEQ ID NO: 144, maintains a HCDR2 sequence of SEQ ID NO: 83, SEQ ID NO: 127, or SEQ ID NO: 145, maintains a HCDR3 sequence of SEQ ID NO: 84 or SEQ ID NO: 146, maintains a LCDR1 sequence of SEQ ID NO: 85, or SEQ ID NO: 147, maintains a LCDR2 sequence of SEQ ID NO: 86, or SEQ ID NO: 148, and maintains a LCDR3 sequence SEQ ID NO: 95.

In some embodiments, the light chain of the antibody, or antigen binding fragment thereof, comprises a light chain variable region having at least 85%, 86%, 87%, 88%, 89%, 90%, 91%, 92%, 93%, 94%, 95%, 96%, 97%, 98%, 99%, or 100% identity to SEQ ID NO: 34, wherein the antibody, or antigen binding fragment thereof, maintains a HCDR1 sequence of SEQ ID NO: 82, SEQ ID NO: 126, or SEQ ID NO: 144, maintains a HCDR2 sequence of SEQ ID NO: 83, SEQ ID NO: 127, or SEQ ID NO: 145, maintains a HCDR3 sequence of SEQ ID NO: 96 or SEQ ID NO: 153, maintains a LCDR1 sequence of SEQ ID NO: 85, or SEQ ID NO: 147, maintains a LCDR2 sequence of SEQ ID NO: 86, or SEQ ID NO: 148, and maintains a LCDR3 sequence SEQ ID NO: 97.

In some embodiments, the light chain of the antibody, or antigen binding fragment thereof, comprises a light chain variable region having at least 85%, 86%, 87%, 88%, 89%, 90%, 91%, 92%, 93%, 94%, 95%, 96%, 97%, 98%, 99%, or 100% identity to SEQ ID NO: 36, wherein the antibody, or antigen binding fragment thereof, maintains a HCDR1 sequence of SEQ ID NO: 82, SEQ ID NO: 126, or SEQ ID NO: 144, maintains a HCDR2 sequence of SEQ ID NO: 83, SEQ ID NO: 127, or SEQ ID NO: 145, maintains a HCDR3 sequence of SEQ ID NO: 98 or SEQ ID NO: 154, maintains a LCDR1 sequence of SEQ ID NO: 85, or SEQ ID NO: 147, maintains a LCDR2 sequence of SEQ ID NO: 86, or SEQ ID NO: 148, and maintains a LCDR3 sequence SEQ ID NO: 99.

In some embodiments, the light chain of the antibody, or antigen binding fragment thereof, comprises a light chain variable region having at least 85%, 86%, 87%, 88%, 89%, 90%, 91%, 92%, 93%, 94%, 95%, 96%, 97%, 98%, 99%, or 100% identity to SEQ ID NO: 38, wherein the antibody, or antigen binding fragment thereof, maintains a HCDR1 sequence of SEQ ID NO: 82, SEQ ID NO: 126, or SEQ ID NO: 144, maintains a HCDR2 sequence of SEQ ID NO: 83, SEQ ID NO: 127, or SEQ ID NO: 145, maintains a HCDR3 sequence of SEQ ID NO: 100 or SEQ ID NO: 155, maintains a LCDR1 sequence of SEQ ID NO: 85, or SEQ ID NO: 147, maintains a LCDR2 sequence of SEQ ID NO: 86, or SEQ ID NO: 148, and maintains a LCDR3 sequence SEQ ID NO: 101.

In some embodiments, the light chain of the antibody, or antigen binding fragment thereof, comprises a light chain variable region having at least 85%, 86%, 87%, 88%, 89%, 90%, 91%, 92%, 93%, 94%, 95%, 96%, 97%, 98%, 99%, or 100% identity to SEQ ID NO: 40, wherein the antibody, or antigen binding fragment thereof, maintains a HCDR1 sequence of SEQ ID NO: 82, SEQ ID NO: 126, or SEQ ID NO: 144, maintains a HCDR2 sequence of SEQ ID NO: 83, SEQ ID NO: 127, or SEQ ID NO: 145, maintains a HCDR3 sequence of SEQ ID NO: 100 or SEQ ID NO: 155, maintains a LCDR1 sequence of SEQ ID NO: 85, or SEQ ID NO: 147, maintains a LCDR2 sequence of SEQ ID NO: 86, or SEQ ID NO: 148, and maintains a LCDR3 sequence SEQ ID NO: 102.

In some embodiments, the light chain of the antibody, or antigen binding fragment thereof, comprises a light chain variable region having at least 85%, 86%, 87%, 88%, 89%, 90%, 91%, 92%, 93%, 94%, 95%, 96%, 97%, 98%, 99%, or 100% identity to SEQ ID NO: 42, wherein the antibody, or antigen binding fragment thereof, maintains a HCDR1 sequence of SEQ ID NO: 103, SEQ ID NO: 128, or SEQ ID NO: 156, maintains a HCDR2 sequence of SEQ ID NO: 104, SEQ ID NO: 129, or SEQ ID NO: 157, maintains a HCDR3 sequence of SEQ ID NO: 105 or SEQ ID NO: 158, maintains a LCDR1 sequence of SEQ ID NO: 106, or SEQ ID NO: 159, maintains a LCDR2 sequence of SEQ ID NO: 107, or SEQ ID NO: 160, and maintains a LCDR3 sequence SEQ ID NO: 108.

In some embodiments, the light chain of the antibody, or antigen binding fragment thereof, comprises a light chain variable region having at least 85%, 86%, 87%, 88%, 89%, 90%, 91%, 92%, 93%, 94%, 95%, 96%, 97%, 98%, 99%, or 100% identity to SEQ ID NO: 44, wherein the antibody, or antigen binding fragment thereof, maintains a HCDR1 sequence of SEQ ID NO: 103, SEQ ID NO: 128, or SEQ ID NO: 156, maintains a HCDR2 sequence of SEQ ID NO: 104, SEQ ID NO: 129, or SEQ ID NO: 157, maintains a HCDR3 sequence of SEQ ID NO: 109 or SEQ ID NO: 161, maintains a LCDR1 sequence of SEQ ID NO: 106, or SEQ ID NO:

159, maintains a LCDR2 sequence of SEQ ID NO: 107, or SEQ ID NO: 160, and maintains a LCDR3 sequence SEQ ID NO: 110.

In some embodiments, the light chain of the antibody, or antigen binding fragment thereof, comprises a light chain variable region having at least 85%, 86%, 87%, 88%, 89%, 90%, 91%, 92%, 93%, 94%, 95%, 96%, 97%, 98%, 99%, or 100% identity to SEQ ID NO: 46, wherein the antibody, or antigen binding fragment thereof, maintains a HCDR1 sequence of SEQ ID NO: 103, SEQ ID NO: 128, or SEQ ID NO: 156, maintains a HCDR2 sequence of SEQ ID NO: 104, SEQ ID NO: 129, or SEQ ID NO: 157, maintains a HCDR3 sequence of SEQ ID NO: 111 or SEQ ID NO: 162, maintains a LCDR1 sequence of SEQ ID NO: 106, or SEQ ID NO: 159, maintains a LCDR2 sequence of SEQ ID NO: 107, or SEQ ID NO: 160, and maintains a LCDR3 sequence SEQ ID NO: 112.

In some embodiments, the light chain of the antibody, or antigen binding fragment thereof, comprises a light chain variable region having at least 85%, 86%, 87%, 88%, 89%, 90%, 91%, 92%, 93%, 94%, 95%, 96%, 97%, 98%, 99%, or 100% identity to SEQ ID NO: 48, wherein the antibody, or antigen binding fragment thereof, maintains a HCDR1 sequence of SEQ ID NO: 103, SEQ ID NO: 128, or SEQ ID NO: 156, maintains a HCDR2 sequence of SEQ ID NO: 104, SEQ ID NO: 129, or SEQ ID NO: 157, maintains a HCDR3 sequence of SEQ ID NO: 105 or SEQ ID NO: 158, maintains a LCDR1 sequence of SEQ ID NO: 106, or SEQ ID NO: 159, maintains a LCDR2 sequence of SEQ ID NO: 107, or SEQ ID NO: 160, and maintains a LCDR3 sequence SEQ ID NO: 113.

In some embodiments, the light chain of the antibody, or antigen binding fragment thereof, comprises a light chain variable region having at least 85%, 86%, 87%, 88%, 89%, 90%, 91%, 92%, 93%, 94%, 95%, 96%, 97%, 98%, 99%, or 100% identity to SEQ ID NO: 50, wherein the antibody, or antigen binding fragment thereof, maintains a HCDR1 sequence of SEQ ID NO: 103, SEQ ID NO: 128, or SEQ ID NO: 156, maintains a HCDR2 sequence of SEQ ID NO: 104, SEQ ID NO: 129, or SEQ ID NO: 157, maintains a HCDR3 sequence of SEQ ID NO: 114 or SEQ ID NO: 163, maintains a LCDR1 sequence of SEQ ID NO: 106, or SEQ ID NO: 159, maintains a LCDR2 sequence of SEQ ID NO: 107, or SEQ ID NO: 160, and maintains a LCDR3 sequence SEQ ID NO: 115.

In some embodiments, the light chain of the antibody, or antigen binding fragment thereof, comprises a light chain variable region having at least 85%, 86%, 87%, 88%, 89%, 90%, 91%, 92%, 93%, 94%, 95%, 96%, 97%, 98%, 99%, or 100% identity to SEQ ID NO: 52, wherein the antibody, or antigen binding fragment thereof, maintains a HCDR1 sequence of SEQ ID NO: 103, SEQ ID NO: 128, or SEQ ID NO: 156, maintains a HCDR2 sequence of SEQ ID NO: 104, SEQ ID NO: 129, or SEQ ID NO: 157, maintains a HCDR3 sequence of SEQ ID NO: 116 or SEQ ID NO: 164, maintains a LCDR1 sequence of SEQ ID NO: 106, or SEQ ID NO: 159, maintains a LCDR2 sequence of SEQ ID NO: 107, or SEQ ID NO: 160, and maintains a LCDR3 sequence SEQ ID NO: 113.

In some embodiments, the light chain of the antibody, or antigen binding fragment thereof, comprises a light chain variable region having at least 85%, 86%, 87%, 88%, 89%, 90%, 91%, 92%, 93%, 94%, 95%, 96%, 97%, 98%, 99%, or 100% identity to SEQ ID NO: 54, wherein the antibody, or antigen binding fragment thereof, maintains a HCDR1 sequence of SEQ ID NO: 103, SEQ ID NO: 128, or SEQ ID NO: 156, maintains a HCDR2 sequence of SEQ ID NO: 104, SEQ ID NO: 129, or SEQ ID NO: 157, maintains a HCDR3 sequence of SEQ ID NO: 117 or SEQ ID NO: 165, maintains a LCDR1 sequence of SEQ ID NO: 106, or SEQ ID NO: 159, maintains a LCDR2 sequence of SEQ ID NO: 107, or SEQ ID NO: 160, and maintains a LCDR3 sequence SEQ ID NO: 118.

In some embodiments, the light chain of the antibody, or antigen binding fragment thereof, comprises a light chain variable region having at least 85%, 86%, 87%, 88%, 89%, 90%, 91%, 92%, 93%, 94%, 95%, 96%, 97%, 98%, 99%, or 100% identity to SEQ ID NO: 56, wherein the antibody, or antigen binding fragment thereof, maintains a HCDR1 sequence of SEQ ID NO: 103, SEQ ID NO: 128, or SEQ ID NO: 156, maintains a HCDR2 sequence of SEQ ID NO: 104, SEQ ID NO: 129, or SEQ ID NO: 157, maintains a HCDR3 sequence of SEQ ID NO: 116 or SEQ ID NO: 164, maintains a LCDR1 sequence of SEQ ID NO: 106, or SEQ ID NO: 159, maintains a LCDR2 sequence of SEQ ID NO: 107, or SEQ ID NO: 160, and maintains a LCDR3 sequence SEQ ID NO: 119.

In some embodiments, the light chain of the antibody, or antigen binding fragment thereof, comprises a light chain variable region having at least 85%, 86%, 87%, 88%, 89%, 90%, 91%, 92%, 93%, 94%, 95%, 96%, 97%, 98%, 99%, or 100% identity to SEQ ID NO: 58, wherein the antibody, or antigen binding fragment thereof, maintains a HCDR1 sequence of SEQ ID NO: 103, SEQ ID NO: 128, or SEQ ID NO: 156, maintains a HCDR2 sequence of SEQ ID NO: 104, SEQ ID NO: 129, or SEQ ID NO: 157, maintains a HCDR3 sequence of SEQ ID NO: 120 or SEQ ID NO: 166, maintains a LCDR1 sequence of SEQ ID NO: 106, or SEQ ID NO: 159, maintains a LCDR2 sequence of SEQ ID NO: 107, or SEQ ID NO: 160, and maintains a LCDR3 sequence SEQ ID NO: 121.

In some embodiments, the light chain of the antibody, or antigen binding fragment thereof, comprises a light chain variable region having at least 85%, 86%, 87%, 88%, 89%, 90%, 91%, 92%, 93%, 94%, 95%, 96%, 97%, 98%, 99%, or 100% identity to SEQ ID NO: 60, wherein the antibody, or antigen binding fragment thereof, maintains a HCDR1 sequence of SEQ ID NO: 103, SEQ ID NO: 128, or SEQ ID NO: 156, maintains a HCDR2 sequence of SEQ ID NO: 104, SEQ ID NO: 129, or SEQ ID NO: 157, maintains a HCDR3 sequence of SEQ ID NO: 122 or SEQ ID NO: 167, maintains a LCDR1 sequence of SEQ ID NO: 106, or SEQ ID NO: 159, maintains a LCDR2 sequence of SEQ ID NO: 107, or SEQ ID NO: 160, and maintains a LCDR3 sequence SEQ ID NO: 123.

The VH and the VL sequences can be in any format, including, but not limited to an scFv format where the VH and VL regions are linked with a peptide linker. Examples of peptide linkers that can be used to link various peptides provided for herein include, but are not limited to: (GGGGS)$_n$ (SEQ ID NO: 266; (GGGGA)$_n$ (SEQ ID NO: 267, or any combination thereof, wherein each n is independently 1-5. In some embodiments, each n is, independently, 1. In some embodiments, each n is, independently, 2. In some embodiments, each n is, independently, 3. In some embodiments, each n is, independently, 4. In some embodiments, each n is, independently, 5. In some embodiments, the variable regions are not linked with a peptide linker.

In some embodiments, the antibody comprises SEQ ID NO: 1 and SEQ ID NO: 2. In some embodiments, the antibody comprises SEQ ID NO: 3 and SEQ ID NO: 4. In some embodiments, the antibody comprises SEQ ID NO: 5 and SEQ ID NO: 6. In some embodiments, the antibody comprises SEQ ID NO: 7 and SEQ ID NO: 8. In some embodiments, the antibody comprises SEQ ID NO: 9 and SEQ ID NO: 10. In some embodiments, the antibody comprises SEQ ID NO: 11 and SEQ ID NO: 12. In some embodiments, the antibody comprises SEQ ID NO: 13 and SEQ ID NO: 14. In some embodiments, the antibody comprises SEQ ID NO: 15 and SEQ ID NO: 16. In some embodiments, the antibody comprises SEQ ID NO: 17 and SEQ ID NO: 18. In some embodiments, the antibody comprises SEQ ID NO: 19 and SEQ ID NO: 20. In some embodiments, the antibody comprises SEQ ID NO: 21 and SEQ ID NO: 22. In some embodiments, the antibody comprises SEQ ID NO: 23 and SEQ ID NO: 24. In some embodiments, the antibody comprises SEQ ID NO: 25 and SEQ ID NO: 26. In some embodiments, the antibody comprises SEQ ID NO: 27 and SEQ ID NO: 28. In some embodiments, the antibody comprises SEQ ID NO: 29 and SEQ ID NO: 30. In some embodiments, the antibody comprises SEQ ID NO: 31 and SEQ ID NO: 32. In some embodiments, the antibody comprises SEQ ID NO: 33 and SEQ ID NO: 34. In some embodiments, the antibody comprises SEQ ID NO: 35 and SEQ ID NO: 36. In some embodiments, the antibody comprises SEQ ID NO: 37 and SEQ ID NO: 38. In some embodiments, the antibody comprises SEQ ID NO: 39 and SEQ ID NO: 40. In some embodiments, the antibody comprises SEQ ID NO: 41 and SEQ ID NO: 42. In some embodiments, the antibody comprises SEQ ID NO: 43 and SEQ ID NO: 44. In some embodiments, the antibody comprises SEQ ID NO: 45 and SEQ ID NO: 46. In some embodiments, the antibody comprises SEQ ID NO: 47 and SEQ ID NO: 48. In some embodiments, the antibody comprises SEQ ID NO: 49 and SEQ ID NO: 50. In some embodiments, the antibody comprises SEQ ID NO: 51 and SEQ ID NO: 52. In some embodiments, the antibody comprises SEQ ID NO: 53 and SEQ ID NO: 54. In some embodiments, the antibody comprises SEQ ID NO: 55 and SEQ ID NO: 56. In some embodiments, the antibody comprises SEQ ID NO: 57 and SEQ ID NO: 58. In some embodiments, the antibody comprises SEQ ID NO: 59 and SEQ ID NO: 60. In some embodiments, the antibody comprises SEQ ID NO: 334 and SEQ ID NO: 2. In some embodiments, the antibody comprises SEQ ID NO: 335 and SEQ ID NO: 4. In some embodiments, the antibody comprises SEQ ID NO: 336 and SEQ ID NO: 6. In some embodiments, the antibody comprises SEQ ID NO: 337 and SEQ ID NO: 8. In some embodiments, the antibody comprises SEQ ID NO: 338 and SEQ ID NO: 10. In some embodiments, the antibody comprises SEQ ID NO: 339 and SEQ ID NO: 12. In some embodiments, the antibody comprises SEQ ID NO: 340 and SEQ ID NO: 14. In some embodiments, the antibody comprises SEQ ID NO: 341 and SEQ ID NO: 16. In some embodiments, the antibody comprises SEQ ID NO: 342 and SEQ ID NO: 18. In some embodiments, the antibody comprises SEQ ID NO: 343 and SEQ ID NO: 20. In some embodiments, the antibody comprises SEQ ID NO: 344 and SEQ ID NO: 22. In some embodiments, the antibody comprises SEQ ID NO: 345 and SEQ ID NO: 24. In some embodiments, the antibody comprises SEQ ID NO: 346 and SEQ ID NO: 26. In some embodiments, the antibody comprises SEQ ID NO: 347 and SEQ ID NO: 28. In some embodiments, the antibody comprises SEQ ID NO: 348 and SEQ ID NO: 30. In some embodiments, the antibody comprises SEQ ID NO: 349 and SEQ ID NO: 32. In some embodiments, the antibody comprises SEQ ID NO: 350 and SEQ ID NO: 34. In some embodiments, the antibody comprises SEQ ID NO: 351 and SEQ ID NO: 36. In some embodiments, the antibody comprises SEQ ID NO: 352 and SEQ ID NO: 38. In some embodiments, the antibody comprises SEQ ID NO: 353 and SEQ ID NO: 40. In some embodiments, the antibody comprises SEQ ID NO: 354 and SEQ ID NO: 42. In some embodiments, the antibody comprises SEQ ID NO: 355 and SEQ ID NO: 44. In some embodiments, the antibody comprises SEQ ID NO: 356 and SEQ ID NO: 46. In some embodiments, the antibody comprises SEQ ID NO: 357 and SEQ ID NO: 48. In some embodiments, the antibody comprises SEQ ID NO: 358 and SEQ ID NO: 50. In some embodiments, the antibody comprises SEQ ID NO: 359 and SEQ ID NO: 52. In some embodiments, the antibody comprises SEQ ID NO: 360 and SEQ ID NO: 54. In some embodiments, the antibody comprises SEQ ID NO: 361 and SEQ ID NO: 56. In some embodiments, the antibody comprises SEQ ID NO: 362 and SEQ ID NO: 58. In some embodiments, the antibody comprises SEQ ID NO: 363 and SEQ ID NO: 60.

As provided for herein, the different peptides ($V_H$ or $V_L$) described herein can be linked with a peptide linker or not linked with a peptide linker and instead form a contiguous sequence. In some embodiments, the heavy chain variable region and the light chain variable region are not linked by a linker. In some embodiments, the heavy chain variable region and the light chain variable region are linked via a peptide linker. In some embodiments, the peptide linker comprises a sequence of $(GGGGS)_n$ (SEQ ID NO: 266); $(GGGGA)_n$ (SEQ ID NO: 267), or any combination thereof, wherein each n is independently 1-5. In some embodiments, each n is, independently, 1. In some embodiments, each n is, independently, 2. In some embodiments, each n is, independently, 3. In some embodiments, each n is, independently, 4. In some embodiments, each n is, independently, 5. The linked peptide format can be represented by a formula of $V_H$-Z-$V_L$ or $V_L$-Z-$V_H$, wherein Z is the peptide linker. In some embodiments, Z is $(GGGGS)_n$ (SEQ ID NO: 266); $(GGGGA)_n$ (SEQ ID NO: 267), or any combination thereof, wherein each n is independently 1-5. In some embodiments, each n is, independently, 1. In some embodiments, each n is, independently, 2. In some embodiments, each n is, independently, 3. In some embodiments, each n is, independently, 4. In some embodiments, each n is, independently, 5.

In some embodiments, the VH and VL polypeptides are linked to a Fc region, such as "IgG4 S228P L235E LS" or "IgG4 S228P L235E YTE". In some embodiments, the Fc region is as provided for herein. In some embodiments, the Fc region is "IgG4 S228P L235E LS". In some embodiments, the Fc region is "IgG4 S228 L235E YTE".

In some embodiments, an antibody, or antigen binding fragment thereof, comprises a $V_H$ peptide and a $V_L$ peptide as provided for herein. In some embodiments, the VH and VL each, independently, comprise 1, 2, 3, 4, or 5 conservative amino acid substitutions. In some embodiments, the CDRs of the VH and VL comprise no more than 1 amino acid conservative amino acid substitution. Therefore, in some embodiments the HCDR1, HCDR2, or HCDR3 could comprise one or no conservative amino acid substitutions. Additionally, in some embodiments the LCDR1, LCDR2, or LCDR3 could comprise one or no conservative amino acid substitutions.

In some embodiments, the antibody or antigen-binding fragment thereof comprises a light chain variable region and a heavy chain variable region, wherein the light chain variable region of the light chain has at least 85%, 86%, 87%, 88%, 89%, 90%, 91%, 92%, 93%, 94%, 95%, 96%, 97%, 98%, 99%, or 100% identity to SEQ ID NO: 2, the heavy chain variable region of the heavy chain has at least 85%, 86%, 87%, 88%, 89%, 90%, 91%, 92%, 93%, 94%, 95%, 96%, 97%, 98%, 99%, or 100% identity to SEQ ID NO: 1 and wherein the antibody, or antigen binding fragment thereof, maintains a HCDR1 sequence of SEQ ID NO: 61, SEQ ID NO: 124, or SEQ ID NO: 130, maintains a HCDR2 sequence of SEQ ID NO: 62, SEQ ID NO: 125, or SEQ ID NO: 131, maintains a HCDR3 sequence of SEQ ID NO: 63 or SEQ ID NO: 132, maintains a LCDR1 sequence of SEQ ID NO: 64, or SEQ ID NO: 133, maintains a LCDR2 sequence of SEQ ID NO: 65, or SEQ ID NO: 134, and maintains a LCDR3 sequence of SEQ ID NO: 66.

In some embodiments, the antibody or antigen-binding fragment thereof comprises a light chain variable region and a heavy chain variable region, wherein the light chain variable region of the light chain has at least 85%, 86%, 87%, 88%, 89%, 90%, 91%, 92%, 93%, 94%, 95%, 96%, 97%, 98%, 99%, or 100% identity to SEQ ID NO: 4, the heavy chain variable region of the heavy chain has at least 85%, 86%, 87%, 88%, 89%, 90%, 91%, 92%, 93%, 94%, 95%, 96%, 97%, 98%, 99%, or 100% identity to SEQ ID NO: 3, and wherein the antibody, or antigen binding fragment thereof, maintains a HCDR1 sequence of SEQ ID NO: 61, SEQ ID NO: 124, or SEQ ID NO: 130, maintains a HCDR2 sequence of SEQ ID NO: 62, SEQ ID NO: 125, or SEQ ID NO: 131, maintains a HCDR3 sequence of SEQ ID NO: 67 or SEQ ID NO: 135, maintains a LCDR1 sequence of SEQ ID NO: 64, or SEQ ID NO: 1339, maintains a LCDR2 sequence of SEQ ID NO: 65, or SEQ ID NO: 134, and maintains a LCDR3 sequence SEQ ID NO: 68.

In some embodiments, the antibody or antigen-binding fragment thereof comprises a light chain variable region and a heavy chain variable region, wherein the light chain variable region of the light chain has at least 85%, 86%, 87%, 88%, 89%, 90%, 91%, 92%, 93%, 94%, 95%, 96%, 97%, 98%, 99%, or 100% identity to SEQ ID NO: 6, the heavy chain variable region of the heavy chain has at least 85%, 86%, 87%, 88%, 89%, 90%, 91%, 92%, 93%, 94%, 95%, 96%, 97%, 98%, 99%, or 100% identity to SEQ ID NO: 5, and wherein the antibody, or antigen binding fragment thereof, maintains a HCDR1 sequence of SEQ ID NO: 61, SEQ ID NO: 124, or SEQ ID NO: 130, maintains a HCDR2 sequence of SEQ ID NO: 62, SEQ ID NO: 125, or SEQ ID NO: 131, maintains a HCDR3 sequence of SEQ ID NO: 69 or SEQ ID NO: 136, maintains a LCDR1 sequence of SEQ ID NO: 64, or SEQ ID NO: 133, maintains a LCDR2 sequence of SEQ ID NO: 65, or SEQ ID NO: 134, and maintains a LCDR3 sequence SEQ ID NO: 68.

In some embodiments, the antibody or antigen-binding fragment thereof comprises a light chain variable region and a heavy chain variable region, wherein the light chain variable region of the light chain has at least 85%, 86%, 87%, 88%, 89%, 90%, 91%, 92%, 93%, 94%, 95%, 96%, 97%, 98%, 99%, or 100% identity to SEQ ID NO: 8, the heavy chain variable region of the heavy chain has at least 85%, 86%, 87%, 88%, 89%, 90%, 91%, 92%, 93%, 94%, 95%, 96%, 97%, 98%, 99%, or 100% identity to SEQ ID NO: 7, and wherein the antibody, or antigen binding fragment thereof, maintains a HCDR1 sequence of SEQ ID NO: 61, SEQ ID NO: 124, or SEQ ID NO: 130, maintains a HCDR2 sequence of SEQ ID NO: 62, SEQ ID NO: 125, or SEQ ID NO: 131, maintains a HCDR3 sequence of SEQ ID NO: 70 or SEQ ID NO: 137, maintains a LCDR1 sequence of SEQ ID NO: 64, or SEQ ID NO: 133, maintains a LCDR2 sequence of SEQ ID NO: 65, or SEQ ID NO: 134, and maintains a LCDR3 sequence SEQ ID NO: 71.

In some embodiments, the antibody or antigen-binding fragment thereof comprises a light chain variable region and a heavy chain variable region, wherein the light chain variable region of the light chain has at least 85%, 86%, 87%, 88%, 89%, 90%, 91%, 92%, 93%, 94%, 95%, 96%, 97%, 98%, 99%, or 100% identity to SEQ ID NO: 10, the heavy chain variable region of the heavy chain has at least 85%, 86%, 87%, 88%, 89%, 90%, 91%, 92%, 93%, 94%, 95%, 96%, 97%, 98%, 99%, or 100% identity to SEQ ID NO: 9, and wherein the antibody, or antigen binding fragment thereof, maintains a HCDR1 sequence of SEQ ID NO: 61, SEQ ID NO: 124, or SEQ ID NO: 130, maintains a HCDR2 sequence of SEQ ID NO: 62, SEQ ID NO: 125, or SEQ ID NO: 131, maintains a HCDR3 sequence of SEQ ID NO: 72 or SEQ ID NO: 138, maintains a LCDR1 sequence of SEQ ID NO: 64, or SEQ ID NO: 133, maintains a LCDR2 sequence of SEQ ID NO: 65, or SEQ ID NO: 134, and maintains a LCDR3 sequence SEQ ID NO: 71.

In some embodiments, the antibody or antigen-binding fragment thereof comprises a light chain variable region and a heavy chain variable region, wherein the light chain variable region of the light chain has at least 85%, 86%, 87%, 88%, 89%, 90%, 91%, 92%, 93%, 94%, 95%, 96%, 97%, 98%, 99%, or 100% identity to SEQ ID NO: 12, the heavy chain variable region of the heavy chain has at least 85%, 86%, 87%, 88%, 89%, 90%, 91%, 92%, 93%, 94%, 95%, 96%, 97%, 98%, 99%, or 100% identity to SEQ ID NO: 11, and wherein the antibody, or antigen binding fragment thereof, maintains a HCDR1 sequence of SEQ ID NO: 61, SEQ ID NO: 124, or SEQ ID NO: 130, maintains a HCDR2 sequence of SEQ ID NO: 62, SEQ ID NO: 125, or SEQ ID NO: 131, maintains a HCDR3 sequence of SEQ ID NO: 73 or SEQ ID NO: 139, maintains a LCDR1 sequence of SEQ ID NO: 64, or SEQ ID NO: 133, maintains a LCDR2 sequence of SEQ ID NO: 65, or SEQ ID NO: 134, and maintains a LCDR3 sequence SEQ ID NO: 71.

In some embodiments, the antibody or antigen-binding fragment thereof comprises a light chain variable region and a heavy chain variable region, wherein the light chain variable region of the light chain has at least 85%, 86%, 87%, 88%, 89%, 90%, 91%, 92%, 93%, 94%, 95%, 96%, 97%, 98%, 99%, or 100% identity to SEQ ID NO: 14, the heavy chain variable region of the heavy chain has at least 85%, 86%, 87%, 88%, 89%, 90%, 91%, 92%, 93%, 94%, 95%, 96%, 97%, 98%, 99%, or 100% identity to SEQ ID NO: 13, and wherein the antibody, or antigen binding fragment thereof, maintains a HCDR1 sequence of SEQ ID NO: 61, SEQ ID NO: 124, or SEQ ID NO: 130, maintains a HCDR2 sequence of SEQ ID NO: 62, SEQ ID NO: 125, or SEQ ID NO: 131, maintains a HCDR3 sequence of SEQ ID NO: 74 or SEQ ID NO: 140, maintains a LCDR1 sequence of SEQ ID NO: 64, or SEQ ID NO: 133, maintains a LCDR2 sequence of SEQ ID NO: 65, or SEQ ID NO: 134, and maintains a LCDR3 sequence SEQ ID NO: 75.

In some embodiments, the antibody or antigen-binding fragment thereof comprises a light chain variable region and a heavy chain variable region, wherein the light chain variable region of the light chain has at least 85%, 86%, 87%, 88%, 89%, 90%, 91%, 92%, 93%, 94%, 95%, 96%, 97%, 98%, 99%, or 100% identity to SEQ ID NO: 16, the heavy chain variable region of the heavy chain has at least 85%, 86%, 87%, 88%, 89%, 90%, 91%, 92%, 93%, 94%, 95%, 96%, 97%, 98%, 99%, or 100% identity to SEQ ID NO: 15, and wherein the antibody, or antigen binding fragment thereof, maintains a HCDR1 sequence of SEQ ID NO: 61, SEQ ID NO: 124, or SEQ ID NO: 130, maintains a HCDR2 sequence of SEQ ID NO: 62, SEQ ID NO: 125, or SEQ ID NO: 131, maintains a HCDR3 sequence of SEQ ID NO: 76 or SEQ ID NO: 141, maintains a LCDR1 sequence of SEQ ID NO: 64, or SEQ ID NO: 133, maintains a LCDR2 sequence of SEQ ID NO: 65, or SEQ ID NO: 134, and maintains a LCDR3 sequence SEQ ID NO: 77.

In some embodiments, the antibody or antigen-binding fragment thereof comprises a light chain variable region and a heavy chain variable region, wherein the light chain variable region of the light chain has at least 85%, 86%, 87%, 88%, 89%, 90%, 91%, 92%, 93%, 94%, 95%, 96%, 97%, 98%, 99%, or 100% identity to SEQ ID NO: 18, the heavy chain variable region of the heavy chain has at least 85%, 86%, 87%, 88%, 89%, 90%, 91%, 92%, 93%, 94%, 95%, 96%, 97%, 98%, 99%, or 100% identity to SEQ ID NO: 17, and wherein the antibody, or antigen binding fragment thereof, maintains a HCDR1 sequence of SEQ ID NO: 61, SEQ ID NO: 124, or SEQ ID NO: 130, maintains a HCDR2 sequence of SEQ ID NO: 62, SEQ ID NO: 125, or SEQ ID NO: 131, maintains a HCDR3 sequence of SEQ ID NO: 78 or SEQ ID NO: 142, maintains a LCDR1 sequence of SEQ ID NO: 64, or SEQ ID NO: 133, maintains a LCDR2 sequence of SEQ ID NO: 65, or SEQ ID NO: 134, and maintains a LCDR3 sequence SEQ ID NO: 79.

In some embodiments, the antibody or antigen-binding fragment thereof comprises a light chain variable region and a heavy chain variable region, wherein the light chain variable region of the light chain has at least 85%, 86%, 87%, 88%, 89%, 90%, 91%, 92%, 93%, 94%, 95%, 96%, 97%, 98%, 99%, or 100% identity to SEQ ID NO: 20, the heavy chain variable region of the heavy chain has at least 85%, 86%, 87%, 88%, 89%, 90%, 91%, 92%, 93%, 94%, 95%, 96%, 97%, 98%, 99%, or 100% identity to SEQ ID NO: 19, and wherein the antibody, or antigen binding fragment thereof, maintains a HCDR1 sequence of SEQ ID NO: 61, SEQ ID NO: 124, or SEQ ID NO: 130, maintains a HCDR2 sequence of SEQ ID NO: 62, SEQ ID NO: 125, or SEQ ID NO: 131, maintains a HCDR3 sequence of SEQ ID NO: 80 or SEQ ID NO: 143, maintains a LCDR1 sequence of SEQ ID NO: 64, or SEQ ID NO: 133, maintains a LCDR2 sequence of SEQ ID NO: 65, or SEQ ID NO: 134, and maintains a LCDR3 sequence SEQ ID NO: 81.

In some embodiments, the antibody or antigen-binding fragment thereof comprises a light chain variable region and a heavy chain variable region, wherein the light chain variable region of the light chain has at least 85%, 86%, 87%, 88%, 89%, 90%, 91%, 92%, 93%, 94%, 95%, 96%, 97%, 98%, 99%, or 100% identity to SEQ ID NO: 22, the heavy chain variable region of the heavy chain has at least 85%, 86%, 87%, 88%, 89%, 90%, 91%, 92%, 93%, 94%, 95%, 96%, 97%, 98%, 99%, or 100% identity to SEQ ID NO: 21, and wherein the antibody, or antigen binding fragment thereof, maintains a HCDR1 sequence of SEQ ID NO: 82, SEQ ID NO: 126, or SEQ ID NO: 144, maintains a HCDR2 sequence of SEQ ID NO: 83, SEQ ID NO: 127, or SEQ ID NO: 145, maintains a HCDR3 sequence of SEQ ID NO: 84 or SEQ ID NO: 146, maintains a LCDR1 sequence of SEQ ID NO: 85, or SEQ ID NO: 147, maintains a LCDR2 sequence of SEQ ID NO: 86, or SEQ ID NO: 148, and maintains a LCDR3 sequence SEQ ID NO: 87.

In some embodiments, the antibody or antigen-binding fragment thereof comprises a light chain variable region and a heavy chain variable region, wherein the light chain variable region of the light chain has at least 85%, 86%, 87%, 88%, 89%, 90%, 91%, 92%, 93%, 94%, 95%, 96%, 97%, 98%, 99%, or 100% identity to SEQ ID NO: 24, the heavy chain variable region of the heavy chain has at least 85%, 86%, 87%, 88%, 89%, 90%, 91%, 92%, 93%, 94%, 95%, 96%, 97%, 98%, 99%, or 100% identity to SEQ ID NO: 23, and wherein the antibody, or antigen binding fragment thereof, maintains a HCDR1 sequence of SEQ ID NO: 82, SEQ ID NO: 126, or SEQ ID NO: 144, maintains a HCDR2 sequence of SEQ ID NO: 83, SEQ ID NO: 127, or SEQ ID NO: 145, maintains a HCDR3 sequence of SEQ ID NO: 88 or SEQ ID NO: 149, maintains a LCDR1 sequence of SEQ ID NO: 85, or SEQ ID NO: 147, maintains a LCDR2 sequence of SEQ ID NO: 86, or SEQ ID NO: 148, and maintains a LCDR3 sequence SEQ ID NO: 89.

In some embodiments, the antibody or antigen-binding fragment thereof comprises a light chain variable region and a heavy chain variable region, wherein the light chain variable region of the light chain has at least 85%, 86%, 87%, 88%, 89%, 90%, 91%, 92%, 93%, 94%, 95%, 96%, 97%, 98%, 99%, or 100% identity to SEQ ID NO: 26, the heavy chain variable region of the heavy chain has at least 85%, 86%, 87%, 88%, 89%, 90%, 91%, 92%, 93%, 94%, 95%, 96%, 97%, 98%, 99%, or 100% identity to SEQ ID NO: 25, and wherein the antibody, or antigen binding fragment thereof, maintains a HCDR1 sequence of SEQ ID NO: 82, SEQ ID NO: 126, or SEQ ID NO: 144, maintains a HCDR2 sequence of SEQ ID NO: 83, SEQ ID NO: 127, or SEQ ID NO: 145, maintains a HCDR3 sequence of SEQ ID NO: 90 or SEQ ID NO: 150, maintains a LCDR1 sequence of SEQ ID NO: 85, or SEQ ID NO: 147, maintains a LCDR2 sequence of SEQ ID NO: 86, or SEQ ID NO: 148, and maintains a LCDR3 sequence SEQ ID NO: 89.

In some embodiments, the antibody or antigen-binding fragment thereof comprises a light chain variable region and a heavy chain variable region, wherein the light chain variable region of the light chain has at least 85%, 86%, 87%, 88%, 89%, 90%, 91%, 92%, 93%, 94%, 95%, 96%, 97%, 98%, 99%, or 100% identity to SEQ ID NO: 28, the heavy chain variable region of the heavy chain has at least 85%, 86%, 87%, 88%, 89%, 90%, 91%, 92%, 93%, 94%, 95%, 96%, 97%, 98%, 99%, or 100% identity to SEQ ID NO: 27, and wherein the antibody, or antigen binding fragment thereof, maintains a HCDR1 sequence of SEQ ID NO: 82, SEQ ID NO: 126, or SEQ ID NO: 144, maintains a HCDR2 sequence of SEQ ID NO: 83, SEQ ID NO: 127, or SEQ ID NO: 145, maintains a HCDR3 sequence of SEQ ID NO: 91 or SEQ ID NO: 151, maintains a LCDR1 sequence of SEQ ID NO: 85, or SEQ ID NO: 147, maintains a LCDR2 sequence of SEQ ID NO: 86, or SEQ ID NO: 148, and maintains a LCDR3 sequence SEQ ID NO: 92.

In some embodiments, the antibody or antigen-binding fragment thereof comprises a light chain variable region and a heavy chain variable region, wherein the light chain variable region of the light chain has at least 85%, 86%, 87%, 88%, 89%, 90%, 91%, 92%, 93%, 94%, 95%, 96%, 97%, 98%, 99%, or 100% identity to SEQ ID NO: 30, the heavy chain variable region of the heavy chain has at least 85%, 86%, 87%, 88%, 89%, 90%, 91%, 92%, 93%, 94%, 95%, 96%, 97%, 98%, 99%, or 100% identity to SEQ ID NO: 29, and wherein the antibody, or antigen binding fragment thereof, maintains a HCDR1 sequence of SEQ ID NO: 82, SEQ ID NO: 126, or SEQ ID NO: 144, maintains a HCDR2 sequence of SEQ ID NO: 83, SEQ ID NO: 127, or SEQ ID NO: 145, maintains a HCDR3 sequence of SEQ ID NO: 93 or SEQ ID NO: 152, maintains a LCDR1 sequence of SEQ ID NO: 85, or SEQ ID NO: 147, maintains a LCDR2 sequence of SEQ ID NO: 86, or SEQ ID NO: 148, and maintains a LCDR3 sequence SEQ ID NO: 94.

In some embodiments, the antibody or antigen-binding fragment thereof comprises a light chain variable region and a heavy chain variable region, wherein the light chain variable region of the light chain has at least 85%, 86%, 87%, 88%, 89%, 90%, 91%, 92%, 93%, 94%, 95%, 96%, 97%, 98%, 99%, or 100% identity to SEQ ID NO: 32, the heavy chain variable region of the heavy chain has at least 85%, 86%, 87%, 88%, 89%, 90%, 91%, 92%, 93%, 94%, 95%, 96%, 97%, 98%, 99%, or 100% identity to SEQ ID NO: 31, and wherein the antibody, or antigen binding fragment thereof, maintains a HCDR1 sequence of SEQ ID NO: 82, SEQ ID NO: 126, or SEQ ID NO: 144, maintains a HCDR2 sequence of SEQ ID NO: 83, SEQ ID NO: 127, or SEQ ID NO: 145, maintains a HCDR3 sequence of SEQ ID NO: 84 or SEQ ID NO: 146, maintains a LCDR1 sequence of SEQ ID NO: 85, or SEQ ID NO: 147, maintains a LCDR2 sequence of SEQ ID NO: 86, or SEQ ID NO: 148, and maintains a LCDR3 sequence SEQ ID NO: 95.

In some embodiments, the antibody or antigen-binding fragment thereof comprises a light chain variable region and a heavy chain variable region, wherein the light chain variable region of the light chain has at least 85%, 86%, 87%, 88%, 89%, 90%, 91%, 92%, 93%, 94%, 95%, 96%, 97%, 98%, 99%, or 100% identity to SEQ ID NO: 34, the heavy chain variable region of the heavy chain has at least 85%, 86%, 87%, 88%, 89%, 90%, 91%, 92%, 93%, 94%, 95%, 96%, 97%, 98%, 99%, or 100% identity to SEQ ID NO: 33, and wherein the antibody, or antigen binding fragment thereof, maintains a HCDR1 sequence of SEQ ID NO: 82, SEQ ID NO: 126, or SEQ ID NO: 144, maintains a HCDR2 sequence of SEQ ID NO: 83, SEQ ID NO: 127, or SEQ ID NO: 145, maintains a HCDR3 sequence of SEQ ID NO: 96 or SEQ ID NO: 153, maintains a LCDR1 sequence of SEQ ID NO: 85, or SEQ ID NO: 147, maintains a LCDR2 sequence of SEQ ID NO: 86, or SEQ ID NO: 148, and maintains a LCDR3 sequence SEQ ID NO: 97.

In some embodiments, the antibody or antigen-binding fragment thereof comprises a light chain variable region and a heavy chain variable region, wherein the light chain variable region of the light chain has at least 85%, 86%, 87%, 88%, 89%, 90%, 91%, 92%, 93%, 94%, 95%, 96%, 97%, 98%, 99%, or 100% identity to SEQ ID NO: 36, the heavy chain variable region of the heavy chain has at least 85%, 86%, 87%, 88%, 89%, 90%, 91%, 92%, 93%, 94%, 95%, 96%, 97%, 98%, 99%, or 100% identity to SEQ ID NO: 35, and wherein the antibody, or antigen binding fragment thereof, maintains a HCDR1 sequence of SEQ ID NO: 82, SEQ ID NO: 126, or SEQ ID NO: 144, maintains a HCDR2 sequence of SEQ ID NO: 83, SEQ ID NO: 127, or SEQ ID NO: 145, maintains a HCDR3 sequence of SEQ ID NO: 98 or SEQ ID NO: 154, maintains a LCDR1 sequence of SEQ ID NO: 85, or SEQ ID NO: 147, maintains a LCDR2 sequence of SEQ ID NO: 86, or SEQ ID NO: 148, and maintains a LCDR3 sequence SEQ ID NO: 99.

In some embodiments, the antibody or antigen-binding fragment thereof comprises a light chain variable region and a heavy chain variable region, wherein the light chain variable region of the light chain has at least 85%, 86%, 87%, 88%, 89%, 90%, 91%, 92%, 93%, 94%, 95%, 96%, 97%, 98%, 99%, or 100% identity to SEQ ID NO: 38, the heavy chain variable region of the heavy chain has at least 85%, 86%, 87%, 88%, 89%, 90%, 91%, 92%, 93%, 94%, 95%, 96%, 97%, 98%, 99%, or 100% identity to SEQ ID NO: 37, and wherein the antibody, or antigen binding fragment thereof, maintains a HCDR1 sequence of SEQ ID NO: 82, SEQ ID NO: 126, or SEQ ID NO: 144, maintains a HCDR2 sequence of SEQ ID NO: 83, SEQ ID NO: 127, or SEQ ID NO: 145, maintains a HCDR3 sequence of SEQ ID NO: 100 or SEQ ID NO: 155, maintains a LCDR1 sequence of SEQ ID NO: 85, or SEQ ID NO: 147, maintains a LCDR2 sequence of SEQ ID NO: 86, or SEQ ID NO: 148, and maintains a LCDR3 sequence SEQ ID NO: 101.

In some embodiments, the antibody or antigen-binding fragment thereof comprises a light chain variable region and a heavy chain variable region, wherein the light chain variable region of the light chain has at least 85%, 86%, 87%, 88%, 89%, 90%, 91%, 92%, 93%, 94%, 95%, 96%, 97%, 98%, 99%, or 100% identity to SEQ ID NO: 40, the heavy chain variable region of the heavy chain has at least 85%, 86%, 87%, 88%, 89%, 90%, 91%, 92%, 93%, 94%, 95%, 96%, 97%, 98%, 99%, or 100% identity to SEQ ID NO: 39, and wherein the antibody, or antigen binding fragment thereof, maintains a HCDR1 sequence of SEQ ID NO: 82, SEQ ID NO: 126, or SEQ ID NO: 144, maintains a HCDR2 sequence of SEQ ID NO: 83, SEQ ID NO: 127, or SEQ ID NO: 145, maintains a HCDR3 sequence of SEQ ID NO: 100 or SEQ ID NO: 155, maintains a LCDR1 sequence of SEQ ID NO: 85, or SEQ ID NO: 147, maintains a LCDR2 sequence of SEQ ID NO: 86, or SEQ ID NO: 148, and maintains a LCDR3 sequence SEQ ID NO: 102.

In some embodiments, the antibody or antigen-binding fragment thereof comprises a light chain variable region and a heavy chain variable region, wherein the light chain variable region of the light chain has at least 85%, 86%, 87%, 88%, 89%, 90%, 91%, 92%, 93%, 94%, 95%, 96%, 97%, 98%, 99%, or 100% identity to SEQ ID NO: 44, the heavy chain variable region of the heavy chain has at least 85%, 86%, 87%, 88%, 89%, 90%, 91%, 92%, 93%, 94%, 95%, 96%, 97%, 98%, 99%, or 100% identity to SEQ ID NO: 41, and wherein the antibody, or antigen binding fragment thereof, maintains a HCDR1 sequence of SEQ ID NO: 103, SEQ ID NO: 128, or SEQ ID NO: 156, maintains a HCDR2 sequence of SEQ ID NO: 104, SEQ ID NO: 129, or SEQ ID NO: 157, maintains a HCDR3 sequence of SEQ ID NO: 105 or SEQ ID NO: 158, maintains a LCDR1 sequence of SEQ ID NO: 106, or SEQ ID NO: 159, maintains a LCDR2 sequence of SEQ ID NO: 107, or SEQ ID NO: 160, and maintains a LCDR3 sequence SEQ ID NO: 108.

In some embodiments, the antibody or antigen-binding fragment thereof comprises a light chain variable region and a heavy chain variable region, wherein the light chain variable region of the light chain has at least 85%, 86%, 87%, 88%, 89%, 90%, 91%, 92%, 93%, 94%, 95%, 96%, 97%, 98%, 99%, or 100% identity to SEQ ID NO: 44, the heavy chain variable region of the heavy chain has at least 85%, 86%, 87%, 88%, 89%, 90%, 91%, 92%, 93%, 94%, 95%, 96%, 97%, 98%, 99%, or 100% identity to SEQ ID NO: 43, and wherein the antibody, or antigen binding fragment thereof, maintains a HCDR1 sequence of SEQ ID NO: 103, SEQ ID NO: 128, or SEQ ID NO: 156, maintains a HCDR2 sequence of SEQ ID NO: 104, SEQ ID NO: 129, or SEQ ID NO: 157, maintains a HCDR3 sequence of SEQ ID NO: 109 or SEQ ID NO: 161, maintains a LCDR1 sequence of SEQ ID NO: 106, or SEQ ID NO: 159, maintains a LCDR2 sequence of SEQ ID NO: 107, or SEQ ID NO: 160, and maintains a LCDR3 sequence SEQ ID NO: 110.

In some embodiments, the antibody or antigen-binding fragment thereof comprises a light chain variable region and a heavy chain variable region, wherein the light chain variable region of the light chain has at least 85%, 86%, 87%, 88%, 89%, 90%, 91%, 92%, 93%, 94%, 95%, 96%, 97%, 98%, 99%, or 100% identity to SEQ ID NO: 46, the heavy chain variable region of the heavy chain has at least 85%, 86%, 87%, 88%, 89%, 90%, 91%, 92%, 93%, 94%, 95%, 96%, 97%, 98%, 99%, or 100% identity to SEQ ID NO: 45, and wherein the antibody, or antigen binding fragment thereof, maintains a HCDR1 sequence of SEQ ID NO: 103, SEQ ID NO: 128, or SEQ ID NO: 156, maintains a HCDR2 sequence of SEQ ID NO: 104, SEQ ID NO: 129, or SEQ ID NO: 157, maintains a HCDR3 sequence of SEQ ID NO: 111 or SEQ ID NO: 162, maintains a LCDR1 sequence of SEQ ID NO: 106, or SEQ ID NO: 159, maintains a LCDR2 sequence of SEQ ID NO: 107, or SEQ ID NO: 160, and maintains a LCDR3 sequence SEQ ID NO: 112.

In some embodiments, the antibody or antigen-binding fragment thereof comprises a light chain variable region and a heavy chain variable region, wherein the light chain variable region of the light chain has at least 85%, 86%, 87%, 88%, 89%, 90%, 91%, 92%, 93%, 94%, 95%, 96%, 97%, 98%, 99%, or 100% identity to SEQ ID NO: 48, the heavy chain variable region of the heavy chain has at least 85%, 86%, 87%, 88%, 89%, 90%, 91%, 92%, 93%, 94%, 95%, 96%, 97%, 98%, 99%, or 100% identity to SEQ ID NO: 47, and wherein the antibody, or antigen binding fragment thereof, maintains a HCDR1 sequence of SEQ ID NO: 103, SEQ ID NO: 128, or SEQ ID NO: 156, maintains a HCDR2 sequence of SEQ ID NO: 104, SEQ ID NO: 129, or SEQ ID NO: 157, maintains a HCDR3 sequence of SEQ ID NO: 105 or SEQ ID NO: 158, maintains a LCDR1 sequence of SEQ ID NO: 106, or SEQ ID NO: 159, maintains a LCDR2 sequence of SEQ ID NO: 107, or SEQ ID NO: 160, and maintains a LCDR3 sequence SEQ ID NO: 113.

In some embodiments, the antibody or antigen-binding fragment thereof comprises a light chain variable region and a heavy chain variable region, wherein the light chain variable region of the light chain has at least 85%, 86%, 87%, 88%, 89%, 90%, 91%, 92%, 93%, 94%, 95%, 96%, 97%, 98%, 99%, or 100% identity to SEQ ID NO: 50, the heavy chain variable region of the heavy chain has at least 85%, 86%, 87%, 88%, 89%, 90%, 91%, 92%, 93%, 94%, 95%, 96%, 97%, 98%, 99%, or 100% identity to SEQ ID NO: 49, and wherein the antibody, or antigen binding fragment thereof, maintains a HCDR1 sequence of SEQ ID NO: 103, SEQ ID NO: 128, or SEQ ID NO: 156, maintains a HCDR2 sequence of SEQ ID NO: 104, SEQ ID NO: 129, or SEQ ID NO: 157, maintains a HCDR3 sequence of SEQ ID NO: 114 or SEQ ID NO: 163, maintains a LCDR1 sequence of SEQ ID NO: 106, or SEQ ID NO: 159, maintains a LCDR2 sequence of SEQ ID NO: 107, or SEQ ID NO: 160, and maintains a LCDR3 sequence SEQ ID NO: 115.

In some embodiments, the antibody or antigen-binding fragment thereof comprises a light chain variable region and a heavy chain variable region, wherein the light chain variable region of the light chain has at least 85%, 86%, 87%, 88%, 89%, 90%, 91%, 92%, 93%, 94%, 95%, 96%, 97%, 98%, 99%, or 100% identity to SEQ ID NO: 52, the heavy chain variable region of the heavy chain has at least 85%, 86%, 87%, 88%, 89%, 90%, 91%, 92%, 93%, 94%, 95%, 96%, 97%, 98%, 99%, or 100% identity to SEQ ID NO: 51, and wherein the antibody, or antigen binding fragment thereof, maintains a HCDR1 sequence of SEQ ID NO: 103, SEQ ID NO: 128, or SEQ ID NO: 156, maintains a HCDR2 sequence of SEQ ID NO: 104, SEQ ID NO: 129, or SEQ ID NO: 157, maintains a HCDR3 sequence of SEQ ID NO: 116 or SEQ ID NO: 164, maintains a LCDR1 sequence of SEQ ID NO: 106, or SEQ ID NO: 159, maintains a LCDR2 sequence of SEQ ID NO: 107, or SEQ ID NO: 160, and maintains a LCDR3 sequence SEQ ID NO: 113.

In some embodiments, the antibody or antigen-binding fragment thereof comprises a light chain variable region and a heavy chain variable region, wherein the light chain variable region of the light chain has at least 85%, 86%, 87%, 88%, 89%, 90%, 91%, 92%, 93%, 94%, 95%, 96%, 97%, 98%, 99%, or 100% identity to SEQ ID NO: 54, the heavy chain variable region of the heavy chain has at least 85%, 86%, 87%, 88%, 89%, 90%, 91%, 92%, 93%, 94%, 95%, 96%, 97%, 98%, 99%, or 100% identity to SEQ ID NO: 55, and wherein the antibody, or antigen binding fragment thereof, maintains a HCDR1 sequence of SEQ ID NO: 103, SEQ ID NO: 128, or SEQ ID NO: 156, maintains a HCDR2 sequence of SEQ ID NO: 104, SEQ ID NO: 129, or SEQ ID NO: 157, maintains a HCDR3 sequence of SEQ ID NO: 117 or SEQ ID NO: 165, maintains a LCDR1 sequence of SEQ ID NO: 106, or SEQ ID NO: 159, maintains a LCDR2 sequence of SEQ ID NO: 107, or SEQ ID NO: 160, and maintains a LCDR3 sequence SEQ ID NO: 118.

In some embodiments, the antibody or antigen-binding fragment thereof comprises a light chain variable region and a heavy chain variable region, wherein the light chain variable region of the light chain has at least 85%, 86%, 87%, 88%, 89%, 90%, 91%, 92%, 93%, 94%, 95%, 96%, 97%, 98%, 99%, or 100% identity to SEQ ID NO: 56, the heavy chain variable region of the heavy chain has at least 85%, 86%, 87%, 88%, 89%, 90%, 91%, 92%, 93%, 94%, 95%, 96%, 97%, 98%, 99%, or 100% identity to SEQ ID NO: 55, and wherein the antibody, or antigen binding fragment thereof, maintains a HCDR1 sequence of SEQ ID NO: 103, SEQ ID NO: 128, or SEQ ID NO: 156, maintains a HCDR2 sequence of SEQ ID NO: 104, SEQ ID NO: 129, or SEQ ID NO: 157, maintains a HCDR3 sequence of SEQ ID NO: 116 or SEQ ID NO: 164, maintains a LCDR1 sequence of SEQ ID NO: 106, or SEQ ID NO: 159, maintains a LCDR2 sequence of SEQ ID NO: 107, or SEQ ID NO: 160, and maintains a LCDR3 sequence SEQ ID NO: 119.

In some embodiments, the antibody or antigen-binding fragment thereof comprises a light chain variable region and a heavy chain variable region, wherein the light chain variable region of the light chain has at least 85%, 86%, 87%, 88%, 89%, 90%, 91%, 92%, 93%, 94%, 95%, 96%, 97%, 98%, 99%, or 100% identity to SEQ ID NO: 58, the heavy chain variable region of the heavy chain has at least 85%, 86%, 87%, 88%, 89%, 90%, 91%, 92%, 93%, 94%, 95%, 96%, 97%, 98%, 99%, or 100% identity to SEQ ID NO: 57, and wherein the antibody, or antigen binding fragment thereof, maintains a HCDR1 sequence of SEQ ID NO: 103, SEQ ID NO: 128, or SEQ ID NO: 156, maintains a HCDR2 sequence of SEQ ID NO: 104, SEQ ID NO: 129, or SEQ ID NO: 157, maintains a HCDR3 sequence of SEQ ID NO: 120 or SEQ ID NO: 166, maintains a LCDR1 sequence of SEQ ID NO: 106, or SEQ ID NO: 159, maintains a LCDR2 sequence of SEQ ID NO: 107, or SEQ ID NO: 160, and maintains a LCDR3 sequence SEQ ID NO: 121.

In some embodiments, the antibody or antigen-binding fragment thereof comprises a light chain variable region and a heavy chain variable region, wherein the light chain variable region of the light chain has at least 85%, 86%, 87%, 88%, 89%, 90%, 91%, 92%, 93%, 94%, 95%, 96%, 97%, 98%, 99%, or 100% identity to SEQ ID NO: 60, the heavy chain variable region of the heavy chain has at least 85%, 86%, 87%, 88%, 89%, 90%, 91%, 92%, 93%, 94%, 95%, 96%, 97%, 98%, 99%, or 100% identity to SEQ ID NO: 59, and wherein the antibody, or antigen binding fragment thereof, maintains a HCDR1 sequence of SEQ ID NO: 103, SEQ ID NO: 128, or SEQ ID NO: 156, maintains a HCDR2 sequence of SEQ ID NO: 104, SEQ ID NO: 129, or SEQ ID NO: 157, maintains a HCDR3 sequence of SEQ ID NO: 122 or SEQ ID NO: 167, maintains a LCDR1 sequence of SEQ ID NO: 106, or SEQ ID NO: 159, maintains a LCDR2 sequence of SEQ ID NO: 107, or SEQ ID NO: 160, and maintains a LCDR3 sequence SEQ ID NO: 123.

In some embodiments, the antibody or antigen-binding fragment thereof comprises a light chain variable region and a heavy chain variable region, wherein the light chain variable region of the light chain has at least 85%, 86%, 87%, 88%, 89%, 90%, 91%, 92%, 93%, 94%, 95%, 96%, 97%, 98%, 99%, or 100% identity to SEQ ID NO: 2, the heavy chain variable region of the heavy chain has at least 85%, 86%, 87%, 88%, 89%, 90%, 91%, 92%, 93%, 94%, 95%, 96%, 97%, 98%, 99%, or 100% identity to SEQ ID NO: 334 and wherein the antibody, or antigen binding fragment thereof, maintains a HCDR1 sequence of SEQ ID NO: 61, SEQ ID NO: 124, or SEQ ID NO: 130, maintains a HCDR2 sequence of SEQ ID NO: 62, SEQ ID NO: 125, or SEQ ID NO: 131, maintains a HCDR3 sequence of SEQ ID NO: 63 or SEQ ID NO: 132, maintains a LCDR1 sequence of SEQ ID NO: 64, or SEQ ID NO: 133, maintains a LCDR2 sequence of SEQ ID NO: 65, or SEQ ID NO: 134, and maintains a LCDR3 sequence of SEQ ID NO: 66.

In some embodiments, the antibody or antigen-binding fragment thereof comprises a light chain variable region and a heavy chain variable region, wherein the light chain variable region of the light chain has at least 85%, 86%, 87%, 88%, 89%, 90%, 91%, 92%, 93%, 94%, 95%, 96%, 97%, 98%, 99%, or 100% identity to SEQ ID NO: 4, the heavy chain variable region of the heavy chain has at least 85%, 86%, 87%, 88%, 89%, 90%, 91%, 92%, 93%, 94%, 95%, 96%, 97%, 98%, 99%, or 100% identity to SEQ ID NO: 335, and wherein the antibody, or antigen binding fragment thereof, maintains a HCDR1 sequence of SEQ ID NO: 61, SEQ ID NO: 124, or SEQ ID NO: 130, maintains a HCDR2 sequence of SEQ ID NO: 62, SEQ ID NO: 125, or SEQ ID NO: 131, maintains a HCDR3 sequence of SEQ ID NO: 67 or SEQ ID NO: 135, maintains a LCDR1 sequence of SEQ ID NO: 64, or SEQ ID NO: 1339, maintains a LCDR2 sequence of SEQ ID NO: 65, or SEQ ID NO: 134, and maintains a LCDR3 sequence SEQ ID NO: 68.

In some embodiments, the antibody or antigen-binding fragment thereof comprises a light chain variable region and a heavy chain variable region, wherein the light chain variable region of the light chain has at least 85%, 86%, 87%, 88%, 89%, 90%, 91%, 92%, 93%, 94%, 95%, 96%, 97%, 98%, 99%, or 100% identity to SEQ ID NO: 6, the heavy chain variable region of the heavy chain has at least 85%, 86%, 87%, 88%, 89%, 90%, 91%, 92%, 93%, 94%, 95%, 96%, 97%, 98%, 99%, or 100% identity to SEQ ID NO: 336, and wherein the antibody, or antigen binding fragment thereof, maintains a HCDR1 sequence of SEQ ID NO: 61, SEQ ID NO: 124, or SEQ ID NO: 130, maintains a HCDR2 sequence of SEQ ID NO: 62, SEQ ID NO: 125, or SEQ ID NO: 131, maintains a HCDR3 sequence of SEQ ID NO: 69 or SEQ ID NO: 136, maintains a LCDR1 sequence of SEQ ID NO: 64, or SEQ ID NO: 133, maintains a LCDR2 sequence of SEQ ID NO: 65, or SEQ ID NO: 134, and maintains a LCDR3 sequence SEQ ID NO: 68.

In some embodiments, the antibody or antigen-binding fragment thereof comprises a light chain variable region and a heavy chain variable region, wherein the light chain variable region of the light chain has at least 85%, 86%, 87%, 88%, 89%, 90%, 91%, 92%, 93%, 94%, 95%, 96%, 97%, 98%, 99%, or 100% identity to SEQ ID NO: 8, the heavy chain variable region of the heavy chain has at least 85%, 86%, 87%, 88%, 89%, 90%, 91%, 92%, 93%, 94%, 95%, 96%, 97%, 98%, 99%, or 100% identity to SEQ ID NO: 337, and wherein the antibody, or antigen binding fragment thereof, maintains a HCDR1 sequence of SEQ ID NO: 61, SEQ ID NO: 124, or SEQ ID NO: 130, maintains a HCDR2 sequence of SEQ ID NO: 62, SEQ ID NO: 125, or SEQ ID NO: 131, maintains a HCDR3 sequence of SEQ ID NO: 70 or SEQ ID NO: 137, maintains a LCDR1 sequence of SEQ ID NO: 64, or SEQ ID NO: 133, maintains a LCDR2 sequence of SEQ ID NO: 65, or SEQ ID NO: 134, and maintains a LCDR3 sequence SEQ ID NO: 71.

In some embodiments, the antibody or antigen-binding fragment thereof comprises a light chain variable region and a heavy chain variable region, wherein the light chain variable region of the light chain has at least 85%, 86%, 87%, 88%, 89%, 90%, 91%, 92%, 93%, 94%, 95%, 96%, 97%, 98%, 99%, or 100% identity to SEQ ID NO: 10, the heavy chain variable region of the heavy chain has at least 85%, 86%, 87%, 88%, 89%, 90%, 91%, 92%, 93%, 94%, 95%, 96%, 97%, 98%, 99%, or 100% identity to SEQ ID NO: 338, and wherein the antibody, or antigen binding fragment thereof, maintains a HCDR1 sequence of SEQ ID NO: 61, SEQ ID NO: 124, or SEQ ID NO: 130, maintains a HCDR2 sequence of SEQ ID NO: 62, SEQ ID NO: 125, or SEQ ID NO: 131, maintains a HCDR3 sequence of SEQ ID NO: 72 or SEQ ID NO: 138, maintains a LCDR1 sequence of SEQ ID NO: 64, or SEQ ID NO: 133, maintains a LCDR2 sequence of SEQ ID NO: 65, or SEQ ID NO: 134, and maintains a LCDR3 sequence SEQ ID NO: 71.

In some embodiments, the antibody or antigen-binding fragment thereof comprises a light chain variable region and a heavy chain variable region, wherein the light chain variable region of the light chain has at least 85%, 86%, 87%, 88%, 89%, 90%, 91%, 92%, 93%, 94%, 95%, 96%, 97%, 98%, 99%, or 100% identity to SEQ ID NO: 12, the heavy chain variable region of the heavy chain has at least 85%, 86%, 87%, 88%, 89%, 90%, 91%, 92%, 93%, 94%, 95%, 96%, 97%, 98%, 99%, or 100% identity to SEQ ID NO: 1339, and wherein the antibody, or antigen binding fragment thereof, maintains a HCDR1 sequence of SEQ ID NO: 61, SEQ ID NO: 124, or SEQ ID NO: 130, maintains a HCDR2 sequence of SEQ ID NO: 62, SEQ ID NO: 125, or SEQ ID NO: 131, maintains a HCDR3 sequence of SEQ ID NO: 73 or SEQ ID NO: 139, maintains a LCDR1 sequence of SEQ ID NO: 64, or SEQ ID NO: 133, maintains a LCDR2 sequence of SEQ ID NO: 65, or SEQ ID NO: 134, and maintains a LCDR3 sequence SEQ ID NO: 71.

In some embodiments, the antibody or antigen-binding fragment thereof comprises a light chain variable region and a heavy chain variable region, wherein the light chain variable region of the light chain has at least 85%, 86%, 87%, 88%, 89%, 90%, 91%, 92%, 93%, 94%, 95%, 96%, 97%, 98%, 99%, or 100% identity to SEQ ID NO: 14, the heavy chain variable region of the heavy chain has at least 85%, 86%, 87%, 88%, 89%, 90%, 91%, 92%, 93%, 94%, 95%, 96%, 97%, 98%, 99%, or 100% identity to SEQ ID NO: 340, and wherein the antibody, or antigen binding fragment thereof, maintains a HCDR1 sequence of SEQ ID NO: 61, SEQ ID NO: 124, or SEQ ID NO: 130, maintains a HCDR2 sequence of SEQ ID NO: 62, SEQ ID NO: 125, or SEQ ID NO: 131, maintains a HCDR3 sequence of SEQ ID NO: 74 or SEQ ID NO: 140, maintains a LCDR1 sequence of SEQ ID NO: 64, or SEQ ID NO: 133, maintains a LCDR2 sequence of SEQ ID NO: 65, or SEQ ID NO: 134, and maintains a LCDR3 sequence SEQ ID NO: 75.

In some embodiments, the antibody or antigen-binding fragment thereof comprises a light chain variable region and a heavy chain variable region, wherein the light chain variable region of the light chain has at least 85%, 86%, 87%, 88%, 89%, 90%, 91%, 92%, 93%, 94%, 95%, 96%, 97%, 98%, 99%, or 100% identity to SEQ ID NO: 16, the heavy chain variable region of the heavy chain has at least 85%, 86%, 87%, 88%, 89%, 90%, 91%, 92%, 93%, 94%, 95%, 96%, 97%, 98%, 99%, or 100% identity to SEQ ID NO: 341, and wherein the antibody, or antigen binding fragment thereof, maintains a HCDR1 sequence of SEQ ID NO: 61, SEQ ID NO: 124, or SEQ ID NO: 130, maintains a HCDR2 sequence of SEQ ID NO: 62, SEQ ID NO: 125, or SEQ ID NO: 131, maintains a HCDR3 sequence of SEQ ID NO: 76 or SEQ ID NO: 141, maintains a LCDR1 sequence of SEQ ID NO: 64, or SEQ ID NO: 133, maintains a LCDR2 sequence of SEQ ID NO: 65, or SEQ ID NO: 134, and maintains a LCDR3 sequence SEQ ID NO: 77.

In some embodiments, the antibody or antigen-binding fragment thereof comprises a light chain variable region and a heavy chain variable region, wherein the light chain variable region of the light chain has at least 85%, 86%, 87%, 88%, 89%, 90%, 91%, 92%, 93%, 94%, 95%, 96%, 97%, 98%, 99%, or 100% identity to SEQ ID NO: 18, the heavy chain variable region of the heavy chain has at least 85%, 86%, 87%, 88%, 89%, 90%, 91%, 92%, 93%, 94%, 95%, 96%, 97%, 98%, 99%, or 100% identity to SEQ ID NO: 342, and wherein the antibody, or antigen binding fragment thereof, maintains a HCDR1 sequence of SEQ ID NO: 61, SEQ ID NO: 124, or SEQ ID NO: 130, maintains a HCDR2 sequence of SEQ ID NO: 62, SEQ ID NO: 125, or SEQ ID NO: 131, maintains a HCDR3 sequence of SEQ ID NO: 78 or SEQ ID NO: 142, maintains a LCDR1 sequence of SEQ ID NO: 64, or SEQ ID NO: 133, maintains a LCDR2 sequence of SEQ ID NO: 65, or SEQ ID NO: 134, and maintains a LCDR3 sequence SEQ ID NO: 79.

In some embodiments, the antibody or antigen-binding fragment thereof comprises a light chain variable region and a heavy chain variable region, wherein the light chain variable region of the light chain has at least 85%, 86%, 87%, 88%, 89%, 90%, 91%, 92%, 93%, 94%, 95%, 96%, 97%, 98%, 99%, or 100% identity to SEQ ID NO: 20, the heavy chain variable region of the heavy chain has at least 85%, 86%, 87%, 88%, 89%, 90%, 91%, 92%, 93%, 94%, 95%, 96%, 97%, 98%, 99%, or 100% identity to SEQ ID NO: 343, and wherein the antibody, or antigen binding fragment thereof, maintains a HCDR1 sequence of SEQ ID NO: 61, SEQ ID NO: 124, or SEQ ID NO: 130, maintains a HCDR2 sequence of SEQ ID NO: 62, SEQ ID NO: 125, or SEQ ID NO: 131, maintains a HCDR3 sequence of SEQ ID NO: 80 or SEQ ID NO: 143, maintains a LCDR1 sequence of SEQ ID NO: 64, or SEQ ID NO: 133, maintains a LCDR2 sequence of SEQ ID NO: 65, or SEQ ID NO: 134, and maintains a LCDR3 sequence SEQ ID NO: 81.

In some embodiments, the antibody or antigen-binding fragment thereof comprises a light chain variable region and a heavy chain variable region, wherein the light chain variable region of the light chain has at least 85%, 86%, 87%, 88%, 89%, 90%, 91%, 92%, 93%, 94%, 95%, 96%, 97%, 98%, 99%, or 100% identity to SEQ ID NO: 22, the heavy chain variable region of the heavy chain has at least 85%, 86%, 87%, 88%, 89%, 90%, 91%, 92%, 93%, 94%, 95%, 96%, 97%, 98%, 99%, or 100% identity to SEQ ID NO: 344, and wherein the antibody, or antigen binding fragment thereof, maintains a HCDR1 sequence of SEQ ID NO: 82, SEQ ID NO: 126, or SEQ ID NO: 144, maintains a HCDR2 sequence of SEQ ID NO: 83, SEQ ID NO: 127, or SEQ ID NO: 145, maintains a HCDR3 sequence of SEQ ID NO: 84 or SEQ ID NO: 146, maintains a LCDR1 sequence of SEQ ID NO: 85, or SEQ ID NO: 147, maintains a LCDR2 sequence of SEQ ID NO: 86, or SEQ ID NO: 148, and maintains a LCDR3 sequence SEQ ID NO: 87.

In some embodiments, the antibody or antigen-binding fragment thereof comprises a light chain variable region and a heavy chain variable region, wherein the light chain variable region of the light chain has at least 85%, 86%, 87%, 88%, 89%, 90%, 91%, 92%, 93%, 94%, 95%, 96%, 97%, 98%, 99%, or 100% identity to SEQ ID NO: 24, the heavy chain variable region of the heavy chain has at least 85%, 86%, 87%, 88%, 89%, 90%, 91%, 92%, 93%, 94%, 95%, 96%, 97%, 98%, 99%, or 100% identity to SEQ ID NO: 345, and wherein the antibody, or antigen binding fragment thereof, maintains a HCDR1 sequence of SEQ ID NO: 82, SEQ ID NO: 126, or SEQ ID NO: 144, maintains a HCDR2 sequence of SEQ ID NO: 83, SEQ ID NO: 127, or SEQ ID NO: 145, maintains a HCDR3 sequence of SEQ ID NO: 88 or SEQ ID NO: 149, maintains a LCDR1 sequence of SEQ ID NO: 85, or SEQ ID NO: 147, maintains a LCDR2 sequence of SEQ ID NO: 86, or SEQ ID NO: 148, and maintains a LCDR3 sequence SEQ ID NO: 89.

In some embodiments, the antibody or antigen-binding fragment thereof comprises a light chain variable region and a heavy chain variable region, wherein the light chain variable region of the light chain has at least 85%, 86%, 87%, 88%, 89%, 90%, 91%, 92%, 93%, 94%, 95%, 96%, 97%, 98%, 99%, or 100% identity to SEQ ID NO: 26, the heavy chain variable region of the heavy chain has at least 85%, 86%, 87%, 88%, 89%, 90%, 91%, 92%, 93%, 94%, 95%, 96%, 97%, 98%, 99%, or 100% identity to SEQ ID NO: 346, and wherein the antibody, or antigen binding fragment thereof, maintains a HCDR1 sequence of SEQ ID NO: 82, SEQ ID NO: 126, or SEQ ID NO: 144, maintains a HCDR2 sequence of SEQ ID NO: 83, SEQ ID NO: 127, or SEQ ID NO: 145, maintains a HCDR3 sequence of SEQ ID NO: 90 or SEQ ID NO: 150, maintains a LCDR1 sequence of SEQ ID NO: 85, or SEQ ID NO: 147, maintains a LCDR2 sequence of SEQ ID NO: 86, or SEQ ID NO: 148, and maintains a LCDR3 sequence SEQ ID NO: 89.

In some embodiments, the antibody or antigen-binding fragment thereof comprises a light chain variable region and a heavy chain variable region, wherein the light chain variable region of the light chain has at least 85%, 86%, 87%, 88%, 89%, 90%, 91%, 92%, 93%, 94%, 95%, 96%, 97%, 98%, 99%, or 100% identity to SEQ ID NO: 28, the heavy chain variable region of the heavy chain has at least 85%, 86%, 87%, 88%, 89%, 90%, 91%, 92%, 93%, 94%, 95%, 96%, 97%, 98%, 99%, or 100% identity to SEQ ID NO: 347, and wherein the antibody, or antigen binding fragment thereof, maintains a HCDR1 sequence of SEQ ID NO: 82, SEQ ID NO: 126, or SEQ ID NO: 144, maintains a HCDR2 sequence of SEQ ID NO: 83, SEQ ID NO: 127, or SEQ ID NO: 145, maintains a HCDR3 sequence of SEQ ID NO: 91 or SEQ ID NO: 151, maintains a LCDR1 sequence of SEQ ID NO: 85, or SEQ ID NO: 147, maintains a LCDR2 sequence of SEQ ID NO: 86, or SEQ ID NO: 148, and maintains a LCDR3 sequence SEQ ID NO: 92.

In some embodiments, the antibody or antigen-binding fragment thereof comprises a light chain variable region and a heavy chain variable region, wherein the light chain variable region of the light chain has at least 85%, 86%, 87%, 88%, 89%, 90%, 91%, 92%, 93%, 94%, 95%, 96%, 97%, 98%, 99%, or 100% identity to SEQ ID NO: 30, the heavy chain variable region of the heavy chain has at least 85%, 86%, 87%, 88%, 89%, 90%, 91%, 92%, 93%, 94%, 95%, 96%, 97%, 98%, 99%, or 100% identity to SEQ ID NO: 348, and wherein the antibody, or antigen binding fragment thereof, maintains a HCDR1 sequence of SEQ ID NO: 82, SEQ ID NO: 126, or SEQ ID NO: 144, maintains a HCDR2 sequence of SEQ ID NO: 83, SEQ ID NO: 127, or SEQ ID NO: 145, maintains a HCDR3 sequence of SEQ ID NO: 93 or SEQ ID NO: 152, maintains a LCDR1 sequence of SEQ ID NO: 85, or SEQ ID NO: 147, maintains a LCDR2 sequence of SEQ ID NO: 86, or SEQ ID NO: 148, and maintains a LCDR3 sequence SEQ ID NO: 94.

In some embodiments, the antibody or antigen-binding fragment thereof comprises a light chain variable region and a heavy chain variable region, wherein the light chain variable region of the light chain has at least 85%, 86%, 87%, 88%, 89%, 90%, 91%, 92%, 93%, 94%, 95%, 96%, 97%, 98%, 99%, or 100% identity to SEQ ID NO: 32, the heavy chain variable region of the heavy chain has at least 85%, 86%, 87%, 88%, 89%, 90%, 91%, 92%, 93%, 94%, 95%, 96%, 97%, 98%, 99%, or 100% identity to SEQ ID NO: 349, and wherein the antibody, or antigen binding fragment thereof, maintains a HCDR1 sequence of SEQ ID NO: 82, SEQ ID NO: 126, or SEQ ID NO: 144, maintains a HCDR2 sequence of SEQ ID NO: 83, SEQ ID NO: 127, or SEQ ID NO: 145, maintains a HCDR3 sequence of SEQ ID NO: 84 or SEQ ID NO: 146, maintains a LCDR1 sequence of SEQ ID NO: 85, or SEQ ID NO: 147, maintains a LCDR2 sequence of SEQ ID NO: 86, or SEQ ID NO: 148, and maintains a LCDR3 sequence SEQ ID NO: 95.

In some embodiments, the antibody or antigen-binding fragment thereof comprises a light chain variable region and a heavy chain variable region, wherein the light chain variable region of the light chain has at least 85%, 86%, 87%, 88%, 89%, 90%, 91%, 92%, 93%, 94%, 95%, 96%, 97%, 98%, 99%, or 100% identity to SEQ ID NO: 34, the heavy chain variable region of the heavy chain has at least 85%, 86%, 87%, 88%, 89%, 90%, 91%, 92%, 93%, 94%, 95%, 96%, 97%, 98%, 99%, or 100% identity to SEQ ID NO: 350, and wherein the antibody, or antigen binding fragment thereof, maintains a HCDR1 sequence of SEQ ID NO: 82, SEQ ID NO: 126, or SEQ ID NO: 144, maintains a HCDR2 sequence of SEQ ID NO: 83, SEQ ID NO: 127, or SEQ ID NO: 145, maintains a HCDR3 sequence of SEQ ID NO: 96 or SEQ ID NO: 153, maintains a LCDR1 sequence of SEQ ID NO: 85, or SEQ ID NO: 147, maintains a LCDR2 sequence of SEQ ID NO: 86, or SEQ ID NO: 148, and maintains a LCDR3 sequence SEQ ID NO: 97.

In some embodiments, the antibody or antigen-binding fragment thereof comprises a light chain variable region and a heavy chain variable region, wherein the light chain variable region of the light chain has at least 85%, 86%, 87%, 88%, 89%, 90%, 91%, 92%, 93%, 94%, 95%, 96%, 97%, 98%, 99%, or 100% identity to SEQ ID NO: 36, the heavy chain variable region of the heavy chain has at least 85%, 86%, 87%, 88%, 89%, 90%, 91%, 92%, 93%, 94%, 95%, 96%, 97%, 98%, 99%, or 100% identity to SEQ ID NO: 351, and wherein the antibody, or antigen binding fragment thereof, maintains a HCDR1 sequence of SEQ ID NO: 82, SEQ ID NO: 126, or SEQ ID NO: 144, maintains a HCDR2 sequence of SEQ ID NO: 83, SEQ ID NO: 127, or SEQ ID NO: 145, maintains a HCDR3 sequence of SEQ ID NO: 98 or SEQ ID NO: 154, maintains a LCDR1 sequence of SEQ ID NO: 85, or SEQ ID NO: 147, maintains a LCDR2 sequence of SEQ ID NO: 86, or SEQ ID NO: 148, and maintains a LCDR3 sequence SEQ ID NO: 99.

In some embodiments, the antibody or antigen-binding fragment thereof comprises a light chain variable region and a heavy chain variable region, wherein the light chain variable region of the light chain has at least 85%, 86%, 87%, 88%, 89%, 90%, 91%, 92%, 93%, 94%, 95%, 96%, 97%, 98%, 99%, or 100% identity to SEQ ID NO: 38, the heavy chain variable region of the heavy chain has at least 85%, 86%, 87%, 88%, 89%, 90%, 91%, 92%, 93%, 94%, 95%, 96%, 97%, 98%, 99%, or 100% identity to SEQ ID NO: 352, and wherein the antibody, or antigen binding fragment thereof, maintains a HCDR1 sequence of SEQ ID NO: 82, SEQ ID NO: 126, or SEQ ID NO: 144, maintains a HCDR2 sequence of SEQ ID NO: 83, SEQ ID NO: 127, or SEQ ID NO: 145, maintains a HCDR3 sequence of SEQ ID NO: 100 or SEQ ID NO: 155, maintains a LCDR1 sequence of SEQ ID NO: 85, or SEQ ID NO: 147, maintains a LCDR2 sequence of SEQ ID NO: 86, or SEQ ID NO: 148, and maintains a LCDR3 sequence SEQ ID NO: 101.

In some embodiments, the antibody or antigen-binding fragment thereof comprises a light chain variable region and a heavy chain variable region, wherein the light chain variable region of the light chain has at least 85%, 86%, 87%, 88%, 89%, 90%, 91%, 92%, 93%, 94%, 95%, 96%, 97%, 98%, 99%, or 100% identity to SEQ ID NO: 40, the heavy chain variable region of the heavy chain has at least 85%, 86%, 87%, 88%, 89%, 90%, 91%, 92%, 93%, 94%, 95%, 96%, 97%, 98%, 99%, or 100% identity to SEQ ID NO: 353, and wherein the antibody, or antigen binding fragment thereof, maintains a HCDR1 sequence of SEQ ID NO: 82, SEQ ID NO: 126, or SEQ ID NO: 144, maintains a HCDR2 sequence of SEQ ID NO: 83, SEQ ID NO: 127, or SEQ ID NO: 145, maintains a HCDR3 sequence of SEQ ID NO: 100 or SEQ ID NO: 155, maintains a LCDR1 sequence of SEQ ID NO: 85, or SEQ ID NO: 147, maintains a LCDR2 sequence of SEQ ID NO: 86, or SEQ ID NO: 148, and maintains a LCDR3 sequence SEQ ID NO: 102.

In some embodiments, the antibody or antigen-binding fragment thereof comprises a light chain variable region and a heavy chain variable region, wherein the light chain variable region of the light chain has at least 85%, 86%, 87%, 88%, 89%, 90%, 91%, 92%, 93%, 94%, 95%, 96%, 97%, 98%, 99%, or 100% identity to SEQ ID NO: 44, the heavy chain variable region of the heavy chain has at least 85%, 86%, 87%, 88%, 89%, 90%, 91%, 92%, 93%, 94%, 95%, 96%, 97%, 98%, 99%, or 100% identity to SEQ ID NO: 354, and wherein the antibody, or antigen binding fragment thereof, maintains a HCDR1 sequence of SEQ ID NO: 103, SEQ ID NO: 128, or SEQ ID NO: 156, maintains a HCDR2 sequence of SEQ ID NO: 104, SEQ ID NO: 129, or SEQ ID NO: 157, maintains a HCDR3 sequence of SEQ ID NO: 105 or SEQ ID NO: 158, maintains a LCDR1 sequence of SEQ ID NO: 106, or SEQ ID NO: 159, maintains a LCDR2 sequence of SEQ ID NO: 107, or SEQ ID NO: 160, and maintains a LCDR3 sequence SEQ ID NO: 108.

In some embodiments, the antibody or antigen-binding fragment thereof comprises a light chain variable region and a heavy chain variable region, wherein the light chain variable region of the light chain has at least 85%, 86%, 87%, 88%, 89%, 90%, 91%, 92%, 93%, 94%, 95%, 96%, 97%, 98%, 99%, or 100% identity to SEQ ID NO: 44, the heavy chain variable region of the heavy chain has at least 85%, 86%, 87%, 88%, 89%, 90%, 91%, 92%, 93%, 94%, 95%, 96%, 97%, 98%, 99%, or 100% identity to SEQ ID NO: 355, and wherein the antibody, or antigen binding fragment thereof, maintains a HCDR1 sequence of SEQ ID NO: 103, SEQ ID NO: 128, or SEQ ID NO: 156, maintains a HCDR2 sequence of SEQ ID NO: 104, SEQ ID NO: 129, or SEQ ID NO: 157, maintains a HCDR3 sequence of SEQ ID NO: 109 or SEQ ID NO: 161, maintains a LCDR1 sequence of SEQ ID NO: 106, or SEQ ID NO: 159, maintains a LCDR2 sequence of SEQ ID NO: 107, or SEQ ID NO: 160, and maintains a LCDR3 sequence SEQ ID NO: 110.

In some embodiments, the antibody or antigen-binding fragment thereof comprises a light chain variable region and a heavy chain variable region, wherein the light chain variable region of the light chain has at least 85%, 86%, 87%, 88%, 89%, 90%, 91%, 92%, 93%, 94%, 95%, 96%, 97%, 98%, 99%, or 100% identity to SEQ ID NO: 46, the heavy chain variable region of the heavy chain has at least 85%, 86%, 87%, 88%, 89%, 90%, 91%, 92%, 93%, 94%, 95%, 96%, 97%, 98%, 99%, or 100% identity to SEQ ID NO: 356, and wherein the antibody, or antigen binding fragment thereof, maintains a HCDR1 sequence of SEQ ID NO: 103, SEQ ID NO: 128, or SEQ ID NO: 156, maintains a HCDR2 sequence of SEQ ID NO: 104, SEQ ID NO: 129, or SEQ ID NO: 157, maintains a HCDR3 sequence of SEQ ID NO: 111 or SEQ ID NO: 162, maintains a LCDR1 sequence of SEQ ID NO: 106, or SEQ ID NO: 159, maintains a LCDR2 sequence of SEQ ID NO: 107, or SEQ ID NO: 160, and maintains a LCDR3 sequence SEQ ID NO: 112.

In some embodiments, the antibody or antigen-binding fragment thereof comprises a light chain variable region and a heavy chain variable region, wherein the light chain variable region of the light chain has at least 85%, 86%, 87%, 88%, 89%, 90%, 91%, 92%, 93%, 94%, 95%, 96%, 97%, 98%, 99%, or 100% identity to SEQ ID NO: 48, the heavy chain variable region of the heavy chain has at least 85%, 86%, 87%, 88%, 89%, 90%, 91%, 92%, 93%, 94%, 95%, 96%, 97%, 98%, 99%, or 100% identity to SEQ ID NO: 357, and wherein the antibody, or antigen binding fragment thereof, maintains a HCDR1 sequence of SEQ ID NO: 103, SEQ ID NO: 128, or SEQ ID NO: 156, maintains a HCDR2 sequence of SEQ ID NO: 104, SEQ ID NO: 129, or SEQ ID NO: 157, maintains a HCDR3 sequence of SEQ ID NO: 105 or SEQ ID NO: 158, maintains a LCDR1 sequence of SEQ ID NO: 106, or SEQ ID NO: 159, maintains a LCDR2 sequence of SEQ ID NO: 107, or SEQ ID NO: 160, and maintains a LCDR3 sequence SEQ ID NO: 113.

In some embodiments, the antibody or antigen-binding fragment thereof comprises a light chain variable region and a heavy chain variable region, wherein the light chain variable region of the light chain has at least 85%, 86%, 87%, 88%, 89%, 90%, 91%, 92%, 93%, 94%, 95%, 96%, 97%, 98%, 99%, or 100% identity to SEQ ID NO: 50, the heavy chain variable region of the heavy chain has at least 85%, 86%, 87%, 88%, 89%, 90%, 91%, 92%, 93%, 94%, 95%, 96%, 97%, 98%, 99%, or 100% identity to SEQ ID NO: 358, and wherein the antibody, or antigen binding fragment thereof, maintains a HCDR1 sequence of SEQ ID NO: 103, SEQ ID NO: 128, or SEQ ID NO: 156, maintains a HCDR2 sequence of SEQ ID NO: 104, SEQ ID NO: 129, or SEQ ID NO: 157, maintains a HCDR3 sequence of SEQ ID NO: 114 or SEQ ID NO: 163, maintains a LCDR1 sequence of SEQ ID NO: 106, or SEQ ID NO: 159, maintains a LCDR2 sequence of SEQ ID NO: 107, or SEQ ID NO: 160, and maintains a LCDR3 sequence SEQ ID NO: 115.

In some embodiments, the antibody or antigen-binding fragment thereof comprises a light chain variable region and a heavy chain variable region, wherein the light chain variable region of the light chain has at least 85%, 86%, 87%, 88%, 89%, 90%, 91%, 92%, 93%, 94%, 95%, 96%, 97%, 98%, 99%, or 100% identity to SEQ ID NO: 52, the heavy chain variable region of the heavy chain has at least 85%, 86%, 87%, 88%, 89%, 90%, 91%, 92%, 93%, 94%, 95%, 96%, 97%, 98%, 99%, or 100% identity to SEQ ID NO: 359, and wherein the antibody, or antigen binding fragment thereof, maintains a HCDR1 sequence of SEQ ID NO: 103, SEQ ID NO: 128, or SEQ ID NO: 156, maintains a HCDR2 sequence of SEQ ID NO: 104, SEQ ID NO: 129, or SEQ ID NO: 157, maintains a HCDR3 sequence of SEQ ID NO: 116 or SEQ ID NO: 164, maintains a LCDR1 sequence of SEQ ID NO: 106, or SEQ ID NO: 159, maintains a LCDR2 sequence of SEQ ID NO: 107, or SEQ ID NO: 160, and maintains a LCDR3 sequence SEQ ID NO: 113.

In some embodiments, the antibody or antigen-binding fragment thereof comprises a light chain variable region and a heavy chain variable region, wherein the light chain variable region of the light chain has at least 85%, 86%, 87%, 88%, 89%, 90%, 91%, 92%, 93%, 94%, 95%, 96%, 97%, 98%, 99%, or 100% identity to SEQ ID NO: 54, the heavy chain variable region of the heavy chain has at least 85%, 86%, 87%, 88%, 89%, 90%, 91%, 92%, 93%, 94%, 95%, 96%, 97%, 98%, 99%, or 100% identity to SEQ ID NO: 360, and wherein the antibody, or antigen binding fragment thereof, maintains a HCDR1 sequence of SEQ ID NO: 103, SEQ ID NO: 128, or SEQ ID NO: 156, maintains a HCDR2 sequence of SEQ ID NO: 104, SEQ ID NO: 129, or SEQ ID NO: 157, maintains a HCDR3 sequence of SEQ ID NO: 117 or SEQ ID NO: 165, maintains a LCDR1 sequence of SEQ ID NO: 106, or SEQ ID NO: 159, maintains a LCDR2 sequence of SEQ ID NO: 107, or SEQ ID NO: 160, and maintains a LCDR3 sequence SEQ ID NO: 118.

In some embodiments, the antibody or antigen-binding fragment thereof comprises a light chain variable region and a heavy chain variable region, wherein the light chain variable region of the light chain has at least 85%, 86%, 87%, 88%, 89%, 90%, 91%, 92%, 93%, 94%, 95%, 96%, 97%, 98%, 99%, or 100% identity to SEQ ID NO: 56, the heavy chain variable region of the heavy chain has at least 85%, 86%, 87%, 88%, 89%, 90%, 91%, 92%, 93%, 94%, 95%, 96%, 97%, 98%, 99%, or 100% identity to SEQ ID NO: 361, and wherein the antibody, or antigen binding fragment thereof, maintains a HCDR1 sequence of SEQ ID NO: 103, SEQ ID NO: 128, or SEQ ID NO: 156, maintains a HCDR2 sequence of SEQ ID NO: 104, SEQ ID NO: 129, or SEQ ID NO: 157, maintains a HCDR3 sequence of SEQ ID NO: 116 or SEQ ID NO: 164, maintains a LCDR1 sequence of SEQ ID NO: 106, or SEQ ID NO: 159, maintains a LCDR2 sequence of SEQ ID NO: 107, or SEQ ID NO: 160, and maintains a LCDR3 sequence SEQ ID NO: 119.

In some embodiments, the antibody or antigen-binding fragment thereof comprises a light chain variable region and a heavy chain variable region, wherein the light chain variable region of the light chain has at least 85%, 86%, 87%, 88%, 89%, 90%, 91%, 92%, 93%, 94%, 95%, 96%, 97%, 98%, 99%, or 100% identity to SEQ ID NO: 58, the heavy chain variable region of the heavy chain has at least 85%, 86%, 87%, 88%, 89%, 90%, 91%, 92%, 93%, 94%, 95%, 96%, 97%, 98%, 99%, or 100% identity to SEQ ID NO: 362, and wherein the antibody, or antigen binding fragment thereof, maintains a HCDR1 sequence of SEQ ID NO: 103, SEQ ID NO: 128, or SEQ ID NO: 156, maintains a HCDR2 sequence of SEQ ID NO: 104, SEQ ID NO: 129, or SEQ ID NO: 157, maintains a HCDR3 sequence of SEQ ID NO: 120 or SEQ ID NO: 166, maintains a LCDR1 sequence of SEQ ID NO: 106, or SEQ ID NO: 159, maintains a LCDR2 sequence of SEQ ID NO: 107, or SEQ ID NO: 160, and maintains a LCDR3 sequence SEQ ID NO: 121.

In some embodiments, the antibody or antigen-binding fragment thereof comprises a light chain variable region and a heavy chain variable region, wherein the light chain variable region of the light chain has at least 85%, 86%, 87%, 88%, 89%, 90%, 91%, 92%, 93%, 94%, 95%, 96%, 97%, 98%, 99%, or 100% identity to SEQ ID NO: 60, the heavy chain variable region of the heavy chain has at least 85%, 86%, 87%, 88%, 89%, 90%, 91%, 92%, 93%, 94%, 95%, 96%, 97%, 98%, 99%, or 100% identity to SEQ ID NO: 363, and wherein the antibody, or antigen binding fragment thereof, maintains a HCDR1 sequence of SEQ ID NO: 103, SEQ ID NO: 128, or SEQ ID NO: 156, maintains a HCDR2 sequence of SEQ ID NO: 104, SEQ ID NO: 129, or SEQ ID NO: 157, maintains a HCDR3 sequence of SEQ ID NO: 122 or SEQ ID NO: 167, maintains a LCDR1 sequence of SEQ ID NO: 106, or SEQ ID NO: 159, maintains a LCDR2 sequence of SEQ ID NO: 107, or SEQ ID NO: 160, and maintains a LCDR3 sequence SEQ ID NO: 123.

In some embodiments, an antibody, or antigen binding fragment thereof, comprises a $V_H$ peptide and a $V_L$ peptide, wherein the $V_H$ peptide comprises a sequence of SEQ ID NO: 1 and the $V_L$ peptide comprises a sequence of SEQ ID NO: 2.

In some embodiments, an antibody, or antigen binding fragment thereof, comprises a $V_H$ peptide and a $V_L$ peptide, wherein the $V_H$ peptide comprises a sequence of SEQ ID NO: 3 and the $V_L$ peptide comprises a sequence of SEQ ID NO: 4.

In some embodiments, an antibody, or antigen binding fragment thereof, comprises a $V_H$ peptide and a $V_L$ peptide, wherein the $V_H$ peptide comprises a sequence of SEQ ID NO: 5 and the $V_L$ peptide comprises a sequence of SEQ ID NO: 6.

In some embodiments, an antibody, or antigen binding fragment thereof, comprises a VH peptide and a VL peptide, wherein the VH peptide comprises a sequence of SEQ ID NO: 7 and the VL peptide comprises a sequence of SEQ ID NO: 8.

In some embodiments, an antibody, or antigen binding fragment thereof, comprises a VH peptide and a VL peptide, wherein the VH peptide comprises a sequence of SEQ ID NO: 9 and the VL peptide comprises a sequence of SEQ ID NO: 10.

In some embodiments, an antibody, or antigen binding fragment thereof, comprises a VH peptide and a VL peptide, wherein the VH peptide comprises a sequence of SEQ ID NO: 11 and the VL peptide comprises a sequence of SEQ ID NO: 12.

In some embodiments, an antibody, or antigen binding fragment thereof, comprises a VH peptide and a VL peptide, wherein the VH peptide comprises a sequence of SEQ ID NO: 13 and the VL peptide comprises a sequence of SEQ ID NO: 14.

In some embodiments, an antibody, or antigen binding fragment thereof, comprises a VH peptide and a VL peptide, wherein the VH peptide comprises a sequence of SEQ ID NO: 15 and the VL peptide comprises a sequence of SEQ ID NO: 16.

In some embodiments, an antibody, or antigen binding fragment thereof, comprises a VH peptide and a VL peptide, wherein the VH peptide comprises a sequence of SEQ ID NO: 17 and the VL peptide comprises a sequence of SEQ ID NO: 18.

In some embodiments, an antibody, or antigen binding fragment thereof, comprises a VH peptide and a VL peptide, wherein the VH peptide comprises a sequence of SEQ ID NO: 19 and the VL peptide comprises a sequence of SEQ ID NO: 20.

In some embodiments, an antibody, or antigen binding fragment thereof, comprises a VH peptide and a VL peptide, wherein the VH peptide comprises a sequence of SEQ ID NO: 21 and the VL peptide comprises a sequence of SEQ ID NO: 22.

In some embodiments, an antibody, or antigen binding fragment thereof, comprises a VH peptide and a VL peptide, wherein the VH peptide comprises a sequence of SEQ ID NO: 23 and the VL peptide comprises a sequence of SEQ ID NO: 24.

In some embodiments, an antibody, or antigen binding fragment thereof, comprises a VH peptide and a VL peptide, wherein the VH peptide comprises a sequence of SEQ ID NO: 25 and the VL peptide comprises a sequence of SEQ ID NO: 26.

In some embodiments, an antibody, or antigen binding fragment thereof, comprises a VH peptide and a VL peptide, wherein the VH peptide comprises a sequence of SEQ ID NO: 27 and the VL peptide comprises a sequence of SEQ ID NO: 28.

In some embodiments, an antibody, or antigen binding fragment thereof, comprises a VH peptide and a VL peptide, wherein the VH peptide comprises a sequence of SEQ ID NO: 29 and the VL peptide comprises a sequence of SEQ ID NO: 30.

In some embodiments, an antibody, or antigen binding fragment thereof, comprises a VH peptide and a VL peptide, wherein the VH peptide comprises a sequence of SEQ ID NO: 31 and the VL peptide comprises a sequence of SEQ ID NO: 32.

In some embodiments, an antibody, or antigen binding fragment thereof, comprises a VH peptide and a VL peptide, wherein the VH peptide comprises a sequence of SEQ ID NO: 33 and the VL peptide comprises a sequence of SEQ ID NO: 34.

In some embodiments, an antibody, or antigen binding fragment thereof, comprises a VH peptide and a VL peptide, wherein the VH peptide comprises a sequence of SEQ ID NO: 35 and the VL peptide comprises a sequence of SEQ ID NO: 36.

In some embodiments, an antibody, or antigen binding fragment thereof, comprises a VH peptide and a VL peptide, wherein the VH peptide comprises a sequence of SEQ ID NO: 37 and the VL peptide comprises a sequence of SEQ ID NO: 38.

In some embodiments, an antibody, or antigen binding fragment thereof, comprises a VH peptide and a VL peptide, wherein the VH peptide comprises a sequence of SEQ ID NO: 39 and the VL peptide comprises a sequence of SEQ ID NO: 40.

In some embodiments, an antibody, or antigen binding fragment thereof, comprises a VH peptide and a VL peptide, wherein the VH peptide comprises a sequence of SEQ ID NO: 41 and the VL peptide comprises a sequence of SEQ ID NO: 42.

In some embodiments, an antibody, or antigen binding fragment thereof, comprises a VH peptide and a VL peptide, wherein the VH peptide comprises a sequence of SEQ ID NO: 43 and the VL peptide comprises a sequence of SEQ ID NO: 44.

In some embodiments, an antibody, or antigen binding fragment thereof, comprises a VH peptide and a VL peptide, wherein the VH peptide comprises a sequence of SEQ ID NO: 45 and the VL peptide comprises a sequence of SEQ ID NO: 46.

In some embodiments, an antibody, or antigen binding fragment thereof, comprises a VH peptide and a VL peptide, wherein the VH peptide comprises a sequence of SEQ ID NO: 47 and the VL peptide comprises a sequence of SEQ ID NO: 48.

In some embodiments, an antibody, or antigen binding fragment thereof, comprises a VH peptide and a VL peptide, wherein the VH peptide comprises a sequence of SEQ ID NO: 49 and the VL peptide comprises a sequence of SEQ ID NO: 50.

In some embodiments, an antibody, or antigen binding fragment thereof, comprises a VH peptide and a VL peptide, wherein the VH peptide comprises a sequence of SEQ ID NO: 51 and the VL peptide comprises a sequence of SEQ ID NO: 52.

In some embodiments, an antibody, or antigen binding fragment thereof, comprises a VH peptide and a VL peptide, wherein the VH peptide comprises a sequence of SEQ ID NO: 53 and the VL peptide comprises a sequence of SEQ ID NO: 54.

In some embodiments, an antibody, or antigen binding fragment thereof, comprises a VH peptide and a VL peptide, wherein the VH peptide comprises a sequence of SEQ ID NO: 55 and the VL peptide comprises a sequence of SEQ ID NO: 56.

In some embodiments, an antibody, or antigen binding fragment thereof, comprises a VH peptide and a VL peptide, wherein the VH peptide comprises a sequence of SEQ ID NO: 57 and the VL peptide comprises a sequence of SEQ ID NO: 58.

In some embodiments, an antibody, or antigen binding fragment thereof, comprises a VH peptide and a VL peptide, wherein the VH peptide comprises a sequence of SEQ ID NO: 59 and the VL peptide comprises a sequence of SEQ ID NO: 60.

In some embodiments, an antibody, or antigen binding fragment thereof, comprises a $V_H$ peptide and a $V_L$ peptide, wherein the $V_H$ peptide comprises a sequence of SEQ ID NO: 334 and the $V_L$ peptide comprises a sequence of SEQ ID NO: 2.

In some embodiments, an antibody, or antigen binding fragment thereof, comprises a $V_H$ peptide and a $V_L$ peptide, wherein the $V_H$ peptide comprises a sequence of SEQ ID NO: 335 and the $V_L$ peptide comprises a sequence of SEQ ID NO: 4.

In some embodiments, an antibody, or antigen binding fragment thereof, comprises a $V_H$ peptide and a $V_L$ peptide, wherein the $V_H$ peptide comprises a sequence of SEQ ID NO: 336 and the $V_L$ peptide comprises a sequence of SEQ ID NO: 6.

In some embodiments, an antibody, or antigen binding fragment thereof, comprises a VH peptide and a VL peptide, wherein the VH peptide comprises a sequence of SEQ ID NO: 337 and the VL peptide comprises a sequence of SEQ ID NO: 8.

In some embodiments, an antibody, or antigen binding fragment thereof, comprises a VH peptide and a VL peptide, wherein the VH peptide comprises a sequence of SEQ ID NO: 338 and the VL peptide comprises a sequence of SEQ ID NO: 10.

In some embodiments, an antibody, or antigen binding fragment thereof, comprises a VH peptide and a VL peptide, wherein the VH peptide comprises a sequence of SEQ ID NO: 339 and the VL peptide comprises a sequence of SEQ ID NO: 12.

In some embodiments, an antibody, or antigen binding fragment thereof, comprises a VH peptide and a VL peptide, wherein the VH peptide comprises a sequence of SEQ ID NO: 340 and the VL peptide comprises a sequence of SEQ ID NO: 14.

In some embodiments, an antibody, or antigen binding fragment thereof, comprises a VH peptide and a VL peptide, wherein the VH peptide comprises a sequence of SEQ ID NO: 341 and the VL peptide comprises a sequence of SEQ ID NO: 16.

In some embodiments, an antibody, or antigen binding fragment thereof, comprises a VH peptide and a VL peptide, wherein the VH peptide comprises a sequence of SEQ ID NO: 342 and the VL peptide comprises a sequence of SEQ ID NO: 18.

In some embodiments, an antibody, or antigen binding fragment thereof, comprises a VH peptide and a VL peptide, wherein the VH peptide comprises a sequence of SEQ ID NO: 343 and the VL peptide comprises a sequence of SEQ ID NO: 20.

In some embodiments, an antibody, or antigen binding fragment thereof, comprises a VH peptide and a VL peptide, wherein the VH peptide comprises a sequence of SEQ ID NO: 344 and the VL peptide comprises a sequence of SEQ ID NO: 22.

In some embodiments, an antibody, or antigen binding fragment thereof, comprises a VH peptide and a VL peptide, wherein the VH peptide comprises a sequence of SEQ ID NO: 345 and the VL peptide comprises a sequence of SEQ ID NO: 24.

In some embodiments, an antibody, or antigen binding fragment thereof, comprises a VH peptide and a VL peptide, wherein the VH peptide comprises a sequence of SEQ ID NO: 346 and the VL peptide comprises a sequence of SEQ ID NO: 26.

In some embodiments, an antibody, or antigen binding fragment thereof, comprises a VH peptide and a VL peptide, wherein the VH peptide comprises a sequence of SEQ ID NO: 347 and the VL peptide comprises a sequence of SEQ ID NO: 28.

In some embodiments, an antibody, or antigen binding fragment thereof, comprises a VH peptide and a VL peptide, wherein the VH peptide comprises a sequence of SEQ ID NO: 348 and the VL peptide comprises a sequence of SEQ ID NO: 30.

In some embodiments, an antibody, or antigen binding fragment thereof, comprises a VH peptide and a VL peptide, wherein the VH peptide comprises a sequence of SEQ ID NO: 349 and the VL peptide comprises a sequence of SEQ ID NO: 32.

In some embodiments, an antibody, or antigen binding fragment thereof, comprises a VH peptide and a VL peptide, wherein the VH peptide comprises a sequence of SEQ ID NO: 350 and the VL peptide comprises a sequence of SEQ ID NO: 34.

In some embodiments, an antibody, or antigen binding fragment thereof, comprises a VH peptide and a VL peptide, wherein the VH peptide comprises a sequence of SEQ ID NO: 351 and the VL peptide comprises a sequence of SEQ ID NO: 36.

In some embodiments, an antibody, or antigen binding fragment thereof, comprises a VH peptide and a VL peptide, wherein the VH peptide comprises a sequence of SEQ ID NO: 352 and the VL peptide comprises a sequence of SEQ ID NO: 38.

In some embodiments, an antibody, or antigen binding fragment thereof, comprises a VH peptide and a VL peptide, wherein the VH peptide comprises a sequence of SEQ ID NO: 353 and the VL peptide comprises a sequence of SEQ ID NO: 40.

In some embodiments, an antibody, or antigen binding fragment thereof, comprises a VH peptide and a VL peptide, wherein the VH peptide comprises a sequence of SEQ ID NO: 354 and the VL peptide comprises a sequence of SEQ ID NO: 42.

In some embodiments, an antibody, or antigen binding fragment thereof, comprises a VH peptide and a VL peptide, wherein the VH peptide comprises a sequence of SEQ ID NO: 355 and the VL peptide comprises a sequence of SEQ ID NO: 44.

In some embodiments, an antibody, or antigen binding fragment thereof, comprises a VH peptide and a VL peptide, wherein the VH peptide comprises a sequence of SEQ ID NO: 356 and the VL peptide comprises a sequence of SEQ ID NO: 46.

In some embodiments, an antibody, or antigen binding fragment thereof, comprises a VH peptide and a VL peptide, wherein the VH peptide comprises a sequence of SEQ ID NO: 357 and the VL peptide comprises a sequence of SEQ ID NO: 48.

In some embodiments, an antibody, or antigen binding fragment thereof, comprises a VH peptide and a VL peptide, wherein the VH peptide comprises a sequence of SEQ ID NO: 358 and the VL peptide comprises a sequence of SEQ ID NO: 50.

In some embodiments, an antibody, or antigen binding fragment thereof, comprises a VH peptide and a VL peptide, wherein the VH peptide comprises a sequence of SEQ ID NO: 359 and the VL peptide comprises a sequence of SEQ ID NO: 52.

In some embodiments, an antibody, or antigen binding fragment thereof, comprises a VH peptide and a VL peptide, wherein the VH peptide comprises a sequence of SEQ ID NO: 360 and the VL peptide comprises a sequence of SEQ ID NO: 54.

In some embodiments, an antibody, or antigen binding fragment thereof, comprises a VH peptide and a VL peptide, wherein the VH peptide comprises a sequence of SEQ ID NO: 361 and the VL peptide comprises a sequence of SEQ ID NO: 56.

In some embodiments, an antibody, or antigen binding fragment thereof, comprises a VH peptide and a VL peptide, wherein the VH peptide comprises a sequence of SEQ ID NO: 362 and the VL peptide comprises a sequence of SEQ ID NO: 58.

In some embodiments, an antibody, or antigen binding fragment thereof, comprises a VH peptide and a VL peptide, wherein the VH peptide comprises a sequence of SEQ ID NO: 363 and the VL peptide comprises a sequence of SEQ ID NO: 60.

In some embodiments, the antibody comprises a heavy chain as set forth below, which includes the variable region and the constant domain:

TABLE 7

| SEQ ID NO: | AB ID NO. | Heavy Chain Sequence |
|---|---|---|
| 168 | MAB1 with constant domain PE and LS mutations | QVQLVESGGGLVKPGGSLRLSCAASGFTFSDYYMSWIRQAP GKGLEWVSYISRSGSTKYYADSVKGRFTISRDNAKNSLYLQ MNSLRAEDTAVYYCARDQEDYALDYWGQGTLVTVSSAST KGPSVFPLAPCSRSTSESTAALGCLVKDYFPEPVTVSWNSGA LTSGVHTFPAVLQSSGLYSLSSVVTVPSSSLGTKTYTCNVDH KPSNTKVDKRVESKYGPPCPPCPAPEFEGGPSVFLFPPKPKD TLMISRTPEVTCVVVDVSQEDPEVQFNWYVDGVEVHNAKT KPREEQFNSTYRVVSVLTVLHQDWLNGKEYKCKVSNKGLP SSIEKTISKAKGQPREPQVYTLPPSQEEMTKNQVSLTCLVKG FYPSDIAVEWESNGQPENNYKTTPPVLDSDGSFFLYSRLTVD KSRWQEGNVFSCSVLHEALHSHYTQKSLSLSLG |
| 169 | MAB1 with constant domain PE and YTE mutations | QVQLVESGGGLVKPGGSLRLSCAASGFTFSDYYMSWIRQAP GKGLEWVSYISRSGSTKYYADSVKGRFTISRDNAKNSLYLQ MNSLRAEDTAVYYCARDQEDYALDYWGQGTLVTVSS ASTKGPSVFPLAPCSRSTSESTAALGCLVKDYFPEPVTVSWN SGALTSGVHTFPAVLQSSGLYSLSSVVTVPSSSLGTKTYTCN VDHKPSNTKVDKRVESKYGPPCPPCPAPEFEGGPSVFLFPPK PKDTLYITREPEVTCVVVDVSQEDPEVQFNWYVDGVEVHN AKTKPREEQFNSTYRVVSVLTVLHQDWLNGKEYKCKVSNK GLPSSIEKTISKAKGQPREPQVYTLPPSQEEMTKNQVSLTCLV KGFYPSDIAVEWESNGQPENNYKTTPPVLDSDGSFFLYSRLT VDKSRWQEGNVFSCSVMHEALHNHYTQKSLSLSLG |
| 170 | MAB2 with constant domain PE and LS mutations | QVQLVESGGGLVKPGGSLRLSCAASGFTFSDYYMSWIRQAP GKGLEWVSYISRSGSTKYYADSVKGRFTISRDNAKNSLYLQ MNSLRAEDTAVYYCARDETDYGWDYWGQGTLVTVSSAST KGPSVFPLAPCSRSTSESTAALGCLVKDYFPEPVTVSWNSGA LTSGVHTFPAVLQSSGLYSLSSVVTVPSSSLGTKTYTCNVDH KPSNTKVDKRVESKYGPPCPPCPAPEFEGGPSVFLFPPKPKD TLMISRTPEVTCVVVDVSQEDPEVQFNWYVDGVEVHNAKT KPREEQFNSTYRVVSVLTVLHQDWLNGKEYKCKVSNKGLP SSIEKTISKAKGQPREPQVYTLPPSQEEMTKNQVSLTCLVKG FYPSDIAVEWESNGQPENNYKTTPPVLDSDGSFFLYSRLTVD KSRWQEGNVFSCSVLHEALHSHYTQKSLSLSLG |

TABLE 7-continued

| SEQ ID NO: | AB ID NO. | Heavy Chain Sequence |
|---|---|---|
| 171 | MAB2 with constant domain PE and YTE mutations | QVQLVESGGGLVKPGGSLRLSCAASGFTFSDYYMSWIRQAP GKGLEWVSYISRSGSTKYYADSVKGRFTISRDNAKNSLYLQ MNSLRAEDTAVYYCARDETDYGWDYWGQGTLVTVSSAST KGPSVFPLAPCSRSTSESTAALGCLVKDYFPEPVTVSWNSGA LTSGVHTFPAVLQSSGLYSLSSVVTVPSSSLGTKTYTCNVDH KPSNTKVDKRVESKYGPPCPPCPAPEFEGGPSVFLFPPKPKD TLYITREPEVTCVVVDVSQEDPEVQFNWYVDGVEVHNAKT KPREEQFNSTYRVVSVLTVLHQDWLNGKEYKCKVSNKGLP SSIEKTISKAKGQPREPQVYTLPPSQEEMTKNQVSLTCLVKG FYPSDIAVEWESNGQPENNYKTTPPVLDSDGSFFLYSRLTVD KSRWQEGNVFSCSVMHEALHNHYTQKSLSLSLG |
| 172 | MAB3 with constant domain PE and LS mutations | QVQLVESGGGLVKPGGSLRLSCAASGFTFSDYYMSWIRQAP GKGLEWVSYISRSGSTKYYADSVKGRFTISRDNAKNSLYLQ MNSLRAEDTAVYYCARDETDYAFDEWGQGTLVTVSS ASTKGPSVFPLAPCSRSTSESTAALGCLVKDYFPEPVTVSWN SGALTSGVHTFPAVLQSSGLYSLSSVVTVPSSSLGTKTYTCN VDHKPSNTKVDKRVESKYGPPCPPCPAPEFEGGPSVFLFPPK PKDTLMISRTPEVTCVVVDVSQEDPEVQFNWYVDGVEVHN AKTKPREEQFNSTYRVVSVLTVLHQDWLNGKEYKCKVSNK GLPSSIEKTISKAKGQPREPQVYTLPPSQEEMTKNQVSLTCLV KGFYPSDIAVEWESNGQPENNYKTTPPVLDSDGSFFLYSRLT VDKSRWQEGNVFSCSVLHEALHSHYTQKSLSLSLG |
| 173 | MAB3 with constant domain PE and YTE mutations | QVQLVESGGGLVKPGGSLRLSCAASGFTFSDYYMSWIRQAP GKGLEWVSYISRSGSTKYYADSVKGRFTISRDNAKNSLYLQ MNSLRAEDTAVYYCARDETDYAFDEWGQGTLVTVSS ASTKGPSVFPLAPCSRSTSESTAALGCLVKDYFPEPVTVSWN SGALTSGVHTFPAVLQSSGLYSLSSVVTVPSSSLGTKTYTCN VDHKPSNTKVDKRVESKYGPPCPPCPAPEFEGGPSVFLFPPK PKDTLYITREPEVTCVVVDVSQEDPEVQFNWYVDGVEVHN AKTKPREEQFNSTYRVVSVLTVLHQDWLNGKEYKCKVSNK GLPSSIEKTISKAKGQPREPQVYTLPPSQEEMTKNQVSLTCLV KGFYPSDIAVEWESNGQPENNYKTTPPVLDSDGSFFLYSRLT VDKSRWQEGNVFSCSVMHEALHNHYTQKSLSLSLG |
| 174 | MAB4 with constant domain PE and LS mutations | QVQLVESGGGLVKPGGSLRLSCAASGFTFSDYYMSWIRQAP GKGLEWVSYISRSGSTKYYADSVKGRFTISRDNAKNSLYLQ MNSLRAEDTAVYYCARDESQYALDYWGQGTLVTVSS ASTKGPSVFPLAPCSRSTSESTAALGCLVKDYFPEPVTVSWN SGALTSGVHTFPAVLQSSGLYSLSSVVTVPSSSLGTKTYTCN VDHKPSNTKVDKRVESKYGPPCPPCPAPEFEGGPSVFLFPPK PKDTLMISRTPEVTCVVVDVSQEDPEVQFNWYVDGVEVHN AKTKPREEQFNSTYRVVSVLTVLHQDWLNGKEYKCKVSNK GLPSSIEKTISKAKGQPREPQVYTLPPSQEEMTKNQVSLTCLV KGFYPSDIAVEWESNGQPENNYKTTPPVLDSDGSFFLYSRLT VDKSRWQEGNVFSCSVLHEALHSHYTQKSLSLSLG |
| 175 | MAB4 with constant domain PE and YTE mutations | QVQLVESGGGLVKPGGSLRLSCAASGFTFSDYYMSWIRQAP GKGLEWVSYISRSGSTKYYADSVKGRFTISRDNAKNSLYLQ MNSLRAEDTAVYYCARDESQYALDYWGQGTLVTVSS ASTKGPSVFPLAPCSRSTSESTAALGCLVKDYFPEPVTVSWN SGALTSGVHTFPAVLQSSGLYSLSSVVTVPSSSLGTKTYTCN VDHKPSNTKVDKRVESKYGPPCPPCPAPEFEGGPSVFLFPPK PKDTLYITREPEVTCVVVDVSQEDPEVQFNWYVDGVEVHN AKTKPREEQFNSTYRVVSVLTVLHQDWLNGKEYKCKVSNK GLPSSIEKTISKAKGQPREPQVYTLPPSQEEMTKNQVSLTCLV KGFYPSDIAVEWESNGQPENNYKTTPPVLDSDGSFFLYSRLT VDKSRWQEGNVFSCSVMHEALHNHYTQKSLSLSLG |
| 176 | MAB5 with constant domain PE and LS mutations | QVQLVESGGGLVKPGGSLRLSCAASGFTFSDYYMSWIRQAP GKGLEWVSYISRSGSTKYYAHSVKGRFTISRDNAKNSLYLQ MNSLRAEDTAVYYCARDNTDYALDWGQGTLVTVSS ASTKGPSVFPLAPCSRSTSESTAALGCLVKDYFPEPVTVSWN SGALTSGVHTFPAVLQSSGLYSLSSVVTVPSSSLGTKTYTCN VDHKPSNTKVDKRVESKYGPPCPPCPAPEFEGGPSVFLFPPK PKDTLMISRTPEVTCVVVDVSQEDPEVQFNWYVDGVEVHN AKTKPREEQFNSTYRVVSVLTVLHQDWLNGKEYKCKVSNK GLPSSIEKTISKAKGQPREPQVYTLPPSQEEMTKNQVSLTCLV KGFYPSDIAVEWESNGQPENNYKTTPPVLDSDGSFFLYSRLT VDKSRWQEGNVFSCSVLHEALHSHYTQKSLSLSLG |
| 177 | MAB5 with constant domain PE and YTE mutations | QVQLVESGGGLVKPGGSLRLSCAASGFTFSDYYMSWIRQAP GKGLEWVSYISRSGSTKYYAHSVKGRFTISRDNAKNSLYLQ MNSLRAEDTAVYYCARDNTDYALDWGQGTLVTVSS ASTKGPSVFPLAPCSRSTSESTAALGCLVKDYFPEPVTVSWN SGALTSGVHTFPAVLQSSGLYSLSSVVTVPSSSLGTKTYTCN |

TABLE 7-continued

| SEQ ID NO: | AB ID NO. | Heavy Chain Sequence |
|---|---|---|
| | | VDHKPSNTKVDKRVESKYGPPCPPCPAPEFEGGPSVFLFPPK PKDTLYITREPEVTCVVVDVSQEDPEVQFNWYVDGVEVHN AKTKPREEQFNSTYRVVSVLTVLHQDWLNGKEYKCKVSNK GLPSSIEKTISKAKGQPREPQVYTLPPSQEEMTKNQVSLTCLV KGFYPSDIAVEWESNGQPENNYKTTPPVLDSDGSFFLYSRLT VDKSRWQEGNVFSCSVMHEALHNHYTQKSLSLSLG |
| 178 | MAB6 with constant domain PE and LS mutations | QVQLVESGGGLVKPGGSLRLSCAASGFTFSDYYMSWIRQAP GKGLEWVSYISRSGSTKYYAHSVKGRFTISRDNAKNSLYLQ MNSLRAEDTAVYYCARDETDYAYDEWGQGTLVTVSS ASTKGPSVFPLAPCSRSTSESTAALGCLVKDYFPEPVTVSWN SGALTSGVHTFPAVLQSSGLYSLSSVVTVPSSSLGTKTYTCN VDHKPSNTKVDKRVESKYGPPCPPCPAPEFEGGPSVFLFPPK PKDTLMISRTPEVTCVVVDVSQEDPEVQFNWYVDGVEVHN AKTKPREEQFNSTYRVVSVLTVLHQDWLNGKEYKCKVSNK GLPSSIEKTISKAKGQPREPQVYTLPPSQEEMTKNQVSLTCLV KGFYPSDIAVEWESNGQPENNYKTTPPVLDSDGSFFLYSRLT VDKSRWQEGNVFSCSVLHEALHSHYTQKSLSLSLG |
| 179 | MAB6 with constant domain PE and YTE mutations | QVQLVESGGGLVKPGGSLRLSCAASGFTFSDYYMSWIRQAP GKGLEWVSYISRSGSTKYYAHSVKGRFTISRDNAKNSLYLQ MNSLRAEDTAVYYCARDETDYAYDEWGQGTLVTVSS ASTKGPSVFPLAPCSRSTSESTAALGCLVKDYFPEPVTVSWN SGALTSGVHTFPAVLQSSGLYSLSSVVTVPSSSLGTKTYTCN VDHKPSNTKVDKRVESKYGPPCPPCPAPEFEGGPSVFLFPPK PKDTLYITREPEVTCVVVDVSQEDPEVQFNWYVDGVEVHN AKTKPREEQFNSTYRVVSVLTVLHQDWLNGKEYKCKVSNK GLPSSIEKTISKAKGQPREPQVYTLPPSQEEMTKNQVSLTCLV KGFYPSDIAVEWESNGQPENNYKTTPPVLDSDGSFFLYSRLT VDKSRWQEGNVFSCSVMHEALHNHYTQKSLSLSLG |
| 180 | MAB7 with constant domain PE and LS mutations | QVQLVESGGGLVKPGGSLRLSCAASGFTFSDYYMSWIRQAP GKGLEWVSYISRSGSTKYYADSVKGRFTISRDNAKNSLYLQ MNSLRAEDTAVYYCARDETDYAYDNWGQGTLVTVSS ASTKGPSVFPLAPCSRSTSESTAALGCLVKDYFPEPVTVSWN SGALTSGVHTFPAVLQSSGLYSLSSVVTVPSSSLGTKTYTCN VDHKPSNTKVDKRVESKYGPPCPPCPAPEFEGGPSVFLFPPK PKDTLMISRTPEVTCVVVDVSQEDPEVQFNWYVDGVEVHN AKTKPREEQFNSTYRVVSVLTVLHQDWLNGKEYKCKVSNK GLPSSIEKTISKAKGQPREPQVYTLPPSQEEMTKNQVSLTCLV KGFYPSDIAVEWESNGQPENNYKTTPPVLDSDGSFFLYSRLT VDKSRWQEGNVFSCSVLHEALHSHYTQKSLSLSLG |
| 181 | MAB7 with constant domain PE and YTE mutations | QVQLVESGGGLVKPGGSLRLSCAASGFTFSDYYMSWIRQAP GKGLEWVSYISRSGSTKYYADSVKGRFTISRDNAKNSLYLQ MNSLRAEDTAVYYCARDETDYAYDNWGQGTLVTVSS ASTKGPSVFPLAPCSRSTSESTAALGCLVKDYFPEPVTVSWN SGALTSGVHTFPAVLQSSGLYSLSSVVTVPSSSLGTKTYTCN VDHKPSNTKVDKRVESKYGPPCPPCPAPEFEGGPSVFLFPPK PKDTLYITREPEVTCVVVDVSQEDPEVQFNWYVDGVEVHN AKTKPREEQFNSTYRVVSVLTVLHQDWLNGKEYKCKVSNK GLPSSIEKTISKAKGQPREPQVYTLPPSQEEMTKNQVSLTCLV KGFYPSDIAVEWESNGQPENNYKTTPPVLDSDGSFFLYSRLT VDKSRWQEGNVFSCSVMHEALHNHYTQKSLSLSLG |
| 182 | MAB8 with constant domain PE and LS mutations | QVQLVESGGGLVKPGGSLRLSCAASGFTFSDYYMSWIRQAP GKGLEWVSYISRSGSTKYYADSVKGRFTISRDNAKNSLYLQ MNSLRAEDTAVYYCARDESDYAYDYWGQGTLVTVSS ASTKGPSVFPLAPCSRSTSESTAALGCLVKDYFPEPVTVSWN SGALTSGVHTFPAVLQSSGLYSLSSVVTVPSSSLGTKTYTCN VDHKPSNTKVDKRVESKYGPPCPPCPAPEFEGGPSVFLFPPK PKDTLMISRTPEVTCVVVDVSQEDPEVQFNWYVDGVEVHN AKTKPREEQFNSTYRVVSVLTVLHQDWLNGKEYKCKVSNK GLPSSIEKTISKAKGQPREPQVYTLPPSQEEMTKNQVSLTCLV KGFYPSDIAVEWESNGQPENNYKTTPPVLDSDGSFFLYSRLT VDKSRWQEGNVFSCSVLHEALHSHYTQKSLSLSLG |
| 183 | MAB8 with constant domain PE and YTE mutations | QVQLVESGGGLVKPGGSLRLSCAASGFTFSDYYMSWIRQAP GKGLEWVSYISRSGSTKYYADSVKGRFTISRDNAKNSLYLQ MNSLRAEDTAVYYCARDESDYAYDYWGQGTLVTVSS ASTKGPSVFPLAPCSRSTSESTAALGCLVKDYFPEPVTVSWN SGALTSGVHTFPAVLQSSGLYSLSSVVTVPSSSLGTKTYTCN VDHKPSNTKVDKRVESKYGPPCPPCPAPEFEGGPSVFLFPPK PKDTLYITREPEVTCVVVDVSQEDPEVQFNWYVDGVEVHN AKTKPREEQFNSTYRVVSVLTVLHQDWLNGKEYKCKVSNK GLPSSIEKTISKAKGQPREPQVYTLPPSQEEMTKNQVSLTCLV KGFYPSDIAVEWESNGQPENNYKTTPPVLDSDGSFFLYSRLT VDKSRWQEGNVFSCSVMHEALHNHYTQKSLSLSLG |

TABLE 7-continued

| SEQ ID NO: | AB ID NO. | Heavy Chain Sequence |
|---|---|---|
| 184 | MAB9 with constant domain PE and LS mutations | QVQLVESGGGLVKPGGSLRLSCAASGFTFSDYYMSWIRQAP GKGLEWVSYISRSGSTKYYADSVKGRFTISRDNAKNSLYLQ MNSLRAEDTAVYYCARDENYALDWWGQGTLVTVSS ASTKGPSVFPLAPCSRSTSESTAALGCLVKDYFPEPVTVSWN SGALTSGVHTFPAVLQSSGLYSLSSVVTVPSSSLGTKTYTCN VDHKPSNTKVDKRVESKYGPPCPPCPAPEFEGGPSVFLFPPK PKDTLMISRTPEVTCVVVDVSQEDPEVQFNWYVDGVEVHN AKTKPREEQFNSTYRVVSVLTVLHQDWLNGKEYKCKVSNK GLPSSIEKTISKAKGQPREPQVYTLPPSQEEMTKNQVSLTCLV KGFYPSDIAVEWESNGQPENNYKTTPPVLDSDGSFFLYSRLT VDKSRWQEGNVFSCSVLHEALHSHYTQKSLSLSLG |
| 185 | MAB9 with constant domain PE and YTE mutations | QVQLVESGGGLVKPGGSLRLSCAASGFTFSDYYMSWIRQAP GKGLEWVSYISRSGSTKYYADSVKGRFTISRDNAKNSLYLQ MNSLRAEDTAVYYCARDENYALDWWGQGTLVTVSS ASTKGPSVFPLAPCSRSTSESTAALGCLVKDYFPEPVTVSWN SGALTSGVHTFPAVLQSSGLYSLSSVVTVPSSSLGTKTYTCN VDHKPSNTKVDKRVESKYGPPCPPCPAPEFEGGPSVFLFPPK PKDTLYITREPEVTCVVVDVSQEDPEVQFNWYVDGVEVHN AKTKPREEQFNSTYRVVSVLTVLHQDWLNGKEYKCKVSNK GLPSSIEKTISKAKGQPREPQVYTLPPSQEEMTKNQVSLTCLV KGFYPSDIAVEWESNGQPENNYKTTPPVLDSDGSFFLYSRLT VDKSRWQEGNVFSCSVMHEALHNHYTQKSLSLSLG |
| 186 | MAB 10 with constant domain PE and LS mutations | QVQLVESGGGLVKPGGSLRLSCAASGFTFSDYYMSWIRQAP GKGLEWVSYISRSGSTKYYADSVKGRFTISRDNAKNSLYLQ MNSLRAEDTAVYYCARDESDYALDFWGQGTLVTVSS ASTKGPSVFPLAPCSRSTSESTAALGCLVKDYFPEPVTVSWN SGALTSGVHTFPAVLQSSGLYSLSSVVTVPSSSLGTKTYTCN VDHKPSNTKVDKRVESKYGPPCPPCPAPEFEGGPSVFLFPPK PKDTLMISRTPEVTCVVVDVSQEDPEVQFNWYVDGVEVHN AKTKPREEQFNSTYRVVSVLTVLHQDWLNGKEYKCKVSNK GLPSSIEKTISKAKGQPREPQVYTLPPSQEEMTKNQVSLTCLV KGFYPSDIAVEWESNGQPENNYKTTPPVLDSDGSFFLYSRLT VDKSRWQEGNVFSCSVLHEALHSHYTQKSLSLSLG |
| 187 | MAB 10 with constant domain PE and YTE mutations | QVQLVESGGGLVKPGGSLRLSCAASGFTFSDYYMSWIRQAP GKGLEWVSYISRSGSTKYYADSVKGRFTISRDNAKNSLYLQ MNSLRAEDTAVYYCARDESDYALDFWGQGTLVTVSS ASTKGPSVFPLAPCSRSTSESTAALGCLVKDYFPEPVTVSWN SGALTSGVHTFPAVLQSSGLYSLSSVVTVPSSSLGTKTYTCN VDHKPSNTKVDKRVESKYGPPCPPCPAPEFEGGPSVFLFPPK PKDTLYITREPEVTCVVVDVSQEDPEVQFNWYVDGVEVHN AKTKPREEQFNSTYRVVSVLTVLHQDWLNGKEYKCKVSNK GLPSSIEKTISKAKGQPREPQVYTLPPSQEEMTKNQVSLTCLV KGFYPSDIAVEWESNGQPENNYKTTPPVLDSDGSFFLYSRLT VDKSRWQEGNVFSCSVMHEALHNHYTQKSLSLSLG |
| 188 | MAB11 with constant domain PE and LS mutations | QVQLVQSGAEVKKPGASVKVSCKVSGDTLTELSMHWVRQ APGKGLEWMGTFDPEEGETIYAQKFQGRVTMTEDTSTDTA YMELSSLRSEDTAVYYCVTEGLAGVPFDLWGQGTLVTVSS ASTKGPSVFPLAPCSRSTSESTAALGCLVKDYFPEPVTVSWN SGALTSGVHTFPAVLQSSGLYSLSSVVTVPSSSLGTKTYTCN VDHKPSNTKVDKRVESKYGPPCPPCPAPEFEGGPSVFLFPPK PKDTLMISRTPEVTCVVVDVSQEDPEVQFNWYVDGVEVHN AKTKPREEQFNSTYRVVSVLTVLHQDWLNGKEYKCKVSNK GLPSSIEKTISKAKGQPREPQVYTLPPSQEEMTKNQVSLTCLV KGFYPSDIAVEWESNGQPENNYKTTPPVLDSDGSFFLYSRLT VDKSRWQEGNVFSCSVLHEALHSHYTQKSLSLSLG |
| 189 | MAB11 with constant domain PE and YTE mutations | QVQLVQSGAEVKKPGASVKVSCKVSGDTLTELSMHWVRQ APGKGLEWMGTFDPEEGETIYAQKFQGRVTMTEDTSTDTA YMELSSLRSEDTAVYYCVTEGLAGVPFDLWGQGTLVTVSS ASTKGPSVFPLAPCSRSTSESTAALGCLVKDYFPEPVTVSWN SGALTSGVHTFPAVLQSSGLYSLSSVVTVPSSSLGTKTYTCN VDHKPSNTKVDKRVESKYGPPCPPCPAPEFEGGPSVFLFPPK PKDTLYITREPEVTCVVVDVSQEDPEVQFNWYVDGVEVHN AKTKPREEQFNSTYRVVSVLTVLHQDWLNGKEYKCKVSNK GLPSSIEKTISKAKGQPREPQVYTLPPSQEEMTKNQVSLTCLV KGFYPSDIAVEWESNGQPENNYKTTPPVLDSDGSFFLYSRLT VDKSRWQEGNVFSCSVMHEALHNHYTQKSLSLSLG |
| 190 | MAB12 with constant domain PE and LS mutations | QVQLVQSGAEVKKPGASVKVSCKVSGDTLTELSMHWVRQ APGKGLEWMGTFDPEEGETIYAQKFQGRVTMTEDTSTDTA YMELSSLRSEDTAVYYCVTEGLGGRPFDHWGQGTLVTVSS ASTKGPSVFPLAPCSRSTSESTAALGCLVKDYFPEPVTVSWN SGALTSGVHTFPAVLQSSGLYSLSSVVTVPSSSLGTKTYTCN |

TABLE 7-continued

| SEQ ID NO: | AB ID NO. | Heavy Chain Sequence |
|---|---|---|
| | | VDHKPSNTKVDKRVESKYGPPCPPCPAPEFEGGPSVFLFPPK<br>PKDTLMISRTPEVTCVVVDVSQEDPEVQFNWYVDGVEVHN<br>AKTKPREEQFNSTYRVVSVLTVLHQDWLNGKEYKCKVSNK<br>GLPSSIEKTISKAKGQPREPQVYTLPPSQEEMTKNQVSLTCLV<br>KGFYPSDIAVEWESNGQPENNYKTTPPVLDSDGSFFLYSRLT<br>VDKSRWQEGNVFSCSVLHEALHSHYTQKSLSLSLG |
| 191 | MAB12 with constant domain PE and YTE mutations | QVQLVQSGAEVKKPGASVKVSCKVSGDTLTELSMHWVRQ<br>APGKGLEWMGTFDPEEGETIYAQKFQGRVTMTEDTSTDTA<br>YMELSSLRSEDTAVYYCVTEGLGGRPFDHWGQGTLVTVSS<br>ASTKGPSVFPLAPCSRSTSESTAALGCLVKDYFPEPVTVSWN<br>SGALTSGVHTFPAVLQSSGLYSLSSVVTVPSSSLGTKTYTCN<br>VDHKPSNTKVDKRVESKYGPPCPPCPAPEFEGGPSVFLFPPK<br>PKDTLYITREPEVTCVVVDVSQEDPEVQFNWYVDGVEVHN<br>AKTKPREEQFNSTYRVVSVLTVLHQDWLNGKEYKCKVSNK<br>GLPSSIEKTISKAKGQPREPQVYTLPPSQEEMTKNQVSLTCLV<br>KGFYPSDIAVEWESNGQPENNYKTTPPVLDSDGSFFLYSRLT<br>VDKSRWQEGNVFSCSVMHEALHNHYTQKSLSLSLG |
| 192 | MAB13 with constant domain PE and LS mutations | QVQLVQSGAEVKKPGASVKVSCKVSGDTLTELSMHWVRQ<br>APGKGLEWMGTFDPEEGETIYAQKFQGRVTMTEDTSTDTA<br>YMELSSLRSEDTAVYYCVTEGLAGFPFDIWGQGTLVTVSS<br>ASTKGPSVFPLAPCSRSTSESTAALGCLVKDYFPEPVTVSWN<br>SGALTSGVHTFPAVLQSSGLYSLSSVVTVPSSSLGTKTYTCN<br>VDHKPSNTKVDKRVESKYGPPCPPCPAPEFEGGPSVFLFPPK<br>PKDTLMISRTPEVTCVVVDVSQEDPEVQFNWYVDGVEVHN<br>AKTKPREEQFNSTYRVVSVLTVLHQDWLNGKEYKCKVSNK<br>GLPSSIEKTISKAKGQPREPQVYTLPPSQEEMTKNQVSLTCLV<br>KGFYPSDIAVEWESNGQPENNYKTTPPVLDSDGSFFLYSRLT<br>VDKSRWQEGNVFSCSVLHEALHSHYTQKSLSLSLG |
| 193 | MAB13 with constant domain PE and YTE mutations | QVQLVQSGAEVKKPGASVKVSCKVSGDTLTELSMHWVRQ<br>APGKGLEWMGTFDPEEGETIYAQKFQGRVTMTEDTSTDTA<br>YMELSSLRSEDTAVYYCVTEGLAGFPFDIWGQGTLVTVSS<br>ASTKGPSVFPLAPCSRSTSESTAALGCLVKDYFPEPVTVSWN<br>SGALTSGVHTFPAVLQSSGLYSLSSVVTVPSSSLGTKTYTCN<br>VDHKPSNTKVDKRVESKYGPPCPPCPAPEFEGGPSVFLFPPK<br>PKDTLYITREPEVTCVVVDVSQEDPEVQFNWYVDGVEVHN<br>AKTKPREEQFNSTYRVVSVLTVLHQDWLNGKEYKCKVSNK<br>GLPSSIEKTISKAKGQPREPQVYTLPPSQEEMTKNQVSLTCLV<br>KGFYPSDIAVEWESNGQPENNYKTTPPVLDSDGSFFLYSRLT<br>VDKSRWQEGNVFSCSVMHEALHNHYTQKSLSLSLG |
| 194 | MAB14 with constant domain PE and LS mutations | QVQLVQSGAEVKKPGASVKVSCKVSGDTLTELSMHWVRQ<br>APGKGLEWMGTFDPEEGETIYAQKFQGRVTMTEDTSTDTA<br>YMELSSLRSEDTAVYYCVTEGLAWRPTDSWGQGTLVTVSS<br>ASTKGPSVFPLAPCSRSTSESTAALGCLVKDYFPEPVTVSWN<br>SGALTSGVHTFPAVLQSSGLYSLSSVVTVPSSSLGTKTYTCN<br>VDHKPSNTKVDKRVESKYGPPCPPCPAPEFEGGPSVFLFPPK<br>PKDTLMISRTPEVTCVVVDVSQEDPEVQFNWYVDGVEVHN<br>AKTKPREEQFNSTYRVVSVLTVLHQDWLNGKEYKCKVSNK<br>GLPSSIEKTISKAKGQPREPQVYTLPPSQEEMTKNQVSLTCLV<br>KGFYPSDIAVEWESNGQPENNYKTTPPVLDSDGSFFLYSRLT<br>VDKSRWQEGNVFSCSVLHEALHSHYTQKSLSLSLG |
| 195 | MAB14 with constant domain PE and YTE mutations | QVQLVQSGAEVKKPGASVKVSCKVSGDTLTELSMHWVRQ<br>APGKGLEWMGTFDPEEGETIYAQKFQGRVTMTEDTSTDTA<br>YMELSSLRSEDTAVYYCVTEGLAWRPTDSWGQGTLVTVSS<br>ASTKGPSVFPLAPCSRSTSESTAALGCLVKDYFPEPVTVSWN<br>SGALTSGVHTFPAVLQSSGLYSLSSVVTVPSSSLGTKTYTCN<br>VDHKPSNTKVDKRVESKYGPPCPPCPAPEFEGGPSVFLFPPK<br>PKDTLYITREPEVTCVVVDVSQEDPEVQFNWYVDGVEVHN<br>AKTKPREEQFNSTYRVVSVLTVLHQDWLNGKEYKCKVSNK<br>GLPSSIEKTISKAKGQPREPQVYTLPPSQEEMTKNQVSLTCLV<br>KGFYPSDIAVEWESNGQPENNYKTTPPVLDSDGSFFLYSRLT<br>VDKSRWQEGNVFSCSVMHEALHNHYTQKSLSLSLG |
| 196 | MAB15 with constant domain PE and LS mutations | QVQLVQSGAEVKKPGASVKVSCKVSGDTLTELSMHWVRQ<br>APGKGLEWMGTFDPEEGETIYAQKFQGRVTMTEDTSTDTA<br>YMELSSLRSEDTAVYYCVTKGLAWLPYYSWGQGTLVTVSS<br>ASTKGPSVFPLAPCSRSTSESTAALGCLVKDYFPEPVTVSWN<br>SGALTSGVHTFPAVLQSSGLYSLSSVVTVPSSSLGTKTYTCN<br>VDHKPSNTKVDKRVESKYGPPCPPCPAPEFEGGPSVFLFPPK<br>PKDTLMISRTPEVTCVVVDVSQEDPEVQFNWYVDGVEVHN<br>AKTKPREEQFNSTYRVVSVLTVLHQDWLNGKEYKCKVSNK<br>GLPSSIEKTISKAKGQPREPQVYTLPPSQEEMTKNQVSLTCLV<br>KGFYPSDIAVEWESNGQPENNYKTTPPVLDSDGSFFLYSRLT<br>VDKSRWQEGNVFSCSVLHEALHSHYTQKSLSLSLG |

TABLE 7-continued

| SEQ ID NO: | AB ID NO. | Heavy Chain Sequence |
|---|---|---|
| 197 | MAB15 with constant domain PE and YTE mutations | QVQLVQSGAEVKKPGASVKVSCKVSGDTLTELSMHWVRQ APGKGLEWMGTFDPEEGETIYAQKFQGRVTMTEDTSTDTA YMELSSLRSEDTAVYYCVTKGLAWLPYYSWGQGTLVTVSS ASTKGPSVFPLAPCSRSTSESTAALGCLVKDYFPEPVTVSWN SGALTSGVHTFPAVLQSSGLYSLSSVVTVPSSSLGTKTYTCN VDHKPSNTKVDKRVESKYGPPCPPCPAPEFEGGPSVFLFPPK PKDTLYITREPEVTCVVVDVSQEDPEVQFNWYVDGVEVHN AKTKPREEQFNSTYRVVSVLTVLHQDWLNGKEYKCKVSNK GLPSSIEKTISKAKGQPREPQVYTLPPSQEEMTKNQVSLTCLV KGFYPSDIAVEWESNGQPENNYKTTPPVLDSDGSFFLYSRLT VDKSRWQEGNVFSCSVMHEALHNHYTQKSLSLSLG |
| 198 | MAB 16 with constant domain PE and LS mutations | QVQLVQSGAEVKKPGASVKVSCKVSGDTLTELSMHWVRQ APGKGLEWMGTFDPEEGETIYAQKFQGRVTMTEDTSTDTA YMELSSLRSEDTAVYYCVTEGLAGVPFDLWGQGTLVTVSS ASTKGPSVFPLAPCSRSTSESTAALGCLVKDYFPEPVTVSWN SGALTSGVHTFPAVLQSSGLYSLSSVVTVPSSSLGTKTYTCN VDHKPSNTKVDKRVESKYGPPCPPCPAPEFEGGPSVFLFPPK PKDTLMISRTPEVTCVVVDVSQEDPEVQFNWYVDGVEVHN AKTKPREEQFNSTYRVVSVLTVLHQDWLNGKEYKCKVSNK GLPSSIEKTISKAKGQPREPQVYTLPPSQEEMTKNQVSLTCLV KGFYPSDIAVEWESNGQPENNYKTTPPVLDSDGSFFLYSRLT VDKSRWQEGNVFSCSVLHEALHSHYTQKSLSLSLG |
| 199 | MAB16 with constant domain PE and YTE mutations | QVQLVQSGAEVKKPGASVKVSCKVSGDTLTELSMHWVRQ APGKGLEWMGTFDPEEGETIYAQKFQGRVTMTEDTSTDTA YMELSSLRSEDTAVYYCVTEGLAGVPFDLWGQGTLVTVSS ASTKGPSVFPLAPCSRSTSESTAALGCLVKDYFPEPVTVSWN SGALTSGVHTFPAVLQSSGLYSLSSVVTVPSSSLGTKTYTCN VDHKPSNTKVDKRVESKYGPPCPPCPAPEFEGGPSVFLFPPK PKDTLYITREPEVTCVVVDVSQEDPEVQFNWYVDGVEVHN AKTKPREEQFNSTYRVVSVLTVLHQDWLNGKEYKCKVSNK GLPSSIEKTISKAKGQPREPQVYTLPPSQEEMTKNQVSLTCLV KGFYPSDIAVEWESNGQPENNYKTTPPVLDSDGSFFLYSRLT VDKSRWQEGNVFSCSVMHEALHNHYTQKSLSLSLG |
| 200 | MAB17 with constant domain PE and LS mutations | QVQLVQSGAEVKKPGASVKVSCKVSGDTLTELSMHWVRQ APGKGLEWMGTFDPEEGETIYAQKFQGRVTMTEDTSTDTA YMELSSLRSEDTAVYYCVTEGEAGRPFDAWGQGTLVTVSS ASTKGPSVFPLAPCSRSTSESTAALGCLVKDYFPEPVTVSWN SGALTSGVHTFPAVLQSSGLYSLSSVVTVPSSSLGTKTYTCN VDHKPSNTKVDKRVESKYGPPCPPCPAPEFEGGPSVFLFPPK PKDTLMISRTPEVTCVVVDVSQEDPEVQFNWYVDGVEVHN AKTKPREEQFNSTYRVVSVLTVLHQDWLNGKEYKCKVSNK GLPSSIEKTISKAKGQPREPQVYTLPPSQEEMTKNQVSLTCLV KGFYPSDIAVEWESNGQPENNYKTTPPVLDSDGSFFLYSRLT VDKSRWQEGNVFSCSVLHEALHSHYTQKSLSLSLG |
| 201 | MAB17 with constant domain PE and YTE mutations | QVQLVQSGAEVKKPGASVKVSCKVSGDTLTELSMHWVRQ APGKGLEWMGTFDPEEGETIYAQKFQGRVTMTEDTSTDTA YMELSSLRSEDTAVYYCVTEGEAGRPFDAWGQGTLVTVSS ASTKGPSVFPLAPCSRSTSESTAALGCLVKDYFPEPVTVSWN SGALTSGVHTFPAVLQSSGLYSLSSVVTVPSSSLGTKTYTCN VDHKPSNTKVDKRVESKYGPPCPPCPAPEFEGGPSVFLFPPK PKDTLYITREPEVTCVVVDVSQEDPEVQFNWYVDGVEVHN AKTKPREEQFNSTYRVVSVLTVLHQDWLNGKEYKCKVSNK GLPSSIEKTISKAKGQPREPQVYTLPPSQEEMTKNQVSLTCLV KGFYPSDIAVEWESNGQPENNYKTTPPVLDSDGSFFLYSRLT VDKSRWQEGNVFSCSVMHEALHNHYTQKSLSLSLG |
| 202 | MAB18 with constant domain PE and LS mutations | QVQLVQSGAEVKKPGASVKVSCKVSGDTLTELSMHWVRQ APGKGLEWMGTFDPEEGETIYAQKFQGRVTMTEDTSTDTA YMELSSLRSEDTAVYYCVTEGLAGRPYDVWGQGTLVTVSS ASTKGPSVFPLAPCSRSTSESTAALGCLVKDYFPEPVTVSWN SGALTSGVHTFPAVLQSSGLYSLSSVVTVPSSSLGTKTYTCN VDHKPSNTKVDKRVESKYGPPCPPCPAPEFEGGPSVFLFPPK PKDTLMISRTPEVTCVVVDVSQEDPEVQFNWYVDGVEVHN AKTKPREEQFNSTYRVVSVLTVLHQDWLNGKEYKCKVSNK GLPSSIEKTISKAKGQPREPQVYTLPPSQEEMTKNQVSLTCLV KGFYPSDIAVEWESNGQPENNYKTTPPVLDSDGSFFLYSRLT VDKSRWQEGNVFSCSVLHEALHSHYTQKSLSLSLG |
| 203 | MAB18 with constant domain PE and YTE mutations | QVQLVQSGAEVKKPGASVKVSCKVSGDTLTELSMHWVRQ APGKGLEWMGTFDPEEGETIYAQKFQGRVTMTEDTSTDTA YMELSSLRSEDTAVYYCVTEGLAGRPYDVWGQGTLVTVSS ASTKGPSVFPLAPCSRSTSESTAALGCLVKDYFPEPVTVSWN SGALTSGVHTFPAVLQSSGLYSLSSVVTVPSSSLGTKTYTCN |

TABLE 7-continued

| SEQ ID NO: | AB ID NO. | Heavy Chain Sequence |
|---|---|---|
| | | VDHKPSNTKVDKRVESKYGPPCPPCPAPEFEGGPSVFLFPPK PKDTLYITREPEVTCVVVDVSQEDPEVQFNWYVDGVEVHN AKTKPREEQFNSTYRVVSVLTVLHQDWLNGKEYKCKVSNK GLPSSIEKTISKAKGQPREPQVYTLPPSQEEMTKNQVSLTCLV KGFYPSDIAVEWESNGQPENNYKTTPPVLDSDGSFFLYSRLT VDKSRWQEGNVFSCSVMHEALHNHYTQKSLSLSLG |
| 204 | MAB 19 with constant domain PE and LS mutations | QVQLVQSGAEVKKPGASVKVSCKVSGDTLTELSMHWVRQ APGKGLEWMGTFDPEEGETIYAQKFQGRVTMTEDTSTDTA YMELSYLRSEDTAVYYCVTEGLAGIPFDSWGQGTLVTVSS ASTKGPSVFPLAPCSRSTSESTAALGCLVKDYFPEPVTVSWN SGALTSGVHTFPAVLQSSGLYSLSSVVTVPSSSLGTKTYTCN VDHKPSNTKVDKRVESKYGPPCPPCPAPEFEGGPSVFLFPPK PKDTLMISRTPEVTCVVVDVSQEDPEVQFNWYVDGVEVHN AKTKPREEQFNSTYRVVSVLTVLHQDWLNGKEYKCKVSNK GLPSSIEKTISKAKGQPREPQVYTLPPSQEEMTKNQVSLTCLV KGFYPSDIAVEWESNGQPENNYKTTPPVLDSDGSFFLYSRLT VDKSRWQEGNVFSCSVLHEALHSHYTQKSLSLSLG |
| 205 | MAB 19 with constant domain PE and YTE mutations | QVQLVQSGAEVKKPGASVKVSCKVSGDTLTELSMHWVRQ APGKGLEWMGTFDPEEGETIYAQKFQGRVTMTEDTSTDTA YMELSYLRSEDTAVYYCVTEGLAGIPFDSWGQGTLVTVSS ASTKGPSVFPLAPCSRSTSESTAALGCLVKDYFPEPVTVSWN SGALTSGVHTFPAVLQSSGLYSLSSVVTVPSSSLGTKTYTCN VDHKPSNTKVDKRVESKYGPPCPPCPAPEFEGGPSVFLFPPK PKDTLYITREPEVTCVVVDVSQEDPEVQFNWYVDGVEVHN AKTKPREEQFNSTYRVVSVLTVLHQDWLNGKEYKCKVSNK GLPSSIEKTISKAKGQPREPQVYTLPPSQEEMTKNQVSLTCLV KGFYPSDIAVEWESNGQPENNYKTTPPVLDSDGSFFLYSRLT VDKSRWQEGNVFSCSVMHEALHNHYTQKSLSLSLG |
| 206 | MAB20 with constant domain PE and LS mutations | QVQLVQSGAEVKKPGASVKVSCKVSGDTLTELSMHWVRQ APGKGLEWMGTFDPEEGETIYAQKFQGRVTMTEDTSTDTA YMELSYLRSEDTAVYYCVTEGLAGIPFDSWGQGTLVTVSS ASTKGPSVFPLAPCSRSTSESTAALGCLVKDYFPEPVTVSWN SGALTSGVHTFPAVLQSSGLYSLSSVVTVPSSSLGTKTYTCN VDHKPSNTKVDKRVESKYGPPCPPCPAPEFEGGPSVFLFPPK PKDTLMISRTPEVTCVVVDVSQEDPEVQFNWYVDGVEVHN AKTKPREEQFNSTYRVVSVLTVLHQDWLNGKEYKCKVSNK GLPSSIEKTISKAKGQPREPQVYTLPPSQEEMTKNQVSLTCLV KGFYPSDIAVEWESNGQPENNYKTTPPVLDSDGSFFLYSRLT VDKSRWQEGNVFSCSVLHEALHSHYTQKSLSLSLG |
| 207 | MAB20 with constant domain PE and YTE mutations | QVQLVQSGAEVKKPGASVKVSCKVSGDTLTELSMHWVRQ APGKGLEWMGTFDPEEGETIYAQKFQGRVTMTEDTSTDTA YMELSYLRSEDTAVYYCVTEGLAGIPFDSWGQGTLVTVSS ASTKGPSVFPLAPCSRSTSESTAALGCLVKDYFPEPVTVSWN SGALTSGVHTFPAVLQSSGLYSLSSVVTVPSSSLGTKTYTCN VDHKPSNTKVDKRVESKYGPPCPPCPAPEFEGGPSVFLFPPK PKDTLYITREPEVTCVVVDVSQEDPEVQFNWYVDGVEVHN AKTKPREEQFNSTYRVVSVLTVLHQDWLNGKEYKCKVSNK GLPSSIEKTISKAKGQPREPQVYTLPPSQEEMTKNQVSLTCLV KGFYPSDIAVEWESNGQPENNYKTTPPVLDSDGSFFLYSRLT VDKSRWQEGNVFSCSVMHEALHNHYTQKSLSLSLG |
| 208 | MAB21 with constant domain PE and LS mutations | EVQLVESGGGVVRPGGSLRLSCAASGFTFDDYGMSWVRQA PGKGLEWVSGINWEGGSTGYADSVKGRFTISRDNAKNSLYL QMNSLRAEDTALYYCARDEQLGGTTYYYYYMDVWGKGTT VTVSSASTKGPSVFPLAPCSRSTSESTAALGCLVKDYFPEPVT VSWNSGALTSGVHTFPAVLQSSGLYSLSSVVTVPSSSLGTKT YTCNVDHKPSNTKVDKRVESKYGPPCPPCPAPEFEGGPSVFL FPPKPKDTLMISRTPEVTCVVVDVSQEDPEVQFNWYVDGVE VHNAKTKPREEQFNSTYRVVSVLTVLHQDWLNGKEYKCKV SNKGLPSSIEKTISKAKGQPREPQVYTLPPSQEEMTKNQVSLT CLVKGFYPSDIAVEWESNGQPENNYKTTPPVLDSDGSFFLYS RLTVDKSRWQEGNVFSCSVLHEALHSHYTQKSLSLSLG |
| 209 | MAB21 with constant domain PE and YTE mutations | EVQLVESGGGVVRPGGSLRLSCAASGFTFDDYGMSWVRQA PGKGLEWVSGINWEGGSTGYADSVKGRFTISRDNAKNSLYL QMNSLRAEDTALYYCARDEQLGGTTYYYYYMDVWGKGTT VTVSSASTKGPSVFPLAPCSRSTSESTAALGCLVKDYFPEPVT VSWNSGALTSGVHTFPAVLQSSGLYSLSSVVTVPSSSLGTKT YTCNVDHKPSNTKVDKRVESKYGPPCPPCPAPEFEGGPSVFL FPPKPKDTLYITREPEVTCVVVDVSQEDPEVQFNWYVDGVE VHNAKTKPREEQFNSTYRVVSVLTVLHQDWLNGKEYKCKV SNKGLPSSIEKTISKAKGQPREPQVYTLPPSQEEMTKNQVSLT CLVKGFYPSDIAVEWESNGQPENNYKTTPPVLDSDGSFFLYS RLTVDKSRWQEGNVFSCSVMHEALHNHYTQKSLSLSLG |

TABLE 7-continued

| SEQ ID NO: | AB ID NO. | Heavy Chain Sequence |
|---|---|---|
| 210 | MAB22 with constant domain PE and LS mutations | EVQLVESGGGVVRPGGSLRLSCAASGFTFDDYGMSWVRQA PGKGLEWVSGINWEGGSTGYADSVKGRFTISRDNAKNSLYL QMNSLRAEDTALYYCARDEQLGGKYYYYYMDVWGKGT TVTVSSASTKGPSVFPLAPCSRSTSESTAALGCLVKDYFPEPV TVSWNSGALTSGVHTFPAVLQSSGLYSLSSVVTVPSSSLGTK TYTCNVDHKPSNTKVDKRVESKYGPPCPPCPAPEFEGGPSVF LFPPKPKDTLMISRTPEVTCVVVDVSQEDPEVQFNWYVDGV EVHNAKTKPREEQFNSTYRVVSVLTVLHQDWLNGKEYKCK VSNKGLPSSIEKTISKAKGQPREPQVYTLPPSQEEMTKNQVS LTCLVKGFYPSDIAVEWESNGQPENNYKTTPPVLDSDGSFFL YSRLTVDKSRWQEGNVFSCSVLHEALHSHYTQKSLSLSLG |
| 211 | MAB22 with constant domain PE and YTE mutations | EVQLVESGGGVVRPGGSLRLSCAASGFTFDDYGMSWVRQA PGKGLEWVSGINWEGGSTGYADSVKGRFTISRDNAKNSLYL QMNSLRAEDTALYYCARDEQLGGKYYYYYMDVWGKGT TVTVSSASTKGPSVFPLAPCSRSTSESTAALGCLVKDYFPEPV TVSWNSGALTSGVHTFPAVLQSSGLYSLSSVVTVPSSSLGTK TYTCNVDHKPSNTKVDKRVESKYGPPCPPCPAPEFEGGPSVF LFPPKPKDTLYITREPEVTCVVVDVSQEDPEVQFNWYVDGV EVHNAKTKPREEQFNSTYRVVSVLTVLHQDWLNGKEYKCK VSNKGLPSSIEKTISKAKGQPREPQVYTLPPSQEEMTKNQVS LTCLVKGFYPSDIAVEWESNGQPENNYKTTPPVLDSDGSFFL YSRLTVDKSRWQEGNVFSCSVMHEALHNHYTQKSLSLSLG |
| 212 | MAB23 with constant domain PE and LS mutations | EVQLVESGGGVVRPGGSLRLSCAASGFTFDDYGMSWVRQA PGKGLEWVSGINWEGGSTGYADSVKGRFTISRDNAKNSLYL QMNSLRAEDTALYYCARDEQLGGQTYYYYYMDVWGKGT TVTVSSASTKGPSVFPLAPCSRSTSESTAALGCLVKDYFPEPV TVSWNSGALTSGVHTFPAVLQSSGLYSLSSVVTVPSSSLGTK TYTCNVDHKPSNTKVDKRVESKYGPPCPPCPAPEFEGGPSVF LFPPKPKDTLMISRTPEVTCVVVDVSQEDPEVQFNWYVDGV EVHNAKTKPREEQFNSTYRVVSVLTVLHQDWLNGKEYKCK VSNKGLPSSIEKTISKAKGQPREPQVYTLPPSQEEMTKNQVS LTCLVKGFYPSDIAVEWESNGQPENNYKTTPPVLDSDGSFFL YSRLTVDKSRWQEGNVFSCSVLHEALHSHYTQKSLSLSLG |
| 213 | MAB23 with constant domain PE and YTE mutations | EVQLVESGGGVVRPGGSLRLSCAASGFTFDDYGMSWVRQA PGKGLEWVSGINWEGGSTGYADSVKGRFTISRDNAKNSLYL QMNSLRAEDTALYYCARDEQLGGQTYYYYYMDVWGKGT TVTVSSASTKGPSVFPLAPCSRSTSESTAALGCLVKDYFPEPV TVSWNSGALTSGVHTFPAVLQSSGLYSLSSVVTVPSSSLGTK TYTCNVDHKPSNTKVDKRVESKYGPPCPPCPAPEFEGGPSVF LFPPKPKDTLYITREPEVTCVVVDVSQEDPEVQFNWYVDGV EVHNAKTKPREEQFNSTYRVVSVLTVLHQDWLNGKEYKCK VSNKGLPSSIEKTISKAKGQPREPQVYTLPPSQEEMTKNQVS LTCLVKGFYPSDIAVEWESNGQPENNYKTTPPVLDSDGSFFL YSRLTVDKSRWQEGNVFSCSVMHEALHNHYTQKSLSLSLG |
| 214 | MAB24 with constant domain PE and LS mutations | EVQLVESGGGVVRPGGSLRLSCAASGFTFDDYGMSWVRQA PGKGLEWVSGINWEGGSTGYADSVKGRFTISRDNAKNSLYL QMNSLRAEDTALYYCARDEQLGGTTYYYYYMDVWGKGTT VTVSSASTKGPSVFPLAPCSRSTSESTAALGCLVKDYFPEPVT VSWNSGALTSGVHTFPAVLQSSGLYSLSSVVTVPSSSLGTKT YTCNVDHKPSNTKVDKRVESKYGPPCPPCPAPEFEGGPSVFL FPPKPKDTLMISRTPEVTCVVVDVSQEDPEVQFNWYVDGVE VHNAKTKPREEQFNSTYRVVSVLTVLHQDWLNGKEYKCKV SNKGLPSSIEKTISKAKGQPREPQVYTLPPSQEEMTKNQVSLT CLVKGFYPSDIAVEWESNGQPENNYKTTPPVLDSDGSFFLYS RLTVDKSRWQEGNVFSCSVLHEALHSHYTQKSLSLSLG |
| 215 | MAB24 with constant domain PE and YTE mutations | EVQLVESGGGVVRPGGSLRLSCAASGFTFDDYGMSWVRQA PGKGLEWVSGINWEGGSTGYADSVKGRFTISRDNAKNSLYL QMNSLRAEDTALYYCARDEQLGGTTYYYYYMDVWGKGTT VTVSSASTKGPSVFPLAPCSRSTSESTAALGCLVKDYFPEPVT VSWNSGALTSGVHTFPAVLQSSGLYSLSSVVTVPSSSLGTKT YTCNVDHKPSNTKVDKRVESKYGPPCPPCPAPEFEGGPSVFL FPPKPKDTLYITREPEVTCVVVDVSQEDPEVQFNWYVDGVE VHNAKTKPREEQFNSTYRVVSVLTVLHQDWLNGKEYKCKV SNKGLPSSIEKTISKAKGQPREPQVYTLPPSQEEMTKNQVSLT CLVKGFYPSDIAVEWESNGQPENNYKTTPPVLDSDGSFFLYS RLTVDKSRWQEGNVFSCSVMHEALHNHYTQKSLSLSLG |
| 216 | MAB25 with constant domain PE and LS mutations | EVQLVESGGGVVRPGGSLRLSCAASGFTFDDYGMSWVRQA PGKGLEWVSGINWEGGSTGYADSVKGRFTISRDNAKNSLYL QMNSLRAEDTALYYCARDEQLGGIKYYYYYMDVWGKGTT VTVSSASTKGPSVFPLAPCSRSTSESTAALGCLVKDYFPEPVT VSWNSGALTSGVHTFPAVLQSSGLYSLSSVVTVPSSSLGTKT |

TABLE 7-continued

| SEQ ID NO: | AB ID NO. | Heavy Chain Sequence |
|---|---|---|
| | | YTCNVDHKPSNTKVDKRVESKYGPPCPPCPAPEFEGGPSVFL<br>FPPKPKDTLMISRTPEVTCVVVDVSQEDPEVQFNWYVDGVE<br>VHNAKTKPREEQFNSTYRVVSVLTVLHQDWLNGKEYKCKV<br>SNKGLPSSIEKTISKAKGQPREPQVYTLPPSQEEMTKNQVSLT<br>CLVKGFYPSDIAVEWESNGQPENNYKTTPPVLDSDGSFFLYS<br>RLTVDKSRWQEGNVFSCSVLHEALHSHYTQKSLSLSLG |
| 217 | MAB25 with constant domain PE and YTE mutations | EVQLVESGGGVVRPGGSLRLCAASGFTFDDYGMSWVRQA<br>PGKGLEWVSGINWEGGSTGYADSVKGRFTISRDNAKNSLYL<br>QMNSLRAEDTALYYCARDEQLGGIKYYYYYMDVWGKGTT<br>VTVSSASTKGPSVFPLAPCSRSTSESTAALGCLVKDYFPEPVT<br>VSWNSGALTSGVHTFPAVLQSSGLYSLSSVVTVPSSSLGTKT<br>YTCNVDHKPSNTKVDKRVESKYGPPCPPCPAPEFEGGPSVFL<br>FPPKPKDTLYITREPEVTCVVVDVSQEDPEVQFNWYVDGVE<br>VHNAKTKPREEQFNSTYRVVSVLTVLHQDWLNGKEYKCKV<br>SNKGLPSSIEKTISKAKGQPREPQVYTLPPSQEEMTKNQVSLT<br>CLVKGFYPSDIAVEWESNGQPENNYKTTPPVLDSDGSFFLYS<br>RLTVDKSRWQEGNVFSCSVMHEALHNHYTQKSLSLSLG |
| 218 | MAB26 with constant domain PE and LS mutations | EVQLVESGGGVVRPGGSLRLCAASGFTFDDYGMSWVRQA<br>PGKGLEWVSGINWEGGSTGYADSVKGRFSISRDNAKNSLYL<br>QMNSLRAEDTALYYCARDEQLGGLKYYYYYMDVWGKGT<br>TVTVSSASTKGPSVFPLAPCSRSTSESTAALGCLVKDYFPEPV<br>TVSWNSGALTSGVHTFPAVLQSSGLYSLSSVVTVPSSSLGTK<br>TYTCNVDHKPSNTKVDKRVESKYGPPCPPCPAPEFEGGPSVF<br>LFPPKPKDTLMISRTPEVTCVVVDVSQEDPEVQFNWYVDGV<br>EVHNAKTKPREEQFNSTYRVVSVLTVLHQDWLNGKEYKCK<br>VSNKGLPSSIEKTISKAKGQPREPQVYTLPPSQEEMTKNQVS<br>LTCLVKGFYPSDIAVEWESNGQPENNYKTTPPVLDSDGSFFL<br>YSRLTVDKSRWQEGNVFSCSVLHEALHSHYTQKSLSLSLG |
| 219 | MAB26 with constant domain PE and YTE mutations | EVQLVESGGGVVRPGGSLRLCAASGFTFDDYGMSWVRQA<br>PGKGLEWVSGINWEGGSTGYADSVKGRFSISRDNAKNSLYL<br>QMNSLRAEDTALYYCARDEQLGGLKYYYYYMDVWGKGT<br>TVTVSSASTKGPSVFPLAPCSRSTSESTAALGCLVKDYFPEPV<br>TVSWNSGALTSGVHTFPAVLQSSGLYSLSSVVTVPSSSLGTK<br>TYTCNVDHKPSNTKVDKRVESKYGPPCPPCPAPEFEGGPSVF<br>LFPPKPKDTLYITREPEVTCVVVDVSQEDPEVQFNWYVDGV<br>EVHNAKTKPREEQFNSTYRVVSVLTVLHQDWLNGKEYKCK<br>VSNKGLPSSIEKTISKAKGQPREPQVYTLPPSQEEMTKNQVS<br>LTCLVKGFYPSDIAVEWESNGQPENNYKTTPPVLDSDGSFFL<br>YSRLTVDKSRWQEGNVFSCSVMHEALHNHYTQKSLSLSLG |
| 220 | MAB27 with constant domain PE and LS mutations | EVQLVESGGGVVRPGGSLRLCAASGFTFDDYGMSWVRQA<br>PGKGLEWVSGINWEGGSTGYADSVKGRFTISRDNAKNSLYL<br>QMNSLRAEDTALYYCARDEQLGGKVYYYYYMDVWGKGT<br>TVTVSSASTKGPSVFPLAPCSRSTSESTAALGCLVKDYFPEPV<br>TVSWNSGALTSGVHTFPAVLQSSGLYSLSSVVTVPSSSLGTK<br>TYTCNVDHKPSNTKVDKRVESKYGPPCPPCPAPEFEGGPSVF<br>LFPPKPKDTLMISRTPEVTCVVVDVSQEDPEVQFNWYVDGV<br>EVHNAKTKPREEQFNSTYRVVSVLTVLHQDWLNGKEYKCK<br>VSNKGLPSSIEKTISKAKGQPREPQVYTLPPSQEEMTKNQVS<br>LTCLVKGFYPSDIAVEWESNGQPENNYKTTPPVLDSDGSFFL<br>YSRLTVDKSRWQEGNVFSCSVLHEALHSHYTQKSLSLSLG |
| 221 | MAB27 with constant domain PE and YTE mutations | EVQLVESGGGVVRPGGSLRLCAASGFTFDDYGMSWVRQA<br>PGKGLEWVSGINWEGGSTGYADSVKGRFTISRDNAKNSLYL<br>QMNSLRAEDTALYYCARDEQLGGKVYYYYYMDVWGKGT<br>TVTVSSASTKGPSVFPLAPCSRSTSESTAALGCLVKDYFPEPV<br>TVSWNSGALTSGVHTFPAVLQSSGLYSLSSVVTVPSSSLGTK<br>TYTCNVDHKPSNTKVDKRVESKYGPPCPPCPAPEFEGGPSVF<br>LFPPKPKDTLYITREPEVTCVVVDVSQEDPEVQFNWYVDGV<br>EVHNAKTKPREEQFNSTYRVVSVLTVLHQDWLNGKEYKCK<br>VSNKGLPSSIEKTISKAKGQPREPQVYTLPPSQEEMTKNQVS<br>LTCLVKGFYPSDIAVEWESNGQPENNYKTTPPVLDSDGSFFL<br>YSRLTVDKSRWQEGNVFSCSVMHEALHNHYTQKSLSLSLG |
| 222 | MAB28 with constant domain PE and LS mutations | EVQLVESGGGVVRPGGSLRLCAASGFTFDDYGMSWVRQA<br>PGKGLEWVSGINWEGGSTGYADSVKGRFSISRDNAKNSLYL<br>QMNSLRAEDTALYYCARDEQLGGLKYYYYYMDVWGKGT<br>TVTVSSASTKGPSVFPLAPCSRSTSESTAALGCLVKDYFPEPV<br>TVSWNSGALTSGVHTFPAVLQSSGLYSLSSVVTVPSSSLGTK<br>TYTCNVDHKPSNTKVDKRVESKYGPPCPPCPAPEFEGGPSVF<br>LFPPKPKDTLMISRTPEVTCVVVDVSQEDPEVQFNWYVDGV<br>EVHNAKTKPREEQFNSTYRVVSVLTVLHQDWLNGKEYKCK<br>VSNKGLPSSIEKTISKAKGQPREPQVYTLPPSQEEMTKNQVS<br>LTCLVKGFYPSDIAVEWESNGQPENNYKTTPPVLDSDGSFFL<br>YSRLTVDKSRWQEGNVFSCSVLHEALHSHYTQKSLSLSLG |

TABLE 7-continued

| SEQ ID NO: | AB ID NO. | Heavy Chain Sequence |
|---|---|---|
| 223 | MAB28 with constant domain PE and YTE mutations | EVQLVESGGGVVRPGGSLRLSCAASGFTFDDYGMSWVRQA PGKGLEWVSGINWEGGSTGYADSVKGRFSISRDNAKNSLYL QMNSLRAEDTALYYCARDEQLGGLKYYYYYMDVWGKGT TVTVSSASTKGPSVFPLAPCSRSTSESTAALGCLVKDYFPEPV TVSWNSGALTSGVHTFPAVLQSSGLYSLSSVVTVPSSSLGTK TYTCNVDHKPSNTKVDKRVESKYGPPCPPCPAPEFEGGPSVF LFPPKPKDTLYITREPEVTCVVVDVSQEDPEVQFNWYVDGV EVHNAKTKPREEQFNSTYRVVSVLTVLHQDWLNGKEYKCK VSNKGLPSSIEKTISKAKGQPREPQVYTLPPSQEEMTKNQVS LTCLVKGFYPSDIAVEWESNGQPENNYKTTPPVLDSDGSFFL YSRLTVDKSRWQEGNVFSCSVMHEALHNHYTQKSLSLSLG |
| 224 | MAB29 with constant domain PE and LS mutations | EVQLVESGGGVVRPGGSLRLSCAASGFTFDDYGMSWVRQA PGKGLEWVSGINWEGGSTGYADSVKGRFTISRDNAKNSLYL QMNSLRAEDTALYYCARDEQLGGNHYYYYYMDAWGKGT TVTVSSASTKGPSVFPLAPCSRSTSESTAALGCLVKDYFPEPV TVSWNSGALTSGVHTFPAVLQSSGLYSLSSVVTVPSSSLGTK TYTCNVDHKPSNTKVDKRVESKYGPPCPPCPAPEFEGGPSVF LFPPKPKDTLMISRTPEVTCVVVDVSQEDPEVQFNWYVDGV EVHNAKTKPREEQFNSTYRVVSVLTVLHQDWLNGKEYKCK VSNKGLPSSIEKTISKAKGQPREPQVYTLPPSQEEMTKNQVS LTCLVKGFYPSDIAVEWESNGQPENNYKTTPPVLDSDGSFFL YSRLTVDKSRWQEGNVFSCSVLHEALHSHYTQKSLSLSLG |
| 225 | MAB29 with constant domain PE and YTE mutations | EVQLVESGGGVVRPGGSLRLSCAASGFTFDDYGMSWVRQA PGKGLEWVSGINWEGGSTGYADSVKGRFTISRDNAKNSLYL QMNSLRAEDTALYYCARDEQLGGNHYYYYYMDAWGKGT TVTVSSASTKGPSVFPLAPCSRSTSESTAALGCLVKDYFPEPV TVSWNSGALTSGVHTFPAVLQSSGLYSLSSVVTVPSSSLGTK TYTCNVDHKPSNTKVDKRVESKYGPPCPPCPAPEFEGGPSVF LFPPKPKDTLYITREPEVTCVVVDVSQEDPEVQFNWYVDGV EVHNAKTKPREEQFNSTYRVVSVLTVLHQDWLNGKEYKCK VSNKGLPSSIEKTISKAKGQPREPQVYTLPPSQEEMTKNQVS LTCLVKGFYPSDIAVEWESNGQPENNYKTTPPVLDSDGSFFL YSRLTVDKSRWQEGNVFSCSVMHEALHNHYTQKSLSLSLG |
| 226 | MAB30 with constant domain PE and LS mutations | EVQLVESGGGVVRPGGSLRLSCAASGFTFDDYGMSWVRQA PGKGLEWVSGINWEGGSTGYADSVKGRFTISRDNAKNSLYL QMNSLRAEDTALYYCARDEQLGGRHYYYYYMDVWGKGT TVTVSSASTKGPSVFPLAPCSRSTSESTAALGCLVKDYFPEPV TVSWNSGALTSGVHTFPAVLQSSGLYSLSSVVTVPSSSLGTK TYTCNVDHKPSNTKVDKRVESKYGPPCPPCPAPEFEGGPSVF LFPPKPKDTLMISRTPEVTCVVVDVSQEDPEVQFNWYVDGV EVHNAKTKPREEQFNSTYRVVSVLTVLHQDWLNGKEYKCK VSNKGLPSSIEKTISKAKGQPREPQVYTLPPSQEEMTKNQVS LTCLVKGFYPSDIAVEWESNGQPENNYKTTPPVLDSDGSFFL YSRLTVDKSRWQEGNVFSCSVLHEALHSHYTQKSLSLSLG |
| 227 | MAB30 with constant domain PE and YTE mutations | EVQLVESGGGVVRPGGSLRLSCAASGFTFDDYGMSWVRQA PGKGLEWVSGINWEGGSTGYADSVKGRFTISRDNAKNSLYL QMNSLRAEDTALYYCARDEQLGGRHYYYYYMDVWGKGT TVTVSSASTKGPSVFPLAPCSRSTSESTAALGCLVKDYFPEPV TVSWNSGALTSGVHTFPAVLQSSGLYSLSSVVTVPSSSLGTK TYTCNVDHKPSNTKVDKRVESKYGPPCPPCPAPEFEGGPSVF LFPPKPKDTLYITREPEVTCVVVDVSQEDPEVQFNWYVDGV EVHNAKTKPREEQFNSTYRVVSVLTVLHQDWLNGKEYKCK VSNKGLPSSIEKTISKAKGQPREPQVYTLPPSQEEMTKNQVS LTCLVKGFYPSDIAVEWESNGQPENNYKTTPPVLDSDGSFFL YSRLTVDKSRWQEGNVFSCSVMHEALHNHYTQKSLSLSLG |
| 364 | MAB31 with constant domain PE and LS mutations | EVQLVESGGGLVKPGGSLRLSCAASGFTFSDYYMSWIRQAP GKGLEWVSYISRSGSTKYYADSVKGRFTISRDNAKNSLYLQ MNSLRAEDTAVYYCARDQEDYALDYWGQGTLVTVSSAST KGPSVFPLAPCSRSTSESTAALGCLVKDYFPEPVTVSWNSGA LTSGVHTFPAVLQSSGLYSLSSVVTVPSSSLGTKTYTCNVDH KPSNTKVDKRVESKYGPPCPPCPAPEFEGGPSVFLFPPKPKD TLMISRTPEVTCVVVDVSQEDPEVQFNWYVDGVEVHNAKT KPREEQFNSTYRVVSVLTVLHQDWLNGKEYKCKVSNKGLP SSIEKTISKAKGQPREPQVYTLPPSQEEMTKNQVSLTCLVKG FYPSDIAVEWESNGQPENNYKTTPPVLDSDGSFFLYSRLTVD KSRWQEGNVFSCSVLHEALHSHYTQKSLSLSLG |
| 365 | MAB31 with constant domain PE and YTE mutations | EVQLVESGGGLVKPGGSLRLSCAASGFTFSDYYMSWIRQAP GKGLEWVSYISRSGSTKYYADSVKGRFTISRDNAKNSLYLQ MNSLRAEDTAVYYCARDQEDYALDYWGQGTLVTVSS ASTKGPSVFPLAPCSRSTSESTAALGCLVKDYFPEPVTVSWN SGALTSGVHTFPAVLQSSGLYSLSSVVTVPSSSLGTKTYTCN |

TABLE 7-continued

| SEQ ID NO: | AB ID NO. | Heavy Chain Sequence |
|---|---|---|
| | | VDHKPSNTKVDKRVESKYGPPCPPCPAPEFEGGPSVFLFPPK PKDTLYITREPEVTCVVVDVSQEDPEVQFNWYVDGVEVHN AKTKPREEQFNSTYRVVSVLTVLHQDWLNGKEYKCKVSNK GLPSSIEKTISKAKGQPREPQVYTLPPSQEEMTKNQVSLTCLV KGFYPSDIAVEWESNGQPENNYKTTPPVLDSDGSFFLYSRLT VDKSRWQEGNVFSCSVMHEALHNHYTQKSLSLSLG |
| 366 | MAB32 with constant domain PE and LS mutations | EVQLVESGGGLVKPGGSLRLSCAASGFTFSDYYMSWIRQAP GKGLEWVSYISRSGSTKYYADSVKGRFTISRDNAKNSLYLQ MNSLRAEDTAVYYCARDETDYGWDYWGQGTLVTVSSAST KGPSVFPLAPCSRSTSESTAALGCLVKDYFPEPVTVSWNSGA LTSGVHTFPAVLQSSGLYSLSSVVTVPSSSLGTKTYTCNVDH KPSNTKVDKRVESKYGPPCPPCPAPEFEGGPSVFLFPPKPKD TLMISRTPEVTCVVVDVSQEDPEVQFNWYVDGVEVHNAKT KPREEQFNSTYRVVSVLTVLHQDWLNGKEYKCKVSNKGLP SSIEKTISKAKGQPREPQVYTLPPSQEEMTKNQVSLTCLVKG FYPSDIAVEWESNGQPENNYKTTPPVLDSDGSFFLYSRLTVD KSRWQEGNVFSCSVLHEALHSHYTQKSLSLSLG |
| 367 | MAB32 with constant domain PE and YTE mutations | EVQLVESGGGLVKPGGSLRLSCAASGFTFSDYYMSWIRQAP GKGLEWVSYISRSGSTKYYADSVKGRFTISRDNAKNSLYLQ MNSLRAEDTAVYYCARDETDYGWDYWGQGTLVTVSSAST KGPSVFPLAPCSRSTSESTAALGCLVKDYFPEPVTVSWNSGA LTSGVHTFPAVLQSSGLYSLSSVVTVPSSSLGTKTYTCNVDH KPSNTKVDKRVESKYGPPCPPCPAPEFEGGPSVFLFPPKPKD TLYITREPEVTCVVVDVSQEDPEVQFNWYVDGVEVHNAKT KPREEQFNSTYRVVSVLTVLHQDWLNGKEYKCKVSNKGLP SSIEKTISKAKGQPREPQVYTLPPSQEEMTKNQVSLTCLVKG FYPSDIAVEWESNGQPENNYKTTPPVLDSDGSFFLYSRLTVD KSRWQEGNVFSCSVMHEALHNHYTQKSLSLSLG |
| 368 | MAB33 with constant domain PE and LS mutations | EVQLVESGGGLVKPGGSLRLSCAASGFTFSDYYMSWIRQAP GKGLEWVSYISRSGSTKYYADSVKGRFTISRDNAKNSLYLQ MNSLRAEDTAVYYCARDETDYAFDEWGQGTLVTVSS ASTKGPSVFPLAPCSRSTSESTAALGCLVKDYFPEPVTVSWN SGALTSGVHTFPAVLQSSGLYSLSSVVTVPSSSLGTKTYTCN VDHKPSNTKVDKRVESKYGPPCPPCPAPEFEGGPSVFLFPPK PKDTLMISRTPEVTCVVVDVSQEDPEVQFNWYVDGVEVHN AKTKPREEQFNSTYRVVSVLTVLHQDWLNGKEYKCKVSNK GLPSSIEKTISKAKGQPREPQVYTLPPSQEEMTKNQVSLTCLV KGFYPSDIAVEWESNGQPENNYKTTPPVLDSDGSFFLYSRLT VDKSRWQEGNVFSCSVLHEALHSHYTQKSLSLSLG |
| 369 | MAB33 with constant domain PE and YTE mutations | EVQLVESGGGLVKPGGSLRLSCAASGFTFSDYYMSWIRQAP GKGLEWVSYISRSGSTKYYADSVKGRFTISRDNAKNSLYLQ MNSLRAEDTAVYYCARDETDYAFDEWGQGTLVTVSS ASTKGPSVFPLAPCSRSTSESTAALGCLVKDYFPEPVTVSWN SGALTSGVHTFPAVLQSSGLYSLSSVVTVPSSSLGTKTYTCN VDHKPSNTKVDKRVESKYGPPCPPCPAPEFEGGPSVFLFPPK PKDTLYITREPEVTCVVVDVSQEDPEVQFNWYVDGVEVHN AKTKPREEQFNSTYRVVSVLTVLHQDWLNGKEYKCKVSNK GLPSSIEKTISKAKGQPREPQVYTLPPSQEEMTKNQVSLTCLV KGFYPSDIAVEWESNGQPENNYKTTPPVLDSDGSFFLYSRLT VDKSRWQEGNVFSCSVMHEALHNHYTQKSLSLSLG |
| 370 | MAB34 with constant domain PE and LS mutations | EVQLVESGGGLVKPGGSLRLSCAASGFTFSDYYMSWIRQAP GKGLEWVSYISRSGSTKYYADSVKGRFTISRDNAKNSLYLQ MNSLRAEDTAVYYCARDESQYALDYWGQGTLVTVSS ASTKGPSVFPLAPCSRSTSESTAALGCLVKDYFPEPVTVSWN SGALTSGVHTFPAVLQSSGLYSLSSVVTVPSSSLGTKTYTCN VDHKPSNTKVDKRVESKYGPPCPPCPAPEFEGGPSVFLFPPK PKDTLMISRTPEVTCVVVDVSQEDPEVQFNWYVDGVEVHN AKTKPREEQFNSTYRVVSVLTVLHQDWLNGKEYKCKVSNK GLPSSIEKTISKAKGQPREPQVYTLPPSQEEMTKNQVSLTCLV KGFYPSDIAVEWESNGQPENNYKTTPPVLDSDGSFFLYSRLT VDKSRWQEGNVFSCSVLHEALHSHYTQKSLSLSLG |
| 371 | MAB34 with constant domain PE and YTE mutations | EVQLVESGGGLVKPGGSLRLSCAASGFTFSDYYMSWIRQAP GKGLEWVSYISRSGSTKYYADSVKGRFTISRDNAKNSLYLQ MNSLRAEDTAVYYCARDESQYALDYWGQGTLVTVSS ASTKGPSVFPLAPCSRSTSESTAALGCLVKDYFPEPVTVSWN SGALTSGVHTFPAVLQSSGLYSLSSVVTVPSSSLGTKTYTCN VDHKPSNTKVDKRVESKYGPPCPPCPAPEFEGGPSVFLFPPK PKDTLYITREPEVTCVVVDVSQEDPEVQFNWYVDGVEVHN AKTKPREEQFNSTYRVVSVLTVLHQDWLNGKEYKCKVSNK GLPSSIEKTISKAKGQPREPQVYTLPPSQEEMTKNQVSLTCLV KGFYPSDIAVEWESNGQPENNYKTTPPVLDSDGSFFLYSRLT VDKSRWQEGNVFSCSVMHEALHNHYTQKSLSLSLG |

TABLE 7-continued

| SEQ ID NO: | AB ID NO. | Heavy Chain Sequence |
| --- | --- | --- |
| 372 | MAB35 with constant domain PE and LS mutations | EVQLVESGGGLVKPGGSLRLSCAASGFTFSDYYMSWIRQAP GKGLEWVSYISRSGSTKYYAHSVKGRFTISRDNAKNSLYLQ MNSLRAEDTAVYYCARDNTDYALDLWGQGTLVTVSS ASTKGPSVFPLAPCSRSTSESTAALGCLVKDYFPEPVTVSWN SGALTSGVHTFPAVLQSSGLYSLSSVVTVPSSSLGTKTYTCN VDHKPSNTKVDKRVESKYGPPCPPCPAPEFEGGPSVFLFPPK PKDTLMISRTPEVTCVVVDVSQEDPEVQFNWYVDGVEVHN AKTKPREEQFNSTYRVVSVLTVLHQDWLNGKEYKCKVSNK GLPSSIEKTISKAKGQPREPQVYTLPPSQEEMTKNQVSLTCLV KGFYPSDIAVEWESNGQPENNYKTTPPVLDSDGSFFLYSRLT VDKSRWQEGNVFSCSVLHEALHSHYTQKSLSLSLG |
| 373 | MAB35 with constant domain PE and YTE mutations | EVQLVESGGGLVKPGGSLRLSCAASGFTFSDYYMSWIRQAP GKGLEWVSYISRSGSTKYYAHSVKGRFTISRDNAKNSLYLQ MNSLRAEDTAVYYCARDNTDYALDLWGQGTLVTVSS ASTKGPSVFPLAPCSRSTSESTAALGCLVKDYFPEPVTVSWN SGALTSGVHTFPAVLQSSGLYSLSSVVTVPSSSLGTKTYTCN VDHKPSNTKVDKRVESKYGPPCPPCPAPEFEGGPSVFLFPPK PKDTLYITREPEVTCVVVDVSQEDPEVQFNWYVDGVEVHN AKTKPREEQFNSTYRVVSVLTVLHQDWLNGKEYKCKVSNK GLPSSIEKTISKAKGQPREPQVYTLPPSQEEMTKNQVSLTCLV KGFYPSDIAVEWESNGQPENNYKTTPPVLDSDGSFFLYSRLT VDKSRWQEGNVFSCSVMHEALHNHYTQKSLSLSLG |
| 374 | MAB36 with constant domain PE and LS mutations | EVQLVESGGGLVKPGGSLRLSCAASGFTFSDYYMSWIRQAP GKGLEWVSYISRSGSTKYYAHSVKGRFTISRDNAKNSLYLQ MNSLRAEDTAVYYCARDETDYAYDEWGQGTLVTVSS ASTKGPSVFPLAPCSRSTSESTAALGCLVKDYFPEPVTVSWN SGALTSGVHTFPAVLQSSGLYSLSSVVTVPSSSLGTKTYTCN VDHKPSNTKVDKRVESKYGPPCPPCPAPEFEGGPSVFLFPPK PKDTLMISRTPEVTCVVVDVSQEDPEVQFNWYVDGVEVHN AKTKPREEQFNSTYRVVSVLTVLHQDWLNGKEYKCKVSNK GLPSSIEKTISKAKGQPREPQVYTLPPSQEEMTKNQVSLTCLV KGFYPSDIAVEWESNGQPENNYKTTPPVLDSDGSFFLYSRLT VDKSRWQEGNVFSCSVLHEALHSHYTQKSLSLSLG |
| 375 | MAB36 with constant domain PE and YTE mutations | EVQLVESGGGLVKPGGSLRLSCAASGFTFSDYYMSWIRQAP GKGLEWVSYISRSGSTKYYAHSVKGRFTISRDNAKNSLYLQ MNSLRAEDTAVYYCARDETDYAYDEWGQGTLVTVSS ASTKGPSVFPLAPCSRSTSESTAALGCLVKDYFPEPVTVSWN SGALTSGVHTFPAVLQSSGLYSLSSVVTVPSSSLGTKTYTCN VDHKPSNTKVDKRVESKYGPPCPPCPAPEFEGGPSVFLFPPK PKDTLYITREPEVTCVVVDVSQEDPEVQFNWYVDGVEVHN AKTKPREEQFNSTYRVVSVLTVLHQDWLNGKEYKCKVSNK GLPSSIEKTISKAKGQPREPQVYTLPPSQEEMTKNQVSLTCLV KGFYPSDIAVEWESNGQPENNYKTTPPVLDSDGSFFLYSRLT VDKSRWQEGNVFSCSVMHEALHNHYTQKSLSLSLG |
| 376 | MAB37 with constant domain PE and LS mutations | EVQLVESGGGLVKPGGSLRLSCAASGFTFSDYYMSWIRQAP GKGLEWVSYISRSGSTKYYADSVKGRFTISRDNAKNSLYLQ MNSLRAEDTAVYYCARDETDYAYDNWGQGTLVTVSS ASTKGPSVFPLAPCSRSTSESTAALGCLVKDYFPEPVTVSWN SGALTSGVHTFPAVLQSSGLYSLSSVVTVPSSSLGTKTYTCN VDHKPSNTKVDKRVESKYGPPCPPCPAPEFEGGPSVFLFPPK PKDTLMISRTPEVTCVVVDVSQEDPEVQFNWYVDGVEVHN AKTKPREEQFNSTYRVVSVLTVLHQDWLNGKEYKCKVSNK GLPSSIEKTISKAKGQPREPQVYTLPPSQEEMTKNQVSLTCLV KGFYPSDIAVEWESNGQPENNYKTTPPVLDSDGSFFLYSRLT VDKSRWQEGNVFSCSVLHEALHSHYTQKSLSLSLG |
| 377 | MAB37 with constant domain PE and YTE mutations | EVQLVESGGGLVKPGGSLRLSCAASGFTFSDYYMSWIRQAP GKGLEWVSYISRSGSTKYYADSVKGRFTISRDNAKNSLYLQ MNSLRAEDTAVYYCARDETDYAYDNWGQGTLVTVSS ASTKGPSVFPLAPCSRSTSESTAALGCLVKDYFPEPVTVSWN SGALTSGVHTFPAVLQSSGLYSLSSVVTVPSSSLGTKTYTCN VDHKPSNTKVDKRVESKYGPPCPPCPAPEFEGGPSVFLFPPK PKDTLYITREPEVTCVVVDVSQEDPEVQFNWYVDGVEVHN AKTKPREEQFNSTYRVVSVLTVLHQDWLNGKEYKCKVSNK GLPSSIEKTISKAKGQPREPQVYTLPPSQEEMTKNQVSLTCLV KGFYPSDIAVEWESNGQPENNYKTTPPVLDSDGSFFLYSRLT VDKSRWQEGNVFSCSVMHEALHNHYTQKSLSLSLG |
| 378 | MAB38 with constant domain PE and LS mutations | EVQLVESGGGLVKPGGSLRLSCAASGFTFSDYYMSWIRQAP GKGLEWVSYISRSGSTKYYADSVKGRFTISRDNAKNSLYLQ MNSLRAEDTAVYYCARDESDYAYDWGQGTLVTVSS ASTKGPSVFPLAPCSRSTSESTAALGCLVKDYFPEPVTVSWN SGALTSGVHTFPAVLQSSGLYSLSSVVTVPSSSLGTKTYTCN |

TABLE 7-continued

| SEQ ID NO: | AB ID NO. | Heavy Chain Sequence |
|---|---|---|
| | | VDHKPSNTKVDKRVESKYGPPCPPCPAPEFEGGPSVFLFPPK PKDTLMISRTPEVTCVVVDVSQEDPEVQFNWYVDGVEVHN AKTKPREEQFNSTYRVVSVLTVLHQDWLNGKEYKCKVSNK GLPSSIEKTISKAKGQPREPQVYTLPPSQEEMTKNQVSLTCLV KGFYPSDIAVEWESNGQPENNYKTTPPVLDSDGSFFLYSRLT VDKSRWQEGNVFSCSVLHEALHSHYTQKSLSLSLG |
| 379 | MAB38 with constant domain PE and YTE mutations | EVQLVESGGGLVKPGGSLRLSCAASGFTFSDYYMSWIRQAP GKGLEWVSYISRSGSTKYYADSVKGRFTISRDNAKNSLYLQ MNSLRAEDTAVYYCARDESDYAYDYWGQGTLVTVSS ASTKGPSVFPLAPCSRSTSESTAALGCLVKDYFPEPVTVSWN SGALTSGVHTFPAVLQSSGLYSLSSVVTVPSSSLGTKTYTCN VDHKPSNTKVDKRVESKYGPPCPPCPAPEFEGGPSVFLFPPK PKDTLYITREPEVTCVVVDVSQEDPEVQFNWYVDGVEVHN AKTKPREEQFNSTYRVVSVLTVLHQDWLNGKEYKCKVSNK GLPSSIEKTISKAKGQPREPQVYTLPPSQEEMTKNQVSLTCLV KGFYPSDIAVEWESNGQPENNYKTTPPVLDSDGSFFLYSRLT VDKSRWQEGNVFSCSVMHEALHNHYTQKSLSLSLG |
| 380 | MAB39 with constant domain PE and LS mutations | EVQLVESGGGLVKPGGSLRLSCAASGFTFSDYYMSWIRQAP GKGLEWVSYISRSGSTKYYADSVKGRFTISRDNAKNSLYLQ MNSLRAEDTAVYYCARDENYALDWWGQGTLVTVSSASTK GPSVFPLAPCSRSTSESTAALGCLVKDYFPEPVTVSWNSGAL TSGVHTFPAVLQSSGLYSLSSVVTVPSSSLGTKTYTCNVDHK PSNTKVDKRVESKYGPPCPPCPAPEFEGGPSVFLFPPKPKDTL MISRTPEVTCVVVDVSQEDPEVQFNWYVDGVEVHNAKTKP REEQFNSTYRVVSVLTVLHQDWLNGKEYKCKVSNKGLPSSI EKTISKAKGQPREPQVYTLPPSQEEMTKNQVSLTCLVKGFYP SDIAVEWESNGQPENNYKTTPPVLDSDGSFFLYSRLTVDKSR WQEGNVFSCSVLHEALHSHYTQKSLSLSLG |
| 381 | MAB39 with constant domain PE and YTE mutations | EVQLVESGGGLVKPGGSLRLSCAASGFTFSDYYMSWIRQAP GKGLEWVSYISRSGSTKYYADSVKGRFTISRDNAKNSLYLQ MNSLRAEDTAVYYCARDENYALDWWGQGTLVTVSSASTK GPSVFPLAPCSRSTSESTAALGCLVKDYFPEPVTVSWNSGAL TSGVHTFPAVLQSSGLYSLSSVVTVPSSSLGTKTYTCNVDHK PSNTKVDKRVESKYGPPCPPCPAPEFEGGPSVFLFPPKPKDTL YITREPEVTCVVVDVSQEDPEVQFNWYVDGVEVHNAKTKP REEQFNSTYRVVSVLTVLHQDWLNGKEYKCKVSNKGLPSSI EKTISKAKGQPREPQVYTLPPSQEEMTKNQVSLTCLVKGFYP SDIAVEWESNGQPENNYKTTPPVLDSDGSFFLYSRLTVDKSR WQEGNVFSCSVMHEALHNHYTQKSLSLSLG |
| 382 | MAB40 with constant domain PE and LS mutations | EVQLVESGGGLVKPGGSLRLSCAASGFTFSDYYMSWIRQAP GKGLEWVSYISRSGSTKYYADSVKGRFTISRDNAKNSLYLQ MNSLRAEDTAVYYCARDESDYALDFWGQGTLVTVSS ASTKGPSVFPLAPCSRSTSESTAALGCLVKDYFPEPVTVSWN SGALTSGVHTFPAVLQSSGLYSLSSVVTVPSSSLGTKTYTCN VDHKPSNTKVDKRVESKYGPPCPPCPAPEFEGGPSVFLFPPK PKDTLMISRTPEVTCVVVDVSQEDPEVQFNWYVDGVEVHN AKTKPREEQFNSTYRVVSVLTVLHQDWLNGKEYKCKVSNK GLPSSIEKTISKAKGQPREPQVYTLPPSQEEMTKNQVSLTCLV KGFYPSDIAVEWESNGQPENNYKTTPPVLDSDGSFFLYSRLT VDKSRWQEGNVFSCSVLHEALHSHYTQKSLSLSLG |
| 383 | MAB40 with constant domain PE and YTE mutations | EVQLVESGGGLVKPGGSLRLSCAASGFTFSDYYMSWIRQAP GKGLEWVSYISRSGSTKYYADSVKGRFTISRDNAKNSLYLQ MNSLRAEDTAVYYCARDESDYALDFWGQGTLVTVSS ASTKGPSVFPLAPCSRSTSESTAALGCLVKDYFPEPVTVSWN SGALTSGVHTFPAVLQSSGLYSLSSVVTVPSSSLGTKTYTCN VDHKPSNTKVDKRVESKYGPPCPPCPAPEFEGGPSVFLFPPK PKDTLYITREPEVTCVVVDVSQEDPEVQFNWYVDGVEVHN AKTKPREEQFNSTYRVVSVLTVLHQDWLNGKEYKCKVSNK GLPSSIEKTISKAKGQPREPQVYTLPPSQEEMTKNQVSLTCLV KGFYPSDIAVEWESNGQPENNYKTTPPVLDSDGSFFLYSRLT VDKSRWQEGNVFSCSVMHEALHNHYTQKSLSLSLG |
| 384 | MAB41 with constant domain PE and LS mutations | EVQLVQSGAEVKKPGASVKVSCKVSGDTLTELSMHWVRQA PGKGLEWMGTFDPEEGETIYAQKFQGRVTMTEDTSTDTAY MELSSLRSEDTAVYYCVTEGLAGVPFDLWGQGTLVTVSS ASTKGPSVFPLAPCSRSTSESTAALGCLVKDYFPEPVTVSWN SGALTSGVHTFPAVLQSSGLYSLSSVVTVPSSSLGTKTYTCN VDHKPSNTKVDKRVESKYGPPCPPCPAPEFEGGPSVFLFPPK PKDTLMISRTPEVTCVVVDVSQEDPEVQFNWYVDGVEVHN AKTKPREEQFNSTYRVVSVLTVLHQDWLNGKEYKCKVSNK GLPSSIEKTISKAKGQPREPQVYTLPPSQEEMTKNQVSLTCLV KGFYPSDIAVEWESNGQPENNYKTTPPVLDSDGSFFLYSRLT VDKSRWQEGNVFSCSVLHEALHSHYTQKSLSLSLG |

TABLE 7-continued

| SEQ ID NO: | AB ID NO. | Heavy Chain Sequence |
|---|---|---|
| 385 | MAB41 with constant domain PE and YTE mutations | EVQLVQSGAEVKKPGASVKVSCKVSGDTLTELSMHWVRQA PGKGLEWMGTFDPEEGETIYAQKFQGRVTMTEDTSTDTAY MELSSLRSEDTAVYYCVTEGLAGVPFDLWGQGTLVTVSS ASTKGPSVFPLAPCSRSTSESTAALGCLVKDYFPEPVTVSWN SGALTSGVHTFPAVLQSSGLYSLSSVVTVPSSSLGTKTYTCN VDHKPSNTKVDKRVESKYGPPCPPCPAPEFEGGPSVFLFPPK PKDTLYITREPEVTCVVVDVSQEDPEVQFNWYVDGVEVHN AKTKPREEQFNSTYRVVSVLTVLHQDWLNGKEYKCKVSNK GLPSSIEKTISKAKGQPREPQVYTLPPSQEEMTKNQVSLTCLV KGFYPSDIAVEWESNGQPENNYKTTPPVLDSDGSFFLYSRLT VDKSRWQEGNVFSCSVMHEALHNHYTQKSLSLSLG |
| 386 | MAB42 with constant domain PE and LS mutations | EVQLVQSGAEVKKPGASVKVSCKVSGDTLTELSMHWVRQA PGKGLEWMGTFDPEEGETIYAQKFQGRVTMTEDTSTDTAY MELSSLRSEDTAVYYCVTEGLGGRPFDHWGQGTLVTVSS ASTKGPSVFPLAPCSRSTSESTAALGCLVKDYFPEPVTVSWN SGALTSGVHTFPAVLQSSGLYSLSSVVTVPSSSLGTKTYTCN VDHKPSNTKVDKRVESKYGPPCPPCPAPEFEGGPSVFLFPPK PKDTLMISRTPEVTCVVVDVSQEDPEVQFNWYVDGVEVHN AKTKPREEQFNSTYRVVSVLTVLHQDWLNGKEYKCKVSNK GLPSSIEKTISKAKGQPREPQVYTLPPSQEEMTKNQVSLTCLV KGFYPSDIAVEWESNGQPENNYKTTPPVLDSDGSFFLYSRLT VDKSRWQEGNVFSCSVLHEALHSHYTQKSLSLSLG |
| 387 | MAB42 with constant domain PE and YTE mutations | EVQLVQSGAEVKKPGASVKVSCKVSGDTLTELSMHWVRQA PGKGLEWMGTFDPEEGETIYAQKFQGRVTMTEDTSTDTAY MELSSLRSEDTAVYYCVTEGLGGRPFDHWGQGTLVTVSS ASTKGPSVFPLAPCSRSTSESTAALGCLVKDYFPEPVTVSWN SGALTSGVHTFPAVLQSSGLYSLSSVVTVPSSSLGTKTYTCN VDHKPSNTKVDKRVESKYGPPCPPCPAPEFEGGPSVFLFPPK PKDTLYITREPEVTCVVVDVSQEDPEVQFNWYVDGVEVHN AKTKPREEQFNSTYRVVSVLTVLHQDWLNGKEYKCKVSNK GLPSSIEKTISKAKGQPREPQVYTLPPSQEEMTKNQVSLTCLV KGFYPSDIAVEWESNGQPENNYKTTPPVLDSDGSFFLYSRLT VDKSRWQEGNVFSCSVMHEALHNHYTQKSLSLSLG |
| 388 | MAB43 with constant domain PE and LS mutations | EVQLVQSGAEVKKPGASVKVSCKVSGDTLTELSMHWVRQA PGKGLEWMGTFDPEEGETIYAQKFQGRVTMTEDTSTDTAY MELSSLRSEDTAVYYCVTEGLAGFPPFDIWGQGTLVTVSS ASTKGPSVFPLAPCSRSTSESTAALGCLVKDYFPEPVTVSWN SGALTSGVHTFPAVLQSSGLYSLSSVVTVPSSSLGTKTYTCN VDHKPSNTKVDKRVESKYGPPCPPCPAPEFEGGPSVFLFPPK PKDTLMISRTPEVTCVVVDVSQEDPEVQFNWYVDGVEVHN AKTKPREEQFNSTYRVVSVLTVLHQDWLNGKEYKCKVSNK GLPSSIEKTISKAKGQPREPQVYTLPPSQEEMTKNQVSLTCLV KGFYPSDIAVEWESNGQPENNYKTTPPVLDSDGSFFLYSRLT VDKSRWQEGNVFSCSVLHEALHSHYTQKSLSLSLG |
| 389 | MAB43 with constant domain PE and YTE mutations | EVQLVQSGAEVKKPGASVKVSCKVSGDTLTELSMHWVRQA PGKGLEWMGTFDPEEGETIYAQKFQGRVTMTEDTSTDTAY MELSSLRSEDTAVYYCVTEGLAGFPPFDIWGQGTLVTVSS ASTKGPSVFPLAPCSRSTSESTAALGCLVKDYFPEPVTVSWN SGALTSGVHTFPAVLQSSGLYSLSSVVTVPSSSLGTKTYTCN VDHKPSNTKVDKRVESKYGPPCPPCPAPEFEGGPSVFLFPPK PKDTLYITREPEVTCVVVDVSQEDPEVQFNWYVDGVEVHN AKTKPREEQFNSTYRVVSVLTVLHQDWLNGKEYKCKVSNK GLPSSIEKTISKAKGQPREPQVYTLPPSQEEMTKNQVSLTCLV KGFYPSDIAVEWESNGQPENNYKTTPPVLDSDGSFFLYSRLT VDKSRWQEGNVFSCSVMHEALHNHYTQKSLSLSLG |
| 390 | MAB44 with constant domain PE and LS mutations | EVQLVQSGAEVKKPGASVKVSCKVSGDTLTELSMHWVRQA PGKGLEWMGTFDPEEGETIYAQKFQGRVTMTEDTSTDTAY MELSSLRSEDTAVYYCVTEGLAWRPTDSWGQGTLVTVSS ASTKGPSVFPLAPCSRSTSESTAALGCLVKDYFPEPVTVSWN SGALTSGVHTFPAVLQSSGLYSLSSVVTVPSSSLGTKTYTCN VDHKPSNTKVDKRVESKYGPPCPPCPAPEFEGGPSVFLFPPK PKDTLMISRTPEVTCVVVDVSQEDPEVQFNWYVDGVEVHN AKTKPREEQFNSTYRVVSVLTVLHQDWLNGKEYKCKVSNK GLPSSIEKTISKAKGQPREPQVYTLPPSQEEMTKNQVSLTCLV KGFYPSDIAVEWESNGQPENNYKTTPPVLDSDGSFFLYSRLT VDKSRWQEGNVFSCSVLHEALHSHYTQKSLSLSLG |
| 391 | MAB44 with constant domain PE and YTE mutations | EVQLVQSGAEVKKPGASVKVSCKVSGDTLTELSMHWVRQA PGKGLEWMGTFDPEEGETIYAQKFQGRVTMTEDTSTDTAY MELSSLRSEDTAVYYCVTEGLAWRPTDSWGQGTLVTVSS ASTKGPSVFPLAPCSRSTSESTAALGCLVKDYFPEPVTVSWN SGALTSGVHTFPAVLQSSGLYSLSSVVTVPSSSLGTKTYTCN |

TABLE 7-continued

| SEQ ID NO: | AB ID NO. | Heavy Chain Sequence |
|---|---|---|
| | | VDHKPSNTKVDKRVESKYGPPCPPCPAPEFEGGPSVFLFPPK
PKDTLYITREPEVTCVVVDVSQEDPEVQFNWYVDGVEVHN
AKTKPREEQFNSTYRVVSVLTVLHQDWLNGKEYKCKVSNK
GLPSSIEKTISKAKGQPREPQVYTLPPSQEEMTKNQVSLTCLV
KGFYPSDIAVEWESNGQPENNYKTTPPVLDSDGSFFLYSRLT
VDKSRWQEGNVFSCSVMHEALHNHYTQKSLSLSLG |
| 392 | MAB45 with constant domain PE and LS mutations | EVQLVQSGAEVKKPGASVKVSCKVSGDTLTELSMHWVRQA
PGKGLEWMGTFDPEEGETIYAQKFQGRVTMTEDTSTDTAY
MELSSLRSEDTAVYYCVTKGLAWLPYYSWGQGTLVTVSSA
STKGPSVFPLAPCSRSTSESTAALGCLVKDYFPEPVTVSWNS
GALTSGVHTFPAVLQSSGLYSLSSVVTVPSSSLGTKTYTCNV
DHKPSNTKVDKRVESKYGPPCPPCPAPEFEGGPSVFLFPPKP
KDTLMISRTPEVTCVVVDVSQEDPEVQFNWYVDGVEVHNA
KTKPREEQFNSTYRVVSVLTVLHQDWLNGKEYKCKVSNKG
LPSSIEKTISKAKGQPREPQVYTLPPSQEEMTKNQVSLTCLVK
GFYPSDIAVEWESNGQPENNYKTTPPVLDSDGSFFLYSRLTV
DKSRWQEGNVFSCSVLHEALHSHYTQKSLSLSLG |
| 393 | MAB45 with constant domain PE and YTE mutations | EVQLVQSGAEVKKPGASVKVSCKVSGDTLTELSMHWVRQA
PGKGLEWMGTFDPEEGETIYAQKFQGRVTMTEDTSTDTAY
MELSSLRSEDTAVYYCVTKGLAWLPYYSWGQGTLVTVSSA
STKGPSVFPLAPCSRSTSESTAALGCLVKDYFPEPVTVSWNS
GALTSGVHTFPAVLQSSGLYSLSSVVTVPSSSLGTKTYTCNV
DHKPSNTKVDKRVESKYGPPCPPCPAPEFEGGPSVFLFPPKP
KDTLYITREPEVTCVVVDVSQEDPEVQFNWYVDGVEVHNA
KTKPREEQFNSTYRVVSVLTVLHQDWLNGKEYKCKVSNKG
LPSSIEKTISKAKGQPREPQVYTLPPSQEEMTKNQVSLTCLVK
GFYPSDIAVEWESNGQPENNYKTTPPVLDSDGSFFLYSRLTV
DKSRWQEGNVFSCSVMHEALHNHYTQKSLSLSLG |
| 394 | MAB46 with constant domain PE and LS mutations | EVQLVQSGAEVKKPGASVKVSCKVSGDTLTELSMHWVRQA
PGKGLEWMGTFDPEEGETIYAQKFQGRVTMTEDTSTDTAY
MELSSLRSEDTAVYYCVTEGLAGVPFDLWGQGTLVTVSS
ASTKGPSVFPLAPCSRSTSESTAALGCLVKDYFPEPVTVSWN
SGALTSGVHTFPAVLQSSGLYSLSSVVTVPSSSLGTKTYTCN
VDHKPSNTKVDKRVESKYGPPCPPCPAPEFEGGPSVFLFPPK
PKDTLMISRTPEVTCVVVDVSQEDPEVQFNWYVDGVEVHN
AKTKPREEQFNSTYRVVSVLTVLHQDWLNGKEYKCKVSNK
GLPSSIEKTISKAKGQPREPQVYTLPPSQEEMTKNQVSLTCLV
KGFYPSDIAVEWESNGQPENNYKTTPPVLDSDGSFFLYSRLT
VDKSRWQEGNVFSCSVLHEALHSHYTQKSLSLSLG |
| 395 | MAB46 with constant domain PE and YTE mutations | EVQLVQSGAEVKKPGASVKVSCKVSGDTLTELSMHWVRQA
PGKGLEWMGTFDPEEGETIYAQKFQGRVTMTEDTSTDTAY
MELSSLRSEDTAVYYCVTEGLAGVPFDLWGQGTLVTVSS
ASTKGPSVFPLAPCSRSTSESTAALGCLVKDYFPEPVTVSWN
SGALTSGVHTFPAVLQSSGLYSLSSVVTVPSSSLGTKTYTCN
VDHKPSNTKVDKRVESKYGPPCPPCPAPEFEGGPSVFLFPPK
PKDTLYITREPEVTCVVVDVSQEDPEVQFNWYVDGVEVHN
AKTKPREEQFNSTYRVVSVLTVLHQDWLNGKEYKCKVSNK
GLPSSIEKTISKAKGQPREPQVYTLPPSQEEMTKNQVSLTCLV
KGFYPSDIAVEWESNGQPENNYKTTPPVLDSDGSFFLYSRLT
VDKSRWQEGNVFSCSVMHEALHNHYTQKSLSLSLG |
| 396 | MAB47 with constant domain PE and LS mutations | EVQLVQSGAEVKKPGASVKVSCKVSGDTLTELSMHWVRQA
PGKGLEWMGTFDPEEGETIYAQKFQGRVTMTEDTSTDTAY
MELSSLRSEDTAVYYCVTEGEAGRPFDAWGQGTLVTVSS
ASTKGPSVFPLAPCSRSTSESTAALGCLVKDYFPEPVTVSWN
SGALTSGVHTFPAVLQSSGLYSLSSVVTVPSSSLGTKTYTCN
VDHKPSNTKVDKRVESKYGPPCPPCPAPEFEGGPSVFLFPPK
PKDTLMISRTPEVTCVVVDVSQEDPEVQFNWYVDGVEVHN
AKTKPREEQFNSTYRVVSVLTVLHQDWLNGKEYKCKVSNK
GLPSSIEKTISKAKGQPREPQVYTLPPSQEEMTKNQVSLTCLV
KGFYPSDIAVEWESNGQPENNYKTTPPVLDSDGSFFLYSRLT
VDKSRWQEGNVFSCSVLHEALHSHYTQKSLSLSLG |
| 397 | MAB47 with constant domain PE and YTE mutations | EVQLVQSGAEVKKPGASVKVSCKVSGDTLTELSMHWVRQA
PGKGLEWMGTFDPEEGETIYAQKFQGRVTMTEDTSTDTAY
MELSSLRSEDTAVYYCVTEGEAGRPFDAWGQGTLVTVSS
ASTKGPSVFPLAPCSRSTSESTAALGCLVKDYFPEPVTVSWN
SGALTSGVHTFPAVLQSSGLYSLSSVVTVPSSSLGTKTYTCN
VDHKPSNTKVDKRVESKYGPPCPPCPAPEFEGGPSVFLFPPK
PKDTLYITREPEVTCVVVDVSQEDPEVQFNWYVDGVEVHN
AKTKPREEQFNSTYRVVSVLTVLHQDWLNGKEYKCKVSNK
GLPSSIEKTISKAKGQPREPQVYTLPPSQEEMTKNQVSLTCLV
KGFYPSDIAVEWESNGQPENNYKTTPPVLDSDGSFFLYSRLT
VDKSRWQEGNVFSCSVMHEALHNHYTQKSLSLSLG |

TABLE 7-continued

| SEQ ID NO: | AB ID NO. | Heavy Chain Sequence |
|---|---|---|
| 398 | MAB48 with constant domain PE and LS mutations | EVQLVQSGAEVKKPGASVKVSCKVSGDTLTELSMHWVRQA PGKGLEWMGTFDPEEGETIYAQKFQGRVTMTEDTSTDTAY MELSSLRSEDTAVYYCVTEGLAGRPYDVWGQGTLVTVSS ASTKGPSVFPLAPCSRSTSESTAALGCLVKDYFPEPVTVSWN SGALTSGVHTFPAVLQSSGLYSLSSVVTVPSSSLGTKTYTCN VDHKPSNTKVDKRVESKYGPPCPPCPAPEFEGGPSVFLFPPK PKDTLMISRTPEVTCVVVDVSQEDPEVQFNWYVDGVEVHN AKTKPREEQFNSTYRVVSVLTVLHQDWLNGKEYKCKVSNK GLPSSIEKTISKAKGQPREPQVYTLPPSQEEMTKNQVSLTCLV KGFYPSDIAVEWESNGQPENNYKTTPPVLDSDGSFFLYSRLT VDKSRWQEGNVFSCSVLHEALHSHYTQKSLSLSLG |
| 399 | MAB48 with constant domain PE and YTE mutations | EVQLVQSGAEVKKPGASVKVSCKVSGDTLTELSMHWVRQA PGKGLEWMGTFDPEEGETIYAQKFQGRVTMTEDTSTDTAY MELSSLRSEDTAVYYCVTEGLAGRPYDVWGQGTLVTVSS ASTKGPSVFPLAPCSRSTSESTAALGCLVKDYFPEPVTVSWN SGALTSGVHTFPAVLQSSGLYSLSSVVTVPSSSLGTKTYTCN VDHKPSNTKVDKRVESKYGPPCPPCPAPEFEGGPSVFLFPPK PKDTLYITREPEVTCVVVDVSQEDPEVQFNWYVDGVEVHN AKTKPREEQFNSTYRVVSVLTVLHQDWLNGKEYKCKVSNK GLPSSIEKTISKAKGQPREPQVYTLPPSQEEMTKNQVSLTCLV KGFYPSDIAVEWESNGQPENNYKTTPPVLDSDGSFFLYSRLT VDKSRWQEGNVFSCSVMHEALHNHYTQKSLSLSLG |
| 400 | MAB49 with constant domain PE and LS mutations | EVQLVQSGAEVKKPGASVKVSCKVSGDTLTELSMHWVRQA PGKGLEWMGTFDPEEGETIYAQKFQGRVTMTEDTSTDTAY MELSYLRSEDTAVYYCVTEGLAGIPFDSWGQGTLVTVSS ASTKGPSVFPLAPCSRSTSESTAALGCLVKDYFPEPVTVSWN SGALTSGVHTFPAVLQSSGLYSLSSVVTVPSSSLGTKTYTCN VDHKPSNTKVDKRVESKYGPPCPPCPAPEFEGGPSVFLFPPK PKDTLMISRTPEVTCVVVDVSQEDPEVQFNWYVDGVEVHN AKTKPREEQFNSTYRVVSVLTVLHQDWLNGKEYKCKVSNK GLPSSIEKTISKAKGQPREPQVYTLPPSQEEMTKNQVSLTCLV KGFYPSDIAVEWESNGQPENNYKTTPPVLDSDGSFFLYSRLT VDKSRWQEGNVFSCSVLHEALHSHYTQKSLSLSLG |
| 401 | MAB49 with constant domain PE and YTE mutations | EVQLVQSGAEVKKPGASVKVSCKVSGDTLTELSMHWVRQA PGKGLEWMGTFDPEEGETIYAQKFQGRVTMTEDTSTDTAY MELSYLRSEDTAVYYCVTEGLAGIPFDSWGQGTLVTVSS ASTKGPSVFPLAPCSRSTSESTAALGCLVKDYFPEPVTVSWN SGALTSGVHTFPAVLQSSGLYSLSSVVTVPSSSLGTKTYTCN VDHKPSNTKVDKRVESKYGPPCPPCPAPEFEGGPSVFLFPPK PKDTLYITREPEVTCVVVDVSQEDPEVQFNWYVDGVEVHN AKTKPREEQFNSTYRVVSVLTVLHQDWLNGKEYKCKVSNK GLPSSIEKTISKAKGQPREPQVYTLPPSQEEMTKNQVSLTCLV KGFYPSDIAVEWESNGQPENNYKTTPPVLDSDGSFFLYSRLT VDKSRWQEGNVFSCSVMHEALHNHYTQKSLSLSLG |
| 402 | MAB50 with constant domain PE and LS mutations | EVQLVQSGAEVKKPGASVKVSCKVSGDTLTELSMHWVRQA PGKGLEWMGTFDPEEGETIYAQKFQGRVTMTEDTSTDTAY MELSYLRSEDTAVYYCVTEGLAGIPFDSWGQGTLVTVSS ASTKGPSVFPLAPCSRSTSESTAALGCLVKDYFPEPVTVSWN SGALTSGVHTFPAVLQSSGLYSLSSVVTVPSSSLGTKTYTCN VDHKPSNTKVDKRVESKYGPPCPPCPAPEFEGGPSVFLFPPK PKDTLMISRTPEVTCVVVDVSQEDPEVQFNWYVDGVEVHN AKTKPREEQFNSTYRVVSVLTVLHQDWLNGKEYKCKVSNK GLPSSIEKTISKAKGQPREPQVYTLPPSQEEMTKNQVSLTCLV KGFYPSDIAVEWESNGQPENNYKTTPPVLDSDGSFFLYSRLT VDKSRWQEGNVFSCSVLHEALHSHYTQKSLSLSLG |
| 403 | MAB50 with constant domain PE and YTE mutations | EVQLVQSGAEVKKPGASVKVSCKVSGDTLTELSMHWVRQA PGKGLEWMGTFDPEEGETIYAQKFQGRVTMTEDTSTDTAY MELSYLRSEDTAVYYCVTEGLAGIPFDSWGQGTLVTVSS ASTKGPSVFPLAPCSRSTSESTAALGCLVKDYFPEPVTVSWN SGALTSGVHTFPAVLQSSGLYSLSSVVTVPSSSLGTKTYTCN VDHKPSNTKVDKRVESKYGPPCPPCPAPEFEGGPSVFLFPPK PKDTLYITREPEVTCVVVDVSQEDPEVQFNWYVDGVEVHN AKTKPREEQFNSTYRVVSVLTVLHQDWLNGKEYKCKVSNK GLPSSIEKTISKAKGQPREPQVYTLPPSQEEMTKNQVSLTCLV KGFYPSDIAVEWESNGQPENNYKTTPPVLDSDGSFFLYSRLT VDKSRWQEGNVFSCSVMHEALHNHYTQKSLSLSLG |
| 404 | MAB51 with constant domain PE and LS mutations | QVQLVESGGGVVRPGGSLRLSCAASGFTFDDYGMSWVRQA PGKGLEWVSGINWEGGSTGYADSVKGRFTISRDNAKNSLYL QMNSLRAEDTALYYCARDEQLGGTTYYYYMDVWGKGTT VTVSSASTKGPSVFPLAPCSRSTSESTAALGCLVKDYFPEPVT VSWNSGALTSGVHTFPAVLQSSGLYSLSSVVTVPSSSLGTKT |

TABLE 7-continued

| SEQ ID NO: | AB ID NO. | Heavy Chain Sequence |
|---|---|---|
| | | YTCNVDHKPSNTKVDKRVESKYGPPCPPCPAPEFEGGPSVFL<br>FPPKPKDTLMISRTPEVTCVVVDVSQEDPEVQFNWYVDGVE<br>VHNAKTKPREEQFNSTYRVVSVLTVLHQDWLNGKEYKCKV<br>SNKGLPSSIEKTISKAKGQPREPQVYTLPPSQEEMTKNQVSLT<br>CLVKGFYPSDIAVEWESNGQPENNYKTTPPVLDSDGSFFLYS<br>RLTVDKSRWQEGNVFSCSVLHEALHSHYTQKSLSLSLG |
| 405 | MAB51 with constant domain PE and YTE mutations | QVQLVESGGGVVRPGGSLRLSCAASGFTFDDYGMSWVRQA<br>PGKGLEWVSGINWEGGSTGYADSVKGRFTISRDNAKNSLYL<br>QMNSLRAEDTALYYCARDEQLGGTTYYYYYMDVWGKGTT<br>VTVSSASTKGPSVFPLAPCSRSTSESTAALGCLVKDYFPEPVT<br>VSWNSGALTSGVHTFPAVLQSSGLYSLSSVVTVPSSSLGTKT<br>YTCNVDHKPSNTKVDKRVESKYGPPCPPCPAPEFEGGPSVFL<br>FPPKPKDTLYITREPEVTCVVVDVSQEDPEVQFNWYVDGVE<br>VHNAKTKPREEQFNSTYRVVSVLTVLHQDWLNGKEYKCKV<br>SNKGLPSSIEKTISKAKGQPREPQVYTLPPSQEEMTKNQVSLT<br>CLVKGFYPSDIAVEWESNGQPENNYKTTPPVLDSDGSFFLYS<br>RLTVDKSRWQEGNVFSCSVMHEALHNHYTQKSLSLSLG |
| 406 | MAB52 with constant domain PE and LS mutations | QVQLVESGGGVVRPGGSLRLSCAASGFTFDDYGMSWVRQA<br>PGKGLEWVSGINWEGGSTGYADSVKGRFTISRDNAKNSLYL<br>QMNSLRAEDTALYYCARDEQLGGKYYYYYMDVWGKGT<br>TVTVSSASTKGPSVFPLAPCSRSTSESTAALGCLVKDYFPEPV<br>TVSWNSGALTSGVHTFPAVLQSSGLYSLSSVVTVPSSSLGTK<br>TYTCNVDHKPSNTKVDKRVESKYGPPCPPCPAPEFEGGPSVF<br>LFPPKPKDTLMISRTPEVTCVVVDVSQEDPEVQFNWYVDGV<br>EVHNAKTKPREEQFNSTYRVVSVLTVLHQDWLNGKEYKCK<br>VSNKGLPSSIEKTISKAKGQPREPQVYTLPPSQEEMTKNQVS<br>LTCLVKGFYPSDIAVEWESNGQPENNYKTTPPVLDSDGSFFL<br>YSRLTVDKSRWQEGNVFSCSVLHEALHSHYTQKSLSLSLG |
| 407 | MAB52 with constant domain PE and YTE mutations | QVQLVESGGGVVRPGGSLRLSCAASGFTFDDYGMSWVRQA<br>PGKGLEWVSGINWEGGSTGYADSVKGRFTISRDNAKNSLYL<br>QMNSLRAEDTALYYCARDEQLGGKYYYYYMDVWGKGT<br>TVTVSSASTKGPSVFPLAPCSRSTSESTAALGCLVKDYFPEPV<br>TVSWNSGALTSGVHTFPAVLQSSGLYSLSSVVTVPSSSLGTK<br>TYTCNVDHKPSNTKVDKRVESKYGPPCPPCPAPEFEGGPSVF<br>LFPPKPKDTLYITREPEVTCVVVDVSQEDPEVQFNWYVDGV<br>EVHNAKTKPREEQFNSTYRVVSVLTVLHQDWLNGKEYKCK<br>VSNKGLPSSIEKTISKAKGQPREPQVYTLPPSQEEMTKNQVS<br>LTCLVKGFYPSDIAVEWESNGQPENNYKTTPPVLDSDGSFFL<br>YSRLTVDKSRWQEGNVFSCSVMHEALHNHYTQKSLSLSLG |
| 408 | MAB53 with constant domain PE and LS mutations | QVQLVESGGGVVRPGGSLRLSCAASGFTFDDYGMSWVRQA<br>PGKGLEWVSGINWEGGSTGYADSVKGRFTISRDNAKNSLYL<br>QMNSLRAEDTALYYCARDEQLGGQTYYYYYMDVWGKGT<br>TVTVSSASTKGPSVFPLAPCSRSTSESTAALGCLVKDYFPEPV<br>TVSWNSGALTSGVHTFPAVLQSSGLYSLSSVVTVPSSSLGTK<br>TYTCNVDHKPSNTKVDKRVESKYGPPCPPCPAPEFEGGPSVF<br>LFPPKPKDTLMISRTPEVTCVVVDVSQEDPEVQFNWYVDGV<br>EVHNAKTKPREEQFNSTYRVVSVLTVLHQDWLNGKEYKCK<br>VSNKGLPSSIEKTISKAKGQPREPQVYTLPPSQEEMTKNQVS<br>LTCLVKGFYPSDIAVEWESNGQPENNYKTTPPVLDSDGSFFL<br>YSRLTVDKSRWQEGNVFSCSVLHEALHSHYTQKSLSLSLG |
| 409 | MAB53 with constant domain PE and YTE mutations | QVQLVESGGGVVRPGGSLRLSCAASGFTFDDYGMSWVRQA<br>PGKGLEWVSGINWEGGSTGYADSVKGRFTISRDNAKNSLYL<br>QMNSLRAEDTALYYCARDEQLGGQTYYYYYMDVWGKGT<br>TVTVSSASTKGPSVFPLAPCSRSTSESTAALGCLVKDYFPEPV<br>TVSWNSGALTSGVHTFPAVLQSSGLYSLSSVVTVPSSSLGTK<br>TYTCNVDHKPSNTKVDKRVESKYGPPCPPCPAPEFEGGPSVF<br>LFPPKPKDTLYITREPEVTCVVVDVSQEDPEVQFNWYVDGV<br>EVHNAKTKPREEQFNSTYRVVSVLTVLHQDWLNGKEYKCK<br>VSNKGLPSSIEKTISKAKGQPREPQVYTLPPSQEEMTKNQVS<br>LTCLVKGFYPSDIAVEWESNGQPENNYKTTPPVLDSDGSFFL<br>YSRLTVDKSRWQEGNVFSCSVMHEALHNHYTQKSLSLSLG |
| 410 | MAB54 with constant domain PE and LS mutations | QVQLVESGGGVVRPGGSLRLSCAASGFTFDDYGMSWVRQA<br>PGKGLEWVSGINWEGGSTGYADSVKGRFTISRDNAKNSLYL<br>QMNSLRAEDTALYYCARDEQLGGTTYYYYYMDVWGKGTT<br>VTVSSASTKGPSVFPLAPCSRSTSESTAALGCLVKDYFPEPVT<br>VSWNSGALTSGVHTFPAVLQSSGLYSLSSVVTVPSSSLGTKT<br>YTCNVDHKPSNTKVDKRVESKYGPPCPPCPAPEFEGGPSVFL<br>FPPKPKDTLMISRTPEVTCVVVDVSQEDPEVQFNWYVDGVE<br>VHNAKTKPREEQFNSTYRVVSVLTVLHQDWLNGKEYKCKV<br>SNKGLPSSIEKTISKAKGQPREPQVYTLPPSQEEMTKNQVSLT<br>CLVKGFYPSDIAVEWESNGQPENNYKTTPPVLDSDGSFFLYS<br>RLTVDKSRWQEGNVFSCSVLHEALHSHYTQKSLSLSLG |

TABLE 7-continued

| SEQ ID NO: | AB ID NO. | Heavy Chain Sequence |
|---|---|---|
| 411 | MAB54 with constant domain PE and YTE mutations | QVQLVESGGGVVRPGGSLRLSCAASGFTFDDYGMSWVRQA PGKGLEWVSGINWEGGSTGYADSVKGRFTISRDNAKNSLYL QMNSLRAEDTALYYCARDEQLGGTTYYYYYMDVWGKGTT VTVSSASTKGPSVFPLAPCSRSTSESTAALGCLVKDYFPEPVT VSWNSGALTSGVHTFPAVLQSSGLYSLSSVVTVPSSSLGTKT YTCNVDHKPSNTKVDKRVESKYGPPCPPCPAPEFEGGPSVFL FPPKPKDTLYITREPEVTCVVVDVSQEDPEVQFNWYVDGVE VHNAKTKPREEQFNSTYRVVSVLTVLHQDWLNGKEYKCKV SNKGLPSSIEKTISKAKGQPREPQVYTLPPSQEEMTKNQVSLT CLVKGFYPSDIAVEWESNGQPENNYKTTPPVLDSDGSFFLYS RLTVDKSRWQEGNVFSCSVMHEALHNHYTQKSLSLSLG |
| 412 | MAB55 with constant domain PE and LS mutations | QVQLVESGGGVVRPGGSLRLSCAASGFTFDDYGMSWVRQA PGKGLEWVSGINWEGGSTGYADSVKGRFTISRDNAKNSLYL QMNSLRAEDTALYYCARDEQLGGIKYYYYYMDVWGKGTT VTVSSASTKGPSVFPLAPCSRSTSESTAALGCLVKDYFPEPVT VSWNSGALTSGVHTFPAVLQSSGLYSLSSVVTVPSSSLGTKT YTCNVDHKPSNTKVDKRVESKYGPPCPPCPAPEFEGGPSVFL FPPKPKDTLMISRTPEVTCVVVDVSQEDPEVQFNWYVDGVE VHNAKTKPREEQFNSTYRVVSVLTVLHQDWLNGKEYKCKV SNKGLPSSIEKTISKAKGQPREPQVYTLPPSQEEMTKNQVSLT CLVKGFYPSDIAVEWESNGQPENNYKTTPPVLDSDGSFFLYS RLTVDKSRWQEGNVFSCSVLHEALHSHYTQKSLSLSLG |
| 413 | MAB55 with constant domain PE and YTE mutations | QVQLVESGGGVVRPGGSLRLSCAASGFTFDDYGMSWVRQA PGKGLEWVSGINWEGGSTGYADSVKGRFTISRDNAKNSLYL QMNSLRAEDTALYYCARDEQLGGIKYYYYYMDVWGKGTT VTVSSASTKGPSVFPLAPCSRSTSESTAALGCLVKDYFPEPVT VSWNSGALTSGVHTFPAVLQSSGLYSLSSVVTVPSSSLGTKT YTCNVDHKPSNTKVDKRVESKYGPPCPPCPAPEFEGGPSVFL FPPKPKDTLYITREPEVTCVVVDVSQEDPEVQFNWYVDGVE VHNAKTKPREEQFNSTYRVVSVLTVLHQDWLNGKEYKCKV SNKGLPSSIEKTISKAKGQPREPQVYTLPPSQEEMTKNQVSLT CLVKGFYPSDIAVEWESNGQPENNYKTTPPVLDSDGSFFLYS RLTVDKSRWQEGNVFSCSVMHEALHNHYTQKSLSLSLG |
| 414 | MAB56 with constant domain PE and LS mutations | QVQLVESGGGVVRPGGSLRLSCAASGFTFDDYGMSWVRQA PGKGLEWVSGINWEGGSTGYADSVKGRFSISRDNAKNSLYL QMNSLRAEDTALYYCARDEQLGGLKYYYYYMDVWGKGTT TVTVSSASTKGPSVFPLAPCSRSTSESTAALGCLVKDYFPEPV TVSWNSGALTSGVHTFPAVLQSSGLYSLSSVVTVPSSSLGTK TYTCNVDHKPSNTKVDKRVESKYGPPCPPCPAPEFEGGPSVF LFPPKPKDTLMISRTPEVTCVVVDVSQEDPEVQFNWYVDGV EVHNAKTKPREEQFNSTYRVVSVLTVLHQDWLNGKEYKCK VSNKGLPSSIEKTISKAKGQPREPQVYTLPPSQEEMTKNQVS LTCLVKGFYPSDIAVEWESNGQPENNYKTTPPVLDSDGSFFL YSRLTVDKSRWQEGNVFSCSVLHEALHSHYTQKSLSLSLG |
| 415 | MAB56 with constant domain PE and YTE mutations | QVQLVESGGGVVRPGGSLRLSCAASGFTFDDYGMSWVRQA PGKGLEWVSGINWEGGSTGYADSVKGRFSISRDNAKNSLYL QMNSLRAEDTALYYCARDEQLGGLKYYYYYMDVWGKGT TVTVSSASTKGPSVFPLAPCSRSTSESTAALGCLVKDYFPEPV TVSWNSGALTSGVHTFPAVLQSSGLYSLSSVVTVPSSSLGTK TYTCNVDHKPSNTKVDKRVESKYGPPCPPCPAPEFEGGPSVF LFPPKPKDTLYITREPEVTCVVVDVSQEDPEVQFNWYVDGV EVHNAKTKPREEQFNSTYRVVSVLTVLHQDWLNGKEYKCK VSNKGLPSSIEKTISKAKGQPREPQVYTLPPSQEEMTKNQVS LTCLVKGFYPSDIAVEWESNGQPENNYKTTPPVLDSDGSFFL YSRLTVDKSRWQEGNVFSCSVMHEALHNHYTQKSLSLSLG |
| 416 | MAB57 with constant domain PE and LS mutations | QVQLVESGGGVVRPGGSLRLSCAASGFTFDDYGMSWVRQA PGKGLEWVSGINWEGGSTGYADSVKGRFTISRDNAKNSLYL QMNSLRAEDTALYYCARDEQLGGVYYYYYMDVWGKGT TVTVSSASTKGPSVFPLAPCSRSTSESTAALGCLVKDYFPEPV TVSWNSGALTSGVHTFPAVLQSSGLYSLSSVVTVPSSSLGTK TYTCNVDHKPSNTKVDKRVESKYGPPCPPCPAPEFEGGPSVF LFPPKPKDTLMISRTPEVTCVVVDVSQEDPEVQFNWYVDGV EVHNAKTKPREEQFNSTYRVVSVLTVLHQDWLNGKEYKCK VSNKGLPSSIEKTISKAKGQPREPQVYTLPPSQEEMTKNQVS LTCLVKGFYPSDIAVEWESNGQPENNYKTTPPVLDSDGSFFL YSRLTVDKSRWQEGNVFSCSVLHEALHSHYTQKSLSLSLG |
| 417 | MAB57 with constant domain PE and YTE mutations | QVQLVESGGGVVRPGGSLRLSCAASGFTFDDYGMSWVRQA PGKGLEWVSGINWEGGSTGYADSVKGRFTISRDNAKNSLYL QMNSLRAEDTALYYCARDEQLGGVYYYYYMDVWGKGT TVTVSSASTKGPSVFPLAPCSRSTSESTAALGCLVKDYFPEPV TVSWNSGALTSGVHTFPAVLQSSGLYSLSSVVTVPSSSLGTK |

TABLE 7-continued

| SEQ ID NO: | AB ID NO. | Heavy Chain Sequence |
|---|---|---|
| | | TYTCNVDHKPSNTKVDKRVESKYGPPCPPCPAPEFEGGPSVF
LFPPKPKDTLYITREPEVTCVVVDVSQEDPEVQFNWYVDGV
EVHNAKTKPREEQFNSTYRVVSVLTVLHQDWLNGKEYKCK
VSNKGLPSSIEKTISKAKGQPREPQVYTLPPSQEEMTKNQVS
LTCLVKGFYPSDIAVEWESNGQPENNYKTTPPVLDSDGSFFL
YSRLTVDKSRWQEGNVFSCSVMHEALHNHYTQKSLSLSLG |
| 418 | MAB58 with constant domain PE and LS mutations | QVQLVESGGGVVRPGGSLRLSCAASGFTFDDYGMSWVRQA
PGKGLEWVSGINWEGGSTGYADSVKGRFSISRDNAKNSLYL
QMNSLRAEDTALYYCARDEQLGGLKYYYYYMDVWGKGT
TVTVSSASTKGPSVFPLAPCSRSTSESTAALGCLVKDYFPEPV
TVSWNSGALTSGVHTFPAVLQSSGLYSLSSVVTVPSSSLGTK
TYTCNVDHKPSNTKVDKRVESKYGPPCPPCPAPEFEGGPSVF
LFPPKPKDTLMISRTPEVTCVVVDVSQEDPEVQFNWYVDGV
EVHNAKTKPREEQFNSTYRVVSVLTVLHQDWLNGKEYKCK
VSNKGLPSSIEKTISKAKGQPREPQVYTLPPSQEEMTKNQVS
LTCLVKGFYPSDIAVEWESNGQPENNYKTTPPVLDSDGSFFL
YSRLTVDKSRWQEGNVFSCSVLHEALHSHYTQKSLSLSLG |
| 419 | MAB58 with constant domain PE and YTE mutations | QVQLVESGGGVVRPGGSLRLSCAASGFTFDDYGMSWVRQA
PGKGLEWVSGINWEGGSTGYADSVKGRFSISRDNAKNSLYL
QMNSLRAEDTALYYCARDEQLGGLKYYYYYMDVWGKGT
TVTVSSASTKGPSVFPLAPCSRSTSESTAALGCLVKDYFPEPV
TVSWNSGALTSGVHTFPAVLQSSGLYSLSSVVTVPSSSLGTK
TYTCNVDHKPSNTKVDKRVESKYGPPCPPCPAPEFEGGPSVF
LFPPKPKDTLYITREPEVTCVVVDVSQEDPEVQFNWYVDGV
EVHNAKTKPREEQFNSTYRVVSVLTVLHQDWLNGKEYKCK
VSNKGLPSSIEKTISKAKGQPREPQVYTLPPSQEEMTKNQVS
LTCLVKGFYPSDIAVEWESNGQPENNYKTTPPVLDSDGSFFL
YSRLTVDKSRWQEGNVFSCSVMHEALHNHYTQKSLSLSLG |
| 420 | MAB59 with constant domain PE and LS mutations | QVQLVESGGGVVRPGGSLRLSCAASGFTFDDYGMSWVRQA
PGKGLEWVSGINWEGGSTGYADSVKGRFTISRDNAKNSLYL
QMNSLRAEDTALYYCARDEQLGGNHYYYYYMDAWGKGT
TVTVSSASTKGPSVFPLAPCSRSTSESTAALGCLVKDYFPEPV
TVSWNSGALTSGVHTFPAVLQSSGLYSLSSVVTVPSSSLGTK
TYTCNVDHKPSNTKVDKRVESKYGPPCPPCPAPEFEGGPSVF
LFPPKPKDTLMISRTPEVTCVVVDVSQEDPEVQFNWYVDGV
EVHNAKTKPREEQFNSTYRVVSVLTVLHQDWLNGKEYKCK
VSNKGLPSSIEKTISKAKGQPREPQVYTLPPSQEEMTKNQVS
LTCLVKGFYPSDIAVEWESNGQPENNYKTTPPVLDSDGSFFL
YSRLTVDKSRWQEGNVFSCSVLHEALHSHYTQKSLSLSLG |
| 421 | MAB59 with constant domain PE and YTE mutations | QVQLVESGGGVVRPGGSLRLSCAASGFTFDDYGMSWVRQA
PGKGLEWVSGINWEGGSTGYADSVKGRFTISRDNAKNSLYL
QMNSLRAEDTALYYCARDEQLGGNHYYYYYMDAWGKGT
TVTVSSASTKGPSVFPLAPCSRSTSESTAALGCLVKDYFPEPV
TVSWNSGALTSGVHTFPAVLQSSGLYSLSSVVTVPSSSLGTK
TYTCNVDHKPSNTKVDKRVESKYGPPCPPCPAPEFEGGPSVF
LFPPKPKDTLYITREPEVTCVVVDVSQEDPEVQFNWYVDGV
EVHNAKTKPREEQFNSTYRVVSVLTVLHQDWLNGKEYKCK
VSNKGLPSSIEKTISKAKGQPREPQVYTLPPSQEEMTKNQVS
LTCLVKGFYPSDIAVEWESNGQPENNYKTTPPVLDSDGSFFL
YSRLTVDKSRWQEGNVFSCSVMHEALHNHYTQKSLSLSLG |
| 422 | MAB60 with constant domain PE and LS mutations | QVQLVESGGGVVRPGGSLRLSCAASGFTFDDYGMSWVRQA
PGKGLEWVSGINWEGGSTGYADSVKGRFTISRDNAKNSLYL
QMNSLRAEDTALYYCARDEQLGGRHYYYYYMDVWGKGT
TVTVSSASTKGPSVFPLAPCSRSTSESTAALGCLVKDYFPEPV
TVSWNSGALTSGVHTFPAVLQSSGLYSLSSVVTVPSSSLGTK
TYTCNVDHKPSNTKVDKRVESKYGPPCPPCPAPEFEGGPSVF
LFPPKPKDTLMISRTPEVTCVVVDVSQEDPEVQFNWYVDGV
EVHNAKTKPREEQFNSTYRVVSVLTVLHQDWLNGKEYKCK
VSNKGLPSSIEKTISKAKGQPREPQVYTLPPSQEEMTKNQVS
LTCLVKGFYPSDIAVEWESNGQPENNYKTTPPVLDSDGSFFL
YSRLTVDKSRWQEGNVFSCSVLHEALHSHYTQKSLSLSLG |
| 423 | MAB60 with constant domain PE and YTE mutations | QVQLVESGGGVVRPGGSLRLSCAASGFTFDDYGMSWVRQA
PGKGLEWVSGINWEGGSTGYADSVKGRFTISRDNAKNSLYL
QMNSLRAEDTALYYCARDEQLGGRHYYYYYMDVWGKGT
TVTVSSASTKGPSVFPLAPCSRSTSESTAALGCLVKDYFPEPV
TVSWNSGALTSGVHTFPAVLQSSGLYSLSSVVTVPSSSLGTK
TYTCNVDHKPSNTKVDKRVESKYGPPCPPCPAPEFEGGPSVF |

TABLE 7-continued

| SEQ ID NO: AB ID NO. | Heavy Chain Sequence |
|---|---|
| | LFPPKPKDTLYITREPEVTCVVVDVSQEDPEVQFNWYVDGV EVHNAKTKPREEQFNSTYRVVSVLTVLHQDWLNGKEYKCK VSNKGLPSSIEKTISKAKGQPREPQVYTLPPSQEEMTKNQVS LTCLVKGFYPSDIAVEWESNGQPENNYKTTPPVLDSDGSFFL YSRLTVDKSRWQEGNVFSCSVMHEALHNHYTQKSLSLSLG |

In some embodiments, the antibody comprises a light chain as set forth below, which includes the variable region and a constant domain, such as the human kappa constant domain:

TABLE 8

| SEQ ID NO: AB ID NO. | Light Chain Sequence |
|---|---|
| 228 MAB1/MAB31 plus kappa constant domain | DIQMTQSPSSLSASVGDRVTITCQASQDISNYLNWYQQKPG KAPKLLIYDASNLETGVPSRFSGSGSGTDFTFTISSLQPEDIAT YYCEQYEDYPLTFGGGTKVEIKRTVAAPSVFIFPPSDEQLKS GTASVVCLLNNFYPREAKVQWKVDNALQSGNSQESVTEQD SKDSTYSLSSTLTLSKADYEKHKVYACEVTHQGLSSPVTKSF NRGEC |
| 229 MAB2/MAB32 plus kappa constant domain | DIQMTQSPSSLSASVGDRVTITCQASQDISNYLNWYQQKPG KAPKLLIYDASNLETGVPSRFSGSGSGTDFTFTISSLQPEDIAT YYCKQYEDYPLTFGGGTKVEIKRTVAAPSVFIFPPSDEQLKS GTASVVCLLNNFYPREAKVQWKVDNALQSGNSQESVTEQD SKDSTYSLSSTLTLSKADYEKHKVYACEVTHQGLSSPVTKSF NRGEC |
| 230 MAB3/MAB33 plus kappa constant domain | DIQMTQSPSSLSASVGDRVTITCQASQDISNYLNWYQQKPG KAPKLLIYDASNLETGVPSRFSGSGSGTDFTFTISSLQPEDIAT YYCKQYEDYPLTFGGGTKVEIKRTVAAPSVFIFPPSDEQLKS GTASVVCLLNNFYPREAKVQWKVDNALQSGNSQESVTEQD SKDSTYSLSSTLTLSKADYEKHKVYACEVTHQGLSSPVTKSF NRGEC |
| 231 MAB4/MAB34 plus kappa constant domain | DIQMTQSPSSLSASVGDRVTITCQASQDISNYLNWYQQKPG KAPKLLIYDASNLETGVPSRFSGSGSGTDFTFTISSLQPEDIAT YYCHQYEDYPLTFGGGTKVEIKRTVAAPSVFIFPPSDEQLKS GTASVVCLLNNFYPREAKVQWKVDNALQSGNSQESVTEQD SKDSTYSLSSTLTLSKADYEKHKVYACEVTHQGLSSPVTKSF NRGEC |
| 232 MAB5/MAB35 plus kappa constant domain | DIQMTQSPSSLSASVGDRVTITCQASQDISNYLNWYQQKPG KAPKLLIYDASNLETGVPSRFSGSGSGTDFTFTISSLQPEDIAT YYCHQYEDYPLTFGGGTKVEIKRTVAAPSVFIFPPSDEQLKS GTASVVCLLNNFYPREAKVQWKVDNALQSGNSQESVTEQD SKDSTYSLSSTLTLSKADYEKHKVYACEVTHQGLSSPVTKSF NRGEC |
| 233 MAB6//MAB36 plus kappa constant domain | DIQMTQSPSSLSASVGDRVTITCQASQDISNYLNWYQQKPG KAPKLLIYDASNLETGVPSRFSGSGSGTDFTFTISSLQPEDIAT YYCHQYEDYPLTFGGGTKVEIKRTVAAPSVFIFPPSDEQLKS GTASVVCLLNNFYPREAKVQWKVDNALQSGNSQESVTEQD SKDSTYSLSSTLTLSKADYEKHKVYACEVTHQGLSSPVTKSF NRGEC |
| 234 MAB7//MAB37 plus kappa constant domain | DIQMTQSPSSLSASVGDRVTITCQASQDISNYLNWYQQKPG KAPKLLIYDASNLETGVPSRFSGSGSGTDFTFTISSLQPEDIAT YYCQQYEDYPLVFGGGTKVEIKRTVAAPSVFIFPPSDEQLKS GTASVVCLLNNFYPREAKVQWKVDNALQSGNSQESVTEQD SKDSTYSLSSTLTLSKADYEKHKVYACEVTHQGLSSPVTKSF NRGEC |
| 235 MAB8//MAB38 plus kappa constant domain | DIQMTQSPSSLSASVGDRVTITCQASQDISNYLNWYQQKPG KAPKLLIYDASNLETGVPSRFSGSGSGTDFTFTISSLQPEDIAT YYCQQHEDYPLTFGGGTKVEIKRTVAAPSVFIFPPSDEQLKS GTASVVCLLNNFYPREAKVQWKVDNALQSGNSQESVTEQD SKDSTYSLSSTLTLSKADYEKHKVYACEVTHQGLSSPVTKSF NRGEC |

TABLE 8-continued

| SEQ ID NO: | AB ID NO. | Light Chain Sequence |
|---|---|---|
| 236 | MAB9/MAB39 plus kappa constant domain | DIQMTQSPSSLSASVGDRVTITCQASQDISNYLNWYQQKPG KAPKLLIYDASNLETGVPSRFSGSGSGTDFTFTISSLQPEDIAT YYCQHYEDYPLTFGGGTKVEIKRTVAAPSVFIFPPSDEQLKS GTASVVCLLNNFYPREAKVQWKVDNALQSGNSQESVTEQD SKDSTYSLSSTLTLSKADYEKHKVYACEVTHQGLSSPVTKSF NRGEC |
| 237 | MAB10/MAB40 plus kappa constant domain | DIQMTQSPSSLSASVGDRVTITCQASQDISNYLNWYQQKPG KAPKLLIYDASNLETGVPSRFSGSGSGTDFTFTISSLQPEDIAT YYCQQYEDLIPTFGGGTKVEIKRTVAAPSVFIFPPSDEQLKSG TASVVCLLNNFYPREAKVQWKVDNALQSGNSQESVTEQDS KDSTYSLSSTLTLSKADYEKHKVYACEVTHQGLSSPVTKSF NRGEC |
| 238 | MAB11//MAB41 plus kappa constant domain | DIQMTQSPSTLSASVGDRVTITCRASQSISSWLAWYQQKPGK APKLLIYKASSLESGVPSRFSGSGSGTEFTLTISSLQPDDFATY YCQSYNSYVWTFGQGTKVEIKRTVAAPSVFIFPPSDEQLKSG TASVVCLLNNFYPREAKVQWKVDNALQSGNSQESVTEQDS KDSTYSLSSTLTLSKADYEKHKVYACEVTHQGLSSPVTKSF NRGEC |
| 239 | MAB12/MAB42 plus kappa constant domain | DIQMTQSPSTLSASVGDRVTITCRASQSISSWLAWYQQKPGK APKLLIYKASSLESGVPSRFSGSGSGTEFTLTISSLQPDDFATY YCQQVNSYDWTFGQGTKVEIKRTVAAPSVFIFPPSDEQLKSG TASVVCLLNNFYPREAKVQWKVDNALQSGNSQESVTEQDS KDSTYSLSSTLTLSKADYEKHKVYACEVTHQGLSSPVTKSF NRGEC |
| 240 | MAB13//MAB43 plus kappa constant domain | DIQMTQSPSTLSASVGDRVTITCRASQSISSWLAWYQQKPGK APKLLIYKASSLESGVPSRFSGSGSGTEFTLTISSLQPDDFATY YCQQVNSYDWTFGQGTKVEIKRTVAAPSVFIFPPSDEQLKSG TASVVCLLNNFYPREAKVQWKVDNALQSGNSQESVTEQDS KDSTYSLSSTLTLSKADYEKHKVYACEVTHQGLSSPVTKSF NRGEC |
| 241 | MAB14/MAB44 plus kappa constant domain | DIQMTQSPSTLSASVGDRVTITCRASQSISSWLAWYQQKPGK APKLLIYKASSLESGVPSRFSGSGSGTEFTLTISSLQPDDFATY YCQQYSSYAWTFGQGTKVEIKRTVAAPSVFIFPPSDEQLKSG TASVVCLLNNFYPREAKVQWKVDNALQSGNSQESVTEQDS KDSTYSLSSTLTLSKADYEKHKVYACEVTHQGLSSPVTKSF NRGEC |
| 242 | MAB15/MAB45 plus kappa constant domain | DIQMTQSPSTLSASVGDRVTITCRASQSISSWLAWYQQKPGK APKLLIYKASSLESGVPSRFSGSGSGTEFTLTISSLQPDDFATY YCQQARSYSWTFGQGTKVEIKRTVAAPSVFIFPPSDEQLKSG TASVVCLLNNFYPREAKVQWKVDNALQSGNSQESVTEQDS KDSTYSLSSTLTLSKADYEKHKVYACEVTHQGLSSPVTKSF NRGEC |
| 243 | MAB16/MAB46 plus kappa constant domain | DIQMTQSPSTLSASVGDRVTITCRASQSISSWLAWYQQKPGK APKLLIYKASSLESGVPSRFSGSGSGTEFTLTISSLQPDDFATY YCQQHNSYRWTFGQGTKVEIKRTVAAPSVFIFPPSDEQLKSG TASVVCLLNNFYPREAKVQWKVDNALQSGNSQESVTEQDS KDSTYSLSSTLTLSKADYEKHKVYACEVTHQGLSSPVTKSF NRGEC |
| 244 | MAB17/MAB47 plus kappa constant domain | DIQMTQSPSTLSASVGDRVTITCRASQSISSWLAWYQQKPGK APKLLIYKASSLESGVPSRFSGSGSGTEFTLTISSLQPDDFATY YCVQYPSYSWTFGQGTKVEIKRTVAAPSVFIFPPSDEQLKSG TASVVCLLNNFYPREAKVQWKVDNALQSGNSQESVTEQDS KDSTYSLSSTLTLSKADYEKHKVYACEVTHQGLSSPVTKSF NRGEC |
| 245 | MAB18/MAB48 plus kappa constant domain | DIQMTQSPSTLSASVGDRVTITCRASQSISSWLAWYQQKPGK APKLLIYKASSLESGVPSRFSGSGSGTEFTLTISSLQPDDFATY YCQQYNSYKLTFGQGTKVEIKRTVAAPSVFIFPPSDEQLKSG TASVVCLLNNFYPREAKVQWKVDNALQSGNSQESVTEQDS KDSTYSLSSTLTLSKADYEKHKVYACEVTHQGLSSPVTKSF NRGEC |

TABLE 8-continued

| SEQ ID NO: | AB ID NO. | Light Chain Sequence |
|---|---|---|
| 246 | MAB19//MAB49 plus kappa constant domain | DIQMTQSPSTLSASVGDRVTITCRASQSISSWLAWYQQKPGK APKLLIYKASSLESGVPSRFSGSGSGTEFTLTISSLQPDDFATY YCQQYNSPSWLFGQGTKVEIKRTVAAPSVFIFPPSDEQLKSG TASVVCLLNNFYPREAKVQWKVDNALQSGNSQESVTEQDS KDSTYSLSSTLTLSKADYEKHKVYACEVTHQGLSSPVTKSF NRGEC |
| 247 | MAB20/MAB50 plus kappa constant domain | DIQMTQSPSTLSASVGDRVTITCRASQSISSWLAWYQQKPGK APKLLIYKASSLESGVPSRFSGSGSGTEFTLTISSLQPDDFATY YCQQVNSLSWTFGQGTKVEIKRTVAAPSVFIFPPSDEQLKSG TASVVCLLNNFYPREAKVQWKVDNALQSGNSQESVTEQDS KDSTYSLSSTLTLSKADYEKHKVYACEVTHQGLSSPVTKSF NRGEC |
| 248 | MAB21/MAB51 plus kappa constant domain | DIQMTQSPSSLSASVGDRVTITCRASQGIRNDLGWYQQKPG KAPKRLIYTASNLQSGVPSRFSGSGSGTEFTLTISSLQPEDFAT YYCFQYNSYPLGFGGGTKVEIKRTVAAPSVFIFPPSDEQLKS GTASVVCLLNNFYPREAKVQWKVDNALQSGNSQESVTEQD SKDSTYSLSSTLTLSKADYEKHKVYACEVTHQGLSSPVTKSF NRGEC |
| 249 | MAB22/MAB52 plus kappa constant domain | DIQMTQSPSSLSASVGDRVTITCRASQGIRNDLGWYQQKPG KAPKRLIYTASNLQSGVPSRFSGSGSGTEFTLTISSLQPEDFAT YYCLQYRSHPLTFGGGTKVEIKRTVAAPSVFIFPPSDEQLKS GTASVVCLLNNFYPREAKVQWKVDNALQSGNSQESVTEQD SKDSTYSLSSTLTLSKADYEKHKVYACEVTHQGLSSPVTKSF NRGEC |
| 250 | MAB23/MAB53 plus kappa constant domain | DIQMTQSPSSLSASVGDRVTITCRASQGIRNDLGWYQQKPG KAPKRLIYTASNLQSGVPSRFSGSGSGTEFTLTISSLQPEDFAT YYCLQYNQVPLTFGGGTKVEIKRTVAAPSVFIFPPSDEQLKS GTASVVCLLNNFYPREAKVQWKVDNALQSGNSQESVTEQD SKDSTYSLSSTLTLSKADYEKHKVYACEVTHQGLSSPVTKSF NRGEC |
| 251 | MAB24/MAB54 plus kappa constant domain | DIQMTQSPSSLSASVGDRVTITCRASQGIRNDLGWYQQKPG KAPKRLIYTASNLQSGVPSRFSGSGSGTEFTLTISSLQPEDFAT YYCLQTNIYPLTFGGGTKVEIKRTVAAPSVFIFPPSDEQLKSG TASVVCLLNNFYPREAKVQWKVDNALQSGNSQESVTEQDS KDSTYSLSSTLTLSKADYEKHKVYACEVTHQGLSSPVTKSF NRGEC |
| 252 | MAB25/MAB55 plus kappa constant domain | DIQMTQSPSSLSASVGDRVTITCRASQGIRNDLGWYQQKPG KAPKRLIYTASNLQSGVPSRFSGSGSGTEFTLTISSLQPEDFAT YYCLQYKQYPLTFGGGTKVEIKRTVAAPSVFIFPPSDEQLKS GTASVVCLLNNFYPREAKVQWKVDNALQSGNSQESVTEQD SKDSTYSLSSTLTLSKADYEKHKVYACEVTHQGLSSPVTKSF NRGEC |
| 253 | MAB26/MAB56 plus kappa constant domain | DIQMTQSPSSLSASVGDRVTITCRASQGIRNDLGWYQQKPG KAPKRLIYTASNLQSGVPSRFSGSGSGTEFTLTISSLQPEDFAT YYCLQTNIYPLTFGGGTKVEIKRTVAAPSVFIFPPSDEQLKSG TASVVCLLNNFYPREAKVQWKVDNALQSGNSQESVTEQDS KDSTYSLSSTLTLSKADYEKHKVYACEVTHQGLSSPVTKSF NRGEC |
| 254 | MAB27/MAB57 plus kappa constant domain | DIQMTQSPSSLSASVGDRVTITCRASQGIRNDLGWYQQKPG KAPKRLIYTASNLQSGVPSRFSGSGSGTEFTLTISSLQPEDFAT YYCLQYNSYPLAFGGGTKVEIKRTVAAPSVFIFPPSDEQLKS GTASVVCLLNNFYPREAKVQWKVDNALQSGNSQESVTEQD SKDSTYSLSSTLTLSKADYEKHKVYACEVTHQGLSSPVTKSF NRGEC |
| 255 | MAB28/MAB58 plus kappa constant domain | DIQMTQSPSSLSASVGDRVTITCRASQGIRNDLGWYQQKPG KAPKRLIYTASNLQSGVPSRFSGSGSGTEFTLTISSLQPEDFAT YYCLQYHSYPLRFGGGTKVEIKRTVAAPSVFIFPPSDEQLKS GTASVVCLLNNFYPREAKVQWKVDNALQSGNSQESVTEQD SKDSTYSLSSTLTLSKADYEKHKVYACEVTHQGLSSPVTKSF NRGEC |
| 256 | MAB29/MAB59 plus kappa constant domain | DIQMTQSPSSLSASVGDRVTITCRASQGIRNDLGWYQQKPG KAPKRLIYTASNLQSGVPSRFSGSGSGTEFTLTISSLQPEDFAT YYCLQYASYPLKFGGGTKVEIKRTVAAPSVFIFPPSDEQLKS GTASVVCLLNNFYPREAKVQWKVDNALQSGNSQESVTEQD SKDSTYSLSSTLTLSKADYEKHKVYACEVTHQGLSSPVTKSF NRGEC |

TABLE 8-continued

| SEQ ID NO: | AB ID NO. | Light Chain Sequence |
|---|---|---|
| 257 | MAB30/MAB60 plus kappa constant domain | DIQMTQSPSSLSASVGDRVTITCRASQGIRNDLGWYQQKPG KAPKRLIYTASNLQSGVPSRFSGSGSGTEFTLTISSLQPEDFAT YYCLQYNAYPLIFGGGTKVEIKRTVAAPSVFIFPPSDEQLKSG TASVVCLLNNFYPREAKVQWKVDNALQSGNSQESVTEQDS KDSTYSLSSTLTLSKADYEKHKVYACEVTHQGLSSPVTKSF NRGEC |

In some embodiments, the antibody, or antigen binding fragment thereof, of any of the embodiments as provided for herein may comprise any constant domain known, such as but not limited to an IgG constant domain. In some embodiments, the constant domain is as provided for herein. In some non-limiting embodiments, the constant domain is selected from the group including, but not limited to, SEQ ID NO: 261, 262, 263, 264, 265, or a variant thereof as provided for herein. In some embodiments, the constant domain has at least 90, 91, 92, 93, 94, 95, 96, 97, 98, or 99% sequence identity to a sequence selected from the group including, but not limited to, SEQ ID NO: 261, 262, 263, 264, 265, or a variant thereof as provided for herein. In some embodiments, the constant domain has at least 90, 91, 92, 93, 94, 95, 96, 97, 98, or 99% sequence identity to a sequence selected from the group including, but not limited to, SEQ ID NO: 261, 262, 263, 264, 265, provided that the constant domain comprises the PE, YTE, and/or LS mutations as described herein.

In some embodiments, the antibody or antigen-binding fragment thereof, comprises a light chain that has at least 90, 91, 92, 93, 94, 95, 96, 97, 98, 99% sequence identity to SEQ ID NO: 228, and a heavy chain that has at least 90, 91, 92, 93, 94, 95, 96, 97, 98, or 99% sequence identity to SEQ ID NO: 168 or SEQ ID NO: 169 (HC of MAB1), wherein the antibody, or antigen binding fragment thereof, maintains the sequences of the heavy chain and light chain CDRs of MAB1. In some embodiments, the antibody or antigen-binding fragment thereof, comprises a light chain that has at least 90, 91, 92, 93, 94, 95, 96, 97, 98, or 99% sequence identity to SEQ ID NO: 228, and a heavy chain that has at least 90, 91, 92, 93, 94, 95, 96, 97, 98, or 99% sequence identity to SEQ ID NO: 168 or SEQ ID NO: 169, wherein the antibody, or antigen binding fragment thereof, maintains a HCDR1 sequence of SEQ ID NO: 61, SEQ ID NO: 124, or SEQ ID NO: 130, maintains a HCDR2 sequence of SEQ ID NO: 62, SEQ ID NO: 125, or SEQ ID NO: 131, maintains a HCDR3 sequence of SEQ ID NO: 63 or SEQ ID NO: 132, maintains a LCDR1 sequence of SEQ ID NO: 64, or SEQ ID NO: 133, maintains a LCDR2 sequence of SEQ ID NO: 65, or SEQ ID NO: 134, and maintains a LCDR3 sequence of SEQ ID NO: 66.

In some embodiments, the antibody or antigen-binding fragment thereof, comprises a light chain that has at least 90, 91, 92, 93, 94, 95, 96, 97, 98, or 99% sequence identity to SEQ ID NO: 229, and a heavy chain that has at least 90, 91, 92, 93, 94, 95, 96, 97, 98, or 99% sequence identity to SEQ ID NO: 170 or SEQ ID NO: 171 (HC of MAB2), wherein the antibody, or antigen binding fragment thereof, maintains the sequences of the heavy chain and light chain CDRs of MAB2. In some embodiments, the antibody or antigen-binding fragment thereof, comprises a light chain that has at least 90, 91, 92, 93, 94, 95, 96, 97, 98, or 99% sequence identity to SEQ ID NO: 229, and a heavy chain that has at least 90, 91, 92, 93, 94, 95, 96, 97, 98, or 99% sequence identity to SEQ ID NO: 170 or SEQ ID NO: 171, wherein the antibody, or antigen binding fragment thereof, maintains a HCDR1 sequence of SEQ ID NO: 61, SEQ ID NO: 124, or SEQ ID NO: 130, maintains a HCDR2 sequence of SEQ ID NO: 62, SEQ ID NO: 125, or SEQ ID NO: 131, maintains a HCDR3 sequence of SEQ ID NO: 67 or SEQ ID NO: 135, maintains a LCDR1 sequence of SEQ ID NO: 64, or SEQ ID NO: 133, maintains a LCDR2 sequence of SEQ ID NO: 65, or SEQ ID NO: 134, and maintains a LCDR3 sequence SEQ ID NO: 68.

In some embodiments, the antibody or antigen-binding fragment thereof, comprises a light chain that has at least 90, 91, 92, 93, 94, 95, 96, 97, 98, or 99% sequence identity to SEQ ID NO: 230, and a heavy chain that has at least 90, 91, 92, 93, 94, 95, 96, 97, 98, or 99% sequence identity to SEQ ID NO: 172 or SEQ ID NO: 173 (HC of MAB3), wherein the antibody, or antigen binding fragment thereof, maintains the sequences of the heavy chain and light chain CDRs of MAB3. In some embodiments, the antibody or antigen-binding fragment thereof, comprises a light chain that has at least 90, 91, 92, 93, 94, 95, 96, 97, 98, or 99% sequence identity to SEQ ID NO: 230, and a heavy chain that has at least 90, 91, 92, 93, 94, 95, 96, 97, 98, or 99% sequence identity to SEQ ID NO: 172 or SEQ ID NO: 173, wherein the antibody, or antigen binding fragment thereof, maintains a HCDR1 sequence of SEQ ID NO: 61, SEQ ID NO: 124, or SEQ ID NO: 130, maintains a HCDR2 sequence of SEQ ID NO: 62, SEQ ID NO: 125, or SEQ ID NO: 131, maintains a HCDR3 sequence of SEQ ID NO: 69 or SEQ ID NO: 136, maintains a LCDR1 sequence of SEQ ID NO: 64, or SEQ ID NO: 133, maintains a LCDR2 sequence of SEQ ID NO: 65, or SEQ ID NO: 134, and maintains a LCDR3 sequence SEQ ID NO: 68.

In some embodiments, the antibody or antigen-binding fragment thereof, comprises a light chain that has at least 90, 91, 92, 93, 94, 95, 96, 97, 98, or 99% sequence identity to SEQ ID NO: 231, and a heavy chain that has at least 90, 91, 92, 93, 94, 95, 96, 97, 98, or 99% sequence identity to SEQ ID NO: 174 or SEQ ID NO: 175 (HC of MAB4), wherein the antibody, or antigen binding fragment thereof, maintains the sequences of the heavy chain and light chain CDRs of MAB4. In some embodiments, the antibody or antigen-binding fragment thereof, comprises a light chain that has at least 90, 91, 92, 93, 94, 95, 96, 97, 98, or 99% sequence identity to SEQ ID NO: 231, and a heavy chain that has at least 90, 91, 92, 93, 94, 95, 96, 97, 98, or 99% sequence identity to SEQ ID NO: 174 or SEQ ID NO: 175, wherein the antibody, or antigen binding fragment thereof, maintains a HCDR1 sequence of SEQ ID NO: 61, SEQ ID NO: 124, or SEQ ID NO: 130, maintains a HCDR2 sequence of SEQ ID NO: 62, SEQ ID NO: 125, or SEQ ID NO: 131, maintains a HCDR3 sequence of SEQ ID NO: 70 or SEQ ID NO: 137, maintains a LCDR1 sequence of SEQ ID NO: 64, or SEQ ID NO: 133, maintains a LCDR2 sequence of SEQ ID NO: 65, or SEQ ID NO: 134, and maintains a LCDR3 sequence SEQ ID NO: 71.

In some embodiments, the antibody or antigen-binding fragment thereof, comprises a light chain that has at least 90, 91, 92, 93, 94, 95, 96, 97, 98, or 99% sequence identity to SEQ ID NO: 232, and a heavy chain that has at least 90, 91, 92, 93, 94, 95, 96, 97, 98, or 99% sequence identity to SEQ ID NO: 176 or SEQ ID NO: 177 (HC of MAB5), wherein the antibody, or antigen binding fragment thereof, maintains the sequences of the heavy chain and light chain CDRs of MAB5. In some embodiments, the antibody or antigen-binding fragment thereof, comprises a light chain that has at least 90, 91, 92, 93, 94, 95, 96, 97, 98, or 99% sequence identity to SEQ ID NO: 232, and a heavy chain that has at least 90, 91, 92, 93, 94, 95, 96, 97, 98, or 99% sequence identity to SEQ ID NO: 176 or SEQ ID NO: 177, wherein the antibody, or antigen binding fragment thereof, maintains a HCDR1 sequence of SEQ ID NO: 61, SEQ ID NO: 124, or SEQ ID NO: 130, maintains a HCDR2 sequence of SEQ ID NO: 62, SEQ ID NO: 125, or SEQ ID NO: 131, maintains a HCDR3 sequence of SEQ ID NO: 72 or SEQ ID NO: 138, maintains a LCDR1 sequence of SEQ ID NO: 64, or SEQ ID NO: 133, maintains a LCDR2 sequence of SEQ ID NO: 65, or SEQ ID NO: 134, and maintains a LCDR3 sequence SEQ ID NO: 71.

In some embodiments, the antibody or antigen-binding fragment thereof, comprises a light chain that has at least 90, 91, 92, 93, 94, 95, 96, 97, 98, or 99% sequence identity to SEQ ID NO: 233, and a heavy chain that has at least 90, 91, 92, 93, 94, 95, 96, 97, 98, or 99% sequence identity to SEQ ID NO: 178 or SEQ ID NO: 179 (HC of MAB6), wherein the antibody, or antigen binding fragment thereof, maintains the sequences of the heavy chain and light chain CDRs of MAB6. In some embodiments, the antibody or antigen-binding fragment thereof, comprises a light chain that has at least 90, 91, 92, 93, 94, 95, 96, 97, 98, or 99% sequence identity to SEQ ID NO: 233, and a heavy chain that has at least 90, 91, 92, 93, 94, 95, 96, 97, 98, or 99% sequence identity to SEQ ID NO: 178 or SEQ ID NO: 179, wherein the antibody, or antigen binding fragment thereof, maintains a HCDR1 sequence of SEQ ID NO: 61, SEQ ID NO: 124, or SEQ ID NO: 130, maintains a HCDR2 sequence of SEQ ID NO: 62, SEQ ID NO: 125, or SEQ ID NO: 131, maintains a HCDR3 sequence of SEQ ID NO: 73 or SEQ ID NO: 139, maintains a LCDR1 sequence of SEQ ID NO: 64, or SEQ ID NO: 133, maintains a LCDR2 sequence of SEQ ID NO: 65, or SEQ ID NO: 134, and maintains a LCDR3 sequence SEQ ID NO: 71.

In some embodiments, the antibody or antigen-binding fragment thereof, comprises a light chain that has at least 90, 91, 92, 93, 94, 95, 96, 97, 98, or 99% sequence identity to SEQ ID NO: 234, and a heavy chain that has at least 90, 91, 92, 93, 94, 95, 96, 97, 98, or 99% sequence identity to SEQ ID NO: 180 or SEQ ID NO: 181 (HC of MAB7), wherein the antibody, or antigen binding fragment thereof, maintains the sequences of the heavy chain and light chain CDRs of MAB7. In some embodiments, the antibody or antigen-binding fragment thereof, comprises a light chain that has at least 90, 91, 92, 93, 94, 95, 96, 97, 98, or 99% sequence identity to SEQ ID NO: 234, and a heavy chain that has at least 90, 91, 92, 93, 94, 95, 96, 97, 98, or 99% sequence identity to SEQ ID NO: 180 or SEQ ID NO: 181, wherein the antibody, or antigen binding fragment thereof, maintains a HCDR1 sequence of SEQ ID NO: 61, SEQ ID NO: 124, or SEQ ID NO: 130, maintains a HCDR2 sequence of SEQ ID NO: 62, SEQ ID NO: 125, or SEQ ID NO: 131, maintains a HCDR3 sequence of SEQ ID NO: 74 or SEQ ID NO: 140, maintains a LCDR1 sequence of SEQ ID NO: 64, or SEQ ID NO: 133, maintains a LCDR2 sequence of SEQ ID NO: 65, or SEQ ID NO: 134, and maintains a LCDR3 sequence SEQ ID NO: 75.

In some embodiments, the antibody or antigen-binding fragment thereof, comprises a light chain that has at least 90, 91, 92, 93, 94, 95, 96, 97, 98, or 99% sequence identity to SEQ ID NO: 235, and a heavy chain that has at least 90, 91, 92, 93, 94, 95, 96, 97, 98, or 99% sequence identity to SEQ ID NO: 182 or SEQ ID NO: 183 (HC of MAB8), wherein the antibody, or antigen binding fragment thereof, maintains the sequences of the heavy chain and light chain CDRs of MAB8. In some embodiments, the antibody or antigen-binding fragment thereof, comprises a light chain that has at least 90, 91, 92, 93, 94, 95, 96, 97, 98, or 99% sequence identity to SEQ ID NO: 235, and a heavy chain that has at least 90, 91, 92, 93, 94, 95, 96, 97, 98, or 99% sequence identity to SEQ ID NO: 182 or SEQ ID NO: 183, wherein the antibody, or antigen binding fragment thereof, maintains a HCDR1 sequence of SEQ ID NO: 61, SEQ ID NO: 124, or SEQ ID NO: 130, maintains a HCDR2 sequence of SEQ ID NO: 62, SEQ ID NO: 125, or SEQ ID NO: 131, maintains a HCDR3 sequence of SEQ ID NO: 76 or SEQ ID NO: 141, maintains a LCDR1 sequence of SEQ ID NO: 64, or SEQ ID NO: 133, maintains a LCDR2 sequence of SEQ ID NO: 65, or SEQ ID NO: 134, and maintains a LCDR3 sequence SEQ ID NO: 77.

In some embodiments, the antibody or antigen-binding fragment thereof, comprises a light chain that has at least 90, 91, 92, 93, 94, 95, 96, 97, 98, or 99% sequence identity to SEQ ID NO: 236, and a heavy chain that has at least 90, 91, 92, 93, 94, 95, 96, 97, 98, or 99% sequence identity to SEQ ID NO: 184 or SEQ ID NO: 185 (HC of MAB9), wherein the antibody, or antigen binding fragment thereof, maintains the sequences of the heavy chain and light chain CDRs of MAB9. In some embodiments, the antibody or antigen-binding fragment thereof, comprises a light chain that has at least 90, 91, 92, 93, 94, 95, 96, 97, 98, or 99% sequence identity to SEQ ID NO: 236, and a heavy chain that has at least 90, 91, 92, 93, 94, 95, 96, 97, 98, or 99% sequence identity to SEQ ID NO: 184 or SEQ ID NO: 185, wherein the antibody, or antigen binding fragment thereof, maintains a HCDR1 sequence of SEQ ID NO: 61, SEQ ID NO: 124, or SEQ ID NO: 130, maintains a HCDR2 sequence of SEQ ID NO: 62, SEQ ID NO: 125, or SEQ ID NO: 131, maintains a HCDR3 sequence of SEQ ID NO: 78 or SEQ ID NO: 142, maintains a LCDR1 sequence of SEQ ID NO: 64, or SEQ ID NO: 133, maintains a LCDR2 sequence of SEQ ID NO: 65, or SEQ ID NO: 134, and maintains a LCDR3 sequence SEQ ID NO: 79.

In some embodiments, the antibody or antigen-binding fragment thereof, comprises a light chain that has at least 90, 91, 92, 93, 94, 95, 96, 97, 98, or 99% sequence identity to SEQ ID NO: 237, and a heavy chain that has at least 90, 91, 92, 93, 94, 95, 96, 97, 98, or 99% sequence identity to SEQ ID NO: 186 or SEQ ID NO: 187 (HC of MAB10), wherein the antibody, or antigen binding fragment thereof, maintains the sequences of the heavy chain and light chain CDRs of MAB10. In some embodiments, the antibody or antigen-binding fragment thereof, comprises a light chain that has at least 90, 91, 92, 93, 94, 95, 96, 97, 98, or 99% sequence identity to SEQ ID NO: 237, and a heavy chain that has at least 90, 91, 92, 93, 94, 95, 96, 97, 98, or 99% sequence identity to SEQ ID NO: 186 or SEQ ID NO: 187, wherein the antibody, or antigen binding fragment thereof, maintains a HCDR1 sequence of SEQ ID NO: 61, SEQ ID NO: 124, or SEQ ID NO: 130, maintains a HCDR2 sequence of SEQ ID NO: 62, SEQ ID NO: 125, or SEQ ID NO: 131, maintains a HCDR3 sequence of SEQ ID NO: 80 or SEQ ID NO: 143, maintains a LCDR1 sequence of SEQ ID NO: 64, or SEQ ID NO: 133, maintains a LCDR2 sequence of SEQ ID NO: 65, or SEQ ID NO: 134, and maintains a LCDR3 sequence SEQ ID NO: 81.

In some embodiments, the antibody or antigen-binding fragment thereof, comprises a light chain that has at least 90, 91, 92, 93, 94, 95, 96, 97, 98, or 99% sequence identity to SEQ ID NO: 238, and a heavy chain that has at least 90, 91, 92, 93, 94, 95, 96, 97, 98, or 99% sequence identity to SEQ ID NO: 188 or SEQ ID NO: 189 (HC of MAB11), wherein the antibody, or antigen binding fragment thereof, maintains the sequences of the heavy chain and light chain CDRs of MAB11. In some embodiments, the antibody or antigen-binding fragment thereof, comprises a light chain that has at least 90, 91, 92, 93, 94, 95, 96, 97, 98, or 99% sequence identity to SEQ ID NO: 238, and a heavy chain that has at least 90, 91, 92, 93, 94, 95, 96, 97, 98, or 99% sequence identity to SEQ ID NO: 188 or SEQ ID NO: 189, wherein the antibody, or antigen binding fragment thereof, maintains a HCDR1 sequence of SEQ ID NO: 82, SEQ ID NO: 126, or SEQ ID NO: 144, maintains a HCDR2 sequence of SEQ ID NO: 83, SEQ ID NO: 127, or SEQ ID NO: 145, maintains a HCDR3 sequence of SEQ ID NO: 84 or SEQ ID NO: 146, maintains a LCDR1 sequence of SEQ ID NO: 85, or SEQ ID NO: 147, maintains a LCDR2 sequence of SEQ ID NO: 86, or SEQ ID NO: 148, and maintains a LCDR3 sequence SEQ ID NO: 87.

In some embodiments, the antibody or antigen-binding fragment thereof, comprises a light chain that has at least 90, 91, 92, 93, 94, 95, 96, 97, 98, or 99% sequence identity to SEQ ID NO: 239, and a heavy chain that has at least 90, 91, 92, 93, 94, 95, 96, 97, 98, or 99% sequence identity to SEQ ID NO: 190 or SEQ ID NO: 191 (HC of MAB12), wherein the antibody, or antigen binding fragment thereof, maintains the sequences of the heavy chain and light chain CDRs of MAB12. In some embodiments, the antibody or antigen-binding fragment thereof, comprises a light chain that has at least 90, 91, 92, 93, 94, 95, 96, 97, 98, or 99% sequence identity to SEQ ID NO: 239, and a heavy chain that has at least 90, 91, 92, 93, 94, 95, 96, 97, 98, or 99% sequence identity to SEQ ID NO: 190 or SEQ ID NO: 191, wherein the antibody, or antigen binding fragment thereof, maintains a HCDR1 sequence of SEQ ID NO: 82, SEQ ID NO: 126, or SEQ ID NO: 144, maintains a HCDR2 sequence of SEQ ID NO: 83, SEQ ID NO: 127, or SEQ ID NO: 145, maintains a HCDR3 sequence of SEQ ID NO: 88 or SEQ ID NO: 149, maintains a LCDR1 sequence of SEQ ID NO: 85, or SEQ ID NO: 147, maintains a LCDR2 sequence of SEQ ID NO: 86, or SEQ ID NO: 148, and maintains a LCDR3 sequence SEQ ID NO: 89.

In some embodiments, the antibody or antigen-binding fragment thereof, comprises a light chain that has at least 90, 91, 92, 93, 94, 95, 96, 97, 98, or 99% sequence identity to SEQ ID NO: 240, and a heavy chain that has at least 90, 91, 92, 93, 94, 95, 96, 97, 98, or 99% sequence identity to SEQ ID NO: 192 or SEQ ID NO: 193 (HC of MAB13), wherein the antibody, or antigen binding fragment thereof, maintains the sequences of the heavy chain and light chain CDRs of MAB13. In some embodiments, the antibody or antigen-binding fragment thereof, comprises a light chain that has at least 90, 91, 92, 93, 94, 95, 96, 97, 98, or 99% sequence identity to SEQ ID NO: 240, and a heavy chain that has at least 90, 91, 92, 93, 94, 95, 96, 97, 98, or 99% sequence identity to SEQ ID NO: 192 or SEQ ID NO: 193, wherein the antibody, or antigen binding fragment thereof, maintains a HCDR1 sequence of SEQ ID NO: 82, SEQ ID NO: 126, or SEQ ID NO: 144, maintains a HCDR2 sequence of SEQ ID NO: 83, SEQ ID NO: 127, or SEQ ID NO: 145, maintains a HCDR3 sequence of SEQ ID NO: 90 or SEQ ID NO: 150, maintains a LCDR1 sequence of SEQ ID NO: 85, or SEQ ID NO: 147, maintains a LCDR2 sequence of SEQ ID NO: 86, or SEQ ID NO: 148, and maintains a LCDR3 sequence SEQ ID NO: 89.

In some embodiments, the antibody or antigen-binding fragment thereof, comprises a light chain that has at least 90, 91, 92, 93, 94, 95, 96, 97, 98, or 99% sequence identity to SEQ ID NO: 241, and a heavy chain that has at least 90, 91, 92, 93, 94, 95, 96, 97, 98, or 99% sequence identity to SEQ ID NO: 194 or SEQ ID NO: 195 (HC of MAB14), wherein the antibody, or antigen binding fragment thereof, maintains the sequences of the heavy chain and light chain CDRs of MAB14. In some embodiments, the antibody or antigen-binding fragment thereof, comprises a light chain that has at least 90, 91, 92, 93, 94, 95, 96, 97, 98, or 99% sequence identity to SEQ ID NO: 241, and a heavy chain that has at least 90, 91, 92, 93, 94, 95, 96, 97, 98, or 99% sequence identity to SEQ ID NO: 194 or SEQ ID NO: 195, wherein the antibody, or antigen binding fragment thereof, maintains a HCDR1 sequence of SEQ ID NO: 82, SEQ ID NO: 126, or SEQ ID NO: 144, maintains a HCDR2 sequence of SEQ ID NO: 83, SEQ ID NO: 127, or SEQ ID NO: 145, maintains a HCDR3 sequence of SEQ ID NO: 91 or SEQ ID NO: 151, maintains a LCDR1 sequence of SEQ ID NO: 85, or SEQ ID NO: 147, maintains a LCDR2 sequence of SEQ ID NO: 86, or SEQ ID NO: 148, and maintains a LCDR3 sequence SEQ ID NO: 92.

In some embodiments, the antibody or antigen-binding fragment thereof, comprises a light chain that has at least 90, 91, 92, 93, 94, 95, 96, 97, 98, or 99% sequence identity to SEQ ID NO: 242, and a heavy chain that has at least 90, 91, 92, 93, 94, 95, 96, 97, 98, or 99% sequence identity to SEQ ID NO: 196 or SEQ ID NO: 197 (HC of MAB15), wherein the antibody, or antigen binding fragment thereof, maintains the sequences of the heavy chain and light chain CDRs of MAB15. In some embodiments, the antibody or antigen-binding fragment thereof, comprises a light chain that has at least 90, 91, 92, 93, 94, 95, 96, 97, 98, or 99% sequence identity to SEQ ID NO: 242, and a heavy chain that has at least 90, 91, 92, 93, 94, 95, 96, 97, 98, or 99% sequence identity to SEQ ID NO: 196 or SEQ ID NO: 197, wherein the antibody, or antigen binding fragment thereof, maintains a HCDR1 sequence of SEQ ID NO: 82, SEQ ID NO: 126, or SEQ ID NO: 144, maintains a HCDR2 sequence of SEQ ID NO: 83, SEQ ID NO: 127, or SEQ ID NO: 145, maintains a HCDR3 sequence of SEQ ID NO: 93 or SEQ ID NO: 152, maintains a LCDR1 sequence of SEQ ID NO: 85, or SEQ ID NO: 147, maintains a LCDR2 sequence of SEQ ID NO: 86, or SEQ ID NO: 148, and maintains a LCDR3 sequence SEQ ID NO: 94.

In some embodiments, the antibody or antigen-binding fragment thereof, comprises a light chain that has at least 90, 91, 92, 93, 94, 95, 96, 97, 98, or 99% sequence identity to SEQ ID NO: 243, and a heavy chain that has at least 90, 91, 92, 93, 94, 95, 96, 97, 98, or 99% sequence identity to SEQ ID NO: 198 or SEQ ID NO: 199 (HC of MAB16), wherein the antibody, or antigen binding fragment thereof, maintains the sequences of the heavy chain and light chain CDRs of MAB16. In some embodiments, the antibody or antigen-binding fragment thereof, comprises a light chain that has at least 90, 91, 92, 93, 94, 95, 96, 97, 98, or 99% sequence identity to SEQ ID NO: 243, and a heavy chain that has at least 90, 91, 92, 93, 94, 95, 96, 97, 98, or 99% sequence identity to SEQ ID NO: 198 or SEQ ID NO: 199, wherein the antibody, or antigen binding fragment thereof, maintains a HCDR1 sequence of SEQ ID NO: 82, SEQ ID NO: 126, or SEQ ID NO: 144, maintains a HCDR2 sequence of SEQ ID NO: 83, SEQ ID NO: 127, or SEQ ID NO: 145, maintains a HCDR3 sequence of SEQ ID NO: 84 or SEQ ID NO: 146, maintains a LCDR1 sequence of SEQ ID NO: 85, or SEQ ID NO: 147, maintains a LCDR2 sequence of SEQ ID NO: 86, or SEQ ID NO: 148, and maintains a LCDR3 sequence SEQ ID NO: 95.

In some embodiments, the antibody or antigen-binding fragment thereof, comprises a light chain that has at least 90, 91, 92, 93, 94, 95, 96, 97, 98, or 99% sequence identity to SEQ ID NO: 244, and a heavy chain that has at least 90, 91, 92, 93, 94, 95, 96, 97, 98, or 99% sequence identity to SEQ ID NO: 200 or SEQ ID NO: 201 (HC of MAB17), wherein the antibody, or antigen binding fragment thereof, maintains the sequences of the heavy chain and light chain CDRs of MAB17. In some embodiments, the antibody or antigen-binding fragment thereof, comprises a light chain that has at least 90, 91, 92, 93, 94, 95, 96, 97, 98, or 99% sequence identity to SEQ ID NO: 244, and a heavy chain that has at least 90, 91, 92, 93, 94, 95, 96, 97, 98, or 99% sequence identity to SEQ ID NO: 200 or SEQ ID NO: 201, wherein the antibody, or antigen binding fragment thereof, maintains a HCDR1 sequence of SEQ ID NO: 82, SEQ ID NO: 126, or SEQ ID NO: 144, maintains a HCDR2 sequence of SEQ ID NO: 83, SEQ ID NO: 127, or SEQ ID NO: 145, maintains a HCDR3 sequence of SEQ ID NO: 96 or SEQ ID NO: 153, maintains a LCDR1 sequence of SEQ ID NO: 85, or SEQ ID NO: 147, maintains a LCDR2 sequence of SEQ ID NO: 86, or SEQ ID NO: 148, and maintains a LCDR3 sequence SEQ ID NO: 97.

In some embodiments, the antibody or antigen-binding fragment thereof, comprises a light chain that has at least 90, 91, 92, 93, 94, 95, 96, 97, 98, or 99% sequence identity to SEQ ID NO: 245, and a heavy chain that has at least 90, 91, 92, 93, 94, 95, 96, 97, 98, or 99% sequence identity to SEQ ID NO: 202 or SEQ ID NO: 203 (HC of MAB18), wherein the antibody, or antigen binding fragment thereof, maintains the sequences of the heavy chain and light chain CDRs of MAB18. In some embodiments, the antibody or antigen-binding fragment thereof, comprises a light chain that has at least 90, 91, 92, 93, 94, 95, 96, 97, 98, or 99% sequence identity to SEQ ID NO: 245, and a heavy chain that has at least 90, 91, 92, 93, 94, 95, 96, 97, 98, or 99% sequence identity to SEQ ID NO: 202 or SEQ ID NO: 203, wherein the antibody, or antigen binding fragment thereof, maintains a HCDR1 sequence of SEQ ID NO: 82, SEQ ID NO: 126, or SEQ ID NO: 144, maintains a HCDR2 sequence of SEQ ID NO: 83, SEQ ID NO: 127, or SEQ ID NO: 145, maintains a HCDR3 sequence of SEQ ID NO: 98 or SEQ ID NO: 154, maintains a LCDR1 sequence of SEQ ID NO: 85, or SEQ ID NO: 147, maintains a LCDR2 sequence of SEQ ID NO: 86, or SEQ ID NO: 148, and maintains a LCDR3 sequence SEQ ID NO: 99.

In some embodiments, the antibody or antigen-binding fragment thereof, comprises a light chain that has at least 90, 91, 92, 93, 94, 95, 96, 97, 98, or 99% sequence identity to SEQ ID NO: 246, and a heavy chain that has at least 90, 91, 92, 93, 94, 95, 96, 97, 98, or 99% sequence identity to SEQ ID NO: 204 or SEQ ID NO: 205 (HC of MAB19), wherein the antibody, or antigen binding fragment thereof, maintains the sequences of the heavy chain and light chain CDRs of MAB19. In some embodiments, the antibody or antigen-binding fragment thereof, comprises a light chain that has at least 90, 91, 92, 93, 94, 95, 96, 97, 98, or 99% sequence identity to SEQ ID NO: 246, and a heavy chain that has at least 90, 91, 92, 93, 94, 95, 96, 97, 98, or 99% sequence identity to SEQ ID NO: 204 or SEQ ID NO: 205, wherein the antibody, or antigen binding fragment thereof, maintains a HCDR1 sequence of SEQ ID NO: 82, SEQ ID NO: 126, or SEQ ID NO: 144, maintains a HCDR2 sequence of SEQ ID NO: 83, SEQ ID NO: 127, or SEQ ID NO: 145, maintains a HCDR3 sequence of SEQ ID NO: 100 or SEQ ID NO: 155, maintains a LCDR1 sequence of SEQ ID NO: 85, or SEQ ID NO: 147, maintains a LCDR2 sequence of SEQ ID NO: 86, or SEQ ID NO: 148, and maintains a LCDR3 sequence SEQ ID NO: 101.

In some embodiments, the antibody or antigen-binding fragment thereof, comprises a light chain that has at least 90, 91, 92, 93, 94, 95, 96, 97, 98, or 99% sequence identity to SEQ ID NO: 247, and a heavy chain that has at least 90, 91, 92, 93, 94, 95, 96, 97, 98, or 99% sequence identity to SEQ ID NO: 206 or SEQ ID NO: 207 (HC of MAB20), wherein the antibody, or antigen binding fragment thereof, maintains the sequences of the heavy chain and light chain CDRs of MAB20. In some embodiments, the antibody or antigen-binding fragment thereof, comprises a light chain that has at least 90, 91, 92, 93, 94, 95, 96, 97, 98, or 99% sequence identity to SEQ ID NO: 247, and a heavy chain that has at least 90, 91, 92, 93, 94, 95, 96, 97, 98, or 99% sequence identity to SEQ ID NO: 206 or SEQ ID NO: 207, wherein the antibody, or antigen binding fragment thereof, maintains a HCDR1 sequence of SEQ ID NO: 82, SEQ ID NO: 126, or SEQ ID NO: 144, maintains a HCDR2 sequence of SEQ ID NO: 83, SEQ ID NO: 127, or SEQ ID NO: 145, maintains a HCDR3 sequence of SEQ ID NO: 100 or SEQ ID NO: 155, maintains a LCDR1 sequence of SEQ ID NO: 85, or SEQ ID NO: 147, maintains a LCDR2 sequence of SEQ ID NO: 86, or SEQ ID NO: 148, and maintains a LCDR3 sequence SEQ ID NO: 102.

In some embodiments, the antibody or antigen-binding fragment thereof, comprises a light chain that has at least 90, 91, 92, 93, 94, 95, 96, 97, 98, or 99% sequence identity to SEQ ID NO: 248, and a heavy chain that has at least 90, 91, 92, 93, 94, 95, 96, 97, 98, or 99% sequence identity to SEQ ID NO: 208 or SEQ ID NO: 209 (HC of MAB21), wherein the antibody, or antigen binding fragment thereof, maintains the sequences of the heavy chain and light chain CDRs of MAB21. In some embodiments, the antibody or antigen-binding fragment thereof, comprises a light chain that has at least 90, 91, 92, 93, 94, 95, 96, 97, 98, or 99% sequence identity to SEQ ID NO: 248, and a heavy chain that has at least 90, 91, 92, 93, 94, 95, 96, 97, 98, or 99% sequence identity to SEQ ID NO: 208 or SEQ ID NO: 209, wherein the antibody, or antigen binding fragment thereof, maintains a HCDR1 sequence of SEQ ID NO: 103, SEQ ID NO: 128, or SEQ ID NO: 156, maintains a HCDR2 sequence of SEQ ID NO: 104, SEQ ID NO: 129, or SEQ ID NO: 157, maintains a HCDR3 sequence of SEQ ID NO: 105 or SEQ ID NO: 158, maintains a LCDR1 sequence of SEQ ID NO: 106, or SEQ ID NO: 159, maintains a LCDR2 sequence of SEQ ID NO: 107, or SEQ ID NO: 160, and maintains a LCDR3 sequence SEQ ID NO: 108.

In some embodiments, the antibody or antigen-binding fragment thereof, comprises a light chain that has at least 90, 91, 92, 93, 94, 95, 96, 97, 98, or 99% sequence identity to SEQ ID NO: 249, and a heavy chain that has at least 90, 91, 92, 93, 94, 95, 96, 97, 98, or 99% sequence identity to SEQ ID NO: 210 or SEQ ID NO: 211 (HC of MAB22), wherein the antibody, or antigen binding fragment thereof, maintains the sequences of the heavy chain and light chain CDRs of MAB22. In some embodiments, the antibody or antigen-binding fragment thereof, comprises a light chain that has at least 90, 91, 92, 93, 94, 95, 96, 97, 98, or 99% sequence identity to SEQ ID NO: 249, and a heavy chain that has at least 90, 91, 92, 93, 94, 95, 96, 97, 98, or 99% sequence identity to SEQ ID NO: 210 or SEQ ID NO: 211, wherein the antibody, or antigen binding fragment thereof, maintains a HCDR1 sequence of SEQ ID NO: 103, SEQ ID NO: 128, or SEQ ID NO: 156, maintains a HCDR2 sequence of SEQ ID NO: 104, SEQ ID NO: 129, or SEQ ID NO: 157, maintains a HCDR3 sequence of SEQ ID NO: 109 or SEQ ID NO: 161, maintains a LCDR1 sequence of SEQ ID NO: 106, or SEQ ID NO: 159, maintains a LCDR2 sequence of SEQ ID NO: 107, or SEQ ID NO: 160, and maintains a LCDR3 sequence SEQ ID NO: 110.

In some embodiments, the antibody or antigen-binding fragment thereof, comprises a light chain that has at least 90, 91, 92, 93, 94, 95, 96, 97, 98, or 99% sequence identity to SEQ ID NO: 250, and a heavy chain that has at least 90, 91, 92, 93, 94, 95, 96, 97, 98, or 99% sequence identity to SEQ ID NO: 212 or SEQ ID NO: 213 (HC of MAB23), wherein the antibody, or antigen binding fragment thereof, maintains the sequences of the heavy chain and light chain CDRs of MAB23. In some embodiments, the antibody or antigen-binding fragment thereof, comprises a light chain that has at least 90, 91, 92, 93, 94, 95, 96, 97, 98, or 99% sequence identity to SEQ ID NO: 250, and a heavy chain that has at least 90, 91, 92, 93, 94, 95, 96, 97, 98, or 99% sequence identity to SEQ ID NO: 212 or SEQ ID NO: 213, wherein the antibody, or antigen binding fragment thereof, maintains a HCDR1 sequence of SEQ ID NO: 103, SEQ ID NO: 128, or SEQ ID NO: 156, maintains a HCDR2 sequence of SEQ ID NO: 104, SEQ ID NO: 129, or SEQ ID NO: 157, maintains a HCDR3 sequence of SEQ ID NO: 111 or SEQ ID NO: 162, maintains a LCDR1 sequence of SEQ ID NO: 106, or SEQ ID NO: 159, maintains a LCDR2 sequence of SEQ ID NO: 107, or SEQ ID NO: 160, and maintains a LCDR3 sequence SEQ ID NO: 112.

In some embodiments, the antibody or antigen-binding fragment thereof, comprises a light chain that has at least 90, 91, 92, 93, 94, 95, 96, 97, 98, or 99% sequence identity to SEQ ID NO: 251, and a heavy chain that has at least 90, 91, 92, 93, 94, 95, 96, 97, 98, or 99% sequence identity to SEQ ID NO: 214 or SEQ ID NO: 215 (HC of MAB24), wherein the antibody, or antigen binding fragment thereof, maintains the sequences of the heavy chain and light chain CDRs of MAB24. In some embodiments, the antibody or antigen-binding fragment thereof, comprises a light chain that has at least 90, 91, 92, 93, 94, 95, 96, 97, 98, or 99% sequence identity to SEQ ID NO: 251, and a heavy chain that has at least 90, 91, 92, 93, 94, 95, 96, 97, 98, or 99% sequence identity to SEQ ID NO: 214 or SEQ ID NO: 215, wherein the antibody, or antigen binding fragment thereof, maintains a HCDR1 sequence of SEQ ID NO: 103, SEQ ID NO: 128, or SEQ ID NO: 156, maintains a HCDR2 sequence of SEQ ID NO: 104, SEQ ID NO: 129, or SEQ ID NO: 157, maintains a HCDR3 sequence of SEQ ID NO: 105 or SEQ ID NO: 158, maintains a LCDR1 sequence of SEQ ID NO: 106, or SEQ ID NO: 159, maintains a LCDR2 sequence of SEQ ID NO: 107, or SEQ ID NO: 160, and maintains a LCDR3 sequence SEQ ID NO: 113.

In some embodiments, the antibody or antigen-binding fragment thereof, comprises a light chain that has at least 90, 91, 92, 93, 94, 95, 96, 97, 98, or 99% sequence identity to SEQ ID NO: 252, and a heavy chain that has at least 90, 91, 92, 93, 94, 95, 96, 97, 98, or 99% sequence identity to SEQ ID NO: 216 or SEQ ID NO: 217 (HC of MAB25), wherein the antibody, or antigen binding fragment thereof, maintains the sequences of the heavy chain and light chain CDRs of MAB25. In some embodiments, the antibody or antigen-binding fragment thereof, comprises a light chain that has at least 90, 91, 92, 93, 94, 95, 96, 97, 98, or 99% sequence identity to SEQ ID NO: 252, and a heavy chain that has at least 90, 91, 92, 93, 94, 95, 96, 97, 98, or 99% sequence identity to SEQ ID NO: 216 or SEQ ID NO: 217, wherein the antibody, or antigen binding fragment thereof, maintains a HCDR1 sequence of SEQ ID NO: 103, SEQ ID NO: 128, or SEQ ID NO: 156, maintains a HCDR2 sequence of SEQ ID NO: 104, SEQ ID NO: 129, or SEQ ID NO: 157, maintains a HCDR3 sequence of SEQ ID NO: 114 or SEQ ID NO: 163, maintains a LCDR1 sequence of SEQ ID NO: 106, or SEQ ID NO: 159, maintains a LCDR2 sequence of SEQ ID NO: 107, or SEQ ID NO: 160, and maintains a LCDR3 sequence SEQ ID NO: 115.

In some embodiments, the antibody or antigen-binding fragment thereof, comprises a light chain that has at least 90, 91, 92, 93, 94, 95, 96, 97, 98, or 99% sequence identity to SEQ ID NO: 253, and a heavy chain that has at least 90, 91, 92, 93, 94, 95, 96, 97, 98, or 99% sequence identity to SEQ ID NO: 218 or SEQ ID NO: 219 (HC of MAB26), wherein the antibody, or antigen binding fragment thereof, maintains the sequences of the heavy chain and light chain CDRs of MAB26. In some embodiments, the antibody or antigen-binding fragment thereof, comprises a light chain that has at least 90, 91, 92, 93, 94, 95, 96, 97, 98, or 99% sequence identity to SEQ ID NO: 253, and a heavy chain that has at least 90, 91, 92, 93, 94, 95, 96, 97, 98, or 99% sequence identity to SEQ ID NO: 218 or SEQ ID NO: 219, wherein the antibody, or antigen binding fragment thereof, maintains a HCDR1 sequence of SEQ ID NO: 103, SEQ ID NO: 128, or SEQ ID NO: 156, maintains a HCDR2 sequence of SEQ ID NO: 104, SEQ ID NO: 129, or SEQ ID NO: 157, maintains a HCDR3 sequence of SEQ ID NO: 116 or SEQ ID NO: 164, maintains a LCDR1 sequence of SEQ ID NO: 106, or SEQ ID NO: 159, maintains a LCDR2 sequence of SEQ ID NO: 107, or SEQ ID NO: 160, and maintains a LCDR3 sequence SEQ ID NO: 113.

In some embodiments, the antibody or antigen-binding fragment thereof, comprises a light chain that has at least 90, 91, 92, 93, 94, 95, 96, 97, 98, or 99% sequence identity to SEQ ID NO: 254, and a heavy chain that has at least 90, 91, 92, 93, 94, 95, 96, 97, 98, or 99% sequence identity to SEQ ID NO: 220 or SEQ ID NO: 221 (HC of MAB27), wherein the antibody, or antigen binding fragment thereof, maintains the sequences of the heavy chain and light chain CDRs of MAB27. In some embodiments, the antibody or antigen-binding fragment thereof, comprises a light chain that has at least 90, 91, 92, 93, 94, 95, 96, 97, 98, or 99% sequence identity to SEQ ID NO: 254, and a heavy chain that has at least 90, 91, 92, 93, 94, 95, 96, 97, 98, or 99% sequence identity to SEQ ID NO: 220 or SEQ ID NO: 221, wherein the antibody, or antigen binding fragment thereof, maintains a HCDR1 sequence of SEQ ID NO: 103, SEQ ID NO: 128, or SEQ ID NO: 156, maintains a HCDR2 sequence of SEQ ID NO: 104, SEQ ID NO: 129, or SEQ ID NO: 157, maintains a HCDR3 sequence of SEQ ID NO: 117 or SEQ ID NO: 165, maintains a LCDR1 sequence of SEQ ID NO: 106, or SEQ ID NO: 159, maintains a LCDR2 sequence of SEQ ID NO: 107, or SEQ ID NO: 160, and maintains a LCDR3 sequence SEQ ID NO: 118.

In some embodiments, the antibody or antigen-binding fragment thereof, comprises a light chain that has at least 90, 91, 92, 93, 94, 95, 96, 97, 98, or 99% sequence identity to SEQ ID NO: 255, and a heavy chain that has at least 90, 91, 92, 93, 94, 95, 96, 97, 98, or 99% sequence identity to SEQ ID NO: 222 or SEQ ID NO: 223 (HC of MAB28), wherein the antibody, or antigen binding fragment thereof, maintains the sequences of the heavy chain and light chain CDRs of MAB28. In some embodiments, the antibody or antigen-binding fragment thereof, comprises a light chain that has at least 90, 91, 92, 93, 94, 95, 96, 97, 98, or 99% sequence identity to SEQ ID NO: 255, and a heavy chain that has at least 90, 91, 92, 93, 94, 95, 96, 97, 98, or 99% sequence identity to SEQ ID NO: 222 or SEQ ID NO: 223, wherein the antibody, or antigen binding fragment thereof, maintains a HCDR1 sequence of SEQ ID NO: 103, SEQ ID NO: 128, or SEQ ID NO: 156, maintains a HCDR2 sequence of SEQ ID NO: 104, SEQ ID NO: 129, or SEQ ID NO: 157, maintains a HCDR3 sequence of SEQ ID NO: 116 or SEQ ID NO: 164, maintains a LCDR1 sequence of SEQ ID NO: 106, or SEQ ID NO: 159, maintains a LCDR2 sequence of SEQ ID NO: 107, or SEQ ID NO: 160, and maintains a LCDR3 sequence SEQ ID NO: 119.

In some embodiments, the antibody or antigen-binding fragment thereof, comprises a light chain that has at least 90, 91, 92, 93, 94, 95, 96, 97, 98, or 99% sequence identity to SEQ ID NO: 256, and a heavy chain that has at least 90, 91, 92, 93, 94, 95, 96, 97, 98, or 99% sequence identity to SEQ ID NO: 224 or SEQ ID NO: 225 (HC of MAB29), wherein the antibody, or antigen binding fragment thereof, maintains the sequences of the heavy chain and light chain CDRs of MAB29. In some embodiments, the antibody or antigen-binding fragment thereof, comprises a light chain that has at least 90, 91, 92, 93, 94, 95, 96, 97, 98, or 99% sequence identity to SEQ ID NO: 256, and a heavy chain that has at least 90, 91, 92, 93, 94, 95, 96, 97, 98, or 99% sequence identity to SEQ ID NO: 224 or SEQ ID NO: 225, wherein the antibody, or antigen binding fragment thereof, maintains a HCDR1 sequence of SEQ ID NO: 103, SEQ ID NO: 128, or SEQ ID NO: 156, maintains a HCDR2 sequence of SEQ ID NO: 104, SEQ ID NO: 129, or SEQ ID NO: 157, maintains a HCDR3 sequence of SEQ ID NO: 120 or SEQ ID NO: 166, maintains a LCDR1 sequence of SEQ ID NO: 106, or SEQ ID NO: 159, maintains a LCDR2 sequence of SEQ ID NO: 107, or SEQ ID NO: 160, and maintains a LCDR3 sequence SEQ ID NO: 121.

In some embodiments, the antibody or antigen-binding fragment thereof, comprises a light chain that has at least 90, 91, 92, 93, 94, 95, 96, 97, 98, or 99% sequence identity to SEQ ID NO: 257, and a heavy chain that has at least 90, 91, 92, 93, 94, 95, 96, 97, 98, or 99% sequence identity to SEQ ID NO: 226 or SEQ ID NO: 227 (HC of MAB30), wherein the antibody, or antigen binding fragment thereof, maintains the sequences of the heavy chain and light chain CDRs of MAB30. In some embodiments, the antibody or antigen-binding fragment thereof, comprises a light chain that has at least 90, 91, 92, 93, 94, 95, 96, 97, 98, or 99% sequence identity to SEQ ID NO: 257, and a heavy chain that has at least 90, 91, 92, 93, 94, 95, 96, 97, 98, or 99% sequence identity to SEQ ID NO: 226 or SEQ ID NO: 227, wherein the antibody, or antigen binding fragment thereof, maintains a HCDR1 sequence of SEQ ID NO: 103, SEQ ID NO: 128, or SEQ ID NO: 156, maintains a HCDR2 sequence of SEQ ID NO: 104, SEQ ID NO: 129, or SEQ ID NO: 157, maintains a HCDR3 sequence of SEQ ID NO: 122 or SEQ ID NO: 167, maintains a LCDR1 sequence of SEQ ID NO: 106, or SEQ ID NO: 159, maintains a LCDR2 sequence of SEQ ID NO: 107, or SEQ ID NO: 160, and maintains a LCDR3 sequence SEQ ID NO: 123.

In some embodiments, the antibody or antigen-binding fragment thereof, comprises a light chain that has at least 90, 91, 92, 93, 94, 95, 96, 97, 98, 99% sequence identity to SEQ ID NO: 228, and a heavy chain that has at least 90, 91, 92, 93, 94, 95, 96, 97, 98, or 99% sequence identity to SEQ ID NO: 364 or SEQ ID NO: 365 (HC of MAB31), wherein the antibody, or antigen binding fragment thereof, maintains the sequences of the heavy chain and light chain CDRs of MAB31. In some embodiments, the antibody or antigen-binding fragment thereof, comprises a light chain that has at least 90, 91, 92, 93, 94, 95, 96, 97, 98, or 99% sequence identity to SEQ ID NO: 228, and a heavy chain that has at least 90, 91, 92, 93, 94, 95, 96, 97, 98, or 99% sequence identity to SEQ ID NO: 364 or SEQ ID NO: 365, wherein the antibody, or antigen binding fragment thereof, maintains a HCDR1 sequence of SEQ ID NO: 61, SEQ ID NO: 124, or SEQ ID NO: 130, maintains a HCDR2 sequence of SEQ ID NO: 62, SEQ ID NO: 125, or SEQ ID NO: 131, maintains a HCDR3 sequence of SEQ ID NO: 63 or SEQ ID NO: 132, maintains a LCDR1 sequence of SEQ ID NO: 64, or SEQ ID NO: 133, maintains a LCDR2 sequence of SEQ ID NO: 65, or SEQ ID NO: 134, and maintains a LCDR3 sequence of SEQ ID NO: 66.

In some embodiments, the antibody or antigen-binding fragment thereof, comprises a light chain that has at least 90, 91, 92, 93, 94, 95, 96, 97, 98, or 99% sequence identity to SEQ ID NO: 229, and a heavy chain that has at least 90, 91, 92, 93, 94, 95, 96, 97, 98, or 99% sequence identity to SEQ ID NO: 366 or SEQ ID NO: 367 (HC of MAB32), wherein the antibody, or antigen binding fragment thereof, maintains the sequences of the heavy chain and light chain CDRs of MAB32. In some embodiments, the antibody or antigen-binding fragment thereof, comprises a light chain that has at least 90, 91, 92, 93, 94, 95, 96, 97, 98, or 99% sequence identity to SEQ ID NO: 229, and a heavy chain that has at least 90, 91, 92, 93, 94, 95, 96, 97, 98, or 99% sequence identity to SEQ ID NO: 366 or SEQ ID NO: 367, wherein the antibody, or antigen binding fragment thereof, maintains a HCDR1 sequence of SEQ ID NO: 61, SEQ ID NO: 124, or SEQ ID NO: 130, maintains a HCDR2 sequence of SEQ ID NO: 62, SEQ ID NO: 125, or SEQ ID NO: 131, maintains a HCDR3 sequence of SEQ ID NO: 67 or SEQ ID NO: 135, maintains a LCDR1 sequence of SEQ ID NO: 64, or SEQ ID NO: 133, maintains a LCDR2 sequence of SEQ ID NO: 65, or SEQ ID NO: 134, and maintains a LCDR3 sequence SEQ ID NO: 68.

In some embodiments, the antibody or antigen-binding fragment thereof, comprises a light chain that has at least 90, 91, 92, 93, 94, 95, 96, 97, 98, or 99% sequence identity to SEQ ID NO: 230, and a heavy chain that has at least 90, 91, 92, 93, 94, 95, 96, 97, 98, or 99% sequence identity to SEQ ID NO: 368 or SEQ ID NO: 369 (HC of MAB33), wherein the antibody, or antigen binding fragment thereof, maintains the sequences of the heavy chain and light chain CDRs of MAB33. In some embodiments, the antibody or antigen-binding fragment thereof, comprises a light chain that has at least 90, 91, 92, 93, 94, 95, 96, 97, 98, or 99% sequence identity to SEQ ID NO: 230, and a heavy chain that has at least 90, 91, 92, 93, 94, 95, 96, 97, 98, or 99% sequence identity to SEQ ID NO: 368 or SEQ ID NO: 369, wherein the antibody, or antigen binding fragment thereof, maintains a HCDR1 sequence of SEQ ID NO: 61, SEQ ID NO: 124, or SEQ ID NO: 130, maintains a HCDR2 sequence of SEQ ID NO: 62, SEQ ID NO: 125, or SEQ ID NO: 131, maintains a HCDR3 sequence of SEQ ID NO: 69 or SEQ ID NO: 136, maintains a LCDR1 sequence of SEQ ID NO: 64, or SEQ ID NO: 133, maintains a LCDR2 sequence of SEQ ID NO: 65, or SEQ ID NO: 134, and maintains a LCDR3 sequence SEQ ID NO: 68.

In some embodiments, the antibody or antigen-binding fragment thereof, comprises a light chain that has at least 90, 91, 92, 93, 94, 95, 96, 97, 98, or 99% sequence identity to SEQ ID NO: 231, and a heavy chain that has at least 90, 91, 92, 93, 94, 95, 96, 97, 98, or 99% sequence identity to SEQ ID NO: 370 or SEQ ID NO: 371 (HC of MAB34), wherein the antibody, or antigen binding fragment thereof, maintains the sequences of the heavy chain and light chain CDRs of MAB34. In some embodiments, the antibody or antigen-binding fragment thereof, comprises a light chain that has at least 90, 91, 92, 93, 94, 95, 96, 97, 98, or 99% sequence identity to SEQ ID NO: 231, and a heavy chain that has at least 90, 91, 92, 93, 94, 95, 96, 97, 98, or 99% sequence identity to SEQ ID NO: 370 or SEQ ID NO: 371, wherein the antibody, or antigen binding fragment thereof, maintains a HCDR1 sequence of SEQ ID NO: 61, SEQ ID NO: 124, or SEQ ID NO: 130, maintains a HCDR2 sequence of SEQ ID NO: 62, SEQ ID NO: 125, or SEQ ID NO: 131, maintains a HCDR3 sequence of SEQ ID NO: 70 or SEQ ID NO: 137, maintains a LCDR1 sequence of SEQ ID NO: 64, or SEQ ID NO: 133, maintains a LCDR2 sequence of SEQ ID NO: 65, or SEQ ID NO: 134, and maintains a LCDR3 sequence SEQ ID NO: 71.

In some embodiments, the antibody or antigen-binding fragment thereof, comprises a light chain that has at least 90, 91, 92, 93, 94, 95, 96, 97, 98, or 99% sequence identity to SEQ ID NO: 232, and a heavy chain that has at least 90, 91, 92, 93, 94, 95, 96, 97, 98, or 99% sequence identity to SEQ ID NO: 372 or SEQ ID NO: 373 (HC of MAB35), wherein the antibody, or antigen binding fragment thereof, maintains the sequences of the heavy chain and light chain CDRs of MAB35. In some embodiments, the antibody or antigen-binding fragment thereof, comprises a light chain that has at least 90, 91, 92, 93, 94, 95, 96, 97, 98, or 99% sequence identity to SEQ ID NO: 232, and a heavy chain that has at least 90, 91, 92, 93, 94, 95, 96, 97, 98, or 99% sequence identity to SEQ ID NO: 372 or SEQ ID NO: 373, wherein the antibody, or antigen binding fragment thereof, maintains a HCDR1 sequence of SEQ ID NO: 61, SEQ ID NO: 124, or SEQ ID NO: 130, maintains a HCDR2 sequence of SEQ ID NO: 62, SEQ ID NO: 125, or SEQ ID NO: 131, maintains a HCDR3 sequence of SEQ ID NO: 72 or SEQ ID NO: 138, maintains a LCDR1 sequence of SEQ ID NO: 64, or SEQ ID NO: 133, maintains a LCDR2 sequence of SEQ ID NO: 65, or SEQ ID NO: 134, and maintains a LCDR3 sequence SEQ ID NO: 71.

In some embodiments, the antibody or antigen-binding fragment thereof, comprises a light chain that has at least 90, 91, 92, 93, 94, 95, 96, 97, 98, or 99% sequence identity to SEQ ID NO: 233, and a heavy chain that has at least 90, 91, 92, 93, 94, 95, 96, 97, 98, or 99% sequence identity to SEQ ID NO: 374 or SEQ ID NO: 375 (HC of MAB36), wherein the antibody, or antigen binding fragment thereof, maintains the sequences of the heavy chain and light chain CDRs of MAB36. In some embodiments, the antibody or antigen-binding fragment thereof, comprises a light chain that has at least 90, 91, 92, 93, 94, 95, 96, 97, 98, or 99% sequence identity to SEQ ID NO: 233, and a heavy chain that has at least 90, 91, 92, 93, 94, 95, 96, 97, 98, or 99% sequence identity to SEQ ID NO: 374 or SEQ ID NO: 375, wherein the antibody, or antigen binding fragment thereof, maintains a HCDR1 sequence of SEQ ID NO: 61, SEQ ID NO: 124, or SEQ ID NO: 130, maintains a HCDR2 sequence of SEQ ID NO: 62, SEQ ID NO: 125, or SEQ ID NO: 131, maintains a HCDR3 sequence of SEQ ID NO: 73 or SEQ ID NO: 139, maintains a LCDR1 sequence of SEQ ID NO: 64, or SEQ ID NO: 133, maintains a LCDR2 sequence of SEQ ID NO: 65, or SEQ ID NO: 134, and maintains a LCDR3 sequence SEQ ID NO: 71.

In some embodiments, the antibody or antigen-binding fragment thereof, comprises a light chain that has at least 90, 91, 92, 93, 94, 95, 96, 97, 98, or 99% sequence identity to SEQ ID NO: 234, and a heavy chain that has at least 90, 91, 92, 93, 94, 95, 96, 97, 98, or 99% sequence identity to SEQ ID NO: 376 or SEQ ID NO: 377 (HC of MAB37), wherein the antibody, or antigen binding fragment thereof, maintains the sequences of the heavy chain and light chain CDRs of MAB37. In some embodiments, the antibody or antigen-binding fragment thereof, comprises a light chain that has at least 90, 91, 92, 93, 94, 95, 96, 97, 98, or 99% sequence identity to SEQ ID NO: 234, and a heavy chain that has at least 90, 91, 92, 93, 94, 95, 96, 97, 98, or 99% sequence identity to SEQ ID NO: 376 or SEQ ID NO: 377, wherein the antibody, or antigen binding fragment thereof, maintains a HCDR1 sequence of SEQ ID NO: 61, SEQ ID NO: 124, or SEQ ID NO: 130, maintains a HCDR2 sequence of SEQ ID NO: 62, SEQ ID NO: 125, or SEQ ID NO: 131, maintains a HCDR3 sequence of SEQ ID NO: 74 or SEQ ID NO: 140, maintains a LCDR1 sequence of SEQ ID NO: 64, or SEQ ID NO: 133, maintains a LCDR2 sequence of SEQ ID NO: 65, or SEQ ID NO: 134, and maintains a LCDR3 sequence SEQ ID NO: 75.

In some embodiments, the antibody or antigen-binding fragment thereof, comprises a light chain that has at least 90, 91, 92, 93, 94, 95, 96, 97, 98, or 99% sequence identity to SEQ ID NO: 235, and a heavy chain that has at least 90, 91, 92, 93, 94, 95, 96, 97, 98, or 99% sequence identity to SEQ ID NO: 378 or SEQ ID NO: 379 (HC of MAB38), wherein the antibody, or antigen binding fragment thereof, maintains the sequences of the heavy chain and light chain CDRs of MAB38. In some embodiments, the antibody or antigen-binding fragment thereof, comprises a light chain that has at least 90, 91, 92, 93, 94, 95, 96, 97, 98, or 99% sequence identity to SEQ ID NO: 235, and a heavy chain that has at least 90, 91, 92, 93, 94, 95, 96, 97, 98, or 99% sequence identity to SEQ ID NO: 378 or SEQ ID NO: 379, wherein the antibody, or antigen binding fragment thereof, maintains a HCDR1 sequence of SEQ ID NO: 61, SEQ ID NO: 124, or SEQ ID NO: 130, maintains a HCDR2 sequence of SEQ ID NO: 62, SEQ ID NO: 125, or SEQ ID NO: 131, maintains a HCDR3 sequence of SEQ ID NO: 76 or SEQ ID NO: 141, maintains a LCDR1 sequence of SEQ ID NO: 64, or SEQ ID NO: 133, maintains a LCDR2 sequence of SEQ ID NO: 65, or SEQ ID NO: 134, and maintains a LCDR3 sequence SEQ ID NO: 77.

In some embodiments, the antibody or antigen-binding fragment thereof, comprises a light chain that has at least 90, 91, 92, 93, 94, 95, 96, 97, 98, or 99% sequence identity to SEQ ID NO: 236, and a heavy chain that has at least 90, 91, 92, 93, 94, 95, 96, 97, 98, or 99% sequence identity to SEQ ID NO: 380 or SEQ ID NO: 381 (HC of MAB39), wherein the antibody, or antigen binding fragment thereof, maintains the sequences of the heavy chain and light chain CDRs of MAB39. In some embodiments, the antibody or antigen-binding fragment thereof, comprises a light chain that has at least 90, 91, 92, 93, 94, 95, 96, 97, 98, or 99% sequence identity to SEQ ID NO: 236, and a heavy chain that has at least 90, 91, 92, 93, 94, 95, 96, 97, 98, or 99% sequence identity to SEQ ID NO: 380 or SEQ ID NO: 381, wherein the antibody, or antigen binding fragment thereof, maintains a HCDR1 sequence of SEQ ID NO: 61, SEQ ID NO: 124, or SEQ ID NO: 130, maintains a HCDR2 sequence of SEQ ID NO: 62, SEQ ID NO: 125, or SEQ ID NO: 131, maintains a HCDR3 sequence of SEQ ID NO: 78 or SEQ ID NO: 142, maintains a LCDR1 sequence of SEQ ID NO: 64, or SEQ ID NO: 133, maintains a LCDR2 sequence of SEQ ID NO: 65, or SEQ ID NO: 134, and maintains a LCDR3 sequence SEQ ID NO: 79.

In some embodiments, the antibody or antigen-binding fragment thereof, comprises a light chain that has at least 90, 91, 92, 93, 94, 95, 96, 97, 98, or 99% sequence identity to SEQ ID NO: 237, and a heavy chain that has at least 90, 91, 92, 93, 94, 95, 96, 97, 98, or 99% sequence identity to SEQ ID NO: 382 or SEQ ID NO: 383 (HC of MAB40), wherein the antibody, or antigen binding fragment thereof, maintains the sequences of the heavy chain and light chain CDRs of MAB40. In some embodiments, the antibody or antigen-binding fragment thereof, comprises a light chain that has at least 90, 91, 92, 93, 94, 95, 96, 97, 98, or 99% sequence identity to SEQ ID NO: 237, and a heavy chain that has at least 90, 91, 92, 93, 94, 95, 96, 97, 98, or 99% sequence identity to SEQ ID NO: 382 or SEQ ID NO: 383, wherein the antibody, or antigen binding fragment thereof, maintains a HCDR1 sequence of SEQ ID NO: 61, SEQ ID NO: 124, or SEQ ID NO: 130, maintains a HCDR2 sequence of SEQ ID NO: 62, SEQ ID NO: 125, or SEQ ID NO: 131, maintains a HCDR3 sequence of SEQ ID NO: 80 or SEQ ID NO: 143, maintains a LCDR1 sequence of SEQ ID NO: 64, or SEQ ID NO: 133, maintains a LCDR2 sequence of SEQ ID NO: 65, or SEQ ID NO: 134, and maintains a LCDR3 sequence SEQ ID NO: 81.

In some embodiments, the antibody or antigen-binding fragment thereof, comprises a light chain that has at least 90, 91, 92, 93, 94, 95, 96, 97, 98, or 99% sequence identity to SEQ ID NO: 238, and a heavy chain that has at least 90, 91, 92, 93, 94, 95, 96, 97, 98, or 99% sequence identity to SEQ ID NO: 384 or SEQ ID NO: 385 (HC of MAB41), wherein the antibody, or antigen binding fragment thereof, maintains the sequences of the heavy chain and light chain CDRs of MAB41. In some embodiments, the antibody or antigen-binding fragment thereof, comprises a light chain that has at least 90, 91, 92, 93, 94, 95, 96, 97, 98, or 99% sequence identity to SEQ ID NO: 238, and a heavy chain that has at least 90, 91, 92, 93, 94, 95, 96, 97, 98, or 99% sequence identity to SEQ ID NO: 384 or SEQ ID NO: 385, wherein the antibody, or antigen binding fragment thereof, maintains a HCDR1 sequence of SEQ ID NO: 82, SEQ ID NO: 126, or SEQ ID NO: 144, maintains a HCDR2 sequence of SEQ ID NO: 83, SEQ ID NO: 127, or SEQ ID NO: 145, maintains a HCDR3 sequence of SEQ ID NO: 84 or SEQ ID NO: 146, maintains a LCDR1 sequence of SEQ ID NO: 85, or SEQ ID NO: 147, maintains a LCDR2 sequence of SEQ ID NO: 86, or SEQ ID NO: 148, and maintains a LCDR3 sequence SEQ ID NO: 87.

In some embodiments, the antibody or antigen-binding fragment thereof, comprises a light chain that has at least 90, 91, 92, 93, 94, 95, 96, 97, 98, or 99% sequence identity to SEQ ID NO: 239, and a heavy chain that has at least 90, 91, 92, 93, 94, 95, 96, 97, 98, or 99% sequence identity to SEQ ID NO: 386 or SEQ ID NO: 387 (HC of MAB42), wherein the antibody, or antigen binding fragment thereof, maintains the sequences of the heavy chain and light chain CDRs of MAB42. In some embodiments, the antibody or antigen-binding fragment thereof, comprises a light chain that has at least 90, 91, 92, 93, 94, 95, 96, 97, 98, or 99% sequence identity to SEQ ID NO: 239, and a heavy chain that has at least 90, 91, 92, 93, 94, 95, 96, 97, 98, or 99% sequence identity to SEQ ID NO: 386 or SEQ ID NO: 387, wherein the antibody, or antigen binding fragment thereof, maintains a HCDR1 sequence of SEQ ID NO: 82, SEQ ID NO: 126, or SEQ ID NO: 144, maintains a HCDR2 sequence of SEQ ID NO: 83, SEQ ID NO: 127, or SEQ ID NO: 145, maintains a HCDR3 sequence of SEQ ID NO: 88 or SEQ ID NO: 149, maintains a LCDR1 sequence of SEQ ID NO: 85, or SEQ ID NO: 147, maintains a LCDR2 sequence of SEQ ID NO: 86, or SEQ ID NO: 148, and maintains a LCDR3 sequence SEQ ID NO: 89.

In some embodiments, the antibody or antigen-binding fragment thereof, comprises a light chain that has at least 90, 91, 92, 93, 94, 95, 96, 97, 98, or 99% sequence identity to SEQ ID NO: 240, and a heavy chain that has at least 90, 91, 92, 93, 94, 95, 96, 97, 98, or 99% sequence identity to SEQ ID NO: 388 or SEQ ID NO: 389 (HC of MAB43), wherein the antibody, or antigen binding fragment thereof, maintains the sequences of the heavy chain and light chain CDRs of MAB43. In some embodiments, the antibody or antigen-binding fragment thereof, comprises a light chain that has at least 90, 91, 92, 93, 94, 95, 96, 97, 98, or 99% sequence identity to SEQ ID NO: 240, and a heavy chain that has at least 90, 91, 92, 93, 94, 95, 96, 97, 98, or 99% sequence identity to SEQ ID NO: 388 or SEQ ID NO: 389, wherein the antibody, or antigen binding fragment thereof, maintains a HCDR1 sequence of SEQ ID NO: 82, SEQ ID NO: 126, or SEQ ID NO: 144, maintains a HCDR2 sequence of SEQ ID NO: 83, SEQ ID NO: 127, or SEQ ID NO: 145, maintains a HCDR3 sequence of SEQ ID NO: 90 or SEQ ID NO: 150, maintains a LCDR1 sequence of SEQ ID NO: 85, or SEQ ID NO: 147, maintains a LCDR2 sequence of SEQ ID NO: 86, or SEQ ID NO: 148, and maintains a LCDR3 sequence SEQ ID NO: 89.

In some embodiments, the antibody or antigen-binding fragment thereof, comprises a light chain that has at least 90, 91, 92, 93, 94, 95, 96, 97, 98, or 99% sequence identity to SEQ ID NO: 241, and a heavy chain that has at least 90, 91, 92, 93, 94, 95, 96, 97, 98, or 99% sequence identity to SEQ ID NO: 390 or SEQ ID NO: 391 (HC of MAB44), wherein the antibody, or antigen binding fragment thereof, maintains the sequences of the heavy chain and light chain CDRs of MAB44. In some embodiments, the antibody or antigen-binding fragment thereof, comprises a light chain that has at least 90, 91, 92, 93, 94, 95, 96, 97, 98, or 99% sequence identity to SEQ ID NO: 241, and a heavy chain that has at least 90, 91, 92, 93, 94, 95, 96, 97, 98, or 99% sequence identity to SEQ ID NO: 390 or SEQ ID NO: 391, wherein the antibody, or antigen binding fragment thereof, maintains a HCDR1 sequence of SEQ ID NO: 82, SEQ ID NO: 126, or SEQ ID NO: 144, maintains a HCDR2 sequence of SEQ ID NO: 83, SEQ ID NO: 127, or SEQ ID NO: 145, maintains a HCDR3 sequence of SEQ ID NO: 91 or SEQ ID NO: 151, maintains a LCDR1 sequence of SEQ ID NO: 85, or SEQ ID NO: 147, maintains a LCDR2 sequence of SEQ ID NO: 86, or SEQ ID NO: 148, and maintains a LCDR3 sequence SEQ ID NO: 92.

In some embodiments, the antibody or antigen-binding fragment thereof, comprises a light chain that has at least 90, 91, 92, 93, 94, 95, 96, 97, 98, or 99% sequence identity to SEQ ID NO: 242, and a heavy chain that has at least 90, 91, 92, 93, 94, 95, 96, 97, 98, or 99% sequence identity to SEQ ID NO: 392 or SEQ ID NO: 393 (HC of MAB45), wherein the antibody, or antigen binding fragment thereof, maintains the sequences of the heavy chain and light chain CDRs of MAB45. In some embodiments, the antibody or antigen-binding fragment thereof, comprises a light chain that has at least 90, 91, 92, 93, 94, 95, 96, 97, 98, or 99% sequence identity to SEQ ID NO: 242, and a heavy chain that has at least 90, 91, 92, 93, 94, 95, 96, 97, 98, or 99% sequence identity to SEQ ID NO: 392 or SEQ ID NO: 393, wherein the antibody, or antigen binding fragment thereof, maintains a HCDR1 sequence of SEQ ID NO: 82, SEQ ID NO: 126, or SEQ ID NO: 144, maintains a HCDR2 sequence of SEQ ID NO: 83, SEQ ID NO: 127, or SEQ ID NO: 145, maintains a HCDR3 sequence of SEQ ID NO: 93 or SEQ ID NO: 152, maintains a LCDR1 sequence of SEQ ID NO: 85, or SEQ ID NO: 147, maintains a LCDR2 sequence of SEQ ID NO: 86, or SEQ ID NO: 148, and maintains a LCDR3 sequence SEQ ID NO: 94.

In some embodiments, the antibody or antigen-binding fragment thereof, comprises a light chain that has at least 90, 91, 92, 93, 94, 95, 96, 97, 98, or 99% sequence identity to SEQ ID NO: 243, and a heavy chain that has at least 90, 91, 92, 93, 94, 95, 96, 97, 98, or 99% sequence identity to SEQ ID NO: 394 or SEQ ID NO: 395 (HC of MAB46), wherein the antibody, or antigen binding fragment thereof, maintains the sequences of the heavy chain and light chain CDRs of MAB46. In some embodiments, the antibody or antigen-binding fragment thereof, comprises a light chain that has at least 90, 91, 92, 93, 94, 95, 96, 97, 98, or 99% sequence identity to SEQ ID NO: 243, and a heavy chain that has at least 90, 91, 92, 93, 94, 95, 96, 97, 98, or 99% sequence identity to SEQ ID NO: 394 or SEQ ID NO: 395, wherein the antibody, or antigen binding fragment thereof, maintains a HCDR1 sequence of SEQ ID NO: 82, SEQ ID NO: 126, or SEQ ID NO: 144, maintains a HCDR2 sequence of SEQ ID NO: 83, SEQ ID NO: 127, or SEQ ID NO: 145, maintains a HCDR3 sequence of SEQ ID NO: 84 or SEQ ID NO: 146, maintains a LCDR1 sequence of SEQ ID NO: 85, or SEQ ID NO: 147, maintains a LCDR2 sequence of SEQ ID NO: 86, or SEQ ID NO: 148, and maintains a LCDR3 sequence SEQ ID NO: 95.

In some embodiments, the antibody or antigen-binding fragment thereof, comprises a light chain that has at least 90, 91, 92, 93, 94, 95, 96, 97, 98, or 99% sequence identity to SEQ ID NO: 244, and a heavy chain that has at least 90, 91, 92, 93, 94, 95, 96, 97, 98, or 99% sequence identity to SEQ ID NO: 396 or SEQ ID NO: 397 (HC of MAB47), wherein the antibody, or antigen binding fragment thereof, maintains the sequences of the heavy chain and light chain CDRs of MAB47. In some embodiments, the antibody or antigen-binding fragment thereof, comprises a light chain that has at least 90, 91, 92, 93, 94, 95, 96, 97, 98, or 99% sequence identity to SEQ ID NO: 244, and a heavy chain that has at least 90, 91, 92, 93, 94, 95, 96, 97, 98, or 99% sequence identity to SEQ ID NO: 396 or SEQ ID NO: 397, wherein the antibody, or antigen binding fragment thereof, maintains a HCDR1 sequence of SEQ ID NO: 82, SEQ ID NO: 126, or SEQ ID NO: 144, maintains a HCDR2 sequence of SEQ ID NO: 83, SEQ ID NO: 127, or SEQ ID NO: 145, maintains a HCDR3 sequence of SEQ ID NO: 96 or SEQ ID NO: 153, maintains a LCDR1 sequence of SEQ ID NO: 85, or SEQ ID NO: 147, maintains a LCDR2 sequence of SEQ ID NO: 86, or SEQ ID NO: 148, and maintains a LCDR3 sequence SEQ ID NO: 97.

In some embodiments, the antibody or antigen-binding fragment thereof, comprises a light chain that has at least 90, 91, 92, 93, 94, 95, 96, 97, 98, or 99% sequence identity to SEQ ID NO: 245, and a heavy chain that has at least 90, 91, 92, 93, 94, 95, 96, 97, 98, or 99% sequence identity to SEQ ID NO: 398 or SEQ ID NO: 399 (HC of MAB48), wherein the antibody, or antigen binding fragment thereof, maintains the sequences of the heavy chain and light chain CDRs of MAB48. In some embodiments, the antibody or antigen-binding fragment thereof, comprises a light chain that has at least 90, 91, 92, 93, 94, 95, 96, 97, 98, or 99% sequence identity to SEQ ID NO: 245, and a heavy chain that has at least 90, 91, 92, 93, 94, 95, 96, 97, 98, or 99% sequence identity to SEQ ID NO: 398 or SEQ ID NO: 399, wherein the antibody, or antigen binding fragment thereof, maintains a HCDR1 sequence of SEQ ID NO: 82, SEQ ID NO: 126, or SEQ ID NO: 144, maintains a HCDR2 sequence of SEQ ID NO: 83, SEQ ID NO: 127, or SEQ ID NO: 145, maintains a HCDR3 sequence of SEQ ID NO: 98 or SEQ ID NO: 154, maintains a LCDR1 sequence of SEQ ID NO: 85, or SEQ ID NO: 147, maintains a LCDR2 sequence of SEQ ID NO: 86, or SEQ ID NO: 148, and maintains a LCDR3 sequence SEQ ID NO: 99.

In some embodiments, the antibody or antigen-binding fragment thereof, comprises a light chain that has at least 90, 91, 92, 93, 94, 95, 96, 97, 98, or 99% sequence identity to SEQ ID NO: 246, and a heavy chain that has at least 90, 91, 92, 93, 94, 95, 96, 97, 98, or 99% sequence identity to SEQ ID NO: 400 or SEQ ID NO: 401 (HC of MAB49), wherein the antibody, or antigen binding fragment thereof, maintains the sequences of the heavy chain and light chain CDRs of MAB49. In some embodiments, the antibody or antigen-binding fragment thereof, comprises a light chain that has at least 90, 91, 92, 93, 94, 95, 96, 97, 98, or 99% sequence identity to SEQ ID NO: 246, and a heavy chain that has at least 90, 91, 92, 93, 94, 95, 96, 97, 98, or 99% sequence identity to SEQ ID NO: 400 or SEQ ID NO: 401, wherein the antibody, or antigen binding fragment thereof, maintains a HCDR1 sequence of SEQ ID NO: 82, SEQ ID NO: 126, or SEQ ID NO: 144, maintains a HCDR2 sequence of SEQ ID NO: 83, SEQ ID NO: 127, or SEQ ID NO: 145, maintains a HCDR3 sequence of SEQ ID NO: 100 or SEQ ID NO: 155, maintains a LCDR1 sequence of SEQ ID NO: 85, or SEQ ID NO: 147, maintains a LCDR2 sequence of SEQ ID NO: 86, or SEQ ID NO: 148, and maintains a LCDR3 sequence SEQ ID NO: 101.

In some embodiments, the antibody or antigen-binding fragment thereof, comprises a light chain that has at least 90, 91, 92, 93, 94, 95, 96, 97, 98, or 99% sequence identity to SEQ ID NO: 247, and a heavy chain that has at least 90, 91, 92, 93, 94, 95, 96, 97, 98, or 99% sequence identity to SEQ ID NO: 402 or SEQ ID NO: 403 (HC of MAB50), wherein the antibody, or antigen binding fragment thereof, maintains the sequences of the heavy chain and light chain CDRs of MAB50. In some embodiments, the antibody or antigen-binding fragment thereof, comprises a light chain that has at least 90, 91, 92, 93, 94, 95, 96, 97, 98, or 99% sequence identity to SEQ ID NO: 247, and a heavy chain that has at least 90, 91, 92, 93, 94, 95, 96, 97, 98, or 99% sequence identity to SEQ ID NO: 402 or SEQ ID NO: 403, wherein the antibody, or antigen binding fragment thereof, maintains a HCDR1 sequence of SEQ ID NO: 82, SEQ ID NO: 126, or SEQ ID NO: 144, maintains a HCDR2 sequence of SEQ ID NO: 83, SEQ ID NO: 127, or SEQ ID NO: 145, maintains a HCDR3 sequence of SEQ ID NO: 100 or SEQ ID NO: 155, maintains a LCDR1 sequence of SEQ ID NO: 85, or SEQ ID NO: 147, maintains a LCDR2 sequence of SEQ ID NO: 86, or SEQ ID NO: 148, and maintains a LCDR3 sequence SEQ ID NO: 102.

In some embodiments, the antibody or antigen-binding fragment thereof, comprises a light chain that has at least 90, 91, 92, 93, 94, 95, 96, 97, 98, or 99% sequence identity to SEQ ID NO: 248, and a heavy chain that has at least 90, 91, 92, 93, 94, 95, 96, 97, 98, or 99% sequence identity to SEQ ID NO: 404 or SEQ ID NO: 405 (HC of MAB51), wherein the antibody, or antigen binding fragment thereof, maintains the sequences of the heavy chain and light chain CDRs of MAB51. In some embodiments, the antibody or antigen-binding fragment thereof, comprises a light chain that has at least 90, 91, 92, 93, 94, 95, 96, 97, 98, or 99% sequence identity to SEQ ID NO: 248, and a heavy chain that has at least 90, 91, 92, 93, 94, 95, 96, 97, 98, or 99% sequence identity to SEQ ID NO: 404 or SEQ ID NO: 405, wherein the antibody, or antigen binding fragment thereof, maintains a HCDR1 sequence of SEQ ID NO: 103, SEQ ID NO: 128, or SEQ ID NO: 156, maintains a HCDR2 sequence of SEQ ID NO: 104, SEQ ID NO: 129, or SEQ ID NO: 157, maintains a HCDR3 sequence of SEQ ID NO: 105 or SEQ ID NO: 158, maintains a LCDR1 sequence of SEQ ID NO: 106, or SEQ ID NO: 159, maintains a LCDR2 sequence of SEQ ID NO: 107, or SEQ ID NO: 160, and maintains a LCDR3 sequence SEQ ID NO: 108.

In some embodiments, the antibody or antigen-binding fragment thereof, comprises a light chain that has at least 90, 91, 92, 93, 94, 95, 96, 97, 98, or 99% sequence identity to SEQ ID NO: 249, and a heavy chain that has at least 90, 91, 92, 93, 94, 95, 96, 97, 98, or 99% sequence identity to SEQ ID NO: 406 or SEQ ID NO: 407 (HC of MAB52), wherein the antibody, or antigen binding fragment thereof, maintains the sequences of the heavy chain and light chain CDRs of MAB52. In some embodiments, the antibody or antigen-binding fragment thereof, comprises a light chain that has at least 90, 91, 92, 93, 94, 95, 96, 97, 98, or 99% sequence identity to SEQ ID NO: 249, and a heavy chain that has at least 90, 91, 92, 93, 94, 95, 96, 97, 98, or 99% sequence identity to SEQ ID NO: 406 or SEQ ID NO: 407, wherein the antibody, or antigen binding fragment thereof, maintains a HCDR1 sequence of SEQ ID NO: 103, SEQ ID NO: 128, or SEQ ID NO: 156, maintains a HCDR2 sequence of SEQ ID NO: 104, SEQ ID NO: 129, or SEQ ID NO: 157, maintains a HCDR3 sequence of SEQ ID NO: 109 or SEQ ID NO: 161, maintains a LCDR1 sequence of SEQ ID NO: 106, or SEQ ID NO: 159, maintains a LCDR2 sequence of SEQ ID NO: 107, or SEQ ID NO: 160, and maintains a LCDR3 sequence SEQ ID NO: 110.

In some embodiments, the antibody or antigen-binding fragment thereof, comprises a light chain that has at least 90, 91, 92, 93, 94, 95, 96, 97, 98, or 99% sequence identity to SEQ ID NO: 250, and a heavy chain that has at least 90, 91, 92, 93, 94, 95, 96, 97, 98, or 99% sequence identity to SEQ ID NO: 408 or SEQ ID NO: 409 (HC of MAB53), wherein the antibody, or antigen binding fragment thereof, maintains the sequences of the heavy chain and light chain CDRs of MAB53. In some embodiments, the antibody or antigen-binding fragment thereof, comprises a light chain that has at least 90, 91, 92, 93, 94, 95, 96, 97, 98, or 99% sequence identity to SEQ ID NO: 250, and a heavy chain that has at least 90, 91, 92, 93, 94, 95, 96, 97, 98, or 99% sequence identity to SEQ ID NO: 408 or SEQ ID NO: 409, wherein the antibody, or antigen binding fragment thereof, maintains a HCDR1 sequence of SEQ ID NO: 103, SEQ ID NO: 128, or SEQ ID NO: 156, maintains a HCDR2 sequence of SEQ ID NO: 104, SEQ ID NO: 129, or SEQ ID NO: 157, maintains a HCDR3 sequence of SEQ ID NO: 111 or SEQ ID NO: 162, maintains a LCDR1 sequence of SEQ ID NO: 106, or SEQ ID NO: 159, maintains a LCDR2 sequence of SEQ ID NO: 107, or SEQ ID NO: 160, and maintains a LCDR3 sequence SEQ ID NO: 112.

In some embodiments, the antibody or antigen-binding fragment thereof, comprises a light chain that has at least 90, 91, 92, 93, 94, 95, 96, 97, 98, or 99% sequence identity to SEQ ID NO: 251, and a heavy chain that has at least 90, 91, 92, 93, 94, 95, 96, 97, 98, or 99% sequence identity to SEQ ID NO: 410 or SEQ ID NO: 411 (HC of MAB54), wherein the antibody, or antigen binding fragment thereof, maintains the sequences of the heavy chain and light chain CDRs of MAB54. In some embodiments, the antibody or antigen-binding fragment thereof, comprises a light chain that has at least 90, 91, 92, 93, 94, 95, 96, 97, 98, or 99% sequence identity to SEQ ID NO: 251, and a heavy chain that has at least 90, 91, 92, 93, 94, 95, 96, 97, 98, or 99% sequence identity to SEQ ID NO: 410 or SEQ ID NO: 411, wherein the antibody, or antigen binding fragment thereof, maintains a HCDR1 sequence of SEQ ID NO: 103, SEQ ID NO: 128, or SEQ ID NO: 156, maintains a HCDR2 sequence of SEQ ID NO: 104, SEQ ID NO: 129, or SEQ ID NO: 157, maintains a HCDR3 sequence of SEQ ID NO: 105 or SEQ ID NO: 158, maintains a LCDR1 sequence of SEQ ID NO: 106, or SEQ ID NO: 159, maintains a LCDR2 sequence of SEQ ID NO: 107, or SEQ ID NO: 160, and maintains a LCDR3 sequence SEQ ID NO: 113.

In some embodiments, the antibody or antigen-binding fragment thereof, comprises a light chain that has at least 90, 91, 92, 93, 94, 95, 96, 97, 98, or 99% sequence identity to SEQ ID NO: 252, and a heavy chain that has at least 90, 91, 92, 93, 94, 95, 96, 97, 98, or 99% sequence identity to SEQ ID NO: 412 or SEQ ID NO: 413 (HC of MAB55), wherein the antibody, or antigen binding fragment thereof, maintains the sequences of the heavy chain and light chain CDRs of MAB55. In some embodiments, the antibody or antigen-binding fragment thereof, comprises a light chain that has at least 90, 91, 92, 93, 94, 95, 96, 97, 98, or 99% sequence identity to SEQ ID NO: 252, and a heavy chain that has at least 90, 91, 92, 93, 94, 95, 96, 97, 98, or 99% sequence identity to SEQ ID NO: 412 or SEQ ID NO: 413, wherein the antibody, or antigen binding fragment thereof, maintains a HCDR1 sequence of SEQ ID NO: 103, SEQ ID NO: 128, or SEQ ID NO: 156, maintains a HCDR2 sequence of SEQ ID NO: 104, SEQ ID NO: 129, or SEQ ID NO: 157, maintains a HCDR3 sequence of SEQ ID NO: 114 or SEQ ID NO: 163, maintains a LCDR1 sequence of SEQ ID NO: 106, or SEQ ID NO: 159, maintains a LCDR2 sequence of SEQ ID NO: 107, or SEQ ID NO: 160, and maintains a LCDR3 sequence SEQ ID NO: 115.

In some embodiments, the antibody or antigen-binding fragment thereof, comprises a light chain that has at least 90, 91, 92, 93, 94, 95, 96, 97, 98, or 99% sequence identity to SEQ ID NO: 253, and a heavy chain that has at least 90, 91, 92, 93, 94, 95, 96, 97, 98, or 99% sequence identity to SEQ ID NO: 414 or SEQ ID NO: 415 (HC of MAB56), wherein the antibody, or antigen binding fragment thereof, maintains the sequences of the heavy chain and light chain CDRs of MAB56. In some embodiments, the antibody or antigen-binding fragment thereof, comprises a light chain that has at least 90, 91, 92, 93, 94, 95, 96, 97, 98, or 99% sequence identity to SEQ ID NO: 253, and a heavy chain that has at least 90, 91, 92, 93, 94, 95, 96, 97, 98, or 99% sequence identity to SEQ ID NO: 414 or SEQ ID NO: 415, wherein the antibody, or antigen binding fragment thereof, maintains a HCDR1 sequence of SEQ ID NO: 103, SEQ ID NO: 128, or SEQ ID NO: 156, maintains a HCDR2 sequence of SEQ ID NO: 104, SEQ ID NO: 129, or SEQ ID NO: 157, maintains a HCDR3 sequence of SEQ ID NO: 116 or SEQ ID NO: 164, maintains a LCDR1 sequence of SEQ ID NO: 106, or SEQ ID NO: 159, maintains a LCDR2 sequence of SEQ ID NO: 107, or SEQ ID NO: 160, and maintains a LCDR3 sequence SEQ ID NO: 113.

In some embodiments, the antibody or antigen-binding fragment thereof, comprises a light chain that has at least 90, 91, 92, 93, 94, 95, 96, 97, 98, or 99% sequence identity to SEQ ID NO: 254, and a heavy chain that has at least 90, 91, 92, 93, 94, 95, 96, 97, 98, or 99% sequence identity to SEQ ID NO: 416 or SEQ ID NO: 417 (HC of MAB57), wherein the antibody, or antigen binding fragment thereof, maintains the sequences of the heavy chain and light chain CDRs of MAB57. In some embodiments, the antibody or antigen-binding fragment thereof, comprises a light chain that has at least 90, 91, 92, 93, 94, 95, 96, 97, 98, or 99% sequence identity to SEQ ID NO: 254, and a heavy chain that has at least 90, 91, 92, 93, 94, 95, 96, 97, 98, or 99% sequence identity to SEQ ID NO: 416 or SEQ ID NO: 417, wherein the antibody, or antigen binding fragment thereof, maintains a HCDR1 sequence of SEQ ID NO: 103, SEQ ID NO: 128, or SEQ ID NO: 156, maintains a HCDR2 sequence of SEQ ID NO: 104, SEQ ID NO: 129, or SEQ ID NO: 157, maintains a HCDR3 sequence of SEQ ID NO: 117 or SEQ ID NO: 165, maintains a LCDR1 sequence of SEQ ID NO: 106, or SEQ ID NO: 159, maintains a LCDR2 sequence of SEQ ID NO: 107, or SEQ ID NO: 160, and maintains a LCDR3 sequence SEQ ID NO: 118.

In some embodiments, the antibody or antigen-binding fragment thereof, comprises a light chain that has at least 90, 91, 92, 93, 94, 95, 96, 97, 98, or 99% sequence identity to SEQ ID NO: 255, and a heavy chain that has at least 90, 91, 92, 93, 94, 95, 96, 97, 98, or 99% sequence identity to SEQ ID NO: 418 or SEQ ID NO: 419 (HC of MAB58), wherein the antibody, or antigen binding fragment thereof, maintains the sequences of the heavy chain and light chain CDRs of MAB58. In some embodiments, the antibody or antigen-binding fragment thereof, comprises a light chain that has at least 90, 91, 92, 93, 94, 95, 96, 97, 98, or 99% sequence identity to SEQ ID NO: 255, and a heavy chain that has at least 90, 91, 92, 93, 94, 95, 96, 97, 98, or 99% sequence identity to SEQ ID NO: 418 or SEQ ID NO: 419, wherein the antibody, or antigen binding fragment thereof, maintains a HCDR1 sequence of SEQ ID NO: 103, SEQ ID NO: 128, or SEQ ID NO: 156, maintains a HCDR2 sequence of SEQ ID NO: 104, SEQ ID NO: 129, or SEQ ID NO: 157, maintains a HCDR3 sequence of SEQ ID NO: 116 or SEQ ID NO: 164, maintains a LCDR1 sequence of SEQ ID NO: 106, or SEQ ID NO: 159, maintains a LCDR2 sequence of SEQ ID NO: 107, or SEQ ID NO: 160, and maintains a LCDR3 sequence SEQ ID NO: 119.

In some embodiments, the antibody or antigen-binding fragment thereof, comprises a light chain that has at least 90, 91, 92, 93, 94, 95, 96, 97, 98, or 99% sequence identity to SEQ ID NO: 256, and a heavy chain that has at least 90, 91, 92, 93, 94, 95, 96, 97, 98, or 99% sequence identity to SEQ ID NO: 420 or SEQ ID NO: 421 (HC of MAB59), wherein the antibody, or antigen binding fragment thereof, maintains the sequences of the heavy chain and light chain CDRs of MAB59. In some embodiments, the antibody or antigen-binding fragment thereof, comprises a light chain that has at least 90, 91, 92, 93, 94, 95, 96, 97, 98, or 99% sequence identity to SEQ ID NO: 256, and a heavy chain that has at least 90, 91, 92, 93, 94, 95, 96, 97, 98, or 99% sequence identity to SEQ ID NO: 420 or SEQ ID NO: 421, wherein the antibody, or antigen binding fragment thereof, maintains a HCDR1 sequence of SEQ ID NO: 103, SEQ ID NO: 128, or SEQ ID NO: 156, maintains a HCDR2 sequence of SEQ ID NO: 104, SEQ ID NO: 129, or SEQ ID NO: 157, maintains a HCDR3 sequence of SEQ ID NO: 120 or SEQ ID NO: 166, maintains a LCDR1 sequence of SEQ ID NO: 106, or SEQ ID NO: 159, maintains a LCDR2 sequence of SEQ ID NO: 107, or SEQ ID NO: 160, and maintains a LCDR3 sequence SEQ ID NO: 121.

In some embodiments, the antibody or antigen-binding fragment thereof, comprises a light chain that has at least 90, 91, 92, 93, 94, 95, 96, 97, 98, or 99% sequence identity to SEQ ID NO: 257, and a heavy chain that has at least 90, 91, 92, 93, 94, 95, 96, 97, 98, or 99% sequence identity to SEQ ID NO: 422 or SEQ ID NO: 423 (HC of MAB60), wherein the antibody, or antigen binding fragment thereof, maintains the sequences of the heavy chain and light chain CDRs of MAB60. In some embodiments, the antibody or antigen-binding fragment thereof, comprises a light chain that has at least 90, 91, 92, 93, 94, 95, 96, 97, 98, or 99% sequence identity to SEQ ID NO: 257, and a heavy chain that has at least 90, 91, 92, 93, 94, 95, 96, 97, 98, or 99% sequence identity to SEQ ID NO: 422 or SEQ ID NO: 423, wherein the antibody, or antigen binding fragment thereof, maintains a HCDR1 sequence of SEQ ID NO: 103, SEQ ID NO: 128, or SEQ ID NO: 156, maintains a HCDR2 sequence of SEQ ID NO: 104, SEQ ID NO: 129, or SEQ ID NO: 157, maintains a HCDR3 sequence of SEQ ID NO: 122 or SEQ ID NO: 167, maintains a LCDR1 sequence of SEQ ID NO: 106, or SEQ ID NO: 159, maintains a LCDR2 sequence of SEQ ID NO: 107, or SEQ ID NO: 160, and maintains a LCDR3 sequence SEQ ID NO: 123.

In some embodiments, the antibody, or antigen-binding fragment thereof, comprises a light chain having a sequence of SEQ ID NO: 228 and a heavy chain that comprises a sequence of SEQ ID NO: 168 or SEQ ID NO: 169.

In some embodiments, the antibody, or antigen-binding fragment thereof, comprises a light chain having a sequence of SEQ ID NO: 229 and a heavy chain that comprises a sequence of SEQ ID NO: 170 or SEQ ID NO: 171.

In some embodiments, the antibody, or antigen-binding fragment thereof, comprises a light chain having a sequence of SEQ ID NO: 230 and a heavy chain that comprises a sequence of SEQ ID NO: 172 or SEQ ID NO: 173.

In some embodiments, the antibody, or antigen-binding fragment thereof, comprises a light chain having a sequence of SEQ ID NO: 231 and a heavy chain that comprises a sequence of SEQ ID NO: 174 or SEQ ID NO: 175.

In some embodiments, the antibody, or antigen-binding fragment thereof, comprises a light chain having a sequence of SEQ ID NO: 232 and a heavy chain that comprises a sequence of SEQ ID NO: 176 or SEQ ID NO: 177.

In some embodiments, the antibody, or antigen-binding fragment thereof, comprises a light chain having a sequence of SEQ ID NO: 233 and a heavy chain that comprises a sequence of SEQ ID NO: 178 or SEQ ID NO: 179.

In some embodiments, the antibody, or antigen-binding fragment thereof, comprises a light chain having a sequence of SEQ ID NO: 234 and a heavy chain that comprises a sequence of SEQ ID NO: 180 or SEQ ID NO: 181.

In some embodiments, the antibody, or antigen-binding fragment thereof, comprises a light chain having a sequence of SEQ ID NO: 235 and a heavy chain that comprises a sequence of SEQ ID NO: 182 or SEQ ID NO: 183.

In some embodiments, the antibody, or antigen-binding fragment thereof, comprises a light chain having a sequence of SEQ ID NO: 236 and a heavy chain that comprises a sequence of SEQ ID NO: 184 or SEQ ID NO: 185.

In some embodiments, the antibody, or antigen-binding fragment thereof, comprises a light chain having a sequence of SEQ ID NO: 237 and a heavy chain that comprises a sequence of SEQ ID NO: 186 or SEQ ID NO: 187.

In some embodiments, the antibody, or antigen-binding fragment thereof, comprises a light chain having a sequence of SEQ ID NO: 238 and a heavy chain that comprises a sequence of SEQ ID NO: 188 or SEQ ID NO: 189.

In some embodiments, the antibody, or antigen-binding fragment thereof, comprises a light chain having a sequence of SEQ ID NO: 239 and a heavy chain that comprises a sequence of SEQ ID NO: 190 or SEQ ID NO: 191.

In some embodiments, the antibody, or antigen-binding fragment thereof, comprises a light chain having a sequence of SEQ ID NO: 240 and a heavy chain that comprises a sequence of SEQ ID NO: 192 or SEQ ID NO: 193.

In some embodiments, the antibody, or antigen-binding fragment thereof, comprises a light chain having a sequence of SEQ ID NO: 241 and a heavy chain that comprises a sequence of SEQ ID NO: 194 or SEQ ID NO: 195.

In some embodiments, the antibody, or antigen-binding fragment thereof, comprises a light chain having a sequence of SEQ ID NO: 242 and a heavy chain that comprises a sequence of SEQ ID NO: 196 or SEQ ID NO: 197.

In some embodiments, the antibody, or antigen-binding fragment thereof, comprises a light chain having a sequence of SEQ ID NO: 243 and a heavy chain that comprises a sequence of SEQ ID NO: 198 or SEQ ID NO: 199.

In some embodiments, the antibody, or antigen-binding fragment thereof, comprises a light chain having a sequence of SEQ ID NO: 244 and a heavy chain that comprises a sequence of SEQ ID NO: 200 or SEQ ID NO: 201.

In some embodiments, the antibody, or antigen-binding fragment thereof, comprises a light chain having a sequence of SEQ ID NO: 245 and a heavy chain that comprises a sequence of SEQ ID NO: 202 or SEQ ID NO: 203.

In some embodiments, the antibody, or antigen-binding fragment thereof, comprises a light chain having a sequence of SEQ ID NO: 246 and a heavy chain that comprises a sequence of SEQ ID NO: 204 or SEQ ID NO: 205.

In some embodiments, the antibody, or antigen-binding fragment thereof, comprises a light chain having a sequence of SEQ ID NO: 247 and a heavy chain that comprises a sequence of SEQ ID NO: 206 or SEQ ID NO: 207.

In some embodiments, the antibody, or antigen-binding fragment thereof, comprises a light chain having a sequence of SEQ ID NO: 248 and a heavy chain that comprises a sequence of SEQ ID NO: 208 or SEQ ID NO: 209.

In some embodiments, the antibody, or antigen-binding fragment thereof, comprises a light chain having a sequence of SEQ ID NO: 249 and a heavy chain that comprises a sequence of SEQ ID NO: 210 or SEQ ID NO: 211.

In some embodiments, the antibody, or antigen-binding fragment thereof, comprises a light chain having a sequence of SEQ ID NO: 250 and a heavy chain that comprises a sequence of SEQ ID NO: 212 or SEQ ID NO: 213.

In some embodiments, the antibody, or antigen-binding fragment thereof, comprises a light chain having a sequence of SEQ ID NO: 251 and a heavy chain that comprises a sequence of SEQ ID NO: 214 or SEQ ID NO: 215.

In some embodiments, the antibody, or antigen-binding fragment thereof, comprises a light chain having a sequence of SEQ ID NO: 252 and a heavy chain that comprises a sequence of SEQ ID NO: 216 or SEQ ID NO: 217.

In some embodiments, the antibody, or antigen-binding fragment thereof, comprises a light chain having a sequence of SEQ ID NO: 253 and a heavy chain that comprises a sequence of SEQ ID NO: 218 or SEQ ID NO: 219.

In some embodiments, the antibody, or antigen-binding fragment thereof, comprises a light chain having a sequence of SEQ ID NO: 254 and a heavy chain that comprises a sequence of SEQ ID NO: 220 or SEQ ID NO: 221.

In some embodiments, the antibody, or antigen-binding fragment thereof, comprises a light chain having a sequence of SEQ ID NO: 255 and a heavy chain that comprises a sequence of SEQ ID NO: 222 or SEQ ID NO: 223.

In some embodiments, the antibody, or antigen-binding fragment thereof, comprises a light chain having a sequence of SEQ ID NO: 256 and a heavy chain that comprises a sequence of SEQ ID NO: 224 or SEQ ID NO: 225.

In some embodiments, the antibody, or antigen-binding fragment thereof, comprises a light chain having a sequence of SEQ ID NO: 257 and a heavy chain that comprises a sequence of SEQ ID NO: 226 or SEQ ID NO: 227.

In some embodiments, the antibody, or antigen-binding fragment thereof, comprises a light chain having a sequence of SEQ ID NO: 228 and a heavy chain that comprises a sequence of SEQ ID NO: 364 or SEQ ID NO: 365.

In some embodiments, the antibody, or antigen-binding fragment thereof, comprises a light chain having a sequence of SEQ ID NO: 229 and a heavy chain that comprises a sequence of SEQ ID NO: 366 or SEQ ID NO: 367.

In some embodiments, the antibody, or antigen-binding fragment thereof, comprises a light chain having a sequence of SEQ ID NO: 230 and a heavy chain that comprises a sequence of SEQ ID NO: 368 or SEQ ID NO: 369.

In some embodiments, the antibody, or antigen-binding fragment thereof, comprises a light chain having a sequence of SEQ ID NO: 231 and a heavy chain that comprises a sequence of SEQ ID NO: 370 or SEQ ID NO: 371.

In some embodiments, the antibody, or antigen-binding fragment thereof, comprises a light chain having a sequence of SEQ ID NO: 232 and a heavy chain that comprises a sequence of SEQ ID NO: 372 or SEQ ID NO: 373.

In some embodiments, the antibody, or antigen-binding fragment thereof, comprises a light chain having a sequence of SEQ ID NO: 233 and a heavy chain that comprises a sequence of SEQ ID NO: 374 or SEQ ID NO: 375.

In some embodiments, the antibody, or antigen-binding fragment thereof, comprises a light chain having a sequence of SEQ ID NO: 234 and a heavy chain that comprises a sequence of SEQ ID NO: 376 or SEQ ID NO: 377.

In some embodiments, the antibody, or antigen-binding fragment thereof, comprises a light chain having a sequence of SEQ ID NO: 235 and a heavy chain that comprises a sequence of SEQ ID NO: 378 or SEQ ID NO: 379.

In some embodiments, the antibody, or antigen-binding fragment thereof, comprises a light chain having a sequence of SEQ ID NO: 236 and a heavy chain that comprises a sequence of SEQ ID NO: 380 or SEQ ID NO: 381.

In some embodiments, the antibody, or antigen-binding fragment thereof, comprises a light chain having a sequence of SEQ ID NO: 237 and a heavy chain that comprises a sequence of SEQ ID NO: 382 or SEQ ID NO: 383.

In some embodiments, the antibody, or antigen-binding fragment thereof, comprises a light chain having a sequence of SEQ ID NO: 238 and a heavy chain that comprises a sequence of SEQ ID NO: 384 or SEQ ID NO: 385.

In some embodiments, the antibody, or antigen-binding fragment thereof, comprises a light chain having a sequence of SEQ ID NO: 239 and a heavy chain that comprises a sequence of SEQ ID NO: 386 or SEQ ID NO: 387.

In some embodiments, the antibody, or antigen-binding fragment thereof, comprises a light chain having a sequence of SEQ ID NO: 240 and a heavy chain that comprises a sequence of SEQ ID NO: 388 or SEQ ID NO: 389.

In some embodiments, the antibody, or antigen-binding fragment thereof, comprises a light chain having a sequence of SEQ ID NO: 241 and a heavy chain that comprises a sequence of SEQ ID NO: 390 or SEQ ID NO: 391.

In some embodiments, the antibody, or antigen-binding fragment thereof, comprises a light chain having a sequence of SEQ ID NO: 242 and a heavy chain that comprises a sequence of SEQ ID NO: 392 or SEQ ID NO: 393.

In some embodiments, the antibody, or antigen-binding fragment thereof, comprises a light chain having a sequence of SEQ ID NO: 243 and a heavy chain that comprises a sequence of SEQ ID NO: 394 or SEQ ID NO: 395.

In some embodiments, the antibody, or antigen-binding fragment thereof, comprises a light chain having a sequence of SEQ ID NO: 244 and a heavy chain that comprises a sequence of SEQ ID NO: 396 or SEQ ID NO: 397.

In some embodiments, the antibody, or antigen-binding fragment thereof, comprises a light chain having a sequence of SEQ ID NO: 245 and a heavy chain that comprises a sequence of SEQ ID NO: 398 or SEQ ID NO: 399.

In some embodiments, the antibody, or antigen-binding fragment thereof, comprises a light chain having a sequence of SEQ ID NO: 246 and a heavy chain that comprises a sequence of SEQ ID NO: 400 or SEQ ID NO: 401.

In some embodiments, the antibody, or antigen-binding fragment thereof, comprises a light chain having a sequence of SEQ ID NO: 247 and a heavy chain that comprises a sequence of SEQ ID NO: 402 or SEQ ID NO: 403.

In some embodiments, the antibody, or antigen-binding fragment thereof, comprises a light chain having a sequence of SEQ ID NO: 248 and a heavy chain that comprises a sequence of SEQ ID NO: 404 or SEQ ID NO: 405.

In some embodiments, the antibody, or antigen-binding fragment thereof, comprises a light chain having a sequence of SEQ ID NO: 249 and a heavy chain that comprises a sequence of SEQ ID NO: 406 or SEQ ID NO: 407.

In some embodiments, the antibody, or antigen-binding fragment thereof, comprises a light chain having a sequence of SEQ ID NO: 250 and a heavy chain that comprises a sequence of SEQ ID NO: 408 or SEQ ID NO: 409.

In some embodiments, the antibody, or antigen-binding fragment thereof, comprises a light chain having a sequence of SEQ ID NO: 251 and a heavy chain that comprises a sequence of SEQ ID NO: 410 or SEQ ID NO: 411.

In some embodiments, the antibody, or antigen-binding fragment thereof, comprises a light chain having a sequence of SEQ ID NO: 252 and a heavy chain that comprises a sequence of SEQ ID NO: 412 or SEQ ID NO: 413.

In some embodiments, the antibody, or antigen-binding fragment thereof, comprises a light chain having a sequence of SEQ ID NO: 253 and a heavy chain that comprises a sequence of SEQ ID NO: 414 or SEQ ID NO: 415.

In some embodiments, the antibody, or antigen-binding fragment thereof, comprises a light chain having a sequence of SEQ ID NO: 254 and a heavy chain that comprises a sequence of SEQ ID NO: 416 or SEQ ID NO: 417.

In some embodiments, the antibody, or antigen-binding fragment thereof, comprises a light chain having a sequence of SEQ ID NO: 255 and a heavy chain that comprises a sequence of SEQ ID NO: 418 or SEQ ID NO: 419.

In some embodiments, the antibody, or antigen-binding fragment thereof, comprises a light chain having a sequence of SEQ ID NO: 256 and a heavy chain that comprises a sequence of SEQ ID NO: 420 or SEQ ID NO: 421.

In some embodiments, the antibody, or antigen-binding fragment thereof, comprises a light chain having a sequence of SEQ ID NO: 257 and a heavy chain that comprises a sequence of SEQ ID NO: 422 or SEQ ID NO: 423.

In some embodiments, an antibody is provided that binds (e.g., specifically binds) to the active form of C1s. In some embodiments, the antibody has a $K_D$ of less than $7\times10^{-9}$ M, $6\times10^{-9}$ M, $5\times10^{-9}$ M, $4\times10^{-9}$ M, $3\times10^{-9}$ M, $2\times10^{-9}$ M, $1\times10^{-9}$ M, $9\times10^{-10}$ M, $8\times10^{-10}$ M, $7\times10^{-10}$ M, $6\times10^{-10}$ M, $5\times10^{-10}$ M, $4\times10^{-10}$ M. In some embodiments, the $K_D$ is determined by surface plasmon resonance (SPR). In some embodiments, the $K_D$ is measured as provided for herein, such as in Example 3. Briefly, and without being bound to any particular SPR method, in an SPR method, the antibody can be immobilized on a sensor surface and a buffer containing the target antigen (e.g., active C1s or the precursor form to show specificity) is passed over the antibody at various concentrations and the binding is determined using the sensor. In some embodiments, the antibody that has a $K_D$ of less than $7\times10^{-9}$ M, $6\times10^{-9}$ M, $5\times10^{-9}$ M, $4\times10^{-9}$ M, $3\times10^{-9}$ M, $2\times10^{-9}$ M, $1\times10^{-9}$ M, $9\times10^{-10}$ M, $8\times10^{-10}$ M, $7\times10^{-10}$ M, $6\times10^{-10}$ M, $5\times10^{-10}$ M, or $4\times10^{-10}$ M is an antibody as provided for herein.

In some embodiments, an antibody is provided that specifically binds to active C1s and inhibits the Wieslab complement classical pathway with an $IC_{50}$ of about 1 to 5 nM, about 0.1 to 1 nM, about 0.5 to about 3 nM, about 1 to about 2 nM, less than 5 nM, less than 4.5 nM, less than 3 nM, or less than 1 nM. In some embodiments, the $IC_{50}$ is determined by binding IgM to a surface (e.g., plate) to activate the complement classical pathway when human serum is added to the wells leading to deposition of components of the membrane attach complex (MAC) in the wells of the plate. Activation can then be measured by detecting the MAC by, for example, an ELISA, with an alkaline phosphatase labelled antibody specific to the neoantigen expressed during MAC formation. To determine the $IC_{50}$ of an inhibitory antibody, such as those provided for herein, in this assay, the assay can be modified by preincubating aliquots of the human serum with varying amounts of the inhibitory anti-C1s antibody for 15 minutes before initiating the assay, which then allows for the $IC_{50}$ to be determined for inhibition of C5bC9 formation. An assay for such determination can be performed using a kit SVAR LifeSciences, Malmo, Sweden and purchased from Eagle Bioscience, Amherst, NH (catalog number COMPL CL310). In some embodiments, the assay is performed as provided for in Example 4. In some embodiments, the antibody that specifically binds to active C1s and inhibits the Wieslab complement classical pathway with an $IC_{50}$ of about 1 to 5 nM, about 0.1 to 1 nM, about 0.5 to about 3 nM, about 1 to about 2 nM, less than 5 nM, less than 4.5 nM, less than 3 nM, or less than 1 nM is an antibody as provided for herein.

In some embodiments, an antibody is provided that specifically binds to active C1s and inhibits human serum complement-mediated human RBC lysis with an $IC_{50}$ of less than 20 nM, less than 19 nM, less than 18 nM, less than 15 nM, less than 13 nM, less than 12 nM, less than 12.5 nM, about 11 to about 20 nM, about 11 to about 15 nM, about 11 to about 13 nM, about 11 to about 12 nM, about 12 to about 15 nM. In some embodiments, the $IC_{50}$ is less than less than 10 nM, about 2 to about 10 nM, about 3 to about 10 nM, about 5 to about 10 nM, less than 25 nM, about 15 to about 25 nM, about 15 to about 21 nM, or about 20 to about 25 nM. In some embodiments, the inhibition of human serum complement-mediated human RBC lysis is determined by sensitizing human red blood cells (hRBCs) to IgG in human serum (such as, but not limited to, rabbit IgG). The percent human serum can be, for example, 20-30% human serum, or 25% human serum. In some embodiments, the assay is performed by incubating the test antibody with aliquots of diluted human serum added to sensitized hRBCs to determine inhibition of lysis. The lysis can be measured by taking measurements, for example, at an absorbance of about 415 nm. In some embodiments, the assay is performed as set forth in Example 5. In some embodiments, the antibody that specifically binds to active C1s and inhibits human serum complement-mediated human RBC lysis with an $IC_{50}$ of less than 20 nM, less than 19 nM, less than 18 nM, less than 15 nM, less than 13 nM, less than 12 nM, less than 12.5 nM, about 11 to about 20 nM, about 11 to about 15 nM, about 11 to about 13 nM, about 11 to about 12 nM, about 12 to about 15 nM is as provided for herein. In some embodiments, the antibody as provided for herein has an $IC_{50}$ that is less than less than 10 nM, about 2 to about 10 nM, about 3 to about 10 nM, about 5 to about 10 nM, less than 25 nM, about 15 to about 25 nM, about 15 to about 21 nM, or about 20 to about 25 nM. In some embodiments, the antibody has an $IC_{50}$ that is less (more potent) than the antibody referred to at TNT020, which is described in WO2018071676A1, which is hereby incorporated by reference in its entirety.

In some embodiments, the antibody has a $K_D$ of less than $7 \times 10^{-9}$ M, $6 \times 10^{-9}$ M, $5 \times 10^{-9}$ M, $4 \times 10^{-9}$ M, $3 \times 10^{-9}$ M, $2 \times 10^{-9}$ M, $1 \times 10^{-9}$ M, $9 \times 10^{-10}$ M, $8 \times 10^{-10}$ M, $7 \times 10^{-10}$ M, $6 \times 10^{-10}$ M, $5 \times 10^{-10}$ M, or $4 \times 10^{-10}$ M and inhibits the Wieslab complement classical pathway with an $IC_{50}$ of about 1 to 5 nM, about 0.1 to 1 nM, about 0.5 to about 3 nM, about 1 to about 2 nM, less than 5 nM, less than 4.5 nM, less than 3 nM, or less than 1 nM.

In some embodiments, the antibody has a $K_D$ of about $3 \times 10^{-10}$ to about $2.5 \times 10^{-9}$ and an $IC_{50}$ of inhibiting the Wieslab complement classical pathway of about 1 to 5 nM, about 0.1 to 1 nM, about 0.5 to about 3 nM, about 1 to about 2 nM, less than 5 nM, less than 4.5 nM, less than 3 nM, or less than 1 nM. In some embodiments, the $IC_{50}$ is about 4 to about 5 nM. In some embodiments, the $IC_{50}$ is about 2 to about 3 nM. In some embodiments, the $IC_{50}$ is about 0.5 to about 1 nM. In some embodiments, the $K_D$ is about $2.0 \times 10^{-9}$ to about $2.5 \times 10^{-9}$. In some embodiments, the $K_D$ is about $1.0 \times 10^{-9}$ to about $1.5 \times 10^{-9}$. In some embodiments, the $K_D$ is about $3.0 \times 10^{-10}$ to about $3.5 \times 10^{-10}$. In some embodiments, the $IC_{50}$ or $K_D$ is about equal to that of MAB4, MAB9 or MAB17. In some embodiments, the antibody is an IgG4 isotype.

As provided for herein, the antibodies, or antigen binding fragments thereof can be variants of the sequences. Accordingly, in some embodiments, a variant of an antibody, or antigen binding fragment thereof, provided for herein is provided. In some embodiments, the variant comprises mutations selected from substitutions, deletions, insertions, or a combination thereof. In some embodiments, the variant comprises between 1 and 20 mutations. In some embodiments, the variant comprises between 1 and 10 mutations. In some embodiments, the variant comprises between 1 and 5 mutations. In some embodiments, the variant comprises 1, 2, 3, 4, 5, 6, 7, 8, 9, 10, 11, 12, 13, 14, 15, 16, 17, 18, 19, or 20 mutations. In some embodiments, the variant comprises at least 1 mutation. Accordingly, in some embodiments, the variant comprises up to or more than 20 mutations. In some embodiments, the variant comprises 1-10 mutations, wherein the mutations are selected from substitutions, deletions, insertions, or a combination thereof. In some embodiments, the variant comprises 1-10 mutations, wherein the mutations are conservative substitutions. Examples of conservative substitutions are as provided for herein (Table 1). Further, one of skill in the art will recognize and understand the substitutions that are encompassed by the term "conservative substitutions". Such substitutions are within the scope of the present disclosure.

The antibody or antigen binding fragment may comprise an antibody fragment as defined and provided for herein. In some embodiments, the antibody binding fragment is as provided for herein. In some embodiments, the antibody fragment is an scFv antibody, a Fab fragment, a Fab' fragment, or a F(ab')$_2$ fragment. In some embodiments, the antibody fragment is an scFv antibody. In some embodiments, the antibody fragment is a Fab fragment. In some embodiments, the antibody fragment is a Fab' fragment. In some embodiments, the antibody fragment is a F(ab')$_2$ fragment.

The sequences of the antibodies can be modified to yield human IgG antibodies. The conversion of the sequences provided herein can be modified to yield other types of antibodies. The CDRs can also be linked to other antibodies, proteins, or molecules to create antibody fragments that bind C1s. This can be in the form of an antibody drug conjugate ("ADC"), or a multi-specific molecule. The sequences can also be made into chimeric antibodies as described herein.

In some embodiments, the antibody comprises an amino acid sequence comprising a sequence provided for herein or a fragment thereof. In some embodiments, the antibody is a monoclonal antibody. In some embodiments, the antibody is a polyclonal antibody. In some embodiments, the antibody is a humanized antibody. In some embodiments, the antibody comprises one or more amino acid sequences as provided herein, an antigen binding fragments, thereof, or a human IgG variant thereof. "A human IgG variant thereof" refers to an antibody that has been modified to be a human IgG when the starting antibody is not a human IgG antibody.

As described herein the production of antibodies with a known sequence is routine and can be done by any method. Accordingly, in some embodiments, a nucleic acid molecule encoding an antibody or fragment thereof is provided. In some embodiments, the nucleic acid encodes a sequence provided for herein. The antibodies can also be modified to be chimeric antibodies or human antibodies. The antibodies can also be used in injectable pharmaceutical compositions. As also described herein, the antibodies can be isolated antibodies or engineered antibodies.

In some embodiments, an isolated nucleic acid molecule is provided. In some embodiments, the nucleic acid molecule encodes for an antibody, or antigen binding fragment thereof as provided for herein. In some embodiments, the nucleic acid molecule encodes for an antibody, or antigen binding fragment thereof comprising a heavy chain variable region, a light chain variable region, a heavy chain constant region, a light chain constant region or any combination thereof as provided for herein. In some embodiments, the nucleic acid molecule encoding the variable heavy chain is as set forth below:

TABLE 9

| SEQ ID NO: | AB ID NO. | Sequence |
|---|---|---|
| 268 | MAB1 | CAGGTGCAGCTTGTTGAAAGTGGTGGGGGTTTG GTTAAACCTGGCGGTTCCCTTCGACTTAGCTGC GCGGCGTCAGGGTTCACATTCTCAGATTATTAC ATGTCTTGGATTCGGCAAGCCCCTGGTAAGGGA CTGGAGTGGGTAAGCTACATATCTCGGTCAGGA AGTACAAAGTACTATGCAGATTCAGTGAAGGGC AGGTTTACGATTAGCCGAGACAACGCAAAGAA CTCTCTTTATCTGCAGATGAATTCACTGAGAGC AGAAGATACCGCTGTCTATTATTGTGCCAGAGA CCAGGAAGATTACGCTCTTGACTACTGGGGCCA AGGTACGCTGGTTACGGTC |
| 270 | MAB2 | CAGGTGCAGCTTGTTGAAAGTGGTGGGGGTTTG GTTAAACCTGGCGGTTCCCTTCGACTTAGCTGC GCGGCGTCAGGGTTCACATTCTCAGATTATTAC ATGTCTTGGATTCGGCAAGCCCCTGGTAAGGGA CTGGAGTGGGTAAGCTACATATCTCGGTCAGGA AGTACAAAGTACTATGCAGATTCAGTGAAGGGC |

TABLE 9-continued

| SEQ ID NO: | AB ID | Sequence |
|---|---|---|
| | | AGGTTTACGATTAGCCGAGACAACGCAAAGAA CTCTCTTTATCTGCAGATGAATTCACTGAGAGC AGAAGATACCGCTGTCTATTATTGTGCCAGAGA CGAGACCGATTACGGCTGGGACTACTGGGGCCA AGGTACGCTGGTTACGGTC |
| 272 | MAB3 | CAGGTGCAGCTTGTTGAAAGTGGTGGGGGTTTG GTTAAACCTGGCGGTTCCCTTCGACTTAGCTGC GCGGCGTCAGGGTTCACATTCTCAGATTATTAC ATGTCTTGGATTCGGCAAGCCCCTGGTAAGGGA CTGGAGTGGGTAAGCTACATATCTCGGTCAGGA AGTACAAAGTACTATGCAGATTCAGTGAAGGGC AGGTTTACGATTAGCCGAGACAACGCAAAGAA CTCTCTTTATCTGCAGATGAATTCACTGAGAGC AGAAGATACCGCTGTCTATTATTGTGCCAGAGA CGAGACCGATTACGCTTTCGACGAATGGGGCCA AGGTACGCTGGTTACGGTC |
| 274 | MAB4 | CAGGTGCAGCTTGTTGAAAGTGGTGGGGGTTTG GTTAAACCTGGCGGTTCCCTTCGACTTAGCTGC GCGGCGTCAGGGTTCACATTCTCAGATTATTAC ATGTCTTGGATTCGGCAAGCCCCTGGTAAGGGA CTGGAGTGGGTAAGCTACATATCTCGGTCAGGA AGTACAAAGTACTATGCAGATTCAGTGAAGGGC AGGTTTACGATTAGCCGAGACAACGCAAAGAA CTCTCTTTATCTGCAGATGAATTCACTGAGAGC AGAAGATACCGCTGTCTATTATTGTGCCAGAGA CGAGAGTCAGTACGCTCTTGACTACTGGGGCCA AGGTACGCTGGTTACGGTC |
| 276 | MAB5 | CAGGTGCAGCTTGTTGAAAGTGGTGGGGGTTTG GTTAAACCTGGCGGTTCCCTTCGACTTAGCTGC GCGGCGTCAGGGTTCACATTCTCAGATTATTAC ATGTCTTGGATTCGGCAAGCCCCTGGTAAGGGA CTGGAGTGGGTAAGCTACATATCTCGGTCAGGA AGTACAAAGTACTATGCACATTCAGTGAAGGGC AGGTTTACGATTAGCCGAGACAACGCAAAGAA CTCTCTTTATCTGCAGATGAATTCACTGAGAGC AGAAGATACCGCTGTCTATTATTGTGCCAGAGA CAACACCGATTACGCTCTTGACCTGTGGGGCCA AGGTACGCTGGTTACGGTC |
| 278 | MAB6 | CAGGTGCAGCTTGTTGAAAGTGGTGGGGGTTTG GTTAAACCTGGCGGTTCCCTTCGACTTAGCTGC GCGGCGTCAGGGTTCACATTCTCAGATTATTAC ATGTCTTGGATTCGGCAAGCCCCTGGTAAGGGA CTGGAGTGGGTAAGCTACATATCTCGGTCAGGA AGTACAAAGTACTATGCATTCAGTGAAGGGC AGGTTTACGATTAGCCGAGACAACGCAAAGAA CTCTCTTTATCTGCAGATGAATTCACTGAGAGC AGAAGATACCGCTGTCTATTATTGTGCCAGAGA CGAGACCGATTACGCTTACGACGAATGGGGCCA AGGTACGCTGGTTACGGTC |
| 280 | MAB7 | CAGGTGCAGCTTGTTGAAAGTGGTGGGGGTTTG GTTAAACCTGGCGGTTCCCTTCGACTTAGCTGC GCGGCGTCAGGGTTCACATTCTCAGATTATTAC ATGTCTTGGATTCGGCAAGCCCCTGGTAAGGGA CTGGAGTGGGTAAGCTACATATCTCGGTCAGGA AGTACAAAGTACTATGCAGATTCAGTGAAGGGC AGGTTTACGATTAGCCGAGACAACGCAAAGAA CTCTCTTTATCTGCAGATGAATTCACTGAGAGC AGAAGATACCGCTGTCTATTATTGTGCCAGAGA CGAGACCGATTACGCTTACGACAACTGGGGCCA AGGTACGCTGGTTACGGTC |
| 282 | MAB8 | CAGGTGCAGCTTGTTGAAAGTGGTGGGGGTTTG GTTAAACCTGGCGGTTCCCTTCGACTTAGCTGC GCGGCGTCAGGGTTCACATTCTCAGATTATTAC ATGTCTTGGATTCGGCAAGCCCCTGGTAAGGGA CTGGAGTGGGTAAGCTACATATCTCGGTCAGGA AGTACAAAGTACTATGCAGATTCAGTGAAGGGC AGGTTTACGATTAGCCGAGACAACGCAAAGAA CTCTCTTTATCTGCAGATGAATTCACTGAGAGC AGAAGATACCGCTGTCTATTATTGTGCCAGAGA CGAGAGTGATTACGCTTACGACTACTGGGGCCA AGGTACGCTGGTTACGGTC |
| 284 | MAB9 | CAGGTGCAGCTTGTTGAAAGTGGTGGGGGTTTG GTTAAACCTGGCGGTTCCCTTCGACTTAGCTGC GCGGCGTCAGGGTTCACATTCTCAGATTATTAC ATGTCTTGGATTCGGCAAGCCCCTGGTAAGGGA CTGGAGTGGGTAAGCTACATATCTCGGTCAGGA AGTACAAAGTACTATGCAGATTCAGTGAAGGGC AGGTTTACGATTAGCCGAGACAACGCAAAGAA CTCTCTTTATCTGCAGATGAATTCACTGAGAGC AGAAGATACCGCTGTCTATTATTGTGCCAGAGA CGAGAATTACGCTCTTGACTGGTGGGGCCAAGG TACGCTGGTTACGGTCTCG |
| 286 | MAB10 | CAGGTGCAGCTTGTTGAAAGTGGTGGGGGTTTG GTTAAACCTGGCGGTTCCCTTCGACTTAGCTGC GCGGCGTCAGGGTTCACATTCTCAGATTATTAC ATGTCTTGGATTCGGCAAGCCCCTGGTAAGGGA CTGGAGTGGGTAAGCTACATATCTCGGTCAGGA AGTACAAAGTACTATGCAGATTCAGTGAAGGGC AGGTTTACGATTAGCCGAGACAACGCAAAGAA CTCTCTTTATCTGCAGATGAATTCACTGAGAGC AGAAGATACCGCTGTCTATTATTGTGCCAGAGA CGAGAGTGATTACGCTCTTGACTTCTGGGGCCA AGGTACGCTGGTTACGGTC |
| 288 | MAB11 | CAAGTTCAACTGGTTCAAAGCGGGGCCGAGGTA AAGAAGCCAGGCGCTTCTGTGAAAGTCAGTTGC AAGGTGAGTGGGGATACATTGACCGAGCTGAG TATGCACTGGGTCCGGCAAGCTCCTGGCAAGGG TTTGGAATGGATGGGTACTTTTGACCCGGAGGA GGGAGAGACCATCTACGCGCAAAAATTCCAAG GTAGGGTGACCATGACGGAGGATACCAGCACG GATACTGCTTACATGGAGCTCAGCTCCCTCAGA AGTGAAGATACTGCCGTCTACTACTGTGTGACC GAGGGGTTTGCCGGGGTGCCGTTTGATCTGTGG GGGCAGGGGACGCTGGTAACGGTCTCGAGT |
| 290 | MAB12 | CAAGTTCAACTGGTTCAAAGCGGGGCCGAGGTA AAGAAGCCAGGCGCTTCTGTGAAAGTCAGTTGC AAGGTGAGTGGGGATACATTGACCGAGCTGAG TATGCACTGGGTCCGGCAAGCTCCTGGCAAGGG TTTGGAATGGATGGGTACTTTTGACCCGGAGGA GGGAGAGACCATCTACGCGCAAAAATTCCAAG GTAGGGTGACCATGACGGAGGATACCAGCACG GATACTGCTTACATGGAGCTCAGCTCCCTCAGA AGTGAAGATACTGCCGTCTACTACTGTGTGACC GAGGGGTTTGGGCGGGCGCCCGTTTGATCACTGG GGGCAGGGGACGCTGGTAACGGTCTCGAGT |
| 292 | MAB13 | CAAGTTCAACTGGTTCAAAGCGGGGCCGAGGTA AAGAAGCCAGGCGCTTCTGTGAAAGTCAGTTGC AAGGTGAGTGGGGATACATTGACCGAGCTGAG TATGCACTGGGTCCGGCAAGCTCCTGGCAAGGG TTTGGAATGGATGGGTACTTTTGACCCGGAGGA GGGAGAGACCATCTACGCGCAAAAATTCCAAG GTAGGGTGACCATGACGGAGGATACCAGCACG GATACTGCTTACATGGAGCTCAGCTCCCTCAGA AGTGAAGATACTGCCGTCTACTACTGTGTGACC GAGGGGTTTGGCCGGGTTCCCGTTTGATATCTGG GGGCAGGGGACGCTGGTAACGGTCTCGAGT |
| 294 | MAB14 | CAAGTTCAACTGGTTCAAAGCGGGGCCGAGGTA AAGAAGCCAGGCGCTTCTGTGAAAGTCAGTTGC AAGGTGAGTGGGGATACATTGACCGAGCTGAG TATGCACTGGGTCCGGCAAGCTCCTGGCAAGGG TTTGGAATGGATGGGTACTTTTGACCCGGAGGA GGGAGAGACCATCTACGCGCAAAAATTCCAAG GTAGGGTGACCATGACGGAGGATACCAGCACG GATACTGCTTACATGGAGCTCAGCTCCCTCAGA AGTGAAGATACTGCCGTCTACTACTGTGTGACC GAGGGGTTTGCCTGGCGCCCGACCGATTCATGG GGGCAGGGGACGCTGGTAACGGTCTCGAGT |

TABLE 9-continued

| SEQ ID NO: | AB ID NO. | Sequence |
|---|---|---|
| 296 | MAB15 | CAAGTTCAACTGGTTCAAAGCGGGGCCGAGGTA<br>AAGAAGTCAGGCGCTTCTGTGAAAGTCAGTTGC<br>AAGGTGAGTGGGGATACATTGACCGAGCTGAG<br>TATGCACTGGGTCCGGCAAGCTCCTGGCAAGGG<br>TTTGGAATGGATGGGTACTTTTGACCCGGAGGA<br>GGGAGAGACCATCTACGCGCAAAAATTCCAAG<br>GTAGGGTGACCATGACGGAGGATACCAGCACG<br>GATACTGCTTACATGGAGCTCAGCTCCCTCAGA<br>AGTGAAGATACTGCCGTCTACTACTGTGTGACC<br>AAGGGTTTGGCCGGGCTGCCGTACTACTCATGG<br>GGGCAGGGGACGCTGGTAACGGTCTCGAGT |
| 298 | MAB16 | CAAGTTCAACTGGTTCAAAGCGGGGCCGAGGTA<br>AAGAAGCCAGGCGCTTCTGTGAAAGTCAGTTGC<br>AAGGTGAGTGGGGATACATTGACCGAGCTGAG<br>TATGCACTGGGTCCGGCAAGCTCCTGGCAAGGG<br>TTTGGAATGGATGGGTACTTTTGACCCGGAGGA<br>GGGAGAGACCATCTACGCGCAAAAATTCCAAG<br>GTAGGGTGACCATGACGGAGGATACCAGCACG<br>GATACTGCTTACATGGAGCTCAGCTCCCTCAGA<br>AGTGAAGATACTGCCGTCTACTACTGTGTGACC<br>GAGGGTTTGGCCGGGGTGCCGTTTGATCTGTGG<br>GGGCAGGGGACGCTGGTAACGGTCTCGAGT |
| 300 | MAB17 | CAAGTTCAACTGGTTCAAAGCGGGGCCGAGGTA<br>AAGAAGCCAGGCGCTTCTGTGAAAGTCAGTTGC<br>AAGGTGAGTGGGGATACATTGACCGAGCTGAG<br>TATGCACTGGGTCCGGCAAGCTCCTGGCAAGGG<br>TTTGGAATGGATGGGTACTTTTGACCCGGAGGA<br>GGGAGAGACCATCTACGCGCAAAAATTCCAAG<br>GTAGGGTGACCATGACGGAGGATACCAGCACG<br>GATACTGCTTACATGGAGCTCAGCTCCCTCAGA<br>AGTGAAGATACTGCCGTCTACTACTGTGTGACC<br>GAGGGTGAGGCCGGGCGCCCGTTTGATGCCTGG<br>GGGCAGGGGACGCTGGTAACGGTCTCGAGT |
| 302 | MAB18 | CAAGTTCAACTGGTTCAAAGCGGGGCCGAGGTA<br>AAGAAGCCAGGCGCTTCTGTGAAAGTCAGTTGC<br>AAGGTGAGTGGGGATACATTGACCGAGCTGAG<br>TATGCACTGGGTCCGGCAAGCTCCTGGCAAGGG<br>TTTGGAATGGATGGGTACTTTTGACCCGGAGGA<br>GGGAGAGACCATCTACGCGCAAAAATTCCAAG<br>GTAGGGTGACCATGACGGAGGATACCAGCACG<br>GATACTGCTTACATGGAGCTCAGCTCCCTCAGA<br>AGTGAAGATACTGCCGTCTACTACTGTGTGACC<br>GAGGGTTTGGCCGGGCGCCCGTACGATGTGTGG<br>GGGCAGGGGACGCTGGTAACGGTCTCGAGT |
| 304 | MAB19 | CAAGTTCAACTGGTTCAAAGCGGGGCCGAGGTA<br>AAGAAGCCAGGCGCTTCTGTGAAAGTCAGTTGC<br>AAGGTGAGTGGGGATACATTGACCGAGCTGAG<br>TATGCACTGGGTCCGGCAAGCTCCTGGCAAGGG<br>TTTGGAATGGATGGGTACTTTTGACCCGGAGGA<br>GGGAGAGACCATCTACGCGCAAAAATTCCAAG<br>GTAGGGTGACCATGACGGAGGATACCAGCACG<br>GATACTGCTTACATGGAGCTCAGCTACCTCAGA<br>AGTGAAGATACTGCCGTCTACTACTGTGTGACC<br>GAGGGTTTGGCCGGGATCCCGTTTGATTCATGG<br>GGGCAGGGGACGCTGGTAACGGTCTCGAGT |
| 306 | MAB20 | CAAGTTCAACTGGTTCAAAGCGGGGCCGAGGTA<br>AAGAAGCCAGGCGCTTCTGTGAAAGTCAGTTGC<br>AAGGTGAGTGGGGATACATTGACCGAGCTGAG<br>TATGCACTGGGTCCGGCAAGCTCCTGGCAAGGG<br>TTTGGAATGGATGGGTACTTTTGACCCGGAGGA<br>GGGAGAGACCATCTACGCGCAAAAATTCCAAG<br>GTAGGGTGACCATGACGGAGGATACCAGCACG<br>GATACTGCTTACATGGAGCTCAGCTACCTCAGA<br>AGTGAAGATACTGCCGTCTACTACTGTGTGACC<br>GAGGGTTTGGCCGGGATCCCGTTTGATTCATGG<br>GGGCAGGGGACGCTGGTAACGGTCTCGAGT |
| 308 | MAB21 | GAAGTCCAGCTTGTTGAGTCTGGCGGAGGGGTG<br>GTTAGGCCAGGAGGTTCCCTTAGGCTTTCCTGT<br>GCGGCATCAGGATTTACCTTCGATGACTACGGA<br>ATGTCATGGGTACGACAAGCTCCCGGCAAAGGC<br>CTCGAATGGGTTTCTGGCATCAACTGGGAGGGC<br>GGTTCCACTGGCTACGCGGACTCAGTTAAGGGT<br>AGGTTCACCATAAGCAGGGACAATGCGAAGAA<br>CTCACTGTATCTCCAAATGAACAGTCTCCGCGC<br>CGAGGATACAGCCCTTTACTATTGTGCACGAGA<br>TGAGCAATTGGGGGGGACTACTTATTATTACTA<br>TTACATGGACGTGTGGGGTAAAGGAACGACCGT<br>CACAGTC |
| 310 | MAB22 | GAAGTCCAGCTTGTTGAGTCTGGCGGAGGGGTG<br>GTTAGGCCAGGAGGTTCCCTTAGGCTTTCCTGT<br>GCGGCATCAGGATTTACCTTCGATGACTACGGA<br>ATGTCATGGGTACGACAAGCTCCCGGCAAAGGC<br>CTCGAATGGGTTTCTGGCATCAACTGGGAGGGC<br>GGTTCCACTGGCTACGCGGACTCAGTTAAGGGT<br>AGGTTCACCATAAGCAGGGACAATGCGAAGAA<br>CTCACTGTATCTCCAAATGAACAGTCTCCGCGC<br>CGAGGATACAGCCCTTTACTATTGTGCACGAGA<br>TGAGCAATTGGGGGGGAAGTATTACTATTACTA<br>TTACATGGACGTGTGGGGTAAAGGAACGACCGT<br>CACAGTC |
| 312 | MAB23 | GAAGTCCAGCTTGTTGAGTCTGGCGGAGGGGTG<br>GTTAGGCCAGGAGGTTCCCTTAGGCTTTCCTGT<br>GCGGCATCAGGATTTACCTTCGATGACTACGGA<br>ATGTCATGGGTACGACAAGCTCCCGGCAAAGGC<br>CTCGAATGGGTTTCTGGCATCAACTGGGAGGGC<br>GGTTCCACTGGCTACGCGGACTCAGTTAAGGGT<br>AGGTTCACCATAAGCAGGGACAATGCGAAGAA<br>CTCACTGTATCTCCAAATGAACAGTCTCCGCGC<br>CGAGGATACAGCCCTTTACTATTGTGCACGAGA<br>TGAGCAATTGGGGGGGCAGACTTATTATTACTA<br>TTACATGGACGTGTGGGGTAAAGGAACGACCGT<br>CACAGTC |
| 314 | MAB24 | GAAGTCCAGCTTGTTGAGTCTGGCGGAGGGGTG<br>GTTAGGCCAGGAGGTTCCCTTAGGCTTTCCTGT<br>GCGGCATCAGGATTTACCTTCGATGACTACGGA<br>ATGTCATGGGTACGACAAGCTCCCGGCAAAGGC<br>CTCGAATGGGTTTCTGGCATCAACTGGGAGGGC<br>GGTTCCACTGGCTACGCGGACTCAGTTAAGGGT<br>AGGTTCACCATAAGCAGGGACAATGCGAAGAA<br>CTCACTGTATCTCCAAATGAACAGTCTCCGCGC<br>CGAGGATACAGCCCTTTACTATTGTGCACGAGA<br>TGAGCAATTGGGGGGGACCACCTATTATTACTA<br>TTACATGGACGTGTGGGGTAAAGGAACGACCGT<br>CACAGTC |
| 316 | MAB25 | GAAGTCCAGCTTGTTGAGTCTGGCGGAGGGGTG<br>GTTAGGCCAGGAGGTTCCCTTAGGCTTTCCTGT<br>GCGGCATCAGGATTTACCTTCGATGACTACGGA<br>ATGTCATGGGTACGACAAGCTCCCGGCAAAGGC<br>CTCGAATGGGTTTCTGGCATCAACTGGGAGGGC<br>GGTTCCACTGGCTACGCGGACTCAGTTAAGGGT<br>AGGTTCACCATAAGCAGGGACAATGCGAAGAA<br>CTCACTGTATCTCCAAATGAACAGTCTCCGCGC<br>CGAGGATACAGCCCTTTACTATTGTGCACGAGA<br>TGAGCAATTGGGGGGGATCAAGTATTATTACTA<br>TTACATGGACGTGTGGGGTAAAGGAACGACCGT<br>CACAGTC |
| 318 | MAB26 | GAAGTCCAGCTTGTTGAGTCTGGCGGAGGGGTG<br>GTTAGGCCAGGAGGTTCCCTTAGGCTTTCCTGT<br>GCGGCATCAGGATTTACTTTCGATGACTACGGA<br>ATGTCATGGGTACGACAAGCTCCCGGCAAAGGC<br>CTTGAATGGGTTTCTGGCATCAACTGGGAGGGC<br>GGTTCCACTGGCTACGCGGACTCAGTTAAGGAA<br>AGGTTCAGCATAAGCAGGGACAATGCGAAGAA<br>CTCACTGTATCTCCAAATGAACAGTCTCCGCGC<br>CGAGGATACAGCCCTTTACTATTGTGCACGAGA<br>TGAGCAATTGGGGGGCTGAAGTATTATTACTA<br>TTACATGGACGTGTGGGGTAAAGGAACGACCGT<br>CACAGTC |

TABLE 9-continued

| SEQ ID NO: | AB ID NO. | Sequence |
|---|---|---|
| 320 | MAB27 | GAAGTCCAGCTTGTTGAGTCTGGCGGAGGGGTG GTTAGGCCAGGAGGTTCCCTTAGGCTTTCCTGT GCGGCATCAGGATTTACCTTCGATGACTACGGA ATGTCATGGGTACGACAAGCTCCCGGCAAAGGC CTCGAATGGGTTTCTGGCATCAACTGGGAGGGC GGTTCCACTGGCTACGCGGACTCAGTTAAGGGT AGGTTCACCATAAGCAGGGACAATGCGAAGAA CTCACTGTATCTCCAAATGAACAGTCTCCGCGC CGAGGATACAGCCCTTTACTATTGTGCACGAGA TGAGCAATTGGGGGGAAGGTGTATTATTACTA TTACATGGACGTGTGGGGTAAAGGAACGACCGT CACAGTC |
| 322 | MAB28 | GAAGTCCAGCTTGTTGAGTCTGGCGGAGGGGTG GTTAGGCCAGGAGGTTCCCTTAGGCTTTCCTGT GCGGCATCAGGATTTACTTTCGATGACTACGGA ATGTCATGGGTACGACAAGCTCCCGGCAAAGGC CTTGAATGGGTTTCTGGCATCAACTGGGAGGGC GGTTCCACTGGCTACGCGGACTCAGTTAAGGGT AGGTTCAGCATAAGCAGGGACAATGCGAAGAA CTCACTGTATCTCCAAATGAACAGTCTCCGCGC CGAGGATACAGCCCTTTACTATTGTGCACGAGA TGAGCAATTGGGGGGGCTGAAGTATTATTACTA TTACATGGACGTGTGGGGTAAAGGAACGACCGT CACAGTC |
| 324 | MAB29 | GAAGTCCAGCTTGTTGAGTCTGGCGGAGGGGTG GTTAGGCCAGGAGGTTCCCTTAGGCTTTCCTGT GCGGCATCAGGATTTACCTTCGATGACTACGGA ATGTCATGGGTACGACAAGCTCCCGGCAAAGGC CTCGAATGGGTTTCTGGCATCAACTGGGAGGGC GGTTCCACTGGCTACGCGGACTCAGTTAAGGGT AGGTTCACCATAAGCAGGGACAATGCGAAGAA CTCACTGTATCTCCAAATGAACAGTCTCCGCGC CGAGGATACAGCCCTTTACTATTGTGCACGAGA TGAGCAATTGGGGGGGAATCACTATTATTACTA TTACATGGACGCTTGGGGTAAAGGAACGACCGT CACAGTC |
| 326 | MAB30 | GAAGTCCAGCTTGTTGAGTCTGGCGGAGGGGTG GTTAGGCCAGGAGGTTCCCTTAGGCTTTCCTGT GCGGCATCAGGATTTACCTTCGATGACTACGGA ATGTCATGGGTACGACAAGCTCCCGGCAAAGGC CTCGAATGGGTTTCTGGCATCAACTGGGAGGGC GGTTCCACTGGCTACGCGGACTCAGTTAAGGGT AGGTTCACCATAAGCAGGGACAATGCGAAGAA CTCACTGTATCTCCAAATGAACAGTCTCCGCGC CGAGGATACAGCCCTTTACTATTGTGCACGAGA TGAGCAATTGGGGGGCGCCACTATTATTACTA TTACATGGACGTGTGGGGTAAAGGAACGACCGT CACAGTC |
| 424 | MAB31 | GAAGTGCAGCTTGTTGAAAGTGGTGGGGGTTTG GTTAAACCTGGCGGTTCCCTTCGACTTAGCTGC GCGGCGTCAGGGTTCACATTCTCAGATTATTAC ATGTCTTGGATTCGGCAAGCCCCTGGTAAGGGA CTGGAGTGGGTAAGCTACATATCTCGGTCAGGA AGTACAAAGTACTATGCAGATTCAGTGAAGGGC AGGTTTACGATTAGCCGAGACAACGCAAAGAA CTCTCTTTATCTGCAGATGAATTCACTGAGAGC AGAAGATACCGCTGTCTATTATTGTGCCAGAGA CCAGGAAGATTACGCTCTTGACTACTGGGGCCA AGGTACGCTGGTTACGGTC |
| 425 | MAB32 | GAAGTGCAGCTTGTTGAAAGTGGTGGGGGTTTG GTTAAACCTGGCGGTTCCCTTCGACTTAGCTGC GCGGCGTCAGGGTTCACATTCTCAGATTATTAC ATGTCTTGGATTCGGCAAGCCCCTGGTAAGGGA CTGGAGTGGGTAAGCTACATATCTCGGTCAGGA AGTACAAAGTACTATGCAGATTCAGTGAAGGGC AGGTTTACGATTAGCCGAGACAACGCAAAGAA CTCTCTTTATCTGCAGATGAATTCACTGAGAGC AGAAGATACCGCTGTCTATTATTGTGCCAGAGA CGAGACCGATTACGCTGGGACTACTGGGGCCA AGGTACGCTGGTTACGGTC |
| 426 | MAB33 | GAAGTGCAGCTTGTTGAAAGTGGTGGGGGTTTG GTTAAACCTGGCGGTTCCCTTCGACTTAGCTGC GCGGCGTCAGGGTTCACATTCTCAGATTATTAC ATGTCTTGGATTCGGCAAGCCCCTGGTAAGGGA CTGGAGTGGGTAAGCTACATATCTCGGTCAGGA AGTACAAAGTACTATGCAGATTCAGTGAAGGGC AGGTTTACGATTAGCCGAGACAACGCAAAGAA CTCTCTTTATCTGCAGATGAATTCACTGAGAGC AGAAGATACCGCTGTCTATTATTGTGCCAGAGA CGAGACCGATTACGCTTTCGACGAATGGGGCCA AGGTACGCTGGTTACGGTC |
| 427 | MAB34 | GAAGTGCAGCTTGTTGAAAGTGGTGGGGGTTTG GTTAAACCTGGCGGTTCCCTTCGACTTAGCTGC GCGGCGTCAGGGTTCACATTCTCAGATTATTAC ATGTCTTGGATTCGGCAAGCCCCTGGTAAGGGA CTGGAGTGGTAAGCTACATATCTCGGTCAGGA AGTACAAAGTACTATGCAGATTCAGTGAAGGGC AGGTTTACGATTAGCCGAGACAACGCAAAGAA CTCTCTTTATCTGCAGATGAATTCACTGAGAGC AGAAGATACCGCTGTCTATTATTGTGCCAGAGA CGAGAGTCAGTACGCTCTTGACTACTGGGGCCA AGGTACGCTGGTTACGGTC |
| 428 | MAB35 | GAAGTGCAGCTTGTTGAAAGTGGTGGGGGTTTG GTTAAACCTGGCGGTTCCCTTCGACTTAGCTGC GCGGCGTCAGGGTTCACATTCTCAGATTATTAC ATGTCTTGGATTCGGCAAGCCCCTGGTAAGGGA CTGGAGTGGGTAAGCTACATATCTCGGTCAGGA AGTACAAAGTACTATGCACATTCAGTGAAGGGC AGGTTTACGATTAGCCGAGACAACGCAAAGAA CTCTCTTTATCTGCAGATGAATTCACTGAGAGC AGAAGATACCGCTGTCTATTATTGTGCCAGAGA CAACACCGATTACGCTCTTGACCGTGGGGCCA AGGTACGCTGGTTACGGTC |
| 429 | MAB36 | GAAGTGCAGCTTGTTGAAAGTGGTGGGGGTTTG GTTAAACCTGGCGGTTCCCTTCGACTTAGCTGC GCGGCGTCAGGGTTCACATTCTCAGATTATTAC ATGTCTTGGATTCGGCAAGCCCCTGGTAAGGGA CTGGAGTGGGTAAGCTACATATCTCGGTCAGGA AGTACAAAGTACTATGCACATTCAGTGAAGGGC AGGTTTACGATTAGCCGAGACAACGCAAAGAA CTCTCTTTATCTGCAGATGAATTCACTGAGAGC AGAAGATACCGCTGTCTATTATTGTGCCAGAGA CGAGACCGATTACGCTTACGACGAATGGGGCCA AGGTACGCTGGTTACGGTC |
| 430 | MAB37 | GAAGTGCAGCTTGTTGAAAGTGGTGGGGGTTTG GTTAAACCTGGCGGTTCCCTTCGACTTAGCTGC GCGGCGTCAGGGTTCACATTCTCAGATTATTAC ATGTCTTGGATTCGGCAAGCCCCTGGTAAGGGA CTGGAGTGGGTAAGCTACATATCTCGGTCAGGA AGTACAAAGTACTATGCAGATTCAGTGAAGGGC AGGTTTACGATTAGCCGAGACAACGCAAAGAA CTCTCTTTATCTGCAGATGAATTCACTGAGAGC AGAAGATACCGCTGTCTATTATTGTGCCAGAGA CGAGACCGATTACGCTTACGACAACTGGGGCCA AGGTACGCTGGTTACGGTC |
| 431 | MAB38 | GAAGTGCAGCTTGTTGAAAGTGGTGGGGGTTTG GTTAAACCTGGCGGTTCCCTTCGACTTAGCTGC GCGGCGTCAGGGTTCACATTCTCAGATTATTAC ATGTCTTGGATTCGGCAAGCCCCTGGTAAGGGA CTGGAGTGGGTAAGCTACATATCTCGGTCAGGA AGTACAAAGTACTATGCAGATTCAGTGAAGGGC AGGTTTACGATTAGCCGAGACAACGCAAAGAA CTCTCTTTATCTGCAGATGAATTCACTGAGAGC AGAAGATACCGCTGTCTATTATTGTGCCAGAGA CGAGACCGATTACGCTTACGACTACTGGGGCCA AGGTACGCTGGTTACGGTC |
| 432 | MAB39 | GAAGTGCAGCTTGTTGAAAGTGGTGGGGGTTTG GTTAAACCTGGCGGTTCCCTTCGACTTAGCTGC GCGGCGTCAGGGTTCACATTCTCAGATTATTAC |

TABLE 9-continued

| SEQ ID NO: | AB ID NO. | Sequence |
|---|---|---|
|  |  | ATGTCTTGGATTCGGCAAGCCCTGGTAAGGGA CTGGAGTGGGTAAGCTACATATCTCGGTCAGGA AGTACAAAGTACTATGCAGATTCAGTGAAGGGC AGGTTTACGATTAGCCGAGACAACGCAAAGAA CTCTCTTTATCTGCAGATGAATTCACTGAGAGC AGAAGATACCGCTGTCTATTATTGTGCCAGAGA CGAGAATTACGCTCTTGACTGGTGGGGCCAAGG TACGCTGGTTACGGTCTCG |
| 433 | MAB40 | GAAGTGCAGCTTGTTGAAAGTGGTGGGGGTTTG GTTAAACCTGGCGGTTCCCTTCGACTTAGCTGC GCGGCGTCAGGGTTCACATTCTCAGATTATTAC ATGTCTTGGATTCGGCAAGCCCTGGTAAGGGA CTGGAGTGGGTAAGCTACATATCTCGGTCAGGA AGTACAAAGTACTATGCAGATTCAGTGAAGGGC AGGTTTACGATTAGCCGAGACAACGCAAAGAA CTCTCTTTATCTGCAGATGAATTCACTGAGAGC AGAAGATACCGCTGTCTATTATTGTGCCAGAGA CGAGAGTGATTACGCTCTTGACTTCTGGGGCCA AGGTACGCTGGTTACGGTC |
| 434 | MAB41 | GAAGTTCAACTGGTTCAAAGCGGGGCCGAGGT AAAGAAGCCAGGCGCTTCTGTGAAAGTCAGTTG CAAGGTGAGTGGGGATACATTGACCGAGCTGA GTATGCACTGGGTCCGGCAAGCTCCTGGCAAGG GTTTGGAATGGATGGGTACTTTTGACCCGGAGG AGGGAGAGACCATCTACGCGCAAAAATTCCAA GGTAGGGTGACCATGACGGAGGATACCAGCAC GGATACTGCTTACATGGAGCTCAGCTCCCTCAG AAGTGAAGATACTGCCGTCTACTACTGTGTGAC CGAGGGTTTGGCCGGGGTGCCGTTTGATCTGTG GGGGCAGGGGACGCTGGTAACGGTCTCGAGT |
| 435 | MAB42 | GAAGTTCAACTGGTTCAAAGCGGGGCCGAGGT AAAGAAGCCAGGCGCTTCTGTGAAAGTCAGTTG CAAGGTGAGTGGGGATACATTGACCGAGCTGA GTATGCACTGGGTCCGGCAAGCTCCTGGCAAGG GTTTGGAATGGATGGGTACTTTTGACCCGGAGG AGGGAGAGACCATCTACGCGCAAAAATTCCAA GGTAGGGTGACCATGACGGAGGATACCAGCAC GGATACTGCTTACATGGAGCTCAGCTCCCTCAG AAGTGAAGATACTGCCGTCTACTACTGTGTGAC CGAGGGTTTGGGCGGGCGCCCGTTTGATCACTG GGGGCAGGGGACGCTGGTAACGGTCTCGAGT |
| 436 | MAB43 | GAAGTTCAACTGGTTCAAAGCGGGGCCGAGGT AAAGAAGCCAGGCGCTTCTGTGAAAGTCAGTTG CAAGGTGAGTGGGGATACATTGACCGAGCTGA GTATGCACTGGGTCCGGCAAGCTCCTGGCAAGG GTTTGGAATGGATGGGTACTTTTGACCCGGAGG AGGGAGAGACCATCTACGCGCAAAAATTCCAA GGTAGGGTGACCATGACGGAGGATACCAGCAC GGATACTGCTTACATGGAGCTCAGCTCCCTCAG AAGTGAAGATACTGCCGTCTACTACTGTGTGAC CGAGGGTTTGGCCGGGTTCCCGTTTGATATCTG GGGGCAGGGGACGCTGGTAACGGTCTCGAGT |
| 437 | MAB44 | GAAGTTCAACTGGTTCAAAGCGGGGCCGAGGT AAAGAAGCCAGGCGCTTCTGTGAAAGTCAGTTG CAAGGTGAGTGGGGATACATTGACCGAGCTGA GTATGCACTGGGTCCGGCAAGCTCCTGGCAAGG GTTTGGAATGGATGGGTACTTTTGACCCGGAGG AGGGAGAGACCATCTACGCGCAAAAATTCCAA GGTAGGGTGACCATGACGGAGGATACCAGCAC GGATACTGCTTACATGGAGCTCAGCTCCCTCAG AAGTGAAGATACTGCCGTCTACTACTGTGTGAC CGAGGGTTTGGCCTGGCGCCCGACCGATTCATG GGGGCAGGGGACGCTGGTAACGGTCTCGAGT |
| 438 | MAB45 | GAAGTTCAACTGGTTCAAAGCGGGGCCGAGGT AAAGAAGCCAGGCGCTTCTGTGAAAGTCAGTTG CAAGGTGAGTGGGGATACATTGACCGAGCTGA GTATGCACTGGGTCCGGCAAGCTCCTGGCAAGG GTTTGGAATGGATGGGTACTTTTGACCCGGAGG AGGGAGAGACCATCTACGCGCAAAAATTCCAA GGTAGGGTGACCATGACGGAGGATACCAGCAC GGATACTGCTTACATGGAGCTCAGCTCCCTCAG AAGTGAAGATACTGCCGTCTACTACTGTGTGAC CAAGGGGTTTGGCCGGGCTGCCGTACTACTCATG GGGGCAGGGGACGCTGGTAACGGTCTCGAGT |
| 439 | MAB46 | GAAGTTCAACTGGTTCAAAGCGGGGCCGAGGT AAAGAAGCCAGGCGCTTCTGTGAAAGTCAGTTG CAAGGTGAGTGGGGATACATTGACCGAGCTGA GTATGCACTGGGTCCGGCAAGCTCCTGGCAAGG GTTTGGAATGGATGGGTACTTTTGACCCGGAGG AGGGAGAGACCATCTACGCGCAAAAATTCCAA GGTAGGGTGACCATGACGGAGGATACCAGCAC GGATACTGCTTACATGGAGCTCAGCTCCCTCAG AAGTGAAGATACTGCCGTCTACTACTGTGTGAC CGAGGGTTTGGCCGGGGTGCCGTTTGATCTGTG GGGGCAGGGGACGCTGGTAACGGTCTCGAGT |
| 440 | MAB47 | GAAGTTCAACTGGTTCAAAGCGGGGCCGAGGT AAAGAAGCCAGGCGCTTCTGTGAAAGTCAGTTG CAAGGTGAGTGGGGATACATTGACCGAGCTGA GTATGCACTGGGTCCGGCAAGCTCCTGGCAAGG GTTTGGAATGGATGGGTACTTTTGACCCGGAGG AGGGAGAGACCATCTACGCGCAAAAATTCCAA GGTAGGGTGACCATGACGGAGGATACCAGCAC GGATACTGCTTACATGGAGCTCAGCTCCCTCAG AAGTGAAGATACTGCCGTCTACTACTGTGTGAC CGAGGGTGAGGCCGGGCGCCCGTTTGATGCCTG GGGGCAGGGGACGCTGGTAACGGTCTCGAGT |
| 441 | MAB48 | GAAGTTCAACTGGTTCAAAGCGGGGCCGAGGT AAAGAAGCCAGGCGCTTCTGTGAAAGTCAGTTG CAAGGTGAGTGGGGATACATTGACCGAGCTGA GTATGCACTGGGTCCGGCAAGCTCCTGGCAAGG GTTTGGAATGGATGGGTACTTTTGACCCGGAGG AGGGAGAGACCATCTACGCGCAAAAATTCCAA GGTAGGGTGACCATGACGGAGGATACCAGCAC GGATACTGCTTACATGGAGCTCAGCTCCCTCAG AAGTGAAGATACTGCCGTCTACTACTGTGTGAC CGAGGGTTTGGCCGGGCGCCCGTACGATGTGTG GGGGCAGGGGACGCTGGTAACGGTCTCGAGT |
| 442 | MAB49 | GAAGTTCAACTGGTTCAAAGCGGGGCCGAGGT AAAGAAGCCAGGCGCTTCTGTGAAAGTCAGTTG CAAGGTGAGTGGGGATACATTGACCGAGCTGA GTATGCACTGGGTCCGGCAAGCTCCTGGCAAGG GTTTGGAATGGATGGGTACTTTTGACCCGGAGG AGGGAGAGACCATCTACGCGCAAAAATTCCAA GGTAGGGTGACCATGACGGAGGATACCAGCAC GGATACTGCTTACATGGAGCTCAGCTACCTCAG AAGTGAAGATACTGCCGTCTACTACTGTGTGAC CGAGGGTTTGGCCGGGATCCCGTTTGATTCATG GGGGCAGGGGACGCTGGTAACGGTCTCGAGT |
| 443 | MAB50 | GAAGTTCAACTGGTTCAAAGCGGGGCCGAGGT AAAGAAGCCAGGCGCTTCTGTGAAAGTCAGTTG CAAGGTGAGTGGGGATACATTGACCGAGCTGA GTATGCACTGGGTCCGGCAAGCTCCTGGCAAGG GTTTGGAATGGATGGGTACTTTTGACCCGGAGG AGGGAGAGACCATCTACGCGCAAAAATTCCAA GGTAGGGTGACCATGACGGAGGATACCAGCAC GGATACTGCTTACATGGAGCTCAGCTACCTCAG AAGTGAAGATACTGCCGTCTACTACTGTGTGAC CGAGGGTTTGGCCGGGATCCCGTTTGATTCATG GGGGCAGGGGACGCTGGTAACGGTCTCGAGT |
| 444 | MAB51 | CAAGTCCAGCTTGTTGAGTCTGGCGGAGGGGTG GTTAGGCCAGGAGGTTCCCTTAGGCTTTCCTGT GCGGCATCAGGATTTACCTTCGATGACTACGGA ATGTCATGGGTACGACAAGCTCCCGGCAAAGGC CTCGAATGGGTTTCTGGCATCAACTGGGAGGGC GGTTCCACTGGCTACGCGGACTCAGTTAAGGGT AGGTTCACCATAAGCAGGGACAATGCGAAGAA |

TABLE 9-continued

| SEQ ID NO: | AB ID NO. | Sequence |
|---|---|---|
|  |  | CTCACTGTATCTCCAAATGAACAGTCTCCGCGC CGAGGATACAGCCCTTTACTATTGTGCACGAGA TGAGCAATTGGGGGGACTACTTATTATTACTA TTACATGGACGTGTGGGGTAAAGGAACGACCGT CACAGTC |
| 445 | MAB52 | CAAGTCCAGCTTGTTGAGTCTGGCGGAGGGGTG GTTAGGCCAGGAGGTTCCCTTAGGCTTTCCTGT GCGGCATCAGGATTTACCTTCGATGACTACGGA ATGTCATGGGTACGACAAGCTCCCGGCAAAGGC CTCGAATGGGTTTCTGGCATCAACTGGGAGGGC GGTTCCACTGGCTACGCGGACTCAGTTAAGGGT AGGTTCACCATAAGCAGGGACAATGCGAAGAA CTCACTGTATCTCCAAATGAACAGTCTCCGCGC CGAGGATACAGCCCTTTACTATTGTGCACGAGA TGAGCAATTGGGGGGAAGTATTACTATTACTA TTACATGGACGTGTGGGGTAAAGGAACGACCGT CACAGTC |
| 446 | MAB53 | CAAGTCCAGCTTGTTGAGTCTGGCGGAGGGGTG GTTAGGCCAGGAGGTTCCCTTAGGCTTTCCTGT GCGGCATCAGGATTTACCTTCGATGACTACGGA ATGTCATGGGTACGACAAGCTCCCGGCAAAGGC CTCGAATGGGTTTCTGGCATCAACTGGGAGGGC GGTTCCACTGGCTACGCGGACTCAGTTAAGGGT AGGTTCACCATAAGCAGGGACAATGCGAAGAA CTCACTGTATCTCCAAATGAACAGTCTCCGCGC CGAGGATACAGCCCTTTACTATTGTGCACGAGA TGAGCAATTGGGGGGGCAGACTTATTATTACTA TTACATGGACGTGTGGGGTAAAGGAACGACCGT CACAGTC |
| 447 | MAB54 | CAAGTCCAGCTTGTTGAGTCTGGCGGAGGGGTG GTTAGGCCAGGAGGTTCCCTTAGGCTTTCCTGT GCGGCATCAGGATTTACCTTCGATGACTACGGA ATGTCATGGGTACGACAAGCTCCCGGCAAAGGC CTCGAATGGGTTTCTGGCATCAACTGGGAGGGC GGTTCCACTGGCTACGCGGACTCAGTTAAGGGT AGGTTCACCATAAGCAGGGACAATGCGAAGAA CTCACTGTATCTCCAAATGAACAGTCTCCGCGC CGAGGATACAGCCCTTTACTATTGTGCACGAGA TGAGCAATTGGGGGGGACCACCTATTATTACTA TTACATGGACGTGTGGGGTAAAGGAACGACCGT CACAGTC |
| 448 | MAB55 | CAAGTCCAGCTTGTTGAGTCTGGCGGAGGGGTG GTTAGGCCAGGAGGTTCCCTTAGGCTTTCCTGT GCGGCATCAGGATTTACCTTCGATGACTACGGA ATGTCATGGGTACGACAAGCTCCCGGCAAAGGC CTCGAATGGGTTTCTGGCATCAACTGGGAGGGC GGTTCCACTGGCTACGCGGACTCAGTTAAGGGT AGGTTCACCATAAGCAGGGACAATGCGAAGAA CTCACTGTATCTCCAAATGAACAGTCTCCGCGC CGAGGATACAGCCCTTTACTATTGTGCACGAGA TGAGCAATTGGGGGGGATCAAGTATTATTACTA TTACATGGACGTGTGGGGTAAAGGAACGACCGT CACAGTC |
| 449 | MAB56 | CAAGTCCAGCTTGTTGAGTCTGGCGGAGGGGTG GTTAGGCCAGGAGGTTCCCTTAGGCTTTCCTGT GCGGCATCAGGATTTACTTTCGATGACTACGGA ATGTCATGGGTACGACAAGCTCCCGGCAAAGGC CTTGAATGGGTTTCTGGCATCAACTGGGAGGGC GGTTCCACTGGCTACGCGGACTCAGTTAAGGGT AGGTTCAGCATAAGCAGGGACAATGCGAAGAA CTCACTGTATCTCCAAATGAACAGTCTCCGCGC CGAGGATACAGCCCTTTACTATTGTGCACGAGA TGAGCAATTGGGGGGGCTGAAGTATTATTACTA TTACATGGACGTGTGGGGTAAAGGAACGACCGT CACAGTC |
| 450 | MAB57 | CAAGTCCAGCTTGTTGAGTCTGGCGGAGGGGTG GTTAGGCCAGGAGGTTCCCTTAGGCTTTCCTGT GCGGCATCAGGATTTACCTTCGATGACTACGGA ATGTCATGGGTACGACAAGCTCCCGGCAAAGGC CTCGAATGGGTTTCTGGCATCAACTGGGAGGGC GGTTCCACTGGCTACGCGGACTCAGTTAAGGGT AGGTTCACCATAAGCAGGGACAATGCGAAGAA CTCACTGTATCTCCAAATGAACAGTCTCCGCGC CGAGGATACAGCCCTTTACTATTGTGCACGAGA TGAGCAATTGGGGGGGAAGGTGTATTATTACTA TTACATGGACGTGTGGGGTAAAGGAACGACCGT CACAGTC |
| 451 | MAB58 | CAAGTCCAGCTTGTTGAGTCTGGCGGAGGGGTG GTTAGGCCAGGAGGTTCCCTTAGGCTTTCCTGT GCGGCATCAGGATTTACTTTCGATGACTACGGA ATGTCATGGGTACGACAAGCTCCCGGCAAAGGC CTTGAATGGGTTTCTGGCATCAACTGGGAGGGC GGTTCCACTGGCTACGCGGACTCAGTTAAGGGT AGGTTCAGCATAAGCAGGGACAATGCGAAGAA CTCACTGTATCTCCAAATGAACAGTCTCCGCGC CGAGGATACAGCCCTTTACTATTGTGCACGAGA TGAGCAATTGGGGGGGCTGAAGTATTATTACTA TTACATGGACGTGTGGGGTAAAGGAACGACCGT CACAGTC |
| 452 | MAB59 | CAAGTCCAGCTTGTTGAGTCTGGCGGAGGGGTG GTTAGGCCAGGAGGTTCCCTTAGGCTTTCCTGT GCGGCATCAGGATTTACCTTCGATGACTACGGA ATGTCATGGGTACGACAAGCTCCCGGCAAAGGC CTCGAATGGGTTTCTGGCATCAACTGGGAGGGC GGTTCCACTGGCTACGCGGACTCAGTTAAGGGT AGGTTCACCATAAGCAGGGACAATGCGAAGAA CTCACTGTATCTCCAAATGAACAGTCTCCGCGC CGAGGATACAGCCCTTTACTATTGTGCACGAGA TGAGCAATTGGGGGGGAATCACTATTATTACTA TTACATGGACGCTTGGGGTAAAGGAACGACCGT CACAGTC |
| 453 | MAB60 | CAAGTCCAGCTTGTTGAGTCTGGCGGAGGGGTG GTTAGGCCAGGAGGTTCCCTTAGGCTTTCCTGT GCGGCATCAGGATTTACCTTCGATGACTACGGA ATGTCATGGGTACGACAAGCTCCCGGCAAAGGC CTCGAATGGGTTTCTGGCATCAACTGGGAGGGC GGTTCCACTGGCTACGCGGACTCAGTTAAGGGT AGGTTCACCATAAGCAGGGACAATGCGAAGAA CTCACTGTATCTCCAAATGAACAGTCTCCGCGC CGAGGATACAGCCCTTTACTATTGTGCACGAGA TGAGCAATTGGGGGGGCGCCACTATTATTACTA TTACATGGACGTGTGGGGTAAAGGAACGACCGT CACAGTC |

In some embodiments, the nucleic acid molecule encoding the variable light chain is as set forth below:

TABLE 10

| SEQ ID NO: | AB ID NO. | Sequence |
|---|---|---|
| 269 | MAB1 | GACATTCAGATGACGCAAAGCCCCTCTAGCTTG TCCGCTAGTGTGGGTGACAGGGTCACCATTACC TGCCAGGCTTCACAAGACATCAGTAATTACCTC AACTGGTATCAGCAGAAACCTGGGAAGGCCCCT AAGCTGTTGATTTACGATGCTAGTAACTTGGAG ACCGGGGTACCCAGCAGATTTAGCGGGAGCGG AAGTGGTACGGATTTTACGTTTACCATTAGCAG CTTGCAGCCCGAGGACATCGCTACATATTACTG TGAACAGTATGAGGACTACCCTCTTACCTTCGG CGGTGGAACGAAAGTTGAGATTAAGCGAACC |
| 271 | MAB2 | GACATTCAGATGACGCAAAGCCCCTCTAGCTTG TCCGCTAGTGTGGGTGACAGGGTCACCATTACC TGCCAGGCTTCACAAGACATCAGTAATTACCTC AACTGGTATCAGCAGAAACCTGGGAAGGCCCCT AAGCTGTTGATTTACGATGCTAGTAACTTGGAG ACCGGGGTACCCAGCAGATTTAGCGGGAGCGG AAGTGGTACGGATTTTACGTTTACCATTAGCAG |

TABLE 10-continued

| SEQ ID NO: | AB ID NO. | Sequence |
|---|---|---|
|  |  | CTTGCAGCCCGAGGACATCGCTACATATTACTG TAAGCAGTATGAGGACTACCCTCTTACCTTCGG CGGTGGAACGAAAGTTGAGATTAAGCGAACC |
| 273 | MAB3 | GACATTCAGATGACGCAAAGCCCCTCTAGCTTG TCCGCTAGTGTGGGTGACAGGGTCACCATTACC TGCCAGGCTTCACAAGACATCAGTAATTACCTC AACTGGTATCAGCAGAAACCTGGGAAGGCCCCT AAGCTGTTGATTTACGATGCTAGTAACTTGGAG ACCGGGGTACCCAGCAGATTTAGCGGGAGCGG AAGTGGTACGGATTTTACGTTTACCATTAGCAG CTTGCAGCCCGAGGACATCGCTACATATTACTG TAAGCAGTATGAGGACTACCCTCTTACCTTCGG CGGTGGAACGAAAGTTGAGATTAAGCGAACC |
| 275 | MAB4 | GACATTCAGATGACGCAAAGCCCCTCTAGCTTG TCCGCTAGTGTGGGTGACAGGGTCACCATTACC TGCCAGGCTTCACAAGACATCAGTAATTACCTC AACTGGTATCAGCAGAAACCTGGGAAGGCCCCT AAGCTGTTGATTTACGATGCTAGTAACTTGGAG ACCGGGGTACCCAGCAGATTTAGCGGGAGCGG AAGTGGTACGGATTTTACGTTTACCATTAGCAG CTTGCAGCCCGAGGACATCGCTACATATTACTG TCACCAGTATGAGGACTACCCTCTTACCTTCGG CGGTGGAACGAAAGTTGAGATTAAGCGAACC |
| 277 | MAB5 | GACATTCAGATGACGCAAAGCCCCTCTAGCTTG TCCGCTAGTGTGGGTGACAGGGTCACCATTACC TGCCAGGCTTCACAAGACATCAGTAATTACCTC AACTGGTATCAGCAGAAACCTGGGAAGGCCCCT AAGCTGTTGATTTACGATGCTAGTAACTTGGAG ACCGGGGTACCCAGCAGATTTAGCGGGAGCGG AAGTGGTACGGATTTTACGTTTACCATTAGCAG CTTGCAGCCCGAGGACATCGCTACATATTACTG TCACCAGTATGAGGACTACCCTCTTACCTTCGG CGGTGGAACGAAAGTTGAGATTAAGCGAACC |
| 279 | MAB6 | GACATTCAGATGACGCAAAGCCCCTCTAGCTTG TCCGCTAGTGTGGGTGACAGGGTCACCATTACC TGCCAGGCTTCACAAGACATCAGTAATTACCTC AACTGGTATCAGCAGAAACCTGGGAAGGCCCCT AAGCTGTTGATTTACGATGCTAGTAACTTGGAG ACCGGGGTACCCAGCAGATTTAGCGGGAGCGG AAGTGGTACGGATTTTACGTTTACCATTAGCAG CTTGCAGCCCGAGGACATCGCTACATATTACTG TCACCAGTATGAGGACTACCCTCTTACCTTCGG CGGTGGAACGAAAGTTGAGATTAAGCGAACC |
| 281 | MAB7 | GACATTCAGATGACGCAAAGCCCCTCTAGCTTG TCCGCTAGTGTGGGTGACAGGGTCACCATTACC TGCCAGGCTTCACAAGACATCAGTAATTACCTC AACTGGTATCAGCAGAAACCTGGGAAGGCCCCT AAGCTGTTGATTTACGATGCTAGTAACTTGGAG ACCGGGGTACCCAGCAGATTTAGCGGGAGCGG AAGTGGTACGGATTTTACGTTTACCATTAGCAG CTTGCAGCCCGAGGACATCGCTACATATTACTG TCAGCAGTATGAGGACTACCCTCTTGTGTTCGG CGGTGGAACGAAAGTTGAGATTAAGCGAACC |
| 283 | MAB8 | GACATTCAGATGACGCAAAGCCCCTCTAGCTTG TCCGCTAGTGTGGGTGACAGGGTCACCATTACC TGCCAGGCTTCACAAGACATCAGTAATTACCTC AACTGGTATCAGCAGAAACCTGGGAAGGCCCCT AAGCTGTTGATTTACGATGCTAGTAACTTGGAG ACCGGGGTACCCAGCAGATTTAGCGGGAGCGG AAGTGGTACGGATTTACGTTTACCATTAGCAG CTTGCAGCCCGAGGACATCGCTACATATTACTG TCAGCAGCACGAGGACTACCCTCTTACCTTCGG CGGTGGAACGAAAGTTGAGATTAAGCGAACC |
| 285 | MAB9 | GACATTCAGATGACGCAAAGCCCCTCTAGCTTG TCCGCTAGTGTGGGTGACAGGGTCACCATTACC TGCCAGGCTTCACAAGACATCAGTAATTACCTC AACTGGTATCAGCAGAAACCTGGGAAGGCCCCT AAGCTGTTGATTTACGATGCTAGTAACTTGGAG ACCGGGGTACCCAGCAGATTTAGCGGGAGCGG AAGTGGTACGGATTTTACGTTTACCATTAGCAG CTTGCAGCCCGAGGACATCGCTACATATTACTG TCAGCACTATGAGGACTACCCTCTTACCTTCGG CGGTGGAACGAAAGTTGAGATTAAGCGAACC |
| 287 | MAB10 | GACATTCAGATGACGCAAAGCCCCTCTAGCTTG TCCGCTAGTGTGGGTGACAGGGTCACCATTACC TGCCAGGCTTCACAAGACATCAGTAATTACCTC AACTGGTATCAGCAGAAACCTGGGAAGGCCCCT AAGCTGTTGATTTACGATGCTAGTAACTTGGAG ACCGGGGTACCCAGCAGATTTAGCGGGAGCGG AAGTGGTACGGATTTTACGTTTACCATTAGCAG CTTGCAGCCCGAGGACATCGCTACATATTACTG TCAGCAGTATGAGGACCTCATCCCCACCTTCGG CGGTGGAACGAAAGTTGAGATTAAGCGAACC |
| 289 | MAB11 | GACATACAAATGACTCAATCACCCTCTACACTT TCCGCCTCTGTCGGCGACAGGGTAACGATAACT TGCCGGGCAAGTCAATCAATCAGCTCCTGGCTT GCTTGGTATCAACAAAAACCAGGCAAGGCACCT AAGCTCCTCATTTACAAGGCGTCATCACTTGAA TCAGGGGTGCCTTCACGATTCAGTGGATCAGGA TCTGGTACTGAATTCACTCTGACCATTTCAAGTC TTCAGCCTGATGACTTTGCGACCTATTATTGCCA GAGCTACAATAGCTACGTGTGGACGTTCGGGCA GGGTACTAAAGTCGAGATTAAACGAACC |
| 291 | MAB12 | GACATACAAATGACTCAATCACCCTCTACACTT TCCGCCTCTGTCGGCGACAGGGTAACGATAACT TGCCGGGCAAGTCAATCAATCAGCTCCTGGCTT GCTTGGTATCAACAAAAACCAGGCAAGGCACCT AAGCTCCTCATTTACAAGGCGTCATCACTTGAA TCAGGGGTGCCTTCACGATTCAGTGGATCAGGA TCTGGTACTGAATTCACTCTGACCATTTCAAGTC TTCAGCCTGATGACTTTGCGACCTATTATTGCCA GCAGGTAATAGCTACGACTGGACGTTCGGGCA GGGTACTAAAGTCGAGATTAAACGAACC |
| 293 | MAB13 | GACATACAAATGACTCAATCACCCTCTACACTT TCCGCCTCTGTCGGCGACAGGGTAACGATAACT TGCCGGGCAAGTCAATCAATCAGCTCCTGGCTT GCTTGGTATCAACAAAAACCAGGCAAGGCACCT AAGCTCCTCATTTACAAGGCGTCATCACTTGAA TCAGGGGTGCCTTCACGATTCAGTGGATCAGGA TCTGGTACTGAATTCACTCTGACCATTTCAAGTC TTCAGCCTGATGACTTTGCGACCTATTATTGCCA GCAGGTAATAGCTACGACTGGACGTTCGGGCA GGGTACTAAAGTCGAGATTAAACGAACC |
| 295 | MAB14 | GACATACAAATGACTCAATCACCCTCTACACTT TCCGCCTCTGTCGGCGACAGGGTAACGATAACT TGCCGGGCAAGTCAATCAATCAGCTCCTGGCTT GCTTGGTATCAACAAAAACCAGGCAAGGCACCT AAGCTCCTCATTTACAAGGCGTCATCACTTGAA TCAGGGGTGCCTTCACGATTCAGCGGATCAGGA TCTGGTACTGAATTCACTCTGACCATTTCAAGTC TTCAGCCTGATGACTTTGCGACCTATTATTGCCA GCAGTACAGCAGCTACGCCTGGACGTTCGGGCA GGGTACTAAAGTCGAGATTAAACGAACC |
| 297 | MAB15 | GACATACAAATGACTCAATCACCCTCTACACTT TCCGCCTCTGTCGGCACAGGGTAACGATAACT TGCCGGGCAAGTCAATCAATCAGCTCCTGGCTT GCTTGGTATCAACAAAAACCAGGCAAGGCACCT AAGCTCCTCATTTACAAGGCGTCATCACTTGAA TCAGGGGTGCCTTCACGATTCAGCGGATCAGGA TCTGGTACTGAATTCACTCTGACCATTTCAAGTC TTCAGCCTGATGACTTTGCGACCTATTATTGCCA GCAGGCCCGCAGCTACTCATGGACGTTCGGGCA GGGTACTAAAGTCGAGATTAAACGAACC |
| 299 | MAB16 | GACATACAAATGACTCAATCACCCTCTACACTT TCCGCCTCTGTCGGCGACAGGGTAACGATAACT TGCCGGGCAAGTCAATCAATCAGCTCCTGGCTT GCTTGGTATCAACAAAAACCAGGCAAGGCACCT AAGCTCCTCATTTACAAGGCGTCATCACTTGAA |

TABLE 10-continued

| SEQ ID NO: | AB ID NO. | Sequence |
|---|---|---|
| | | TCAGGGGTGCCTTCACGATTCAGCGGATCAGGA<br>TCTGGTACTGAATTCACTCTGACCATTTCAAGTC<br>TTCAGCCTGATGACTTTGCGACCTATTATTGCCA<br>GCAGCACAATAGCTACCGCTGGACGTTCGGGCA<br>GGGTACTAAAGTCGAGATTAAACGAACC |
| 301 | MAB17 | GACATACAAATGACTCAATCACCCTCTACACTT<br>TCCGCCTCTGTCGGCGACAGGGTAACGATAACT<br>TGCCGGGCAAGTCAATCAATCAGCTCCTGGCTT<br>GCTTGGTATCAACAAAAACCAGGCAAGGCACCT<br>AAGCTCCTCATTTACAAGGCGTCATCACTTGAA<br>TCAGGGGTGCCTTCACGATTCAGCGGATCAGGA<br>TCTGGTACTGAATTCACTCTGACCATTTCAAGTC<br>TTCAGCCTGATGACTTTGCGACCTATTATTGCGT<br>GCAGTACCCCAGCTACTCATGGACGTTCGGGCA<br>GGGTACTAAAGTCGAGATTAAACGAACC |
| 303 | MAB18 | GACATACAAATGACTCAATCACCCTCTACACTT<br>TCCGCCTCTGTCGGCGACAGGGTAACGATAACT<br>TGCCGGGCAAGTCAATCAATCAGCTCCTGGCTT<br>GCTTGGTATCAACAAAAACCAGGCAAGGCACCT<br>AAGCTCCTCATTTACAAGGCGTCATCACTTGAA<br>TCAGGGGTGCCTTCACGATTCAGCGGATCAGGA<br>TCTGGTACTGAATTCACTCTGACCATTTCAAGTC<br>TTCAGCCTGATGACTTTGCGACCTATTATTGCCA<br>GCAGTACAATAGCTACAAGCTGACGTTCGGGCA<br>GGGTACTAAAGTCGAGATTAAACGAACC |
| 305 | MAB19 | GACATACAAATGACTCAATCACCCTCTACACTT<br>TCCGCCTCTGTCGGCGACAGGGTAACGATAACT<br>TGCCGGGCAAGTCAATCAATCAGCTCCTGGCTT<br>GCTTGGTATCAACAAAAACCAGGCAAGGCACCT<br>AAGCTCCTCATTTACAAAGGCGTCATCACTTGAA<br>TCAGGGGTGCCTTCACGATTCAGCGGATCAGGA<br>TCTGGTACTGAATTCACTCTGACCATTTCAAGTC<br>TTCAGCCTGATGACTTTGCGACCTATTATTGCCA<br>GCAGTACAATAGCCCCTCATGGCTGTTCGGGCA<br>GGGTACTAAAGTCGAGATTAAACGAACC |
| 307 | MAB20 | GACATACAAATGACTCAATCACCCTCTACACTT<br>TCCGCCTCTGTCGGCGACAGGGTAACGATAACT<br>TGCCGGGCAAGTCAATCAATCAGCTCCTGGCTT<br>GCTTGGTATCAACAAAAACCAGGCAAGGCACCT<br>AAGCTCCTCATTTACAAGGCGTCATCACTTGAA<br>TCAGGGGTGCCTTCACGATTCAGCGGATCAGGA<br>TCTGGTACTGAATTCACTCTGACCATTTCAAGTC<br>TTCAGCCTGATGACTTTGCGACCTATTATTGCCA<br>GCAGGTAATAGCCTGTCATGGACGTTCGGGCA<br>GGGTACTAAAGTCGAGATTAAACGAACC |
| 309 | MAB21 | GACATACAGATGACTCAGTCCCCAAGTAGTCTG<br>AGCGCCTCTGTCGGCGACCGCGTTACCATTACT<br>TGCCGGGCGAGTCAAGGGATACGCAACGATTTG<br>GGTTGGTATCAGCAAAAGCCCGGAAAGGCCCC<br>AAAGCGGCTGATATACACCGCCTCAAACCTCCA<br>GTCTGGAGTTCCATCAAGGTTTAGTGGATCTGG<br>ATCTGGCACTGAGTTACTCTCACTATAAGCTCC<br>CTTCAGCCTGAAGACTTCGCAACTTATTATTGCT<br>TCCAGTATAATAGTTATCCTCTCGGCTTTGGCGG<br>TGGCACCAAAGTGGAGATTAAGCGAACC |
| 311 | MAB22 | GACATACAGATGACTCAGTCCCCAAGTAGTCTG<br>AGCGCCTCTGTCGGCGACCGCGTTACCATTACT<br>TGCCGGGCGAGTCAAGGGATACGCAACGATTTG<br>GGTTGGTATCAGCAAAAGCCCGAAAGGCCCC<br>AAAGCGGCTGATATACACCGCCTCAAACCTCCA<br>GTCTGGAGTTCCATCAAGGTTTAGTGGATCTGG<br>ATCTGGCACTGAGTTTACTCTCACTATAAGCTCC<br>CTTCAGCCTGAAGACTTCGCAACTTATTATTGCT<br>TGCAGTACCGCAGTCACTATCCTCTCACTTTTGG<br>CGGTGGCACCAAAGTGGAGATTAAGCGAACC |
| 313 | MAB23 | GACATACAGATGACTCAGTCCCCAAGTAGTCTG<br>AGCGCCTCTGTCGGCGACCGCGTTACCATTACT<br>TGCCGGGCGAGTCAAGGGATACGCAACGATTTG<br>GGTTGGTATCAGCAAAAGCCCGGAAAGGCCCC |

TABLE 10-continued

| SEQ ID NO: | AB ID NO. | Sequence |
|---|---|---|
| | | AAAGCGGCTGATATACACCGCCTCAAACCTCCA<br>GTCTGGAGTTCCATCAAGGTTTAGTGGATCTGG<br>ATCTGGCACTGAGTTTACTCTCACTATAAGCTCC<br>CTTCAGCCTGAAGACTTCGCAACTTATTATTGCT<br>TGCAGTATAATCAGGTGCCTCTCACTTTTGCG<br>GTGGCACCAAAGTGGAGATTAAGCGAACC |
| 315 | MAB24 | GACATACAGATGACTCAGTCCCCAAGTAGTCTG<br>AGCGCCTCTGTCGGCGACCGCGTTACCATTACT<br>TGCCGGGCGAGTCAAGGGATACGCAACGATTTG<br>GGTTGGTATCAGCAAAAGCCCGGAAAGGCCCC<br>AAAGCGGCTGATATACACCGCCTCAAACCTCCA<br>GTCTGGAGTTCCATCAAGGTTTAGTGGATCTGG<br>ATCTGGCACTGAGTTACTCTCACTATAAGCTCC<br>CTTCAGCCTGAAGACTTCGCAACTTATTATTGCT<br>TGCAGACCAATATCTATCCTCTCACTTTTGGCGG<br>TGGCACCAAAGTGGAGATTAAGCGAACC |
| 317 | MAB25 | GACATACAGATGACTCAGTCCCCAAGTAGTCTG<br>AGCGCCTCTGTCGGCGACCGCGTTACCATTACT<br>TGCCGGGCGAGTCAAGGGATACGCAACGATTTG<br>GGTTGGTATCAGCAAAAGCCCGGAAAGGCCCC<br>AAAGCGGCTGATATACACCGCCTCAAACCTCCA<br>GTCTGGAGTTCCATCAAGGTTTAGTGGATCTGG<br>ATCTGGCACTGAGTTACTCTCACTATAAGCTCC<br>CTTCAGCCTGAAGACTTCGCAACTTATTATTGCT<br>TGCAGTATAAGCAGTATCCTCTCACTTTTGGCG<br>GTGGCACCAAAGTGGAGATTAAGCGAACC |
| 319 | MAB26 | GACATACAGATGACTCAGTCCCCAAGTAGTCTG<br>AGCGCCTCTGTCGGCGACCGCGTTACCATTACT<br>TGCCGGGCGAGTCAAGGGATACGCAACGATTTG<br>GGTTGGTATCAGCAAAAGCCCGGAAAGGCCCC<br>AAAGCGGCTGATATACACCGCCTCAAACCTCCA<br>GTCTGGAGTTCCATCAAGGTTTAGTGGATCTGG<br>ATCTGGCACTGAGTTACTCTCACTATAAGCTCC<br>CTTCAGCCTGAAGACTTCGCAACTTATTATTGCT<br>TGCAGACCAATATCTATCCTCTCACTTTTGGCGG<br>TGGCACCAAAGTGGAGATTAAGCGAACC |
| 321 | MAB27 | GACATACAGATGACTCAGTCCCCAAGTAGTCTG<br>AGCGCCTCTGTCGGCGACCGCGTTACCATTACT<br>TGCCGGGCGAGTCAAGGGATACGCAACGATTTG<br>GGTTGGTATCAGCAAAAGCCCGGAAAGGCCCC<br>AAAGCGGCTGATATACACCGCCTCAAACCTCCA<br>GTCTGGAGTTCCATCAAGGTTTAGTGGATCTGG<br>ATCTGGCACTGAGTTACTCTCACTATAAGCTCC<br>CTTCAGCCTGAAGACTTCGCAACTTATTATTGCT<br>TGCAGTATAATAGTTATCCTCTCGCCTTTGGCGG<br>TGGCACCAAAGTGGAGATTAAGCGAACC |
| 323 | MAB28 | GACATACAGATGACTCAGTCCCCAAGTAGTCTG<br>AGCGCCTCTGTCGGCGACCGCGTTACCATTACT<br>TGCCGGGCGAGTCAAGGGATACGCAACGATTTG<br>GGTTGGTATCAGCAAAAGCCCGGAAAGGCCCC<br>AAAGCGGCTGATATACACCGCCTCAAACCTCCA<br>GTCTGGAGTTCCATCAAGGTTTAGTGGATCTGG<br>ATCTGGCACTGAGTTACTCTCACTATAAGCTCC<br>CTTCAGCCTGAAGACTTCGCAACTTATTATTGCT<br>TGCAGTATCACAGTTATCCTCTCCGCCTTTGGCGG<br>TGGCACCAAAGTGGAGATTAAGCGAACC |
| 325 | MAB29 | GACATACAGATGACTCAGTCCCCAAGTAGTCTG<br>AGCGCCTCTGTCGGCGACCGCGTTACCATTACT<br>TGCCGGGCGAGTCAAGGGATACGCAACGATTTG<br>GGTTGGTATCAGCAAAAGCCCGGAAAGGCCCC<br>AAAGCGGCTGATATACACCGCCTCAAACCTCCA<br>GTCTGGAGTTCCATCAAGGTTTAGTGGATCTGG<br>ATCTGGCACTGAGTTACTCTCACTATAAGCTCC<br>CTTCAGCCTGAAGACTTCGCAACTTATTATTGCT<br>TGCAGTATGCCAGTTATCCTCTCAAGTTTGGCG<br>GTGGCACCAAAGTGGAGATTAAGCGAACC |
| 327 | MAB30 | GACATACAGATGACTCAGTCCCCAAGTAGTCTG<br>AGCGCCTCTGTCGGCGACCGCGTTACCATTACT<br>TGCCGGGCGAGTCAAGGGATACGCAACGATTTG |

TABLE 10-continued

| SEQ ID NO: | AB ID NO. | Sequence |
|---|---|---|
| | | GGTTGGTATCAGCAAAAGCCCGGAAAGGCCCC AAAGCGGCTGATATACACCGCCTCAAACCTCCA GTCTGGAGTTCCATCAAGGTTTAGTGGATCTGG ATCTGGCACTGAGTTTACTCTCACTATAAGCTCC CTTCAGCCTGAAGACTTCGCAACTTATTATTGCT TGCAGTATAATGCCTATCCTCTCATCTTTGGCGG TGGCACCAAAGTGGAGATTAAGCGAACC |

In some embodiments, the nucleic acid molecule comprises a sequence of SEQ ID NO: 268, SEQ ID NO: 269, SEQ ID NO: 270, SEQ ID NO: 271, SEQ ID NO: 272, SEQ ID NO: 273, SEQ ID NO: 274, SEQ ID NO: 275, SEQ ID NO: 276, SEQ ID NO: 277, SEQ ID NO: 278, SEQ ID NO: 279, SEQ ID NO: 280, SEQ ID NO: 281, SEQ ID NO: 282, SEQ ID NO: 283, SEQ ID NO: 284, SEQ ID NO: 285, SEQ ID NO: 286, SEQ ID NO: 287, SEQ ID NO: 288, SEQ ID NO: 289, SEQ ID NO: 290, SEQ ID NO: 291, SEQ ID NO: 292, SEQ ID NO: 293, SEQ ID NO: 294, SEQ ID NO: 295, SEQ ID NO: 296, SEQ ID NO: 297, SEQ ID NO: 298, SEQ ID NO: 299, SEQ ID NO: 300, SEQ ID NO: 301, SEQ ID NO: 302, SEQ ID NO: 303, SEQ ID NO: 304, SEQ ID NO: 305, SEQ ID NO: 306, SEQ ID NO: 307, SEQ ID NO: 308, SEQ ID NO: 309, SEQ ID NO: 310, SEQ ID NO: 311, SEQ ID NO: 312, SEQ ID NO: 313, SEQ ID NO: 314, SEQ ID NO: 315, SEQ ID NO: 316, SEQ ID NO: 317, SEQ ID NO: 318, SEQ ID NO: 319, SEQ ID NO: 320, SEQ ID NO: 321, SEQ ID NO: 322, SEQ ID NO: 323, SEQ ID NO: 324, SEQ ID NO: 325, SEQ ID NO: 326, SEQ ID NO: 327, SEQ ID NO: 424, SEQ ID NO: 425, SEQ ID NO: 426, SEQ ID NO: 427, SEQ ID NO: 428, SEQ ID NO: 429, SEQ ID NO: 430, SEQ ID NO: 431, SEQ ID NO: 432, SEQ ID NO: 433, SEQ ID NO: 434, SEQ ID NO: 435 SEQ ID NO: 436, SEQ ID NO: 437, SEQ ID NO: 438, SEQ ID NO: 439, SEQ ID NO: 440, SEQ ID NO: 441, SEQ ID NO: 442, SEQ ID NO: 443, SEQ ID NO: 444, SEQ ID NO: 445, SEQ ID NO: 446, SEQ ID NO: 447, SEQ ID NO: 448, SEQ ID NO: 449, SEQ ID NO: 450, SEQ ID NO: 451, SEQ ID NO: 452, or SEQ ID NO: 453, as set forth in the table above. It is to be understood that the nucleotide sequences of are exemplary sequences and are not meant to be limiting in any way. Due to the degenerate nature of codons, other nucleic acid molecules can be used. In some embodiments, the nucleic acid molecule is codon optimized for expression in a bacterial system. In some embodiments, the nucleic acid molecule is codon optimized for expression in a eukaryotic system or cell. In some embodiments, the nucleic acid molecule is a DNA or RNA molecule that encodes a polypeptide as provided for herein. In some embodiments, the RNA molecule is an mRNA molecule. Accordingly, in some embodiments, the nucleic acid molecule comprises a sequence that is substantially similar to those provided for herein. In some embodiments, the nucleic acid molecule comprises a sequence that has at least 60%, 65%, 70%, 75%, 80%, 85%, 90%, 95%, or 100% identity to the sequences provided for herein, or any percent identity falling within any of the recited percent identities. In some embodiments, the nucleic acid molecule comprises a sequence that has at least 60%, 65%, 70%, 75%, 80%, 85%, 90%, 95%, or 100% identity to the nucleic acid molecules provided for herein, or any percent identity falling within any of the recited percent identities.

In some embodiments, an expression vector is provided. In some embodiments, the expression vector comprises a nucleic acid molecule encoding an antibody or antigen-binding fragment thereof as provided for herein. In some embodiments, the expression vector comprises a nucleic acid molecule as provided for herein. The vector may be any vector known in the art. In some embodiments the vector is as provided for herein. In some embodiments, the vector is a plasmid. In some embodiments the vector is a virus.

In some embodiments, "derivatives" of the antibodies, fragments, regions or derivatives thereof, which term includes those proteins encoded by truncated or modified genes to yield molecular species functionally resembling the immunoglobulin fragments are provided. The modifications include, but are not limited to, addition of genetic sequences coding for cytotoxic proteins such as plant and bacterial toxins. The modification can also include a reporter protein, such as a fluorescent or chemiluminescent tag. The fragments and derivatives can be produced in any manner.

The identification of these antibodies, or antigen binding fragments thereof, provide the information necessary to generate additional monoclonal antibodies with similar binding characteristics and therapeutic or diagnostic utility that parallel the embodiments of this application.

The antibodies can be generated according to the examples provided herein. Once the sequences are known, the antibodies can also be generated according to known methods. The antibodies can also be converted to different types, such as being converted to Human IgGs and the like. By converting the antibodies to a human antibody, a human subject should not identify the antibodies as foreign. The conversion of a non-human IgG antibody to a human IgG antibody is well known and can routinely be done once the native sequence is known. As discussed herein, the antibodies can be modified according to known methods. Such methods are described in, for example, Riechmann L, Clark M, Waldmann H, Winter G (1988). Reshaping human antibodies for therapy". Nature 332 (6162): 332-323; Tsurushita N, Park M, Pakabunto K, Ong K, Avdalovic A, Fu H, Jia A, Visquez M, Kumar S. (2004), which is incorporated by reference in its entirety.

In some embodiments, a host cell is provided. In some embodiments, the host cell comprises an antibody or antigen-binding fragment thereof as provided for herein. In some embodiments, the host cell comprises a nucleic acid molecule encoding for antibody or antigen-binding fragment thereof as provided for herein. In some embodiments, the host cell comprises nucleic acid molecules as provided for herein, or any variants thereof as provided for herein, or any combination thereof. In some embodiments, the host cell comprises a vector, said vector comprising comprises a nucleic acid molecule encoding for antibody or antigen-binding fragment thereof as provided for herein. In some embodiments, the vector comprises nucleic acid molecules as provided for herein, any variants thereof as provided for herein, or any combination thereof.

In some embodiments, the host cell produces an antibody or antigen-binding fragment thereof as provided for herein. In some embodiments, an antibody or antigen-binding fragment thereof as provided for herein is provided, wherein the antibody or antigen-binding fragment thereof as provided for herein is produced by the host cell.

In some embodiments, a method of producing a polypeptide is provided. In some embodiments, the polypeptide comprises a heavy chain variable region as provided for herein, a light chain variable region as provided for herein, or a combination thereof. In some embodiments, the method comprises growing a host cell under conditions so that the host cell expresses the polypeptide comprising the heavy chain variable region, light chain variable region, or combination thereof, and purifying the polypeptide comprising the heavy chain variable region, the light chain variable region, or a combination thereof, thereby producing the polypeptide. In some embodiments, the host cell is a host cell as provided for herein.

In some embodiments, a method of producing an antibody, or antigen binding fragment thereof, is provided. In some embodiments, the antibody binds human C1s. In some embodiments, the antigen binding fragment binds human C1s. In some embodiments, the method comprises growing a host cell under conditions so that the host cell expresses a polypeptide or polypeptides comprising the immunoglobulin heavy chain variable region and/or the immunoglobulin light chain variable region, thereby producing the antibody or the antigen binding fragment of the antibody, and purifying the antibody or the antigen binding fragment of the antibody. In some embodiments, the polypeptide or polypeptides comprise the immunoglobulin heavy chain variable region. In some embodiments, the polypeptide or polypeptides comprise the immunoglobulin light chain variable region. In some embodiments, the polypeptide or polypeptides comprise the immunoglobulin heavy chain variable region and the immunoglobulin light chain variable region. In some embodiments, the host cell is a host cell as provided for herein. In some embodiments, the antibody, or antigen binding fragment thereof, is as provided for herein.

The polypeptide or antibody-producing cell contributing the nucleotide sequences encoding the antigen-binding region of the chimeric antibody can also be produced by transformation of a non-human, such as a primate, or a human cell. For example, a B lymphocyte which produces the antibody can be infected and transformed with a virus such as Epstein-Barr virus to yield an immortal antibody producing cell (Kozbor et al., Immunol. Today 4:72 79 (1983)). Alternatively, the B lymphocyte can be transformed by providing a transforming gene or transforming gene product, as is well-known in the art. See, e.g., Ausubel infra, Harlow infra, and Colligan infra, the contents of which references are incorporated entirely herein by reference. The cell fusions are accomplished by standard procedures well known to those skilled in the field of immunology, such as producing cells can also be a hybridoma which is generated by fusing a B-cell with an immortal myeloma cell. Fusion partner cell lines and methods for fusing and selecting hybridomas and screening for mAbs are well known in the art. See, e.g., Ausubel infra, Harlow infra, and Colligan infra, the contents of which references are incorporated entirely herein by reference.

The nucleic acid sequence encoding an antibody described herein can be genomic DNA or cDNA, or RNA (e.g. mRNA) which encodes at least one of the variable regions described herein. A convenient alternative to the use of chromosomal gene fragments as the source of DNA encoding the V region antigen-binding segment is the use of cDNA for the construction of chimeric immunoglobulin genes, e.g., as reported by Liu et al. (Proc. Natl. Acad. Sci., USA 84:3439 (1987) and J. Immunology 139:3521 (1987), which references are hereby entirely incorporated herein by reference. The use of cDNA requires that gene expression elements appropriate for the host cell be combined with the gene in order to achieve synthesis of the desired protein. The use of cDNA sequences is advantageous over genomic sequences (which contain introns), in that cDNA sequences can be expressed in bacteria or other hosts which lack appropriate RNA splicing systems.

For example, a cDNA encoding a V region antigen-binding segment able to detect, bind, to or neutralize Cis can be provided using known methods based on the use of the amino acid sequences provided herein. Because the genetic code is degenerate, more than one codon can be used to encode a particular amino acid (Watson, et al., infra). Using the genetic code, one or more different oligonucleotides can be identified, each of which would be capable of encoding the amino acid. The probability that a particular oligonucleotide will, in fact, constitute the actual XXX-encoding sequence can be estimated by considering abnormal base pairing relationships and the frequency with which a particular codon is actually used (to encode a particular amino acid) in eukaryotic or prokaryotic cells expressing an antibody or fragment. Such "codon usage rules" are disclosed by Lathe, et al., J. Molec. Biol. 183:1 12 (1985). Using the "codon usage rules" of Lathe, a single oligonucleotide, or a set of oligonucleotides, that contains a theoretical "most probable" nucleotide sequence capable of encoding an antibody variable or constant region sequences is identified.

The variable regions described herein can be combined with any type of constant region including a human constant region or murine constant region. Human genes which encode the constant (C) regions of the antibodies, fragments and regions can be derived from a human fetal liver library, by known methods. Human C region genes can be derived from any human cell including those which express and produce human immunoglobulins. The human $C_H$ region can be derived from any of the known classes or isotypes of human H chains, including gamma, μ, α, δ or ε, and subtypes thereof, such as G1, G2, G3 and G4. Since the H chain isotype is responsible for the various effector functions of an antibody, as well as antibody recycling by interaction with FcRn, the choice of $C_H$ region will be guided by the desired effector functions, such as complement fixation, or activity in antibody-dependent cellular cytotoxicity (ADCC). Preferably, the $C_H$ region is derived from gamma 1 (IgG1), gamma 3 (IgG3), gamma 4 (IgG4), or L (IgM). The human $C_L$ region can be derived from either human L chain isotype, kappa or lambda.

Methods of purifying polypeptides or proteins (including antibodies or antigen binding fragments thereof) are known in the art, and any such method is within the scope of the present application. Further, the host cell is not limited by the examples recited above. Any suitable cell may be used to generate the polypeptides or proteins of the present disclosure.

Pharmaceutical Compositions

In some embodiments, a pharmaceutical composition is provided. In some embodiments, the pharmaceutical composition comprises an antibody or antigen-binding fragment thereof as provided for herein.

In some embodiments, to prepare pharmaceutical or sterile compositions of the anti-C1s antibodies or other proteins provided herein, the antibody, or antigen binding fragment thereof, or other proteins provided herein are admixed with a pharmaceutically acceptable carrier or excipient. See, e.g., *Remington's Pharmaceutical Sciences* and U.S. Pharmacopeia: National Formulary, Mack Publishing Company, Easton, PA (1984).

Formulations of therapeutic or the antibodies provided herein may be prepared by mixing with acceptable carriers, excipients, or stabilizers in the form of, e.g., lyophilized powders, slurries, aqueous solutions or suspensions (see, e.g., Hardman, et al. (2001) *Goodman and Gilman's The*

*Pharmacological Basis of Therapeutics*, McGraw-Hill, New York, NY; Gennaro (2000) *Remington: The Science and Practice of Pharmacy*, Lippincott, Williams, and Wilkins, New York, NY; Avis, et al. (eds.) (1993) *Pharmaceutical Dosage Forms: Parenteral Medications*, Marcel Dekker, NY; Lieberman, et al. (eds.) (1990) *Pharmaceutical Dosage Forms: Tablets*, Marcel Dekker, NY; Lieberman, et al. (eds.) (1990) *Pharmaceutical Dosage Forms: Disperse Systems*, Marcel Dekker, NY; Weiner and Kotkoskie (2000) *Excipient Toxicity and Safety*, Marcel Dekker, Inc., New York, NY). In some embodiments, the antibodies are diluted to an appropriate concentration in a sodium acetate solution pH 5-6, and NaCl or sucrose is added for tonicity. Additional agents, such as polysorbate 20 or polysorbate 80, may be added to enhance stability.

Toxicity and therapeutic efficacy of the antibody compositions, administered alone or in combination with another agent, can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index ($LD_{50}/ED_{50}$). In particular aspects, antibodies exhibiting high therapeutic indices are desirable. The data obtained from these cell culture assays and animal studies can be used in formulating a range of dosage for use in human. The dosage of such compounds lies preferably within a range of circulating concentrations that include the $ED_{50}$ with little or no toxicity. The dosage may vary within this range depending upon the dosage form employed and the route of administration.

In some embodiments, a composition is administered to a subject in accordance with the Physicians' Desk Reference 2003 (Thomson Healthcare; 57th edition (Nov. 1, 2002)).

The mode of administration can vary. Suitable routes of administration include oral, rectal, transmucosal, intestinal, parenteral; intramuscular, subcutaneous, intradermal, intramedullary, intrathecal, direct intraventricular, intravenous, intraperitoneal, intranasal, intraocular, inhalation, insufflation, topical, cutaneous, transdermal, or intra-arterial. In some embodiments, the composition is an injectable pharmaceutical composition. In some embodiments, the composition is formulated for intravenous or subcutaneous injection. In some embodiments, the composition is formulated for intravenous injection. In some embodiments, the composition is formulated for subcutaneous injection.

In some embodiments, the antibody, or antigen binding fragment thereof, can be administered by an invasive route such as by injection. In some embodiments, the antibodies or antigen binding fragment thereof, or pharmaceutical composition thereof, is administered intravenously, subcutaneously, intramuscularly, intraarterially, intra-articularly (e.g. in arthritis joints), intratumorally, or by inhalation, aerosol delivery. Administration by non-invasive routes (e.g., orally; for example, in a pill, capsule or tablet) is also within the scope of the present embodiments.

In some embodiments, the anti-C1s antibody, or antigen binding fragment thereof, is administered in combination with at least one additional therapeutic agent, such as, but not limited to any therapeutic used to treat the disorders provided for herein. In some embodiments, the antibody is administered in combination with another treatment for the disorders provided for herein.

Compositions can be administered with medical devices known in the art. For example, a pharmaceutical composition of the invention can be administered by injection with a hypodermic needle, including, e.g., a prefilled syringe or autoinjector.

The pharmaceutical compositions may also be administered with a needleless hypodermic injection device; such as the devices disclosed in U.S. Pat. Nos. 6,620,135; 6,096,002; 5,399,163; 5,383,851; 5,312,335; 5,064,413; 4,941,880; 4,790,824 or 4,596,556.

The pharmaceutical compositions may also be administered by infusion. Examples of well-known implants and modules form administering pharmaceutical compositions include: U.S. Pat. No. 4,487,603, which discloses an implantable micro-infusion pump for dispensing medication at a controlled rate; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments. Many other such implants, delivery systems, and modules are well known to those skilled in the art.

Alternately, one may administer the antibody in a local rather than systemic manner, for example, via injection of the antibody directly into an arthritic joint or pathogen-induced lesion characterized by immunopathology, often in a depot or sustained release formulation. Furthermore, one may administer the antibody in a targeted drug delivery system, for example, in a liposome coated with a tissue-specific antibody, targeting, for example, arthritic joint or pathogen-induced lesion characterized by immunopathology. The liposomes will be targeted to and taken up selectively by the afflicted tissue.

The administration regimen depends on several factors, including the serum or tissue turnover rate of the therapeutic antibody, the level of symptoms, the immunogenicity of the therapeutic antibody, and the accessibility of the target cells in the biological matrix. Preferably, the administration regimen delivers sufficient therapeutic antibody to effect improvement in the target disease state, while simultaneously minimizing undesired side effects. Accordingly, the amount of biologic delivered depends in part on the particular therapeutic antibody and the severity of the condition being treated. Guidance in selecting appropriate doses of therapeutic antibodies is available (see, e.g., Wawrzynczak (1996) *Antibody Therapy*, Bios Scientific Pub. Ltd, Oxfordshire, UK; Kresina (ed.) (1991) *Monoclonal Antibodies, Cytokines and Arthritis*, Marcel Dekker, New York, NY; Bach (ed.) (1993) *Monoclonal Antibodies and Peptide Therapy in Autoimmune Diseases*, Marcel Dekker, New York, NY; Baert, et al. (2003) *New Engl. J. Med.* 348:601-608; Milgrom et al. (1999) *New Engl. J. Med.* 341:1966-1973; Slamon et al. (2001) *New Engl. J. Med.* 344:783-792; Beniaminovitz et al. (2000) *New Engl. J. Med.* 342:613-619; Ghosh et al. (2003) *New Engl. J. Med.* 348:24-32; Lipsky et al. (2000) *New Engl. J. Med.* 343:1594-1602).

Determination of the appropriate dose can be made by the clinician, e.g., using parameters or factors known or suspected in the art to affect treatment. Generally, the dose begins with an amount somewhat less than the optimum dose and it is increased by small increments thereafter until the desired or optimum effect is achieved relative to any negative side effects. Important diagnostic measures include those of symptoms of, e.g., the inflammation or level of inflammatory cytokines produced. In general, it is desirable that a biologic that will be used is derived from the same species as the animal targeted for treatment, thereby minimizing any immune response to the reagent. In the case of human subjects, for example, chimeric, humanized and fully human antibodies may be desirable.

Antibodies or antigen binding fragments thereof can be provided by continuous infusion, or by doses administered, e.g., daily, 1-7 times per week, weekly, bi-weekly, monthly, bimonthly, or quarterly. In some embodiments, a total weekly dose is generally at least 0.05 µg/kg body weight, more generally at least 0.2 µg/kg, 0.5 µg/kg, 1 µg/kg, 10 µg/kg, 100 µg/kg, 0.25 mg/kg, 1.0 mg/kg, 2.0 mg/kg, 5.0 mg/ml, 10 mg/kg, 25 mg/kg, 50 mg/kg or more (see, e.g., Yang, et al. (2003) *New Engl. J. Med.* 349:427-434; Herold, et al. (2002) *New Engl. J. Med.* 346:1692-1698; Liu, et al. (1999) *J. Neurol. Neurosurg. Psych.* 67:451-456; Portielji, et al. (20003) *Cancer Immunol. Immunother.* 52:133-144). Doses may also be provided to achieve a pre-determined target concentration of the antibody in the subject's serum, such as 0.1, 0.3, 1, 3, 10, 30, 100, 300 µg/ml or more. In other embodiments, a fully human antibody is administered subcutaneously or intravenously, on a weekly, biweekly, "every 4 weeks," monthly, bimonthly, or quarterly basis at 10, 20, 50, 80, 100, 200, 500, 1000 or 2500 mg/subject.

As used herein, "inhibit" or "treat" or "treatment" includes a postponement of development of the symptoms associated with a disorder and/or a reduction in the severity of the symptoms of such disorder. The terms further include ameliorating existing uncontrolled or unwanted symptoms, preventing additional symptoms, and ameliorating or preventing the underlying causes of such symptoms. Thus, the terms denote that a beneficial result has been conferred on a vertebrate subject with a disorder, disease or symptom, or with the potential to develop such a disorder, disease or symptom.

As used herein, the terms "therapeutically effective amount", "therapeutically effective dose" and "effective amount" refer to an amount of the antibody, or antigen binding fragment thereof, that, when administered alone or in combination with an additional therapeutic agent to a cell, tissue, or subject, is effective to cause a measurable improvement in one or more symptoms of a disease or condition or the progression of such disease or condition. A therapeutically effective dose further refers to that amount of the binding compound sufficient to result in at least partial amelioration of symptoms, e.g., treatment, healing, prevention or amelioration of the relevant medical condition, or an increase in rate of treatment, healing, prevention or amelioration of such conditions. When applied to an individual active ingredient administered alone, a therapeutically effective dose refers to that ingredient alone. When applied to a combination, a therapeutically effective dose refers to combined amounts of the active ingredients that result in the therapeutic effect, whether administered in combination, serially or simultaneously. An effective amount of a therapeutic will result in an improvement of a diagnostic measure or parameter by at least 10%; usually by at least 20%; preferably at least about 30%; more preferably at least 40%, and most preferably by at least 50%. An effective amount can also result in an improvement in a subjective measure in cases where subjective measures are used to assess disease severity. In some embodiments, an amount is a therapeutically effective amount if it is an amount that can be used to treat or ameliorate tumors or gastric tumors.

The term "subject" as used throughout includes any organism, such as an animal, including a mammal (e.g., rat, mouse, dog, cat, rabbit) and, for example, a human. In one embodiment, the subject is a human. A subject can also be referred to as a patient. In some embodiments, the subject is a subject in need thereof. A subject that is "in need thereof" refers to a subject that has been identified as requiring treatment for the condition that is to be treated and is treated with the specific intent of treating such condition. The conditions can be, for example, any of the conditions described herein.

In some embodiments, the methods comprise administering a therapeutically or prophylactically effective amount of one or more antibodies or antigen binding fragments of the antibodies described herein to a susceptible subject or to one exhibiting a condition in which C1s is known to have caused the pathology observed. Any active form of the antibody can be administered, including, but not limited to scFv, Fab and F(ab')$_2$ fragments and other forms of antibodies provided for herein.

The present disclosure provides a method to treat an individual having a complement-mediated disease or disorder, the method comprising administering to the individual an anti-C1s antibody of any of the embodiments disclosed herein or a pharmaceutical composition thereof. In some embodiments, the individual is a mammal. In some embodiments, the individual is a human. In some embodiments, the administering is intravenous. In some embodiments, the administering is subcutaneous. In some embodiments, the administering is intrathecal. In some embodiments, the administering results in an outcome selected from the group consisting of: (a) a reduction in complement activation; (b) an improvement in cognitive function; (c) a reduction in neuron loss; (d) a reduction in phospho-Tau levels in neurons; (e) a reduction in glial cell activation; (f) a reduction in lymphocyte infiltration; (g) a reduction in macrophage infiltration; (h) a reduction in antibody deposition, (i) a reduction in glial cell loss; (j) a reduction in oligodendrocyte loss; (k) a reduction in dendritic cell infiltration; (l) a reduction in neutrophil infiltration; (m) a reduction in red blood cell lysis; (n) a reduction in red blood cell phagocytosis; (o) a reduction in platelet phagocytosis; (p) a reduction in platelet lysis; (q) an improvement in transplant graft survival; (r) a reduction in macrophage mediated phagocytosis; (s) an improvement in vision; (t) an improvement in motor control; (u) an improvement in thrombus formation; (v) an improvement in clotting; (w) an improvement in kidney function; (x) a reduction in antibody mediated complement activation; (y) a reduction in autoantibody mediated complement activation; (z) an improvement in anemia; (aa) reduction of demyelination; (ab) reduction of eosinophilia; (ac) a reduction in autoantibody mediated blister formation; (ad) a reduction in autoantibody induced pruritis; (ae) a reduction in autoantibody induced erythematosus; (af) a reduction in autoantibody mediated skin erosion; (ag) a reduction in red blood cell destruction due to transfusion reactions; (ah) a reduction in red blood cell lysis due to alloantibodies; (ai) a reduction in hemolysis due to transfusion reactions; (aj) a reduction in allo-antibody mediated platelet lysis; (ak) a reduction in platelet lysis due to transfusion reactions; (al) a reduction in mast cell activation; (am) a reduction in mast cell histamine release; (an) a reduction in vascular permeability; (ao) a reduction in edema; (ap) a reduction in complement deposition on transplant graft endothelium; (aq) a reduction of anaphylatoxin generation in transplant graft endothelium; (ar) a reduction in the separation of the dermal-epidermal junction; (as) a reduction in the generation of anaphylatoxins in the dermal-epidermal junction; (at) a reduction in alloantibody mediated complement activation in transplant graft endothelium; (au) a reduction in antibody mediated loss of the neuromuscular junction; (av) a reduction in complement activation at the neuromuscular junction; (aw) a reduction in anaphylatoxin generation at the neuromuscular junction; (ax) a reduction in complement deposition at the neuromuscular junction; (ay) a reduction in paralysis; (az) a reduction in numbness; (ba) increased bladder control; (bb) increased bowel control; (bc) a reduction in mortality associated with autoantibodies; and (bd) a reduction in morbidity associated with autoantibodies. In some embodiments, the reduction in glial cell activation comprises reduction in astrocyte activation or reduction in microglia activation.

In some embodiments, a method of treating a subject with a C1s mediated disorder is provided. In some embodiments, the method comprises administering to the subject an antibody or antigen-binding fragment thereof as provided for herein or a pharmaceutical composition comprising an antibody or antigen-binding fragment thereof as provided for herein, thereby treating the C1s mediated disorder. The antibody or antigen-binding fragment thereof of any of the embodiments provided for herein or the pharmaceutical compositions of any of the embodiments provided for herein inhibit complement C1s activity in an individual having a complement-mediated disease or disorder. In some embodiments, the individual is a mammal. In some embodiments, the individual is a human. In some embodiments, the administering is intravenous. In some embodiments, the administering is subcutaneous. In some embodiments, the administering is intrathecal. In some embodiments, the administering results in an outcome selected from the group consisting of: (a) a reduction in complement activation; (b) an improvement in cognitive function; (c) a reduction in neuron loss; (d) a reduction in phospho-Tau levels in neurons; (e) a reduction in glial cell activation; (f) a reduction in lymphocyte infiltration; (g) a reduction in macrophage infiltration; (h) a reduction in antibody deposition, (i) a reduction in glial cell loss; (j) a reduction in oligodendrocyte loss; (k) a reduction in dendritic cell infiltration; (l) a reduction in neutrophil infiltration; (m) a reduction in red blood cell lysis; (n) a reduction in red blood cell phagocytosis; (o) a reduction in platelet phagocytosis; (p) a reduction in platelet lysis; (q) an improvement in transplant graft survival; (r) a reduction in macrophage mediated phagocytosis; (s) an improvement in vision; (t) an improvement in motor control; (u) an improvement in thrombus formation; (v) an improvement in clotting; (w) an improvement in kidney function; (x) a reduction in antibody mediated complement activation; (y) a reduction in autoantibody mediated complement activation; (z) an improvement in anemia; (aa) reduction of demyelination; (ab) reduction of eosinophilia; (ac) a reduction in autoantibody mediated blister formation; (ad) a reduction in autoantibody induced pruritis; (ae) a reduction in autoantibody induced erythematosus; (af) a reduction in autoantibody mediated skin erosion; (ag) a reduction in red blood cell destruction due to transfusion reactions; (ah) a reduction in red blood cell lysis due to alloantibodies; (ai) a reduction in hemolysis due to transfusion reactions; (aj) a reduction in allo-antibody mediated platelet lysis; (ak) a reduction in platelet lysis due to transfusion reactions; (al) a reduction in mast cell activation; (am) a reduction in mast cell histamine release; (an) a reduction in vascular permeability; (ao) a reduction in edema; (ap) a reduction in complement deposition on transplant graft endothelium; (aq) a reduction of anaphylatoxin generation in transplant graft endothelium; (ar) a reduction in the separation of the dermal-epidermal junction; (as) a reduction in the generation of anaphylatoxins in the dermal-epidermal junction; (at) a reduction in alloantibody mediated complement activation in transplant graft endothelium; (au) a reduction in antibody mediated loss of the neuromuscular junction; (av) a reduction in complement activation at the neuromuscular junction; (aw) a reduction in anaphylatoxin generation at the neuromuscular junction; (ax) a reduction in complement deposition at the neuromuscular junction; (ay) a reduction in paralysis; (az) a reduction in numbness; (ba) increased bladder control; (bb) increased bowel control; (bc) a reduction in mortality associated with autoantibodies; and (bd) a reduction in morbidity associated with autoantibodies. In some embodiments, the reduction in glial cell activation comprises reduction in astrocyte activation or reduction in microglia activation. In some embodiments, the C1s mediated disorder is selected from the group including, but not limited to, hemolysis, Cold Agglutinin Disease, Immune Thrombocytopenia (ITP), Myasthenia Gravis, Glomerulopathies, Atypical Hemolytic uremic syndrome, antiphospholipid antibody syndrome, transplant rejection, Chronic inflammatory demyelinating polyneuropathy (CIDP), Multifocal motor neuropathy (MMN), Dermatomyositis, or Anti MAG neuropathy. In some embodiments, these conditions can be caused by stroke or due to spinal cord injury. In some embodiments, the C1s mediated disorder is hemolysis. In some embodiments, the C1s mediated disorder is Cold Agglutinin Disease. In some embodiments, the C1s mediated disorder is Immune Thrombocytopenia (ITP). In some embodiments, the C1s mediated disorder is Myasthenia Gravis. In some embodiments, the C1s mediated disorder is Glomerulopathies. In some embodiments, the C1s mediated disorder is Atypical Hemolytic uremic syndrome. In some embodiments, the C1s mediated disorder is antiphospholipid antibody syndrome. In some embodiments, the C1s mediated disorder is transplant rejection. In some embodiments, the C1s mediated disorder is Chronic inflammatory demyelinating polyneuropathy (CIDP). In some embodiments, the C1s mediated disorder is Multifocal motor neuropathy (MMN). In some embodiments, the C1s mediated disorder is Dermatomysositis. In some embodiments, the C1s mediated disorder is Anti MAG neuropathy. In some embodiments, the C1s mediated disorder is due to stroke. In some embodiments, the C1s mediated disorder is due to spinal cord injury.

In some embodiments, the antibody or antigen-binding fragment thereof of any of the embodiments as provided for herein, or a pharmaceutical composition comprising the antibody or antigen-binding fragment thereof of any of the embodiments as provided for herein is for the use in the treatment of a complement-mediated disease or disorder. In some embodiments, the complement-mediated disorder is selected from the group including, but not limited to, hemolysis, Cold Agglutinin Disease, Immune Thrombocytopenia (ITP), Myasthenia Gravis, Glomerulopathies, Atypical Hemolytic uremic syndrome, antiphospholipid antibody syndrome, transplant rejection, Chronic inflammatory demyelinating polyneuropathy (CIDP), Multifocal motor neuropathy (MMN), Dermatomyositis, or Anti MAG neuropathy. In some embodiments, these conditions can be due to stroke or due to spinal cord injury. In some embodiments, the C1s mediated disorder is hemolysis. In some embodiments, the C1s mediated disorder is Cold Agglutinin Disease. In some embodiments, the C1s mediated disorder is Immune Thrombocytopenia (ITP). In some embodiments, the C1s mediated disorder is Myasthenia Gravis. In some embodiments, the C1s mediated disorder is Glomerulopathies. In some embodiments, the C1s mediated disorder is Atypical Hemolytic uremic syndrome. In some embodiments, the C1s mediated disorder is antiphospholipid antibody syndrome. In some embodiments, the C1s mediated disorder is transplant rejection. In some embodiments, the C1s mediated disorder is Chronic inflammatory demyelinating polyneuropathy (CIDP). In some embodiments, the C1s mediated disorder is Multifocal motor neuropathy (MMN). In some embodiments, the C1s mediated disorder is Dermatomyositis. In some embodiments, the C1s mediated disorder is Anti MAG neuropathy. In some embodiments, the C1s mediated disorder is due to stroke. In some embodiments, the C1s mediated disorder is due to spinal cord injury. In some embodiments, the C1s mediated disorder is selected from the group including, but not limited to, hemolysis, Cold Agglutinin Disease, Immune Thrombocytopenia (ITP), Myasthenia Gravis, Glomerulopathies, Atypical Hemolytic uremic syndrome, antiphospholipid antibody syndrome, transplant rejection, Chronic inflammatory demyelinating polyneuropathy (CIDP), Multifocal motor neuropathy (MMN), Dermatomyositis, or Anti MAG neuropathy. In some embodiments, the C1s mediated disorder is hemolysis. In some embodiments, the C1s mediated disorder is Cold Agglutinin Disease. In some embodiments, the C1s mediated disorder is Immune Thrombocytopenia (ITP). In some embodiments, the C1s mediated disorder is Myasthenia Gravis. In some embodiments, the C1s mediated disorder is Glomerulopathies. In some embodiments, the C1s mediated disorder is Atypical Hemolytic uremic syndrome. In some embodiments, the C1s mediated disorder is antiphospholipid antibody syndrome. In some embodiments, the C1s mediated disorder is transplant rejection. In some embodiments, the C1s mediated disorder is Chronic inflammatory demyelinating polyneuropathy (CIDP). In some embodiments, the C1s mediated disorder is Multifocal motor neuropathy (MMN). In some embodiments, the C1s mediated disorder is Dermatomyositis. In some embodiments, the C1s mediated disorder is Anti MAG neuropathy. In some embodiments, the C1s mediated disorder is due to stroke. In some embodiments, the C1s mediated disorder is due to Spinal Cord Injury.

The present disclosure provides use of an anti-C1s antibody of any of the embodiments in the manufacture of a medicament for the treatment of an individual having a complement-mediated disease or disorder. Accordingly, in some embodiments, an antibody, or antigen binding fragment thereof, or a pharmaceutical composition is provided for use as a medicament. In some embodiments, an antibody, or antigen binding fragment thereof, is provided for use as a medicament. In some embodiments, a pharmaceutical composition is provided for use as a medicament. In some embodiments, the antibody, or antigen binding fragment thereof, is an antibody or antigen binding fragment as provided for herein. In some embodiments, the pharmaceutical composition comprises an antibody or antigen binding fragment as provided for herein. In some embodiments, the pharmaceutical composition is as provided for herein. In some embodiments, the medicament is for use in treatment of a C1s mediated disease or disorder. In some embodiments, the complement-mediated disorder is, but not limited to, hemolysis, Cold Agglutinin Disease, Immune Thrombocytopenia (ITP), Myasthenia Gravis, Glomerulopathies, Atypical Hemolytic uremic syndrome, antiphospholipid antibody syndrome, transplant rejection, Chronic inflammatory demyelinating polyneuropathy (CIDP), Multifocal motor neuropathy (MMN), Dermatomyositis, or Anti MAG neuropathy. In some embodiments, the conditions can be due to stroke or due to spinal cord injury. In some embodiments, the C1s mediated disorder is hemolysis. In some embodiments, the C1s mediated disorder is Cold Agglutinin Disease. In some embodiments, the C1s mediated disorder is Immune Thrombocytopenia (ITP). In some embodiments, the C1s mediated disorder is Myasthenia Gravis. In some embodiments, the C1s mediated disorder is Glomerulopathies. In some embodiments, the C1s mediated disorder is Atypical Hemolytic uremic syndrome. In some embodiments, the C1s mediated disorder is antiphospholipid antibody syndrome. In some embodiments, the C1s mediated disorder is transplant rejection. In some embodiments, the C1s mediated disorder is Chronic inflammatory demyelinating polyneuropathy (CIDP). In some embodiments, the C1s mediated disorder is Multifocal motor neuropathy (MMN). In some embodiments, the C1s mediated disorder is Dermatomyositis. In some embodiments, the C1s mediated disorder is Anti MAG neuropathy. In some embodiments, the C1s mediated disorder is due to stroke. In some embodiments, the C1s mediated disorder is due to spinal cord injury.

In some embodiments, a use of an antibody or antigen binding fragment as provided for herein or a pharmaceutical composition as provided for herein is provided. In some embodiments, the use is for the treatment of a C1s mediated disorder. In some embodiments, a use of an antibody or antigen binding fragment as provided for herein is provided, the use for the treatment of a C1s mediated disorder. In some embodiments, a use of a pharmaceutical composition comprising an antibody or antigen binging fragment as provided for herein is provided, the use for the treatment of a C1s mediated disorder. In some embodiments, the pharmaceutical composition is as provided for herein. The antibody of any of the embodiments or pharmaceutical compositions thereof inhibit complement C1s activity in an individual having a complement-mediated disease or disorder. In some embodiments, the complement-mediated disorder is, but not limited to, hemolysis, Cold Agglutinin Disease, Immune Thrombocytopenia (ITP), Myasthenia Gravis, Glomerulopathies, Atypical Hemolytic uremic syndrome, antiphospholipid antibody syndrome, transplant rejection, Chronic inflammatory demyelinating polyneuropathy (CIDP), Multifocal motor neuropathy (MMN), Dermatomyositis, or Anti MAG neuropathy. In some embodiments, the conditions can be due to stroke, or due to spinal cord injury. In some embodiments, the C1s mediated disorder is hemolysis. In some embodiments, the C1s mediated disorder is Cold Agglutinin Disease. In some embodiments, the C1s mediated disorder is Immune Thrombocytopenia (ITP). In some embodiments, the C1s mediated disorder is Myasthenia Gravis. In some embodiments, the C1s mediated disorder is Glomerulopathies. In some embodiments, the C1s mediated disorder is Atypical Hemolytic uremic syndrome. In some embodiments, the C1s mediated disorder is antiphospholipid antibody syndrome. In some embodiments, the C1s mediated disorder is transplant rejection. In some embodiments, the C1s mediated disorder is Chronic inflammatory demyelinating polyneuropathy (CIDP). In some embodiments, the C1s mediated disorder is Multifocal motor neuropathy (MMN). In some embodiments, the C1s mediated disorder is Dermatomyositis. In some embodiments, the C1s mediated disorder is Anti MAG neuropathy. In some embodiments, the C1s mediated disorder is due to stroke. In some embodiments, the C1s mediated disorder is due to spinal cord injury.

The present disclosure provides use of an anti-C1s antibody of any of the embodiments or a pharmaceutical composition thereof in the manufacture of a medicament for inhibiting complement C1s activity. In some embodiments, the present disclosure provides use of an anti-C1s antibody of any of the embodiments or a pharmaceutical composition thereof in the manufacture of a medicament for inhibiting complement C1s activity in an individual having a complement-mediated disease or disorder. In some embodiments, the complement-mediated disorder is, but not limited to, hemolysis, Cold Agglutinin Disease, Immune Thrombocytopenia (ITP), Myasthenia Gravis, Glomerulopathies, Atypical Hemolytic uremic syndrome, antiphospholipid antibody syndrome, transplant rejection, Chronic inflammatory demyelinating polyneuropathy (CIDP), Multifocal motor neuropathy (MMN), Dermatomyositis, or Anti MAG neuropathy. In some embodiments the conditions are caused by a stroke or due to spinal cord injury.

The present disclosure provides an anti-C1s antibody of any of the embodiments or a pharmaceutical composition thereof for use in medical therapy.

The present disclosure provides an anti-C1s antibody of any of the embodiments or a pharmaceutical composition thereof for treating an individual having a complement-mediated disease or disorder. In some embodiments, the complement-mediated disorder is, but not limited to, hemolysis, Cold Agglutinin Disease, Immune Thrombocytopenia (ITP), Myasthenia Gravis, Glomerulopathies, Atypical Hemolytic uremic syndrome, antiphospholipid antibody syndrome, transplant rejection, Chronic inflammatory demyelinating polyneuropathy (CIDP), Multifocal motor neuropathy (MMN), Dermatomyositis, or Anti MAG neuropathy. In some embodiments, the conditions are due to stroke or due to spinal cord injury. In some embodiments, the C1s mediated disorder is hemolysis. In some embodiments, the C1s mediated disorder is Cold Agglutinin Disease. In some embodiments, the C1s mediated disorder is Immune Thrombocytopenia (ITP). In some embodiments, the C1s mediated disorder is Myasthenia Gravis. In some embodiments, the C1s mediated disorder is Glomerulopathies. In some embodiments, the C1s mediated disorder is Atypical Hemolytic uremic syndrome. In some embodiments, the C1s mediated disorder is antiphospholipid antibody syndrome. In some embodiments, the C1s mediated disorder is transplant rejection. In some embodiments, the Cis mediated disorder is Chronic inflammatory demyelinating polyneuropathy (CIDP). In some embodiments, the Cis mediated disorder is Multifocal motor neuropathy (MMN). In some embodiments, the Cis mediated disorder is Dermatomyositis. In some embodiments, the Cis mediated disorder is Anti MAG neuropathy. In some embodiments, the Cis mediated disorder is due to stroke. In some embodiments, the Cis mediated disorder is due to Spinal Cord Injury.

The present disclosure provides an anti-C1s antibody of any of the embodiments or a pharmaceutical composition thereof for inhibiting complement C1s protein activity. The present disclosure provides an anti-C1s antibody of any of the embodiments or a pharmaceutical composition thereof for inhibiting complement Cis protein activity in an individual having a complement-mediated disease or disorder. In some embodiments, the complement-mediated disorder is, but not limited to, hemolysis, Cold Agglutinin Disease, Immune Thrombocytopenia (ITP), Myasthenia Gravis, Glomerulopathies, Atypical Hemolytic uremic syndrome, antiphospholipid antibody syndrome, transplant rejection, Chronic inflammatory demyelinating polyneuropathy (CIDP), Multifocal motor neuropathy (MMN), Dermatomyositis, or Anti MAG neuropathy. In some embodiments, the conditions are caused by a stroke or spinal cord injury. In some embodiments, the C1s mediated disorder is hemolysis. In some embodiments, the C1s mediated disorder is Cold Agglutinin Disease. In some embodiments, the C1s mediated disorder is Immune Thrombocytopenia (ITP). In some embodiments, the C1s mediated disorder is Myasthenia Gravis. In some embodiments, the Cis mediated disorder is Glomerulopathies. In some embodiments, the C1s mediated disorder is Atypical Hemolytic uremic syndrome. In some embodiments, the C1s mediated disorder is antiphospholipid antibody syndrome. In some embodiments, the C1s mediated disorder is transplant rejection. In some embodiments, the C1s mediated disorder is Chronic inflammatory demyelinating polyneuropathy (CIDP). In some embodiments, the C1s mediated disorder is Multifocal motor neuropathy (MMN). In some embodiments, the C1s mediated disorder is Dermatomyositis. In some embodiments, the C1s mediated disorder is Anti MAG neuropathy. In some embodiments, the C1s mediated disorder is due to stroke. In some embodiments, the C1s mediated disorder is due to spinal cord injury.

The present disclosure provides a method to diagnose a complement-mediated disease or disorder in an individual, the method comprising: (a) determining the amount of a complement C1s protein in a biological sample obtained from the individual, wherein the step of determining comprises: (i) contacting the biological sample with an anti-C1s antibody of any of the embodiments; and (ii) quantitating binding of the antibody to complement C1s protein present in the sample; and (b) comparing the amount of the complement Cis protein to a normal control value that indicates the amount of complement C1s protein in a normal control individual, wherein a significant difference between the amount of C1s protein in the biological sample and the normal control value indicates that the individual has a complement-mediated disease or disorder. In some embodiments, the biological sample is selected from the group consisting of blood, serum, plasma, urine, saliva, cerebrospinal fluid, interstitial fluid, ocular fluid, synovial fluid, solid tissue sample, tissue culture sample, and cellular sample.

The present disclosure provides a method to monitor progression of a complement-mediated disease or disorder in an individual, the method comprising: (a) determining a first amount of complement a C1s protein in a biological sample obtained from the individual at a first time point; (b) determining a second amount of complement a Cis protein in a biological sample obtained from the individual at a second time point; and (c) comparing the second amount of complement C1s protein with the first amount of complement C1s protein. The steps of determining comprise: (i) contacting the biological sample with an anti-C1s antibody of any of the embodiments; and (ii) quantitating binding of the antibody to complement C1s protein present in the sample. In some embodiments, the first time point is a time point before initiation of a treatment regimen, and the second time point is a time point after initiation of a treatment regimen. In some embodiments, the biological sample is selected from the group consisting of blood, serum, plasma, urine, saliva, cerebrospinal fluid, interstitial fluid, ocular fluid, synovial fluid, solid tissue sample, tissue culture sample, and cellular sample.

The present disclosure provides an in vitro method to detect complement Cis protein in a biological sample obtained from an individual, the method comprising: (a) contacting the biological sample with an anti-C1s antibody of any of the embodiments; and (b) detecting binding of the antibody to complement C1s protein present in the sample. In some embodiments, the biological sample is selected from the group consisting of blood, serum, plasma, urine, saliva, cerebrospinal fluid, interstitial fluid, ocular fluid, synovial fluid, solid tissue sample, tissue culture sample, and cellular sample. In some embodiments, the method is quantitative.

The present disclosure provides a method to detect complement C1s protein in a living individual in vivo, the method comprising: (a) administering to the individual an anti-C1s antibody of any of the embodiments; and (b) detecting binding of the antibody to complement C1s protein in the individual using an imaging method. In some embodiments, the binding is detected in the individual at a site altered by a complement-mediated disease or disorder. In some embodiments, the binding is detected in the brain of the individual. In some of the embodiments, the antibody comprises a contrast agent suitable for use in the imaging method. In some embodiments, the imaging method is selected from the group consisting of magnetic resonance imaging, positron emission tomography, and IVIS instrumentation. In some embodiments, the method is quantitative.

In some embodiments, the biological sample is selected from the group consisting of blood, serum, plasma, urine, saliva, cerebrospinal fluid, interstitial fluid, ocular fluid, synovial fluid, solid tissue sample, tissue culture sample, and a cellular sample.

In some embodiments, the methods of the present disclosure provide that the individual is suspected of having a complement-mediated disease or disorder, has been diagnosed as having a complement-mediated disease or disorder, or has a genetic predisposition to developing a complement-mediated disease or disorder.

The present disclosure provides a composition comprising: (a) an anti-C1s antibody of any of the embodiments; and (b) a solution comprising one or more agents that maintain an organ or a tissue intended for transplantation into a recipient individual. In some embodiments, the solution is an organ preservation solution or a tissue preservation solution. In some embodiments, the solution is an organ perfusion solution or a tissue perfusion solution. In some embodiments, the solution comprises: i) a salt; ii) an agent that reduces edema; iii) an oxygen free radical scavenger; and iii) an energy supply system component. In some embodiments, the composition comprises potassium lactobionate, $KH_2PO_4$, $MgSO_4$, raffinose, adenosine, glutathione, allopurinol, and/or hydroxyethyl starch.

The present disclosure provides an organ or tissue preservation solution comprising an anti-C1s antibody of any of the embodiments or a pharmaceutical composition thereof.

The present disclosure provides an organ or tissue perfusion solution comprising an anti-C1s antibody of any of the embodiments or a pharmaceutical composition thereof.

The present disclosure provides a method for maintaining an organ or tissue for transplant, the method comprising contacting the organ or the tissue with a composition comprising: (a) an anti-C1s antibody of any of the embodiments; and (b) an organ or tissue preservation solution of any of the embodiments or an organ or tissue perfusion solution of any of the embodiments.

The present disclosure provides an isolated organ or tissue maintained in a composition comprising: (a) an anti-C1s antibody of any of the embodiments; and (b) an organ or tissue preservation solution of any of the embodiments or an organ or tissue perfusion solution of any of the embodiments. In some embodiments, the organ is selected from the group consisting of an eye, a heart, an intestine, a kidney, a liver, a lung, a pancreas, a stomach, and a thymus. In some embodiments, the tissue is selected from the group consisting of bone, bone marrow, cornea, heart valve, islet of Langerhans, tendon, skin, and vein.

The present disclosure provides an in vitro method for inhibiting complement C1s activity in an organ or a tissue, the method comprising contacting the organ or the tissue with an anti-C1s antibody of any of the embodiments or a pharmaceutical composition thereof.

Treatment of individuals may comprise the administration of a therapeutically effective amount of the antibodies described herein. The antibodies can be provided in a kit, such as those provided herein. The antibodies can be used or administered alone or in admixture with another therapeutic, analgesic, or diagnostic agent, such as provided for herein. In providing a patient with an antibody, or fragment thereof, capable of binding to C1s, or an antibody capable of protecting against C1s in a recipient patient, the dosage of administered agent will vary depending upon such factors as the patient's age, weight, height, sex, general medical condition, previous medical history, etc.

An antibody, capable treating a condition associated with C1s activity or use to treat a C1s related pathology, is intended to be provided to subjects in an amount sufficient to affect a reduction, resolution, or amelioration in the C1s related symptom or pathology. Examples of such pathologies are provided for herein.

Accordingly, in some embodiments, methods of treating a subject with a C1s mediated disorder are provided. In some embodiments, the method comprises administering a pharmaceutical composition comprising an antibody, or antigen binding fragment thereof, as provided herein. In some embodiments, the disorder is as provided for herein.

As provided for herein, the antibodies, or antigen binding fragments thereof, can be administered with other therapeutics. These can be administered simultaneously or sequentially.

Kits are also provided which are useful for carrying out embodiments described herein. The present kits can comprise a first container containing or packaged in association with the above-described antibodies. The kit may also comprise another container containing or packaged in association solutions necessary or convenient for carrying out the embodiments. The containers can be made of glass, plastic or foil and can be a vial, bottle, pouch, tube, bag, etc. The kit may also contain written information, such as procedures for carrying out the embodiments or analytical information, such as the amount of reagent contained in the first container means. The container may be in another container apparatus, e.g. a box or a bag, along with the written information.

In some embodiments, antibodies that bind to a C1s protein are provided. In some embodiments, the antibodies are antibodies or antigen binding fragments as provided for herein. In some embodiments, the antibodies or antigen binding fragments comprise an amino acid sequence as provided for herein, or a variant thereof as provided for herein. In some embodiments, the antibody is isolated. In some embodiments, the antibody binds specifically to the active form of C1s.

In some embodiments, the antibody inhibits or neutralizes the function of an active form of C1s protein. As used herein, the term "neutralize" means that the activity or function of the protein is inhibited. The inhibition can be complete or partial. In some embodiments, the activity or function of the protein is inhibited at least 10, 20, 30, 40, 50, 60, 70, 80, 90, 95, or 99%. The percent inhibition can be based upon the function or activity of the protein in the absence of the antibody. In some embodiments, the antibody inhibits the function facilitated by C1s.

In some embodiments, methods are provided comprising administering an antibody provided for herein, or a pharmaceutical composition comprising the same, to a subject, wherein antibody inhibits the membrane attack complex (MAC) deposition in a subject in need thereof, such as a patient with Myasthenia Gravis. The MAC is a complex of proteins that can form from a complex of complement proteins (see, Bayly-Jones et al., 2017 The mystery behind membrane insertion: a review of the complement membrane attack complex Phil. Trans. R. Soc.; Vol. 372, 20160221, which is hereby incorporated by reference in its entirety.). Thus, in some embodiments, the antibody can prevent or reduce the formation of the MAC deposition in patients.

In some embodiments, methods are provided comprising administering an antibody provided for herein, or a pharmaceutical composition comprising the same, to a subject, wherein antibody inhibits or prevents neurotransmission impairment in a subject in need thereof, such as a patient with Myasthenia Gravis. In some embodiments, the method comprises inhibiting neurotransmission impairment. In some embodiments, the method comprises preventing neurotransmission impairment.

In some embodiments, methods are provided comprising administering an antibody provided for herein, or a pharmaceutical composition comprising the same, to a subject, wherein antibody enhances muscle contraction in a subject thereof, such as a patient with Myasthenia Gravis.

In some embodiments, methods are provided comprising administering an antibody provided for herein, or a pharmaceutical composition comprising the same, to a subject, to ameliorate or alleviate muscle paralysis in a subject in need thereof, such as a patient with Myasthenia Gravis. In some embodiments, the method comprises ameliorating muscle paralysis. In some embodiments, the method comprises alleviating muscle paralysis.

In some embodiments, methods are provided comprising administering an antibody provided for herein, or a pharmaceutical composition comprising the same, to a subject, to inhibit the loss of muscle tone or muscle mass in a subject in need thereof, such as a patient with Myasthenia Gravis. In some embodiments, the method comprises inhibiting the loss of muscle tone. In some embodiments, the method comprises inhibiting the loss of muscle mass.

In some embodiments, methods are provided comprising administering an antibody provided for herein, or a pharmaceutical composition comprising the same, to a subject, to reduce the muscle fatigue index in a subject in need thereof, such as a patient with Myasthenia Gravis. In some embodiments, the muscle fatigue index is based on answers to Norwegian version of the FQ (Fatigue Questionnaire) (Loge J H, Ekeberg O, Kaasa S. Fatigue in the general Norwegian population: normative data and associations. J Psychosom Res. 1998; 45:53-65; Chalder T, Berelowitz G, Pawlikowska T, Watts L, Wessely S, Wright D, Wallace EP. Development of a fatigue scale. J Psychosom Res. 1993; 37:147-153, each of which of is hereby incorporated by reference in its entirety. Other examples include, Chalder Fatigue Questionnaire (CFQ) (Chalder T. et al. Development of a fatigue scale; J Psychosom Res. 1993; 37: 147-153); Fatigue Impact Scale (FIS) (Fisk J. D. et al, Measuring the functional impact of fatigue: initial validation of the fatigue impact scale. Clin Infect Dis. 1994; 1: S79-S83); Fatigue Scale for Motor and Cognitive function (FSMC) (Penner I., Raselli C., Stöcklin M., Opwis K., Kappos L., Calabrese P. The fatigue scale for motor and cognitive functions (FSMC): validation of a new instrument to assess multiple sclerosis-related fatigue. 2009; 15(12):1509-17); Fatigue Severity Scale (FSS) (Krupp L. B. et al., The fatigue severity scale. Application to patients with multiple sclerosis and systemic lupus erythematosus, Arch Neurol. 1989; 46: 1121-1123); Fatigue Survey (FS) (Grohar-Murray M. E. et al, Self-care actions to manage fatigue among myasthenia gravis patients, J Neurosci Nursing: J Am Assoc Neurosci Nurses. 1998; 30: 191-199); Myasthenia Gravis Fatigue Scale (MGFS) (Grohar-Murray M. E. et al, Self-care actions to manage fatigue among myasthenia gravis patients. J Neurosci Nursing: J Am Assoc Neurosci Nurses. 1998; 30: 191-199); or Neuro-QoL-Fatigue short form (Neuro-QoL-F-SF) (Cella D. et al., Neuro-QOL. Brief Measur Health-relat Qual Life Clin Res Neurol. 2012; 78: 1860-1867), each of which are hereby incorporated by reference in its entirety.

ENUMERATED EMBODIMENTS

In some embodiments, the following embodiments are provided.

1. An antibody, or an antigen binding fragment thereof, wherein the antibody or antibody fragment comprises:
   (a) a heavy chain variable region comprising heavy chain HCDR1, HCDR2, and HCDR3 sequences, wherein the heavy chain HCDR1 sequence has the amino acid sequence selected from SEQ ID NO: 61 SEQ ID NO: 124, or SEQ ID NO: 130; the heavy chain HCDR2 has the amino acid sequence of SEQ ID NO: 62, SEQ ID NO: 125, or SEQ ID NO: 131, and the heavy chain HCDR3 sequence has the amino acid sequence of SEQ ID NO: 63, or SEQ ID NO: 132, or variants or convention equivalents of any of the foregoing; and (ii) a light chain variable region comprising light chain LCDR1, LCDR2, and LCDR3 sequences, wherein the light chain LCDR1 sequence has the amino acid sequence SEQ ID NO: 64, or SEQ ID NO: 133; the light chain LCDR2 sequence has the amino acid sequence of SEQ ID NO: 65 or SEQ ID NO: 134; and the light chain LCDR3 sequence has the amino acid sequence of SEQ ID NO: 66; or variants or convention equivalents of any of the foregoing;
   (b) a heavy chain variable region comprising heavy chain HCDR1, HCDR2, and HCDR3 sequences, wherein the heavy chain HCDR1 sequence has the amino acid sequence of SEQ ID NO: 61, SEQ ID NO: 124, or SEQ ID NO: 130; the heavy chain HCDR2 has the amino acid sequence of SEQ ID NO: 62, SEQ ID NO: 125, or SEQ ID NO: 131; and the heavy chain HCDR3 sequence has the amino acid sequence of SEQ ID NO: 67, or SEQ ID NO: 135, or variants or convention equivalents of any of the foregoing; and (ii) a light chain variable region comprising light chain LCDR1, LCDR2, and LCDR3 sequences, wherein the light chain LCDR1 sequence has the amino acid sequence SEQ ID NO: 64, or SEQ ID NO: 133; the light chain LCDR2 sequence has the amino acid sequence of SEQ ID NO: 65 or SEQ ID NO: 134; and the light chain LCDR3 sequence has the amino acid sequence of SEQ ID NO: 68; or variants or convention equivalents of any of the foregoing;
   (c) a heavy chain variable region comprising heavy chain HCDR1, HCDR2, and HCDR3 sequences, wherein the heavy chain HCDR1 sequence has the amino acid sequence of SEQ ID NO: 61, SEQ ID NO: 124, or SEQ ID NO: 130; the heavy chain HCDR2 has the amino acid sequence of SEQ ID NO: 62, SEQ ID NO: 125, or SEQ ID NO: 131; and the heavy chain HCDR3 sequence has the amino acid sequence of SEQ ID NO: 69, or SEQ ID NO: 136, or variants or convention equivalents of any of the foregoing; and (ii) a light chain variable region comprising light chain LCDR1, LCDR2, and LCDR3 sequences, wherein the light chain LCDR1 sequence has the amino acid sequence SEQ ID NO: 64, or SEQ ID NO: 133; the light chain LCDR2 sequence has the amino acid sequence of SEQ ID NO: 65, or SEQ ID NO: 134; and the light chain LCDR3 sequence has the amino acid sequence of SEQ ID NO: 68; or variants or convention equivalents of any of the foregoing;

(d) a heavy chain variable region comprising heavy chain HCDR1, HCDR2, and HCDR3 sequences, wherein the heavy chain HCDR1 sequence has the amino acid sequence of SEQ ID NO: 61, SEQ ID NO: 124, or SEQ ID NO: 130; the heavy chain HCDR2 has the amino acid sequence of SEQ ID NO: 62, SEQ ID NO: 125, or SEQ ID NO: 131; and the heavy chain HCDR3 sequence has the amino acid sequence of SEQ ID NO: 70, or SEQ ID NO: 137, or variants or convention equivalents of any of the foregoing; and (ii) a light chain variable region comprising light chain LCDR1, LCDR2, and LCDR3 sequences, wherein the light chain LCDR1 sequence has the amino acid sequence SEQ ID NO: 64, or SEQ ID NO: 133; the light chain LCDR2 sequence has the amino acid sequence of SEQ ID NO: 65, or SEQ ID NO: 134; and the light chain LCDR3 sequence has the amino acid sequence of SEQ ID NO: 71; or variants or convention equivalents of any of the foregoing;

(e) a heavy chain variable region comprising heavy chain HCDR1, HCDR2, and HCDR3 sequences, wherein the heavy chain HCDR1 sequence has the amino acid sequence of SEQ ID NO: 61, SEQ ID NO: 124, or SEQ ID NO: 130; the heavy chain HCDR2 has the amino acid sequence of SEQ ID NO: 62, SEQ ID NO: 125, or SEQ ID NO: 131; and the heavy chain HCDR3 sequence has the amino acid sequence of SEQ ID NO: 72, or SEQ ID NO: 138, or variants or convention equivalents of any of the foregoing; and (ii) a light chain variable region comprising light chain LCDR1, LCDR2, and LCDR3 sequences, wherein the light chain LCDR1 sequence has the amino acid sequence SEQ ID NO: 64, or SEQ ID NO: 133; the light chain LCDR2 sequence has the amino acid sequence of SEQ ID NO: 65, or SEQ ID NO: 134; and the light chain LCDR3 sequence has the amino acid sequence of SEQ ID NO: 71; or variants or convention equivalents of any of the foregoing;

(f) a heavy chain variable region comprising heavy chain HCDR1, HCDR2, and HCDR3 sequences, wherein the heavy chain HCDR1 sequence has the amino acid sequence of SEQ ID NO: 61, SEQ ID NO: 124, or SEQ ID NO: 130; the heavy chain HCDR2 has the amino acid sequence of SEQ ID NO: 62, SEQ ID NO: 125, or SEQ ID NO: 131; and the heavy chain HCDR3 sequence has the amino acid sequence of SEQ ID NO: 73, or SEQ ID NO: 139, or variants or convention equivalents of any of the foregoing; and (ii) a light chain variable region comprising light chain LCDR1, LCDR2, and LCDR3 sequences, wherein the light chain LCDR1 sequence has the amino acid sequence SEQ ID NO: 64, or SEQ ID NO: 133; the light chain LCDR2 sequence has the amino acid sequence of SEQ ID NO: 65, or SEQ ID NO: 134; and the light chain LCDR3 sequence has the amino acid sequence of SEQ ID NO: 71, or variants or convention equivalents of any of the foregoing;

(g) a heavy chain variable region comprising heavy chain HCDR1, HCDR2, and HCDR3 sequences, wherein the heavy chain HCDR1 sequence has the amino acid sequence of SEQ ID NO: 61, SEQ ID NO: 124, or SEQ ID NO: 130; the heavy chain HCDR2 has the amino acid sequence of SEQ ID NO: 62, SEQ ID NO: 125, or SEQ ID NO: 131; and the heavy chain HCDR3 sequence has the amino acid sequence of SEQ ID NO: 74, or SEQ ID NO: 140, or variants or convention equivalents of any of the foregoing; and (ii) a light chain variable region comprising light chain LCDR1, LCDR2, and LCDR3 sequences, wherein the light chain LCDR1 sequence has the amino acid sequence SEQ ID NO: 64, or SEQ ID NO: 133; the light chain LCDR2 sequence has the amino acid sequence of SEQ ID NO: 65, or SEQ ID NO: 134; and the light chain LCDR3 sequence has the amino acid sequence of SEQ ID NO: 75; or variants or convention equivalents of any of the foregoing;

(h) a heavy chain variable region comprising heavy chain HCDR1, HCDR2, and HCDR3 sequences, wherein the heavy chain HCDR1 sequence has the amino acid sequence of SEQ ID NO: 61, SEQ ID NO: 124, or SEQ ID NO: 130; the heavy chain HCDR2 has the amino acid sequence of SEQ ID NO: 62, SEQ ID NO: 125, or SEQ ID NO: 131; and the heavy chain HCDR3 sequence has the amino acid sequence of SEQ ID NO: 76, or SEQ ID NO: 141, or variants or convention equivalents of any of the foregoing; and (ii) a light chain variable region comprising light chain LCDR1, LCDR2, and LCDR3 sequences, wherein the light chain LCDR1 sequence has the amino acid sequence SEQ ID NO: 64, or SEQ ID NO: 133; the light chain LCDR2 sequence has the amino acid sequence of SEQ ID NO: 65, or SEQ ID NO: 134; and the light chain LCDR3 sequence has the amino acid sequence of SEQ ID NO: 77; or variants or convention equivalents of any of the foregoing;

(i) a heavy chain variable region comprising heavy chain HCDR1, HCDR2, and HCDR3 sequences, wherein the heavy chain HCDR1 sequence has the amino acid sequence of SEQ ID NO: 61, SEQ ID NO: 124, or SEQ ID NO: 130; the heavy chain HCDR2 has the amino acid sequence of SEQ ID NO: 62, SEQ ID NO: 125, or SEQ ID NO: 131; and the heavy chain HCDR3 sequence has the amino acid sequence of SEQ ID NO: 78, or SEQ ID NO: 142, or variants or convention equivalents of any of the foregoing; and (ii) a light chain variable region comprising light chain LCDR1, LCDR2, and LCDR3 sequences, wherein the light chain LCDR1 sequence has the amino acid sequence SEQ ID NO: 64, or SEQ ID NO: 133; the light chain LCDR2 sequence has the amino acid sequence of SEQ ID NO: 65, or SEQ ID NO: 134; and the light chain LCDR3 sequence has the amino acid sequence of SEQ ID NO: 79; or variants or convention equivalents of any of the foregoing;

(j) a heavy chain variable region comprising heavy chain HCDR1, HCDR2, and HCDR3 sequences, wherein the heavy chain HCDR1 sequence has the amino acid sequence of SEQ ID NO: 61, SEQ ID NO: 124, or SEQ ID NO: 130; the heavy chain HCDR2 has the amino acid sequence of SEQ ID NO: 62, SEQ ID NO: 125, or SEQ ID NO: 131; and the heavy chain HCDR3 sequence has the amino acid sequence of SEQ ID NO: 80, or SEQ ID NO: 143, or variants or convention equivalents of any of the foregoing; and (ii) a light chain variable region comprising light chain LCDR1, LCDR2, and LCDR3 sequences, wherein the light chain LCDR1 sequence has the amino acid sequence SEQ ID NO: 64, or SEQ ID NO: 133; the light chain LCDR2 sequence has the amino acid sequence of SEQ ID NO: 65, or SEQ ID NO: 134; and the light chain LCDR3 sequence has the amino acid sequence of SEQ ID NO: 81; or variants or convention equivalents of any of the foregoing;

(k) a heavy chain variable region comprising heavy chain HCDR1, HCDR2, and HCDR3 sequences, wherein the heavy chain HCDR1 sequence has the amino acid sequence of SEQ ID NO: 82, SEQ ID NO: 126, or SEQ ID NO: 144; the heavy chain HCDR2 has the amino acid sequence of SEQ ID NO: 83, SEQ ID NO: 127, or SEQ ID NO: 145; and the heavy chain HCDR3 sequence has the amino acid sequence of SEQ ID NO: 84, or SEQ ID NO: 146, or variants or convention equivalents of any of the foregoing; and (ii) a light chain variable region comprising light chain LCDR1, LCDR2, and LCDR3 sequences, wherein the light chain LCDR1 sequence has the amino acid sequence SEQ ID NO: 85, or SEQ ID NO: 147; the light chain LCDR2 sequence has the amino acid sequence of SEQ ID NO: 86, or SEQ ID NO: 148; and the light chain LCDR3 sequence has the amino acid sequence of SEQ ID NO: 87; or variants or convention equivalents of any of the foregoing;

(l) a heavy chain variable region comprising heavy chain HCDR1, HCDR2, and HCDR3 sequences, wherein the heavy chain HCDR1 sequence has the amino acid sequence of SEQ ID NO: 82, SEQ ID NO: 126, or SEQ ID NO: 144; the heavy chain HCDR2 has the amino acid sequence of SEQ ID NO: 83, SEQ ID NO: 127, or SEQ ID NO: 145; and the heavy chain HCDR3 sequence has the amino acid sequence of SEQ ID NO: 88, or SEQ ID NO: 149, or variants or convention equivalents of any of the foregoing; and (ii) a light chain variable region comprising light chain LCDR1, LCDR2, and LCDR3 sequences, wherein the light chain LCDR1 sequence has the amino acid sequence SEQ ID NO: 85, or SEQ ID NO: 147; the light chain LCDR2 sequence has the amino acid sequence of SEQ ID NO: 86, or SEQ ID NO: 148; and the light chain LCDR3 sequence has the amino acid sequence of SEQ ID NO: 89; or variants or convention equivalents of any of the foregoing;

(m) a heavy chain variable region comprising heavy chain HCDR1, HCDR2, and HCDR3 sequences, wherein the heavy chain HCDR1 sequence has the amino acid sequence of SEQ ID NO: 82, SEQ ID NO: 126, or SEQ ID NO: 144; the heavy chain HCDR2 has the amino acid sequence of SEQ ID NO: 83, SEQ ID NO: 127, or SEQ ID NO: 145; and the heavy chain HCDR3 sequence has the amino acid sequence of SEQ ID NO: 90, or SEQ ID NO: 150, or variants or convention equivalents of any of the foregoing; and (ii) a light chain variable region comprising light chain LCDR1, LCDR2, and LCDR3 sequences, wherein the light chain LCDR1 sequence has the amino acid sequence SEQ ID NO: 85, or SEQ ID NO: 147; the light chain LCDR2 sequence has the amino acid sequence of SEQ ID NO: 86, or SEQ ID NO: 148; and the light chain LCDR3 sequence has the amino acid sequence of SEQ ID NO: 89; or variants or convention equivalents of any of the foregoing;

(n) a heavy chain variable region comprising heavy chain HCDR1, HCDR2, and HCDR3 sequences, wherein the heavy chain HCDR1 sequence has the amino acid sequence of SEQ ID NO: 82, SEQ ID NO: 126, or SEQ ID NO: 144; the heavy chain HCDR2 has the amino acid sequence of SEQ ID NO: 83, SEQ ID NO: 127, or SEQ ID NO: 145; and the heavy chain HCDR3 sequence has the amino acid sequence of SEQ ID NO: 91, or SEQ ID NO: 151, or variants or convention equivalents of any of the foregoing; and (ii) a light chain variable region comprising light chain LCDR1, LCDR2, and LCDR3 sequences, wherein the light chain LCDR1 sequence has the amino acid sequence SEQ ID NO: 85, or SEQ ID NO: 147; the light chain LCDR2 sequence has the amino acid sequence of SEQ ID NO: 86, or SEQ ID NO: 148; and the light chain LCDR3 sequence has the amino acid sequence of SEQ ID NO: 92; or variants or convention equivalents of any of the foregoing;

(o) a heavy chain variable region comprising heavy chain HCDR1, HCDR2, and HCDR3 sequences, wherein the heavy chain HCDR1 sequence has the amino acid sequence of SEQ ID NO: 82, SEQ ID NO: 126, or SEQ ID NO: 144; the heavy chain HCDR2 has the amino acid sequence of SEQ ID NO: 83, SEQ ID NO: 127, or SEQ ID NO: 145; and the heavy chain HCDR3 sequence has the amino acid sequence of SEQ ID NO: 93, or SEQ ID NO: 152, or variants or convention equivalents of any of the foregoing; and (ii) a light chain variable region comprising light chain LCDR1, LCDR2, and LCDR3 sequences, wherein the light chain LCDR1 sequence has the amino acid sequence SEQ ID NO: 85, or SEQ ID NO: 147; the light chain LCDR2 sequence has the amino acid sequence of SEQ ID NO: 86, or SEQ ID NO: 148; and the light chain LCDR3 sequence has the amino acid sequence of SEQ ID NO: 94; or variants or convention equivalents of any of the foregoing;

(p) a heavy chain variable region comprising heavy chain HCDR1, HCDR2, and HCDR3 sequences, wherein the heavy chain HCDR1 sequence has the amino acid sequence of SEQ ID NO: 82, SEQ ID NO: 126, or SEQ ID NO: 144; the heavy chain HCDR2 has the amino acid sequence of SEQ ID NO: 83, SEQ ID NO: 127, or SEQ ID NO: 145; and the heavy chain HCDR3 sequence has the amino acid sequence of SEQ ID NO: 84, or SEQ ID NO: 146, or variants or convention equivalents of any of the foregoing; and (ii) a light chain variable region comprising light chain LCDR1, LCDR2, and LCDR3 sequences, wherein the light chain LCDR1 sequence has the amino acid sequence SEQ ID NO: 85, or SEQ ID NO: 147; the light chain LCDR2 sequence has the amino acid sequence of SEQ ID NO: 86, or SEQ ID NO: 148; and the light chain LCDR3 sequence has the amino acid sequence of SEQ ID NO: 95; or variants or convention equivalents of any of the foregoing;

(q) a heavy chain variable region comprising heavy chain HCDR1, HCDR2, and HCDR3 sequences, wherein the heavy chain HCDR1 sequence has the amino acid sequence of SEQ ID NO: 82, SEQ ID NO: 126, or SEQ ID NO: 144; the heavy chain HCDR2 has the amino acid sequence of SEQ ID NO: 83, SEQ ID NO: 127, or SEQ ID NO: 145; and the heavy chain HCDR3 sequence has the amino acid sequence of SEQ ID NO: 96, or SEQ ID NO: 153, or variants or convention equivalents of any of the foregoing; and (ii) a light chain variable region comprising light chain LCDR1, LCDR2, and LCDR3 sequences, wherein the light chain LCDR1 sequence has the amino acid sequence SEQ ID NO: 85, or SEQ ID NO: 147; the light chain LCDR2 sequence has the amino acid sequence of SEQ ID NO: 86, or SEQ ID NO: 148; and the light chain LCDR3 sequence has the amino acid sequence of SEQ ID NO: 97; or variants or convention equivalents of any of the foregoing;

(r) a heavy chain variable region comprising heavy chain HCDR1, HCDR2, and HCDR3 sequences, wherein the heavy chain HCDR1 sequence has the amino acid sequence of SEQ ID NO: 82, SEQ ID NO: 126, or SEQ ID NO: 144; the heavy chain HCDR2 has the amino acid sequence of SEQ ID NO: 83, SEQ ID NO: 127, or SEQ ID NO: 145; and the heavy chain HCDR3 sequence has the amino acid sequence of SEQ ID NO: 98, or SEQ ID NO: 154, or variants or convention equivalents of any of the foregoing; and (ii) a light chain variable region comprising light chain LCDR1, LCDR2, and LCDR3 sequences, wherein the light chain LCDR1 sequence has the amino acid sequence SEQ ID NO: 85, or SEQ ID NO: 147; the light chain LCDR2 sequence has the amino acid sequence of SEQ ID NO: 86, or SEQ ID NO: 148; and the light chain LCDR3 sequence has the amino acid sequence of SEQ ID NO: 99; or variants or convention equivalents of any of the foregoing;

(s) a heavy chain variable region comprising heavy chain HCDR1, HCDR2, and HCDR3 sequences, wherein the heavy chain HCDR1 sequence has the amino acid sequence of SEQ ID NO: 82, SEQ ID NO: 126, or SEQ ID NO: 144; the heavy chain HCDR2 has the amino acid sequence of SEQ ID NO: 83, SEQ ID NO: 127, or SEQ ID NO: 145; and the heavy chain HCDR3 sequence has the amino acid sequence of SEQ ID NO: 100, or SEQ ID NO: 155, or variants or convention equivalents of any of the foregoing; and (ii) a light chain variable region comprising light chain LCDR1, LCDR2, and LCDR3 sequences, wherein the light chain LCDR1 sequence has the amino acid sequence SEQ ID NO: 85, or SEQ ID NO: 147; the light chain LCDR2 sequence has the amino acid sequence of SEQ ID NO: 86, or SEQ ID NO: 148; and the light chain LCDR3 sequence has the amino acid sequence of SEQ ID NO: 101; or variants or convention equivalents of any of the foregoing;

(t) a heavy chain variable region comprising heavy chain HCDR1, HCDR2, and HCDR3 sequences, wherein the heavy chain HCDR1 sequence has the amino acid sequence of SEQ ID NO: 82, SEQ ID NO: 126, or SEQ ID NO: 144; the heavy chain HCDR2 has the amino acid sequence of SEQ ID NO: 83, SEQ ID NO: 127, or SEQ ID NO: 145; and the heavy chain HCDR3 sequence has the amino acid sequence of SEQ ID NO: 100, or SEQ ID NO: 155, or variants or convention equivalents of any of the foregoing; and (ii) a light chain variable region comprising light chain LCDR1, LCDR2, and LCDR3 sequences, wherein the light chain LCDR1 sequence has the amino acid sequence SEQ ID NO: 85, or SEQ ID NO: 147; the light chain LCDR2 sequence has the amino acid sequence of SEQ ID NO: 86, or SEQ ID NO: 148; and the light chain LCDR3 sequence has the amino acid sequence of SEQ ID NO: 102; or variants or convention equivalents of any of the foregoing;

(u) a heavy chain variable region comprising heavy chain HCDR1, HCDR2, and HCDR3 sequences, wherein the heavy chain HCDR1 sequence has the amino acid sequence of SEQ ID NO: 103, SEQ ID NO: 128, or SEQ ID NO: 156; the heavy chain HCDR2 has the amino acid sequence of SEQ ID NO: 104, SEQ ID NO: 129, or SEQ ID NO: 157; and the heavy chain HCDR3 sequence has the amino acid sequence of SEQ ID NO: 105, or SEQ ID NO: 158, or variants or convention equivalents of any of the foregoing; and (ii) a light chain variable region comprising light chain LCDR1, LCDR2, and LCDR3 sequences, wherein the light chain LCDR1 sequence has the amino acid sequence SEQ ID NO: 106, or SEQ ID NO: 159; the light chain LCDR2 sequence has the amino acid sequence of SEQ ID NO: 107, or SEQ ID NO: 160; and the light chain LCDR3 sequence has the amino acid sequence of SEQ ID NO: 108; or variants or convention equivalents of any of the foregoing;

(v) a heavy chain variable region comprising heavy chain HCDR1, HCDR2, and HCDR3 sequences, wherein the heavy chain HCDR1 sequence has the amino acid sequence of SEQ ID NO: 103, SEQ ID NO: 128, or SEQ ID NO: 156; the heavy chain HCDR2 has the amino acid sequence of SEQ ID NO: 104, SEQ ID NO: 129, or SEQ ID NO: 157; and the heavy chain HCDR3 sequence has the amino acid sequence of SEQ ID NO: 109, or SEQ ID NO: 161, or variants or convention equivalents of any of the foregoing; and (ii) a light chain variable region comprising light chain LCDR1, LCDR2, and LCDR3 sequences, wherein the light chain LCDR1 sequence has the amino acid sequence SEQ ID NO: 106, or SEQ ID NO: 159; the light chain LCDR2 sequence has the amino acid sequence of SEQ ID NO: 107, or SEQ ID NO: 160; and the light chain LCDR3 sequence has the amino acid sequence of SEQ ID NO: 110; or variants or convention equivalents of any of the foregoing;

(w) a heavy chain variable region comprising heavy chain HCDR1, HCDR2, and HCDR3 sequences, wherein the heavy chain HCDR1 sequence has the amino acid sequence of SEQ ID NO: 103, SEQ ID NO: 128, or SEQ ID NO: 156; the heavy chain HCDR2 has the amino acid sequence of SEQ ID NO: 104, SEQ ID NO: 129, or SEQ ID NO: 157; and the heavy chain HCDR3 sequence has the amino acid sequence of SEQ ID NO: 111, or SEQ ID NO: 162, or variants or convention equivalents of any of the foregoing; and (ii) a light chain variable region comprising light chain LCDR1, LCDR2, and LCDR3 sequences, wherein the light chain LCDR1 sequence has the amino acid sequence SEQ ID NO: 106, or SEQ ID NO: 159; the light chain LCDR2 sequence has the amino acid sequence of SEQ ID NO: 107, or SEQ ID NO: 160; and the light chain LCDR3 sequence has the amino acid sequence of SEQ ID NO: 112; or variants or convention equivalents of any of the foregoing;

(x) a heavy chain variable region comprising heavy chain HCDR1, HCDR2, and HCDR3 sequences, wherein the heavy chain HCDR1 sequence has the amino acid sequence of SEQ ID NO: 103, SEQ ID NO: 128, or SEQ ID NO: 156; the heavy chain HCDR2 has the amino acid sequence of SEQ ID NO: 104, SEQ ID NO: 129, or SEQ ID NO: 157; and the heavy chain HCDR3 sequence has the amino acid sequence of SEQ ID NO: 105, or SEQ ID NO: 158, or variants or convention equivalents of any of the foregoing; and (ii) a light chain variable region comprising light chain LCDR1, LCDR2, and LCDR3 sequences, wherein the light chain LCDR1 sequence has the amino acid sequence SEQ ID NO: 106, or SEQ ID NO: 159; the light chain LCDR2 sequence has the amino acid sequence of SEQ ID NO: 107, or SEQ ID NO: 160; and the light chain LCDR3 sequence has the amino acid sequence of SEQ ID NO: 113; or variants or convention equivalents of any of the foregoing;

(y) a heavy chain variable region comprising heavy chain HCDR1, HCDR2, and HCDR3 sequences, wherein the heavy chain HCDR1 sequence has the amino acid sequence of SEQ ID NO: 103, SEQ ID NO: 128, or SEQ ID NO: 156; the heavy chain HCDR2 has the amino acid sequence of SEQ ID NO: 104, SEQ ID NO: 129, or SEQ ID NO: 157; and the heavy chain HCDR3 sequence has the amino acid sequence of SEQ ID NO: 114, or SEQ ID NO: 163, or variants or convention equivalents of any of the foregoing; and (ii) a light chain variable region comprising light chain LCDR1, LCDR2, and LCDR3 sequences, wherein the light chain LCDR1 sequence has the amino acid sequence SEQ ID NO: 106, or SEQ ID NO: 159; the light chain LCDR2 sequence has the amino acid sequence of SEQ ID NO: 107, or SEQ ID NO: 160; and the light chain LCDR3 sequence has the amino acid sequence of SEQ ID NO: 115; or variants or convention equivalents of any of the foregoing;

(z) a heavy chain variable region comprising heavy chain HCDR1, HCDR2, and HCDR3 sequences, wherein the heavy chain HCDR1 sequence has the amino acid sequence of SEQ ID NO: 103, SEQ ID NO: 128, or SEQ ID NO: 156; the heavy chain HCDR2 has the amino acid sequence of SEQ ID NO: 104, SEQ ID NO: 129, or SEQ ID NO: 157; and the heavy chain HCDR3 sequence has the amino acid sequence of SEQ ID NO: 116, or SEQ ID NO: 164, or variants or convention equivalents of any of the foregoing; and (ii) a light chain variable region comprising light chain LCDR1, LCDR2, and LCDR3 sequences, wherein the light chain LCDR1 sequence has the amino acid sequence SEQ ID NO: 106, or SEQ ID NO: 159; the light chain LCDR2 sequence has the amino acid sequence of SEQ ID NO: 107, or SEQ ID NO: 160; and the light chain LCDR3 sequence has the amino acid sequence of SEQ ID NO: 113; or variants or convention equivalents of any of the foregoing;

(aa) a heavy chain variable region comprising heavy chain HCDR1, HCDR2, and HCDR3 sequences, wherein the heavy chain HCDR1 sequence has the amino acid sequence of SEQ ID NO: 103, SEQ ID NO: 128, or SEQ ID NO: 156; the heavy chain HCDR2 has the amino acid sequence of SEQ ID NO: 104, SEQ ID NO: 129, or SEQ ID NO: 157; and the heavy chain HCDR3 sequence has the amino acid sequence of SEQ ID NO: 117, or SEQ ID NO: 165, or variants or convention equivalents of any of the foregoing; and (ii) a light chain variable region comprising light chain LCDR1, LCDR2, and LCDR3 sequences, wherein the light chain LCDR1 sequence has the amino acid sequence SEQ ID NO: 106, or SEQ ID NO: 159; the light chain LCDR2 sequence has the amino acid sequence of SEQ ID NO: 107, or SEQ ID NO: 160; and the light chain LCDR3 sequence has the amino acid sequence of SEQ ID NO: 118; or variants or convention equivalents of any of the foregoing;

(ab) a heavy chain variable region comprising heavy chain HCDR1, HCDR2, and HCDR3 sequences, wherein the heavy chain HCDR1 sequence has the amino acid sequence of SEQ ID NO: 103, SEQ ID NO: 128, or SEQ ID NO: 156; the heavy chain HCDR2 has the amino acid sequence of SEQ ID NO: 104, SEQ ID NO: 129, or SEQ ID NO: 157; and the heavy chain HCDR3 sequence has the amino acid sequence of SEQ ID NO: 116, or SEQ ID NO: 164, or variants or convention equivalents of any of the foregoing; and (ii) a light chain variable region comprising light chain LCDR1, LCDR2, and LCDR3 sequences, wherein the light chain LCDR1 sequence has the amino acid sequence SEQ ID NO: 106, or SEQ ID NO: 159; the light chain LCDR2 sequence has the amino acid sequence of SEQ ID NO: 107, or SEQ ID NO: 160; and the light chain LCDR3 sequence has the amino acid sequence of SEQ ID NO: 119; or variants or convention equivalents of any of the foregoing;

(ac) a heavy chain variable region comprising heavy chain HCDR1, HCDR2, and HCDR3 sequences, wherein the heavy chain HCDR1 sequence has the amino acid sequence of SEQ ID NO: 103, SEQ ID NO: 128, or SEQ ID NO: 156; the heavy chain HCDR2 has the amino acid sequence of SEQ ID NO: 104, SEQ ID NO: 129, or SEQ ID NO: 157; and the heavy chain HCDR3 sequence has the amino acid sequence of SEQ ID NO: 120, or SEQ ID NO: 166, or variants or convention equivalents of any of the foregoing; and (ii) a light chain variable region comprising light chain LCDR1, LCDR2, and LCDR3 sequences, wherein the light chain LCDR1 sequence has the amino acid sequence SEQ ID NO: 106, or SEQ ID NO: 159; the light chain LCDR2 sequence has the amino acid sequence of SEQ ID NO: 107, or SEQ ID NO: 160; and the light chain LCDR3 sequence has the amino acid sequence of SEQ ID NO: 121; or variants or convention equivalents of any of the foregoing;

(ad) a heavy chain variable region comprising heavy chain HCDR1, HCDR2, and HCDR3 sequences, wherein the heavy chain HCDR1 sequence has the amino acid sequence of SEQ ID NO: 103, SEQ ID NO: 128, or SEQ ID NO: 156; the heavy chain HCDR2 has the amino acid sequence of SEQ ID NO: 104, SEQ ID NO: 129, or SEQ ID NO: 157; and the heavy chain HCDR3 sequence has the amino acid sequence of SEQ ID NO: 122, or SEQ ID NO: 167, or variants or convention equivalents of any of the foregoing; and (ii) a light chain variable region comprising light chain LCDR1, LCDR2, and LCDR3 sequences, wherein the light chain LCDR1 sequence has the amino acid sequence SEQ ID NO: 106, or SEQ ID NO: 159; the light chain LCDR2 sequence has the amino acid sequence of SEQ ID NO: 107, or SEQ ID NO: 160; and the light chain LCDR3 sequence has the amino acid sequence of SEQ ID NO: 123; or variants or convention equivalents of any of the foregoing.

2. The antibody or antigen-binding fragment thereof of embodiment 1, wherein the heavy chain comprises:
  (a) a heavy chain variable region having at least 90% sequence identity to SEQ ID NO: 1, wherein the antibody, or antigen binding fragment thereof, maintains the sequences of HCDR1, HCDR2, HCDR3, LCDR1, LCDR2, and LCDR3 set forth in subpart a of embodiment 1; or
  (b) a heavy chain variable region having at least 90% sequence identity to SEQ ID NO: 3, wherein the antibody, or antigen binding fragment thereof, maintains the sequences of HCDR1, HCDR2, HCDR3, LCDR1, LCDR2, and LCDR3 set forth in subpart b of embodiment 1; or
  (c) a heavy chain variable region having at least 90% sequence identity to SEQ ID NO: 5, wherein the antibody, or antigen binding fragment thereof, maintains the sequences of HCDR1, HCDR2, HCDR3, LCDR1, LCDR2, and LCDR3 set forth in subpart c of embodiment
  (d) a heavy chain variable region having at least 90% sequence identity to SEQ ID NO: 7, wherein the antibody, or antigen binding fragment thereof, maintains the sequences of HCDR1, HCDR2, HCDR3, LCDR1, LCDR2, and LCDR3 set forth in subpart d of embodiment 1; or
  (e) a heavy chain variable region having at least 90% sequence identity to SEQ ID NO: 9, wherein the antibody, or antigen binding fragment thereof, maintains the sequences of HCDR1, HCDR2, HCDR3, LCDR1, LCDR2, and LCDR3 set forth in subpart e of embodiment 1; or
  (f) a heavy chain variable region having at least 90% sequence identity to SEQ ID NO: 11, wherein the antibody, or antigen binding fragment thereof, maintains the sequences of HCDR1, HCDR2, HCDR3, LCDR1, LCDR2, and LCDR3 set forth in subpart f of embodiment 1; or
  (g) a heavy chain variable region having at least 90% sequence identity to SEQ ID NO: 13, wherein the antibody, or antigen binding fragment thereof, maintains the sequences of HCDR1, HCDR2, HCDR3, LCDR1, LCDR2, and LCDR3 set forth in subpart g of embodiment 1; or
  (h) a heavy chain variable region having at least 90% sequence identity to SEQ ID NO: 15, wherein the antibody, or antigen binding fragment thereof, maintains the sequences of HCDR1, HCDR2, HCDR3, LCDR1, LCDR2, and LCDR3 set forth in subpart h of embodiment 1; or
  (i) a heavy chain variable region having at least 90% sequence identity to SEQ ID NO: 17, wherein the antibody, or antigen binding fragment thereof, maintains the sequences of HCDR1, HCDR2, HCDR3, LCDR1, LCDR2, and LCDR3 set forth in subpart i of embodiment 1; or
  (j) a heavy chain variable region having at least 90% sequence identity to SEQ ID NO: 19, wherein the antibody, or antigen binding fragment thereof, maintains the sequences of HCDR1, HCDR2, HCDR3, LCDR1, LCDR2, and LCDR3 set forth in subpart j of embodiment 1; or
  (k) a heavy chain variable region having at least 90% sequence identity to SEQ ID NO: 21, wherein the antibody, or antigen binding fragment thereof, maintains the sequences of HCDR1, HCDR2, HCDR3, LCDR1, LCDR2, and LCDR3 set forth in subpart k of embodiment 1; or
  (l) a heavy chain variable region having at least 90% sequence identity to SEQ ID NO: 23, wherein the antibody, or antigen binding fragment thereof, maintains the sequences of HCDR1, HCDR2, HCDR3, LCDR1, LCDR2, and LCDR3 set forth in subpart l of embodiment 1; or
  (m) a heavy chain variable region having at least 90% sequence identity to SEQ ID NO: 25, wherein the antibody, or antigen binding fragment thereof, maintains the sequences of HCDR1, HCDR2, HCDR3, LCDR1, LCDR2, and LCDR3 set forth in subpart m of embodiment 1; or
  (n) a heavy chain variable region having at least 90% sequence identity to SEQ ID NO: 27, wherein the antibody, or antigen binding fragment thereof, maintains the sequences of HCDR1, HCDR2, HCDR3, LCDR1, LCDR2, and LCDR3 set forth in subpart n of embodiment 1; or
  (o) a heavy chain variable region having at least 90% sequence identity to SEQ ID NO: 29, wherein the antibody, or antigen binding fragment thereof, maintains the sequences of HCDR1, HCDR2, HCDR3, LCDR1, LCDR2, and LCDR3 set forth in subpart o of embodiment 1; or
  (p) a heavy chain variable region having at least 90% sequence identity to SEQ ID NO: 31, wherein the antibody, or antigen binding fragment thereof, maintains the sequences of HCDR1, HCDR2, HCDR3, LCDR1, LCDR2, and LCDR3 set forth in subpart p of embodiment 1; or
  (q) a heavy chain variable region having at least 90% sequence identity to SEQ ID NO: 33, wherein the antibody, or antigen binding fragment thereof, maintains the sequences of HCDR1, HCDR2, HCDR3, LCDR1, LCDR2, and LCDR3 set forth in subpart q of embodiment 1; or
  (r) a heavy chain variable region having at least 90% sequence identity to SEQ ID NO: 35, wherein the antibody, or antigen binding fragment thereof, maintains the sequences of HCDR1, HCDR2, HCDR3, LCDR1, LCDR2, and LCDR3 set forth in subpart r of embodiment 1; or
  (s) a heavy chain variable region having at least 90% sequence identity to SEQ ID NO: 37, wherein the antibody, or antigen binding fragment thereof, maintains the sequences of HCDR1, HCDR2, HCDR3, LCDR1, LCDR2, and LCDR3 set forth in subpart s of embodiment 1; or
  (t) a heavy chain variable region having at least 90% sequence identity to SEQ ID NO: 39, wherein the antibody, or antigen binding fragment thereof, maintains the sequences of HCDR1, HCDR2, HCDR3, LCDR1, LCDR2, and LCDR3 set forth in subpart t of embodiment 1; or
(u) a heavy chain variable region having at least 90% sequence identity to SEQ ID NO: 41, wherein the antibody, or antigen binding fragment thereof, maintains the sequences of HCDR1, HCDR2, HCDR3, LCDR1, LCDR2, and LCDR3 set forth in subpart u of embodiment 1; or
(v) a heavy chain variable region having at least 90% sequence identity to SEQ ID NO: 43, wherein the antibody, or antigen binding fragment thereof, maintains the sequences of HCDR1, HCDR2, HCDR3, LCDR1, LCDR2, and LCDR3 set forth in subpart v of embodiment 1; or
(w) a heavy chain variable region having at least 90% sequence identity to SEQ ID NO: 45, wherein the antibody, or antigen binding fragment thereof, maintains the sequences of HCDR1, HCDR2, HCDR3, LCDR1, LCDR2, and LCDR3 set forth in subpart w of embodiment 1; or
(x) a heavy chain variable region having at least 90% sequence identity to SEQ ID NO: 47, wherein the antibody, or antigen binding fragment thereof, maintains the sequences of HCDR1, HCDR2, HCDR3, LCDR1, LCDR2, and LCDR3 set forth in subpart x of embodiment 1; or
(y) a heavy chain variable region having at least 90% sequence identity to SEQ ID NO: 49, wherein the antibody, or antigen binding fragment thereof, maintains the sequences of HCDR1, HCDR2, HCDR3, LCDR1, LCDR2, and LCDR3 set forth in subpart y of embodiment 1; or
(z) a heavy chain variable region having at least 90% sequence identity to SEQ ID NO: 51, wherein the antibody, or antigen binding fragment thereof, maintains the sequences of HCDR1, HCDR2, HCDR3, LCDR1, LCDR2, and LCDR3 set forth in subpart z of embodiment 1; or
(aa) a heavy chain variable region having at least 90% sequence identity to SEQ ID NO: 53, wherein the antibody, or antigen binding fragment thereof, maintains the sequences of HCDR1, HCDR2, HCDR3, LCDR1, LCDR2, and LCDR3 set forth in subpart ab of embodiment 1; or
(ab) a heavy chain variable region having at least 90% sequence identity to SEQ ID NO: 55, wherein the antibody, or antigen binding fragment thereof, maintains the sequences of HCDR1, HCDR2, HCDR3, LCDR1, LCDR2, and LCDR3 set forth in subpart ac of embodiment 1; or
(ac) a heavy chain variable region having at least 90% sequence identity to SEQ ID NO: 57, wherein the antibody, or antigen binding fragment thereof, maintains the sequences of HCDR1, HCDR2, HCDR3, LCDR1, LCDR2, and LCDR3 set forth in subpart ad of embodiment 1; or
(ad) a heavy chain variable region having at least 90% sequence identity to SEQ ID NO: 59, wherein the antibody, or antigen binding fragment thereof, maintains the sequences of HCDR1, HCDR2, HCDR3, LCDR1, LCDR2, and LCDR3 set forth in subpart ae of embodiment 1; or
(ae) a heavy chain variable region having at least 90% sequence identity to SEQ ID NO: 334, wherein the antibody, or antigen binding fragment thereof, maintains the sequences of HCDR1, HCDR2, HCDR3, LCDR1, LCDR2, and LCDR3 set forth in subpart a of embodiment 1; or
(af) a heavy chain variable region having at least 90% sequence identity to SEQ ID NO: 335, wherein the antibody, or antigen binding fragment thereof, maintains the sequences of HCDR1, HCDR2, HCDR3, LCDR1, LCDR2, and LCDR3 set forth in subpart b of embodiment 1; or
(ag) a heavy chain variable region having at least 90% sequence identity to SEQ ID NO: 336, wherein the antibody, or antigen binding fragment thereof, maintains the sequences of HCDR1, HCDR2, HCDR3, LCDR1, LCDR2, and LCDR3 set forth in subpart c of embodiment
(ah) a heavy chain variable region having at least 90% sequence identity to SEQ ID NO: 337, wherein the antibody, or antigen binding fragment thereof, maintains the sequences of HCDR1, HCDR2, HCDR3, LCDR1, LCDR2, and LCDR3 set forth in subpart d of embodiment 1; or
(ai) a heavy chain variable region having at least 90% sequence identity to SEQ ID NO: 338, wherein the antibody, or antigen binding fragment thereof, maintains the sequences of HCDR1, HCDR2, HCDR3, LCDR1, LCDR2, and LCDR3 set forth in subpart e of embodiment 1; or
(aj) a heavy chain variable region having at least 90% sequence identity to SEQ ID NO: 339, wherein the antibody, or antigen binding fragment thereof, maintains the sequences of HCDR1, HCDR2, HCDR3, LCDR1, LCDR2, and LCDR3 set forth in subpart f of embodiment 1; or
(ak) a heavy chain variable region having at least 90% sequence identity to SEQ ID NO: 340, wherein the antibody, or antigen binding fragment thereof, maintains the sequences of HCDR1, HCDR2, HCDR3, LCDR1, LCDR2, and LCDR3 set forth in subpart g of embodiment 1; or
(al) a heavy chain variable region having at least 90% sequence identity to SEQ ID NO: 341, wherein the antibody, or antigen binding fragment thereof, maintains the sequences of HCDR1, HCDR2, HCDR3, LCDR1, LCDR2, and LCDR3 set forth in subpart h of embodiment 1; or
(am) a heavy chain variable region having at least 90% sequence identity to SEQ ID NO: 342, wherein the antibody, or antigen binding fragment thereof, maintains the sequences of HCDR1, HCDR2, HCDR3, LCDR1, LCDR2, and LCDR3 set forth in subpart i of embodiment 1; or
(an) a heavy chain variable region having at least 90% sequence identity to SEQ ID NO: 343, wherein the antibody, or antigen binding fragment thereof, maintains the sequences of HCDR1, HCDR2, HCDR3, LCDR1, LCDR2, and LCDR3 set forth in subpart j of embodiment 1; or
(ao) a heavy chain variable region having at least 90% sequence identity to SEQ ID NO: 344, wherein the antibody, or antigen binding fragment thereof, maintains the sequences of HCDR1, HCDR2, HCDR3, LCDR1, LCDR2, and LCDR3 set forth in subpart k of embodiment 1; or
(ap) a heavy chain variable region having at least 90% sequence identity to SEQ ID NO: 345, wherein the antibody, or antigen binding fragment thereof, maintains the sequences of HCDR1, HCDR2, HCDR3, LCDR1, LCDR2, and LCDR3 set forth in subpart l of embodiment 1; or
(aq) a heavy chain variable region having at least 90% sequence identity to SEQ ID NO: 346, wherein the antibody, or antigen binding fragment thereof, maintains the sequences of HCDR1, HCDR2, HCDR3, LCDR1, LCDR2, and LCDR3 set forth in subpart m of embodiment 1; or
(ar) a heavy chain variable region having at least 90% sequence identity to SEQ ID NO: 347, wherein the antibody, or antigen binding fragment thereof, maintains the sequences of HCDR1, HCDR2, HCDR3, LCDR1, LCDR2, and LCDR3 set forth in subpart n of embodiment 1; or
(as) a heavy chain variable region having at least 90% sequence identity to SEQ ID NO: 348, wherein the antibody, or antigen binding fragment thereof, maintains the sequences of HCDR1, HCDR2, HCDR3, LCDR1, LCDR2, and LCDR3 set forth in subpart o of embodiment 1; or
(at) a heavy chain variable region having at least 90% sequence identity to SEQ ID NO: 349, wherein the antibody, or antigen binding fragment thereof, maintains the sequences of HCDR1, HCDR2, HCDR3, LCDR1, LCDR2, and LCDR3 set forth in subpart p of embodiment 1; or
(au) a heavy chain variable region having at least 90% sequence identity to SEQ ID NO: 350, wherein the antibody, or antigen binding fragment thereof, maintains the sequences of HCDR1, HCDR2, HCDR3, LCDR1, LCDR2, and LCDR3 set forth in subpart q of embodiment 1; or
(av) a heavy chain variable region having at least 90% sequence identity to SEQ ID NO: 351, wherein the antibody, or antigen binding fragment thereof, maintains the sequences of HCDR1, HCDR2, HCDR3, LCDR1, LCDR2, and LCDR3 set forth in subpart r of embodiment
(aw) a heavy chain variable region having at least 90% sequence identity to SEQ ID NO: 352, wherein the antibody, or antigen binding fragment thereof, maintains the sequences of HCDR1, HCDR2, HCDR3, LCDR1, LCDR2, and LCDR3 set forth in subpart s of embodiment 1; or
(ax) a heavy chain variable region having at least 90% sequence identity to SEQ ID NO: 353, wherein the antibody, or antigen binding fragment thereof, maintains the sequences of HCDR1, HCDR2, HCDR3, LCDR1, LCDR2, and LCDR3 set forth in subpart t of embodiment 1; or
(ay) a heavy chain variable region having at least 90% sequence identity to SEQ ID NO: 354, wherein the antibody, or antigen binding fragment thereof, maintains the sequences of HCDR1, HCDR2, HCDR3, LCDR1, LCDR2, and LCDR3 set forth in subpart u of embodiment 1; or
(az) a heavy chain variable region having at least 90% sequence identity to SEQ ID NO: 355, wherein the antibody, or antigen binding fragment thereof, maintains the sequences of HCDR1, HCDR2, HCDR3, LCDR1, LCDR2, and LCDR3 set forth in subpart v of embodiment 1; or
(ba) a heavy chain variable region having at least 90% sequence identity to SEQ ID NO: 356, wherein the antibody, or antigen binding fragment thereof, maintains the sequences of HCDR1, HCDR2, HCDR3, LCDR1, LCDR2, and LCDR3 set forth in subpart w of embodiment 1; or
(bb) a heavy chain variable region having at least 90% sequence identity to SEQ ID NO: 357, wherein the antibody, or antigen binding fragment thereof, maintains the sequences of HCDR1, HCDR2, HCDR3, LCDR1, LCDR2, and LCDR3 set forth in subpart x of embodiment 1; or
(bc) a heavy chain variable region having at least 90% sequence identity to SEQ ID NO: 358, wherein the antibody, or antigen binding fragment thereof, maintains the sequences of HCDR1, HCDR2, HCDR3, LCDR1, LCDR2, and LCDR3 set forth in subpart y of embodiment 1; or
(bd) a heavy chain variable region having at least 90% sequence identity to SEQ ID NO: 359, wherein the antibody, or antigen binding fragment thereof, maintains the sequences of HCDR1, HCDR2, HCDR3, LCDR1, LCDR2, and LCDR3 set forth in subpart z of embodiment 1; or
(be) a heavy chain variable region having at least 90% sequence identity to SEQ ID NO: 360, wherein the antibody, or antigen binding fragment thereof, maintains the sequences of HCDR1, HCDR2, HCDR3, LCDR1, LCDR2, and LCDR3 set forth in subpart ab of embodiment 1; or
(bf) a heavy chain variable region having at least 90% sequence identity to SEQ ID NO: 361, wherein the antibody, or antigen binding fragment thereof, maintains the sequences of HCDR1, HCDR2, HCDR3, LCDR1, LCDR2, and LCDR3 set forth in subpart ac of embodiment 1; or
(bg) a heavy chain variable region having at least 90% sequence identity to SEQ ID NO: 362, wherein the antibody, or antigen binding fragment thereof, maintains the sequences of HCDR1, HCDR2, HCDR3, LCDR1, LCDR2, and LCDR3 set forth in subpart ad of embodiment 1; or
(bh) a heavy chain variable region having at least 90% sequence identity to SEQ ID NO: 363, wherein the antibody, or antigen binding fragment thereof, maintains the sequences of HCDR1, HCDR2, HCDR3, LCDR1, LCDR2, and LCDR3 set forth in subpart ae of embodiment 1.
3. The antibody or antigen-binding fragment thereof of embodiments 1 or 2, wherein the light chain comprises:
(a) a light chain variable region having at least 90% sequence identity to SEQ ID NO: 2, wherein the antibody, or antigen binding fragment thereof, maintains the sequences of HCDR1, HCDR2, HCDR3, LCDR1, LCDR2, and LCDR3 set forth in subpart a of embodiment 1; or
(b) a light chain variable region having at least 90% sequence identity to SEQ ID NO: 4, wherein the antibody, or antigen binding fragment thereof, maintains the sequences of HCDR1, HCDR2, HCDR3, LCDR1, LCDR2, and LCDR3 set forth in subpart b of embodiment 1; or
(c) a light chain variable region having at least 90% sequence identity to SEQ ID NO: 6, wherein the antibody, or antigen binding fragment thereof, maintains the sequences of HCDR1, HCDR2, HCDR3, LCDR1, LCDR2, and LCDR3 set forth in subpart c of embodiment 1; or
(d) a light chain variable region having at least 90% sequence identity to SEQ ID NO: 8, wherein the antibody, or antigen binding fragment thereof, maintains the sequences of HCDR1, HCDR2, HCDR3, LCDR1, LCDR2, and LCDR3 set forth in subpart d of embodiment 1; or
(e) a light chain variable region having at least 90% sequence identity to SEQ ID NO: 10, wherein the antibody, or antigen binding fragment thereof, maintains the sequences of HCDR1, HCDR2, HCDR3, LCDR1, LCDR2, and LCDR3 set forth in subpart e of embodiment 1; or
(f) a light chain variable region having at least 90% sequence identity to SEQ ID NO: 12, wherein the antibody, or antigen binding fragment thereof, maintains the sequences of HCDR1, HCDR2, HCDR3, LCDR1, LCDR2, and LCDR3 set forth in subpart f of embodiment 1; or
(g) a light chain variable region having at least 90% sequence identity to SEQ ID NO: 14, wherein the antibody, or antigen binding fragment thereof, maintains the sequences of HCDR1, HCDR2, HCDR3, LCDR1, LCDR2, and LCDR3 set forth in subpart g of embodiment 1; or
(h) a light chain variable region having at least 90% sequence identity to SEQ ID NO: 16, wherein the antibody, or antigen binding fragment thereof, maintains the sequences of HCDR1, HCDR2, HCDR3, LCDR1, LCDR2, and LCDR3 set forth in subpart h of embodiment 1; or
(i) a light chain variable region having at least 90% sequence identity to SEQ ID NO: 18, wherein the antibody, or antigen binding fragment thereof, maintains the sequences of HCDR1, HCDR2, HCDR3, LCDR1, LCDR2, and LCDR3 set forth in subpart i of embodiment 1; or
(j) a light chain variable region having at least 90% sequence identity to SEQ ID NO: 20, wherein the antibody, or antigen binding fragment thereof, maintains the sequences of HCDR1, HCDR2, HCDR3, LCDR1, LCDR2, and LCDR3 set forth in subpart j of embodiment
(k) a light chain variable region having at least 90% sequence identity to SEQ ID NO: 22, wherein the antibody, or antigen binding fragment thereof, maintains the sequences of HCDR1, HCDR2, HCDR3, LCDR1, LCDR2, and LCDR3 set forth in subpart k of embodiment 1; or
(l) a light chain variable region having at least 90% sequence identity to SEQ ID NO: 24, wherein the antibody, or antigen binding fragment thereof, maintains the sequences of HCDR1, HCDR2, HCDR3, LCDR1, LCDR2, and LCDR3 set forth in subpart l of embodiment 1; or
(m) a light chain variable region having at least 90% sequence identity to SEQ ID NO: 26, wherein the antibody, or antigen binding fragment thereof, maintains the sequences of HCDR1, HCDR2, HCDR3, LCDR1, LCDR2, and LCDR3 set forth in subpart m of embodiment 1; or
(n) a light chain variable region having at least 90% sequence identity to SEQ ID NO: 28, wherein the antibody, or antigen binding fragment thereof, maintains the sequences of HCDR1, HCDR2, HCDR3, LCDR1, LCDR2, and LCDR3 set forth in subpart n of embodiment 1; or
(o) a light chain variable region having at least 90% sequence identity to SEQ ID NO: 30, wherein the antibody, or antigen binding fragment thereof, maintains the sequences of HCDR1, HCDR2, HCDR3, LCDR1, LCDR2, and LCDR3 set forth in subpart o of embodiment 1; or
(p) a light chain variable region having at least 90% sequence identity to SEQ ID NO: 32, wherein the antibody, or antigen binding fragment thereof, maintains the sequences of HCDR1, HCDR2, HCDR3, LCDR1, LCDR2, and LCDR3 set forth in subpart p of embodiment 1; or
(q) a light chain variable region having at least 90% sequence identity to SEQ ID NO: 34, wherein the antibody, or antigen binding fragment thereof, maintains the sequences of HCDR1, HCDR2, HCDR3, LCDR1, LCDR2, and LCDR3 set forth in subpart q of embodiment 1; or
(r) a light chain variable region having at least 90% sequence identity to SEQ ID NO: 36, wherein the antibody, or antigen binding fragment thereof, maintains the sequences of HCDR1, HCDR2, HCDR3, LCDR1, LCDR2, and LCDR3 set forth in subpart r of embodiment 1; or
(s) a light chain variable region having at least 90% sequence identity to SEQ ID NO: 38, wherein the antibody, or antigen binding fragment thereof, maintains the sequences of HCDR1, HCDR2, HCDR3, LCDR1, LCDR2, and LCDR3 set forth in subpart s of embodiment 1; or
(t) a light chain variable region having at least 90% sequence identity to SEQ ID NO: 40, wherein the antibody, or antigen binding fragment thereof, maintains the sequences of HCDR1, HCDR2, HCDR3, LCDR1, LCDR2, and LCDR3 set forth in subpart t of embodiment 1; or
(u) a light chain variable region having at least 90% sequence identity to SEQ ID NO: 42, wherein the antibody, or antigen binding fragment thereof, maintains the sequences of HCDR1, HCDR2, HCDR3, LCDR1, LCDR2, and LCDR3 set forth in subpart u of embodiment 1; or
(v) a light chain variable region having at least 90% sequence identity to SEQ ID NO: 44, wherein the antibody, or antigen binding fragment thereof, maintains the sequences of HCDR1, HCDR2, HCDR3, LCDR1, LCDR2, and LCDR3 set forth in subpart v of embodiment 1; or
(w) a light chain variable region having at least 90% sequence identity to SEQ ID NO: 46, wherein the antibody, or antigen binding fragment thereof, maintains the sequences of HCDR1, HCDR2, HCDR3, LCDR1, LCDR2, and LCDR3 set forth in subpart w of embodiment 1; or
(x) a light chain variable region having at least 90% sequence identity to SEQ ID NO: 48, wherein the antibody, or antigen binding fragment thereof, maintains the sequences of HCDR1, HCDR2, HCDR3, LCDR1, LCDR2, and LCDR3 set forth in subpart x of embodiment 1; or
(y) a light chain variable region having at least 90% sequence identity to SEQ ID NO: 50, wherein the antibody, or antigen binding fragment thereof, maintains the sequences of HCDR1, HCDR2, HCDR3, LCDR1, LCDR2, and LCDR3 set forth in subpart y of embodiment
(z) a light chain variable region having at least 90% sequence identity to SEQ ID NO: 52, wherein the antibody, or antigen binding fragment thereof, maintains the sequences of HCDR1, HCDR2, HCDR3, LCDR1, LCDR2, and LCDR3 set forth in subpart z of embodiment 1; or
(aa) a light chain variable region having at least 90% sequence identity to SEQ ID NO: 54, wherein the antibody, or antigen binding fragment thereof, maintains the sequences of HCDR1, HCDR2, HCDR3, LCDR1, LCDR2, and LCDR3 set forth in subpart ab of embodiment 1; or
(ab) a light chain variable region having at least 90% sequence identity to SEQ ID NO: 56, wherein the antibody, or antigen binding fragment thereof, maintains the sequences of HCDR1, HCDR2, HCDR3, LCDR1, LCDR2, and LCDR3 set forth in subpart ac of embodiment 1; or
(ac) a light chain variable region having at least 90% sequence identity to SEQ ID NO: 58, wherein the antibody, or antigen binding fragment thereof, maintains the sequences of HCDR1, HCDR2, HCDR3, LCDR1, LCDR2, and LCDR3 set forth in subpart ad of embodiment 1; or
(ad) a light chain variable region having at least 90% sequence identity to SEQ ID NO: 60, wherein the antibody, or antigen binding fragment thereof, maintains the sequences of HCDR1, HCDR2, HCDR3, LCDR1, LCDR2, and LCDR3 set forth in subpart ae of embodiment 1.

4. The antibody or antigen-binding fragment thereof of any one of embodiments 1-3 wherein the antibody, or antigen binding fragment thereof, comprises:
(a) a light chain variable region of the light chain having at least 90% sequence identity to SEQ ID NO: 2, and a heavy chain variable region of the heavy chain having at least 90% sequence identity to SEQ ID NO: 1, wherein the antibody, or antigen binding fragment thereof, maintains the sequences of HCDR1, HCDR2, HCDR3, LCDR1, LCDR2, and LCDR3 set forth in subpart a of embodiment 1; or
(b) a light chain variable region of the light chain having at least 90% sequence identity to SEQ ID NO: 4, and a heavy chain variable region of the heavy chain having at least 90% sequence identity to SEQ ID NO: 3, wherein the antibody, or antigen binding fragment set forth in subpart b of embodiment 1; or
(c) a light chain variable region of the light chain having at least 90% sequence identity to SEQ ID NO: 6, and a heavy chain variable region of the heavy chain having at least 90% sequence identity to SEQ ID NO: 5, wherein the antibody, or antigen binding fragment thereof, maintains the sequences of HCDR1, HCDR2, HCDR3, LCDR1, LCDR2, and LCDR3 set forth in subpart c of embodiment 1; or
(d) a light chain variable region of the light chain having at least 90% sequence identity to SEQ ID NO: 8, and a heavy chain variable region of the heavy chain having at least 90% sequence identity to SEQ ID NO: 7, wherein the antibody, or antigen binding fragment thereof, maintains the sequences of HCDR1, HCDR2, HCDR3, LCDR1, LCDR2, and LCDR3 set forth in subpart d of embodiment 1; or
(e) a light chain variable region of the light chain having at least 90% sequence identity to SEQ ID NO: 10, and a heavy chain variable region of the heavy chain having at least 90% sequence identity to SEQ ID NO: 9, wherein the antibody, or antigen binding fragment thereof, maintains the sequences of HCDR1, HCDR2, HCDR3, LCDR1, LCDR2, and LCDR3 set forth in subpart e of embodiment 1; or
(f) a light chain variable region of the light chain having at least 90% sequence identity to SEQ ID NO: 12, and a heavy chain variable region of the heavy chain having at least 90% sequence identity to SEQ ID NO: 11, wherein the antibody, or antigen binding fragment thereof, maintains the sequences of HCDR1, HCDR2, HCDR3, LCDR1, LCDR2, and LCDR3 set forth in subpart f of embodiment 1; or
(g) a light chain variable region of the light chain having at least 90% sequence identity to SEQ ID NO: 14, and a heavy chain variable region of the heavy chain having at least 90% sequence identity to SEQ ID NO: 13, wherein the antibody, or antigen binding fragment thereof, maintains the sequences of HCDR1, HCDR2, HCDR3, LCDR1, LCDR2, and LCDR3 set forth in subpart g of embodiment 1; or
(h) a light chain variable region of the light chain having at least 90% sequence identity to SEQ ID NO: 16, and a heavy chain variable region of the heavy chain having at least 90% sequence identity to SEQ ID NO: 15, wherein the antibody, or antigen binding fragment set forth in subpart h of embodiment 1; or
(i) a light chain variable region of the light chain having at least 90% sequence identity to SEQ ID NO: 18, and a heavy chain variable region of the heavy chain having at least 90% sequence identity to SEQ ID NO: 17, wherein the antibody, or antigen binding fragment thereof, maintains the sequences of HCDR1, HCDR2, HCDR3, LCDR1, LCDR2, and LCDR3 set forth in subpart i of embodiment 1; or
(j) a light chain variable region of the light chain having at least 90% sequence identity to SEQ ID NO: 20, and a heavy chain variable region of the heavy chain having at least 90% sequence identity to SEQ ID NO: 19, wherein the antibody, or antigen binding fragment thereof, maintains the sequences of HCDR1, HCDR2, HCDR3, LCDR1, LCDR2, and LCDR3 set forth in subpart j of embodiment 1; or
(k) a light chain variable region of the light chain having at least 90% sequence identity to SEQ ID NO: 22, and a heavy chain variable region of the heavy chain having at least 90% sequence identity to SEQ ID NO: 21, wherein the antibody, or antigen binding fragment thereof, maintains the sequences of HCDR1, HCDR2, HCDR3, LCDR1, LCDR2, and LCDR3 set forth in subpart k of embodiment 1; or
(l) a light chain variable region of the light chain having at least 90% sequence identity to SEQ ID NO: 24, and a heavy chain variable region of the heavy chain having at least 90% sequence identity to SEQ ID NO: 23, wherein the antibody, or antigen binding fragment thereof, maintains the sequences of HCDR1, HCDR2, HCDR3, LCDR1, LCDR2, and LCDR3 set forth in subpart l of embodiment 1; or
(m) a light chain variable region of the light chain having at least 90% sequence identity to SEQ ID NO: 26, and a heavy chain variable region of the heavy chain having at least 90% sequence identity to SEQ ID NO: 25, wherein the antibody, or antigen binding fragment thereof, maintains the sequences of HCDR1, HCDR2, HCDR3, LCDR1, LCDR2, and LCDR3 set forth in subpart m of embodiment 1; or
(n) a light chain variable region of the light chain having at least 90% sequence identity to SEQ ID NO: 28, and a heavy chain variable region of the heavy chain having at least 90% sequence identity to SEQ ID NO: 27, wherein the antibody, or antigen binding fragment set forth in subpart n of embodiment 1; or (o) a light chain variable region of the light chain having at least 90% sequence identity to SEQ ID NO: 30, and a heavy chain variable region of the heavy chain having at least 90% sequence identity to SEQ ID NO: 29, wherein the antibody, or antigen binding fragment thereof, maintains the sequences of HCDR1, HCDR2, HCDR3, LCDR1, LCDR2, and LCDR3 set forth in subpart o of embodiment 1; or (p) a light chain variable region of the light chain having at least 90% sequence identity to SEQ ID NO: 32, and a heavy chain variable region of the heavy chain having at least 90% sequence identity to SEQ ID NO: 31, wherein the antibody, or antigen binding fragment thereof, maintains the sequences of HCDR1, HCDR2, HCDR3, LCDR1, LCDR2, and LCDR3 set forth in subpart p of embodiment 1; or (q) a light chain variable region of the light chain having at least 90% sequence identity to SEQ ID NO: 34, and a heavy chain variable region of the heavy chain having at least 90% sequence identity to SEQ ID NO: 33, wherein the antibody, or antigen binding fragment thereof, maintains the sequences of HCDR1, HCDR2, HCDR3, LCDR1, LCDR2, and LCDR3 set forth in subpart q of embodiment 1; or (r) a light chain variable region of the light chain having at least 90% sequence identity to SEQ ID NO: 36, and a heavy chain variable region of the heavy chain having at least 90% sequence identity to SEQ ID NO: 35, wherein the antibody, or antigen binding fragment thereof, maintains the sequences of HCDR1, HCDR2, HCDR3, LCDR1, LCDR2, and LCDR3 set forth in subpart r of embodiment 1; or (s) a light chain variable region of the light chain having at least 90% sequence identity to SEQ ID NO: 38, and a heavy chain variable region of the heavy chain having at least 90% sequence identity to SEQ ID NO: 37, wherein the antibody, or antigen binding fragment thereof, maintains the sequences of HCDR1, HCDR2, HCDR3, LCDR1, LCDR2, and LCDR3 set forth in subpart s of embodiment 1; or (t) a light chain variable region of the light chain having at least 90% sequence identity to SEQ ID NO: 40, and a heavy chain variable region of the heavy chain having at least 90% sequence identity to SEQ ID NO: 39, wherein the antibody, or antigen binding fragment set forth in subpart t of embodiment 1; or (u) a light chain variable region of the light chain having at least 90% sequence identity to SEQ ID NO: 42, and a heavy chain variable region of the heavy chain having at least 90% sequence identity to SEQ ID NO: 41, wherein the antibody, or antigen binding fragment thereof, maintains the sequences of HCDR1, HCDR2, HCDR3, LCDR1, LCDR2, and LCDR3 set forth in subpart u of embodiment 1; or (v) a light chain variable region of the light chain having at least 90% sequence identity to SEQ ID NO: 44, and a heavy chain variable region of the heavy chain having at least 90% sequence identity to SEQ ID NO: 43, wherein the antibody, or antigen binding fragment thereof, maintains the sequences of HCDR1, HCDR2, HCDR3, LCDR1, LCDR2, and LCDR3 set forth in subpart v of embodiment 1; or (w) a light chain variable region of the light chain having at least 90% sequence identity to SEQ ID NO: 46, and a heavy chain variable region of the heavy chain having at least 90% sequence identity to SEQ ID NO: 45, wherein the antibody, or antigen binding fragment thereof, maintains the sequences of HCDR1, HCDR2, HCDR3, LCDR1, LCDR2, and LCDR3 set forth in subpart w of embodiment 1; or (x) a light chain variable region of the light chain having at least 90% sequence identity to SEQ ID NO: 48, and a heavy chain variable region of the heavy chain having at least 90% sequence identity to SEQ ID NO: 47, wherein the antibody, or antigen binding fragment thereof, maintains the sequences of HCDR1, HCDR2, HCDR3, LCDR1, LCDR2, and LCDR3 set forth in subpart x of embodiment 1; or (y) a light chain variable region of the light chain having at least 90% sequence identity to SEQ ID NO: 50, and a heavy chain variable region of the heavy chain having at least 90% sequence identity to SEQ ID NO: 49, wherein the antibody, or antigen binding fragment thereof, maintains the sequences of HCDR1, HCDR2, HCDR3, LCDR1, LCDR2, and LCDR3 set forth in subpart y of embodiment 1; or (z) a light chain variable region of the light chain having at least 90% sequence identity to SEQ ID NO: 52, and a heavy chain variable region of the heavy chain having at least 90% sequence identity to SEQ ID NO: 51, wherein the antibody, or antigen binding fragment set forth in subpart z of embodiment 1; or (aa) a light chain variable region of the light chain having at least 90% sequence identity to SEQ ID NO: 54, and a heavy chain variable region of the heavy chain having at least 90% sequence identity to SEQ ID NO: 53, wherein the antibody, or antigen binding fragment thereof, maintains the sequences of HCDR1, HCDR2, HCDR3, LCDR1, LCDR2, and LCDR3 set forth in subpart ab of embodiment 1; or (ab) a light chain variable region of the light chain having at least 90% sequence identity to SEQ ID NO: 56, and a heavy chain variable region of the heavy chain having at least 90% sequence identity to SEQ ID NO: 55, wherein the antibody, or antigen binding fragment thereof, maintains the sequences of HCDR1, HCDR2, HCDR3, LCDR1, LCDR2, and LCDR3 set forth in subpart ac of embodiment 1; or (ac) a light chain variable region of the light chain having at least 90% sequence identity to SEQ ID NO: 58, and a heavy chain variable region of the heavy chain having at least 90% sequence identity to SEQ ID NO: 57, wherein the antibody, or antigen binding fragment thereof, maintains the sequences of HCDR1, HCDR2, HCDR3, LCDR1, LCDR2, and LCDR3 set forth in subpart ad of embodiment 1; or (ad) a light chain variable region of the light chain having at least 90% sequence identity to SEQ ID NO: 60, and a heavy chain variable region of the heavy chain having at least 90% sequence identity to SEQ ID NO: 59, wherein the antibody, or antigen binding fragment thereof, maintains the sequences of HCDR1, HCDR2, HCDR3, LCDR1, LCDR2, and LCDR3 set forth in subpart ae of embodiment 1; or (ae) a light chain variable region of the light chain having at least 90% sequence identity to SEQ ID NO: 2, and a heavy chain variable region of the heavy chain having at least 90% sequence identity to SEQ ID NO: 334, wherein the antibody, or antigen binding fragment thereof, maintains the sequences of HCDR1, HCDR2, HCDR3, LCDR1, LCDR2, and LCDR3 set forth in subpart a of embodiment 1; or (af) a light chain variable region of the light chain having at least 90% sequence identity to SEQ ID NO: 4, and a heavy chain variable region of the heavy chain having at least 90% sequence identity to SEQ ID NO: 335, wherein the antibody, or antigen binding fragment set forth in subpart b of embodiment 1; or (ag) a light chain variable region of the light chain having at least 90% sequence identity to SEQ ID NO: 6, and a heavy chain variable region of the heavy chain having at least 90% sequence identity to SEQ ID NO: 336, wherein the antibody, or antigen binding fragment thereof, maintains the sequences of HCDR1, HCDR2, HCDR3, LCDR1, LCDR2, and LCDR3 set forth in subpart c of embodiment 1; or (ah) a light chain variable region of the light chain having at least 90% sequence identity to SEQ ID NO: 8, and a heavy chain variable region of the heavy chain having at least 90% sequence identity to SEQ ID NO: 337, wherein the antibody, or antigen binding fragment thereof, maintains the sequences of HCDR1, HCDR2, HCDR3, LCDR1, LCDR2, and LCDR3 set forth in subpart d of embodiment 1; or (ai) a light chain variable region of the light chain having at least 90% sequence identity to SEQ ID NO: 10, and a heavy chain variable region of the heavy chain having at least 90% sequence identity to SEQ ID NO: 338, wherein the antibody, or antigen binding fragment thereof, maintains the sequences of HCDR1, HCDR2, HCDR3, LCDR1, LCDR2, and LCDR3 set forth in subpart e of embodiment 1; or (aj) a light chain variable region of the light chain having at least 90% sequence identity to SEQ ID NO: 12, and a heavy chain variable region of the heavy chain having at least 90% sequence identity to SEQ ID NO: 339, wherein the antibody, or antigen binding fragment thereof, maintains the sequences of HCDR1, HCDR2, HCDR3, LCDR1, LCDR2, and LCDR3 set forth in subpart f of embodiment 1; or (ak) a light chain variable region of the light chain having at least 90% sequence identity to SEQ ID NO: 14, and a heavy chain variable region of the heavy chain having at least 90% sequence identity to SEQ ID NO: 340, wherein the antibody, or antigen binding fragment thereof, maintains the sequences of HCDR1, HCDR2, HCDR3, LCDR1, LCDR2, and LCDR3 set forth in subpart g of embodiment 1; or (al) a light chain variable region of the light chain having at least 90% sequence identity to SEQ ID NO: 16, and a heavy chain variable region of the heavy chain having at least 90% sequence identity to SEQ ID NO: 341, wherein the antibody, or antigen binding fragment set forth in subpart h of embodiment 1; or (am) a light chain variable region of the light chain having at least 90% sequence identity to SEQ ID NO: 18, and a heavy chain variable region of the heavy chain having at least 90% sequence identity to SEQ ID NO: 342, wherein the antibody, or antigen binding fragment thereof, maintains the sequences of HCDR1, HCDR2, HCDR3, LCDR1, LCDR2, and LCDR3 set forth in subpart i of embodiment 1; or (an) a light chain variable region of the light chain having at least 90% sequence identity to SEQ ID NO: 20, and a heavy chain variable region of the heavy chain having at least 90% sequence identity to SEQ ID NO: 343, wherein the antibody, or antigen binding fragment thereof, maintains the sequences of HCDR1, HCDR2, HCDR3, LCDR1, LCDR2, and LCDR3 set forth in subpart j of embodiment 1; or (ao) a light chain variable region of the light chain having at least 90% sequence identity to SEQ ID NO: 22, and a heavy chain variable region of the heavy chain having at least 90% sequence identity to SEQ ID NO: 344, wherein the antibody, or antigen binding fragment thereof, maintains the sequences of HCDR1, HCDR2, HCDR3, LCDR1, LCDR2, and LCDR3 set forth in subpart k of embodiment 1; or (ap) a light chain variable region of the light chain having at least 90% sequence identity to SEQ ID NO: 24, and a heavy chain variable region of the heavy chain having at least 90% sequence identity to SEQ ID NO: 345, wherein the antibody, or antigen binding fragment thereof, maintains the sequences of HCDR1, HCDR2, HCDR3, LCDR1, LCDR2, and LCDR3 set forth in subpart 1 of embodiment 1; or (aq) a light chain variable region of the light chain having at least 90% sequence identity to SEQ ID NO: 26, and a heavy chain variable region of the heavy chain having at least 90% sequence identity to SEQ ID NO: 346, wherein the antibody, or antigen binding fragment thereof, maintains the sequences of HCDR1, HCDR2, HCDR3, LCDR1, LCDR2, and LCDR3 set forth in subpart m of embodiment 1; or (ar) a light chain variable region of the light chain having at least 90% sequence identity to SEQ ID NO: 28, and a heavy chain variable region of the heavy chain having at least 90% sequence identity to SEQ ID NO: 347, wherein the antibody, or antigen binding fragment set forth in subpart n of embodiment 1; or (as) a light chain variable region of the light chain having at least 90% sequence identity to SEQ ID NO: 30, and a heavy chain variable region of the heavy chain having at least 90% sequence identity to SEQ ID NO: 348, wherein the antibody, or antigen binding fragment thereof, maintains the sequences of HCDR1, HCDR2, HCDR3, LCDR1, LCDR2, and LCDR3 set forth in subpart o of embodiment 1; or (at) a light chain variable region of the light chain having at least 90% sequence identity to SEQ ID NO: 32, and a heavy chain variable region of the heavy chain having at least 90% sequence identity to SEQ ID NO: 349, wherein the antibody, or antigen binding fragment thereof, maintains the sequences of HCDR1, HCDR2, HCDR3, LCDR1, LCDR2, and LCDR3 set forth in subpart p of embodiment 1; or (au) a light chain variable region of the light chain having at least 90% sequence identity to SEQ ID NO: 34, and a heavy chain variable region of the heavy chain having at least 90% sequence identity to SEQ ID NO: 350, wherein the antibody, or antigen binding fragment thereof, maintains the sequences of HCDR1, HCDR2, HCDR3, LCDR1, LCDR2, and LCDR3 set forth in subpart q of embodiment 1; or (av) a light chain variable region of the light chain having at least 90% sequence identity to SEQ ID NO: 36, and a heavy chain variable region of the heavy chain having at least 90% sequence identity to SEQ ID NO: 351, wherein the antibody, or antigen binding fragment thereof, maintains the sequences of HCDR1, HCDR2, HCDR3, LCDR1, LCDR2, and LCDR3 set forth in subpart r of embodiment 1; or
(aw) a light chain variable region of the light chain having at least 90% sequence identity to SEQ ID NO: 38, and a heavy chain variable region of the heavy chain having at least 90% sequence identity to SEQ ID NO: 352, wherein the antibody, or antigen binding fragment thereof, maintains the sequences of HCDR1, HCDR2, HCDR3, LCDR1, LCDR2, and LCDR3 set forth in subpart s of embodiment 1; or
(ax) a light chain variable region of the light chain having at least 90% sequence identity to SEQ ID NO: 40, and a heavy chain variable region of the heavy chain having at least 90% sequence identity to SEQ ID NO: 353, wherein the antibody, or antigen binding fragment set forth in subpart t of embodiment 1; or
(ay) a light chain variable region of the light chain having at least 90% sequence identity to SEQ ID NO: 42, and a heavy chain variable region of the heavy chain having at least 90% sequence identity to SEQ ID NO: 354, wherein the antibody, or antigen binding fragment thereof, maintains the sequences of HCDR1, HCDR2, HCDR3, LCDR1, LCDR2, and LCDR3 set forth in subpart u of embodiment 1; or
(az) a light chain variable region of the light chain having at least 90% sequence identity to SEQ ID NO: 44, and a heavy chain variable region of the heavy chain having at least 90% sequence identity to SEQ ID NO: 355, wherein the antibody, or antigen binding fragment thereof, maintains the sequences of HCDR1, HCDR2, HCDR3, LCDR1, LCDR2, and LCDR3 set forth in subpart v of embodiment 1; or
(ba) a light chain variable region of the light chain having at least 90% sequence identity to SEQ ID NO: 46, and a heavy chain variable region of the heavy chain having at least 90% sequence identity to SEQ ID NO: 356, wherein the antibody, or antigen binding fragment thereof, maintains the sequences of HCDR1, HCDR2, HCDR3, LCDR1, LCDR2, and LCDR3 set forth in subpart w of embodiment 1; or
(bb) a light chain variable region of the light chain having at least 90% sequence identity to SEQ ID NO: 48, and a heavy chain variable region of the heavy chain having at least 90% sequence identity to SEQ ID NO: 357, wherein the antibody, or antigen binding fragment thereof, maintains the sequences of HCDR1, HCDR2, HCDR3, LCDR1, LCDR2, and LCDR3 set forth in subpart x of embodiment 1; or
(bc) a light chain variable region of the light chain having at least 90% sequence identity to SEQ ID NO: 50, and a heavy chain variable region of the heavy chain having at least 90% sequence identity to SEQ ID NO: 358, wherein the antibody, or antigen binding fragment thereof, maintains the sequences of HCDR1, HCDR2, HCDR3, LCDR1, LCDR2, and LCDR3 set forth in subpart y of embodiment 1; or
(bd) a light chain variable region of the light chain having at least 90% sequence identity to SEQ ID NO: 52, and a heavy chain variable region of the heavy chain having at least 90% sequence identity to SEQ ID NO: 359, wherein the antibody, or antigen binding fragment set forth in subpart z of embodiment 1; or
(be) a light chain variable region of the light chain having at least 90% sequence identity to SEQ ID NO: 54, and a heavy chain variable region of the heavy chain having at least 90% sequence identity to SEQ ID NO: 360, wherein the antibody, or antigen binding fragment thereof, maintains the sequences of HCDR1, HCDR2, HCDR3, LCDR1, LCDR2, and LCDR3 set forth in subpart ab of embodiment 1; or
(bf) a light chain variable region of the light chain having at least 90% sequence identity to SEQ ID NO: 56, and a heavy chain variable region of the heavy chain having at least 90% sequence identity to SEQ ID NO: 361, wherein the antibody, or antigen binding fragment thereof, maintains the sequences of HCDR1, HCDR2, HCDR3, LCDR1, LCDR2, and LCDR3 set forth in subpart ac of embodiment 1; or
(bg) a light chain variable region of the light chain having at least 90% sequence identity to SEQ ID NO: 58, and a heavy chain variable region of the heavy chain having at least 90% sequence identity to SEQ ID NO: 362, wherein the antibody, or antigen binding fragment thereof, maintains the sequences of HCDR1, HCDR2, HCDR3, LCDR1, LCDR2, and LCDR3 set forth in subpart ad of embodiment 1; or
(bh) a light chain variable region of the light chain having at least 90% sequence identity to SEQ ID NO: 60, and a heavy chain variable region of the heavy chain having at least 90% sequence identity to SEQ ID NO: 363, wherein the antibody, or antigen binding fragment thereof, maintains the sequences of HCDR1, HCDR2, HCDR3, LCDR1, LCDR2, and LCDR3 set forth in subpart ae of embodiment 1.

5. The antibody or antigen-binding fragment thereof of embodiment 4, wherein;
(a) the light chain variable region comprises SEQ ID NO: 2, and the heavy chain variable region comprises SEQ ID NO: 1;
(b) the light chain variable region comprises SEQ ID NO: 4, and the heavy chain variable region comprises SEQ ID NO: 3;
(c) the light chain variable region comprises SEQ ID NO: 6, and the heavy chain variable region comprises SEQ ID NO: 5
(d) the light chain variable region comprises SEQ ID NO: 8, and the heavy chain variable region comprises SEQ ID NO: 7
(e) the light chain variable region comprises SEQ ID NO: 10, and the heavy chain variable region comprises SEQ ID NO: 9
(f) the light chain variable region comprises SEQ ID NO: 12, and the heavy chain variable region comprises SEQ ID NO: 11;
(g) the light chain variable region comprises SEQ ID NO: 14, and the heavy chain variable region comprises SEQ ID NO: 13;
(h) the light chain variable region comprises SEQ ID NO: 16, and the heavy chain variable region comprises SEQ ID NO: 15;
(i) the light chain variable region comprises SEQ ID NO: 18, and the heavy chain variable region comprises SEQ ID NO: 17;
(j) the light chain variable region comprises SEQ ID NO: 20, and the heavy chain variable region comprises SEQ ID NO: 19;
(k) the light chain variable region comprises SEQ ID NO: 22, and the heavy chain variable region comprises SEQ ID NO: 21;

(l) the light chain variable region comprises SEQ ID NO: 24, and the heavy chain variable region comprises SEQ ID NO: 23;
(m) the light chain variable region comprises SEQ ID NO: 26, and the heavy chain variable region comprises SEQ ID NO: 25;
(n) the light chain variable region comprises SEQ ID NO: 28, and the heavy chain variable region comprises SEQ ID NO: 27;
(o) the light chain variable region comprises SEQ ID NO: 30, and the heavy chain variable region comprises SEQ ID NO: 29;
(p) the light chain variable region comprises SEQ ID NO: 32, and the heavy chain variable region comprises SEQ ID NO: 31;
(q) the light chain variable region comprises SEQ ID NO: 34, and the heavy chain variable region comprises SEQ ID NO: 33;
(r) the light chain variable region comprises SEQ ID NO: 36, and the heavy chain variable region comprises SEQ ID NO: 35;
(s) the light chain variable region comprises SEQ ID NO: 38, and the heavy chain variable region comprises SEQ ID NO: 37;
(t) the light chain variable region comprises SEQ ID NO: 40, and the heavy chain variable region comprises SEQ ID NO: 39;
(u) the light chain variable region comprises SEQ ID NO: 42, and the heavy chain variable region comprises SEQ ID NO: 41;
(v) the light chain variable region comprises SEQ ID NO: 44, and the heavy chain variable region comprises SEQ ID NO: 43;
(w) the light chain variable region comprises SEQ ID NO: 46, and the heavy chain variable region comprises SEQ ID NO: 45;
(x) the light chain variable region comprises SEQ ID NO: 48, and the heavy chain variable region comprises SEQ ID NO: 47;
(y) the light chain variable region comprises SEQ ID NO: 50, and the heavy chain variable region comprises SEQ ID NO: 49;
(z) the light chain variable region comprises SEQ ID NO: 52, and the heavy chain variable region comprises SEQ ID NO: 51;
(aa) the light chain variable region comprises SEQ ID NO: 54, and the heavy chain variable region comprises SEQ ID NO: 53;
(ab) the light chain variable region comprises SEQ ID NO: 56, and the heavy chain variable region comprises SEQ ID NO: 55;
(ac) the light chain variable region comprises SEQ ID NO: 58, and the heavy chain variable region comprises SEQ ID NO: 57;
(ad) the light chain variable region comprises SEQ ID NO: 60, and the heavy chain variable region comprises SEQ ID NO: 59; or
(ae) the light chain variable region comprises SEQ ID NO: 2, and the heavy chain variable region comprises SEQ ID NO: 334;
(af) the light chain variable region comprises SEQ ID NO: 4, and the heavy chain variable region comprises SEQ ID NO: 335;
(ag) the light chain variable region comprises SEQ ID NO: 6, and the heavy chain variable region comprises SEQ ID NO: 336;
(ah) the light chain variable region comprises SEQ ID NO: 8, and the heavy chain variable region comprises SEQ ID NO: 337;
(ai) the light chain variable region comprises SEQ ID NO: 10, and the heavy chain variable region comprises SEQ ID NO: 338;
(aj) the light chain variable region comprises SEQ ID NO: 12, and the heavy chain variable region comprises SEQ ID NO: 339;
(ak) the light chain variable region comprises SEQ ID NO: 14, and the heavy chain variable region comprises SEQ ID NO: 340;
(al) the light chain variable region comprises SEQ ID NO: 16, and the heavy chain variable region comprises SEQ ID NO: 341;
(am) the light chain variable region comprises SEQ ID NO: 18, and the heavy chain variable region comprises SEQ ID NO: 342;
(an) the light chain variable region comprises SEQ ID NO: 20, and the heavy chain variable region comprises SEQ ID NO: 343;
(ao) the light chain variable region comprises SEQ ID NO: 22, and the heavy chain variable region comprises SEQ ID NO: 344;
(ap) the light chain variable region comprises SEQ ID NO: 24, and the heavy chain variable region comprises SEQ ID NO: 345;
(aq) the light chain variable region comprises SEQ ID NO: 26, and the heavy chain variable region comprises SEQ ID NO: 346;
(ar) the light chain variable region comprises SEQ ID NO: 28, and the heavy chain variable region comprises SEQ ID NO: 347;
(as) the light chain variable region comprises SEQ ID NO: 30, and the heavy chain variable region comprises SEQ ID NO: 348;
(at) the light chain variable region comprises SEQ ID NO: 32, and the heavy chain variable region comprises SEQ ID NO: 349;
(au) the light chain variable region comprises SEQ ID NO: 34, and the heavy chain variable region comprises SEQ ID NO: 350;
(av) the light chain variable region comprises SEQ ID NO: 36, and the heavy chain variable region comprises SEQ ID NO: 351;
(aw) the light chain variable region comprises SEQ ID NO: 38, and the heavy chain variable region comprises SEQ ID NO: 352;
(ax) the light chain variable region comprises SEQ ID NO: 40, and the heavy chain variable region comprises SEQ ID NO: 353;
(ay) the light chain variable region comprises SEQ ID NO: 42, and the heavy chain variable region comprises SEQ ID NO: 354;
(az) the light chain variable region comprises SEQ ID NO: 44, and the heavy chain variable region comprises SEQ ID NO: 355;
(ba) the light chain variable region comprises SEQ ID NO: 46, and the heavy chain variable region comprises SEQ ID NO: 356;
(bb) the light chain variable region comprises SEQ ID NO: 48, and the heavy chain variable region comprises SEQ ID NO: 357;
(bc) the light chain variable region comprises SEQ ID NO: 50, and the heavy chain variable region comprises SEQ ID NO: 358;

(bd) the light chain variable region comprises SEQ ID NO: 52, and the heavy chain variable region comprises SEQ ID NO: 359;
(be) the light chain variable region comprises SEQ ID NO: 54, and the heavy chain variable region comprises SEQ ID NO: 360;
(bf) the light chain variable region comprises SEQ ID NO: 56, and the heavy chain variable region comprises SEQ ID NO: 361;
(bg) the light chain variable region comprises SEQ ID NO: 58, and the heavy chain variable region comprises SEQ ID NO: 362; or
(bh) the light chain variable region comprises SEQ ID NO: 60, and the heavy chain variable region comprises SEQ ID NO: 363.

6. The antibody or antigen-binding fragment thereof of any one of embodiments 1-5, wherein:

(a) the heavy chain has at least 90% sequence identity to SEQ ID NO: 168 or SEQ ID NO: 169, wherein the antibody, or antigen binding fragment thereof, maintains the sequences of HCDR1, HCDR2, HCDR3, LCDR1, LCDR2, and LCDR3 set forth in subpart a of embodiment (b) the heavy chain has at least 90% sequence identity to SEQ ID NO: 170 or SEQ ID NO: 171, wherein the antibody, or antigen binding fragment thereof, maintains the sequences of HCDR1, HCDR2, HCDR3, LCDR1, LCDR2, and LCDR3 set forth in subpart b of embodiment 1; or (c) the heavy chain has at least 90% sequence identity to SEQ ID NO: 172 or SEQ ID NO: 173, wherein the antibody, or antigen binding fragment thereof, maintains the sequences of HCDR1, HCDR2, HCDR3, LCDR1, LCDR2, and LCDR3 set forth in subpart c of embodiment 1; or (d) the heavy chain has at least 90% sequence identity to SEQ ID NO: 174 or SEQ ID NO: 175, wherein the antibody, or antigen binding fragment thereof, maintains the sequences of HCDR1, HCDR2, HCDR3, LCDR1, LCDR2, and LCDR3 set forth in subpart d of embodiment 1; or (e) the heavy chain has at least 90% sequence identity to SEQ ID NO: 176 or SEQ ID NO: 177, wherein the antibody, or antigen binding fragment thereof, maintains the sequences of HCDR1, HCDR2, HCDR3, LCDR1, LCDR2, and LCDR3 set forth in subpart e of embodiment 1; or (f) the heavy chain has at least 90% sequence identity to SEQ ID NO: 178 or SEQ ID NO: 179, wherein the antibody, or antigen binding fragment thereof, maintains the sequences of HCDR1, HCDR2, HCDR3, LCDR1, LCDR2, and LCDR3 set forth in subpart f of embodiment 1; or (g) the heavy chain has at least 90% sequence identity to SEQ ID NO: 180 or SEQ ID NO: 181, wherein the antibody, or antigen binding fragment thereof, maintains the sequences of HCDR1, HCDR2, HCDR3, LCDR1, LCDR2, and LCDR3 set forth in subpart g of embodiment 1; or (h) the heavy chain has at least 90% sequence identity to SEQ ID NO: 182 or SEQ ID NO: 183, wherein the antibody, or antigen binding fragment thereof, maintains the sequences of HCDR1, HCDR2, HCDR3, LCDR1, LCDR2, and LCDR3 set forth in subpart h of embodiment 1; or (i) the heavy chain has at least 90% sequence identity to SEQ ID NO: 184 or SEQ ID NO: 185, wherein the antibody, or antigen binding fragment thereof, maintains the sequences of HCDR1, HCDR2, HCDR3, LCDR1, LCDR2, and LCDR3 set forth in subpart i of embodiment 1; or (j) the heavy chain has at least 90% sequence identity to SEQ ID NO: 186 or SEQ ID NO: 187, wherein the antibody, or antigen binding fragment thereof, maintains the sequences of HCDR1, HCDR2, HCDR3, LCDR1, LCDR2, and LCDR3 set forth in subpart j of embodiment 1; or (k) the heavy chain has at least 90% sequence identity to SEQ ID NO: 188 or SEQ ID NO: 189, wherein the antibody, or antigen binding fragment thereof, maintains the sequences of HCDR1, HCDR2, HCDR3, LCDR1, LCDR2, and LCDR3 set forth in subpart k of embodiment 1; or (l) the heavy chain has at least 90% sequence identity to SEQ ID NO: 190 or SEQ ID NO: 191, wherein the antibody, or antigen binding fragment thereof, maintains the sequences of HCDR1, HCDR2, HCDR3, LCDR1, LCDR2, and LCDR3 set forth in subpart l of embodiment 1; or (m) the heavy chain has at least 90% sequence identity to SEQ ID NO: 192 or SEQ ID NO: 193, wherein the antibody, or antigen binding fragment thereof, maintains the sequences of HCDR1, HCDR2, HCDR3, LCDR1, LCDR2, and LCDR3 set forth in subpart m of embodiment 1; or (n) the heavy chain has at least 90% sequence identity to SEQ ID NO: 194 or SEQ ID NO: 195, wherein the antibody, or antigen binding fragment thereof, maintains the sequences of HCDR1, HCDR2, HCDR3, LCDR1, LCDR2, and LCDR3 set forth in subpart n of embodiment 1; or (o) the heavy chain has at least 90% sequence identity to SEQ ID NO: 196 or SEQ ID NO: 197, wherein the antibody, or antigen binding fragment thereof, maintains the sequences of HCDR1, HCDR2, HCDR3, LCDR1, LCDR2, and LCDR3 set forth in subpart o of embodiment 1; or (p) the heavy chain has at least 90% sequence identity to SEQ ID NO: 198 or SEQ ID NO: 199, wherein the antibody, or antigen binding fragment thereof, maintains the sequences of HCDR1, HCDR2, HCDR3, LCDR1, LCDR2, and LCDR3 set forth in subpart p of embodiment (q) the heavy chain has at least 90% sequence identity to SEQ ID NO: 200 or SEQ ID NO: 201, wherein the antibody, or antigen binding fragment thereof, maintains the sequences of HCDR1, HCDR2, HCDR3, LCDR1, LCDR2, and LCDR3 set forth in subpart q of embodiment 1; or (r) the heavy chain has at least 90% sequence identity to SEQ ID NO: 202 or SEQ ID NO: 203, wherein the antibody, or antigen binding fragment thereof, maintains the sequences of HCDR1, HCDR2, HCDR3, LCDR1, LCDR2, and LCDR3 set forth in subpart r of embodiment 1; or (s) the heavy chain has at least 90% sequence identity to SEQ ID NO: 204 or SEQ ID NO: 205, wherein the antibody, or antigen binding fragment thereof, maintains the sequences of HCDR1, HCDR2, HCDR3, LCDR1, LCDR2, and LCDR3 set forth in subpart s of embodiment 1; or (t) the heavy chain has at least 90% sequence identity to SEQ ID NO: 206 or SEQ ID NO: 207, wherein the antibody, or antigen binding fragment thereof, maintains the sequences of HCDR1, HCDR2, HCDR3, LCDR1, LCDR2, and LCDR3 set forth in subpart t of embodiment 1; or
(u) the heavy chain has at least 90% sequence identity to SEQ ID NO: 208 or SEQ ID NO: 209, wherein the antibody, or antigen binding fragment thereof, maintains the sequences of HCDR1, HCDR2, HCDR3, LCDR1, LCDR2, and LCDR3 set forth in subpart u of embodiment 1; or
(v) the heavy chain has at least 90% sequence identity to SEQ ID NO: 210 or SEQ ID NO: 211, wherein the antibody, or antigen binding fragment thereof, maintains the sequences of HCDR1, HCDR2, HCDR3, LCDR1, LCDR2, and LCDR3 set forth in subpart v of embodiment 1; or
(w) the heavy chain has at least 90% sequence identity to SEQ ID NO: 212 or SEQ ID NO: 213, wherein the antibody, or antigen binding fragment thereof, maintains the sequences of HCDR1, HCDR2, HCDR3, LCDR1, LCDR2, and LCDR3 set forth in subpart w of embodiment 1; or
(x) the heavy chain has at least 90% sequence identity to SEQ ID NO: 214 or SEQ ID NO: 215, wherein the antibody, or antigen binding fragment thereof, maintains the sequences of HCDR1, HCDR2, HCDR3, LCDR1, LCDR2, and LCDR3 set forth in subpart x of embodiment 1; or
(y) the heavy chain has at least 90% sequence identity to SEQ ID NO: 216 or SEQ ID NO: 217, wherein the antibody, or antigen binding fragment thereof, maintains the sequences of HCDR1, HCDR2, HCDR3, LCDR1, LCDR2, and LCDR3 set forth in subpart y of embodiment 1; or
(z) the heavy chain has at least 90% sequence identity to SEQ ID NO: 218 or SEQ ID NO: 219, wherein the antibody, or antigen binding fragment thereof, maintains the sequences of HCDR1, HCDR2, HCDR3, LCDR1, LCDR2, and LCDR3 set forth in subpart z of embodiment 1; or
(aa) the heavy chain has at least 90% sequence identity to SEQ ID NO: 220 or SEQ ID NO: 221, wherein the antibody, or antigen binding fragment thereof, maintains the sequences of HCDR1, HCDR2, HCDR3, LCDR1, LCDR2, and LCDR3 set forth in subpart ab of embodiment 1; or
(ab) the heavy chain has at least 90% sequence identity to SEQ ID NO: 222 or SEQ ID NO: 223, wherein the antibody, or antigen binding fragment thereof, maintains the sequences of HCDR1, HCDR2, HCDR3, LCDR1, LCDR2, and LCDR3 set forth in subpart ac of embodiment 1; or
(ac) the heavy chain has at least 90% sequence identity to SEQ ID NO: 224 or SEQ ID NO: 225, wherein the antibody, or antigen binding fragment thereof, maintains the sequences of HCDR1, HCDR2, HCDR3, LCDR1, LCDR2, and LCDR3 set forth in subpart ad of embodiment 1; or
(ad) the heavy chain has at least 90% sequence identity to SEQ ID NO: 226 or SEQ ID NO: 227, wherein the antibody, or antigen binding fragment thereof, maintains the sequences of HCDR1, HCDR2, HCDR3, LCDR1, LCDR2, and LCDR3 set forth in subpart ae of embodiment 1; or
(ae) the heavy chain has at least 90% sequence identity to SEQ ID NO: 364 or SEQ ID NO: 365, wherein the antibody, or antigen binding fragment thereof, maintains the sequences of HCDR1, HCDR2, HCDR3, LCDR1, LCDR2, and LCDR3 set forth in subpart a of embodiment 1; or
(af) the heavy chain has at least 90% sequence identity to SEQ ID NO: 366 or SEQ ID NO: 367, wherein the antibody, or antigen binding fragment thereof, maintains the sequences of HCDR1, HCDR2, HCDR3, LCDR1, LCDR2, and LCDR3 set forth in subpart b of embodiment 1; or
(ag) the heavy chain has at least 90% sequence identity to SEQ ID NO: 368 or SEQ ID NO: 369, wherein the antibody, or antigen binding fragment thereof, maintains the sequences of HCDR1, HCDR2, HCDR3, LCDR1, LCDR2, and LCDR3 set forth in subpart c of embodiment 1; or
(ah) the heavy chain has at least 90% sequence identity to SEQ ID NO: 370 or SEQ ID NO: 371, wherein the antibody, or antigen binding fragment thereof, maintains the sequences of HCDR1, HCDR2, HCDR3, LCDR1, LCDR2, and LCDR3 set forth in subpart d of embodiment 1; or
(ai) the heavy chain has at least 90% sequence identity to SEQ ID NO: 372 or SEQ ID NO: 373, wherein the antibody, or antigen binding fragment thereof, maintains the sequences of HCDR1, HCDR2, HCDR3, LCDR1, LCDR2, and LCDR3 set forth in subpart e of embodiment 1; or
(aj) the heavy chain has at least 90% sequence identity to SEQ ID NO: 374 or SEQ ID NO: 375, wherein the antibody, or antigen binding fragment thereof, maintains the sequences of HCDR1, HCDR2, HCDR3, LCDR1, LCDR2, and LCDR3 set forth in subpart f of embodiment 1; or
(ak) the heavy chain has at least 90% sequence identity to SEQ ID NO: 376 or SEQ ID NO: 377, wherein the antibody, or antigen binding fragment thereof, maintains the sequences of HCDR1, HCDR2, HCDR3, LCDR1, LCDR2, and LCDR3 set forth in subpart g of embodiment 1; or
(al) the heavy chain has at least 90% sequence identity to SEQ ID NO: 378 or SEQ ID NO: 379, wherein the antibody, or antigen binding fragment thereof, maintains the sequences of HCDR1, HCDR2, HCDR3, LCDR1, LCDR2, and LCDR3 set forth in subpart h of embodiment 1; or
(am) the heavy chain has at least 90% sequence identity to SEQ ID NO: 380 or SEQ ID NO: 381, wherein the antibody, or antigen binding fragment thereof, maintains the sequences of HCDR1, HCDR2, HCDR3, LCDR1, LCDR2, and LCDR3 set forth in subpart i of embodiment 1; or
(an) the heavy chain has at least 90% sequence identity to SEQ ID NO: 382 or SEQ ID NO: 383, wherein the antibody, or antigen binding fragment thereof, maintains the sequences of HCDR1, HCDR2, HCDR3, LCDR1, LCDR2, and LCDR3 set forth in subpart j of embodiment 1; or
(ao) the heavy chain has at least 90% sequence identity to SEQ ID NO: 384 or SEQ ID NO: 385, wherein the antibody, or antigen binding fragment thereof, maintains the sequences of HCDR1, HCDR2, HCDR3, LCDR1, LCDR2, and LCDR3 set forth in subpart k of embodiment 1; or
(ap) the heavy chain has at least 90% sequence identity to SEQ ID NO: 386 or SEQ ID NO: 387, wherein the antibody, or antigen binding fragment thereof, maintains the sequences of HCDR1, HCDR2, HCDR3, LCDR1, LCDR2, and LCDR3 set forth in subpart l of embodiment 1; or
(aq) the heavy chain has at least 90% sequence identity to SEQ ID NO: 388 or SEQ ID NO: 389, wherein the antibody, or antigen binding fragment thereof, maintains the sequences of HCDR1, HCDR2, HCDR3, LCDR1, LCDR2, and LCDR3 set forth in subpart m of embodiment 1; or
(ar) the heavy chain has at least 90% sequence identity to SEQ ID NO: 390 or SEQ ID NO: 391, wherein the antibody, or antigen binding fragment thereof, maintains the sequences of HCDR1, HCDR2, HCDR3, LCDR1, LCDR2, and LCDR3 set forth in subpart n of embodiment 1; or
(as) the heavy chain has at least 90% sequence identity to SEQ ID NO: 392 or SEQ ID NO: 393, wherein the antibody, or antigen binding fragment thereof, maintains the sequences of HCDR1, HCDR2, HCDR3, LCDR1, LCDR2, and LCDR3 set forth in subpart o of embodiment 1; or
(at) the heavy chain has at least 90% sequence identity to SEQ ID NO: 394 or SEQ ID NO: 395, wherein the antibody, or antigen binding fragment thereof, maintains the sequences of HCDR1, HCDR2, HCDR3, LCDR1, LCDR2, and LCDR3 set forth in subpart p of embodiment
(au) the heavy chain has at least 90% sequence identity to SEQ ID NO: 396 or SEQ ID NO: 397, wherein the antibody, or antigen binding fragment thereof, maintains the sequences of HCDR1, HCDR2, HCDR3, LCDR1, LCDR2, and LCDR3 set forth in subpart q of embodiment 1; or
(av) the heavy chain has at least 90% sequence identity to SEQ ID NO: 398 or SEQ ID NO: 399, wherein the antibody, or antigen binding fragment thereof, maintains the sequences of HCDR1, HCDR2, HCDR3, LCDR1, LCDR2, and LCDR3 set forth in subpart r of embodiment 1; or
(aw) the heavy chain has at least 90% sequence identity to SEQ ID NO: 400 or SEQ ID NO: 401, wherein the antibody, or antigen binding fragment thereof, maintains the sequences of HCDR1, HCDR2, HCDR3, LCDR1, LCDR2, and LCDR3 set forth in subpart s of embodiment 1; or
(ax) the heavy chain has at least 90% sequence identity to SEQ ID NO: 402 or SEQ ID NO: 403, wherein the antibody, or antigen binding fragment thereof, maintains the sequences of HCDR1, HCDR2, HCDR3, LCDR1, LCDR2, and LCDR3 set forth in subpart t of embodiment 1; or
(ay) the heavy chain has at least 90% sequence identity to SEQ ID NO: 404 or SEQ ID NO: 405, wherein the antibody, or antigen binding fragment thereof, maintains the sequences of HCDR1, HCDR2, HCDR3, LCDR1, LCDR2, and LCDR3 set forth in subpart u of embodiment 1; or
(az) the heavy chain has at least 90% sequence identity to SEQ ID NO: 406 or SEQ ID NO: 407, wherein the antibody, or antigen binding fragment thereof, maintains the sequences of HCDR1, HCDR2, HCDR3, LCDR1, LCDR2, and LCDR3 set forth in subpart v of embodiment 1; or
(ba) the heavy chain has at least 90% sequence identity to SEQ ID NO: 408 or SEQ ID NO: 409, wherein the antibody, or antigen binding fragment thereof, maintains the sequences of HCDR1, HCDR2, HCDR3, LCDR1, LCDR2, and LCDR3 set forth in subpart w of embodiment 1; or
(bb) the heavy chain has at least 90% sequence identity to SEQ ID NO: 410 or SEQ ID NO: 411, wherein the antibody, or antigen binding fragment thereof, maintains the sequences of HCDR1, HCDR2, HCDR3, LCDR1, LCDR2, and LCDR3 set forth in subpart x of embodiment 1; or
(be) the heavy chain has at least 90% sequence identity to SEQ ID NO: 412 or SEQ ID NO: 413, wherein the antibody, or antigen binding fragment thereof, maintains the sequences of HCDR1, HCDR2, HCDR3, LCDR1, LCDR2, and LCDR3 set forth in subpart y of embodiment 1; or
(bd) the heavy chain has at least 90% sequence identity to SEQ ID NO: 414 or SEQ ID NO: 415, wherein the antibody, or antigen binding fragment thereof, maintains the sequences of HCDR1, HCDR2, HCDR3, LCDR1, LCDR2, and LCDR3 set forth in subpart z of embodiment 1; or
(be) the heavy chain has at least 90% sequence identity to SEQ ID NO: 416 or SEQ ID NO: 417, wherein the antibody, or antigen binding fragment thereof, maintains the sequences of HCDR1, HCDR2, HCDR3, LCDR1, LCDR2, and LCDR3 set forth in subpart ab of embodiment 1; or
(bf) the heavy chain has at least 90% sequence identity to SEQ ID NO: 418 or SEQ ID NO: 419, wherein the antibody, or antigen binding fragment thereof, maintains the sequences of HCDR1, HCDR2, HCDR3, LCDR1, LCDR2, and LCDR3 set forth in subpart ac of embodiment 1; or
(bg) the heavy chain has at least 90% sequence identity to SEQ ID NO: 420 or SEQ ID NO: 421, wherein the antibody, or antigen binding fragment thereof, maintains the sequences of HCDR1, HCDR2, HCDR3, LCDR1, LCDR2, and LCDR3 set forth in subpart ad of embodiment 1; or
(bh) the heavy chain has at least 90% sequence identity to SEQ ID NO: 422 or SEQ ID NO: 423, wherein the antibody, or antigen binding fragment thereof, maintains the sequences of HCDR1, HCDR2, HCDR3, LCDR1, LCDR2, and LCDR3 set forth in subpart ae of embodiment 1.

7. The antibody or antigen-binding fragment thereof of any one of embodiments 1-6,
wherein the light chain comprises:
(a) the light chain has at least 90% sequence identity to SEQ ID NO: 228, wherein the antibody, or antigen binding fragment thereof, maintains the sequences of HCDR1, HCDR2, HCDR3, LCDR1, LCDR2, and LCDR3 set forth in subpart a of embodiment 1; or
(b) the light chain has least 90% sequence identity to SEQ ID NO: 229, wherein the antibody, or antigen binding fragment thereof, maintains the sequences of HCDR1, HCDR2, HCDR3, LCDR1, LCDR2, and LCDR3 set forth in subpart b of embodiment 1; or
(c) the light chain has at least 90% sequence identity to SEQ ID NO: 230, wherein the antibody, or antigen binding fragment thereof, maintains the sequences of HCDR1, HCDR2, HCDR3, LCDR1, LCDR2, and LCDR3 set forth in subpart c of embodiment 1; or
(d) the light chain has at least 90% sequence identity to SEQ ID NO: 231, wherein the antibody, or antigen binding fragment thereof, maintains the sequences of HCDR1, HCDR2, HCDR3, LCDR1, LCDR2, and LCDR3 set forth in subpart d of embodiment 1; or
(e) the light chain has at least 90% sequence identity to SEQ ID NO: 232, wherein the antibody, or antigen binding fragment thereof, maintains the sequences of HCDR1, HCDR2, HCDR3, LCDR1, LCDR2, and LCDR3 set forth in subpart e of embodiment 1; or
(f) the light chain has at least 90% sequence identity to SEQ ID NO: 233, wherein the antibody, or antigen binding fragment thereof, maintains the sequences of HCDR1, HCDR2, HCDR3, LCDR1, LCDR2, and LCDR3 set forth in subpart f of embodiment 1; or
(g) the light chain has at least 90% sequence identity to SEQ ID NO: 234, wherein the antibody, or antigen binding fragment thereof, maintains the sequences of HCDR1, HCDR2, HCDR3, LCDR1, LCDR2, and LCDR3 set forth in subpart g of embodiment 1; or
(h) the light chain has at least 90% sequence identity to SEQ ID NO: 235, wherein the antibody, or antigen binding fragment thereof, maintains the sequences of HCDR1, HCDR2, HCDR3, LCDR1, LCDR2, and LCDR3 set forth in subpart h of embodiment 1; or
(i) the light chain has at least 90% sequence identity to SEQ ID NO: 236, wherein the antibody, or antigen binding fragment thereof, maintains the sequences of HCDR1, HCDR2, HCDR3, LCDR1, LCDR2, and LCDR3 set forth in subpart i of embodiment 1; or
(j) the light chain has at least 90% sequence identity to SEQ ID NO: 237, wherein the antibody, or antigen binding fragment thereof, maintains the sequences of HCDR1, HCDR2, HCDR3, LCDR1, LCDR2, and LCDR3 set forth in subpart j of embodiment 1; or
(k) the light chain has at least 90% sequence identity to SEQ ID NO: 238, wherein the antibody, or antigen binding fragment thereof, maintains the sequences of HCDR1, HCDR2, HCDR3, LCDR1, LCDR2, and LCDR3 set forth in subpart k of embodiment 1; or
(l) the light chain has at least 90% sequence identity to SEQ ID NO: 239, wherein the antibody, or antigen binding fragment thereof, maintains the sequences of HCDR1, HCDR2, HCDR3, LCDR1, LCDR2, and LCDR3 set forth in subpart l of embodiment 1; or
(m) the light chain has at least 90% sequence identity to SEQ ID NO: 240, wherein the antibody, or antigen binding fragment thereof, maintains the sequences of HCDR1, HCDR2, HCDR3, LCDR1, LCDR2, and LCDR3 set forth in subpart m of embodiment 1; or
(n) the light chain has at least 90% sequence identity to SEQ ID NO: 241, wherein the antibody, or antigen binding fragment thereof, maintains the sequences of HCDR1, HCDR2, HCDR3, LCDR1, LCDR2, and LCDR3 set forth in subpart n of embodiment 1; or
(o) the light chain has at least 90% sequence identity to SEQ ID NO: 242, wherein the antibody, or antigen binding fragment thereof, maintains the sequences of HCDR1, HCDR2, HCDR3, LCDR1, LCDR2, and LCDR3 set forth in subpart o of embodiment 1; or
(p) the light chain has at least 90% sequence identity to SEQ ID NO: 243, wherein the antibody, or antigen binding fragment thereof, maintains the sequences of HCDR1, HCDR2, HCDR3, LCDR1, LCDR2, and LCDR3 set forth in subpart p of embodiment 1; or
(q) the light chain has at least 90% sequence identity to SEQ ID NO: 244, wherein the antibody, or antigen binding fragment thereof, maintains the sequences of HCDR1, HCDR2, HCDR3, LCDR1, LCDR2, and LCDR3 set forth in subpart q of embodiment 1; or
(r) the light chain has at least 90% sequence identity to SEQ ID NO: 245, wherein the antibody, or antigen binding fragment thereof, maintains the sequences of HCDR1, HCDR2, HCDR3, LCDR1, LCDR2, and LCDR3 set forth in subpart r of embodiment 1; or
(s) the light chain has at least 90% sequence identity to SEQ ID NO: 246, wherein the antibody, or antigen binding fragment thereof, maintains the sequences of HCDR1, HCDR2, HCDR3, LCDR1, LCDR2, and LCDR3 set forth in subpart s of embodiment 1; or
(t) the light chain has at least 90% sequence identity to SEQ ID NO: 247, wherein the antibody, or antigen binding fragment thereof, maintains the sequences of HCDR1, HCDR2, HCDR3, LCDR1, LCDR2, and LCDR3 set forth in subpart t of embodiment 1; or
(u) the light chain has at least 90% sequence identity to SEQ ID NO: 248, wherein the antibody, or antigen binding fragment thereof, maintains the sequences of HCDR1, HCDR2, HCDR3, LCDR1, LCDR2, and LCDR3 set forth in subpart u of embodiment 1; or
(v) the light chain has at least 90% sequence identity to SEQ ID NO: 249, wherein the antibody, or antigen binding fragment thereof, maintains the sequences of HCDR1, HCDR2, HCDR3, LCDR1, LCDR2, and LCDR3 set forth in subpart v of embodiment 1; or
(w) the light chain has at least 90% sequence identity to SEQ ID NO: 250, wherein the antibody, or antigen binding fragment thereof, maintains the sequences of HCDR1, HCDR2, HCDR3, LCDR1, LCDR2, and LCDR3 set forth in subpart w of embodiment 1; or
(x) the light chain has at least 90% sequence identity to SEQ ID NO: 251, wherein the antibody, or antigen binding fragment thereof, maintains the sequences of HCDR1, HCDR2, HCDR3, LCDR1, LCDR2, and LCDR3 set forth in subpart x of embodiment 1; or
(y) the light chain has at least 90% sequence identity to SEQ ID NO: 252, wherein the antibody, or antigen binding fragment thereof, maintains the sequences of HCDR1, HCDR2, HCDR3, LCDR1, LCDR2, and LCDR3 set forth in subpart y of embodiment 1; or
(z) the light chain has at least 90% sequence identity to SEQ ID NO: 253, wherein the antibody, or antigen binding fragment thereof, maintains the sequences of HCDR1, HCDR2, HCDR3, LCDR1, LCDR2, and LCDR3 set forth in subpart z of embodiment 1; or
(aa) the light chain has at least 90% sequence identity to SEQ ID NO: 254, wherein the antibody, or antigen binding fragment thereof, maintains the sequences of HCDR1, HCDR2, HCDR3, LCDR1, LCDR2, and LCDR3 set forth in subpart ab of embodiment 1; or
(ab) the light chain has at least 90% sequence identity to SEQ ID NO: 255, wherein the antibody, or antigen binding fragment thereof, maintains the sequences of HCDR1, HCDR2, HCDR3, LCDR1, LCDR2, and LCDR3 set forth in subpart ac of embodiment 1; or
(ac) the light chain has at least 90% sequence identity to SEQ ID NO: 256, wherein the antibody, or antigen binding fragment thereof, maintains the sequences of HCDR1, HCDR2, HCDR3, LCDR1, LCDR2, and LCDR3 set forth in subpart ad of embodiment 1; or
(ad) the light chain has at least 90% sequence identity to SEQ ID NO: 257, wherein the antibody, or antigen binding fragment thereof, maintains the sequences of HCDR1, HCDR2, HCDR3, LCDR1, LCDR2, and LCDR3 set forth in subpart ae of embodiment 1.

8. The antibody, or antigen-binding fragment thereof, of any one of embodiments 1-7, wherein:
- (a) the light chain has at least 90% sequence identity to SEQ ID NO: 228, and the heavy chain has at least 90% sequence identity to SEQ ID NO: 168 or SEQ ID NO: 169, wherein the antibody, or antigen binding fragment thereof, maintains the sequences of HCDR1, HCDR2, HCDR3, LCDR1, LCDR2, and LCDR3 set forth in subpart a of embodiment 1; or
- (b) the light chain has at least 90% sequence identity to SEQ ID NO: 229, and the heavy chain has at least 90% sequence identity to SEQ ID NO: 170 or SEQ ID NO: 171, wherein the antibody, or antigen binding fragment thereof, maintains the sequences of HCDR1, HCDR2, HCDR3, LCDR1, LCDR2, and LCDR3 set forth in subpart b of embodiment 1; or
- (c) the light chain has at least 90% sequence identity to SEQ ID NO: 230, and the heavy chain has at least 90% sequence identity to SEQ ID NO: 172 or SEQ ID NO: 173, wherein the antibody, or antigen binding fragment thereof, maintains the sequences of HCDR1, HCDR2, HCDR3, LCDR1, LCDR2, and LCDR3 set forth in subpart c of embodiment 1; or
- (d) the light chain has at least 90% sequence identity to SEQ ID NO: 231, and the heavy chain has at least 90% sequence identity to SEQ ID NO: 174 or SEQ ID NO: 175, wherein the antibody, or antigen binding fragment thereof, maintains the sequences of HCDR1, HCDR2, HCDR3, LCDR1, LCDR2, and LCDR3 set forth in subpart d of embodiment 1; or
- (e) the light chain has at least 90% sequence identity to SEQ ID NO: 232, and the heavy chain has at least 90% sequence identity to SEQ ID NO: 176 or SEQ ID NO: 177, wherein the antibody, or antigen binding fragment thereof, maintains the sequences of HCDR1, HCDR2, HCDR3, LCDR1, LCDR2, and LCDR3 set forth in subpart e of embodiment 1; or
- (f) the light chain has at least 90% sequence identity to SEQ ID NO: 233, and the heavy chain has at least 90% sequence identity to SEQ ID NO: 178 or SEQ ID NO: 179, wherein the antibody, or antigen binding fragment thereof, maintains the sequences of HCDR1, HCDR2, HCDR3, LCDR1, LCDR2, and LCDR3 set forth in subpart f of embodiment 1; or
- (g) the light chain has at least 90% sequence identity to SEQ ID NO: 234, and the heavy chain has at least 90% sequence identity to SEQ ID NO: 180 or SEQ ID NO: 181, wherein the antibody, or antigen binding fragment thereof, maintains the sequences of HCDR1, HCDR2, HCDR3, LCDR1, LCDR2, and LCDR3 set forth in subpart g of embodiment 1; or
- (h) the light chain has at least 90% sequence identity to SEQ ID NO: 235, and the heavy chain has at least 90% sequence identity to SEQ ID NO: 182 or SEQ ID NO: 183, wherein the antibody, or antigen binding fragment thereof, maintains the sequences of HCDR1, HCDR2, HCDR3, LCDR1, LCDR2, and LCDR3 set forth in subpart h of embodiment 1; or
- (i) the light chain has at least 90% sequence identity to SEQ ID NO: 236, and the heavy chain has at least 90% sequence identity to SEQ ID NO: 184 or SEQ ID NO: 185, wherein the antibody, or antigen binding fragment thereof, maintains the sequences of HCDR1, HCDR2, HCDR3, LCDR1, LCDR2, and LCDR3 set forth in subpart i of embodiment 1; or
- (j) the light chain has at least 90% sequence identity to SEQ ID NO: 237, and the heavy chain has at least 90% sequence identity to SEQ ID NO: 186 or SEQ ID NO: 187, wherein the antibody, or antigen binding fragment thereof, maintains the sequences of HCDR1, HCDR2, HCDR3, LCDR1, LCDR2, and LCDR3 set forth in subpart j of embodiment 1; or
- (k) the light chain has at least 90% sequence identity to SEQ ID NO: 238, and the heavy chain has at least 90% sequence identity to SEQ ID NO: 188 or SEQ ID NO: 189, wherein the antibody, or antigen binding fragment thereof, maintains the sequences of HCDR1, HCDR2, HCDR3, LCDR1, LCDR2, and LCDR3 set forth in subpart k of embodiment 1; or
- (l) the light chain has at least 90% sequence identity to SEQ ID NO: 239, and the heavy chain has at least 90% sequence identity to SEQ ID NO: 190 or SEQ ID NO: 191, wherein the antibody, or antigen binding fragment thereof, maintains the sequences of HCDR1, HCDR2, HCDR3, LCDR1, LCDR2, and LCDR3 set forth in subpart l of embodiment 1; or
- (m) the light chain has at least 90% sequence identity to SEQ ID NO: 240, and the heavy chain has at least 90% sequence identity to SEQ ID NO: 192 or SEQ ID NO: 193, wherein the antibody, or antigen binding fragment thereof, maintains the sequences of HCDR1, HCDR2, HCDR3, LCDR1, LCDR2, and LCDR3 set forth in subpart m of embodiment 1; or
- (n) the light chain has at least 90% sequence identity to SEQ ID NO: 241, and the heavy chain has at least 90% sequence identity to SEQ ID NO: 194 or SEQ ID NO: 195, wherein the antibody, or antigen binding fragment thereof, maintains the sequences of HCDR1, HCDR2, HCDR3, LCDR1, LCDR2, and LCDR3 set forth in subpart n of embodiment 1; or
- (o) the light chain has at least 90% sequence identity to SEQ ID NO: 242, and the heavy chain has at least 90% sequence identity to SEQ ID NO: 196 or SEQ ID NO: 197, wherein the antibody, or antigen binding fragment thereof, maintains the sequences of HCDR1, HCDR2, HCDR3, LCDR1, LCDR2, and LCDR3 set forth in subpart o of embodiment 1; or
- (p) the light chain has at least 90% sequence identity to SEQ ID NO: 243, and the heavy chain has at least 90% sequence identity to SEQ ID NO: 198 or SEQ ID NO: 199, wherein the antibody, or antigen binding fragment thereof, maintains the sequences of HCDR1, HCDR2, HCDR3, LCDR1, LCDR2, and LCDR3 set forth in subpart p of embodiment 1; or
- (q) the light chain has at least 90% sequence identity to SEQ ID NO: 244, and the heavy chain has at least 90% sequence identity to SEQ ID NO: 200 or SEQ ID NO: 201, wherein the antibody, or antigen binding fragment thereof, maintains the sequences of HCDR1, HCDR2, HCDR3, LCDR1, LCDR2, and LCDR3 set forth in subpart q of embodiment 1; or
- (r) the light chain has at least 90% sequence identity to SEQ ID NO: 245, and the heavy chain has at least 90% sequence identity to SEQ ID NO: 202 or SEQ ID NO: 203, wherein the antibody, or antigen binding fragment thereof, maintains the sequences of HCDR1, HCDR2, HCDR3, LCDR1, LCDR2, and LCDR3 set forth in subpart r of embodiment 1; or
- (s) the light chain has at least 90% sequence identity to SEQ ID NO: 246, and the heavy chain has at least 90% sequence identity to SEQ ID NO: 204 or SEQ ID NO: 205, wherein the antibody, or antigen binding fragment thereof, maintains the sequences of HCDR1, HCDR2, HCDR3, LCDR1, LCDR2, and LCDR3 set forth in subpart s of embodiment 1; or
(t) the light chain has at least 90% sequence identity to SEQ ID NO: 247, and the heavy chain has at least 90% sequence identity to SEQ ID NO: 206 or SEQ ID NO: 207, wherein the antibody, or antigen binding fragment thereof, maintains the sequences of HCDR1, HCDR2, HCDR3, LCDR1, LCDR2, and LCDR3 set forth in subpart t of embodiment 1; or
(u) the light chain has at least 90% sequence identity to SEQ ID NO: 248, and the heavy chain has at least 90% sequence identity to SEQ ID NO: 208 or SEQ ID NO: 209, wherein the antibody, or antigen binding fragment thereof, maintains the sequences of HCDR1, HCDR2, HCDR3, LCDR1, LCDR2, and LCDR3 set forth in subpart u of embodiment 1; or
(v) the light chain has at least 90% sequence identity to SEQ ID NO: 249, and the heavy chain has at least 90% sequence identity to SEQ ID NO: 210 or SEQ ID NO: 211, wherein the antibody, or antigen binding fragment thereof, maintains the sequences of HCDR1, HCDR2, HCDR3, LCDR1, LCDR2, and LCDR3 set forth in subpart v of embodiment 1; or
(w) the light chain has at least 90% sequence identity to SEQ ID NO: 250, and the heavy chain has at least 90% sequence identity to SEQ ID NO: 212 or SEQ ID NO: 213, wherein the antibody, or antigen binding fragment thereof, maintains the sequences of HCDR1, HCDR2, HCDR3, LCDR1, LCDR2, and LCDR3 set forth in subpart w of embodiment 1; or
(x) the light chain has at least 90% sequence identity to SEQ ID NO: 251, and the heavy chain has at least 90% sequence identity to SEQ ID NO: 214 or SEQ ID NO: 215, wherein the antibody, or antigen binding fragment thereof, maintains the sequences of HCDR1, HCDR2, HCDR3, LCDR1, LCDR2, and LCDR3 set forth in subpart x of embodiment 1; or
(y) the light chain has at least 90% sequence identity to SEQ ID NO: 252, and the heavy chain has at least 90% sequence identity to SEQ ID NO: 216 or SEQ ID NO: 217, wherein the antibody, or antigen binding fragment thereof, maintains the sequences of HCDR1, HCDR2, HCDR3, LCDR1, LCDR2, and LCDR3 set forth in subpart y of embodiment 1; or
(z) the light chain has at least 90% sequence identity to SEQ ID NO: 253, and the heavy chain has at least 90% sequence identity to SEQ ID NO: 218 or SEQ ID NO: 219, wherein the antibody, or antigen binding fragment thereof, maintains the sequences of HCDR1, HCDR2, HCDR3, LCDR1, LCDR2, and LCDR3 set forth in subpart z of embodiment 1; or
(aa) the light chain has at least 90% sequence identity to SEQ ID NO: 254, and the heavy chain has at least 90% sequence identity to SEQ ID NO: 220 or SEQ ID NO: 221, wherein the antibody, or antigen binding fragment thereof, maintains the sequences of HCDR1, HCDR2, HCDR3, LCDR1, LCDR2, and LCDR3 set forth in subpart aa of embodiment 1; or
(ab) the light chain has at least 90% sequence identity to SEQ ID NO: 255, and the heavy chain has at least 90% sequence identity to SEQ ID NO: 222 or SEQ ID NO: 223, wherein the antibody, or antigen binding fragment thereof, maintains the sequences of HCDR1, HCDR2, HCDR3, LCDR1, LCDR2, and LCDR3 set forth in subpart ab of embodiment 1; or
(ac) the light chain has at least 90% sequence identity to SEQ ID NO: 256, and the heavy chain has at least 90% sequence identity to SEQ ID NO: 224 or SEQ ID NO: 225, wherein the antibody, or antigen binding fragment thereof, maintains the sequences of HCDR1, HCDR2, HCDR3, LCDR1, LCDR2, and LCDR3 set forth in subpart ac of embodiment 1; or
(ad) the light chain has at least 90% sequence identity to SEQ ID NO: 257, and the heavy chain has at least 90% sequence identity to SEQ ID NO: 226 or SEQ ID NO: 227, wherein the antibody, or antigen binding fragment thereof, maintains the sequences of HCDR1, HCDR2, HCDR3, LCDR1, LCDR2, and LCDR3 set forth in subpart ad of embodiment 1; or
(ae) the light chain has at least 90% sequence identity to SEQ ID NO: 228, and the heavy chain has at least 90% sequence identity to SEQ ID NO: 364 or SEQ ID NO: 365, wherein the antibody, or antigen binding fragment thereof, maintains the sequences of HCDR1, HCDR2, HCDR3, LCDR1, LCDR2, and LCDR3 set forth in subpart a of embodiment 1; or
(af) the light chain has at least 90% sequence identity to SEQ ID NO: 229, and the heavy chain has at least 90% sequence identity to SEQ ID NO: 366 or SEQ ID NO: 367, wherein the antibody, or antigen binding fragment thereof, maintains the sequences of HCDR1, HCDR2, HCDR3, LCDR1, LCDR2, and LCDR3 set forth in subpart b of embodiment 1; or
(ag) the light chain has at least 90% sequence identity to SEQ ID NO: 230, and the heavy chain has at least 90% sequence identity to SEQ ID NO: 368 or SEQ ID NO: 369, wherein the antibody, or antigen binding fragment thereof, maintains the sequences of HCDR1, HCDR2, HCDR3, LCDR1, LCDR2, and LCDR3 set forth in subpart c of embodiment 1; or
(ah) the light chain has at least 90% sequence identity to SEQ ID NO: 231, and the heavy chain has at least 90% sequence identity to SEQ ID NO: 370 or SEQ ID NO: 371, wherein the antibody, or antigen binding fragment thereof, maintains the sequences of HCDR1, HCDR2, HCDR3, LCDR1, LCDR2, and LCDR3 set forth in subpart d of embodiment 1; or
(ai) the light chain has at least 90% sequence identity to SEQ ID NO: 232, and the heavy chain has at least 90% sequence identity to SEQ ID NO: 372 or SEQ ID NO: 373, wherein the antibody, or antigen binding fragment thereof, maintains the sequences of HCDR1, HCDR2, HCDR3, LCDR1, LCDR2, and LCDR3 set forth in subpart e of embodiment 1; or
(aj) the light chain has at least 90% sequence identity to SEQ ID NO: 233, and the heavy chain has at least 90% sequence identity to SEQ ID NO: 374 or SEQ ID NO: 375, wherein the antibody, or antigen binding fragment thereof, maintains the sequences of HCDR1, HCDR2, HCDR3, LCDR1, LCDR2, and LCDR3 set forth in subpart f of embodiment 1; or
(ak) the light chain has at least 90% sequence identity to SEQ ID NO: 234, and the heavy chain has at least 90% sequence identity to SEQ ID NO: 376 or SEQ ID NO: 377, wherein the antibody, or antigen binding fragment thereof, maintains the sequences of HCDR1, HCDR2, HCDR3, LCDR1, LCDR2, and LCDR3 set forth in subpart g of embodiment 1; or
(al) the light chain has at least 90% sequence identity to SEQ ID NO: 235, and the heavy chain has at least 90% sequence identity to SEQ ID NO: 378 or SEQ ID NO: 379, wherein the antibody, or antigen binding fragment thereof, maintains the sequences of HCDR1, HCDR2, HCDR3, LCDR1, LCDR2, and LCDR3 set forth in subpart h of embodiment 1; or
(am) the light chain has at least 90% sequence identity to SEQ ID NO: 236, and the heavy chain has at least 90% sequence identity to SEQ ID NO: 380 or SEQ ID NO: 381, wherein the antibody, or antigen binding fragment thereof, maintains the sequences of HCDR1, HCDR2, HCDR3, LCDR1, LCDR2, and LCDR3 set forth in subpart i of embodiment 1; or
(an) the light chain has at least 90% sequence identity to SEQ ID NO: 237, and the heavy chain has at least 90% sequence identity to SEQ ID NO: 382 or SEQ ID NO: 383, wherein the antibody, or antigen binding fragment thereof, maintains the sequences of HCDR1, HCDR2, HCDR3, LCDR1, LCDR2, and LCDR3 set forth in subpart j of embodiment 1; or
(ao) the light chain has at least 90% sequence identity to SEQ ID NO: 238, and the heavy chain has at least 90% sequence identity to SEQ ID NO: 384 or SEQ ID NO: 385, wherein the antibody, or antigen binding fragment thereof, maintains the sequences of HCDR1, HCDR2, HCDR3, LCDR1, LCDR2, and LCDR3 set forth in subpart k of embodiment 1; or
(ap) the light chain has at least 90% sequence identity to SEQ ID NO: 239, and the heavy chain has at least 90% sequence identity to SEQ ID NO: 386 or SEQ ID NO: 387, wherein the antibody, or antigen binding fragment thereof, maintains the sequences of HCDR1, HCDR2, HCDR3, LCDR1, LCDR2, and LCDR3 set forth in subpart l of embodiment 1; or
(aq) the light chain has at least 90% sequence identity to SEQ ID NO: 240, and the heavy chain has at least 90% sequence identity to SEQ ID NO: 388 or SEQ ID NO: 389, wherein the antibody, or antigen binding fragment thereof, maintains the sequences of HCDR1, HCDR2, HCDR3, LCDR1, LCDR2, and LCDR3 set forth in subpart m of embodiment 1; or
(ar) the light chain has at least 90% sequence identity to SEQ ID NO: 241, and the heavy chain has at least 90% sequence identity to SEQ ID NO: 390 or SEQ ID NO: 391, wherein the antibody, or antigen binding fragment thereof, maintains the sequences of HCDR1, HCDR2, HCDR3, LCDR1, LCDR2, and LCDR3 set forth in subpart n of embodiment 1; or
(as) the light chain has at least 90% sequence identity to SEQ ID NO: 242, and the heavy chain has at least 90% sequence identity to SEQ ID NO: 392 or SEQ ID NO: 393, wherein the antibody, or antigen binding fragment thereof, maintains the sequences of HCDR1, HCDR2, HCDR3, LCDR1, LCDR2, and LCDR3 set forth in subpart o of embodiment 1; or
(at) the light chain has at least 90% sequence identity to SEQ ID NO: 243, and the heavy chain has at least 90% sequence identity to SEQ ID NO: 394 or SEQ ID NO: 395, wherein the antibody, or antigen binding fragment thereof, maintains the sequences of HCDR1, HCDR2, HCDR3, LCDR1, LCDR2, and LCDR3 set forth in subpart p of embodiment 1; or
(au) the light chain has at least 90% sequence identity to SEQ ID NO: 244, and the heavy chain has at least 90% sequence identity to SEQ ID NO: 396 or SEQ ID NO: 397, wherein the antibody, or antigen binding fragment thereof, maintains the sequences of HCDR1, HCDR2, HCDR3, LCDR1, LCDR2, and LCDR3 set forth in subpart q of embodiment 1; or
(av) the light chain has at least 90% sequence identity to SEQ ID NO: 245, and the heavy chain has at least 90% sequence identity to SEQ ID NO: 398 or SEQ ID NO: 399, wherein the antibody, or antigen binding fragment thereof, maintains the sequences of HCDR1, HCDR2, HCDR3, LCDR1, LCDR2, and LCDR3 set forth in subpart r of embodiment 1; or
(aw) the light chain has at least 90% sequence identity to SEQ ID NO: 246, and the heavy chain has at least 90% sequence identity to SEQ ID NO: 400 or SEQ ID NO: 401, wherein the antibody, or antigen binding fragment thereof, maintains the sequences of HCDR1, HCDR2, HCDR3, LCDR1, LCDR2, and LCDR3 set forth in subpart s of embodiment 1; or
(ax) the light chain has at least 90% sequence identity to SEQ ID NO: 247, and the heavy chain has at least 90% sequence identity to SEQ ID NO: 402 or SEQ ID NO: 403, wherein the antibody, or antigen binding fragment thereof, maintains the sequences of HCDR1, HCDR2, HCDR3, LCDR1, LCDR2, and LCDR3 set forth in subpart t of embodiment 1; or
(ay) the light chain has at least 90% sequence identity to SEQ ID NO: 248, and the heavy chain has at least 90% sequence identity to SEQ ID NO: 404 or SEQ ID NO: 405, wherein the antibody, or antigen binding fragment thereof, maintains the sequences of HCDR1, HCDR2, HCDR3, LCDR1, LCDR2, and LCDR3 set forth in subpart u of embodiment 1; or
(az) the light chain has at least 90% sequence identity to SEQ ID NO: 249, and the heavy chain has at least 90% sequence identity to SEQ ID NO: 406 or SEQ ID NO: 407, wherein the antibody, or antigen binding fragment thereof, maintains the sequences of HCDR1, HCDR2, HCDR3, LCDR1, LCDR2, and LCDR3 set forth in subpart v of embodiment 1; or
(ba) the light chain has at least 90% sequence identity to SEQ ID NO: 250, and the heavy chain has at least 90% sequence identity to SEQ ID NO: 408 or SEQ ID NO: 409, wherein the antibody, or antigen binding fragment thereof, maintains the sequences of HCDR1, HCDR2, HCDR3, LCDR1, LCDR2, and LCDR3 set forth in subpart w of embodiment 1; or
(bb) the light chain has at least 90% sequence identity to SEQ ID NO: 251, and the heavy chain has at least 90% sequence identity to SEQ ID NO: 410 or SEQ ID NO: 411, wherein the antibody, or antigen binding fragment thereof, maintains the sequences of HCDR1, HCDR2, HCDR3, LCDR1, LCDR2, and LCDR3 set forth in subpart x of embodiment 1; or
(bc) the light chain has at least 90% sequence identity to SEQ ID NO: 252, and the heavy chain has at least 90% sequence identity to SEQ ID NO: 412 or SEQ ID NO: 413, wherein the antibody, or antigen binding fragment thereof, maintains the sequences of HCDR1, HCDR2, HCDR3, LCDR1, LCDR2, and LCDR3 set forth in subpart y of embodiment 1; or
(bd) the light chain has at least 90% sequence identity to SEQ ID NO: 253, and the heavy chain has at least 90% sequence identity to SEQ ID NO: 414 or SEQ ID NO: 415, wherein the antibody, or antigen binding fragment thereof, maintains the sequences of HCDR1, HCDR2, HCDR3, LCDR1, LCDR2, and LCDR3 set forth in subpart z of embodiment 1; or
(be) the light chain has at least 90% sequence identity to SEQ ID NO: 254, and the heavy chain has at least 90% sequence identity to SEQ ID NO: 416 or SEQ ID NO: 417, wherein the antibody, or antigen binding fragment thereof, maintains the sequences of HCDR1, HCDR2, HCDR3, LCDR1, LCDR2, and LCDR3 set forth in subpart ab of embodiment 1; or
(bf) the light chain has at least 90% sequence identity to SEQ ID NO: 255, and the heavy chain has at least 90% sequence identity to SEQ ID NO: 418 or SEQ ID NO: 419, wherein the antibody, or antigen binding fragment thereof, maintains the sequences of HCDR1, HCDR2, HCDR3, LCDR1, LCDR2, and LCDR3 set forth in subpart ac of embodiment 1; or
(bg) the light chain has at least 90% sequence identity to SEQ ID NO: 256, and the heavy chain has at least 90% sequence identity to SEQ ID NO: 420 or SEQ ID NO: 421, wherein the antibody, or antigen binding fragment thereof, maintains the sequences of HCDR1, HCDR2, HCDR3, LCDR1, LCDR2, and LCDR3 set forth in subpart ad of embodiment 1; or
(bh) the light chain has at least 90% sequence identity to SEQ ID NO: 257, and the heavy chain has at least 90% sequence identity to SEQ ID NO: 422 or SEQ ID NO: 423, wherein the antibody, or antigen binding fragment thereof, maintains the sequences of HCDR1, HCDR2, HCDR3, LCDR1, LCDR2, and LCDR3 set forth in subpart ae of embodiment 1.

9. The antibody, or antigen-binding fragment thereof, of embodiment 8, wherein:
(a) the light chain comprises SEQ ID NO: 228, and the heavy chain comprises SEQ ID NO: 168 or SEQ ID NO: 169; or
(b) the light chain comprises SEQ ID NO: 229, and the heavy chain comprises SEQ ID NO: 170 or SEQ ID NO: 171; or
(c) the light chain comprises SEQ ID NO: 230, and the heavy chain comprises SEQ ID NO: 172 or SEQ ID NO: 173; or
(d) the light chain comprises SEQ ID NO: 231, and the heavy chain comprises SEQ ID NO: 174 or SEQ ID NO: 175; or
(e) the light chain comprises SEQ ID NO: 232, and the heavy chain comprises SEQ ID NO: 176 or SEQ ID NO: 177; or
(f) the light chain comprises SEQ ID NO: 233, and the heavy chain comprises SEQ ID NO: 178 or SEQ ID NO: 179; or
(g) the light chain comprises SEQ ID NO: 234, and the heavy chain comprises SEQ ID NO: 180 or SEQ ID NO: 181; or
(h) the light chain comprises SEQ ID NO: 235, and the heavy chain comprises SEQ ID NO: 182 or SEQ ID NO: 183; or
(i) the light chain comprises SEQ ID NO: 236, and the heavy chain comprises SEQ ID NO: 184 or SEQ ID NO: 185; or
(j) the light chain comprises SEQ ID NO: 237, and the heavy chain comprises SEQ ID NO: 186 or SEQ ID NO: 187; or
(k) the light chain comprises SEQ ID NO: 238, and the heavy chain comprises SEQ ID NO: 188 or SEQ ID NO: 189; or
(l) the light chain comprises SEQ ID NO: 239, and the heavy chain comprises SEQ ID NO: 190 or SEQ ID NO: 191; or
(m) the light chain comprises SEQ ID NO: 240, and the heavy chain comprises SEQ ID NO: 192 or SEQ ID NO: 193; or
(n) the light chain comprises SEQ ID NO: 241, and the heavy chain comprises SEQ ID NO: 194 or SEQ ID NO: 195; or
(o) the light chain comprises SEQ ID NO: 242, and the heavy chain comprises SEQ ID NO: 196 or SEQ ID NO: 197; or
(p) the light chain comprises SEQ ID NO: 243, and the heavy chain comprises SEQ ID NO: 198 or SEQ ID NO: 199; or
(q) the light chain comprises SEQ ID NO: 244, and the heavy chain comprises SEQ ID NO: 200 or SEQ ID NO: 201; or
(r) the light chain comprises SEQ ID NO: 245, and the heavy chain comprises SEQ ID NO: 202 or SEQ ID NO: 203; or
(s) the light chain comprises SEQ ID NO: 246, and the heavy chain comprises SEQ ID NO: 204 or SEQ ID NO: 205; or
(t) the light chain comprises SEQ ID NO: 247, and the heavy chain comprises SEQ ID NO: 206 or SEQ ID NO: 207; or
(u) the light chain comprises SEQ ID NO: 248, and the heavy chain comprises SEQ ID NO: 208 or SEQ ID NO: 209; or
(v) the light chain comprises SEQ ID NO: 249, and the heavy chain comprises SEQ ID NO: 210 or SEQ ID NO: 211; or
(w) the light chain comprises SEQ ID NO: 250, and the heavy chain comprises SEQ ID NO: 212 or SEQ ID NO: 213; or
(x) the light chain comprises SEQ ID NO: 251, and the heavy chain comprises SEQ ID NO: 214 or SEQ ID NO: 215; or
(y) the light chain comprises SEQ ID NO: 252, and the heavy chain comprises SEQ ID NO: 216 or SEQ ID NO: 217; or
(z) the light chain comprises SEQ ID NO: 253, and the heavy chain comprises SEQ ID NO: 218 or SEQ ID NO: 219; or
(aa) the light chain comprises SEQ ID NO: 254, and the heavy chain comprises SEQ ID NO: 220 or SEQ ID NO: 221; or
(ab) the light chain comprises SEQ ID NO: 255, and the heavy chain comprises SEQ ID NO: 222 or SEQ ID NO: 223; or
(ac) the light chain comprises SEQ ID NO: 256, and the heavy chain comprises SEQ ID NO: 224 or SEQ ID NO: 225; or
(ad) the light chain comprises SEQ ID NO: 257, and the heavy chain comprises SEQ ID NO: 226 or SEQ ID NO: 227; or
(ae) the light chain comprises SEQ ID NO: 228, and the heavy chain comprises SEQ ID NO: 364 or SEQ ID NO: 365; or
(af) the light chain comprises SEQ ID NO: 229, and the heavy chain comprises SEQ ID NO: 366 or SEQ ID NO: 367; or
(ag) the light chain comprises SEQ ID NO: 230, and the heavy chain comprises SEQ ID NO: 368 or SEQ ID NO: 369; or
(ah) the light chain comprises SEQ ID NO: 231, and the heavy chain comprises SEQ ID NO: 370 or SEQ ID NO: 371; or
(ai) the light chain comprises SEQ ID NO: 232, and the heavy chain comprises SEQ ID NO: 372 or SEQ ID NO: 373; or
(aj) the light chain comprises SEQ ID NO: 233, and the heavy chain comprises SEQ ID NO: 374 or SEQ ID NO: 375; or (ak) the light chain comprises SEQ ID NO: 234, and the heavy chain comprises SEQ ID NO: 376 or SEQ ID NO: 377; or
(al) the light chain comprises SEQ ID NO: 235, and the heavy chain comprises SEQ ID NO: 378 or SEQ ID NO: 379; or
(am) the light chain comprises SEQ ID NO: 236, and the heavy chain comprises SEQ ID NO: 380 or SEQ ID NO: 381; or
(an) the light chain comprises SEQ ID NO: 237, and the heavy chain comprises SEQ ID NO: 382 or SEQ ID NO: 383; or
(ao) the light chain comprises SEQ ID NO: 238, and the heavy chain comprises SEQ ID NO: 384 or SEQ ID NO: 385; or
(ap) the light chain comprises SEQ ID NO: 239, and the heavy chain comprises SEQ ID NO: 386 or SEQ ID NO: 387; or
(aq) the light chain comprises SEQ ID NO: 240, and the heavy chain comprises SEQ ID NO: 388 or SEQ ID NO: 389; or
(ar) the light chain comprises SEQ ID NO: 241, and the heavy chain comprises SEQ ID NO: 390 or SEQ ID NO: 391; or
(as) the light chain comprises SEQ ID NO: 242, and the heavy chain comprises SEQ ID NO: 392 or SEQ ID NO: 393; or
(at) the light chain comprises SEQ ID NO: 243, and the heavy chain comprises SEQ ID NO: 394 or SEQ ID NO: 395; or
(au) the light chain comprises SEQ ID NO: 244, and the heavy chain comprises SEQ ID NO: 396 or SEQ ID NO: 397; or
(av) the light chain comprises SEQ ID NO: 245, and the heavy chain comprises SEQ ID NO: 398 or SEQ ID NO: 399; or
(aw) the light chain comprises SEQ ID NO: 246, and the heavy chain comprises SEQ ID NO: 400 or SEQ ID NO: 401; or
(ax) the light chain comprises SEQ ID NO: 247, and the heavy chain comprises SEQ ID NO: 402 or SEQ ID NO: 403; or
(ay) the light chain comprises SEQ ID NO: 248, and the heavy chain comprises SEQ ID NO: 404 or SEQ ID NO: 405; or
(az) the light chain comprises SEQ ID NO: 249, and the heavy chain comprises SEQ ID NO: 406 or SEQ ID NO: 407; or
(ba) the light chain comprises SEQ ID NO: 250, and the heavy chain comprises SEQ ID NO: 408 or SEQ ID NO: 409; or
(bb) the light chain comprises SEQ ID NO: 251, and the heavy chain comprises SEQ ID NO: 410 or SEQ ID NO: 411; or
(bc) the light chain comprises SEQ ID NO: 252, and the heavy chain comprises SEQ ID NO: 412 or SEQ ID NO: 413; or
(bd) the light chain comprises SEQ ID NO: 253, and the heavy chain comprises SEQ ID NO: 414 or SEQ ID NO: 415; or
(be) the light chain comprises SEQ ID NO: 254, and the heavy chain comprises SEQ ID NO: 416 or SEQ ID NO: 417; or
(bf) the light chain comprises SEQ ID NO: 255, and the heavy chain comprises SEQ ID NO: 418 or SEQ ID NO: 419; or
(bg) the light chain comprises SEQ ID NO: 256, and the heavy chain comprises SEQ ID NO: 420 or SEQ ID NO: 421; or
(bh) the light chain comprises SEQ ID NO: 257, and the heavy chain comprises SEQ ID NO: 422 or SEQ ID NO: 423.

10. The antibody or antigen-binding fragment thereof of any one of the preceding embodiments, wherein the antibody binding fragment is a scFv antibody, a Fab fragment, a Fab' fragment, or an F(ab')$_2$ fragment.

11. The antibody, or antigen binding fragment thereof, of any one of the preceding embodiments, wherein the antibody is a monoclonal antibody.

12. The antibody, or antigen binding fragment thereof, of any one of the preceding embodiments, wherein the antibody is a humanized antibody.

13. The antibody, or antigen binding fragment thereof, of any one of the preceding embodiments, wherein the antibody, or antigen binding fragment thereof, comprises the sequence selected from one or more of the following sequences: SEQ ID NO: 1; SEQ ID NO: 2; SEQ ID NO: 3; SEQ ID NO: 4; SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 334, SEQ ID NO: 335, SEQ ID NO: 336, SEQ ID NO: 337, SEQ ID NO: 338, SEQ ID NO: 339, SEQ ID NO: 340, SEQ ID NO: 341, SEQ ID NO: 342, SEQ ID NO: 343, SEQ ID NO: 344, SEQ ID NO: 345, SEQ ID NO: 346, SEQ ID NO: 347, SEQ ID NO: 348, SEQ ID NO: 349, SEQ ID NO: 350, SEQ ID NO: 351, SEQ ID NO: 352, SEQ ID NO: 353, SEQ ID NO: 354, SEQ ID NO: 355, SEQ ID NO: 356, SEQ ID NO: 357, SEQ ID NO: 358, SEQ ID NO: 359, SEQ ID NO: 360, SEQ ID NO: 361, SEQ ID NO: 362, SEQ ID NO: 363, or a variant thereof.

14. The antibody, or antigen binding fragment thereof, of any one of the preceding embodiments, wherein the antibody, or antigen binding fragment thereof, comprises a $V_L$ peptide of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, or 60, or any variant thereof.

15. The antibody, or antigen binding fragment thereof, of any one of the preceding embodiments, wherein the antibody, or antigen binding fragment thereof, comprises a $V_H$ peptide of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 334, 335, 336, 337, 338, 339, 340, 341, 342, 343, 344, 345, 346, 347, 348, 349, 350, 351, 352, 353, 354, 355, 356, 357, 358, 359, 360, 361, 362, or 363, or any variant thereof.

16. An antibody, or antigen binding fragment thereof, wherein the antibody comprises:
a variable heavy chain comprising a HCDR1 of SEQ ID NO: 128, a HCDR2 of SEQ ID NO: 129, and a HCDR3 of DEQLGGX$_1$X$_2$YYYYYMDX$_3$ (SEQ ID NO: 333), wherein: X$_1$ is N, T, I, Q, L, K, or R; X$_2$ is Y, T, K, H, or V; and X$_3$ is V or A; and
a variable light chain LCDR1 of SEQ ID NO: 106, a LCDR2 of SEQ ID NO: 107, and a LCDR3 comprising an amino acid sequence of: X$_4$QX$_5$X$_6$X$_7$X$_8$PLX$_9$ (SEQ ID NO: 332), wherein: X$_4$ is L or F; X$_5$ is Y or T; X$_6$ is N, K, A, H, or R; X$_7$ is S, Q, I, or A; X$_8$ is Y, V, or H; and X$_9$ is T, G, K, R, I or A.

17. An antibody, or antigen binding fragment thereof, wherein the antibody comprises:
a variable heavy chain comprising a HCDR1 of SEQ ID NO: 61, a HCDR2 of SEQ ID NO: 62, and a HCDR3 of DX$_{10}$X$_{11}$X$_{12}$YX$_{13}$X$_{14}$DX$_{15}$ (SEQ ID NO: 329), wherein: X$_{10}$ is E, Q, or N; X$_{11}$ is T, E, S, or N; X$_{12}$ is D or Q; X$_{13}$ is A or G; X$_{14}$ is L, W, F, or Y; and X$_{15}$ is Y, E, L, N, F, or W; and
a variable light chain comprising a LCDR1 of SEQ ID NO: 64, a LCDR2 of SEQ ID NO: 65, and a LCDR3 comprising an amino acid sequence of X$_{16}$X$_{17}$X$_{18}$EDX$_{19}$X$_{20}$X$_{21}$X$_{22}$ (SEQ ID NO: 328), wherein X$_{16}$ is Q, E, K, or H; X$_{17}$ is Q or H; X$_{18}$ is Y or H, X$_{19}$ is L or Y; X$_{20}$ is P or I; X$_{21}$ is L or P, and X$_{22}$ is T or V.

18. An antibody, or antigen binding fragment thereof, wherein the antibody comprises:
a variable heavy chain comprising a HCDR1 of SEQ ID NO: 82, a HCDR2 of SEQ ID NO: 83, and a HCDR3 of X$_{23}$GX$_{24}$X$_{25}$X$_{26}$X$_{27}$PX$_{28}$X$_{29}$X$_{30}$ (SEQ ID NO: 330), wherein: X23 is E or K, X24 is L or E; X25 is A or G, X26 is G or W, X27 is R, V, L, I, or F, X28 is F, Y, or T, X29 is D or Y, X 30 is A, V, L, S, H, or I; and
a variable light chain comprising a LCDR1 of SEQ ID NO: 85, a LCDR2 of SEQ ID NO: 86, and a LCDR3 of X$_{31}$QX$_{32}$X$_{33}$SX$_{34}$X$_{35}$X$_{36}$X$_{37}$ (SEQ ID NO: 331), wherein X31 is Q or V; X32 is Y, A, V, or H; X33 is N, P, S, or R; X34 is Y, L, or P; X35 is S, K, V, A, D, or R; X36 is W or L; and X37 is T or L.

19. The antibody, or antigen binding fragment thereof, of any one of the preceding embodiments, wherein the antibody, or antigen binding fragment thereof, comprises a constant region as provided for herein.

20. The antibody, or antigen binding fragment thereof, of any one of the preceding embodiments, wherein the heavy chain variable region and the light chain variable region are not linked by a linker.

21. The antibody, or antigen binding fragment thereof, of any one of the preceding embodiments, wherein the heavy chain variable region and the light chain variable region are linked with a peptide linker.

22. The antibody, or antigen binding fragment thereof, of embodiment 21, wherein the peptide linker comprises a sequence of (GGGGS)$_n$ (SEQ ID NO: 266); (GGGGA)$_n$ (SEQ ID NO: 267), or any combination thereof, wherein each n is independently 1-5.

23. A variant of the antibody, or antigen binding fragment thereof, of any one of the preceding embodiments, wherein the variant has 1-10 substitutions, deletions, or insertions.

24. A variant of the antibody, or antigen binding fragment thereof, of any one of the preceding embodiments, wherein the variant has 1-10 conservative substitutions.

25. A recombinant antibody or an antigen binding fragment thereof that binds to a C1s, such as specifically binding to active C1s, wherein the antibody, or antigen binding fragment thereof, comprises an amino acid sequence, or a variant thereof, as provided for herein.

26. An antibody that specifically binds to active C1s, wherein the antibody has a K$_D$ of less than $7\times10^{-9}$ M, $6\times10^{-9}$ M, $5\times10^{-9}$ M, $4\times10^{-9}$ M, $3\times10^{-9}$ M, $2\times10^{-9}$ M, $1\times10^{-9}$ M, $9\times10^{-10}$ M, $8\times10^{-10}$ M, $7\times10^{-10}$ M, $6\times10^{-10}$ M, $5\times10^{-10}$ M, $4\times10^{-10}$ M.

27. The antibody of embodiment 26, wherein the K$_D$ is measured as set forth in Example 3.

28. The antibody of embodiments 26 or 27, wherein the antibody is an antibody of any one of embodiments 1-25.

29. An antibody that specifically binds to active C1s and inhibits the Wieslab complement classical pathway with an IC$_{50}$ of about 1 to 5 nM, about 0.1 to 1 nM, about 0.5 to about 3 nM, about 1 to about 2 nM, less than 5 nM, less than 4.5 nM, less than 3 nM, or less than 1 nM.

30. The antibody of embodiment 29, wherein the IC$_{50}$ is determined as set forth in Example 4.

31. The antibody of embodiments 29 or 30, wherein the antibody is an antibody of any one of embodiments 1-25.

32. An antibody that specifically binds to active C1s and inhibits human serum complement-mediated human RBC lysis with an IC$_{50}$ of less than 20 nM, less than 19 nM, less than 18 nM, less than 15 nM, less than 13 nM, less than 12 nM, less than 12.5 nM, about 11 to about 20 nM, about 11 to about 15 nM, about 11 to about 13 nM, about 11 to about 12 nM, about 12 to about 15 nM.

33. The antibody of embodiment 32, wherein the IC$_{50}$ is determined as set forth in Example 5.

34. The antibody of embodiments 32 or 33, wherein the antibody is an antibody of any one of embodiments 1-25.

35. An isolated nucleic acid molecule encoding an antibody, or an antigen binding fragment thereof, a heavy chain variable region, a light chain variable region, heavy chain, or light chain, of any of the preceding embodiments.

36. The isolated nucleic acid sequence of embodiment 35 comprising a nucleic acid molecule as set forth herein, such as a sequence of SEQ ID NO: 268, SEQ ID NO: 269, SEQ ID NO: 270, SEQ ID NO: 271, SEQ ID NO: 272, SEQ ID NO: 273, SEQ ID NO: 274, SEQ ID NO: 275, SEQ ID NO: 276, SEQ ID NO: 277, SEQ ID NO: 278, SEQ ID NO: 279, SEQ ID NO: 280, SEQ ID NO: 281, SEQ ID NO: 282, SEQ ID NO: 283, SEQ ID NO: 284, SEQ ID NO: 285, SEQ ID NO: 286, SEQ ID NO: 287, SEQ ID NO: 288, SEQ ID NO: 289, SEQ ID NO: 290, SEQ ID NO: 291, SEQ ID NO: 292, SEQ ID NO: 293, SEQ ID NO: 294, SEQ ID NO: 295, SEQ ID NO: 296, SEQ ID NO: 297, SEQ ID NO: 298, SEQ ID NO: 299, SEQ ID NO: 300, SEQ ID NO: 301, SEQ ID NO: 302, SEQ ID NO: 303, SEQ ID NO: 304, SEQ ID NO: 305, SEQ ID NO: 306, SEQ ID NO: 307, SEQ ID NO: 308, SEQ ID NO: 309, SEQ ID NO: 310, SEQ ID NO: 311, SEQ ID NO: 312, SEQ ID NO: 313, SEQ ID NO: 314, SEQ ID NO: 315, SEQ ID NO: 316, SEQ ID NO: 317, SEQ ID NO: 318, SEQ ID NO: 319, SEQ ID NO: 320, SEQ ID NO: 321, SEQ ID NO: 322, SEQ ID NO:

323, SEQ ID NO: 324, SEQ ID NO: 325, SEQ ID NO: 326, SEQ ID NO: 327, SEQ ID NO: 424, SEQ ID NO: 425, SEQ ID NO: 426, SEQ ID NO: 427, SEQ ID NO: 428, SEQ ID NO: 429, SEQ ID NO: 430, SEQ ID NO: 431, SEQ ID NO: 432, SEQ ID NO: 433, SEQ ID NO: 434, SEQ ID NO: 435, SEQ ID NO: 436, SEQ ID NO: 437, SEQ ID NO: 438, SEQ ID NO: 439, SEQ ID NO: 440, SEQ ID NO: 441, SEQ ID NO: 442, SEQ ID NO: 443, SEQ ID NO: 444, SEQ ID NO: 445, SEQ ID NO: 446, SEQ ID NO: 447, SEQ ID NO: 448, SEQ ID NO: 449, SEQ ID NO: 450, SEQ ID NO: 451, SEQ ID NO: 452, or SEQ ID NO: 453.

37. An expression vector comprising the nucleic acid molecule of embodiments 35 or 36.

38. A host cell comprising the nucleic acid molecule of embodiments 35 or 36 or the vector of embodiment 37.

39. An antibody or antigen-binding fragment produced by the host cell of embodiment 38.

40. A pharmaceutical composition comprising an antibody, or antigen binding fragment thereof, of any one of embodiments 1-34.

41. The pharmaceutical composition of embodiment 40, wherein the composition is formulated for intravenous or subcutaneous injection.

42. The pharmaceutical composition of embodiment 40, wherein the composition is an injectable pharmaceutical composition.

43. A method of producing a polypeptide comprising a heavy chain variable region or light chain variable region, the method comprising:
    (a) growing the host cell of embodiment 41 under conditions so that the host cell expresses the polypeptide comprising the heavy chain variable region or the light chain variable region; and
    (b) purifying the polypeptide comprising the heavy chain variable region or the light chain variable region.

44. A method of producing an antibody that binds human C1s, or an antigen binding fragment of the antibody, the method comprising:
    (a) growing the host cell of embodiment 41 under conditions so that the host cell expresses a polypeptide or polypeptides comprising the immunoglobulin heavy chain variable region and/or the immunoglobulin light chain variable region, thereby producing the antibody or the antigen-binding fragment of the antibody; and
    (b) purifying the antibody or the antigen-binding fragment of the antibody.

45. A method of treating a subject with C1s mediated disorder, the method comprising administering to the subject an antibody, or antigen binding fragment thereof, of any one of embodiments 1-34 or 39 or a pharmaceutical composition of any one of embodiments 40-42.

46. The method of embodiment 45, wherein the disorder is hemolysis, Cold Agglutinin Disease, Immune Thrombocytopenia (ITP), Myasthenia Gravis, Glomerulopathies, Atypical Hemolytic uremic syndrome, antiphospholipid antibody syndrome, transplant rejection, Chronic inflammatory demyelinating polyneuropathy (CIDP), Multifocal motor neuropathy (MMN), Dermatomyositis, or Anti MAG neuropathy.

47. The method of embodiment 45, wherein the C1s mediated disorder is Cold Agglutinin Disease or Myasthenia Gravis.

48. A method of inhibiting membrane attack complex (MAC) formation or deposition in a subject in need thereof (e.g. such as a patient with Myasthenia Gravis), the method comprising administering to the subject an antibody, or antigen binding fragment thereof, of any one of embodiments 1-34 or 39 or a pharmaceutical composition of any one of embodiments 40-42.

49. A method of inhibiting or preventing neurotransmission impairment in a subject in need thereof, (e.g. such as a patient with Myasthenia Gravis), the method comprising administering to the subject an antibody, or antigen binding fragment thereof, of any one of embodiments 1-34 or 39 or a pharmaceutical composition of any one of embodiments 40-42.

50. A method of enhancing, allowing, or permitting muscle contraction in a subject in need thereof, (e.g. such as a patient with Myasthenia Gravis), the method comprising administering to the subject an antibody, or antigen binding fragment thereof, of any one of embodiments 1-34 or 39 or a pharmaceutical composition of any one of embodiments 40-42.

51. A method of ameliorating or alleviating muscle paralysis in a subject in need thereof, (e.g. such as a patient with Myasthenia Gravis), the method comprising administering to the subject an antibody, or antigen binding fragment thereof, of any one of embodiments 1-34 or 39 or a pharmaceutical composition of any one of embodiments 40-42.

52. A method of inhibiting the loss of muscle tone or muscle mass in a subject in need thereof, (e.g. such as a patient with Myasthenia Gravis), the method comprising administering to the subject an antibody, or antigen binding fragment thereof, of any one of embodiments 1-34 or 39 or a pharmaceutical composition of any one of embodiments 40-42.

53. A method of reducing the muscle fatigue index in a subject in need thereof, (e.g. such as a patient with Myasthenia Gravis), the method comprising administering to the subject an antibody, or antigen binding fragment thereof, of any one of embodiments 1-34 or 39 or a pharmaceutical composition of any one of embodiments 40-42.

54. The method of any one of embodiments 45-53, wherein the antibody or pharmaceutical composition is administered intravenously.

55. The method of any one of embodiments 45-53, wherein the antibody or pharmaceutical composition is administered subcutaneously.

56. An antibody, or antigen binding fragment thereof, of any one of embodiments 1-34 or 39, or a pharmaceutical composition comprising the antibody or antigen binding fragment thereof, for the use in the treatment of a C1s mediated disorder, such as those provided for herein, such as hemolysis, Cold Agglutinin Disease, Immune Thrombocytopenia (ITP), Myasthenia Gravis, Glomerulopathies, Atypical Hemolytic uremic syndrome, antiphospholipid antibody syndrome, transplant rejection, Chronic inflammatory demyelinating polyneuropathy (CIDP), Multifocal motor neuropathy (MMN), Dermatomyositis, or Anti MAG neuropathy.

57. An antibody, or antigen binding fragment thereof, of any one of embodiments 1-34 or 39, or a pharmaceutical composition comprising the antibody or antigen binding fragment thereof, for the use in the treatment of a C1S mediated disorder, such as Cold Agglutinin Disease or Myasthenia Gravis.

58. An antibody, or antigen binding fragment thereof, of any one of embodiments 1-34 or 39 or a pharmaceutical composition comprising the antibody, or antigen binding fragment thereof, for use as a medicament.
59. The antibody or binding fragment thereof, or pharmaceutical composition of embodiment 58 for use in the treatment of a C1s mediated disorder, such as those provided for herein.
60. Use of the antibody, or antigen binding fragment thereof, of any one of embodiments 1-34 or 39, or a pharmaceutical composition comprising the antibody or antigen binding fragment thereof, for the treatment of a C1s mediated disorder, such as those provided for herein.

In some embodiments, the following embodiments are provided.

1. An antibody, or an antigen binding fragment thereof, wherein the antibody or antibody fragment comprises:
   a heavy chain variable region comprising heavy chain HCDR1, HCDR2, and HCDR3 sequences, wherein the HCDR1 has the amino acid sequence of SEQ ID NO: 61, the HCDR2 has the amino acid sequence of SEQ ID NO: 62, the HCDR3 has the amino acid sequence of SEQ ID NO: 78; and
   a light chain variable region comprising light chain LCDR1, LCDR3, and LCDR3 sequences, wherein the LCDR1 has the amino acid sequence of SEQ ID NO: 64, the LCDR2 has the amino acid sequence of SEQ ID NO: 65, the LCDR3 has the amino acid sequence of SEQ ID NO: 79.
2. The antibody of embodiment 1, or an antigen binding fragment thereof, wherein the heavy chain variable region comprises an amino acid sequence at least 90% identical to the amino acid sequence of SEQ ID NO: 342.
3. The antibody of embodiment 1, or an antigen binding fragment thereof, wherein the heavy chain variable region comprises an amino acid sequence at least 95% identical to the amino acid sequence of SEQ ID NO: 342.
4. The antibody of embodiment 1, or an antigen binding fragment thereof, wherein the heavy chain variable region comprises the amino acid sequence of SEQ ID NO: 342.
5. The antibody of embodiment 1, or an antigen binding fragment thereof, wherein the heavy chain variable region comprises an amino acid sequence at least 90% identical to the amino acid sequence of SEQ ID NO: 17.
6. The antibody of embodiment 1, or an antigen binding fragment thereof, wherein the heavy chain variable region comprises an amino acid sequence at least 95% identical to the amino acid sequence of SEQ ID NO: 17.
7. The antibody of embodiment 1, or an antigen binding fragment thereof, wherein the heavy chain variable region comprises the amino acid sequence of SEQ ID NO: 17.
8. The antibody of embodiment 1, or an antigen binding fragment thereof, wherein the heavy chain variable region comprises an amino acid sequence at least 90% identical to the amino acid sequence of SEQ ID NO: 454.
9. The antibody of embodiment 1, or an antigen binding fragment thereof, wherein the heavy chain variable region comprises an amino acid sequence at least 95% identical to the amino acid sequence of SEQ ID NO: 454.
10. The antibody of embodiment 1, or an antigen binding fragment thereof, wherein the heavy chain variable region comprises the amino acid sequence of SEQ ID NO: 454.
11. The antibody of embodiment 1, or an antigen binding fragment thereof, wherein the antibody comprises a heavy chain that is at least 90% identical to the amino acid sequence of SEQ ID NO: 381.
12. The antibody of embodiment 1, or an antigen binding fragment thereof, wherein the antibody comprises a heavy chain that is at least 95% identical to the amino acid sequence of SEQ ID NO: 381.
13. The antibody of embodiment 1, or an antigen binding fragment thereof, wherein the antibody comprises a heavy chain comprises the amino acid sequence of SEQ ID NO: 381.
14. The antibody of embodiment 1, or an antigen binding fragment thereof, wherein the antibody comprises a heavy chain that is at least 90% identical to the amino acid sequence of SEQ ID NO: 185.
15. The antibody of embodiment 1, or an antigen binding fragment thereof, wherein the antibody comprises a heavy chain that is at least 95% identical to the amino acid sequence of SEQ ID NO: 185.
16. The antibody of embodiment 1, or an antigen binding fragment thereof, wherein the antibody comprises a heavy chain comprises the amino acid sequence of SEQ ID NO: 185.
17. The antibody of any one of embodiments 1-16, or an antigen binding fragment thereof, wherein the light chain variable region comprises an amino acid sequence that is at least 90% identical to the amino acid sequence of SEQ ID NO: 18.
18. The antibody of any one of embodiments 1-16, or an antigen binding fragment thereof, wherein the light chain variable region comprises an amino acid sequence that is at least 95% identical to the amino acid sequence of SEQ ID NO: 18.
19. The antibody of any one of embodiments 1-16, or an antigen binding fragment thereof, wherein the light chain variable region comprises the amino acid sequence of SEQ ID NO: 18.
20. The antibody of any one of embodiments 1-16, or an antigen binding fragment thereof, wherein the antibody comprises a light chain that is at least 90% identical to the amino acid sequence of SEQ ID NO: 236.
21. The antibody of any one of embodiments 1-16, or an antigen binding fragment thereof, wherein the antibody comprises a light chain that is at least 95% identical to the amino acid sequence of SEQ ID NO: 236.
22. The antibody of any one of embodiments 1-16, or an antigen binding fragment thereof, wherein the antibody comprises a heavy chain comprises the amino acid sequence of SEQ ID NO: 236.
23. The antibody of embodiment 1, wherein the antibody, or an antigen binding fragment thereof, comprises a variable heavy chain region comprising the amino acid sequence of SEQ ID NO: 342 and a light chain variable region comprising the sequence of SEQ ID NO 18.
24. The antibody of embodiment 23, wherein the antibody, or an antigen binding fragment thereof, comprises a heavy chain comprising the sequence of SEQ ID NO: 381 and a light chain comprising the sequence of SEQ ID NO: 236.

25. The antibody of embodiment 1, wherein the antibody, or an antigen binding fragment thereof, comprises a variable heavy chain region comprising the amino acid sequence of SEQ ID NO: 17 and a light chain variable region comprising the sequence of SEQ ID NO 18.
26. The antibody of embodiment 23, wherein the antibody, or an antigen binding fragment thereof, comprises a heavy chain comprising the sequence of SEQ ID NO: 185 and a light chain comprising the sequence of SEQ ID NO: 236.
27. An isolated nucleic acid molecule encoding an antibody, or an antigen binding fragment thereof, a heavy chain variable region, a light chain variable region, heavy chain, or light chain, of any of the preceding embodiments.
28. An expression vector comprising the nucleic acid molecule of embodiment 27.
29. A host cell comprising the nucleic acid molecule of embodiments 27 or the vector of embodiment 28.
30. A pharmaceutical composition comprising an antibody, or antigen binding fragment thereof, of any one of embodiments 1-26 and a pharmaceutically acceptable excipient.
31. The pharmaceutical composition of embodiment 30, wherein the composition is formulated for intravenous or subcutaneous injection.
32. A method of producing a polypeptide comprising a heavy chain variable region or light chain variable region, the method comprising:
    (a) growing the host cell of embodiment 29 under conditions so that the host cell expresses the polypeptide comprising the heavy chain variable region or the light chain variable region; and
    (b) purifying the polypeptide comprising the heavy chain variable region and/or the light chain variable region.
33. A method of treating a subject with C1s mediated disorder, the method comprising administering to the subject an antibody, or antigen binding fragment thereof, of any one of embodiments 1-26, or a pharmaceutical composition comprising the same.
34. The method of embodiments 33, wherein the disorder is Myasthenia Gravis, hemolysis, Cold Agglutinin Disease, Immune Thrombocytopenia (ITP), Glomerulopathies, Atypical Hemolytic uremic syndrome, antiphospholipid antibody syndrome, transplant rejection, Chronic inflammatory demyelinating polyneuropathy (CIDP), Multifocal motor neuropathy (MMN), Dermatomyositis, or Anti MAG neuropathy.
35. A method of treating a subject with or Myasthenia Gravis or Cold Agglutinin Disease, the method comprising administering to the subject an antibody, or antigen binding fragment thereof, of any one of embodiments 1-26, or a pharmaceutical composition comprising the same.
36. The method of embodiment 35, wherein the antibody, or an antigen binding fragment thereof, comprises a variable heavy chain region comprising the amino acid sequence of SEQ ID NO: 342 and a light chain variable region comprising the sequence of SEQ ID NO 18.
37. The method of embodiment 35, wherein the antibody, or an antigen binding fragment thereof, comprises a heavy chain comprising the sequence of SEQ ID NO: 381 and a light chain comprising the sequence of SEQ ID NO: 236.
38. A method of inhibiting membrane attack complex (MAC) formation or deposition in a subject in need thereof (e.g. such as a patient with Myasthenia Gravis), the method comprising administering to the subject an antibody, or antigen binding fragment thereof, of any one of embodiments 1-26, or a pharmaceutical composition comprising the same.
39. A method of inhibiting or preventing neurotransmission impairment in a subject in need thereof, (e.g. such as a patient with Myasthenia Gravis), the method comprising administering to the subject an antibody, or antigen binding fragment thereof, of any one of embodiments 1-26, or a pharmaceutical composition comprising the same.
40. A method of enhancing, allowing, or permitting muscle contraction in a subject in need thereof, (e.g. such as a patient with Myasthenia Gravis), the method comprising administering to the subject an antibody, or antigen binding fragment thereof, of any one of embodiments 1-26, or a pharmaceutical composition comprising the same.
41. A method of ameliorating or alleviating muscle paralysis in a subject in need thereof, (e.g. such as a patient with Myasthenia Gravis), the method comprising administering to the subject an antibody, or antigen binding fragment thereof, embodiments 1-26, or a pharmaceutical composition comprising the same.
42. A method of inhibiting the loss of muscle tone or muscle mass in a subject in need thereof, (e.g. such as a patient with Myasthenia Gravis), the method comprising administering to the subject an antibody, or antigen binding fragment thereof, of any one of embodiments 1-26, or a pharmaceutical composition comprising the same.
43. A method of reducing the muscle fatigue index in a subject in need thereof, (e.g. such as a patient with Myasthenia Gravis), the method comprising administering to the subject an antibody, or antigen binding fragment thereof, of any one of embodiments 1-26, or a pharmaceutical composition comprising the same.

The subject matter is now described with reference to the following examples. These examples are provided for the purpose of illustration only and the claims should in no way be construed as being limited to these examples, but rather should be construed to encompass any and all variations which become evident as a result of the teaching provided herein. Those of skill in the art will readily recognize a variety of non-critical parameters that could be changed or modified to yield essentially similar results.

EXAMPLES

Example 1: Expression and Purification of hC1s RQ

For all work with active human C1s, material purified from human serum (CompTech, Tyler, TX, catalog number A104) was used. It was observed that human ProC1s purified from serum is unstable and appears to undergo cleavage, presumably at Arg437, the site cleaved by C1r (Budayova-Spano, M et al. *EMBO J* 21:231-239, 2002, using the C1s numbering in GenBank sequence AAA51852.1) either because of trace amounts of C1r in the material or a slow rate of autocleavage. To stabilize ProC1s for use in binding experiments, recombinant human ProC1s was expressed in mammalian cells in which Arg437 was mutated to glutamine (hProC1s_RQ).

A gene sequence encoding the protein human ProC1s_RQ shown in FIG. 1 was cloned into a high expression mammalian plasmid vector. Suspension Chinese hamster ovary (CHO) or human embryonic kidney (HEK293) cells were seeded in a shake flask and expanded using a serum-free and chemically defined medium. On the day of transfection, the expanded cells were seeded into a new vessel with fresh medium. After transfection with the plasmid expression vector for human ProCis RQ, the cells were maintained as a batch-fed culture for 14 days. Next, the cells were removed from the media by centrifugation and the media containing human ProC1s_RQ was loaded onto an immobilized metal affinity column (Millipore Sigma, St. Louis, MO, catalog GE17-920-07) pre-equilibrated with binding buffer (20 mM sodium phosphate, 1M NaCl, pH 7.2). Washing buffer (20 mM sodium phosphate, 1M NaCl, 40 mM imidazole, pH 7.2) was passed through the column until the $OD_{280}$ value returned to baseline. Human ProC1s_RQ was eluted with a linear gradient of increasing imidazole concentration up to 0.5 M in 20 mM sodium phosphate pH 7.2. The eluate was collected in fractions, and the $OD_{280}$ value of each fraction was recorded. Denaturing capillary electrophoresis (CE-SDS, LabChip GXII, Perkin Elmer) of each fraction was performed and analyzed. Fractions containing the target protein were pooled and dialyzed into 30 mM HEPES, 150 mM NaCl, pH 7.0.

Example 2: Human C1s and hProC1s_RQ ELISA

Human C1s and recombinant hC1s_RQ were biotinylated using the EZ link Sulfo NHS-LC-Biotin kit (ThermoFisher catalog #21327) as described by the vendor. 96-well plates (Maxisorp black 96-well immune plates (Thermofisher Scientific, Waltham, MA, Cat No 437111) were coated with 50 µl/well of a goat anti-human IgG (Jackson ImmunoResearch, West Grove, PA, catalog number 109-001-008) diluted to 2.5 µg/ml in phosphate buffered saline (PBS) and incubated at 4° C. overnight. Plates were washed with PBS and then blocked with 300 µl/well 3% (wt/vol) powdered milk in PBS (3% M-PBS) and incubated at room temperature for 1 hour with agitation and then washed with PBS. For each clone tested, 50 µl of the media from the expression cultures was added to an equal volume of 6% (wt/vol) powdered milk in PBS and added to a well in an anti-human IgG coated plate for 1 h at room temperature. The plate was then washed with PBS and then either 100 µl biotinylated-human C1s or biotinylated-hProC1s_RQ was added to each well and incubated for 1 h at room temperature. After washing the wells with PBS, 50 µl/well of Strep-Eu (Perkin-Elmer, Waltham, MA, Cat No 1244-360) diluted 500-fold in DELFIA® assay buffer (Perkin-Elmer, Waltham, MA, Cat. No 1244-111) was added to each well and incubated at room temperature for 1 h. After washing the wells 3 times with PBS, 50 µL of DELFIA enhancement solution (Perkin-Elmer, Waltham, MA, Cat. No 1244-105) was added to the wells. The plates were agitated gently for 3-5 minutes and read using a PHERAstar FS plate reader (BMG Labtech, Cary, NC), with excitation at 340 nm, emission at 615 nm with a delay time of 400 secs.

Example 3: Optimization of Three Parental Anti-Human C1s Antibodies

Three antibody lineages, 4011, 191 and 5 L3, that bound, as determined by surface plasmon resonance (SPR), to active human C1s with greater selectivity vs. human ProCis RQ than recombinant sutimlimab/BIVV009/TNT009 (sequence contained in US patent application US2021/0115116A1), which binds with high affinity to both human Cis and human ProCis, were identified (Table 11). Having low affinity for ProC1s reduces binding of these three antibodies to serum ProCis versus BIVV009/TNT009 which should improve serum half-life. To further optimize the affinity for human Cis and selectivity versus human ProCis, mutations were introduced into the CDRs of parental antibodies. Before optimization the amino acid sequences of the variable region heavy and light chains, outside of the CDR3 region, were changed to the sequences of the most closely related germline sequences when those changes did not significantly impact potency. Additionally, sequences that could potentially make the antibodies structurally unstable were also changed. For antibody 4011, four variable region heavy chain amino acids were changed (V32L, D55E, I55T and D82E) and three variable region light chain amino acids were changed (E13A, T31S and I62F). The resulting antibody is called 4011 g. For antibody 191, four heavy chain amino acids were changed (V40A, K77N, D100E and G101T) and four light chain amino acids were changed (N45K, G65S, D81E and S80P). The resulting antibody is called 191 g. For antibody 5L3 one heavy chain amino acid was changed (N54E) and one light chain amino acid was changed (E45K). The resulting antibody is called 5L3g.

TABLE 11

Affinity of 4011, 191, 5L3 and TNT009 for human C1s and human ProC1s RQ (as determined by SPR).

| Antibody | Human C1s $K_D$ (nM) | Human ProC1s RQ $K_D$ (nM) |
| --- | --- | --- |
| TNT009 (sutimlimab) | 0.25 | 0.4 |
| 4011 | 0.3 | 3900 |
| 191 | 1.2 | >5000 |
| 5L3 | 3.7 | >5000 |

For each of the three antibodies, 4011 g, 191 g and 5L3g, heavy and light chain CDR3 sequences were diversified by mutating two residues at a time to all 17 alternate amino acids (excluding cysteine, methionine and the original amino acid) using synthetic primers. The resulting libraries were then enriched for Cis binding and counterselection against ProCis RQ binding. The enriched sequences were then screened for: 1) high IgG expression level (for good developability); 2) high binding to labelled Cis at low concentrations (for high affinity and potency); and 3) low binding to labelled ProC1s_RQ at high concentrations (for high selectivity).

High scoring sequences from the screening were expressed at a small scale by conducting transfections into mammalian 293 cells in four 96-well plates for 5-7 days. An ELISA assay was used for initial ranking of affinity to C1s and selectivity against proC1s_RQ.

Figure 2B:
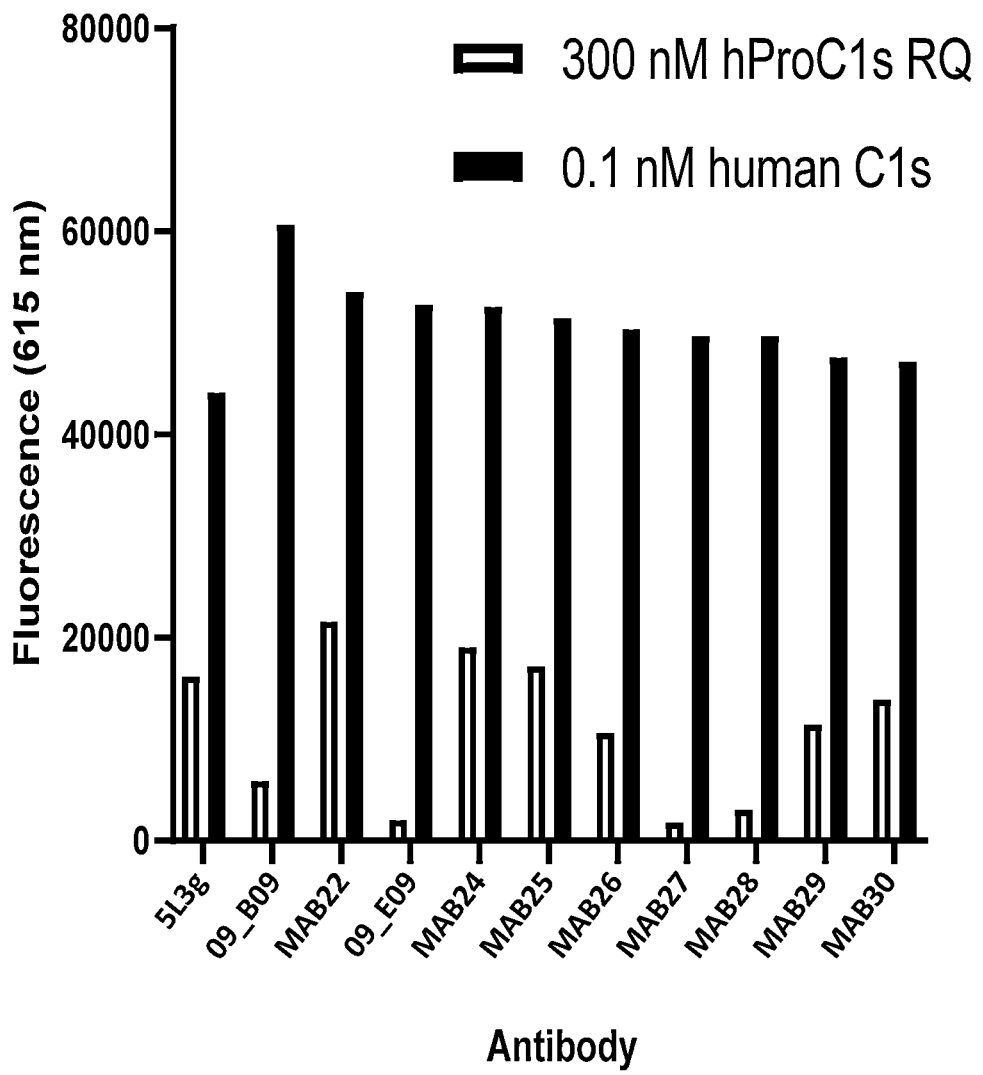

For the initial selection of clones, each was evaluated for binding to both biotinylated-human Cis (0.5 nM for 4011 g and 5L3g clones; 1.0 nM for 191 g clones) and hProC1s_RQ (500 nM) on separate plates. Clones with weak binding to hProC1s_RQ and high affinity binding to human C1s were rescreened by ELISA using biotinylated-human C1s (1 nM for 191 g clones, 0.1 nM for 4011 g and 5L3g clones) and 300 nM biotinylated-hProC1s_RQ and ten clones were chosen from each. See FIG. 2. For a subset of these 30 antibodies, we evaluated by surface plasmon resonance (SPR) the affinity to human C1s (Table 12). We also evaluated by SPR the binding to human ProC1s_RQ and found that for those marked with an asterisk (*) in Table 12 there was no detectable binding above background to 500 nM human ProC1s_RQ.

SPR methods: The binding assays were performed according to the following methods, which are described briefly.

Antibody Immobilization

Affinity-purified goat anti-human Fc antibody (MP Biomedical, Irvine, CA, catalog #55071) was immobilized onto a high-capacity amine (HCA) sensor surface (Bruker, Billerica, MA catalog #1862614) at 1,000 RU-10,000 RU. HBS-EP+running buffer (10 mM HEPES, 150 mM NaCl, 0.05% v/v Tween-20, pH 7.4) was equilibrated with the system by performing a 3× Prime, then the baseline stability was observed over 30 min.

Kinetics

Each antibody analyzed was diluted to 10 nM in HBS-EP+running buffer and captured by injecting at 10 μl/min for 3 minutes on a Sierra Sensors MASS-2 instrument, (Bruker, Billerica, MA).

Buffer was injected for 2 minutes at 25 l/min. Varying concentrations of C1s or ProC1s RQ were injected at 35 l/min for 2 minutes.

The surface was regenerated by injecting Regeneration solution (10 mM glycine-HCl, pH 1.7) at 35 l/min for 30 seconds.

This was repeated for all concentrations of analyte tested and the kinetic parameters (on rate ($K_a$), off rate ($K_d$) and affinity $K_D$ were calculated using instrument software. Table 12. SPR binding of selected clones and parental antibodies from each lineage and recombinant TNT020 to human C1s. Values for the association rate ($K_a$), dissociation rate ($k_d$) and affinity ($K_D$) are shown. Antibodies with an asterisk (*) showed no detectable binding above background by SPR to human ProC1s_RQ. moles/liter (M)

TABLE 12

| Antibody | $K_a$ (M$^{-1}$sec$^{-1}$) | $K_d$ (sec$^{-1}$) | $K_D$ (M) |
|---|---|---|---|
| 5L3g | 8.70 × 10$^4$ | 4.85 × 10$^{-4}$ | 5.58 × 10$^{-9}$ |
| MAB22 | 8.04 × 10$^4$ | 3.35 × 10$^{-4}$ | 4.17 × 10$^{-9}$ |
| MAB29 | 8.41 × 10$^4$ | 5.90 × 10$^{-4}$ | 7.02 × 10$^{-9}$ |
| MAB26 | 8.45 × 10$^4$ | 5.50 × 10$^{-4}$ | 6.52 × 10$^{-9}$ |
| MAB24 | 9.39 × 10$^4$ | 3.28 × 10$^{-4}$ | 3.49 × 10$^{-9}$ |
| MAB25 | 1.11 × 10$^5$ | 6.21 × 10$^{-4}$ | 5.57 × 10$^{-9}$ |
| MAB30 | 1.15 × 10$^5$ | 6.88 × 10$^{-4}$ | 6.01 × 10$^{-9}$ |
| MAB28 | 1.41 × 10$^5$ | 4.09 × 10$^{-4}$ | 2.89 × 10$^{-9}$ |
| MAB27 | 1.92 × 10$^5$ | 2.64 × 10$^{-4}$ | 1.38 × 10$^{-9}$ |
| SCT191g* | 3.57 × 10$^5$ | 1.345 × 10$^{-3}$ | 3.77 × 10$^{-9}$ |
| MAB9* | 4.14 × 10$^5$ | 1.27 × 10$^{-4}$ | 3.06 × 10$^{-10}$ |
| MAB3* | 2.24 × 10$^5$ | 2.09 × 10$^{-4}$ | 9.32 × 10$^{-10}$ |
| MAB1* | 2.68 × 10$^5$ | 2.55 × 10$^{-4}$ | 9.50 × 10$^{-10}$ |
| MAB7* | 1.84 × 10$^5$ | 2.23 × 10$^{-4}$ | 1.22 × 10$^{-9}$ |
| MAB4* | 1.90 × 10$^5$ | 2.32 × 10$^{-4}$ | 1.22 × 10$^{-9}$ |
| MAB5* | 1.89 × 10$^5$ | 2.64 × 10$^{-4}$ | 1.40 × 10$^{-9}$ |
| MAB2* | 1.18 × 10$^5$ | 2.15 × 10$^{-4}$ | 1.83 × 10$^{-9}$ |
| MAB8* | 1.62 × 10$^5$ | 3.45 × 10$^{-4}$ | 2.13 × 10$^{-9}$ |
| 4011g | 1.52 × 10$^5$ | 7.78 × 10$^{-4}$ | 5.12 × 10$^{-9}$ |
| MAB17* | 1.98 × 10$^5$ | 4.14 × 10$^{-4}$ | 2.09 × 10$^{-9}$ |
| MAB13* | 2.04 × 10$^5$ | 1.22 × 10$^{-3}$ | 6.00 × 10$^{-9}$ |
| MAB15* | 1.15 × 10$^5$ | 7.37 × 10$^{-4}$ | 6.39 × 10$^{-9}$ |
| MAB19 | 1.06 × 10$^5$ | 6.57 × 10$^{-4}$ | 6.18 × 10$^{-9}$ |
| TNT020* | 3.57 × 10$^5$ | 1.34 × 10$^{-3}$ | 3.77 × 10$^{-9}$ |

Figure 2C:
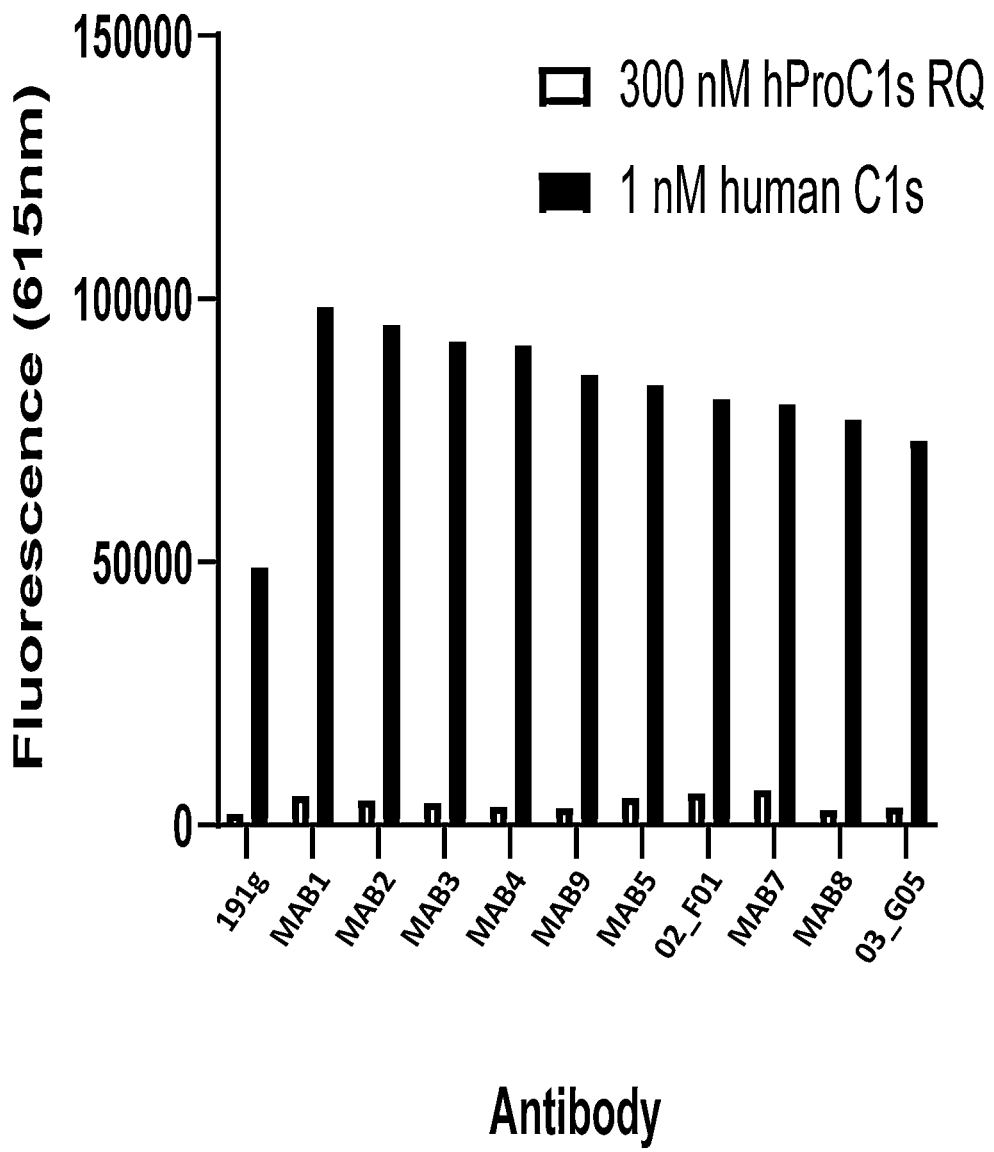
Figure 4A:
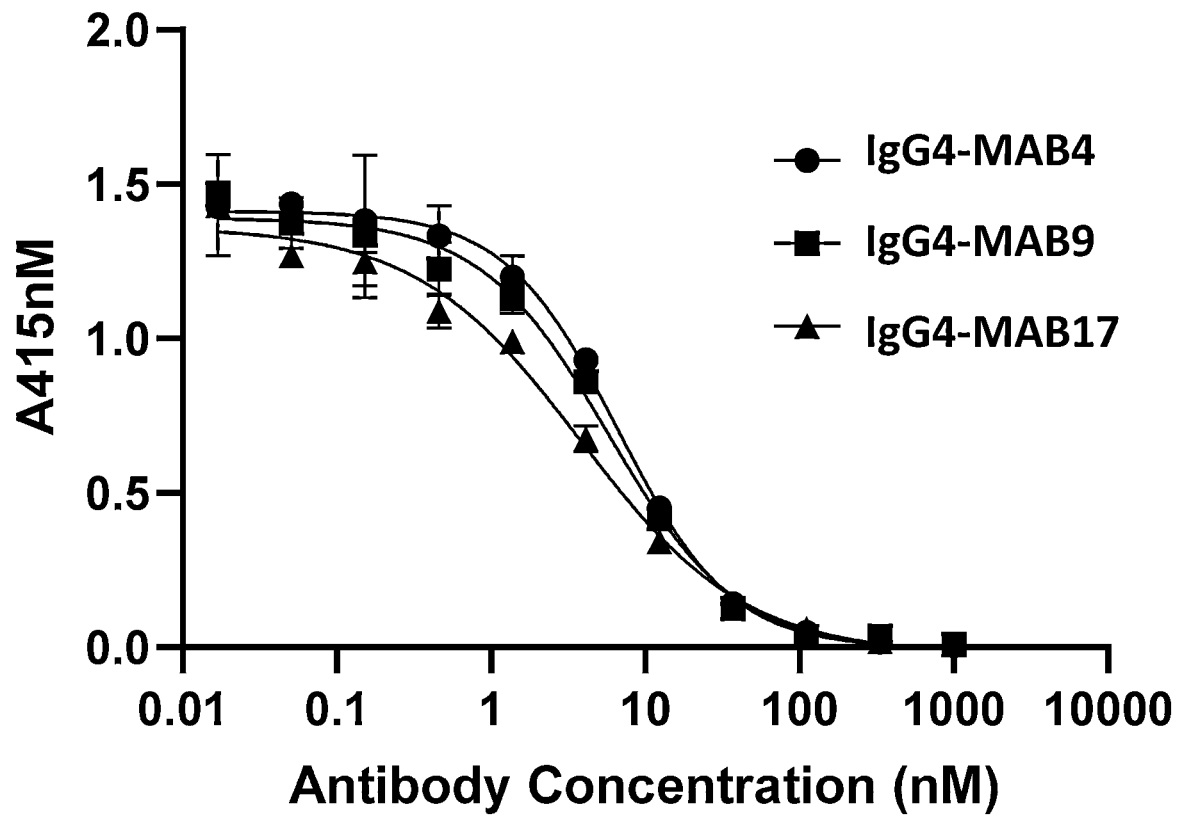
FIGS. 4A-4C depicts the antibody-mediated inhibition of complement-mediated hRBC lysis in 25% human serum by antibodies IgG4-MAB17, IgG4-MAB4, and IgG4-MAB9 (FIG. 4A), by antibodies 191 g, MAB4 and MAB9 (FIG. 4B), and by antibodies MAB2 (US20220380483A1) and MAB9 (FIG. 4C), as disclosed herein.
Figure 4B:
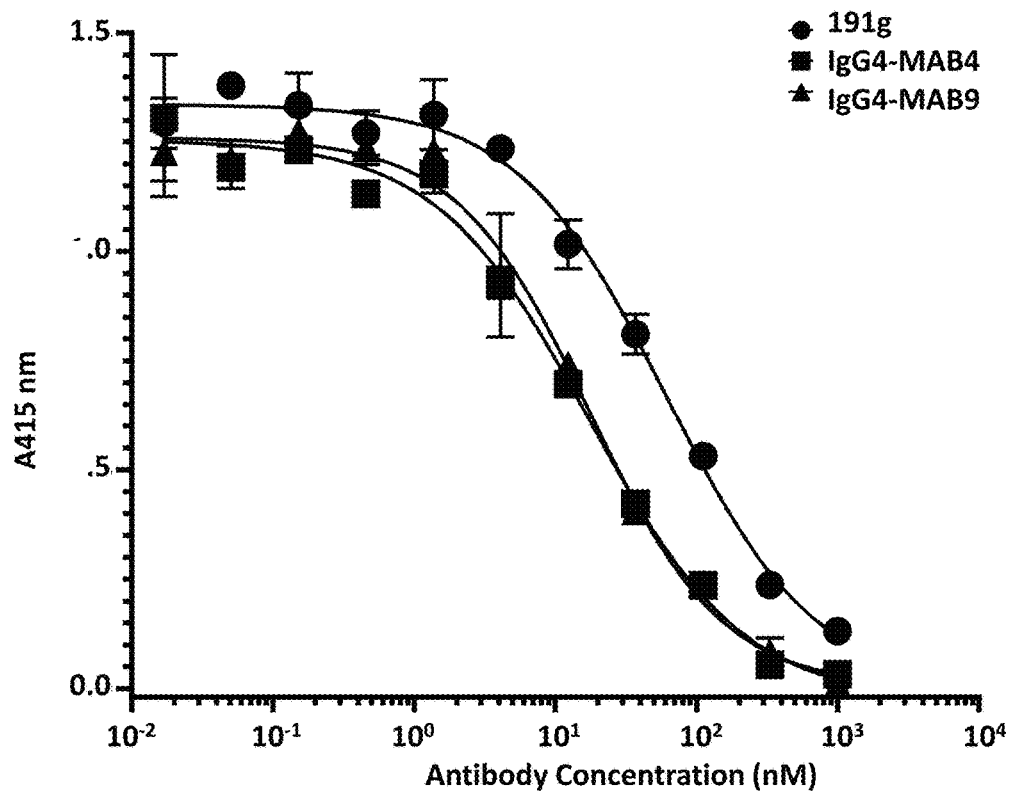

Of the 30 antibodies obtained from the screening process, we chose three for further characterization. MAB17 was chosen because it had reduced binding to human ProC1s_RQ, the precursor to active human C1s, as compared to the parental antibody 4011 g (FIG. 2A) and, therefore, might have a longer serum half-life due to reduced binding to the high level of ProC1s in serum (600 nM). Antibody MAB17 also had higher affinity to the target protein human C1s than its parental 4O11 g and recombinant TNT020, an antibody with selectivity for human C1s vs. human ProC1s (Patent application, US2020/0048332 A1) (Table 12). MAB4 and MAB9 were chosen because they have higher affinity to human C1s than their parental antibody 191 g and recombinant TNT020 (FIG. 2C and Table 12). The higher affinity for human C1s also resulted in improved potency in inhibiting lysis of sensitized human red blood cells in 25% serum versus 191 g (FIG. 4B and Table 14A).

Figure 4C:
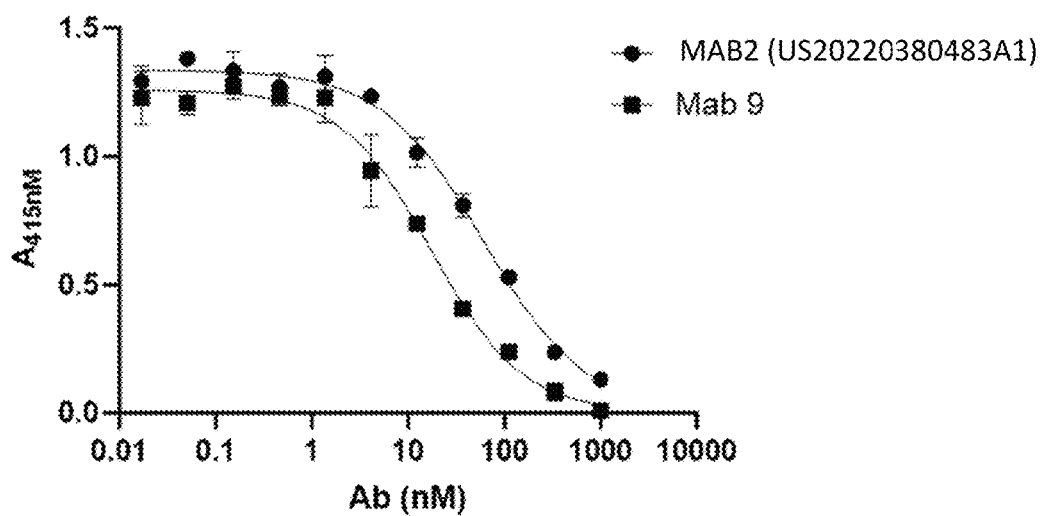

The antibody as referred herein as MAB9 was also compared to a different antibody that binds to the active form of C1s. This comparator antibody is referred to as MAB2 in WO2022246154A2 and US20220380483A1, each of which is hereby incorporated by reference in its entirety (hereinafter referred to as "MAB2 (US20220380483A1)". In the RBC lysis assay the IC50 of MAB2 (US20220380483A1) was calculated to be 61.2 nM and the IC50 of MAB9 (described herein) was calculated to be 17.6 nM. (FIG. 4C) Although a direct comparison of MAB39 to MAB2 (US20220380483A1) was not performed in the same assay, the data provided herein demonstrate that MAB39 and MAB9 have equivalent potency. Accordingly, the MAB9 antibody has over a 3× improvement in potency as compared to MAB2 (US20220380483A1) based upon the IC50 in the RBC lysis assay. This would also apply to MAB39, which would be expected to have more than 3× improvement over MAB2 (US20220380483A1).

We chose to further characterize and express MAB4, MAB9 and MAB17, in a human IgG4 backbone with the following modifications to the heavy chain; YTE: M252Y, S254T, T256E; Hinge region: S228P; CH2 region: L235E. The YTE modification was included to increase FcRn binding and serum half-life (Dall'Acqua, W F et al., *J Immunol*, 169: 5171-5180 (2002). The S228P modification was included to prevent Fab-arm exchange (Silva, J P et al., *J Biol Chem*, 290: 5462-5469 (2015). The L235E modification reduces binding to various FcgRs (Alegre, M L et al., *J Immunol*, 148: 3461-3468 (1992). To denote that these three antibodies are in this IgG4 background, we named these three antibodies IgG4-MAB4, IgG4-MAB9 and IgG4-MAB17.

Example 4: Inhibition of the Complement Classical Pathway

Figure 3:
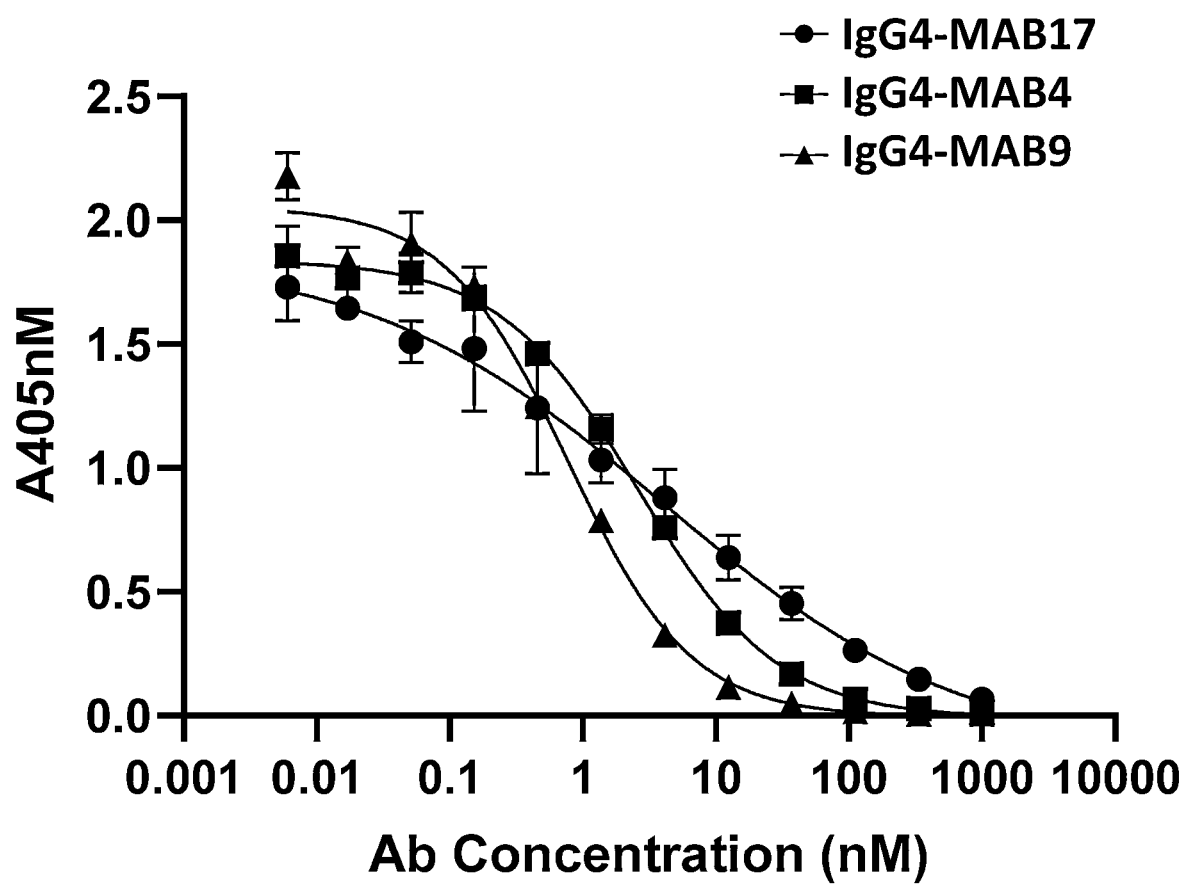
FIG. 3 depicts inhibition of the Wieslab complement classical pathway assay in 1% human serum by the antibodies IgG4-MAB17, IgG4-MAB4, and IgG4-MAB9, as disclosed herein.

An adaptation of the Wieslab® assay produced by SVAR LifeSciences, Malmo, Sweden and purchased from Eagle Bioscience, Amherst, NH (catalog number COMPL CL310) was used to determine the $IC_{50}$ of the antibodies to block the complement classical pathway (Frederikson, G N et al., *J. Imm Meth*, 166: 263-270 (1993)). The Wieslab® assay used plate-bound IgM to activate the complement classical pathway when 1% human serum was added to the wells leading to deposition of components of the membrane attack complex (MAC) in the wells of the plate. After incubation at 37° C. for 1 hour, the wells were washed and the C5bC9 component of the MAC was detected by ELISA with an alkaline phosphatase labelled antibody specific to the neoantigen expressed during MAC formation as described by the makers of the kit. The assay was modified by preincubating aliquots of 1% human serum with varying amounts of inhibitory antibody for 15 minutes at 37° C. before initiating the assay so $IC_{50}$ could be determined for inhibition of C5bC9 formation. The C5bC9 ELISA signal (A405 nm) vs. inhibitory antibody concentration was plotted to determine an $IC_{50}$ value fitting the data to the equation Y=Bottom+ (Top−Bottom)/(1+($IC_{50}$/X)^HillSlope) with GraphPad Prism software, version 9.2 (GraphPad Software, San Diego, CA). Results: The plots from the titration of IgG4-MAB4, IgG4-MAB9 and IgG4-MAB17 in the Wieslab Complement Classical Pathway Assay are shown in FIG. 3 and the $IC_{50}$ values are in Table 13.

TABLE 13

$IC_{50}$ values for inhibition of Wieslab complement classical pathway by IgG4-MAB4, IgG4-MAB9 and IgG4-MAB17.

| Antibody | $IC_{50}$ (nM) | $R^2$ |
|---|---|---|
| IgG4-MAB4 | 2.6 | 0.995 |
| IgG4-MAB9 | 0.78 | 0.991 |
| IgG4-MAB17 | 4.1 | 0.967 |

All three antibodies, IgG4-MAB4, IgG4-MAB9 and IgG4-MAB17, completely inhibited the Wieslab complement classical pathway assay with $IC_{50}$ values of 0.78 to 4.1 nM. In addition to showing that IgG4-MAB4, IgG4-MAB9, IgG4-MAB17 are potent inhibitors of the complement classical pathway, we have also tested these antibodies for inhibition of the Wieslab complement alternative and lectin pathways using similar methods. A selective CIs inhibitory antibody would not be expected to inhibit either the complement alternative or lectin pathways as C1 complex activation is specific for the complement classical pathway. IgG4-MAB4, IgG4-MAB9, IgG4-MAB17 were tested at concentrations up to 1 micromolar and no dose-dependent inhibition of either the complement alternative or lectin pathways using the Wieslab complement alternative pathway and lectin pathway assays was observed (data not shown).

In three separate Wieslab complement classical pathway assays we also compared IgG4-MAB9 to IgG-MAB39. The variable heavy chain region of MAB9 AND MAB39 have the same CDRs, but differ only in the N-terminal amino acid of the variable heavy chain region. IgG4-MAB9 has a glutamine (Q) at this position while IgG-MAB39 has a glutamate (E). IgG4-MAB9 had an $IC_{50}$+standard deviation of 0.69+0.28 nM, while IgG4-MAB39 had an $IC_{50}$+standard deviation of 0.49+0.11 nM. The change of the glutamine at the N-terminus of the VH in MAB9 to the glutamate at the N-terminus of the VH in MAB39 was done for manufacturing purposes. Without wishing to be bound to any particular theory, glutamine at the N-terminus may lead to spontaneous cyclization of the residue to pyroglutamate (pE) in vitro. This process is slower with a glutamate as compared to glutamine. Therefore, the manufacturing of MAB39 is advantageous as compared to MAB9. The antibody referenced in this example and the examples below as MAB9 comprises a VL of SEQ ID NO: 18, a light chain of SEQ ID NO: 236, a VH of SEQ ID NO: 17 and a heavy chain of SEQ ID NO 185, which has the "YTE" mutations in the constant domain. The antibody referenced in this example and the examples below as MAB39 comprises a VL of SEQ ID NO: 18, a light chain of SEQ ID NO: 236, a VH of SEQ ID NO: 342 and a heavy chain of SEQ ID NO 381, which has the "YTE" mutations in the constant domain.

Example 5: Inhibition of Human Serum Complement-Mediated Human RBC Lysis

To evaluate inhibition of MAC formation stimulated by the complement classical pathway at a higher, more physiologically relevant, serum concentration than used in the Wieslab® assay, the ability of the antibodies to inhibit lysis of sensitized human RBCs (hRBCs) was tested in an assay using 25% human serum. Methods: hRBCs were sensitized with a rabbit IgG to hRBCs (LS Bio, Seattle, WA, catalog #LS-C63000-2). Serial dilutions of the anti-C1s antibodies were preincubated with aliquots of human serum diluted in 0.1% gelatin, 5 mM veronal, 145 mM NaCl, 0.15 mM $CaCl_2$, 0.5 mM $MgCl_2$, 0.025% $NaN_3$, pH 7.3 (GVB++), added to sensitized hRBCs in GVB++ at a final human serum concentration of 25% and incubated at 37° C. in microtiter plates. After 1 hour, EDTA was added to 20 mM, the plates centrifuged at 500×g for 5 minutes at 4° C. and the supernatants assayed for absorbance at 415 nm. The data were plotted and used to calculate an $IC_{50}$ value fitting the data to the equation $Y=Bottom+(Top-Bottom)/(1+(IC_{50}/X)^{\wedge}HillSlope)$ with GraphPad Prism software, version 9.2 (GraphPad Software, San Diego, CA). hRBCs were obtained from three different donors and each were tested independently. FIG. 4A shows the plotted data from Donor 3 and Table 14 the $IC_{50}$ values for experiments in which inhibition of lysis of hRBCs from three different donors were tested in the presence of IgG4-MAB4, IgG4-MAB9, IgG4-MAB17 and recombinant TNT020. IgG4-MAB4, IgG4-MAB9 and IgG4-MAB17 showed complete inhibition of complement-mediated hRBC lysis in 25% human serum with $IC_{50}$ values of 3.8-22.1 nM from the three independent hRBC donors. In all cases, the $IC_{50}$ values for IgG4-MAB4, IgG4-MAB9 and IgG4-MAB17 were 1.39-3.84 times lower than the $IC_{50}$ values for recombinant TNT020.

TABLE 14

$IC_{50}$ values for inhibition of hRBC lysis in 25% human serum by IgG4-MAB4, IgG4-MAB9, IgG4-MAB17 and recombinant TNT020 of hRBCs from three independent donors.

| | Donor 1 | | Donor 2 | | Donor 3 | |
|---|---|---|---|---|---|---|
| Antibody | $IC_{50}$ [nM] | $R^2$ | $IC_{50}$ [nM] | $R^2$ | $IC_{50}$ [nM] | $R^2$ |
| IgG4-MAB4 | 14.9 | 0.9953 | 17.1 | 0.9858 | 6.6 | 0.9909 |
| IgG4-MAB9 | 12.9 | 0.9966 | 22.1 | 0.9914 | 5.8 | 0.9919 |
| IgG4-MAB17 | 11.0 | 0.9938 | 20.5 | 0.9979 | 3.8 | 0.9868 |
| TNT020 | 20.9 | 0.9932 | 30.7 | 0.9839 | 14.6 | 0.9848 |

We also compared parental antibody 191 g to two derivatives of 191 g, MAB4 and MAB9, using the inhibition of hRBC lysis assay in 25% human serum as shown in FIG. 4B and Table 14A, which illustrates that MAB4 and MAB9 completely inhibited hRBC lysis in 25% serum and had lower $IC_{50}$ values than the parental antibody 191 g.

TABLE 14A $IC_{50}$ values for inhibition of hRBC lysis in 25% human serum by 191g, IgG4-MAB4 and IgG4-MAB9.

| Antibody | $IC_{50}$ [nM] | $R^2$ |
|---|---|---|
| 191g | 61.2 | 0.989 |
| IgG4-MAB4 | 17.5 | 0.988 |
| IgG4-MAB9 | 17.6 | 0.985 |

Example 6: Inhibition of Human Serum C3b Deposition on hRBCs

In addition to causing cell lysis, complement classical pathway activation also leads to deposition of C3b on sensitized cells which can lead to phagocytosis by macrophages (Brown, Proc Natl Acad Sci USA 99:16969, 2002).

Figure 5:
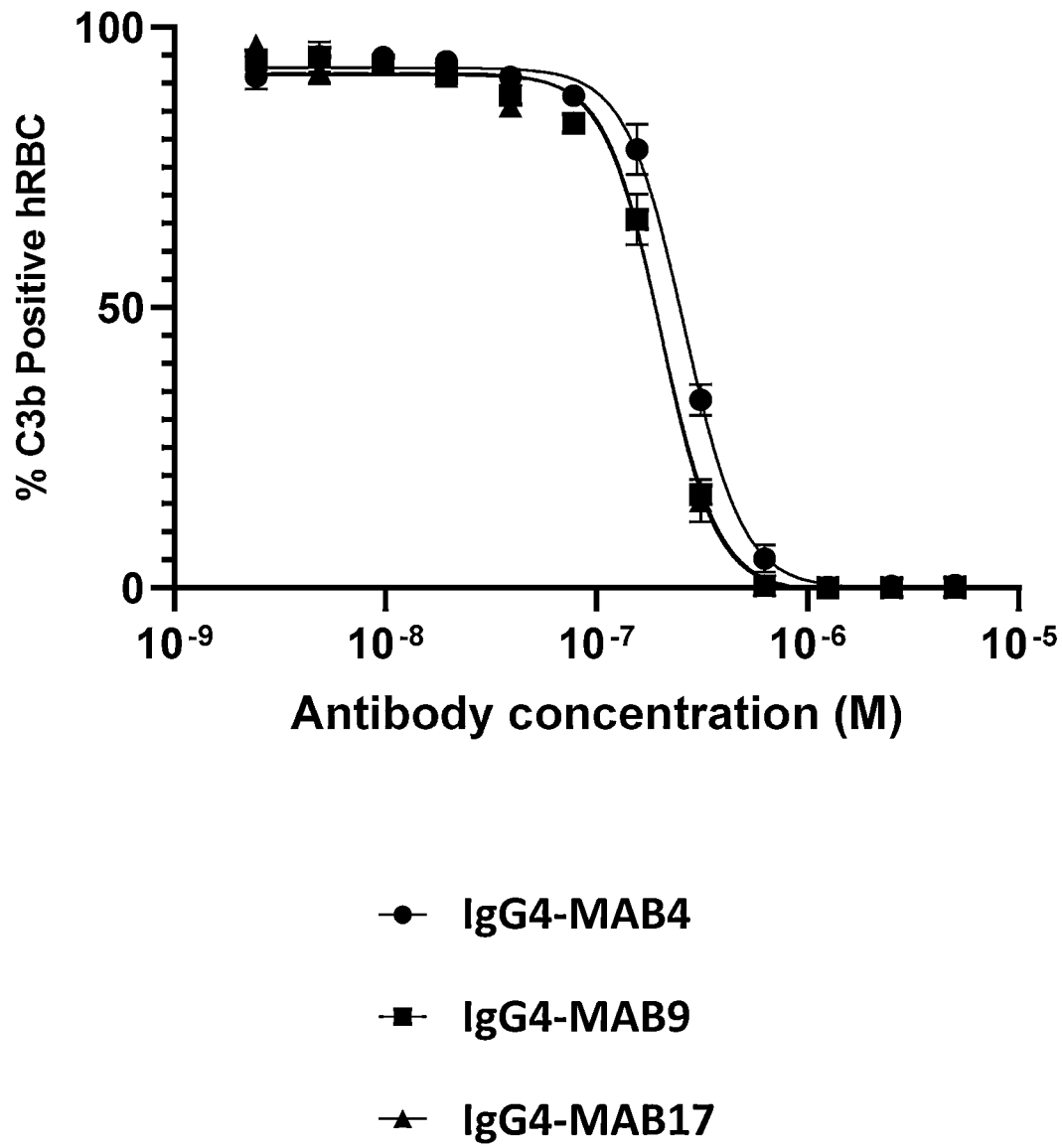
FIG. 5 depicts the antibody-mediated inhibition of C3b deposition on hRBCs by antibodies IgG4-MAB17, IgG4-MAB4, and IgG4-MAB9, as disclosed herein.

The ability of the antibodies to inhibit this endpoint of the complement classical pathway was evaluated using flow cytometry to examine C3b deposition from human serum on hRBCs sensitized with the same rabbit IgG to hRBCs used for hRBC lysis. Methods: hRBCs were sensitized with rabbit anti-hRBCs IgG (LS Bio, Seattle, WA, catalog #LS-C63000-2), using a higher dilution (less antibody) than in the hRBC lysis experiments to avoid too much lysis but still leading to C3b deposition. Human serum pre-incubated with serial dilutions of IgG4-MAB4, IgG4-MAB9, IgG4-MAB17 and recombinant TNT020 in GVB++ was added to the sensitized hRBCs at a final human serum concentration of 7.5%, incubated at 37° C. for 1 hour and then EDTA was added to 10 mM. The hRBCs were pelleted by centrifugation, washed with GVB without $MgCl_2$ or $CaCl_2$) and pelleted again. The resulting hRBCs were stained with a fluorescein isothiocyanate (FITC) conjugated antibody that binds to C3c/C3b (Abcam catalog number ab4212), counterstained with 7 amino-actinomycin D (7AAD) and sorted using an Intellicyte iQue3 to determine the percentage of hRBCs staining positive for C3b. The data were plotted and used to calculate an $IC_{50}$ value fitting the data to the equation Y=Bottom+(Top−Bottom)/(1+(IC50/X)^HillSlope) with GraphPad Prism software version 9.2 (GraphPad Software, San Diego, CA). hRBCs from two different donors were tested in this assay. Donor A was tested once and Donor B was tested twice. FIG. 5 shows the plotted data for inhibition of C3b-deposition 7.5% human serum by IgG4-MAB4, IgG4-MAB9, IgG4-MAB17 and TNT020 from Donor B (2) and Table 15 the $IC_{50}$ values for all three experiments.

TABLE 15

C3b deposition $IC_{50}$ values for IgG4-MAB4, IgG4-MAB9, IgG4-MAB17 and TNT020. RBCs from donor A were tested once while RBCs from donor B were tested twice (1) and (2).

| Antibody | Donor A $IC_{50}$ (nM) [R2] | Donor B (1) $IC_{50}$ (nM) [R2] | Donor B (2) $IC_{50}$ (nM) [R2] |
|---|---|---|---|
| IgG4-MAB4 | 69.2 [0.994] | 193 [0.994] | 262 [0.998] |
| IgG4-MAB9 | 64.1 [0.983] | 124 [0.997] | 202 [0.997] |
| IgG4-MAB17 | 40.7 [0.996] | 112 [0.995] | 202 [0.995] |
| TNT020 | 52.9 [0.980] | 238 [0.988] | 688 [0.995] |

In summary, IgG4-MAB4, IgG4-MAB9 and IgG4-MAB17 showed complete inhibition of C3b deposition on sensitized hRBCs in 7.5% human serum with $IC_{50}$s of 40.7-262 nM.

Example 7: Pharmacokinetics of IgG4-MAB4, IgG4-MAB9 and IgG4-MAB17 Dosed Intravenously (IV) in Cynomolgus Monkeys We dosed IgG4-MAB4, IgG4-MAB9 and IgG4-MAB17 IV in cynomolgus monkeys to understand the pharmacokinetics of the antibodies in a primate species where the amino acid sequence of C1s is 94% identical to human C1s.

IgG4-MAB4, IgG4-MAB9 and IgG4-MAB17 were dosed intravenously in cynomolgus monkeys to understand the pharmacokinetics of the antibodies in a primate species. Two different doses of the antibodies were evaluated, 3 and 30 mpk. Methods: Male cynomolgus monkeys (*Macaca fascicularis*) weighing approximately 2-4 kg each were dosed IV in the cephalic vein with either 3 mg antibody/kg body weight (mpk) or 30 mpk of IgG4-MAB4, IgG4-MAB9 and IgG4-MAB17 in 20 mM Histidine, 8% (weight/volume) sucrose. The antibody solutions were prepared immediately before dosing and a volume of 4 ml/kg body weight was administered over 10 minutes to cohorts of three animals for each of the two doses. Blood was collected and placed in tubes without anticoagulant to obtain serum at the following time points: prior to dosing (pre-dose), and 2 hours (h), 8 h, 24 h, day 2, day 3, day 7, day 10, day 14, day 21, day 28, day 42, day 56 and day 70 post dosing. At the end of the study the serum concentration of the dosed antibodies was determined for each sample using an ELISA to detect total human IgG.

ELISA Materials: High Bind Microplate, Corning (Glendale, CA), Cat #: 9018 Tween-20: Sigma (Burlington, MA), Cat #: P7949-100 mL Proclin300, Sigma (Burlington, MA), Cat #:48912-U Goat anti-Human Antibody, Southern Biotech (Birmingham, AL), Cat #: 2049-01 Human IgG-heavy and light chain monkey-adsorbed Antibody, Bethyl (Montgomery, TX), Cat #A80-319P TMB substrate solutions (A and B), InnoReagents, Cat #: TMB-S-003 10× phosphate buffered saline (PBS): 1370 mM NaCl, 100 mM $Na_2HPO_4$, 27 mM KCl, 20 mM $KH_2PO_4$ 1×PBS: 137 mM NaCl, 10 mM $Na_2HPO_4$, 2.7 mM KCl, 2 mM $KH_2PO_4$ (Dilute from 10×PBS using Milli Q water) Assay Diluent:1×PBS, 1% BSA, 0.05% Tween-20, 0.05% proclin 300, Washing Buffer (PBST): 1×PBS with 0.05% Tween-20 Stop solution: 2N $H_2SO_4$ Male Cynomolgus monkey serum, ELISA plate reader: SpectraMax M2, Molecular Devices (San Jose, CA) SoftMax Pro GxP 5.4.4 software, Molecular Devices (San Jose, CA)

Figure 6:
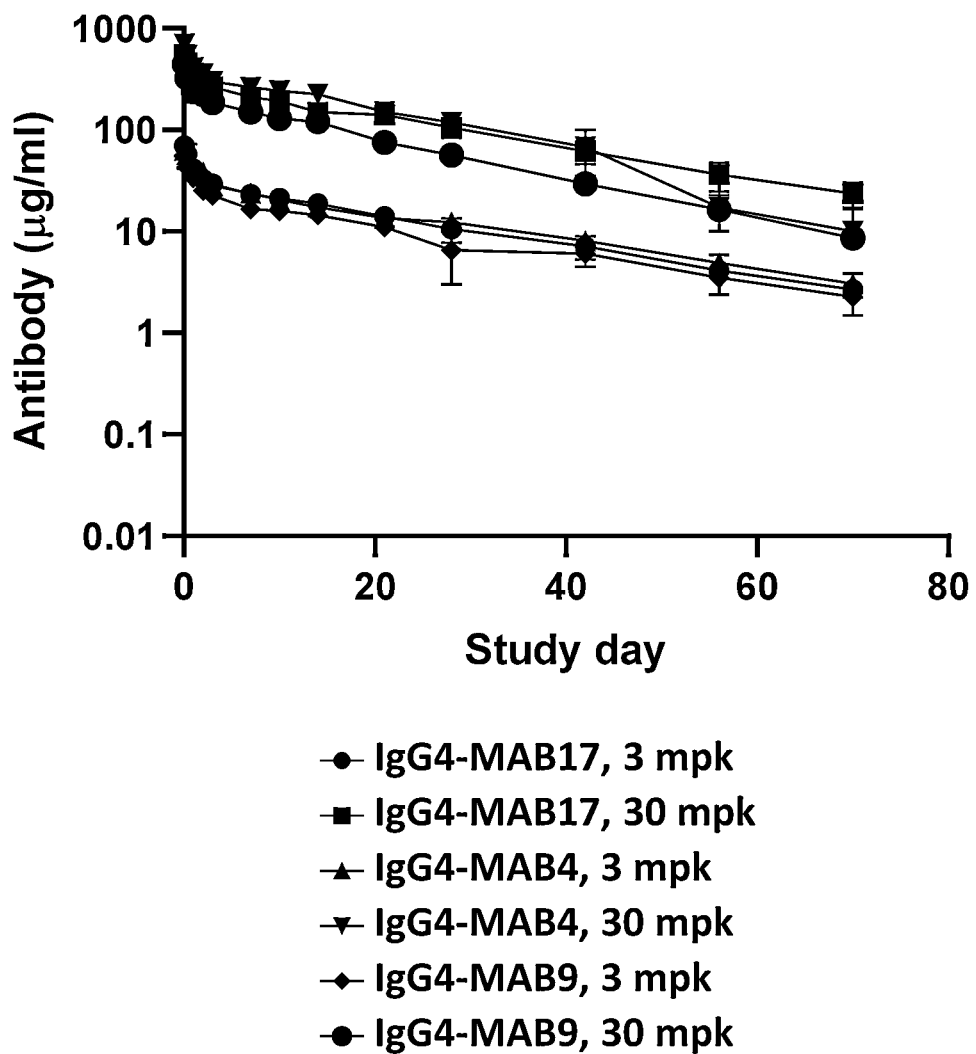
FIG. 6 shows mean concentrations of antibodies after a single IV dose of 3 or 30 mg/kg body weight (mpk) over time in cynomolgus monkeys, by antibodies IgG4-MAB17, IgG4-MAB4, and IgG4-MAB9, as disclosed herein.

For assay plate coating, goat anti-human antibody was diluted in PBS. 50 μL/well was added into the ELISA plate. The plate was sealed and incubated overnight in 4° C. The plate was washed 3 times with 300 μL of washing buffer, then blocked with 200 μL/well blocking buffer. The plate was sealed and incubated at RT for 1-3 hr, constantly shaking at 300 rpm. The plate was then washed 3 times with 300 μL of washing buffer. For preparation of the anti-C1s antibody standard, a 2-fold serial dilution was made in 5% male monkey serum. Eight standards ranged from 50 to 0.391 ng/ml of IgG4-MAB4, IgG4-MAB9 and IgG4-MAB17. For QC preparation, two sets of QCs were prepared in 5% pooled monkey serum for each antibody: HQC (40 ng/mL), MQC (8 ng/mL) and LQC (2 ng/mL). For sample preparation: All serum samples were diluted at 20-fold in Assay Diluent first. Additional dilutions were made in 5% male monkey serum. For sample incubation, the diluted standards/QCs/samples were added at 50 μL/well into the plate. The plate was sealed and incubated at 37° C. for 1 hr. For the detection reagent reaction, the plate was first washed 3 times with 300 μL of washing buffer. Human IgG-heavy and light chain monkey-adsorbed Antibody (A80-319P) was diluted in assay diluent. The diluted detection antibody was added into the assay plate at 100 μL/well. The assay plate was then incubated at 37° C. for 30 min. For substrate reaction and plate reading, the plate was first washed 3 times with 300 μL of washing buffer. TMB working solution was prepared by bringing the substrate to room temperature 30 min before use, mixing equal volume of substrate A and substrate B. 100 μL/well of premixed TMB substrate was added to each well and then incubated at room temperature for about 10 min. 100 μL/well of ELISA stopping solution was then added. The plate was then mixed and read at 450/630 nm wavelength using SpectraMax M2. Data was processed using Soft Max Pro GxP, and the standard curve was fit using 4-PL model. PK parameters were calculated using WinNonlin version 8.2 software, Certara (Princeton, NJ) Results: A plot of the mean IgG4-MAB4, IgG4-MAB9 and IgG4-MAB17 concentrations (n=3 animals/treatment group) for the cynomolgus monkeys dosed with 3 and 30 mg/kg body weight (mpk) are plotted in FIG. 6. The calculated pharmacokinetic parameters are listed in Table 16.

TABLE 16

Pharmacokinetic parameters of IgG4-MAB4, IgG4-MAB9 and IgG4-MAB17 when dosed at 3 or 30 mpk in cynomolgus monkeys.

| Dose and Ab | 3 mpk IgG4-MAB17 IV | 30 mpk IgG4-MAB17 IV | 3 mpk IgG4-MAB9 IV | 30 mpk IgG4-MAB9 IV | 3 mpk IgG4-MAB4 IV | 30 mpk IgG4-MAB4 IV |
|---|---|---|---|---|---|---|
| Mean clearance ± SD (ml/day/kg) | 3.38 ± 0.58 | 3.78 ± 0.65 | 3.16 ± 0.18 | 3.43 ± 0.76 | 4.19 ± 0.33 | 6.22 ± 0.96 |
| Mean volume of distribution steady state ± SD (ml/kg) | 89 ± 11 | 100 ± 7.2 | 92 ± 9.9 | 75.4 ± 4.8 | 124 ± 16 | 139 ± 14 |
| Mean serum half life ± SD (days) | 19.8 ± 4.4 | 19.2 ± 2.7 | 20.7 ± 2.8 | 15.6 ± 3.2 | 21.7 ± 1.3 | 18.3 ± 8.2 |
| Area under the curve through last day (day*mg/ml) | 824 ± 98 | 7407 ± 1027 | 857 ± 20 | 7373 ± 2652 | 556 ± 195 | 4538 ± 542 |

Example 8: Inhibition of the Complement Classical Pathway is Sustained Over Time in Cynomolgus Monkeys Treated with IgG4-MAB39 Dosed Subcutaneously (SC)

Figure 7:
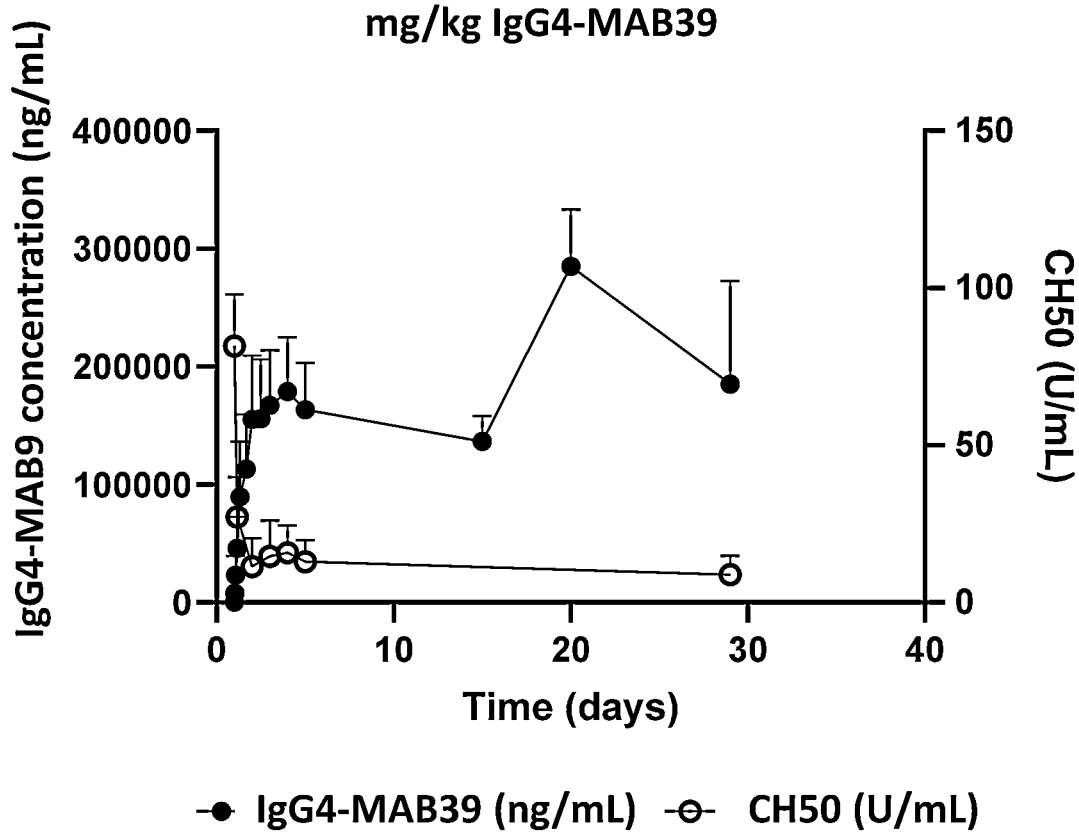
FIG. 7 shows the concentration of IgG4-MAB39 in serum diluted by the dilution factor necessary to obtain 50% lysis of sensibilized sheep RBCs (CH50). The serum was obtained from cynomolgus monkeys treated with a single subcutaneous dose of 20 mg/kg body weight (mpk) of IgG4-MAB39. The concentration of IgG4-MAB39 at CH50 was monitored over time for up to 30 days.
Figure 8:
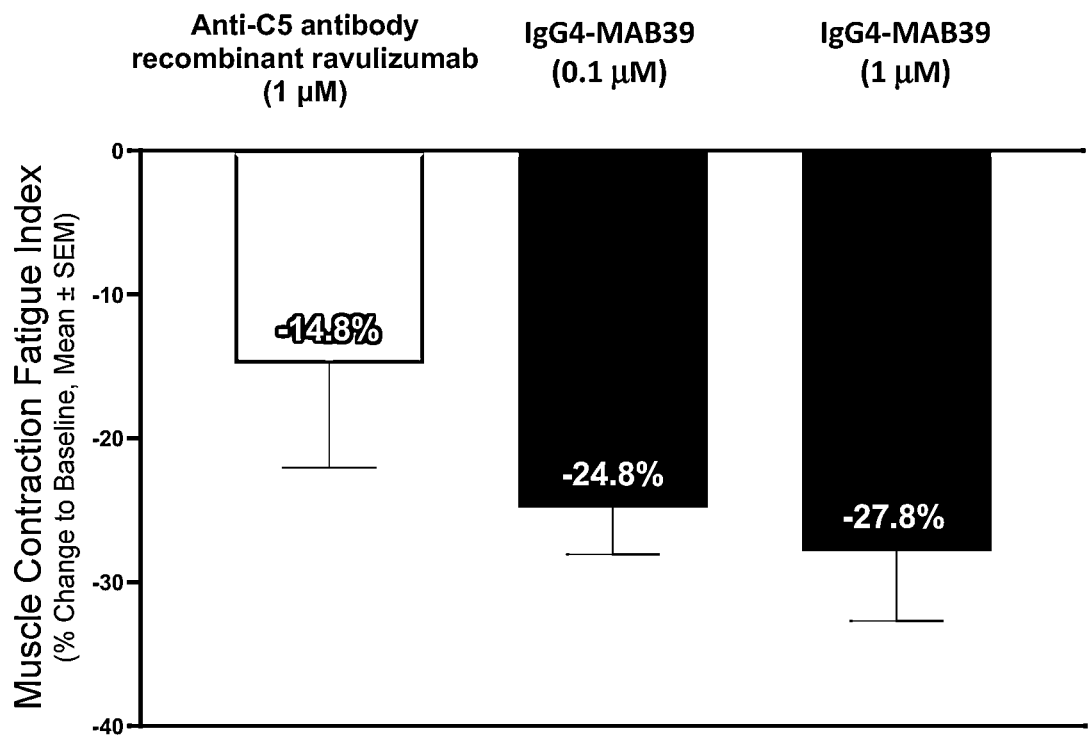
FIG. 8 depicts preclinical cell-based model of myasthenia gravis was used to assess the effect of complement classical pathway inhibition with IgG4-MAB39 on neuromuscular junction functionality. Human induced pluripotent stem cell (iPSC)-derived motor neuron and skeletal muscle cells were co-cultured in a two-chamber compartmentalized microfluidic device with motor neuron on one chamber and muscle cells on the second chamber. Sera (10% concentration) from AChR+MG patients (n=3) supplemented with complement-preserved pooled normal human sera (1%), were added to the skeletal muscle cell reservoir in the absence or presence of IgG4-MAB39 or anti-C5 antibody recombinant ravulizumab (from published patent). The motor neuron chamber received electrical stimulation at 2 Hz for 2 minutes and skeletal muscle contraction was monitored in real-time. The muscle contraction fatigue index score was calculated based on the area under the curve (AUC) of the region of interest (ROI) divided by tetanus response from that myotube (maximum ROI trace height×duration of stimulation). IgG4-MAB39 decreased the muscle contract fatigue index score in AChR+MG patient sera, an indication of improved neurotransmission, neuromuscular junction functionality, and muscle contraction. The response profile of IgG-MAB39 was similar to that of anti-C5 antibody recombinant ravulizumab. IgG4-MAB39 improved neurotransmission impairment in a physiologically relevant in vitro model of AChR+MG. This finding provides a scientific rationale for targeting complement classical pathway in AChR+MG.

The ability of IgG4-MAB39 to sustain classical pathway inhibition over time was evaluated. Serum from cynomolgus monkeys was obtained for up to 30 days following the administration of a single subcutaneous dose of 20 mg/kg of IgG4-MAB39 (n=10 animals). The dilution factor of the serum necessary to obtain 50% lysis of sensitized sheep RBCs (CH50) was determined at multiple time points using the Complement CH50 Test Kit (Haemoscan. Groningen, The Netherlands) according to the manufacturer's instructions. The serum concentration of IgG4-MAB39 was quantified using an electrochemiluminescent immunoassay at the dilution factor of CH50 is depicted over time by the filled circles shown in FIG. 7. In summary, a single subcutaneous dose of IgG4-MAB39 at 20 mg/kg in cynomolgus monkeys led to a rapid and sustained inhibition of complement classical pathway.

Example 9: Comparative Biophysical and Functional Studies of the Anti-Active C1s Antibody MAB39 and its Preclinical Precursor MAB9

Three comparative studies were performed to determine if there are differences between MAB39 and its precursor MAB9 in terms of biophysical and functional properties: Surface Plasmon Resonance analysis to assess binding affinity to human active C1s, Wieslab Classical Pathway assay to assess potency, and Classical pathway mediated cell lysis assay using antibody-sensitized sheep red blood cells to assess potency. Assays assessing potency used 1% human sera.
Materials and Methods
Binding of MAB39 and MAB9 to Human Active C1s at 37° C./pH 7.4 Measured by Surface Plasmon Resonance. Human active C1s purified from serum was procured from Complement Technologies, Tyler, TX (catalog number A104). Studies to evaluate MAB39 and MAB9 binding to human active C1s at 37° C. were performed on a Biacore 4000 and Biacore T100 (Cytiva, Marlborough, MA), respectively. Goat anti-human antibody (ThermoFisher, Waltham, MA, USA, catalog number H10500) was amine-coupled to a C1 sensor chip (Cytiva, Marlborough, MA, USA, catalog number BR100535). MAB39 was diluted to 6.67 nM and MAB9 was diluted to 10 nM in 50 mM HEPES pH 7.4, 150 mM NaCl, 1.3 mM Ca, 0.02% Tween-20, 1 mg/mL BSA (HBS). MAB39 was captured for 60 seconds to produce surface densities of 200 RU and MAB9 was captured for 30 seconds to produce surface densities of 10 to 20 RU. Human active C1s was tested for binding using a 3-fold titration series in HBS with a maximum concentration of 12.3 nM for MAB39 and 16 nM for MAB9. Data were processed by subtracting responses from a reference surface as well as a buffer injection. The processed data were fitted with a 1:1 interaction model including baseline offset and bulk refractive index shifts in the association phase. Surfaces were regenerated with a 12 second injection of 1/100 dilution of H3PO4 for MAB39 and 12 second injection of 1/50 dilution of H3PO4 for MAB9. Replicate experiments were performed (n=2 for MAB9 and n=4 for MAB39).

Potency of MAB39 and MAB9 in the Wieslab Classical Pathway Assay. Inhibition of complement classical pathway by MAB39 and MAB9 was assessed by using the Wieslab Classical Pathway ELISA kit (SVAR LifeSciences, Malmo, Sweden, catalog number COMPLCP310), which measures the amount of C5b9 formed on IgM-coated plates upon addition of human serum. Serial dilutions of MAB39 and MAB9 were prepared using diluent buffer contained in the kit then combined with normal human serum (Complement Technologies, Tyler, TX, USA, catalog number NHS), with final antibody concentrations ranging from 0.01 to 600 nM with a 3-fold sequential serial dilution and final normal human serum concentration of 1%. Test samples, along with reconstituted positive and negative control human sera contained in the kit, diluent alone, and 0 nM antibody NHS control, were added to the plate. Then the plate was sealed with a plate sealer and incubated for 1 hour at 37° C. The plate was processed according to the manufacturer's protocol with reagents contained in the kit. Briefly, the plate was washed 3 times with wash buffer, followed by the addition of anti-C5b9 alkaline phosphatase conjugated detection antibody for 30 minutes at room temperature, washed 3 times with wash buffer, incubated with substrate solution for 30 minutes at ambient temperature, and finally the reaction was quenched with the addition of 5 mM EDTA stop solution. The plate was then read at absorbance 405 nm (SpectraMax 250, Molecular Devices, San Jose, CA, USA). For data analysis, the diluent alone value (blank control) was subtracted from all samples. The % complement classical pathway CCP activity was calculated using the following formula: % CCP activity=(Sample−Negative Control)/(Positive Control−Negative Control)×100. Next, the % CCP activity was normalized using the following formula: (% CCP activity of sample)/(mean of % CCP activity at lowest concentration of each data set)×100. The normalized % complement classical pathway activity was then plotted against inhibitor concentration and fitted to a standard 4-parameter dose-response inhibition using GraphPad (GraphPad Software, San Diego, CA, USA, version 9) to calculate the IC50 values. Three independent experiments were performed. Each experiment had 2 replicates. IgG4 isotype (recombinantly produced at Atum, Newark, CA, USA) served as a negative control antibody.

Potency of MAB39 and MAB9 in an Antibody-sensitized Sheep Red Blood Cell Lysis Assay. Inhibition of complement classical pathway by MAB39 and MAB9 was also determined with a hemolysis assay that utilizes antibody-sensitized sheep red blood cells. In this assay, complement classical pathway and MAC-mediated lysis are induced on antibody-coated sheep red blood cells upon exposure to human sera. Serial dilutions of MAB39 and MAB9 were prepared using GVB++ buffer containing calcium and magnesium (Complement Technologies, Tyler, Texas, USA, catalog number B102) then combined with normal human serum (Quidel, San Diego, CA, USA, catalog number 185487) and antibody-sensitized sheep red blood cells ($5\times10^7$ cells per well, Complement Technologies, Tyler, Texas, USA, catalog number B202) in a tissue culture treated round bottom 96-well plate (Sarstedt, Numbrecht, Germany, catalog number 82.1582001). The final antibody concentrations ranged from 0.05 to 1000 nM with a 3-fold serial dilution and final human serum concentration was 1%. Controls included GVB++ buffer alone (blank), antibody-sensitized sheep red blood cells in GVB++ with 40% water (total lysis control), antibody-sensitized sheep red blood cells in GVB++ with 1% normal human serum final concentration (0 nM antibody NHS control), antibody-sensitized sheep red blood cells in GVB++, antibody-sensitized sheep red blood cells in GVB++ with 10 mM EDTA final concentration, and antibody-sensitized sheep red blood cells in GVB++ with 1% normal human serum final concentration and 10 mM EDTA final concentration. The plate was incubated for 1 hour at 37° C., centrifuged at 1000×gravity (g) for 3 minutes to pellet intact cells, and the supernatants were collected and transferred to a flat bottom 96-well plate (Corning, Corning, NY, USA, catalog number 3596). Hemoglobin release from lysed red blood cells in the supernatant was detected by measuring the optical density (OD) at 412 nm using a spectrophotometer (PHERAStar, BMG Lab Tech, Ortenberg, Germany). For data analysis, the GVB++ alone value (blank control) was subtracted from all samples. The % sheep red blood cell (sRBC) hemolysis was calculated using the following formula: % sRBC hemolysis=(ODtest)−(ODblank)/(ODtotal lysis)−(ODblank)×100. Next, the % sRBC hemolysis was normalized using the following formula: (% sRBC hemolysis of sample/mean of % sRBC hemolysis at lowest concentration of each data set)×100. The normalized % sRBC hemolysis was then plotted against inhibitor concentration and fitted to a standard 4-parameter dose-response inhibition using GraphPad (GraphPad Software, San Diego, CA, version 9) to calculate the IC50 values. Three independent experiments were performed. Each experiment had 2 replicates. IgG4 isotype (recombinantly produced at Atum, Newark, CA, USA) served as a negative control antibody.

Results

Comparison of Binding Affinities of MAB39 and MAB9 to Human Active C1s by Surface Plasmon Resonance. The human active C1s association constant (ka), disassociation constant (kd) and affinity (KD) for MAB39 and MAB9 were determined in separate experiments (Table 17). The KD values±SD of MAB39 and MAB9 for human active C1s were 0.0105±0.0046 nM and 0.0071±0.00054 nM, respectively, and no statistical difference in binding affinity to human active C1s was observed between MAB39 and MAB9. Statistical analysis was performed using paired t-test, with p value of 0.6168.

TABLE 17

Binding Affinity of MAB39 and MAB9 to Human Active C1s

| Antibody | Ligand | $Ka\ (M^{-1}sec^{-1}) \pm$ SD | $Kd\ (sec^{-1}) \pm$ SD | KD (nM) ± SD |
|---|---|---|---|---|
| MAB39 | Human active C1s | $1.19 \pm 0.07 \times 10^7$ | $1.25 \pm 0.62 \times 10^{-4}$ | $0.0105 \pm 0.0046$ |
| MAB9 | Human active C1s | $1.69 \pm 0.01 \times 10^7$ | $1.20 \pm 0.08 \times 10^{-4}$ | $0.0071 \pm 0.0005$ |

These very high affinities represent a significant improvement as compared to a parental antibody, referred to as MAB2 in WO2022246154A2. In a direct comparison between MAB2 (US20220380483A1) and MAB9 in a Surface Plasmon Resonance (SPR) assay and MAB9 was found to have an affinity that is about 10× higher than MAB2 (US20220380483A1). Thus, based on the KD reported above for MAB39 and MAB9, MAB39 would also be expected to have a significant improvement in affinity as compared to MAB2.

Figure 9:
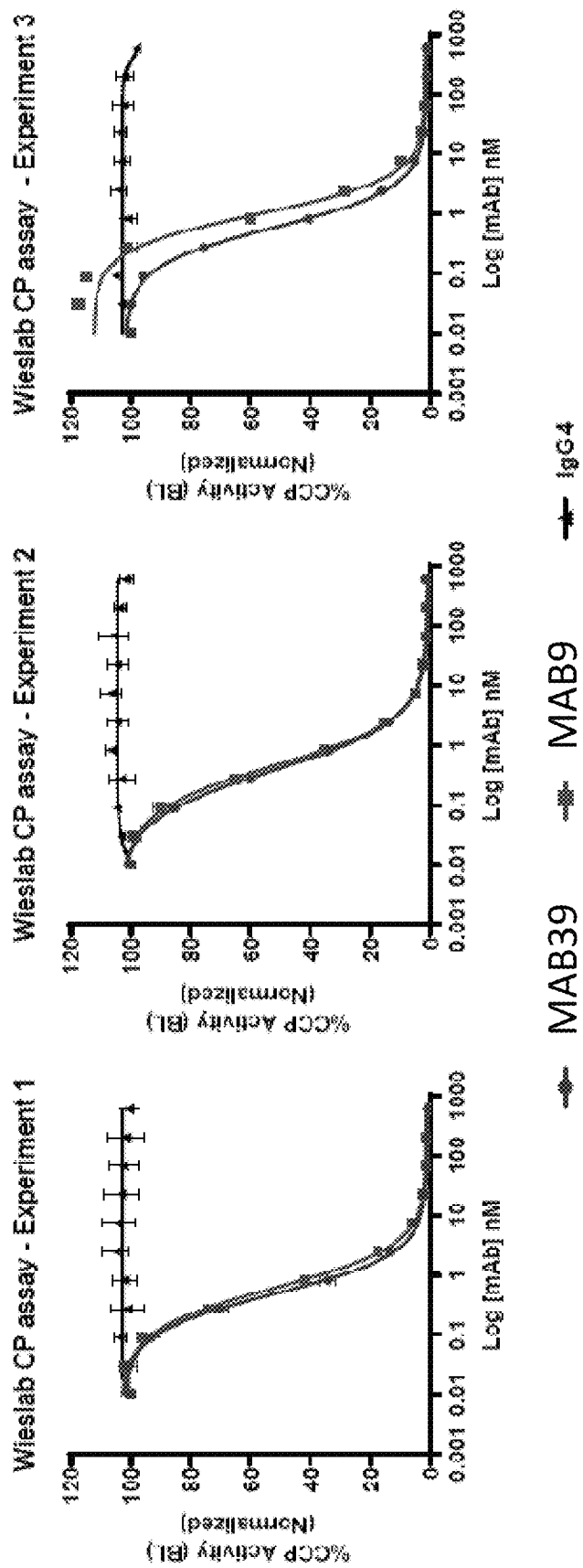
FIG. 9 shows the dose-dependent complete inhibition of the Classical Pathway with MAB39 and its pre-clinical precursor MAB9 in the Wieslab assay.

Comparison of Potency Between MAB39 and MAB9 in the Wieslab Classical Pathway Assay. Complement classical pathway activity versus antibody concentrations were plotted and the IC50 values were calculated. FIG. 9 shows the results from all 3 independent experiments evaluating the potency of MAB39 and MAB9 in the Wieslab Classical Pathway assay. MAB39 and MAB9 exhibited similar dose-dependent and complete inhibition of the classical pathway in the Wieslab ELISA assay at 1% human serum concentration. In contrast, an IgG4 isotype control antibody had minimal effect and did not inhibit the classical pathway. The IC50 value for MAB39 was 0.49±0.11 nM and MAB9 was 0.69±0.28 nM, representing the mean and standard deviation from the 3 independent experiments (Table 18). Thus, no statistical difference in potency was observed between MAB39 and MAB9 in the Wieslab Classical Pathway assay.

TABLE 18

IC50 values for MAB39 and MAB9 in the Wieslab
Classical Pathway Assay with 1%
Human Serum

| Antibody | IC50 (nM) |
| --- | --- |
| MAB39 | 0.49 ± 0.11 |
| MAB9 | 0.69 ± 0.28 |

The values represent the mean and standard deviation from three independent experiments performed in duplicates.

Figure 10:
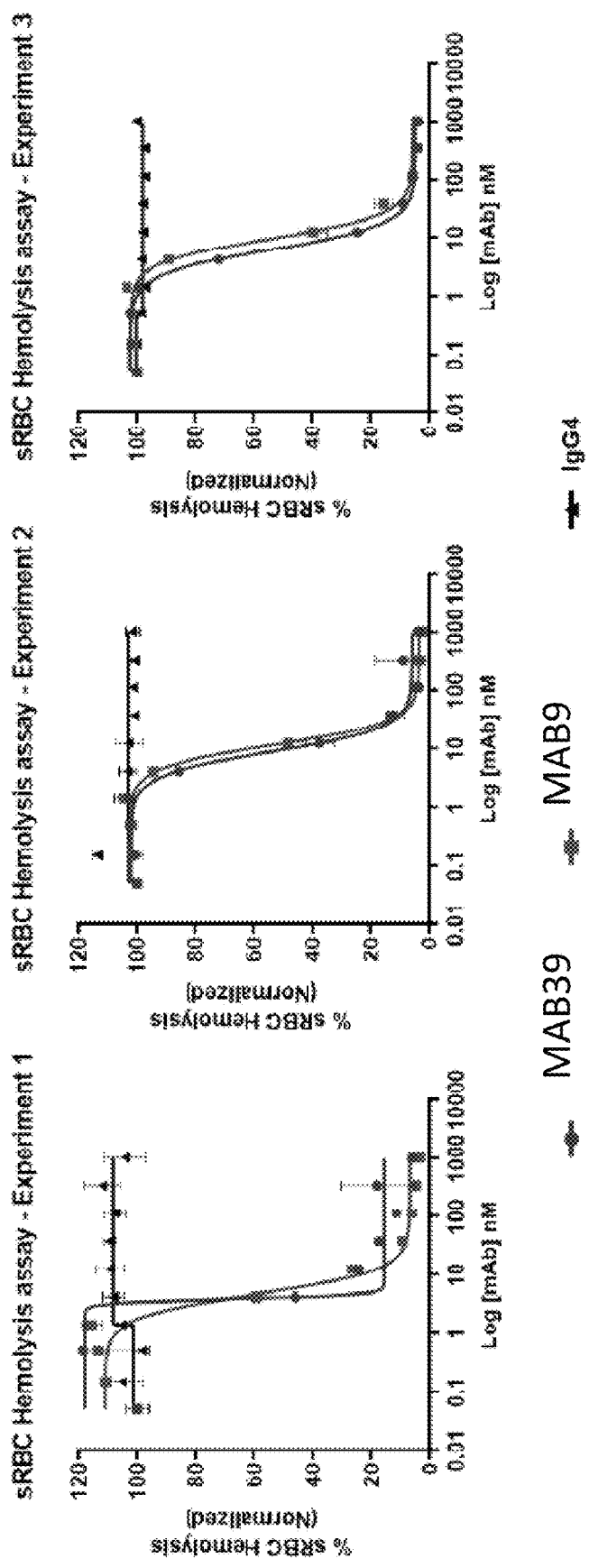
FIG. 10 shows dose-dependent complete inhibition of the Classical Pathway with MAB39 and its pre-clinical precursor MAB9 in the antibody-sensitized sheep red blood cell lysis assay.

Comparison of Potency Between MAB39 and MAB9 in an Antibody-sensitized Sheep Red Blood Cell Lysis Assay. The percentage hemolysis versus antibody concentrations were plotted and the IC50 values were calculated. FIG. 10 shows the graphs from all 3 independent experiments evaluating the potency of MAB39 and MAB9 in the antibody-sensitized sheep red blood cell lysis assay. MAB39 and MAB9 exhibited similar dose-dependent and complete inhibition of the classical pathway in the antibody-sensitized sheep red blood cell lysis assay at 1% human serum concentration. The isotype control antibody did not inhibit the classical pathway mediated cell lysis. The IC50 value for MAB39 was 6.30±2.51 nM and MAB9 was 8.57±3.57 nM, representing the mean and standard deviation from the 3 independent experiments (Table 19). Consistent with the findings in the Wieslab Classical Pathway assay, no statistical difference in potency was observed between MAB39 and MAB9 in the antibody-sensitized sheep red blood cell lysis assay.

TABLE 19

IC50 values for MAB39 and MAB9 in the
antibody-sensitized sheep red blood cell lysis assay

| Antibody | IC50 (nM) |
| --- | --- |
| MAB39 | 6.30 ± 2.51 |
| MAB9 | 8.57 ± 3.57 |

The values represent the mean and standard deviation from 3 independent experiments performed in duplicates.

Results: MAB9 and MAB39 exhibited comparable binding affinities to the target protein human active C1s. The KD values±SD of MAB39 and MAB9 for human active C1s were 0.0105±0.0046 nM and 0.0071±0.00054 nM, respectively. Both antibodies demonstrated comparable potency, with complete inhibition of the classical pathway in the Wieslab and antibody-sensitized red blood cell lysis assays. For the Wieslab Classical Pathway assay using 1% human sera, the IC50 values±standard deviation (SD) for MAB39 was 0.49±0.11 nM and MAB9 was 0.69±0.28 nM. For the antibody-sensitized sheep red blood cell lysis assay using 1% human sera, the IC50 values±SD for MAB39 was 6.30±2.51 nM and MAB9 was 8.57±3.57 nM.

Conclusions: The single amino acid substitution from glutamine (MAB9) to glutamate (MAB39) had no statistically observable effect on the binding affinity to human active C1s by MAB9 or MAB39, and both molecules showed equivalent in vitro inhibition (i.e., IC50 values) of classical pathway activity in 2 well-established complement classical pathway assays. These findings demonstrate that MAB39 and its analog and precursor, MAB9, exhibit indistinguishable biophysical and functional properties, and that preclinical studies conducted with MAB9 can be used to support the clinical evaluation of MAB39.

Example 10: Anti-Active C1s Antibodies Prevent Neurotransmission Impairment in a Functional In Vitro Model of Myasthenia Gravis (MG)

A functional human on-chip model of MG was used to interrogate the effect of IgG4-MAB9 on physiologically relevant readouts that include deposition of the pore-forming membrane attack complex (MAC), neurotransmission and muscle fatigability.

The effect of IgG4-MAB9 on neurotransmission and muscle fatigue was assessed using an in vitro human on-chip model of MG composed of human iPSC-derived motor neurons and primary human skeletal muscle cells in NHS-supplemented AChR+MG patient sera.

Human iPSC-derived motor neurons and primary human skeletal muscle cells were cultured in separate chambers of a two-chamber compartmentalized microfluidic device for one month. On the day of the experiment, 10% AChR+MG patient sera or healthy volunteer sera each containing 1% NHS—supplemented sera was added to the wells. The cells were treated with IgG4-MAB9, recombinant ravulizumab, or left untreated for three hours. Muscle contraction fatigue was assessed by stimulating cells in the motor neuron chamber with electrical stimulation at 2 Hz for 2 minutes and recording the resulting muscle contractions in the skeletal muscle cell chamber. Muscle contraction fatigue index score was calculated based on the area under the curve of the region of interest divided by tetanic response from individual myotubes.

The effect of IgG4-MAB39 and anti-C5 antibody recombinant ravulizumab on the muscle fatigue index in cells incubated in AChR+MG serum from three individual patients is shown in FIG. 8.

Treatment of the cells incubated in AChR+MG patient sera with 0.1 μM and 1 μM IgG4-MAB39 resulted in a reduction of muscle contraction fatigue by 24.8% and 27.8%, respectively, as compared to baseline. Reduced muscle contraction fatigue was also observed in cells incubated in AChR+MG patient sera treated with anti-C5 antibody recombinant ravulizumab, as compared to baseline. This finding provides a scientific rationale for targeting complement classical pathway in AChR+MG.

IgG4-MAB39 was found to be a potent and selective anti-active C1s antibody that prevented complement-mediated MAC formation and complement-mediated hRBC lysis, and blocked activity of the classical complement pathway, but not the alternative or lectin complement pathways for immune surveillance, as discussed in Examples 3, 4, and 5, above. AChR+MG patient sera induced neurotransmission impairment and muscle fatigue in a human on-chip model of MG. Treatment with IgG4-MAB39 inhibited active C1s and prevented neurotransmission impairment and muscle fatigue in a cell-based human on-chip model of MG, allowing for muscle contraction and reducing the muscle fatigue index, providing proof of efficacy data in this indication.

Example 11: MAB39 does not Inhibit *N. meningitidis* Bacteria Killing

It can be important that the anti-C1S antibodies provided herein are specific and do not inhibit other immune pathways that are necessary for a subject's health, such as against bacterial infections. Accordingly, the ability of bacteria to survive in the presence of antibodies specific for the active form of CIS was tested. Briefly, *N. meningitidis* bacteria survival was measured in a culture of complement-containing sera (80% human sera) and anticapsular antibody (α-Nm), which mimics *N. meningitidis* vaccination, with and without test reagents. Anti-C7 antibody and heat-inactivation (HI), were used as controls that inactivate complement and demonstrated that the bacteria survived (see, FIG. 11). Ravulizumab (RAV), a non-specific humanized monoclonal antibody complement inhibitor, resulted in bacterial survival (i.e., no complement-mediated killing). In contrast to ravulizumab, no bacterial survival was observed when MAB39 was added to the complement-containing sera (C') and anticapsular antibody (α-Nm) mixture, which means that MAB39 does not inhibit *N. meningitidis* bacteria complement mediated killing. (FIG. 11) The lack of inhibition of *meningitidis* bacteria complement mediated killing was observed at both 0.3 uM and 1 uM concentrations. (FIG. 11) Accordingly, the antibodies provided herein do not inhibit complement mediated bacteria killing as compared to the non-specific complement antibody inhibitor ravulizumab.

Example 12: Proteolytic Cleavage of Non-Complement Substrates by Active C1s

Several in vitro studies have demonstrated an emerging role of active C1s in the proteolytic cleavage of non-complement substrates that include, for example, collagen, HMC I, HMGB1, IGFBP5, LRP6, NCL, and NPM1. Without being bound to any particular theory, these potential non-complement substrates of active C1s are postulated to be important in the clearance of antigens on apoptotic cells or in the hemostasis of bone, muscle, and connective tissues. Accordingly, it would be preferable for an antibody that targets the active form of ClS not inhibit or not inhibit significantly inhibit the cleavage of these non-complement substrates.

To test this, non-complement substrates in PBS (phosphate buffer saline) are incubated with active C1s (Complement Technologies, Tyler, TX, Catalog A104) in the absence or presence of varying concentrations of MAB39, MAB9, or isotype IgG4 antibody at 37° C. for 30 minutes. Complement component C4 is used a positive control. The reaction is stopped with 10×SDS-PAGE loading buffer with reducing agent DTT (dithiothreitol) and heated to 95° C. for about 10 minutes. Samples are then subjected to SDS-PAGE and cleavage products are detected by Coomassie Blue staining (for native non-complement substrate proteins) or alternatively, Western blot analysis (for recombinant non-complement substrate proteins with His- or Flag-tags).

No significant cleavage of non-complement substrates HMC I, HMGB1, IGFBP5, LRP6, NCL, and NPM1 by MAB39 or MAB9 is observed.

Thus, the antibodies provided for herein can be used as inhibitors of active C1s to treat C1s mediated disorders, such as cold agglutinin disease and Myasthenia Gravis. Due to the specificity of the antibodies to active Cis, the antibodies provided herein do not inhibit complement mediated bacterial killing and are not expected to inhibit the proteolytic cleavage of non-complement substrates of active ClS.

All references cited herein are incorporated by reference to the same extent as if each individual publication, database entry (e.g., Genbank sequences or GeneID entries), patent application, or patent, was specifically and individually indicated to be incorporated by reference. This statement of incorporation by reference is intended by Applicants, pursuant to 37 C.F.R. § 1.57(b)(1), to relate to each and every individual publication, database entry (e.g. Genbank sequences or GeneID entries), patent application, or patent, each of which is clearly identified in compliance with 37 C.F.R. § 1.57(b)(2), even if such citation is not immediately adjacent to a dedicated statement of incorporation by reference. The inclusion of dedicated statements of incorporation by reference, if any, within the specification does not in any way weaken this general statement of incorporation by reference. Citation of the references herein is not intended as an admission that the reference is pertinent prior art, nor does it constitute any admission as to the contents or date of these publications or documents.

The present embodiments are not to be limited in scope by the specific embodiments described herein. Indeed, various modifications in addition to those described herein will become apparent to those skilled in the art from the foregoing description and the accompanying FIGs. Such modifications are intended to fall within the scope of the embodiments and any appended claims.

The present specification is considered to be sufficient to enable one skilled in the art to practice the embodiments. Various modifications in addition to those shown and described herein will become apparent to those skilled in the art from the foregoing description and fall within the scope of the present disclosure and any appended claims.

What is claimed is:

1. An antibody, or an antigen binding fragment thereof, wherein the antibody, or the antigen binding fragment thereof, comprises:
   a heavy chain variable region comprising heavy chain HCDR1, HCDR2, and HCDR3 sequences, wherein the HCDR1 has the amino acid sequence of SEQ ID NO: 61, the HCDR2 has the amino acid sequence of SEQ ID NO: 62, and the HCDR3 has the amino acid sequence of SEQ ID NO: 78; and
   a light chain variable region comprising light chain LCDR1, LCDR3, and LCDR3 sequences, wherein the LCDR1 has the amino acid sequence of SEQ ID NO: 64, the LCDR2 has the amino acid sequence of SEQ ID NO: 65, and the LCDR3 has the amino acid sequence of SEQ ID NO: 79.

2. The antibody, or the antigen binding fragment thereof, of claim 1, wherein the heavy chain variable region comprises an amino acid sequence at least 95% identical to the amino acid sequence of SEQ ID NO: 342.

3. The antibody, or the antigen binding fragment thereof, of claim 1, wherein the heavy chain variable region comprises the amino acid sequence of SEQ ID NO: 342.

4. The antibody, or the antigen binding fragment thereof, of claim 1, wherein the heavy chain variable region comprises an amino acid sequence at least 95% identical to the amino acid sequence of SEQ ID NO: 17.

5. The antibody, or the antigen binding fragment thereof, of claim 1, wherein the heavy chain variable region comprises the amino acid sequence of SEQ ID NO: 17.

6. The antibody, or the antigen binding fragment thereof, of claim 1, wherein the heavy chain variable region comprises an amino acid sequence at least 95% identical to the amino acid sequence of SEQ ID NO: 454.

7. The antibody, or the antigen binding fragment thereof, of claim 1, wherein the heavy chain variable region comprises the amino acid sequence of SEQ ID NO: 454.

8. The antibody, or the antigen binding fragment thereof, of claim 1, wherein the antibody, or the antigen binding fragment thereof, comprises a heavy chain that is at least 95% identical to the amino acid sequence of SEQ ID NO: 381.

9. The antibody, or the antigen binding fragment thereof, of claim 1, o wherein the antibody, or the antigen binding fragment thereof, comprises a heavy chain comprising the amino acid sequence of SEQ ID NO: 381.

10. The antibody, or the antigen binding fragment thereof, of claim 1, herein the antibody, or the antigen binding fragment thereof, comprises a heavy chain that is at least 95% identical to the amino acid sequence of SEQ ID NO: 185.

11. The antibody, or the antigen binding fragment thereof, of claim 1, wherein the antibody, or the antigen binding fragment thereof, comprises a heavy chain comprising the amino acid sequence of SEQ ID NO: 185.

12. The antibody, or the antigen binding fragment thereof, of claim 1, wherein the light chain variable region comprises an amino acid sequence that is at least 95% identical to the amino acid sequence of SEQ ID NO: 18.

13. The antibody, or the antigen binding fragment thereof, of claim 1, wherein the light chain variable region comprises the amino acid sequence of SEQ ID NO: 18.

14. The antibody, or the antigen binding fragment thereof, of claim 1, wherein the antibody, or the antigen binding fragment thereof, comprises a light chain that is at least 95% identical to the amino acid sequence of SEQ ID NO: 236.

15. The antibody, or the antigen binding fragment thereof, of claim 1, wherein the antibody, or the antigen binding fragment thereof, comprises a light chain comprising the amino acid sequence of SEQ ID NO: 236.

16. The antibody, or the antigen binding fragment thereof, of claim 1, wherein the antibody, or the antigen binding fragment thereof, comprises the heavy chain variable region comprising the amino acid sequence of SEQ ID NO: 342, and the light chain variable region comprising the amino acid sequence of SEQ ID NO 18.

17. The antibody, or the antigen binding fragment thereof, of claim 1, wherein the antibody, or the antigen binding fragment thereof, comprises a heavy chain comprising the amino acid sequence of SEQ ID NO: 381, and a light chain comprising the amino acid sequence of SEQ ID NO: 236.

18. The antibody, or the antigen binding fragment thereof, of claim 1, wherein the antibody, or the antigen binding fragment thereof, comprises the heavy chain variable region comprising the amino acid sequence of SEQ ID NO: 17, and the light chain variable region comprising the amino acid sequence of SEQ ID NO 18.

19. The antibody, or the antigen binding fragment thereof, of claim 1, wherein the antibody, or the antigen binding fragment thereof, comprises a heavy chain comprising the amino acid sequence of SEQ ID NO: 185, and a light chain comprising the amino acid sequence of SEQ ID NO: 236.

20. A pharmaceutical composition comprising the antibody, or the antigen binding fragment thereof, of claim 1, and a pharmaceutically acceptable excipient.

21. A method of treating a subject with Myasthenia Gravis, hemolysis, Cold Agglutinin Disease, Immune Thrombocytopenia (ITP), Glomerulopathies, Atypical Hemolytic uremic syndrome, antiphospholipid antibody syndrome, transplant rejection, Chronic inflammatory demyelinating polyneuropathy (CIDP), Multifocal motor neuropathy (MMN), Dermatomyositis, or Anti MAG neuropathy, the method comprising administering to the subject the antibody, or the antigen binding fragment thereof, of claim 1, or a pharmaceutical composition comprising the antibody, or the antigen binding fragment thereof, of claim 1.

22. The method of claim 21, wherein the subject is a subject with Myasthenia Gravis.

23. The method of claim 21, wherein the subject is a subject with Cold Agglutinin Disease.

24. The method of claim 21, wherein the subject is a subject with Chronic inflammatory demyelinating polyneuropathy (CIDP).

25. The method of claim 21, wherein the subject is a subject with Multifocal motor neuropathy (MMN).

* * * * *

UNITED STATES PATENT AND TRADEMARK OFFICE
CERTIFICATE OF CORRECTION

PATENT NO. : 12,110,344 B2
APPLICATION NO. : 18/515714
DATED : October 8, 2024
INVENTOR(S) : Vahe Bedian and Charles A. Omer It is certified that error appears in the above-identified patent and that said Letters Patent is hereby corrected as shown below:

In the Specification

At Column 1, in the section entitled "REFERENCE TO AN ELECTRONIC SEQUENCE LISTING", please replace:
"This application contains a Sequence Listing which has been submitted electronically in XML format and is hereby incorporated by reference in its entirety. The Sequence Listing is named "DIN002WOsequencelisting.xml", was created on November 17, 2023, and is 495,158 bytes in size."
With:
--This application contains a Sequence Listing which has been submitted electronically in XML format and is hereby incorporated by reference in its entirety. The Sequence Listing is named "DIN002WOsequencelisting2.xml", was created on October 31, 2024, and is 495,144 bytes in size.--

At Column 305, in the paragraph beginning with: SEQUENCE: 4, please replace:
"DIQMTQSPSSLSASVGDRVTITCQASQDISNYLNWYQQKPGKAPKLLIYDASNLETGVPSRFSGSGSGTDFTFTISSLQPEDIATYYCEQYEDYPLTFGGGTKVEIK"
With:
--DIQMTQSPSSLSASVGDRVTITCQASQDISNYLNWYQQKPGKAPKLLIYDASNLETGVPSRFSGSGSGTDFTFTISSLQPEDIATYYCKQYEDYPLTFGGGTKVEIK--

At Column 307, in the paragraph beginning with: SEQUENCE: 18, please replace:
"DIQMTQSPSSLSASVGDRVTITCQASQDISNYLNWYQQKPGKAPKLLIYDASNLETGVPSRFSGSGSGTDFTFTISSLQPEDIATYYCQQHEDYPLTFGGGTKVEIK"
With:
--DIQMTQSPSSLSASVGDRVTITCQASQDISNYLNWYQQKPGKAPKLLIYDASNLETGVPSRFSGSGSGTDFTFTISSLQPEDIATYYCQHYEDYPLTFGGGTKVEIK--

At Column 309, in the paragraph beginning with: SEQUENCE: 28, please replace:
"DIQMTQSPSTLSASVGDRVTITCRASQSISSWLAWYQQKPGKAPKLLIYKASSLESGVPSRFSGSGSGTEFTLTISSLQPDDFATYYCQQVNSYDWTFGQGTKVEIK"

Signed and Sealed this
Eleventh Day of March, 2025

Coke Morgan Stewart
*Acting Director of the United States Patent and Trademark Office*

With:
--DIQMTQSPSTLSASVGDRVTITCRASQSISSWLAWYQQKPGKAPKLLIYKASSLESGVPSRF
SGSGSGTEFTLTISSLQPDDFATYYCQQYSSYAWTFGQGTKVEIK--

At Column 349, in the paragraph beginning with: SEQ ID NO: 194, please replace:
"length = 444"
With:
--length = 445--

At Column 349, in the paragraph beginning with: SEQ ID NO: 194, please replace:
"1..444"
With:
--1..445--

At Column 349, in the paragraph beginning with: SEQUENCE: 194, please replace:
"QVQLVQSGAEVKKPGASVKVSCKVSGDTLTELSMHWVRQAPGKGLEWMGTFDPEEGETIY
AQKFQGRVTMTEDTSTDTAYMELSSLRSEDTAVYYCVTEGLAWRPTDSWGQGTLVTVSSAS
TKGPSVFPLAPCSRSTSESTAALGCLVKDYFPEPVTVSWNSGALTSGVHTFPAVLQSSGLYSLS
SVVTVPSSSLGTKTYTCNVDHKPSNTKVDKRVESKYGPPCPPCPAPEFEGGPSVFLEPPKPKDT
LMISRTPEVTCVVVDVSQEDPEVQFNWYVDGVEVHNAKTKPREEQFNSTYRVVSVLTVLHQ
DWLNGKEYKCKVSNKGLPSSIEKTISKAKGQPREPQVYTLPPSQEEMTKNQVSLTCLVKG
FYPSDIAVEWESNGQPENNYKTTPPVLDSDGSFFLYSRLTVDKSRWQEGNVFSCSVLHEALHS
HYTQKSLSLSL"
With:
--QVQLVQSGAEVKKPGASVKVSCKVSGDTLTELSMHWVRQAPGKGLEWMGTFDPEEGET
IYAQKFQGRVTMTEDTSTDTAYMELSSLRSEDTAVYYCVTEGLAWRPTDSWGQGTLVTVSS
ASTKGPSVFPLAPCSRSTSESTAALGCLVKDYFPEPVTVSWNSGALTSGVHTFPAVLQSSGLY
SLSSVVTVPSSSLGTKTYTCNVDHKPSNTKVDKRVESKYGPPCPPCPAPEFEGGPSVFLFPPKP
KDTLMISRTPEVTCVVVDVSQEDPEVQFNWYVDGVEVHNAKTKPREEQFNSTYRVVSVLTV
LHQDWLNGKEYKCKVSNKGLPSSIEKTISKAKGQPREPQVYTLPPSQEEMTKNQVSLTCLVK
GFYPSDIAVEWESNGQPENNYKTTPPVLDSDGSFFLYSRLTVDKSRWQEGNVFSCSVLHEAL
HSHYTQKSLSLSLG--

At Column 375, in the paragraph beginning with: SEQ ID NO: 272, please replace:
"length = 327"
With:
--length = 348--

At Column 375, in the paragraph beginning with: SEQ ID NO: 272, please replace:
"1..327"
With:
--1..348--

At Column 375, in the paragraph beginning with: SEQUENCE: 272, please replace:
"gacattcagatgacgcaaagcccctctagcttgtccgctagtgtgggtgacagggtcaccattacctgccaggcttcacaagacatcagtaattacc
tcaactggtatcagcagaaacctgggaaggcccctaagctgttgatttacgatgctagtaacttggagaccggggtacccagcagatttagc

CERTIFICATE OF CORRECTION (continued)
U.S. Pat. No. 12,110,344 B2 gggagcggaagtggtacggattttacgtttaccattagcagcttgcagcccgaggacatcgctacatattactgtaagcagtatgaggactaccctctt
accttcggoggtggaacgaaagttgagattaagcgaacc"
With:
--caggtgcagcttgttgaaagtggtgggggtttggttaaacctggcggttcccttcgacttagctgcgcggcgtcagggttcacattctcagattatt
acatgtcttggattoggcaagcccctggtaagggactggagtgggtaagctacatatctcggtcaggaagtacaaagtactatgcagattcagtgaa
gggcaggtttacgattagccgagacaacgcaaagaactctctttatctgcagatgaattcactgagagcagaagataccgctgtctattattgtgccag
agacgagaccgattacgctttcgacgaatggggccaaggtacgctggttacggtc--

At Column 399, in the paragraph beginning with: SEQ ID NO: 354, please replace:
"length = 124"
With:
--length = 125--

At Column 399, in the paragraph beginning with: SEQ ID NO: 354, please replace:
"1..124"
With:
--1..125--

At Column 399, in the paragraph beginning with: SEQUENCE: 354, please replace:
"EVOLVESGGGVVRPGGSLRLSCAASGFTFDDYGMSWVRQAPGKGLEWVSGINWEGGSTGY
ADSVKGRFTISRDNAKNSLYLQMNSLRAEDTALYYCARDEQLGGTTYYYYYMDVWGKGTT
VTVS"
With:
--EVQLVESGGGVVRPGGSLRLSCAASGFTFDDYGMSWVRQAPGKGLEWVSGINWEGGST
GYADSVKGRFTISRDNAKNSLYLQMNSLRAEDTALYYCARDEQLGGTTYYYYYMDVWGKG
TTVTVSS --

At Column 409, in the paragraph beginning with: SEQ ID NO: 387, please replace:
"length = 483"
With:
--length = 445--

At Column 409, in the paragraph beginning with: SEQ ID NO: 387, please replace:
"1..483"
With:
--1..445--

At Column 411, in the paragraph beginning with: SEQUENCE: 387, please replace:
"MABWITH:CONSTANTDOMAINPEANDYTEMUTATIONSEVOLVQSGAEVKKPGASVKVSC
KVSGDTLTELSMHWWVRQAPGKGLEWMGTFDPEEGETIYAQKFQGRVTMTEDTSTDTAYM
ELSSLRSEDTAVYYCVTEGLGGRPFDHWGQGTLVTVSSASTKGPSVFPLAPCSRSTSESTAA
LGCLVKDYFPEPVTVSWNSGALTSGVHTFPAVLQSSGLYSLSSVVTVPSSSLGTKTYTCNVD
HKPSNTKVDKRVESKYGPPCPPCPAPEFEGGPSVFLFPPKPKDTLYITREPEVTCVVVDVSQED
PEVQFNWYVDGVEVHNAKTKPREEQFNSTYRVVSVLTVLHQDWLNGKEYKCKVSNKGL
PSSIEKTISKAKGQPREPQVYTLPPSQEEMTKNQVSLTCLVKGFYPSDIAVEWESNGQPENNKT
TPPVLDSDGSFFLYSRLTVDKSRWQEGNVFSCSVMHEALHNHYTQKSLSLSLG"

CERTIFICATE OF CORRECTION (continued)
U.S. Pat. No. 12,110,344 B2

With:
--EVQLVQSGAEVKKPGASVKVSCKVSGDTLTELSMHWVRQAPGKGLEWMGTFDPEEGE
TIYAQKFQGRVTMTEDTSTDTAYMELSSLRSEDTAVYYCVTEGLGGRPFDHWGQGTLVTVSS
SASTKGPSVFPLAPCSRSTSESTAALGCLVKDYFPEPVTVSWNSGALTSGVHTFPAVLQSS
GLYSLSSVVTVPSSSLGTKTYTCNVDHKPSNTKVDKRVESKYGPPCPPCPAPEFEGGPSVFL
FPPKPKDTLYITREPEVTCVVVDVSQEDPEVQFNWYVDGVEVHNAKTKPREEQFNSTYRVV
SVLTVLHQDWLNGKEYKCKVSNKGLPSSIEKTISKAKGQPREPQVYTLPPSQEEMTKNQVSL
TCLVKGFYPSDIAVEWESNGQPENNYKTTPPVLDSDGSFFLYSRLTVDKSRWQEGNVFSCSV
MHEALHNHYTQKSLSLSLG--